US012521431B2

(12) United States Patent
Barnes et al.

(10) Patent No.: US 12,521,431 B2
(45) Date of Patent: Jan. 13, 2026

(54) HBV VACCINE

(71) Applicant: Oxford University Innovation Limited, Oxford (GB)

(72) Inventors: Eleanor Barnes, Oxford (GB); Senthil Chinnakannan, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 18/206,249

(22) Filed: Jun. 6, 2023

(65) Prior Publication Data

US 2024/0115694 A1 Apr. 11, 2024

Related U.S. Application Data

(63) Continuation of application No. 16/604,221, filed as application No. PCT/GB2018/050948 on Apr. 10, 2018, now abandoned.

(30) Foreign Application Priority Data

Apr. 10, 2017 (GB) ..................................... 1705765

(51) Int. Cl.
*C07H 21/02* (2006.01)
*A61K 39/29* (2006.01)
(Continued)

(52) U.S. Cl.
CPC ............ *A61K 39/292* (2013.01); *A61K 39/39* (2013.01); *C07K 14/005* (2013.01); *C12N 7/00* (2013.01);
(Continued)

(58) Field of Classification Search
None
See application file for complete search history.

(56) References Cited

U.S. PATENT DOCUMENTS

2012/0251569 A1 10/2012 Martin et al.
2013/0243805 A1 9/2013 Apelian et al.

FOREIGN PATENT DOCUMENTS

CN 101573449 A 11/2009
CN 103173492 A 6/2013
(Continued)

OTHER PUBLICATIONS

International Search Report and Written Opinion for PCT/GB2018/050948, dated Jun. 26, 2018, pp. 1-12.
(Continued)

*Primary Examiner* — M Franco G Salvoza
(74) *Attorney, Agent, or Firm* — Thomas|Horstemeyer, LLP

(57) ABSTRACT

The invention relates to a multi-HBV immunogen viral vector vaccine comprising: a viral vector comprising an immunogen expression cassette, wherein the expression of a protein encoded by the expression cassette is arranged to be driven by a promoter, wherein the immunogen expression cassette encodes: a) HBV Core; b) a modified HBV polymerase ($P_{mut}$), wherein the modification is a mutation to wild-type HBV polymerase to substantially remove polymerase function; c) HBV surface antigen (HbsAg); and d) an intergenic sequence that is arranged to cause expression of at least the HBV surface antigen (HbsAg) as a separate protein from the HBV core and the modified HBV polymerase ($P_{mut}$), wherein the intergenic sequence is downstream (3') of the sequences encoding the HBV core and the modified HBV polymerase ($P_{mut}$) and upstream (5') of the sequence encoding the HBV surface antigen (HbsAg); and related compositions, vaccination methods and methods of treatment or prophylaxis of HBV infection.

6 Claims, 23 Drawing Sheets

Specification includes a Sequence Listing.

(51) Int. Cl.
*A61K 39/39* (2006.01)
*C07K 14/005* (2006.01)
*C12N 7/00* (2006.01)
*A61K 39/00* (2006.01)

(52) U.S. Cl.
CPC ................ *A61K 2039/5256* (2013.01); *A61K 2039/55516* (2013.01); *C07K 2319/00* (2013.01); *C12N 2710/24134* (2013.01); *C12N 2730/10122* (2013.01); *C12N 2730/10134* (2013.01)

(56) References Cited

FOREIGN PATENT DOCUMENTS

| | | | |
|---|---|---|---|
| JP | 2006-526409 | A | 11/2006 |
| JP | 2013-501038 | A | 1/2013 |
| JP | 2014-527404 | A | 10/2014 |
| WO | 94/12617 | A1 | 6/1994 |
| WO | 2005/017149 | A1 | 2/2005 |
| WO | 2008/020656 | A1 | 2/2008 |
| WO | 2011/015656 | A2 | 2/2011 |
| WO | 2012/109404 | A1 | 8/2012 |
| WO | 2013/007772 | A1 | 1/2013 |
| WO | 2015/082922 | A1 | 6/2015 |

OTHER PUBLICATIONS

United Kingdom Search Report for GB1705765.4, dated Mar. 8, 2018, pp. 1-4.
Perrine Martin et al: "TG1050, an immunotherapeutic to treat chronic hepatitis B, induces robust T cells and exerts an antiviral effect in HBV-persistent mice", GUT, vol. 64, No. 12, Nov. 26, 2014 (Nov. 26, 2014), pp. 1961-1971, XP055453477.
Sarah Kutscher et al: "Design of therapeutic vaccines: hepatitis Bas an example", Microbial Biotechnology, vol. 5, No. 2, Sep. 29, 2011 (Sep. 29, 2011), pp. 270-282, XP055217521, ISSN: 1751-7915, DOI: 10.1111/j.1751-7915.2011.00303.x p. 274-p. 277.
International Preliminary Report on Patentability for PCT/GB2018/050948, dated Oct. 15, 2019, pp. 1-7.
Japanese Office Action for Patent Application No. 2019-555196, dated May 10, 2022, pp. 1-14 (Translation Included).
Korean Office Action for Patent Application No. 10-2019-7031896, dated Sep. 27, 2023, pp. 1-11 (Translation Included).
Journal of Hepatology, 2018.4, vol. 68, pp. S789-S790, #SAT-407.
Vaccines, 2020, vol. 8, #184, <doi: 10.3390/vaccines8020184>.
Chinese Office Action for Patent Application No. 202410387306.0, dated Dec. 27, 2024, pp. 1-10 (Translation Included).

FIG. 1B...

genotype C consensus:

7269.1 HBV isolate JP-02:

acaacattccaccaagctctgctagatcccagagtgaggggcctatactttcctgctggtggctccagttccggaacagtaaaccctgttccgacta -----------------------------------------------t------------------------------------------------- tcacccatatcgtcaatcttctcgaggactggggaccctgcaccgaacatggagaacacaacatcaggattcctaggacccctgctcgtgttacagg ------------------------------------------------------------------------------------------------- tttttcttgttgacaagaatcctcacaataccacagagtctagactcgtggtggacttctctcaattttctaggggagcacccacgtgtcctggcc ------------------------------------------------------------------------------------------------- tcgcagtccccaacctccaatcactcaccaacctcttgtcctccaatttgtcctggctatcgctggatgtgtctgcggcgttttatcatattcctct ------------------------------------------------------------------------------------------------- ctgctgctatgcctcatcttcttgttggttcttctggactaccaaggtatgttgcccgtttgtcctctacttccaggaacatcaactaccagcacgg ------------------------------------------------------------------------------------------------- tgcaagacctgcacgattcctgctcaaggaacctctatgtttccctcttgttgctgtacaaaaccttcggacggaaactgcacttgtattcccatcc ------------------------------------------------------------------------------------------------- tcctgggctttcgcaagattcctatgggagtgggcctcagtccgtttctcctggctcagtttactagtgccatttgttcagtggttcgtagggcttt ------------------------------------------------------------------------------------------------- actgtttggctttcagttatatggatgatgtggtattggggccaagtctgtacaacatcttgagtcccttttttacctctattaccaattttctttt ------------------------------------------------------------------------------------------------- tgggtatacatttgaaccctaataaaaccaaacgttggggctactcccttaacttcatgggatatgtaattggaagttggggtactttaccacagga ------------------------------------------------------------------------------------------------- ttgtactaaaaatcaagcaatgttttcgaaaactgcctgtaaatagacctattgattggaaagtatgtcaaagaattgtgggtcttttgggctttgc ------------------------------------------------------------------------------------------------- cttttacacaatgtggctatcctgccttaatgcctttatatgcatgtatacaatctaagcaggctttcactttctcgccaacttacaggcctttct ----------------------------g-------------------------------------------------------------------- aacaatatctgaacctttaccccgttgcccggcaacggtcaggtctctgccaagtgtttgctgacgcaacccccactggatggggcttggccatagg ------------------------------------------------------------------------------------------------- ggcgcatgcgtggaacctttgtggctcctctgccgatccatactgcggaactcctagcagcttgttttgctcgcagccggtctggagcgaaacttat ------------------------------------------------------------------------------------------------- ccgacaactctgttgtcctctctcggaaatacacctcctttccatggctgctagggtgtgctgccaactggatcctgcgcgggacgtcctttgtcta ------------------------------------------------------------------------------------------------- cgtcggcgctgaatcccgcggacgacccgtctcggggccgtttgggactctaccgtccccttcttcatctgccgttccggccgaccacggggcgcac ------------------------------------------------------------------------------------------------- tttacgcggtctccccgtctgtgccttctcatctgccggaccgtgtgcacttcgcttcacctctgcacgtcgcatggagaccaccgtgaacgcccac

FIG. 1B continued cttgcccaaggtcttacataagaggactcttggactctcagcaatgtcaacgaccgaccttgaggcatacttcaaagactgtttgtttaaagactgg gttgggggaggagattaggttaatgatctttgtactaggaggctgtaggcataaattggtctgttcaccagcaccatgcaactttttcacctctgcc atctcatgttcatgtcctactgttcaagcctccaagctgtgccttgggtggctttggggcatggacattgacccgtataaagaatttggagcttctg ttactctctttttttgccttctgacttctttccttctattcgagatctcctcgacaccgcctctgctctgtatcgggaggccttagagtctccggaac tcacctcaccatacagcactcaggcaagctattctgtgttggggtgagttgatgaatctggccacctgggtgggaagtaatttggaagacccagcat gaattagtagtcagctatgtcaatgttaatatgggcctaaaaatcagacaactattgtggtttcacatttcctgtcttacttttggaagagaaactg gagtatttggtgtcttttggagtgtggattcgcactcctcccgcttacagaccaccaaatgcccctatcttatcaacacttccggaaactactgttg cgacgaggcaggtcccctagaagaagaactccctcgcctcgcagacgaaggtctcaatcgccgcgtcgcagaagatctcaatctcgggaatctcaat tatcccttggactcataaggtgggaaactttactgggctttattcttctactgtacctgtctttaatcctgagtggcaaactccctcctttcctcac tttacaggaggacattattaatagatgtcaacaatatgtgggccctcttacagttaatgaaaaaaggagattaaaattaattatgcctgctaggttc taaccttaccaaatatttgcccttggacaaaggcattaaaccttattatcctgaacatgcagttaatcattacttcaaaactaggcattatttacat g gtggaaggctggcattctatataagagagaaactacacgcagcgcctcatttgtgggtcaccatattcttgggaacaagagctacagcatgggagg cttccaaacctcgacaaggcatggggacgaatctttctgttcccaatcctctgggattctttcccgatcaccagttggaccctgcgttcggagccaa acaatccagattgggacttcaaccccaacaaggatcactggccagaggcaaatcaggtaggagcgggagcattcgggccagggttcaccccaccaca gtcttttggggtggagccctcaggctcagggcatattgacaacagtgccagcagcacctcctcctgcctccaccaatcggcagtcaggaagacagcc ccatctctccacctctaagagacagtcatcctcaggccatgcagtggaa MVA-SIi-HBV-PreS-Pmut-C-S(sh)

MVA-SIi-HBV-PreS-Pmut-C-TPA-S(sh)

MVA-SII-HBV-PreS-Pmut-C-S(sh)

SII-HBV-CPmutPreS-TPA-S(sh)

SEQUENCE LISTING

```
Sequence total quantity: 61
SEQ ID NO: 1            moltype = DNA  length = 3215
FEATURE                 Location/Qualifiers
source                  1..3215
                        mol_type = other DNA
                        organism = Hepatitis B virus
SEQUENCE: 1
ctccacaaca ttccaccaag ctctgctaga tcccagagtg aggggcctat actttcctgc  60
tggtggctcc agttccggaa cagtaaaccc tgttccgact actgcctcac ccatatcgtc  120
aatcttctcg aggactgggg accctgcacc gaacatggag aacacaacat caggattcct  180
aggacccctg ctcgtgttac aggcggggtt tttcttgttg acaagaatcc tcacaatacc  240
acagagtcta gactcgtggt ggacttctct caattttcta gggggagcac ccacgtgtcc  300
tggccaaaat tcgcagtccc caacctccaa tcactcacca acctcttgtc ctccaatttg  360
tcctggctat cgctggatgt gtctgcggcg ttttatcata ttcctcttca tcctgctgct  420
atgcctcatc ttcttgttgg ttcttctgga ctaccaaggt atgttgcccg tttgtcctct  480
acttccagga acatcaacta ccagcacggg accatgcaag acctgcacga ttcctgctca  540
aggaacctct atgtttccct cttgttgctg tacaaaacct tcggacggaa actgcacttg  600
tattcccatc ccatcatcct gggctttcgc aagattccta tgggagtggg cctcagtccg  660
tttctcctgg ctcagtttac tagtgccatt tgttcagtgg ttcgtagggc tttcccccac  720
tgtttggctt tcagttatat ggatgatgtg gtattggggg ccaagtctgt acaacatctt  780
gagtcccttt ttacctctat taccaatttt cttttgtctt tgggtataca tttgaaccct  840
aataaaacca aacgttgggg ctactccctt aacttcatgg gatatgtaat tggaagttgg  900
ggtactttac cacaggaaca tattgtacta aaaatcaagc aatgttttcg aaaactgcct  960
gtaaatagac ctattgattg gaaagtatgt caaagaattg tgggtctttt gggctttgct  1020
gccccttttta cacaatgtgg ctatcctgcc ttaatgcctt tatatgcatg tatacaatct  1080
aagcaggctt tcactttctc gccaacttac aaggcctttc tgtgtaaaca atatctgaac  1140
ctttaccccg ttgcccggca acggtcaggt ctctgccaag tgtttgctga cgcaaccccc  1200
actggatggg gcttggccat aggccatcgg cgcatgcgtg gaacctttgt ggctcctctg  1260
```

-continued

```
ccgatccata ctgcggaact cctagcagct tgttttgctc gcagccggtc tggagcgaaa  1320
cttatcggaa ccgacaactc tgttgtcctc tctcggaaat acacctcctt tccatggctg  1380
ctagggtgtg ctgccaactg gatcctgcgc gggacgtcct ttgtctacgt cccgtcggcg  1440
ctgaatcccg cggacgaccc gtctcggggc cgtttgggac tctaccgtcc ccttcttcat  1500
ctgccgttcc ggccgaccac ggggcgcacc tctctttacg cggtctcccc gtctgtgcct  1560
tctcatctgc cggaccgtgt gcacttcgct tcacctctgc acgtcgcatg gagaccaccg  1620
tgaacgccca ccaggtcttg cccaaggtct tacataagag gactcttgga ctctcagcaa  1680
tgtcaacgac cgaccttgag gcatacttca aagactgttt gtttaaagac tgggaggagt  1740
tgggggagga gattaggtta atgatctttg tactaggagg ctgtaggcat aaattggtct  1800
gttcaccagc accatgcaac tttttcacct ctgcctaatc atctcatgtt catgtcctac  1860
tgttcaagcc tccaagctgt gccttgggtg gctttggggc atggacattg acccgtataa  1920
agaatttgga gcttctgtgg agttactctc tttttgcct tctgacttct ttccttctat  1980
tcgagatctc ctcgacaccg cctctgctct gtatcgggag gccttagagt ctccggaaca  2040
ttgttcacct caccatacag cactcaggca agctattctg tgttggggtg agttgatgaa  2100
tctggccacc tgggtgggaa gtaatttgga agacccagca tccagggaat tagtagtcag  2160
ctatgtcaat gttaatatgg gcctaaaaat cagacaacta ttgtggtttc acatttcctg  2220
tcttactttt ggaagagaaa ctgttcttga gtatttggtg tcttttggag tgtggattcg  2280
cactcctccc gcttacagac caccaaatgc ccctatctta tcaacacttc cggaaactac  2340
tgttgttaga cgacgaggca ggtcccctag aagaagaact ccctcgcctc gcagacgaag  2400
gtctcaatcg ccgcgtcgca gaagatctca atctcgggaa tctcaatgtt agtatccctt  2460
ggactcataa ggtgggaaac tttactgggc tttattcttc tactgtacct gtctttaatc  2520
ctgagtggca aactccctcc tttcctcaca ttcatttaca ggaggacatt attaatagat  2580
gtcaacaata tgtgggccct cttacagtta atgaaaaaag gagattaaaa ttaattatgc  2640
ctgctaggtt ctatcctaac cttaccaaat atttgccctt ggacaaaggc attaaacctt  2700
attatcctga acatgcagtt aatcattact tcaaaactag gcattattta catactctgt  2760
ggaaggctgg cattctatat aagagagaaa ctacacgcag cgcctcattt tgtgggtcac  2820
catattcttg ggaacaagag ctacagcatg ggaggttggt cttccaaacc tcgacaaggc  2880
atggggacga atctttctgt tcccaatcct ctgggattct ttcccgatca ccagttggac  2940
cctgcgttcg gagccaactc aaacaatcca gattgggact tcaaccccaa caaggatcac  3000
tggccagagg caaatcaggt aggagcggga gcattcgggc cagggttcac ccccaccacac  3060
ggcggtcttt tggggtggag ccctcaggct cagggcatat tgacaacagt gccagcagca  3120
cctcctcctg cctccaccaa tcggcagtca ggaagacagc ctactcccat ctctccacct  3180
ctaagagaca gtcatcctca ggccatgcag tggaa                              3215

SEQ ID NO: 2            moltype = DNA  length = 3215
FEATURE                 Location/Qualifiers
misc_feature            1..3215
                        note = HBV consensus sequence
source                  1..3215
                        mol_type = other DNA
                        organism = synthetic construct
SEQUENCE: 2
ctccacaaca ttccaccaag ctctgctaga tcccagagtg aggggcctat attttcctgc  60
tggtggctcc agttccggaa cagtaaaccc tgttccgact actgcctcac ccatatcgtc  120
aatcttctcg aggactgggg accctgcacc gaacatggag aacacaacat caggattcct  180
aggacccctg ctcgtgttac aggcggggtt tttcttgttg acaagaatcc tcacaatacc  240
acagagtcta gactcgtggt ggacttctct caattttcta gggggagcac ccacgtgtcc  300
tggccaaaat tcgcagtccc caacctccaa tcactcacca acctcttgtc ctccaatttg  360
tcctggctat cgctggatgt gtctgcggcg ttttatcata ttcctcttca tcctgctgct  420
atgcctcatc ttcttgttgg ttcttctgga ctaccaaggt atgttgcccg tttgtcctct  480
acttccagga acatcaacta ccagcacggg accatgcaag acctgcacga ttcctgctca  540
aggaacctct atgtttccct cttgttgctg tacaaaacct tcggacggaa actgcacttg  600
tattcccatc ccatcatcct gggctttcgc aagattccta tgggagtggg cctcagtccg  660
tttctcctgg ctcagtttac tagtgccatt tgttcagtgg ttcgtagggc tttcccccac  720
tgtttggctt tcagttatat ggatgatgtg gtattggggg ccaagtctgt acaacatctt  780
gagtcccttt ttacctctat taccaatttt cttttgtctt tgggtataca tttgaaccct  840
aataaaacca aacgttgggg ctactccctt aacttcatgg gatatgtaat tggaagttgg  900
ggtactttac cacaggaaca tattgtacta aaaatcaagc aatgttttcg aaaactgcct  960
gtaaatagac ctattgattg gaaagtatgt caaagaattg tgggtctttt gggctttgct  1020
gccccttta cacaatgtgg ctatcctgcc ttgatgcctt tatatgcatg tatacaatct  1080
aagcaggctt tcactttctc gccaacttac aaggcctttc tgtgtaaaca atatctgaac  1140
ctttaccccg ttgcccggca acggtcaggt ctctgccaag tgtttgctga cgcaaccccc  1200
actggatggg gcttggccat aggccatcgg cgcatgcgtg gaacctttgt ggctcctctg  1260
ccgatccata ctgcggaact cctagcagct tgttttgctc gcagccggtc tggagcgaaa  1320
cttatcggaa ccgacaactc tgttgtcctc tctcggaaat acacctcctt tccatggctg  1380
ctagggtgtg ctgccaactg gatcctgcgc gggacgtcct ttgtctacgt cccgtcggcg  1440
ctgaatcccg cggacgaccc gtctcggggc cgtttgggac tctaccgtcc ccttcttcat  1500
ctgccgttcc ggccgaccac ggggcgcacc tctctttacg cggtctcccc gtctgtgcct  1560
tctcatctgc cggaccgtgt gcacttcgct tcacctctgc acgtcgcatg gagaccaccg  1620
tgaacgccca ccaggtcttg cccaaggtct tacataagag gactcttgga ctctcagcaa  1680
tgtcaacgac cgaccttgag gcatacttca aagactgttt gtttaaagac tgggaggagt  1740
tgggggagga gattaggtta atgatctttg tactaggagg ctgtaggcat aaattggtct  1800
gttcaccagc accatgcaac tttttcacct ctgcctaatc atctcatgtt catgtcctac  1860
tgttcaagcc tccaagctgt gccttgggtg gctttggggc atggacattg acccgtataa  1920
agaatttgga gcttctgtgg agttactctc tttttgcct tctgacttct ttccttctat  1980
tcgagatctc ctcgacaccg cctctgctct gtatcgggag gccttagagt ctccggaaca  2040
ttgttcacct caccatacag cactcaggca agctattctg tgttggggtg agttgatgaa  2100
tctggccacc tgggtgggaa gtaatttgga agacccagca tccagggaat tagtagtcag  2160
ctatgtcaat gttaatatgg gcctaaaaat cagacaacta ttgtggtttc acatttcctg  2220
```

-continued

```
tcttactttt ggaagagaaa ctgttcttga gtatttggtg tcttttggag tgtggattcg  2280
cactcctccc gcttacagac caccaaatgc ccctatctta tcaacacttc cggaaactac  2340
tgttgttaga cgacgaggca ggtcccctag aagaagaact ccctcgcctc gcagacgaag  2400
gtctcaatcg ccgcgtcgca gaagatctca atctcgggaa tctcaatgtt agtatccctt  2460
ggactcataa ggtgggaaac tttactgggc tttattcttc tactgtacct gtctttaatc  2520
ctgagtggca aactccctcc tttcctcaca ttcatttaca ggaggacatt attaatagat  2580
gtcaacaata tgtgggccct cttacagtta atgaaaaaag gagattaaaa ttaattatgc  2640
ctgctaggtt ctatcctaac cttaccaaat atttgccctt ggacaaaggc attaaaccgt  2700
attatcctga acatgcagtt aatcattact tcaaaactag gcattattta catactctgt  2760
ggaaggctgg cattctatat aagagagaaa ctacacgcag cgcctcattt tgtgggtcac  2820
catattcttg ggaacaagag ctacagcatg ggaggttggt cttccaaacc tcgacaaggc  2880
atggggacga atctttctgt tcccaatcct ctgggattct ttcccgatca ccagttggac  2940
cctgcgttcg gagccaactc aaacaatcca gattgggact tcaaccccaa caaggatcac  3000
tggccagagg caaatcaggt aggagcggga gcattcgggc cagggttcac ccccaccacac  3060
ggcggtcttt tggggtggag ccctcaggct cagggcatat tgacaacagt gccagcagca  3120
cctcctcctg cctccaccaa tcggcagtca ggaagacagc ctactcccat ctctccacct  3180
ctaagagaca gtcatcctca ggccatgcag tggaa                              3215

SEQ ID NO: 3           moltype = AA  length = 1525
FEATURE                Location/Qualifiers
REGION                 1..1525
                       note = Vaccine construct
source                 1..1525
                       mol_type = protein
                       organism = synthetic construct
SEQUENCE: 3
MSLLWGGVTV LAAMLIAGQV ASVVFLVKGG GPGGGMQLFH LCLIISCSCP TVQASKLCLG  60
WLWGMDIDPY KEFGASVELL SFLPSDFFPS IRDLLDTASA LYREALESPE HCSPHHTALR  120
QAILCWGELM NLATWVGSNL EDPASRELVV SYVNVNMGLK IRQLLWFHIS CLTFGRETVL  180
EYLVSFGVWI RTPPAYRPPN APILSTLPET TVVRRRGRSP RRRTPSPRRR RSQSPRRRRS  240
QSRESQCGGG SGGGMPLSYQ HFRKLLLLDD EAGPLEEELP RLADEGLNRR VAEDLNLGNL  300
NVSIPWTHKV GNFTGLASST VPVFNPEWQT PSFPHIHLQE DIINRCQQYV GPLTVNEKRR  360
LKLIMPARFY PNLTKYLPLD KGIKPYYPEH AVNHYFKTRH YLHTLWKAGI LYKRETTRSA  420
SFCGSPYSWE QELQHGRLVF QTSTRHGDES FCSQSSGILS RSPVGPCVRS QLKQSRLGLQ  480
PQQGSLARGK SGRSGSIRAR VHPTTRRSFG VEPSGSGHID NSASSTSSCL HQSAVRKTAY  540
SHLSTSKRQS SSGHAVELHN IPPSSARSQS EGPIFSAWWL QFRNSKPASD YALTHIVNLL  600
EDWGPATEHG EHNIRIPRTP ARVTGGVFLV DKNPHNTTES RLVVDFSQFS RGSTHVSWPK  660
FAVPNLQSLT NLLSSNLSWL SLDVSAAFYH IPLHPAAMPH LLVGSSGLPR YVARLSSTSR  720
NINYQHGTMQ DLHDSCSRNL YVSLLLLYKT FGRKLHLYSH PIILGFRKIP MGVGLSPFLL  780
AQFTSAICSV VRRAFPHCLA FSYMDDVVLG AKSVQHLESL FTSITNFLLS LGIHLNPNKT  840
KRWGYSLNFM GYVIGSWGTL PQEHIVLKIK QCFRKLPVNR PIDWKVCQRI VGLLGFAAPF  900
TQCGYPALMP LYACIQSKQA FTFSPTYKAF LCKQYLNLYP VARQRSGLCQ VFADATPTGW  960
GLAIGHRAMR GTFVAPLPIH TAELLAACFA RSRSGAKLIG TDNSVVLSRK YTSFPWLLGC  1020
AANWILRGTS FVYVPSALNP AADPSAGRLG LYRPLLHLPF RPTTGRTSLY AVSPSVPSHL  1080
PDRVHFASPL HVAWRPPRKR RAPVKQTLNF DLLKLAGDVE SNPGPMGGWS SKPRQGMGTN  1140
LSVPNPLGFF PDHQLDPAFG ANSNNPDWDF NPNKDHWPEA NQVGAGAFGP GFTPPHGGLL  1200
GWSPQAQGIL TTVPAAPPPA STNRQSGRQP TPISPPLRDS HPQAMQWNST TFHQALLDPR  1260
VRGLYFPAGG SSSGTVNPVP TTASPISSIF SRTGDPAPNM ENTTSGFLGP LLVLQAGFFL  1320
LTRILTIPQS LDSWWTSLNF LGGAPTCPGQ NSQSPTSNHS PTSCPPICPG YRWMCLRRFI  1380
IFLFILLLCL IFLLVLLDYQ GMLPVCPLLP GTSTTSTGPC KTCTIPAQGT SMFPSCCCTK  1440
PSDGNCTCIP IPSSWAFARF LWEWASVRFS WLSLLVPFVQ WFVGLSPTVW LSVIWMMWYW  1500
GPSLYNILSP FLPLLPIFFC LWVYI                                         1525

SEQ ID NO: 4           moltype = AA  length = 26
FEATURE                Location/Qualifiers
REGION                 1..26
                       note = Shark Invariant Chain
source                 1..26
                       mol_type = protein
                       organism = unidentified
SEQUENCE: 4
SLLWGGVTVL AAMLIAGQVA SVVFLV                                        26

SEQ ID NO: 5           moltype = AA  length = 8
FEATURE                Location/Qualifiers
REGION                 1..8
                       note = Linker peptide
source                 1..8
                       mol_type = protein
                       organism = synthetic construct
SEQUENCE: 5
KGGGPGGG                                                            8

SEQ ID NO: 6           moltype = AA  length = 183
FEATURE                Location/Qualifiers
source                 1..183
                       mol_type = protein
                       organism = Hepatitis B virus
```

-continued

```
SEQUENCE: 6
MDIDPYKEFG ASVELLSFLP SDFFPSIRDL LDTASALYRE ALESPEHCSP HHTALRQAIL  60
CWGELMNLAT WVGSNLEDPA SRELVVSYVN VNMGLKIRQL LWFHISCLTF GRETVLEYLV  120
SFGVWIRTPP AYRPPNAPIL STLPETTVVR RRGRSPRRRT PSPRRRRSQS PRRRRSQSRE  180
SQC                                                               183

SEQ ID NO: 7            moltype = AA  length = 7
FEATURE                 Location/Qualifiers
REGION                  1..7
                        note = Linker peptide
source                  1..7
                        mol_type = protein
                        organism = synthetic construct
SEQUENCE: 7
GGGSGGG                                                           7

SEQ ID NO: 8            moltype = AA  length = 772
FEATURE                 Location/Qualifiers
source                  1..772
                        mol_type = protein
                        organism = Hepatitis B virus
SEQUENCE: 8
MPLSYQHFRK LLLLDDEAGP LEEELPRLAD EGLNRRVAED LNLGNLNVSI PWTHKVGNFT  60
GLASSTVPVF NPEWQTPSFP HIHLQEDIIN RCQQYVGPLT VNEKRRLKLI MPARFYPNLT  120
KYLPLDKGIK PYYPEHAVNH YFKTRHYLHT LWKAGILYKR ETTRSASFCG SPYSWEQELQ  180
HGRLVFQTST RHGDESFCSQ SSGILSRSPV GPCVRSQLKQ SRLGLQPQQG SLARGKSGRS  240
GSIRARVHPT TRRSFGVEPS GSGHIDNSAS STSSCLHQSA VRKTAYSHLS TSKRQSSSGH  300
AVELHNIPPS SARSQSEGPI FSAWWLQFRN SKPASDYALT HIVNLLEDWG PATEHGEHNI  360
RIPRTPARVT GGVFLVDKNP HNTTESRLVV DFSQFSRGST HVSWPKFAVP NLQSLTNLLS  420
SNLSTFGRKL HLYSHPIILG FRKIPMGVGL SPFLLAQFTS AICSVVRRAF PHCLAFSYMD  480
DVVLGAKSVQ HLESLFTSIT NFLLSLGIHL NPNKTKRWGY SLNFMGYVIG SWGTLPQEHI  540
VLKIKQCFRK LPVNRPIDWK VCQRIVGLLG FAAPFTQCGY PALMPLYACI QSKQAFTFSP  600
TYKAFLCKQY LNLYPVARQR SGLCQVFADA TPTGWGLAIG HRAMRGTFVA PLPIHTAELL  660
AACFARSRSG AKLIGTDNSV VLSRKYTSFP WLLGCAANWI LRGTSFVYVP SALNPAADPS  720
AGRLGLYRPL LHLPFRPTTG RTSLYAVSPS VPSHLPDRVH FASPLHVAWR PP          772

SEQ ID NO: 9            moltype = AA  length = 28
FEATURE                 Location/Qualifiers
REGION                  1..28
                        note = Furin 2A
source                  1..28
                        mol_type = protein
                        organism = unidentified
SEQUENCE: 9
RKRRAPVKQT LNFDLLKLAG DVESNPGP                                    28

SEQ ID NO: 10           moltype = AA  length = 226
FEATURE                 Location/Qualifiers
source                  1..226
                        mol_type = protein
                        organism = Hepatitis B virus
SEQUENCE: 10
MENTTSGFLG PLLVLQAGFF LLTRILTIPQ SLDSWWTSLN FLGGAPTCPG QNSQSPTSNH  60
SPTSCPPICP GYRWMCLRRF IIFLFILLLC LIFLLVLLDY QGMLPVCPLL PGTSTTSTGP  120
CKTCTIPAQG TSMFPSCCCT KPSDGNCTCI PIPSSWAFAR FLWEWASVRF SWLSLLVPFV  180
QWFVGLSPTV WLSVIWMMWY WGPSLYNILS PFLPLLPIFF CLWVYI                 226

SEQ ID NO: 11           moltype = AA  length = 1521
FEATURE                 Location/Qualifiers
REGION                  1..1521
                        note = Vaccine construct
source                  1..1521
                        mol_type = protein
                        organism = synthetic construct
SEQUENCE: 11
MSLLWGGVTV LAAMLIAGQV ASVVFLVKGG SMGGWSSKPR QGMGTNLSVP NPLGFFPDHQ  60
LDPAFGANSN NPDWDFNPNK DHWPEANQVG AGAFGPGFTP PHGGLLGWSP QAQGILTTVP  120
AAPPPASTNR QSGRQPTPIS PPLRDSHPQA MQWNSTTFHQ ALLDPRVRGL YFPAGGSSSG  180
TVNPVPTTAS PISSIFSRTG DPAPNMENTT SGFLGPLLVL QAGFFLLTRI LTIPQSLDSW  240
WTSLNFLGGA PTCPGQNSQS PTSNHSPTSC PPICPGYRWM CLRRFIIFLF ILLLCLIFLL  300
VLLDYQGMLP VCPLLPGTST TSTGPCKTCT IPAQGTSMFP SCCCTKPSDG NCTCIPIPSS  360
WAFARFLWEW ASVRFSWLSL LVPFVQWFVG LSPTVWLSVI WMMWYWGPSL YNILSPFLPL  420
LPIFFCLWVY IRKRRAPVKQ TLNFDLLKLA GDVESNPGPM QLFHLCLIIS CSCPTVQASK  480
LCLGWLWGMD IDPYKEFGAS VELLSFLPSD FFPSIRDLLD TASALYREAL ESPEHCSPHH  540
TALRQAILCW GELMNLATWV GSNLEDPASR ELVVSYVNVN MGLKIRQLLW FHISCLTFGR  600
ETVLEYLVSF GVWIRTPPAY RPPNAPILST LPETTVVRRR GRSPRRRTPS PRRRRSQSPR  660
RRRSQSRESQ CGGGSGGGMP LSYQHFRKLL LLDDEAGPLE EELPRLADEG LNRRVAEDLN  720
LGNLNVSIPW THKVGNFTGL ASSTVPVFNP EWQTPSFPHI HLQEDIINRC QQYVGPLTVN  780
EKRRLKLIMP ARFYPNLTKY LPLDKGIKPY YPEHAVNHYF KTRHYLHTLW KAGILYKRET  840
```

-continued

```
TRSASFCGSP YSWEQELQHG RLVFQTSTRH GDESFCSQSS GILSRSPVGP CVRSQLKQSR  900
LGLQPQQGSL ARGKSGRSGS IRARVHPTTR RSFGVEPSGS GHIDNSASST SSCLHQSAVR  960
KTAYSHLSTS KRQSSSGHAV ELHNIPPSSA RSQSEGPIFS AWWLQFRNSK PASDYALTHI  1020
VNLLEDWGPA TEHGEHNIRI PRTPARVTGG VFLVDKNPHN TTESRLVVDF SQFSRGSTHV  1080
SWPKFAVPNL QSLTNLLSSN LSWLSLDVSA AFYHIPLHPA AMPHLLVGSS GLPRYVARLS  1140
STSRNINYQH GTMQDLHDSC SRNLYVSLLL LYKTFGRKLH LYSHPIILGF RKIPMGVGLS  1200
PFLLAQFTSA ICSVVRRAFP HCLAFSYMDD VVLGAKSVQH LESLFTSITN FLLSLGIHLN  1260
PNKTKRWGYS LNFMGYVIGS WGTLPQEHIV LKIKQCFRKL PVNRPIDWKV CQRIVGLLGF  1320
AAPFTQCGYP ALMPLYACIQ SKQAFTFSPT YKAFLCKQYL NLYPVARQRS GLCQVFADAT  1380
PTGWGLAIGH RAMRGTFVAP LPIHTAELLA ACFARSRSGA KLIGTDNSVV LSRKYTSFPW  1440
LLGCAANWIL RGTSFVYVPS ALNPAADPSA GRLGLYRPLL HLPFRPTTGR TSLYAVSPSV  1500
PSHLPDRVHF ASPLHVAWRP P                                            1521

SEQ ID NO: 12          moltype = AA  length = 1490
FEATURE                Location/Qualifiers
REGION                 1..1490
                       note = Vaccine construct
source                 1..1490
                       mol_type = protein
                       organism = synthetic construct
SEQUENCE: 12
MQLFHLCLII SCSCPTVQAS KLCLGWLWGM DIDPYKEFGA SVELLSFLPS DFFPSIRDLL  60
DTASALYREA LESPEHCSPH HTALRQAILC WGELMNLATW VGSNLEDPAS RELVVSYVNV  120
NMGLKIRQLL WFHISCLTFG RETVLEYLVS FGVWIRTPPA YRPPNAPILS TLPETTVVRR  180
RGRSPRRRTP SPRRRRSQSP RRRRSQSRES QCGGGSGGGM PLSYQHFRKL LLLDDEAGPL  240
EEELPRLADE GLNRRVAEDL NLGNLNVSIP WTHKVGNFTG LASSTVPVFN PEWQTPSFPH  300
IHLQEDIINR CQQYVGPLTV NEKRRLKLIM PARFYPNLTK YLPLDKGIKP YYPEHAVNHY  360
FKTRHYLHTL WKAGILYKRE TTRSASFCGS PYSWEQELQH GRLVFQTSTR HGDESFCSQS  420
SGILSRSPVG PCVRSQLKQS RLGLQPQQGS LARGKSGRSG SIRARVHPTT RRSFGVEPSG  480
SGHIDNSASS TSSCLHQSAV RKTAYSHLST SKRQSSSGHA VELHNIPPSS ARSQSEGPIF  540
SAWWLQFRNS KPASDYALTH IVNLLEDWGP ATEHGEHNIR IPRTPARVTG GVFLVDKNPH  600
NTTESRLVVD FSQFSRGSTH VSWPKFAVPN LQSLTNLLSS NLSWLSLDVS AAFYHIPLHP  660
AAMPHLLVGS SGLPRYVARL SSTSRNINYQ HGTMQDLHDS CSRNLYVSLL LLYKTFGRKL  720
HLYSHPIILG FRKIPMGVGL SPFLLAQFTS AICSVVRRAF PHCLAFSYMD DVVLGAKSVQ  780
HLESLFTSIT NFLLSLGIHL NPNKTKRWGY SLNFMGYVIG SWGTLPQEHI VLKIKQCFRK  840
LPVNRPIDWK VCQRIVGLLG FAAPFTQCGY PALMPLYACI QSKQAFTFSP TYKAFLCKQY  900
LNLYPVARQR SGLCQVFADA TPTGWGLAIG HRAMRGTFVA PLPIHTAELL AACFARSRSG  960
AKLIGTDNSV VLSRKYTSFP WLLGCAANWI LRGTSFVYVP SALNPAADPS AGRLGLYRPL  1020
LHLPFRPTTG RTSLYAVSPS VPSHLPDRVH FASPLHVAWR PPRKRRAPVK QTLNFDLLKL  1080
AGDVESNPGP MGGWSSKPRQ GMGTNLSVPN PLGFFPDHQL DPAFGANSNN PDWDFNPNKD  1140
HWPEANQVGA GAFGPGFTPP HGGLLGWSPQ AQGILTTVPA APPPASTNRQ SGRQPTPISP  1200
PLRDSHPQAM QWNSTTFHQA LLDPRVRGLY FPAGGSSSGT VNPVPTTASP ISSIFSRTGD  1260
PAPNMENTTS GFLGPLLVLQ AGFFLLTRIL TIPQSLDSWW TSLNFLGGAP TCPGQNSQSP  1320
TSNHSPTSCP PICPGYRWMC LRRFIIFLFI LLLCLIFLLV LLDYQGMLPV CPLLPGTSTT  1380
STGPCKTCTI PAQGTSMFPS CCCTKPSDGN CTCIPIPSSW AFARFLWEWA SVRFSWLSLL  1440
VPFVQWFVGL SPTVWLSVIW MMWYWGPSLY NILSPFLPLL PIFFCLWVYI             1490

SEQ ID NO: 13          moltype = AA  length = 1492
FEATURE                Location/Qualifiers
REGION                 1..1492
                       note = Vaccine construct
source                 1..1492
                       mol_type = protein
                       organism = synthetic construct
SEQUENCE: 13
MSLLWGGVTV LAAMLIAGQV ASVVFLVKGG GPGGGMQLFH LCLIISCSCP TVQASKLCLG  60
WLWGMDIDPY KEFGASVELL SFLPSDFFPS IRDLLDTASA LYREALESPE HCSPHHTALR  120
QAILCWGELM NLATWVGSNL EDPASRELVV SYVNVNMGLK IRQLLWFHIS CLTFGRETVL  180
EYLVSFGVWI RTPPAYRPPN APILSTLPET TVVRRRGRSP RRRTPSPRRR RSQSPRRRRS  240
QSRESQCGGG SGGGMPLSYQ HFRKLLLLDD EAGPLEEELP RLADEGLNRR VAEDLNLGNL  300
NVSIPWTHKV GNFTGLASST VPVFNPEWQT PSFPHIHLQE DIINRCQQYV GPLTVNEKRR  360
LKLIMPARFY PNLTKYLPLD KGIKPYYPEH AVNHYFKTRH YLHTLWKAGI LYKRETTRSA  420
SFCGSPYSWE QELQHGRLVF QTSTRHGDES FCSQSSGILS RSPVGPCVRS QLKQSRLGLQ  480
PQQGSLARGK SGRSGSIRAR VHPTTRRSFG VEPSGSGHID NSASSTSSCL HQSAVRKTAY  540
SHLSTSKRQS SSGHAVELHN IPPSSARSQS EGPIFSAWWL QFRNSKPASD YALTHIVNLL  600
EDWGPATEHG EHNIRIPRTP ARVTGGVFLV DKNPHNTTES RLVVDFSQFS RGSTHVSWPK  660
FAVPNLQSLT NLLSSNLSTF GRKLHLYSHP IILGFRKIPM GVGLSPFLLA QFTSAICSVV  720
RRAFPHCLAF SYMDDVVLGA KSVQHLESLF TSITNFLLSL GIHLNPNKTK RWGYSLNFMG  780
YVIGSWGTLP QEHIVLKIKQ CFRKLPVNRP IDWKVCQRIV GLLGFAAPFT QCGYPALMPL  840
YACIQSKQAF TFSPTYKAFL CKQYLNLYPV ARQRSGLCQV FADATPTGWG LAIGHRAMRG  900
TFVAPLPIHT AELLAACFAR SRSGAKLIGT DNSVVLSRKY TSFPWLLGCA ANWILRGTSF  960
VYVPSALNPA ADPSAGRLGL YRPLLHLPFR PTTGRTSLYA VSPSVPSHLP DRVHFASPLH  1020
VAWRPPKSPN SNNPDWDFNP NKDHWPEANQ VGAGAFGPGF TPPHGGLLGW SPQAQGILTT  1080
VPAAPPPAST NRQSGRQPTP ISPPLRDSHP QAMQWNSTTF HQALLDPRVR GLYFPAGGSS  1140
SGTVNPVPTT ASPISSIFSR TGDPAPNGSK GKRKRRAPVK QTLNFDLLKL AGDVESNPGP  1200
MGGWSSKPRQ GMGTNLSVPN PLGFFPDHQL DPAFGANSNN PDWDFNPNKD HWPEANQVGL  1260
EGGSGGMENT TSGFLGPLLV LQAGFFLLTR ILTIPQSLDS WWTSLNFLGG APTCPGQNSQ  1320
```

```
SPTSNHSPTS CPPICPGYRW MCLRRFIIFL FILLLCLIFL LVLLDYQGML PVCPLLPGTS  1380
TTSTGPCKTC TIPAQGTSMF PSCCCTKPSD GNCTCIPIPS SWAFARFLWE WASVRFSWLS  1440
LLVPFVQWFV GLSPTVWLSV IWMMWYWGPS LYNILSPFLP LLPIFFCLWV YI          1492

SEQ ID NO: 14          moltype = AA  length = 4
FEATURE                Location/Qualifiers
REGION                 1..4
                       note = Linker peptide
source                 1..4
                       mol_type = protein
                       organism = synthetic construct
SEQUENCE: 14
KGGS                                                               4

SEQ ID NO: 15          moltype = AA  length = 138
FEATURE                Location/Qualifiers
source                 1..138
                       mol_type = protein
                       organism = Hepatitis B virus
SEQUENCE: 15
NSNNPDWDFN PNKDHWPEAN QVGAGAFGPG FTPPHGGLLG WSPQAQGILT TVPAAPPPAS  60
TNRQSGRQPT PISPPLRDSH PQAMQWNSTT FHQALLDPRV RGLYFPAGGS SSGTVNPVPT  120
TASPISSIFS RTGDPAPN                                                138

SEQ ID NO: 16          moltype = AA  length = 29
FEATURE                Location/Qualifiers
source                 1..29
                       mol_type = protein
                       organism = Hepatitis B virus
SEQUENCE: 16
MQLFHLCLII SCSCPTVQAS KLCLGWLWG                                    29

SEQ ID NO: 17          moltype = AA  length = 159
FEATURE                Location/Qualifiers
source                 1..159
                       mol_type = protein
                       organism = Hepatitis B virus
SEQUENCE: 17
SKLCLGWLWG MDIDPYKEFG ASVELLSFLP SDFFPSIRDL LDTASALYRE ALESPEHCSP  60
HHTALRQAIL CWGELMNLAT WVGSNLEDPA SRELVVSYVN VNMGLKIRQL LWFHISCLTF  120
GRETVLEYLV SFGVWIRTPP AYRPPNAPIL STLPETTVV                         159

SEQ ID NO: 18          moltype = AA  length = 226
FEATURE                Location/Qualifiers
source                 1..226
                       mol_type = protein
                       organism = Hepatitis B virus
SEQUENCE: 18
MENTTSGFLG PLLVLQAGFF LLTRILTIPQ SLDSWWTSLN FLGGAPTCPG QNSQSPTSNH  60
SPTSCPPICP GYRWMCLRRF IIFLFILLLC LIFLLVLLDY QGMLPVCPLL PGTSTTSTGP  120
CKTCTIPAQG TSMFPSCCCT KPSDGNCTCI PIPSSWAFAR FLWEWASVRF SWLSLLVPFV  180
QWFVGLSPTV WLSVIWMMWY WGPSLYNILS PFLPLLPIFF CLWVYI                 226

SEQ ID NO: 19          moltype = AA  length = 843
FEATURE                Location/Qualifiers
source                 1..843
                       mol_type = protein
                       organism = Hepatitis B virus
SEQUENCE: 19
MPLSYQHFRK LLLLDDEAGP LEEELPRLAD EGLNRRVAED LNLGNLNVSI PWTHKVGNFT  60
GLYSSTVPVF NPEWQTPSFP HIHLQEDIIN RCQQYVGPLT VNEKRRLKLI MPARFYPNLT  120
KYLPLDKGIK PYYPEHAVNH YFKTRHYLHT LWKAGILYKR ETTRSASFCG SPYSWEQELQ  180
HGRLVFQTST RHGDESFCSQ SSGILSRSPV GPCVRSQLKQ SRLGLQPQQG SLARGKSGRS  240
GSIRARVHPT TRRSFGVEPS GSGHIDNSAS STSSCLHQSA VRKTAYSHLS TSKRQSSSGH  300
AVELHNIPPS SARSQSEGPI FSCWWLQFRN SKPCSDYCLT HIVNLLEDWG PCTEHGEHNI  360
RIPRTPARVT GGVFLVDKNP HNTTESRLVV DFSQFSRGST HVSWPKFAVP NLQSLTNLLS  420
SNLSWLSLDV SAAFYHIPLH PAAMPHLLVG SSGLPRYVAR LSSTSRNINY QHGTMQDLHD  480
SCSRNLYVSL LLLYKTFGRK LHLYSHPIIL GFRKIPMGVG LSPFLLAQFT SAICSVVRRA  540
FPHCLAFSYM DDVVLGAKSV QHLESLFTSI TNFLLSLGIH LNPNKTKRWG YSLNFMGYVI  600
GSWGTLPQEH IVLKIKQCFR KLPVNRPIDW KVCQRIVGLL GFAAPFTQCG YPALMPLYAC  660
IQSKQAFTFS PTYKAFLCKQ YLNLYPVARQ RSGLCQVFAD ATPTGWGLAI GHRRMRGTFV  720
APLPIHTAEL LAACFARSRS GAKLIGTDNS VVLSRKYTSF PWLLGCAANW ILRGTSFVYV  780
PSALNPADDP SRGRLGLYRP LLHLPFRPTT GRTSLYAVSP SVPSHLPDRV HFASPLHVAW  840
RPP                                                                843

SEQ ID NO: 20          moltype = AA  length = 5
FEATURE                Location/Qualifiers
REGION                 1..5
                       note = Linker peptide
```

```
source                  1..5
                        mol_type = protein
                        organism = synthetic construct
SEQUENCE: 20
GSKGK                                                                  5

SEQ ID NO: 21           moltype = AA  length = 59
FEATURE                 Location/Qualifiers
source                  1..59
                        mol_type = protein
                        organism = Hepatitis B virus
SEQUENCE: 21
MGGWSSKPRQ GMGTNLSVPN PLGFFPDHQL DPAFGANSNN PDWDFNPNKD HWPEANQVG   59

SEQ ID NO: 22           moltype = AA  length = 7
FEATURE                 Location/Qualifiers
REGION                  1..7
                        note = Linker peptide
source                  1..7
                        mol_type = protein
                        organism = synthetic construct
SEQUENCE: 22
LEGGSGG                                                                7

SEQ ID NO: 23           moltype = AA  length = 1539
FEATURE                 Location/Qualifiers
source                  1..1539
                        mol_type = protein
                        organism = Hepatitis B virus
SEQUENCE: 23
MSLLWGGVTV LAAMLIAGQV ASVVFLVSKS GPPSGKSNSN NPDWDFNPNK DHWPEANQVG  60
AGAFGPGFTP PHGGLLGWSP QAQGILTTVP AAPPPASTNR QSGRQPTPIS PPLRDSHPQA  120
MQWNSTTFHQ ALLDPRVRGL YFPAGGSSSG TVNPVPTTAS PISSIFSRTG DPAPNGSKSG  180
SKMPLSYQHF RKLLLLDDEA GPLEEELPRL ADEGLNRRVA EDLNLGNLNV SIPWTHKVGN  240
FTGLASSTVP VFNPEWQTPS FPHIHLQEDI INRCQQYVGP LTVNEKRRLK LIMPARFYPN  300
LTKYLPLDKG IKPYYPEHAV NHYFKTRHYL HTLWKAGILY KRETTRSASF CGSPYSWEQE  360
LQHGRLVFQT STRHGDESFC SQSSGILSRS PVGPCVRSQL KQSRLGLQPQ QGSLARGKSG  420
RSGSIRARVH PTTRRSFGVE PSGSGHIDNS ASSTSSCLHQ SAVRKTAYSH LSTSKRQSSS  480
GHAVELHNIP PSSARSQSEG PIFSAWWLQF RNSKPASDYA LTHIVNLLED WGPATEHGEH  540
NIRIPRTPAR VTGGVFLVDK NPHNTTESRL VVDFSQFSRG STHVSWPKFA VPNLQSLTNL  600
LSSNLSWLSL DVSAAFYHIP LHPAAMPHLL VGSSGLPRYV ARLSSTSRNI NYQHGTMQDL  660
HDSCSRNLYV SLLLLYKTFG RKLHLYSHPI ILGFRKIPMG VGLSPFLLAQ FTSAICSVVR  720
RAFPHCLAFS YMDDVVLGAK SVQHLESLFT SITNFLLSLG IHLNPNKTKR WGYSLNFMGY  780
VIGSWGTLPQ EHIVLKIKQC FRKLPVNRPI DWKVCQRIVG LLGFAAPFTQ CGYPALMPLY  840
ACIQSKQAFT FSPTYKAFLC KQYLNLYPVA RQRSGLCQVF ADATPTGWGL AIGHRAMRGT  900
FVAPLPIHTA ELLAACFARS RSGAKLIGTD NSVVLSRKYT SFPWLLGCAA NWILRGTSFV  960
YVPSALNPAA DPSAGRLGLY RPLLHLPFRP TTGRTSLYAV SPSVPSHLPD RVHFASPLHV  1020
AWRPPSKSPG SGPPMQLFHL CLIISCSCPT VQASKLCLGW LWGMDIDPYK EFGASVELLS  1080
FLPSDFFPSI RDLLDTASAL YREALESPEH CSPHHTALRQ AILCWGELMN LATWVGSNLE  1140
DPASRELVVS YVNVNMGLKI RQLLWFHISC LTFGRETVLE YLVSFGVWIR TPPAYRPPNA  1200
PILSTLPETT VVRRRGRSPR RRTPSPRRRR SQSPRRRRSQ SRESQCMGGW SSKPRQGMGT  1260
NLSVPNPLGF FPDHQLDPAF GANSNNPDWD FNPNKDHWPE ANQVGASKGG KSGMENTTSG  1320
FLGPLLVLQA GFFLLTRILT IPQSLDSWWT SLNFLGGAPT CPGQNSQSPT SNHSPTSCPP  1380
ICPGYRWMCL RRFIIFLFIL LLCLIFLLVL LDYQGMLPVC PLLPGTSTTS TGPCKTCTIP  1440
AQGTSMFPSC CCTKPSDGNC TCIPIPSSWA FARFLWEWAS VRFSWLSLLV PFVQWFVGLS  1500
PTVWLSVIWM MWYWGPSLYN ILSPFLPLLP IFFCLWVYI                        1539

SEQ ID NO: 24           moltype = DNA  length = 7143
FEATURE                 Location/Qualifiers
misc_feature            1..7143
                        note = Vaccine construct
source                  1..7143
                        mol_type = other DNA
                        organism = synthetic construct
SEQUENCE: 24
gtaatctatt cgatataccg ttgctaacag tatactggcc caataactgt ggatggaaaa  60
tctataataa tacattaata tcatccgatg gtgctagggt tatttggatg gatgcgtata  120
aattttcttg cggtttatct ttacaagact attgttatca ttggggtagc aaaccagaga  180
gccgaccatt cgatttaata aaaaaatcag atgctaaacg caattctaaa tcgttggtca  240
aagaatctat ggcatccttg aaatccttgt acgaggcatt cgagacacaa tcaggagcgt  300
tagaagtttt aatgagtcca tgtaggatgt tttcgttttc tagaatagaa gacatgttct  360
taactagtgt cattaataga gtatccgaga atactggaat ggggatgtat tatcctacca  420
acgatatacc ttctctattt atcgaatcat ctatctgtct agattatatt atagtaaata  480
atcaggaatc caacaaatat cgtatcaaat ctgttctcga tatcatttct tcaaaacaat  540
accctgcagg acgtcccaac tacgttaaaa atggtacaaa aggaaagtta tatatcgcgt  600
tgtgtaaagt taccgtacct actaacgacc atattccagt agtttatcac gatgatgaca  660
atactaccac ctttattaca gtattgacgt ccgtcgatat tgaaactgct atcagagcag  720
gatattcgat agtcgaatta ggggctttac aatgggataa taatattcca gaacttaaaa  780
acggtttact ggatagtatc aagatgattt atgacttgaa cgcagttaca acaaataatt  840
```

-continued

```
tattggaaca gctcatagaa aatattaact ttaacaactc tagtataatt tcgttgtttt  900
atacatttgc cattagttat tgccgagcat tcatttactc aattatggaa accatagatc  960
cggtgtatat atctcagttc agttataaag aattatacgt tagtagctct tataaagata 1020
ttaatgaatc catgagtcag atggtaaaat tataaaaagt gaaaaacaat attattttta 1080
tcgttggttg ttacactatg tctctgctgt ggggcggagt gacagtgctg gccgctatgc 1140
tgattgctgg acaggtggcc agcgtggtgt tcctggtgtc taagtctgga cctcctagcg 1200
gcaagagcaa cagcaacaac cccgactggg acttcaaccc caacaaggac cattggccag 1260
aggccaatca agtcggagcc ggcgcttttg gccctggctt tacacctcct catggcggac 1320
tgcttggatg gtcacctcag gctcagggca tcctgacaac agtgcctgct gctccacctc 1380
ctgccagcac caatagacag tctggcagac agcccacacc tatcagccct ccactgagag 1440
acagccatcc tcaggccatg cagtggaaca gcaccacctt tcatcaggcc ctgctggacc 1500
ctagagtgcg gggcctttat tttcctgccg gcggatctag cagcggcacc gtgaatcctg 1560
tgcctacaac cgcctctcct atcagcagca tcttcagcag aaccggcgat cccgctccta 1620
acggcagcaa gtctggctcc aagatgcccc tgagctacca gcacttcaga aaactgctgc 1680
tgctggacga cgaggccgga cctctggaag aagaactgcc tagactggcc gacgagggcc 1740
tgaatagaag agtggccgag gacctgaacc tgggcaacct gaatgtgtct atcccctgga 1800
cacacaaagt gggcaacttc acaggcctgg ccagctctac cgtgcctgtg ttcaatcccg 1860
agtggcagac ccctagcttc cctcacatcc atctgcaaga ggacatcatc aaccggtgcc 1920
agcagtacgt gggccctctg accgtgaacg agaagcggag actgaagctg atcatgcccg 1980
ccagattcta ccccaacctg accaagtacc tgcctctgga caagggcatc aagccttact 2040
accctgagca cgccgtgaac cactacttca agacccggca ctacctgcac accctgtgga 2100
aggccggcat cctgtataag agagagacaa ccagaagcgc cagcttctgc ggcagccctt 2160
actcttggga gcaagagctg cagcacggca gactggtgtt ccagacctct acaagacacg 2220
gcgacgagtc tttctgcagc cagagcagcg gaatcctgag cagatctcct gtgggacctt 2280
gtgtgcggag ccagctgaaa cagagtagac tgggcctgca gcctcagcag ggatctctgg 2340
ctagaggaaa gagcggcaga agcggcagca tcagagccag agtgcaccct accaccagaa 2400
gaagctttgg cgtcgagcct agcggctccg gccacatcga taatagcgcc agcagcacca 2460
gcagctgcct gcatcagtcc gccgttagaa agaccgccta cagccacctg agcacctcca 2520
agagacagag cagctctgga cacgccgtgg aactgcacaa catccctcca agcagcgcca 2580
gatctcagag cgagggccct atcttttctg cctggtggct gcagttcaga aacagcaagc 2640
ccgccagcga ctacgccctg acacacatcg tgaacctgct ggaagattgg ggccctgcca 2700
cagaacacgg cgagcacaat atcagaatcc ccagaacacc cgccagagtg acaggcggag 2760
tgtttctggt ggacaagaac cctcacaaca ccaccgagag caggctggtg gtggacttca 2820
gccagtttag cagaggcagc acccacgtgt cctggcctaa attcgccgtg cctaacctgc 2880
agagcctgac caatctgctg agcagcaacc tgagctggct gagcctggat gtgtccgccg 2940
ccttctatca catcccactg catcctgccg ccatgcctca tctgcttgtg ggaagttctg 3000
gcctgcctag atacgtggcc aggctgtcct ctaccagccg gaacatcaat taccagcacg 3060
ggaccatgca ggacctgcac gacagctgta gccggaacct gtacgttagc ctgctcctgc 3120
tgtacaagac cttcggcaga aagctgcacc tgtactctca ccccatcatc ctgggcttca 3180
gaaagatccc catgggcgtg ggcctgtctc catttctgct ggcccagttt accagcgcca 3240
tctgctctgt tgtgcggaga gcctttcctc actgcctggc cttcagctac atggacgatg 3300
tggtgctggg cgccaagtct gtgcagcacc tggaaagcct gtttacctcc atcaccaact 3360
ttctgctgtc cctgggaatc catctgaacc ctaacaagac caagagatgg ggctacagcc 3420
tgaacttcat gggctacgtg atcggcagct ggggcacact gcctcaagag cacatcgtgc 3480
tgaaaatcaa gcagtgcttt cggaagctgc ccgtgaacag acccatcgac tggaaagtgt 3540
gccagcggat cgttggcctg ctgggatttg ccgctccttt cacacagtgc ggctaccccg 3600
ctctcatgcc tctgtatgcc tgtatccaga gcaagcaggc cttcacattc agccctacct 3660
acaaggcctt cctgtgcaag cagtacctga atctgtaccc cgtggccaga cagagaagcg 3720
gcctgtgtca agtgttcgcc gatgccacac ctacaggatg gggactcgcc attggacaca 3780
gggccatgag aggaaccttt gtggcccctc tgcctatcca cacagccgaa ttgctggctg 3840
cctgcttcgc cagaagtaga tccggcgcca agctgatcgg caccgacaat tctgtggtcc 3900
tgagccggaa gtacaccagc tttccatggc tgctgggctg tgccgccaac tggattctga 3960
gaggcaccag cttcgtgtac gtgcccagcg ctcttaaccc tgccgctgat ccttctgctg 4020
ggagactcgg cctgtacaga cctctgctgc atctgccctt cagacccacc acaggcagaa 4080
ccagcctgta tgccgtgtct cctagcgtgc caagccatct gcctgatcgg gtgcactttg 4140
cctctccact tcatgtggct tggcggccac ctagcaagag ccctggatct ggaccaccta 4200
tgcagctgtt tcacctgtgc ctgatcatct cttgcagctg ccctacagtg caggccagca 4260
agctgtgtct cggatggctc tggggcatgg acatcgaccc ctacaaagaa ttcggcgcca 4320
gcgtcgagct gctgagcttc ctgcctagcg acttcttccc ctccatccgg gatctgctgg 4380
atactgctag cgccctgtat cgcgaggccc tggaatctcc tgagcactgt tctccacacc 4440
acactgccct gagacaggct atcctgtgtt ggggcgagct gatgaacctg gccacatggg 4500
tcggaagcaa cctggaagat cccgccagca gagaactggt ggtgtcctac gtgaacgtga 4560
acatgggcct gaagatcaga cagctgctgt ggttccacat ctcctgcctg acctttggcc 4620
gggaaaccgt gctggaatac ctggtgtcct ttggcgtgtg gatcagaacc cctccagcct 4680
accgacctcc taacgctcct atcctgtcta ccctgcctga gacaacagtc gtgcggcgga 4740
gaggaagaag ccctagaaga aggaccccat ctcctcggcg gagaagatca cagtcccctc 4800
ggagaagaag atcccagagc cgggaatccc agtgctgatt tttgttcgac attaaaaatt 4860
gaaaataaat acaaaggttc ttgagggttg tgttaaattg aaagcgagaa ataatcataa 4920
atatgattca ggtgacggat ccatgggagg ctggtccagc aaacccagac aaggcatggg 4980
caccaatctg agcgtgccca atcctctggg attcttccca gaccaccagc tggatcctgc 5040
cttcggcgcc aacagcaaca accccgactg ggacttcaac cccaacaagg accattggcc 5100
agaggccaat caagtgggcg ctagcaaagg cggcaagagc ggcatggaga ataccacctc 5160
tggctttctg ggccctctgc tggttctgca ggccggcttc tttctgctga cccggatcct 5220
gacaatccct cagagcctgg atagctggtg gacaagcctg aacttccttg gcggcgctcc 5280
tacatgccct ggccagaatt ctcagagccc caccagcaat cacagcccca caagctgccc 5340
tccaatctgc cctggctaca gatggatgtg cctgcggcgg ttcatcatct ttctgttcat 5400
cctgctgctg tgcctgatct tcctgctggt gctgctggac tatcagggca tgctgcctgt 5460
gtgtcctctg ctgcctggca ccagcacaac atctacaggc ccttgcaaga cctgcacaat 5520
cccagctcag ggcacctcca tgtttcccag ctgctgttgc accaagccta gcgacggcaa 5580
```

-continued

```
ctgcacatgc atccccattc cttccagctg ggccttcgcc agatttctgt gggaatgggc  5640
cagcgtgcgg ttcagctggc tgtctctgct tgtgcctttc gtgcagtggt tcgtgggcct  5700
gtctcctaca gtgtggctga gcgtgatctg gatgatgtgg tactggggcc ctagcctgta  5760
caatattctg agccccttcc tgcctctgct cccaatcttc ttctgcctgt gggtgtacat  5820
ctgattaacc gagtttctgc attattgtaa ttcgtatgct ggcaccatca aagaatcact  5880
tctaaaagat atcaatatca cacatacaaa tattactacc ctattgaatg agacagccaa  5940
ggttatcaag ttagtaaaat ctctggtaga taaagaagat actgatattg tgaataattt  6000
cattaccaaa gaaattaaaa acagagacaa aatagttaat agtttgtctc tatcaaacct  6060
ggactttcgt ttgtaaattg gggcttttgg tacaataaat gggtgttgcc aatgattcat  6120
cccctgaata tcaatggatg tctccccata gattatcaga tactgttata ttaggagact  6180
gtttgtattt taacaatata atgtcccaat tagatttaca ccaaaattgg gctccatcag  6240
ttagattgtt aaattatttt aagaatttta ataaggaaac actactaaag atagaagaga  6300
atgattacat taattcatcc tttttccaac aaaaggataa acgattttat cctataaacg  6360
acgattttta tcacatatct acaggaggat atggtatagt ctttaagata gataactatg  6420
tagtaaaatt tgtattcgag gccacaaaat tatatagtcc catggaaact acggcggagt  6480
tcacagtacc caaatttcta tacaacaatc taaagggaga tgaaaaaaaa ttaatcgtgt  6540
gtgcgtgggc catgggatta aactataaat taacattttt acatactctg tataaacgtg  6600
ttcttcatat gttgctatta ttgatacaaa ctatggatgg tcaggaacta tcattgagat  6660
attcttctaa agttttttta aaggcgttta acgagagaaa ggacagtatc aaattcgtga  6720
aattactatc ccacttttat ccggcagtta ttaacagtaa tattaatgtt ataaactatt  6780
ttaaccgcat gtttcacttt ttcgaacatg aaaagagaac taactacgaa tacgaaagag  6840
gaaatattat aatttttccc ctagcactgt attcggcaga taaagtagat accgagctag  6900
ctatcaaatt aggatttaaa tctttggtac aatacataaa gtttatcttt ttacagatgg  6960
ctctgttata cattaaaatt tacgaactac catgctgcga caacttttta cacgcagatc  7020
ttaaacccga taatatctta ctttttgatt ccaatgaacc aataataatt catctaaagg  7080
ataaaaagtt tgtttttaat gaacgtatta aatcggcatt aaacgacttt gacttttccc  7140
aag                                                                7143
```

```
SEQ ID NO: 25          moltype = AA  length = 1524
FEATURE                Location/Qualifiers
REGION                 1..1524
                       note = Vaccine construct
source                 1..1524
                       mol_type = protein
                       organism = synthetic construct
SEQUENCE: 25
MSLLWGGVTV LAAMLIAGQV ASVVFLVKGG GPGGGMQLFH LCLIISCSCP TVQASKLCLG  60
WLWGMDIDPY KEFGASVELL SFLPSDFFPS IRDLLDTASA LYREALESPE HCSPHHTALR  120
QAILCWGELM NLATWVGSNL EDPASRELVV SYVNVNMGLK IRQLLWFHIS CLTFGRETVL  180
EYLVSFGVWI RTPPAYRPPN APILSTLPET TVVRRRGRSP RRRTPSPRRR RSQSPRRRRS  240
QSRESQCGGG SGGGMPLSYQ HFRKLLLLDD EAGPLEEELP RLADEGLNRR VAEDLNLGNL  300
NVSIPWTHKV GNFTGLASST VPVFNPEWQT PSFPHIHLQE DIINRCQQYV GPLTVNEKRR  360
LKLIMPARFY PNLTKYLPLD KGIKPYYPEH AVNHYFKTRH YLHTLWKAGI LYKRETTRSA  420
SFCGSPYSWE QELQHGRLVF QTSTRHGDES FCSQSSGILS RSPVGPCVRS QLKQSRLGLQ  480
PQQGSLARGK SGRSGSIRAR VHPTTRRSFG VEPSGSGHID NSASSTSSCL HQSAVRKTAY  540
SHLSTSKRQS SSGHAVELHN IPPSSARSQS EGPIFSAWWL QFRNSKPASD YALTHIVNLL  600
EDWGPATEHG EHNIRIPRTP ARVTGGVFLV DKNPHNTTES RLVVDFSQFS RGSTHVSWPK  660
FAVPNLQSLT NLLSSNLSTF GRKLHLYSHP IILGFRKIPM GVGLSPFLLA QFTSAICSVV  720
RRAFPHCLAF SYMDDVVLGA KSVQHLESLF TSITNFLLSL GIHLNPNKTK RWGYSLNFMG  780
YVIGSWGTLP QEHIVLKIKQ CFRKLPVNRP IDWKVCQRIV GLLGFAAPFT QCGYPALMPL  840
YACIQSKQAF TFSPTYKAFL CKQYLNLYPV ARQRSGLCQV FADATPTGWG LAIGHRAMRG  900
TFVAPLPIHT AELLAACFAR SRSGAKLIGT DNSVVLSRKY TSFPWLLGCA ANWILRGTSF  960
VYVPSALNPA ADPSAGRLGL YRPLLHLPFR PTTGRTSLYA VSPSVPSHLP DRVHFASPLH  1020
VAWRPPKSPN SNNPDWDFNP NKDHWPEANQ VGAGAFGPGF TPPHGGLLGW SPQAQGILTT  1080
VPAAPPPAST NRQSGRQPTP ISPPLRDSHP QAMQWNSTTF HQALLDPRVR GLYFPAGGSS  1140
SGTVNPVPTT ASPISSIFSR TGDPAPNGSK GKRKRRAPVK QTLNFDLLKL AGDVESNPGP  1200
MDAMKRGLCC VLLLCGAVFV SPSQEIHARF RRMGGWSSKP RQGMGTNLSV PNPLGFFPDH  1260
QLDPAFGANS NNPDWDFNPN KDHWPEANQV GLEGGSGGME NTTSGFLGPL LVLQAGFFLL  1320
TRILTIPQSL DSWWTSLNFL GGAPTCPGQN SQSPTSNHSP TSCPPICPGY RWMCLRRFII  1380
FLFILLLCLI FLLVLLDYQG MLPVCPLLPG TSTTSTGPCK TCTIPAQGTS MFPSCCCTKP  1440
SDGNCTCIPI PSSWAFARFL WEWASVRFSW LSLLVPFVQW FVGLSPTVWL SVIWMMWYWG  1500
PSLYNILSPF LPLLPIFFCL WVYI                                         1524
```

```
SEQ ID NO: 26          moltype = AA  length = 1571
FEATURE                Location/Qualifiers
REGION                 1..1571
                       note = Vaccine construct
source                 1..1571
                       mol_type = protein
                       organism = synthetic construct
SEQUENCE: 26
MSLLWGGVTV LAAMLIAGQV ASVVFLVSKS GPPSGKSNSN NPDWDFNPNK DHWPEANQVG  60
AGAFGPGFTP PHGGLLGWSP QAQGILTTVP AAPPPASTNR QSGRQPTPIS PPLRDSHPQA  120
MQWNSTTFHQ ALLDPRVRGL YFPAGGSSSG TVNPVPTTAS PISSIFSRTG DPAPNGSKSG  180
SKMPLSYQHF RKLLLLDDEA GPLEEELPRL ADEGLNRRVA EDLNLGNLNV SIPWTHKVGN  240
FTGLASSTVP VFNPEWQTPS FPHIHLQEDI INRCQQYVGP LTVNEKRRLK LIMPARFYPN  300
LTKYLPLDKG IKPYYPEHAV NHYFKTRHYL HTLWKAGILY KRETTRSASF CGSPYSWEQE  360
LQHGRLVFQT STRHGDESFC SQSSGILSRS PVGPCVRSQL KQSRLGLQPQ QGSLARGKSG  420
RSGSIRARVH PTTRRSFGVE PSGSGHIDNS ASSTSSCLHQ SAVRKTAYSH LSTSKRQSSS  480
```

```
GHAVELHNIP PSSARSQSEG PIFSAWWLQF RNSKPASDYA LTHIVNLLED WGPATEHGEH  540
NIRIPRTPAR VTGGVFLVDK NPHNTTESRL VVDFSQFSRG STHVSWPKFA VPNLQSLTNL  600
LSSNLSWLSL DVSAAFYHIP LHPAAMPHLL VGSSGLPRYV ARLSSTSRNI NYQHGTMQDL  660
HDSCSRNLYV SLLLLYKTFG RKLHLYSHPI ILGFRKIPMG VGLSPFLLAQ FTSAICSVVR  720
RAFPHCLAFS YMDDVVLGAK SVQHLESLFT SITNFLLSLG IHLNPNKTKR WGYSLNFMGY  780
VIGSWGTLPQ EHIVLKIKQC FRKLPVNRPI DWKVCQRIVG LLGFAAPFTQ CGYPALMPLY  840
ACIQSKQAFT FSPTYKAFLC KQYLNLYPVA RQRSGLCQVF ADATPTGWGL AIGHRAMRGT  900
FVAPLPIHTA ELLAACFARS RSGAKLIGTD NSVVLSRKYT SFPWLLGCAA NWILRGTSFV  960
YVPSALNPAA DPSAGRLGLY RPLLHLPFRP TTGRTSLYAV SPSVPSHLPD RVHFASPLHV  1020
AWRPPSKSPG SGPPMQLFHL CLIISCSCPT VQASKLCLGW LWGMDIDPYK EFGASVELLS  1080
FLPSDFFPSI RDLLDTASAL YREALESPEH CSPHHTALRQ AILCWGELMN LATWVGSNLE  1140
DPASRELVVS YVNVNMGLKI RQLLWFHISC LTFGRETVLE YLVSFGVWIR TPPAYRPPNA  1200
PILSTLPETT VVRRRGRSPR RRTPSPRRRR SQSPRRRRSQ SRESQCMDAM KRGLCCVLLL  1260
CGAVFVSPSQ EIHARFRRMG GWSSKPRQGM GTNLSVPNPL GFFPDHQLDP AFGANSNNPD  1320
WDFNPNKDHW PEANQVGASK GGKSGMENTT SGFLGPLLVL QAGFFLLTRI LTIPQSLDSW  1380
WTSLNFLGGA PTCPGQNSQS PTSNHSPTSC PPICPGYRWM CLRRFIIFLF ILLLCLIFLL  1440
VLLDYQGMLP VCPLLPGTST TSTGPCKTCT IPAQGTSMFP SCCCTKPSDG NCTCIPIPSS  1500
WAFARFLWEW ASVRFSWLSL LVPFVQWFVG LSPTVWLSVI WMMWYWGPSL YNILSPFLPL  1560
LPIFFCLWVY I                                                       1571

SEQ ID NO: 27          moltype = DNA  length = 7239
FEATURE                Location/Qualifiers
misc_feature           1..7239
                       note = Vaccine construct
source                 1..7239
                       mol_type = other DNA
                       organism = synthetic construct
SEQUENCE: 27
gtaatctatt cgatataccg ttgctaacag tatactggcc caataactgt ggatggaaaa  60
tctataataa tacattaata tcatccgatg gtgctagggt tatttggatg gatgcgtata  120
aattttcttg cggtttatct ttacaagact attgttatca ttggggtagc aaaccagaga  180
gccgaccatt cgatttaata aaaaaatcag atgctaaacg caattctaaa tcgttggtca  240
aagaatctat ggcatccttg aaatccttgt acgaggcatt cgagacacaa tcaggagcgt  300
tagaagtttt aatgagtcca tgtaggatgt tttcgttttc tagaatagaa gacatgttct  360
taactagtgt cattaataga gtatccgaga atactggaat ggggatgtat tatcctacca  420
acgatatacc ttctctattt atcgaatcat ctatctgtct agattatatt atagtaaata  480
atcaggaatc caacaaatat cgtatcaaat ctgttctcga tatcatttct tcaaaacaat  540
accctgcagg acgtcccaac tacgttaaaa atggtacaaa aggaaagtta tatatcgcgt  600
tgtgtaaagt taccgtacct actaacgacc atattccagt agtttatcac gatgatgaca  660
atactaccac ctttattaca gtattgacgt ccgtcgatat tgaaactgct atcagagcag  720
gatattcgat agtcgaatta ggggctttac aatgggataa taatattcca gaacttaaaa  780
acggtttact ggatagtatc aagatgattt atgacttgaa cgcagttaca acaaataatt  840
tattggaaca gctcatagaa aatattaact ttaacaactc tagtataatt tcgttgtttt  900
atacatttgc cattagttat tgccgagcat tcatttactc aattatggaa accatagatc  960
cggtgtatat atctcagttc agttataaag aattatacgt tagtagctct tataaagata  1020
ttaatgaatc catgagtcag atggtaaaat tataaaaagt gaaaaacaat attattttta  1080
tcgttggttg ttacactatg tctctgctgt ggggcggagt gacagtgctg gccgctatgc  1140
tgattgctgg acaggtggcc agcgtggtgt tcctggtgtc taagtctgga cctcctagcg  1200
gcaagagcaa cagcaacaac cccgactggg acttcaaccc caacaaggac cattggccag  1260
aggccaatca agtcggagcc ggcgcttttg gccctggctt tacacctcct catggcggac  1320
tgcttggatg gtcacctcag gctcagggca tcctgacaac agtgcctgct gctccacctc  1380
ctgccagcac caatagacag tctggcagac agcccacacc tatcagccct ccactgagag  1440
acagccatcc tcaggccatg cagtggaaca gcaccacctt tcatcaggcc ctgctggacc  1500
ctagagtgcg gggcctttat ttcctgccg gcggatctag cagcggcacc gtgaatcctg  1560
tgcctacaac cgcctctcct atcagcagca tcttcagcag aaccggcgat cccgctccta  1620
acggcagcaa gtctggctcc aagatgcccc tgagctacca gcacttcaga aaactgctgc  1680
tgctggacga cgaggccgga cctctggaag aagaactgcc tagactggcc gacgagggcc  1740
tgaatagaag agtggccgag gacctgaacc tgggcaacct gaatgtgtct atcccctgga  1800
cacacaaagt gggcaacttc acaggcctgg ccagctctac cgtgcctgtg ttcaatcccg  1860
agtggcagac ccctagcttc cctcacatcc atctgcaaga ggacatcatc aaccggtgcc  1920
agcagtacgt gggccctctg accgtgaacg agaagcggag actgaagctg atcatgcccg  1980
ccagattcta ccccaacctg accaagtacc tgcctctgga caagggcatc aagccttact  2040
accctgagca cgccgtgaac cactacttca agacccggca ctacctgcac accctgtgga  2100
aggccggcat cctgtataag agagagacaa ccagaagcgc cagcttctgc ggcagccctt  2160
actcttggga gcaagagctg cagcacggca gactggtgtt ccagacctct acaagacacg  2220
gcgacgagtc tttctgcagc cagagcagcg gaatcctgag cagatctcct gtgggacctt  2280
gtgtgcggag ccagctgaaa cagagtagac tgggcctgca gcctcagcag ggatctctgg  2340
ctagaggaaa gagcggcaga agcggcagca tcagagccag agtgcaccct accaccagaa  2400
gaagctttgg cgtcgagcct agcggctccg gccacatcga taatagcgcc agcagcacca  2460
gcagctgcct gcatcagtcc gccgttagaa agaccgccta cagccacctg agcacctcca  2520
agagacagag cagctctgga cacgccgtgg aactgcacaa catccctcca agcagcgcca  2580
gatctcagag cgagggccct atcttttctg cctggtggct gcagttcaga aacagcaagc  2640
ccgccagcga ctacgccctg acacacatcg tgaacctgct ggaagattgg ggccctgcca  2700
cagaacacgg cgagcacaat atcagaatcc ccagaacacc cgccagagtg acaggcggag  2760
tgtttctggt ggacaagaac cctcacaaca ccaccgagag caggctggtg gtggacttca  2820
gccagtttag cagaggcagc acccacgtgt cctggcctaa attcgccgtg cctaacctgc  2880
agagcctgac caatctgctg agcagcaacc tgagctggct gagcctggat gtgtccgccg  2940
ccttctatca catcccactg catcctgccg ccatgcctca tctgcttgtg ggaagttctg  3000
gcctgcctag atacgtggcc aggctgtcct ctaccagccg gaacatcaat taccagcacg  3060
```

-continued

```
ggaccatgca ggacctgcac gacagctgta gccggaacct gtacgttagc ctgctcctgc  3120
tgtacaagac cttcggcaga aagctgcacc tgtactctca ccccatcatc ctgggcttca  3180
gaaagatccc catgggcgtg ggcctgtctc catttctgct ggcccagttt accagcgcca  3240
tctgctctgt tgtgcggaga gcctttcctc actgcctggc cttcagctac atggacgatg  3300
tggtgctggg cgccaagtct gtgcagcacc tggaaagcct gtttacctcc atcaccaact  3360
ttctgctgtc cctgggaatc catctgaacc ctaacaagac caagagatgg ggctacagcc  3420
tgaacttcat gggctacgtg atcggcagct ggggcacact gcctcaagag cacatcgtgc  3480
tgaaaatcaa gcagtgcttt cggaagctgc ccgtgaacag acccatcgac tggaaagtgt  3540
gccagcggat cgttggcctg ctgggatttg ccgctccttt cacacagtgc ggctaccccg  3600
ctctcatgcc tctgtatgcc tgtatccaga gcaagcaggc cttcacattc agccctacct  3660
acaaggcctt cctgtgcaag cagtacctga atctgtaccc cgtggccaga cagagaagcg  3720
gcctgtgtca agtgttcgcc gatgccacac ctacaggatg gggactcgcc attggacaca  3780
gggccatgag aggaaccttt gtggcccctc tgcctatcca cacagccgaa ttgctggctg  3840
cctgcttcgc cagaagtaga tccggcgcca agctgatcgg caccgacaat tctgtggtcc  3900
tgagccggaa gtacaccagc tttccatggc tgctgggctg tgccgccaac tggattctga  3960
gaggcaccag cttcgtgtac gtgcccagcg ctcttaaccc tgccgctgat ccttctgctg  4020
ggagactcgg cctgtacaga cctctgctgc atctgccctt cagacccacc acaggcagaa  4080
ccagcctgta tgccgtgtct cctagcgtgc caagccatct gcctgatcgg gtgcactttg  4140
cctctccact tcatgtggct tggcggccac ctagcaagag ccctggatct ggaccaccta  4200
tgcagctgtt tcacctgtgc ctgatcatct cttgcagctg ccctacagtg caggccagca  4260
agctgtgtct cggatggctc tggggcatgg acatcgaccc ctacaaagaa ttcggcgcca  4320
gcgtcgagct gctgagcttc ctgcctagcg acttcttccc ctccatccgg gatctgctgg  4380
atactgctag cgccctgtat cgcgaggccc tggaatctcc tgagcactgt tctccacacc  4440
acactgccct gagacaggct atcctgtgtt ggggcgagct gatgaacctg gccacatggg  4500
tcggaagcaa cctggaagat cccgccagca gagaactggt ggtgtcctac gtgaacgtga  4560
acatgggcct gaagatcaga cagctgctgt ggttccacat ctcctgcctg acctttggcc  4620
gggaaaccgt gctggaatac ctggtgtcct ttggcgtgtg gatcagaacc cctccagcct  4680
accgacctcc taacgctcct atcctgtcta ccctgcctga gacaacagtc gtgcggcgga  4740
gaggaagaag ccctagaaga aggaccccat ctcctcggcg gagaagatca cagtcccctc  4800
ggagaagaag atcccagagc cgggaatccc agtgctgatt tttgttcgac attaaaaatt  4860
gaaaataaat acaaaggttc ttgagggttg tgttaaattg aaagcgagaa ataatcataa  4920
atatgattca ggtgacggat ccatggacgc tatgaagagg ggcctgtgct gtgtgctgct  4980
gctgtgcgga gctgtgtttg tgtcccctag ccaagagatc cacgccagat tcagaagaat  5040
gggcggctgg tccagcaagc ccagacaagg catgggcacc aatctgagcg tgcccaatcc  5100
tctgggattc ttcccagacc accagctgga tcctgccttc ggcgccaaca gcaacaaccc  5160
cgactgggac ttcaacccca acaaggacca ttggccagag gccaatcaag tgggcgctag  5220
caaaggcggc aagagcggca tggagaatac cacctctggc tttctgggcc ctctgctggt  5280
tctgcaggcc ggcttctttc tgctgacccg gatcctgaca atccctcaga gcctggatag  5340
ctggtggaca agcctgaact tccttggcgg cgctcctaca tgccctggcc agaattctca  5400
gagccccacc agcaatcaca gccccacaag ctgccctcca atctgccctg gctacagatg  5460
gatgtgcctg cggcggttca tcatctttct gttcatcctg ctgctctgcc tgatcttcct  5520
gctggtgctc ctggactatc agggcatgct gcctgtgtgt cctctgctgc ctggcaccag  5580
cacaacatct acaggccctt gcaagacctg cacaatccca gctcagggca cctccatgtt  5640
tcccagctgc tgttgcacca agcctagcga cggcaactgc acatgcatcc ccattccttc  5700
cagctgggcc ttcgccagat ttctgtggga atgggccagc gtgcggttca gctggctgtc  5760
tctgcttgtg cctttcgtgc agtggttcgt gggcctgtct cctacagtgt ggctgagcgt  5820
gatctggatg atgtggtact ggggccctag cctgtacaat attctgagcc ccttcctgcc  5880
tctgctccca atcttcttct gcctgtgggt gtacatctga ttaaccgagt ttctgcatta  5940
ttgtaattcg tatgctggca ccatcaaaga atcacttcta aaagatatca atatcacaca  6000
tacaaatatt actaccctat tgaatgagac agccaaggtt atcaagttag taaaatctct  6060
ggtagataaa gaagatactg atattgtgaa taatttcatt accaaagaaa ttaaaaacag  6120
agacaaaata gttaatagtt tgtctctatc aaacctggac tttcgtttgt aaattggggc  6180
tttttgtaca ataaatgggt gttgccaatg attcatcccc tgaatatcaa tggatgtctc  6240
cccatagatt atcagatact gttatattag gagactgttt gtattttaac aatataatgt  6300
cccaattaga tttacaccaa aattgggctc catcagttag attgttaaat tattttaaga  6360
attttaataa ggaaacacta ctaaagatag aagagaatga ttacattaat tcatcctttt  6420
tccaacaaaa ggataaacga ttttatccta taaacgacga tttttatcac atatctacag  6480
gaggatatgg tatagtcttt aagatagata actatgtagt aaaatttgta ttcgaggcca  6540
caaaattata tagtcccatg gaaactacgg cggagttcac agtacccaaa tttctataca  6600
acaatctaaa gggagatgaa aaaaaattaa tcgtgtgtgc gtgggccatg ggattaaact  6660
ataaattaac atttttacat actctgtata aacgtgttct tcatatgttg ctattattga  6720
tacaaactat ggatggtcag gaactatcat tgagatattc ttctaaagtt tttttaaagg  6780
cgtttaacga gagaaaggac agtatcaaat tcgtgaaatt actatcccac ttttatccgg  6840
cagttattaa cagtaatatt aatgttataa actattttaa ccgcatgttt cactttttcg  6900
aacatgaaaa gagaactaac tacgaatacg aaagaggaaa tattataatt tttcccctag  6960
cactgtattc ggcagataaa gtagataccg agctagctat caaattagga tttaaatctt  7020
tggtacaata cataaagttt atctttttac agatggctct gttatacatt aaaatttacg  7080
aactaccatg ctgcgacaac tttttacacg cagatcttaa acccgataat atcttacttt  7140
ttgattccaa tgaaccaata ataattcatc taaaggataa aaagtttgtt tttaatgaac  7200
gtattaaatc ggcattaaac gactttgact tttcccaag                          7239
```

```
SEQ ID NO: 28          moltype = DNA  length = 97
FEATURE                Location/Qualifiers
misc_feature           1..97
                       note = Promoter
source                 1..97
                       mol_type = other DNA
                       organism = synthetic construct
```

```
SEQUENCE: 28
tcgacattaa aaattgaaaa taaatacaaa ggttcttgag ggttgtgtta aattgaaagc  60
gagaaataat cataaatatg attcaggtga cggatcc                            97

SEQ ID NO: 29          moltype = DNA  length = 96
FEATURE                Location/Qualifiers
misc_feature           1..96
                       note = TPA sequence
source                 1..96
                       mol_type = other DNA
                       organism = synthetic construct
SEQUENCE: 29
atggacgcta tgaagagggg cctgtgctgt gtgctgctgc tgtgcggagc tgtgtttgtg  60
tcccctagcc aagagatcca cgccagattc agaaga                             96

SEQ ID NO: 30          moltype = AA  length = 32
FEATURE                Location/Qualifiers
REGION                 1..32
                       note = TPA peptide
source                 1..32
                       mol_type = protein
                       organism = synthetic construct
SEQUENCE: 30
MDAMKRGLCC VLLLCGAVFV SPSQEIHARF RR                                 32

SEQ ID NO: 31          moltype = AA  length = 10
FEATURE                Location/Qualifiers
REGION                 1..10
                       note = Linker peptide
source                 1..10
                       mol_type = protein
                       organism = synthetic construct
SEQUENCE: 31
SKSGPPSGKS                                                          10

SEQ ID NO: 32          moltype = AA  length = 7
FEATURE                Location/Qualifiers
REGION                 1..7
                       note = Linker peptide
source                 1..7
                       mol_type = protein
                       organism = synthetic construct
SEQUENCE: 32
GSKSGSK                                                             7

SEQ ID NO: 33          moltype = AA  length = 9
FEATURE                Location/Qualifiers
REGION                 1..9
                       note = Linker peptide
source                 1..9
                       mol_type = protein
                       organism = synthetic construct
SEQUENCE: 33
SKSPGSGPP                                                           9

SEQ ID NO: 34          moltype = AA  length = 8
FEATURE                Location/Qualifiers
REGION                 1..8
                       note = Linker peptide
source                 1..8
                       mol_type = protein
                       organism = synthetic construct
SEQUENCE: 34
ASKGGKSG                                                            8

SEQ ID NO: 35          moltype = DNA  length = 1097
FEATURE                Location/Qualifiers
misc_feature           1..1097
                       note = F11 left flank
source                 1..1097
                       mol_type = other DNA
                       organism = synthetic construct
SEQUENCE: 35
gtaatctatt cgatataccg ttgctaacag tatactggcc caataactgt ggatggaaaa  60
tctataataa tacattaata tcatccgatg gtgctagggt tatttggatg gatgcgtata  120
aattttcttg cggtttatct ttacaagact attgttatca ttggggtagc aaaccagaga  180
gccgaccatt cgatttaata aaaaaatcag atgctaaacg caattctaaa tcgttggtca  240
aagaatctat ggcatccttg aaatccttgt acgaggcatt cgagacacaa tcaggagcgt  300
tagaagtttt aatgagtcca tgtaggatgt tttcgttttc tagaatagaa gacatgttct  360
```

```
taactagtgt cattaataga gtatccgaga atactggaat ggggatgtat tatcctacca  420
acgatatacc ttctctattt atcgaatcat ctatctgtct agattatatt atagtaaata  480
atcaggaatc caacaaatat cgtatcaaat ctgttctcga tatcatttct tcaaaacaat  540
accctgcagg acgtcccaac tacgttaaaa atggtacaaa aggaaagtta tatatcgcgt  600
tgtgtaaagt taccgtacct actaacgacc atattccagt agtttatcac gatgatgaca  660
atactaccac ctttattaca gtattgacgt ccgtcgatat tgaaactgct atcagagcag  720
gatattcgat agtcgaatta ggggctttac aatgggataa taatattcca gaacttaaaa  780
acggtttact ggatagtatc aagatgattt atgacttgaa cgcagttaca acaaataatt  840
tattggaaca gctcatagaa aatattaact ttaacaactc tagtataatt tcgttgtttt  900
atacatttgc cattagttat tgccgagcat tcatttactc aattatggaa accatagatc  960
cggtgtatat atctcagttc agttataaag aattatacgt tagtagctct tataaagata  1020
ttaatgaatc catgagtcag atggtaaaat tataaaaagt gaaaaacaat attattttta  1080
tcgttggttg ttacact                                                 1097
```

```
SEQ ID NO: 36          moltype = DNA  length = 1319
FEATURE                Location/Qualifiers
misc_feature           1..1319
                       note = F11 right flank
source                 1..1319
                       mol_type = other DNA
                       organism = synthetic construct
SEQUENCE: 36
ttaaccgagt ttctgcatta ttgtaattcg tatgctggca ccatcaaaga atcacttcta  60
aaagatatca atatcacaca tacaaatatt actaccctat tgaatgagac agccaaggtt  120
atcaagttag taaaatctct ggtagataaa gaagatactg atattgtgaa taatttcatt  180
accaaagaaa ttaaaaacag agacaaaata gttaatagtt tgtctctatc aaacctggac  240
tttcgtttgt aaattggggc tttttgtaca ataaatgggt gttgccaatg attcatcccc  300
tgaatatcaa tggatgtctc cccatagatt atcagatact gttatattag gagactgttt  360
gtattttaac aatataatgt cccaattaga tttacaccaa aattgggctc catcagttag  420
attgttaaat tattttaaga attttaataa ggaaacacta ctaaagatag aagagaatga  480
ttacattaat tcatcctttt tccaacaaaa ggataaacga ttttatccta taaacgacga  540
tttttatcac atatctacag gaggatatgg tatagtcttt aagatagata actatgtagt  600
aaaatttgta ttcgaggcca caaaattata tagtcccatg gaaactacgg cggagttcac  660
agtacccaaa tttctataca acaatctaaa gggagatgaa aaaaaattaa tcgtgtgtgc  720
gtgggccatg ggattaaact ataaattaac atttttacat actctgtata aacgtgttct  780
tcatatgttg ctattattga tacaaactat ggatggtcag gaactatcat tgagatattc  840
ttctaaagtt tttttaaagg cgtttaacga gagaaaggac agtatcaaat tcgtgaaatt  900
actatcccac ttttatccgg cagttattaa cagtaatatt aatgttataa actattttaa  960
ccgcatgttt cactttttcg aacatgaaaa gagaactaac tacgaatacg aaagaggaaa  1020
tattataatt tttcccctag cactgtattc ggcagataaa gtagataccg agctagctat  1080
caaattagga tttaaatctt tggtacaata cataaagttt atctttttac agatggctct  1140
gttatacatt aaaatttacg aactaccatg ctgcgacaac tttttacacg cagatcttaa  1200
acccgataat atcttacttt ttgattccaa tgaaccaata ataattcatc taaaggataa  1260
aaagtttgtt tttaatgaac gtattaaatc ggcattaaac gactttgact tttcccaag   1319
```

```
SEQ ID NO: 37          moltype = DNA  length = 3741
FEATURE                Location/Qualifiers
misc_feature           1..3741
                       note = Vaccine construct
source                 1..3741
                       mol_type = other DNA
                       organism = synthetic construct
SEQUENCE: 37
atgtctctgc tgtggggcgg agtgacagtg ctggccgcta tgctgattgc tggacaggtg  60
gccagcgtgg tgttcctggt gtctaagtct ggacctccta gcggcaagag caacagcaac  120
aaccccgact gggacttcaa ccccaacaag gaccattggc cagaggccaa tcaagtcgga  180
gccggcgctt ttggccctgg ctttacacct cctcatggcg gactgcttgg atggtcacct  240
caggctcagg gcatcctgac aacagtgcct gctgctccac ctcctgccag caccaataga  300
cagtctggca gacagcccac acctatcagc cctccactga gagacagcca tcctcaggcc  360
atgcagtgga acagcaccac ctttcatcag gccctgctgg accctagagt gcggggcctt  420
tattttcctg ccggcggatc tagcagcggc accgtgaatc ctgtgcctac aaccgcctct  480
cctatcagca gcatcttcag cagaaccggc gatcccgctc ctaacggcag caagtctggc  540
tccaagatgc ccctgagcta ccagcacttc agaaaactgc tgctgctgga cgacgaggcc  600
ggacctctgg aagaagaact gcctagactg gccgacgagg gcctgaatag aagagtggcc  660
gaggacctga acctgggcaa cctgaatgtg tctatcccct ggacacacaa agtgggcaac  720
ttcacaggcc tggccagctc taccgtgcct gtgttcaatc ccgagtggca gacccctagc  780
ttccctcaca tccatctgca agaggacatc atcaaccggt gccagcagta cgtgggccct  840
ctgaccgtga acgagaagcg gagactgaag ctgatcatgc ccgccagatt ctaccccaac  900
ctgaccaagt acctgcctct ggacaagggc atcaagcctt actaccctga gcacgccgtg  960
aaccactact tcaagacccg gcactacctg cacaccctgt ggaaggccgg catcctgtat  1020
aagagagaga caaccagaag cgccagcttc tgcggcagcc cttactcttg ggagcaagag  1080
ctgcagcacg gcagactggt gttccagacc tctacaagac acggcgacga gtctttctgc  1140
agccagagca gcggaatcct gagcagatct cctgtgggac cttgtgtgcg gagccagctg  1200
aaacagagta gactgggcct gcagcctcag cagggatctc tggctagagg aaagagcggc  1260
agaagcggca gcatcagagc cagagtgcac cctaccacca gaagaagctt tggcgtcgag  1320
cctagcggct ccggccacat cgataatagc gccagcagca ccagcagctg cctgcatcag  1380
tccgccgtta gaaagaccgc ctacagccac ctgagcacct ccaagagaca gagcagctct  1440
ggacacgccg tggaactgca caacatccct ccaagcagcg ccagatctca gagcgagggc  1500
cctatctttt ctgcctggtg gctgcagttc agaaacagca agcccgccag cgactacgcc  1560
```

-continued

```
ctgacacaca tcgtgaacct gctggaagat tggggccctg ccacagaaca cggcgagcac  1620
aatatcagaa tccccagaac acccgccaga gtgacaggcg gagtgtttct ggtggacaag  1680
aaccctcaca acaccaccga gagcaggctg gtggtggact tcagccagtt tagcagaggc  1740
agcacccacg tgtcctggcc taaattcgcc gtgcctaacc tgcagagcct gaccaatctg  1800
ctgagcagca acctgagctg gctgagcctg gatgtgtccg ccgccttcta tcacatccca  1860
ctgcatcctg ccgccatgcc tcatctgctt gtgggaagtt ctggcctgcc tagatacgtg  1920
gccaggctgt cctctaccag ccggaacatc aattaccagc acgggaccat gcaggacctg  1980
cacgacagct gtagccggaa cctgtacgtt agcctgctcc tgctgtacaa gaccttcggc  2040
agaaagctgc acctgtactc tcaccccatc atcctgggct tcagaaagat ccccatgggc  2100
gtgggcctgt ctccatttct gctggcccag tttaccagcg ccatctgctc tgttgtgcgg  2160
agagcctttc ctcactgcct ggccttcagc tacatggacg atgtggtgct gggcgccaag  2220
tctgtgcagc acctggaaag cctgtttacc tccatcacca actttctgct gtccctggga  2280
atccatctga accctaacaa gaccaagaga tggggctaca gcctgaactt catgggctac  2340
gtgatcggca gctggggcac actgcctcaa gagcacatcg tgctgaaaat caagcagtgc  2400
tttcggaagc tgcccgtgaa cagacccatc gactggaaag tgtgccagcg gatcgttggc  2460
ctgctgggat ttgccgctcc tttcacacag tgcggctacc ccgctctcat gcctctgtat  2520
gcctgtatcc agagcaagca ggccttcaca ttcagcccta cctacaaggc cttcctgtgc  2580
aagcagtacc tgaatctgta ccccgtggcc agacagagaa gcggcctgtg tcaagtgttc  2640
gccgatgcca cacctacagg atggggactc gccattggac acagggccat gagaggaacc  2700
tttgtggccc ctctgcctat ccacacagcc gaattgctgg ctgcctgctt cgccagaagt  2760
agatccggcg ccaagctgat cggcaccgac aattctgtgg tcctgagccg gaagtacacc  2820
agctttccat ggctgctggg ctgtgccgcc aactggattc tgagaggcac cagcttcgtg  2880
tacgtgccca gcgctcttaa ccctgccgct gatccttctg ctgggagact cggcctgtac  2940
agacctctgc tgcatctgcc cttcagaccc accacaggca gaaccagcct gtatgccgtg  3000
tctcctagcg tgccaagcca tctgcctgat cgggtgcact ttgcctctcc acttcatgtg  3060
gcttggcggc cacctagcaa gagccctgga tctggaccac ctatgcagct gtttcacctg  3120
tgcctgatca tctcttgcag ctgccctaca gtgcaggcca gcaagctgtg tctcggatgg  3180
ctctggggca tggacatcga cccctacaaa gaattcggcg ccagcgtcga gctgctgagc  3240
ttcctgccta gcgacttctt cccctccatc cgggatctgc tggatactgc tagcgccctg  3300
tatcgcgagg ccctggaatc tcctgagcac tgttctccac accacactgc cctgagacag  3360
gctatcctgt gttggggcga gctgatgaac ctggccacat gggtcggaag caacctggaa  3420
gatcccgcca gcagagaact ggtggtgtcc tacgtgaacg tgaacatggg cctgaagatc  3480
agacagctgc tgtggttcca catctcctgc ctgacctttg gccgggaaac cgtgctggaa  3540
tacctggtgt cctttggcgt gtggatcaga acccctccag cctaccgacc tcctaacgct  3600
cctatcctgt ctaccctgcc tgagacaaca gtcgtgcggc ggagaggaag aagccctaga  3660
agaaggaccc catctcctcg gcggagaaga tcacagtccc ctcggagaag aagatcccag  3720
agccgggaat cccagtgctg a                                            3741
```

```
SEQ ID NO: 38           moltype = DNA  length = 882
FEATURE                 Location/Qualifiers
source                  1..882
                        mol_type = other DNA
                        organism = Hepatitis B virus
SEQUENCE: 38
atgggaggct ggtccagcaa acccagacaa ggcatgggca ccaatctgag cgtgcccaat  60
cctctgggat tcttcccaga ccaccagctg gatcctgcct tcggcgccaa cagcaacaac  120
cccgactggg acttcaaccc caacaaggac cattggccag aggccaatca agtgggcgct  180
agcaaaggcg gcaagagcgg catggagaat accacctctg gctttctggg ccctctgctg  240
gttctgcagg ccggcttctt tctgctgacc cggatcctga caatccctca gagcctggat  300
agctggtgga caagcctgaa cttccttggc ggcgctccta catgccctgg ccagaattct  360
cagagcccca ccagcaatca cagccccaca agctgccctc caatctgccc tggctacaga  420
tggatgtgcc tgcggcggtt catcatcttt ctgttcatcc tgctgctgtg cctgatcttc  480
ctgctggtgc tgctggacta tcagggcatg ctgcctgtgt gtcctctgct gcctggcacc  540
agcacaacat ctacaggccc ttgcaagacc tgcacaatcc cagctcaggg cacctccatg  600
tttcccagct gctgttgcac caagcctagc gacggcaact gcacatgcat ccccattcct  660
tccagctggg ccttcgccag atttctgtgg gaatgggcca gcgtgcggtt cagctggctg  720
tctctgcttg tgcctttcgt gcagtggttc gtgggcctgt ctcctacagt gtggctgagc  780
gtgatctgga tgatgtggta ctggggccct agcctgtaca atattctgag ccccttcctg  840
cctctgctcc caatcttctt ctgcctgtgg gtgtacatct ga                    882
```

```
SEQ ID NO: 39           moltype = DNA  length = 12012
FEATURE                 Location/Qualifiers
misc_feature            1..12012
                        note = Vector
source                  1..12012
                        mol_type = other DNA
                        organism = synthetic construct
SEQUENCE: 39
ccaccgcctc ggacctggcc gacctcatct tccccgagcg cctcaggctg acgctgcgca  60
acggcctgcc cgactttatg agccaaagca tgttgcaaaa actttcggta aaaaatgtaa  120
ttactccctc ctgcacaggc agcaaagccc ccgctccctc cagaaacaca tacaaagcct  180
cagcgtccat agcttaccga gcacggcagg cgcaagagtc agagaaaagg ctgagctcta  240
acctgactgc ccgctcctgt gctcaatata taagccctaa cctacactga cgtaaaaggg  300
cccaaaagtc taaaaaaata acccgcccaa aatgacacac acgcccagca cacgcccaga  360
aaccggtgac acactcaaaa aaatacgtgc gcttcctcaa acgcccaaac cggcgtcatt  420
tccgggttcc cacgctacgt caccgctcag cgactttcaa attccgtcga ccgttaaaaa  480
cgtcactcgc cccgccccta acggtcgccc ttctctcggc caatcacctt cctcccttcc  540
caaattcaaa cgcctcattt gcatattaac gcgcacaaaa agtttgaggt atatatttga  600
atgatggttt aaacgcggcc gccaggccta cccactagtc aattcgggag gatcgaaacg  660
```

-continued

```
gcagatcgca aaaaacagta catacagaag gagacatgaa catgaacatc aaaaaaattg  720
taaaacaagc cacagttctg acttttacga ctgcacttct ggcaggagga gcgactcaag  780
ccttcgcgaa agaaaataac caaaaagcat acaaagaaac gtacggcgtc tctcatatta  840
cacgccatga tatgctgcag atccctaaac agcagcaaaa cgaaaaatac caagtgcctc  900
aattcgatca atcaacgatt aaaaatattg agtctgcaaa aggacttgat gtgtgggaca  960
gctggccgct gcaaaacgct gacggaacag tagctgaata caacggctat cacgttgtgt  1020
ttgctcttgc gggaagcccg aaagacgctg atgacacatc aatctacatg ttttatcaaa  1080
aggtcggcga caactcaatc gacagctgga aaaacgcggg ccgtgtcttt aaagacagcg  1140
ataagttcga cgccaacgat ccgatcctga aagatcagac gcaagaatgg tccggttctg  1200
caacctttac atctgacgga aaaatccgtt tattctacac tgactattcc ggtaaacatt  1260
acggcaaaca aagcctgaca acagcgcagg taaatgtgtc aaaatctgat gacacactca  1320
aaatcaacgg agtggaagat cacaaaacga tttttgacgg agacggaaaa acatatcaga  1380
acgttcagca gtttatcgat gaaggcaatt atacatccgg cgacaaccat acgctgagag  1440
accctcacta cgttgaagac aaaggccata aataccttgt attcgaagcc aacacgggaa  1500
cagaaaacgg ataccaaggc gaagaatctt tatttaacaa agcgtactac ggcggcggca  1560
cgaacttctt ccgtaaagaa agccagaagc ttcagcagag cgctaaaaaa cgcgatgctg  1620
agttagcgaa cggcgccctc ggtatcatag agttaaataa tgattacaca ttgaaaaaag  1680
taatgaagcc gctgatcact tcaaacacgg taactgatga aatcgagcgc gcgaatgttt  1740
tcaaaatgaa cggcaaatgg tacttgttca ctgattcacg cggttcaaaa atgacgatcg  1800
atggtattaa ctcaaacgat atttacatgc ttggttatgt atcaaactct ttaaccggcc  1860
cttacaagcc gctgaacaaa acagggcttg tgctgcaaat gggtcttgat ccaaacgatg  1920
tgacattcac ttactctcac ttcgcagtgc cgcaagccaa aggcaacaat gtggttatca  1980
caagctacat gacaaacaga ggcttcttcg aggataaaaa ggcaacattt gcgccaagct  2040
tcttaatgaa catcaaaggc aataaaacat ccgttgtcaa aaacagcatc ctggagcaag  2100
gacagctgac agtcaactaa taacagcaaa aagaaaatgc cgatacttca ttggcatttt  2160
cttttatttc tcaacaagat ggtgaattga ctagtgggta gatccacagg acgggtgtgg  2220
tcgccatgat cgcgtagtcg atagtggctc caagtagcga agcgagcagg actgggcggc  2280
ggccaaagcg gtcggacagt gctccgagaa cgggtgcgca tagaaattgc atcaacgcat  2340
atagcgctag cagcacgcca tagtgactgg cgatgctgtc ggaatggacg atatcccgca  2400
agaggcccgg cagtaccggc ataaccaagc ctatgcctac agcatccagg gtgacggtgc  2460
cgaggatgac gatgagcgca ttgttagatt tcatacacgg tgcctgactg cgttagcaat  2520
ttaactgtga taaactaccg cattaaagct tatcgatgat aagctgtcaa acatgagaat  2580
tgatccggaa ccccttaatat aacttcgtat aatgtatgct atacgaagtt attaggtccc  2640
tcgactatag ggtcaccgtc gacagcgaca cacttgcatc ggatgcagcc cggttaacgt  2700
gccggcacgg cctgggtaac caggtatttt gtccacataa ccgtgcgcaa aatgttgtgg  2760
ataagcagga cacagcagca atccacagca ggcatacaac cgcacaccga ggttactccg  2820
ttctacaggt tacgacgaca tgtcaatact tgcccttgac aggcattgat ggaatcgtag  2880
tctcacgctg atagtctgat cgacaataca agtgggaccg tggtcccaga ccgataatca  2940
gaccgacray acgagtggga ycgtggtccc agactaataa tcagaccgac gatacgagtg  3000
ggaccgtggt cccagactaa taatcagacc gacgatacga gtgggaccgt ggtyccagwc  3060
tratwatcag accgacgata cragtggrac mgtggkccca gasakaataw tcagrccgag  3120
wtaygcwktc kggcctgtaa caaaggacat taagtaaaga cagatamrmg tgrgactaaa  3180
acgtggtccc agtctgatta tcagaccgac gatacgagtg ggaccgtggt cccagactaa  3240
taatcagacc gacgatacga gtgggaccgt ggtcccagac taataatcag accgacgata  3300
cgagtgggac cgtggtccca gtctgattat cagaccgacg atacaagtgg aacagtgggc  3360
ccagagagaa tattcaggcc agttatgctt tctggcctgt aacaaaggac attaagtaaa  3420
gacagataaa cgtagactaa aacgtggtcg catcagggtg ctggcttttc aagttcctta  3480
agaatggcct caattttctc tatacactca gttggaacac gagacctgtc caggttaagc  3540
accattttat cgcccttata caatactgtc gctccaggag caaactgatg tcgtgagctt  3600
aaactagttc ttgatgcaga tgacgtttta agcacagaag ttaaaagagt gataacttct  3660
tcagcttcaa atatcacccc agctttttttc tgctcatgaa ggttagatgc ctgctgctta  3720
agtaattcct ctttatctgt aaaggctttt tgaagtgcat cacctgaccg ggcagatagt  3780
tcaccggggt gagaaaaaag agcaacaact gatttaggca atttggcggt gttgatacag  3840
cgggtaataa tcttacgtga aatattttcc gcatcagcca gcgcagaaat atttccagca  3900
aattcattct gcaatcggct tgcataacgc tgaccacgtt cataagcact tgttgggcga  3960
taatcgttac ccaatctgga taatgcagcc atctgctcat catccagctc gccaaccaga  4020
acacgataat cactttcggt aagtgcagca gctttacgac ggcgactccc atcggcaatt  4080
tctatgacac cagatactct tcgaccgaac gccggtgtct gttgaccagt cagtagaaaa  4140
gaagggatga gatcatccag tgcgtcctca gtaagcagct cctggtcacg ttcattacct  4200
gaccataccc gagaggtctt ctcaacacta tcaccccgga gcacttcaag agtaaacttc  4260
acatcccgac cacatacagg caaagtaatg gcattaccgc gagccattac tcctacgcgc  4320
gcaattaacg aatccaccat cggggcagct ggtgtcgata acgaagtatc ttcaaccggt  4380
tgagtattga gcgtatgttt tggaataaca ggcgcacgct tcattatcta atctcccagc  4440
gtggtttaat cagacgatcg aaaatttcat tgcagacagg ttcccaaata gaaagagcat  4500
ttctccaggc accagttgaa gagcgttgat caatggcctg ttcaaaaaca gttctcatcc  4560
ggatctgacc tttaccaact tcatccgttt cacgtacaac attttttaga accatgcttc  4620
cccaggcatc ccgaatttgc tcctccatcc acggggactg agagccatta ctattgctgt  4680
atttggtaag caaaatacgt acatcaggct cgaacccttt aagatcaacg ttcttgagca  4740
gatcacgaag catatcgaaa aactgcagtg cggaggtgta gtcaaacaac tcagcaggcg  4800
tgggaacaat cagcacatca gcagcacata cgacattaat cgtgccgata cccaggttag  4860
gcgcgctgtc aataactatg acatcatagt catgagcaac agtttcaatg gccagtcgga  4920
gcatcaggtg tggatcggtg ggcagtttac cttcatcaaa tttgcccatt aactcagttt  4980
caatacggtg cagagccaga caggaaggaa taatgtcaag ccccggccag caagtgggct  5040
ttattgcata agtgacatcg tccttttccc caagatagaa aggcaggaga gtgtcttctg  5100
catgaatatg aagatctggt acccatccgt gatacattga ggctgttccc tgggggtcgt  5160
taccttccac gagcaaaaca cgtagcccct tcagagccag atcctgagca agatgaacag  5220
aaactgaggt tttgtaaacg ccacctttat gggcagcaac cccgatcacc ggtggaaata  5280
cgtcttcagc acgtcgcaat cgcgtaccaa acacatcacg catatgatta atttgttcaa  5340
ttgtataacc aacacgttgc tcaacccgtc ctcgaatttc catatccggg tgcggtagtc  5400
```

-continued

```
gccctgcttt ctcggcatct ctgatagcct gagaagaaac cccaactaaa tccgctgctt  5460
cacctattct ccagcgccgg gttattttcc tcgcttccgg gctgtcatca ttaaactgtg  5520
caatggcgat agccttcgtc atttcatgac cagcgtttat gcactggtta agtgtttcca  5580
tgagtttcat tctgaacatc ctttaatcat tgctttgcgt tttttttatta aatcttgcaa  5640
tttactgcaa agcaacaaca aaatcgcaaa gtcatcaaaa aaccgcaaag ttgtttaaaa  5700
taagagcaac actacaaaag gagataagaa gagcacatac ctcagtcact tattatcact  5760
agcgctcgcc gcagccgtgt aaccgagcat agcgagcgaa ctggcgagga agcaaagaag  5820
aactgttctg tcagatagct cttacgctca gcgcaagaag aaatatccac cgtgggaaaa  5880
actccaggta gaggtacaca cgcggatagc caattcagag taataaactg tgataatcaa  5940
ccctcatcaa tgatgacgaa ctaacccccg atatcaggtc acatgacgaa gggaaagaga  6000
aggaaatcaa ctgtgacaaa ctgccctcaa atttggcttc cttaaaaatt acagttcaaa  6060
aagtatgaga aaatccatgc aggctgaagg aaacagcaaa actgtgacaa attaccctca  6120
gtaggtcaga acaaatgtga cgaaccaccc tcaaatctgt gacagataac cctcagacta  6180
tcctgtcgtc atggaagtga tatcgcggaa ggaaaatacg atatgagtcg tctggcggcc  6240
tttctttttc tcaatgtatg agaggcgcat tggagttctg ctgttgatct cattaacaca  6300
gacctgcagg aagcggcggc ggaagtcagg catacgctgg taactttgag gcagctggta  6360
acgctctatg atccagtcga ttttcagaga gacgatgcct gagccatccg gcttacgata  6420
ctgacacagg gattcgtata aacgcatggc atacggattg gtgatttctt ttgtttcact  6480
aagccgaaac tgcgtaaacc ggttctgtaa cccgataaag aagggaatga gatatgggtt  6540
gatatgtaca ctgtaaagcc ctctggatgg actgtgcgca cgtttgataa accaaggaaa  6600
agattcatag ccttttcat cgccggcatc ctcttcaggg cgataaaaaa ccacttcctt  6660
ccccgcgaaa ctcttcaatg cctgccgtat atccttactg gcttccgcag aggtcaatcc  6720
gaatatttca gcatatttag caacatggat ctcgcagata ccgtcatgtt cctgtagggt  6780
gccatcagat ttctgatct ggtcaacgaa cagatacagc atacgttttt gatcccggga  6840
gagactatat gccgcctcag tgaggtcgtt tgactggacg attcgcgggc tatttttacg  6900
tttcttgtga ttgataaccg ctgtttccgc catgacagat ccatgtgaag tgtgacaagt  6960
ttttagattg tcacactaaa taaaaaagag tcaataagca gggataactt tgtgaaaaaa  7020
cagcttcttc tgagggcaat ttgtcacagg gttaagggca atttgtcaca gacaggactg  7080
tcatttgagg gtgatttgtc acactgaaag ggcaatttgt cacaacacct tctctagaac  7140
cagcatggat aaaggcctac aaggcgctct aaaaaagaag atctaaaaac tataaaaaaa  7200
ataattataa aaatatcccc gtggataagt ggataacccc aagggaagtt ttttcaggca  7260
tcgtgtgtaa gcagaatata taagtgctgt tccctggtgc ttcctcgctc actcgagggc  7320
ttcgccctgt cgctcaactg cggcgagcac tactggctgt aaaaggacag accacatcat  7380
ggttctgtgt tcattaggtt gttctgtcca ttgctgacat aatccgctcc acttcaacgt  7440
aacaccgcac gaagatttct attgttcctg aaggcatatt caaatcgttt tcgttaccgc  7500
ttgcaggcat catgacagaa cactacttcc tataaacgct acacaggctc ctgagattaa  7560
taatgcggat ctctacgata atgggagatt ttcccgactg tttcgttcgc ttctcagtgg  7620
ataacagcca gcttctctgt ttaacagaca aaaacagcat atccactcag ttccacattt  7680
ccatataaag gccaaggcat ttattctcag gataattgtt tcagcatcgc aaccgcatca  7740
gactccggca tcgcaaactg cacccggtgc cgggcagcca catccagcgc aaaaaccttc  7800
gtgtagactt ccgttgaact gatggactta tgtcccatca ggctttgcag aactttcagc  7860
ggtataccgg catacagcat gtgcatcgca taggaatggc ggaacgtatg tggtgtgacc  7920
ggaacagaga acgtcacacc gtcagcagca gcggcggcaa ccgcctcccc aatccaggtc  7980
ctgaccgttc tgtccgtcac ttcccagatc cgcgctttct ctgtccttcc tgtgcgacgg  8040
ttacgccgct ccatgagctt atcgcgaata aatacctgtg acggaagatc acttcgcaga  8100
ataaataaat cctggtgtcc ctgttgatac cgggaagccc tgggccaact tttggcgaaa  8160
atgagacgtt gatcggcacg taagaggttc caactttcac cataatgaaa taagatcact  8220
accgggcgta ttttttgagt tatcgagatt ttcaggagct aaggaagcta aaatggagaa  8280
aaaaatcact ggatatacca ccgttgatat atcccaatgg catcgtaaag aacattttga  8340
ggcatttcag tcagttgctc aatgtaccta taaccagacc gttcagctgg atattacggc  8400
ctttttaaag accgtaaaga aaaataagca caagttttat ccggccttta ttcacattct  8460
tgcccgcctg atgaatgctc atccggagtt ccgtatggca atgaaagacg gtgagctggt  8520
gatatgggat agtgttcacc cttgttacac cgttttccat gagcaaactg aaacgttttc  8580
atcgctctgg agtgaatacc acgacgattt ccggcagttt ctacacatat attcgcaaga  8640
tgtggcgtgt tacggtgaaa acctggccta tttccctaaa gggtttattg agaatatgtt  8700
tttcgtctca gccaatccct gggtgagttt caccagtttt gatttaaacg tggccaatat  8760
ggacaacttc ttcgcccccg ttttcaccat gggcaaatat tatacgcaag gcgacaaggt  8820
gctgatgccg ctggcgattc aggttcatca tgccgtttgt gatggcttcc atgtcggcag  8880
aatgcttaat gaattacaac agtactgcga tgagtggcag ggcggggcgt aatttttta  8940
aggcagttat tggtgccctt aaacgcctgg ttgctacgcc tgaataagtg ataataagcg  9000
gatgaatggc agaaattcga tgataagctg tcaaacatga gaattggtcg acggcgcgcc  9060
aaagcttgca tgcctgcagc cgcgtaacct ggcaaaatcg gttacggttg agtaataaat  9120
ggatgccctg cgtaagcggg gcacatttca ttacctcttt ctccgcaccc gacatagata  9180
ataacttcgt atagtataca ttatacgaag ttatctagta gacttaatcg cgtttaaacc  9240
catcatcaat aatatacctc aaactttttg tgcgcgttaa tatgcaaatg aggcgtttga  9300
atttgggaag ggaggaaggt gattggccga gagaagggcg accgttaggg gcggggcgag  9360
tgacgttttg atgacgtgac cgcgaggagg agccagtttg caagttctcg tgggaaaagt  9420
gacgtcaaac gaggtgtggt ttgaacacgg aaatactcaa ttttcccgcg ctctctgaca  9480
ggaaatgagg tgtttctagg cggatgcaag tgaaaacggg ccattttcgc gcgaaaactg  9540
aatgaggaag tgaaaatctg agtaatttcg cgtttatgac agggaggagt atttgccgag  9600
ggccgagtag actttgaccg attacgtggg ggtttcgatt accgtgtttt tcacctaaat  9660
ttccgcgtac ggtgtcaaag tccggtgttt ttacgtaggt gtcagctgat cgccagggta  9720
tttaaacctg cgctctccag tcaagaggcc actcttgagt gccagcgaga agagttttct  9780
cctccgcgcg cgagtcagat ctacactttg aaaggcgatc gctagcgaca tcgatcacaa  9840
gtttgtacaa aaaagcaggc tccaccatgg gaacccgcgt tttgagattt ctgtcgccga  9900
ctaaattcat gtcgcgcgat agtggtgttt atcgccgata gagatggcga tattggaaaa  9960
atcgatattt gaaaatatgg catattgaaa atgtcgccga tgtgagtttc tgtgtaactg  10020
atatcgccat ttttccaaaa gtgatttttg ggcatacgcg atatctggcg atagcgctta  10080
tatcgtttac gggggatggc gatagacgac tttggtgact tgggcgattc tgtgtgtcgc  10140
```

```
aaatatcgca gtttcgatat aggtgacaga cgatatgagg ctatatcgcc gatagaggcg  10200
acatcaagct ggcacatggc caatgcatat cgatctatac attgaatcaa tattggccat  10260
tagccatatt attcattggt tatatagcat aaatcaatat tggctattgg ccattgcata  10320
cgttgtatcc atatcataat atgtacattt atattggctc atgtccaaca ttaccgccat  10380
gttgacattg attattgact agttattaat agtaatcaat tacggggtca ttagttcata  10440
gcccatatat ggagttccgc gttacataac ttacggtaaa tggcccgcct ggctgaccgc  10500
ccaacgaccc ccgcccattg acgtcaataa tgacgtatgt tcccatagta acgccaatag  10560
ggactttcca ttgacgtcaa tgggtggagt atttacggta aactgcccac ttggcagtac  10620
atcaagtgta tcatatgcca agtacgcccc ctattgacgt caatgacggt aaatggcccg  10680
cctggcatta tgcccagtac atgaccttat gggactttcc tacttggcag tacatctacg  10740
tattagtcat cgctattacc atggtgatgc ggttttggca gtacatcaat gggcgtggat  10800
agcggtttga ctcacgggga tttccaagtc tccaccccat tgacgtcaat gggagtttgt  10860
tttggcacca aaatcaacgg gactttccaa aatgtcgtaa caactccgcc ccattgacgc  10920
aaatgggcgg taggcgtgta cggtgggagg tctatataag cagagctctc cctatcagtg  10980
atagagatct ccctatcagt gatagagatc gtcgacgagc tcgtttagtg aaccgtcaga  11040
tcgcctggag acgccatcca cgctgttttg acctccatag aagacaccgg gaccgatcca  11100
gcctccgcgg ccgggaacgg tgcattggaa cgcggattcc ccgtgccaag agtgacgtaa  11160
gtaccgccta tagagtctat aggcccaccc ccttggcttc ttatgcatgc tatactgttt  11220
ttggcttggg gtctatacac ccccgcttcc tcatgttata ggtgatggta tagcttagcc  11280
tataggtgtg ggttattgac cattattgac cactccccta ttggtgacga tactttccat  11340
tactaatcca taacatggct ctttgccaca actctcttta ttggctatat gccaatacac  11400
tgtccttcag agactgacac ggactctgta tttttacagg atggggtctc atttattatt  11460
tacaaattca catatacaac accaccgtcc ccagtgcccg cagtttttat taaacataac  11520
gtgggatctc cacgcgaatc tcgggtacgt gttccggaca tgggctcttc tccggtagcg  11580
gcggagcttc tacatccgag ccctgctccc atgcctccag cgactcatgg tcgctcggca  11640
gctccttgct cctaacagtg gaggccagac ttaggcacag cacgatgccc accaccacca  11700
gtgtgccgca caaggccgtg gcggtagggt atgtgtctga aaatgagctc ggggagcggg  11760
cttgcaccgc tgacgcattt ggaagactta aggcagcggc agaagaagat gcaggcagct  11820
gagttgttgt gttctgataa gagtcagagg taactcccgt tgcggtgctg ttaacggtgg  11880
agggcagtgt agtctgagca gtactcgttg ctgccgcgcg cgccaccaga cataatagct  11940
gacagactaa cagactgttc ctttccatgg gtcttttctg cagtcaccgt ccttgacacg  12000
aagcttggta cc                                                      12012

SEQ ID NO: 40           moltype = DNA  length = 29187
FEATURE                 Location/Qualifiers
misc_feature            1..29187
                        note = Vector
source                  1..29187
                        mol_type = other DNA
                        organism = synthetic construct
SEQUENCE: 40
gcggccgctc gagcatgcat ctagagggcc ctattctata gtgtcaccta aatgctagag  60
ctcgctgatc agcctcgact gtgccttcta gttgccagcc atctgttgtt tgcccctccc  120
ccgtgccttc cttgaccctg gaaggtgcca ctcccactgt cctttcctaa taaaatgagg  180
aaattgcatc gcattgtctg agtaggtgtc attctattct ggggggtggg gtggggcagg  240
acagcaaggg ggaggattgg gaagacaata gcaggcatgc tggggatgcg gtgggctcta  300
tggcttctga ggcggaaaga accagctggg gctcgagggg ggatcgatcc cgtcgagata  360
tctagaccca gctttcttgt acaaagtggt gatcgattcg acagatcgcg atcgcagtga  420
gtagtgttct ggggcggggg aggacctgca tgagggccag aatgactgaa atctgtgctt  480
ttctgtgtgt tgcagcatca tgagcggaag cggctccttt gagggagggg tattcagccc  540
ttatctgacg gggcgtctcc cctcctgggc gggagtgcgt cagaatgtga tgggatccac  600
ggtggacggc cggcccgtgc agcccgcgaa ctcttcaacc ctgacctatg caaccctgag  660
ctcttcgtcg gtggacgcag ctgccgccgc agctgctgca tccgccgcca gcgccgtgcg  720
cggaatggcc atgggcgccg gctactacgg cactctggtg gccaactcga gttccaccaa  780
taatcccgcc agcctgaacg aggagaagct gctgctgctg atggcccagc ttgaggcctt  840
gacccagcgc ctgggcgagc tgacccagca ggtggctcag ctgcaggagc agacgcgggc  900
cgcggttgcc acggtgaaat ccaaataaaa aatgaatcaa taaataaacg gagacggttg  960
ttgattttaa cacagagtct gaatctttat ttgatttttc gcgcgcggta ggccctggac  1020
cacccggtctc gatcattgag cacccggtgg atcttttcca ggacccggta gaggtgggct  1080
tggatgttga ggtacatggg catgagcccg tcccgggggt ggaggtagct ccattgcagg  1140
gcctcgtgct cgggggtggt gttgtaaatc acccagtcat agcaggggcg cagggcgtgg  1200
tgttgcacaa tatctttgag gaggagactg atggccacgg gcagcccttt ggtgtaggtg  1260
tttacaaatc tgttgagctg ggagggatgc atgcgggggg agatgaggtg catcttggcc  1320
tggatcttga gattggcgat gttaccgccc agatcccgcc tggggttcat gttgtgcagg  1380
accaccagca cggtgtatcc ggtgcacttg gggaatttat catgcaactt ggaagggaag  1440
gcgtgaaaga atttggcgac gcccttgtgt ccgcccaggt tttccatgca ctcatccatg  1500
atgatggcaa tgggcccgtg ggcggcggcc tgggcaaaga cgtttcgggg gtcggacaca  1560
tcatagttgt ggtcctgggt gaggtcatca taggccattt taatgaattt ggggcggagg  1620
gtgccggact gggggacaaa ggtaccctcg atcccggggg cgtagttccc ctcacagatc  1680
tgcatctccc aggctttgag ctcagagggg gggatcatgt ccacctgcgg ggcgataaag  1740
aacacggttt ccggggcggg ggagatgagc tgggccgaaa gcaagttccg gagcagctgg  1800
gacttgccgc agccggtggg gccgtaaatg accccgatga ccggctgcag gtggtagttg  1860
agggagagac agctgccgtc ctcccggagg aggggggcca cctcgttcat catctcgcgc  1920
acgtgcatgt tctcgcgcac cagttccgcc aggaggcgct ctcccccccag agataggagc  1980
tcctggagcg aggcgaagtt tttcagcggc ttgagtccgt cggccatggg cattttggag  2040
agggtctgtt gcaagagttc caagcggtcc cagagctcgg tgatgtgctc tacggcatct  2100
cgatccagca gacctcctcg tttcgcgggt tgggacgact gcgggagtag ggcaccagac  2160
gatgggcgtc cagcgcagcc agggtccggt ccttccaggg ccgcagcgtc cgcgtcaggg  2220
tggtctccgt cacggtgaag ggtgcgcgc cgggctgggc gcttgcgagg gtgcgcttca  2280
```

```
ggctcatccg gctggtcgaa aaccgctccc gatcggcgcc ctgcgcgtcg gccaggtagc  2340
aattgaccat gagttcgtag ttgagcgcct cggccgcgtg gcctttggcg cggagcttac  2400
ctttggaagt ctgcccgcag gcgggacaga ggagggactt gagggcgtag agcttggggg  2460
cgaggaagac ggaatcgggg gcgtaggcgt ccgcgccgca gtgggcgcag acggtctcgc  2520
actccacgag ccaggtgagg tcgggctggt cggggtcaaa aaccagtttc ccgccgttct  2580
ttttgatgcg tttcttacct ttggtctcca tgagctcgtg tccccgctgg gtgacaaaga  2640
ggctgtccgt gtccccgtag accgacttta tgggccggtc ctcgagcggt gtgccgcggt  2700
cctcctcgta gaggaacccc gcccactccg agacgaaagc ccgggtccag gccagcacga  2760
aggaggccac gtgggacggg tagcggtcgt tgtccaccag cgggtccact tttccaggg   2820
tatgcaaaca catgtccccc tcgtccacat ccaggaaggt gattggcttg taagtgtagg  2880
ccacgtgacc gggggtcccg gccggggggg tataaaaggg ggcgggcccc tgctcgtcct  2940
cactgtcttc cggatcgctg tccaggagcg ccagctgttg ggtaggtat  tccctctcga  3000
aggcgggcat gacctcggca ctcaggttgt cagtttctag aaacgaggag gatttgatat  3060
tgacggtgcc agcggagatg cctttcaaga gcccctcgtc catctggtca gaaaagacga  3120
tttttttgtt gtcgagcttg gtggcgaagg agccgtagag ggcgttggaa aggagcttgg  3180
cgatggagcg catggtctgg tttttttcct tgtcggcgcg ctccttggcc gcgatgttga  3240
gctgcacgta ctcgcgcgcc acgcacttcc attcggggaa gacggtggtc atctcgtcgg  3300
gcacgattct gacctgccaa cctcgattat gcagggtgat gaggtccaca ctggtggcca  3360
cctcgccgcg caggggctcg ttggtccagc agaggcggcc gcccttgcgc gagcagaagg  3420
ggggcagagg gtccagcatg acctcgtcgg gggggtcggc atcgatggtg aagatgccgg  3480
gcaggagatc ggggtcgaag tagctgatgg aagtggccag atcgtccagg gaagcttgcc  3540
attcgcgcac ggccagcgcg cgctcgtagg gactgagggg cgtgccccag ggcatggggt  3600
gggtgagcgc ggaggcgtac atgccgcaga tgtcgtagac gtagaggggc tcctcgagga  3660
tgccgatgta ggtggggtag cagcgccccc cgcggatgct ggcgcgcacg tagtcataca  3720
gctcgtgcga gggcgcgagg agccccgggc ccaggttggt gcgactgggc ttttcggcgc  3780
ggtagacgat ctggcgaaag atggcatgcg agttggagga gatggtgggc ctttggaaga  3840
tgttgaagtg ggcgtggggg aggccgaccg agtcgcggat gaagtgggcg taggagtctt  3900
gcagtttggc gacgagctcg gcggtgacga ggacgtccag agcgcagtag tcgagggtct  3960
cctggatgat gtcatacttg agctggccct tttgtttcca cagctcgcgg ttgagaagga  4020
actcttcgcg gtccttccag tactcttcga gggggaaccc gtcctgatct gcacggtaag  4080
agcctagcat gtagaactgg ttgacggcct tgtaggcgca gcagcccttc tccacgggga  4140
gggcgtaggc ctgggcggcc ttgcgcaggg aggtgtgcgt gagggcgaag gtgtccctga  4200
ccatgacctt gaggaactgg tgcttgaaat cgatatcgtc gcagcccccc tgctcccaga  4260
gctggaagtc cgtgcgcttc ttgtaggcgg ggttgggcaa agcgaaagta acatcgttga  4320
aaaggatctt gcccgcgcgg ggcataaagt tgcgagtgat gcggaaaggc tggggcacct  4380
cggcccggtt gttgatgacc tgggcggcga gcacgatctc gtcgaaaccg ttgatgttgt  4440
ggcccacgat gtagagttcc acgaatcgcg ggcggccctt gacgtggggc agcttcttga  4500
gctcctcgta ggtgagctcg tcggggtcgc tgagaccgtg ctgctcgagc gcccagtcgg  4560
cgagatgggg gttggcgcgg aggaaggaag tccagagatc cacggccagg gcggtttgca  4620
gacggtcccg gtactgacgg aactgctgcc cgacggccat tttttcgggg gtgacgcagt  4680
agaaggtgcg ggggtccccg tgccagcggt cccatttgag ctggagggcg agatcgaggg  4740
cgagctcgac gaggcggtcg tcccctgaga gtttcatgac cagcatgaag ggacgagct   4800
gcttgccgaa ggaccccatc caggtgtagg tttccacatc gtaggtgagg aagagccttt  4860
cggtgcgagg atgcgagccg atggggaaga actggatctc ctgccaccaa ttggaggaat  4920
ggctgttgat gtgatggaag tagaaatgcc gacggcgcgc cgaacactcg tgcttgtgtt  4980
tatacaagcg gccacagtgc tcgcaacgct gcacgggatg cacgtgctgc acgagctgta  5040
cctgagttcc tttgacgagg aatttcagtg ggaagtggag tcgtggcgcc tgcatctcgt  5100
gctgtactac gtcgtggtgg tcggcctggc cctcttctgc ctcgatggtg gtcatgctga  5160
cgagcccgcg cgggaggcag gtccagacct cggcgcgagc gggtcggaga gcgaggacga  5220
gggcgcgcag gccggagctg tccagggtcc tgagacgctg cggagtcagg tcagtgggca  5280
gcggcggcgc gcggttgact tgcaggagtt tttccagggc gcgcgggagg tccagatggt  5340
acttgatctc caccgcgccg ttggtggcga cgtcgatggc ttgcagggtc ccgtgcccct  5400
ggggtgtgac caccgtcccc cgtttcttct tgggcggctg gggcgacggg ggcggtgcct  5460
cttccatggt tagaagcggc ggcgaggacg cgcgccgggc ggcagaggcg gctcggggcc  5520
cggaggcagg ggcggcaggg gcacgtcggc gccgcgcgcg ggtaggttct ggtactgcgc  5580
ccggagaaga ctggcgtgag cgacgacgcg acggttgacg tcctggatct gacgcctctg  5640
ggtgaaggcc acgggacccg tgagtttgaa cctgaaagag agttcgacag aatcaatctc  5700
ggtatcgttg acggcggcct gccgcaggat ctcttgcacg tcgcccgagt tgtcctggta  5760
ggcgatctcg gtcatgaact gctcgatctc ctcctcctga aggtctccgc gaccggcgcg  5820
ctccacggtg gccgcgaggt cgttggagat gcggcccatg agctgcgaga aggcgttcat  5880
gcccgcctcg ttccagacgc ggctgtagac cacgacgccc tcgggatcgc gggcgcgcat  5940
gaccacctgg gcgaggttga gctccacgtg gcgcgtgaag accgcgtagt tgcagaggcg  6000
ctggtagagg tagttgagcg tggtggcgat gtgctcggtg acgaagaaat acatgatcca  6060
gcggcggagc ggcatctcgc tgacgtcgcc cagcgcctcc aagcgttcca tggcctcgta  6120
aaagtccacg gcgaagttga aaaactggga gttgcgcgcc gagacggtca actcctcctc  6180
cagaagacgg atgagctcgg cgatggtggc gcgcacctcg cgctcgaagg cccccgggag  6240
ttcctccact tcctcctctt cttcctcctc cactaacatc tcttctactt cctcctcagg  6300
cggtggtggt ggcgggggag gggcctgcg  tcgccggcgg cgcacgggca gacggtcgat  6360
gaagcgctcg atggtctcgc cgcgccggcg tcgcatggtc tcggtgacgg cgcgcccgtc  6420
ctcgcggggc cgcagcgtga agacgccgcc gcgcatctcc aggtggccgg gggggtcccc  6480
gttgggcagg gagagggcgc tgacgatgca tcttatcaat tgccccgtag ggactccgcg  6540
caaggacctg agcgtctcga gatccacggg atctgaaaac cgttgaacga aggcttcgag  6600
ccagtcgcag tcgcaaggta ggctgagcac ggtttcttct gccgggtcat gttggggagc  6660
ggggcgggcg atgctgctgg tgatgaagtt gaaataggcg gttctgagac ggcggatggt  6720
ggcgaggagc accaggtctt tgggcccggc ttgctggatg cgcagacggt cggccatgcc  6780
ccaggcgtgg tcctgacacc tggccaggtc cttgtagtag tcctgcatga gccgctccac  6840
gggcacctcc tcctcgcccg cgcggccgtg catgcgcgtg agcccgaagc cgcgctgggg  6900
ctggacgagc gccaggtcgg cgacgacgcg ctcggcgagg atggcctgct ggatctgggt  6960
gagggtggtc tggaagtcgt caaagtcgac gaagcggtgg taggctccgg tgttgatggt  7020
```

```
gtaggagcag ttggccatga cggaccagtt gacggtctgg tggcccggac gcacgagctc  7080
gtggtacttg aggcgcgagt aggcgcgcgt gtcgaagatg tagtcgttgc aggtgcgcac  7140
caggtactgg tagccgatga ggaagtgcgg cggcggctgg cggtagagcg gccatcgctc  7200
ggtggcgggg gcgccgggcg cgaggtcctc gagcatggtg cggtggtagc cgtagatgta  7260
cctggacatc caggtgatgc cggcggcggt ggtggaggcg cgcgggaact cgcggacgcg  7320
gttccagatg ttgcgcagcg gcaggaagta gttcatggtg ggcacggtct ggcccgtgag  7380
gcgcgcgcag tcgtggatgc tctatacggg caaaaacgaa agcggtcagc ggctcgactc  7440
cgtggcctgg aggctaagcg aacgggttgg gctgcgcgtg taccccggtt cgaatctcga  7500
atcaggctgg agccgcagct aacgtggtac tggcactccc gtctcgaccc aagcctgcac  7560
caaccctcca ggatacggag gcgggtcgtt ttgcaacttt ttttggaggc cggaaatgaa  7620
actagtaagc gcggaaagcg gccgaccgcg atggctcgct gccgtagtct ggagaagaat  7680
cgccagggtt gcgttgcggt gtgccccggt tcgaggccgg ccggattccg cggctaacga  7740
gggcgtggct gccccgtcgt ttccaagacc ccatagccag ccgacttctc cagttacgga  7800
gcgagcccct cttttgtttt gtttgttttt gccagatgca tcccgtactg cggcagatgc  7860
gcccccacca ccctccaccg caacaacagc cccctcctcc acagccggcg cttctgcccc  7920
cgccccagca gcagcagcaa cttccagcca cgaccgccgc ggccgccgtg agcggggctg  7980
gacagacttc tcagtatgat cacctggcct tggaagaggg cgaggggctg gcgcgcctgg  8040
gggcgtcgtc gccggagcgg cacccgcgcg tgcagatgaa aagggacgct cgcgaggcct  8100
acgtgcccaa gcagaacctg ttcagagaca ggagcggcga ggagcccgag gagatgcgcg  8160
cggcccggtt ccacgcgggg cgggagctgc ggcgcggcct ggaccgaaag agggtgctga  8220
gggacgagga tttcgaggcg gacgagctga cggggatcag ccccgcgcgc gcgcacgtgg  8280
ccgcggccaa cctggtcacg gcgtacgagc agaccgtgaa ggaggagagc aacttccaaa  8340
aatccttcaa caaccacgtg cgcaccctga tcgcgcgcga ggaggtgacc ctgggcctga  8400
tgcacctgtg ggacctgctg gaggccatcg tgcagaaccc caccagcaag ccgctgacgg  8460
cgcagctgtt cctggtggtg cagcatagtc gggacaacga ggcgttcagg gaggcgctgc  8520
tgaatatcac cgagcccgag ggccgctggc tcctggacct ggtgaacatt ctgcagagca  8580
tcgtggtgca ggagcgcggg ctgccgctgt ccgagaagct ggcggccatc aacttctcgg  8640
tgctgagtct gggcaagtac tacgctagga agatctacaa gaccccgtac gtgcccatag  8700
acaaggaggt gaagatcgac gggttttaca tgcgcatgac cctgaaagtg ctgaccctga  8760
gcgacgatct gggggtgtac cgcaacgaca ggatgcaccg cgcggtgagc gccagcaggc  8820
ggcgcgagct gagcgaccag gagctgatgc acagcctgca gcgggccctg accggggccg  8880
ggaccgaggg ggagagctac tttgacatgg gcgcggacct gcactggcag cccagccgcc  8940
gggccttgga ggcggcaggc ggtccccccct acatagaaga ggtggacgat gaggtggacg  9000
aggagggcga gtacctggaa gactgatggc gcgaccgtat ttttgctaga tgcaacaaca  9060
gccacctcct gatcccgcga tgcgggcggc gctgcagagc cagccgtccg gcattaactc  9120
ctcggacgat tggacccagg ccatgcaacg catcatggcg ctgacgaccc gcaaccccga  9180
agcctttaga cagcagcccc aggccaaccg gctctcggcc atcctggagg ccgtggtgcc  9240
ctcgcgctcc aaccccacgc acgagaaggt cctggccatc gtgaacgcgc tggtggagaa  9300
caaggccatc cgcggcgacg aggccggcct ggtgtacaac gcgctgctgg agcgcgtggc  9360
ccgctacaac agcaccaacg tgcagaccaa cctggaccgc atggtgaccg acgtgcgcga  9420
ggccgtggcc cagcgcgagc ggttccaccg cgagtccaac ctgggatcca tggtggcgct  9480
gaacgccttc ctcagcaccc agcccgccaa cgtgccccgg ggccaggagg actacaccaa  9540
cttcatcagc gccctgcgcc tgatggtgac cgaggtgccc cagagcgagg tgtaccagtc  9600
cgggccggac tacttcttcc agaccagtcg ccagggcttg cagaccgtga acctgagcca  9660
ggcgttcaag aacttgcagg gcctgtgggg cgtgcaggcc ccggtcgggg accgcgcgac  9720
ggtgtcgagc ctgctgacgc cgaactcgcg cctgctgctg ctgctggtgg ccccctcac  9780
ggacagcggc agcatcaacc gcaactcgta cctgggctac ctgattaacc tgtaccgcga  9840
ggccatcggc caggcgcacg tggacgagca gacctaccag gagatcaccc acgtgagccg  9900
cgccctgggc caggacgacc cgggcaatct ggaagccacc ctgaactttt tgctgaccaa  9960
ccggtcgcag aagatcccgc cccagtacac gctcagcgcc gaggaggagc gcatcctgcg  10020
atacgtgcag cagagcgtgg gcctgttcct gatgcaggag ggggccaccc ccagcgccgc  10080
gctcgacatg accgcgcgca acatggagcc cagcatgtac gccagcaacc gcccgttcat  10140
caataaactg atggactact tgcatcgggc ggccgccatg aactctgact atttcaccaa  10200
cgccatcctg aatccccact ggctcccgcc gccggggttc tacacgggcg agtacgacat  10260
gcccgacccc aatgacgggt tcctgtggga cgatgtggac agcagcgtgt tctccccccg  10320
accgggtgct aacgagcgcc ccttgtggaa gaaggaaggc agcgaccgac gcccgtcctc  10380
ggcgctgtcc ggccgcgagg gtgctgccgc ggcggtgccc gaggccgcca gtcctttccc  10440
gagcttgccc ttctcgctga acagtattcg cagcagcgag ctgggcagga tcacgcgccc  10500
gcgcttgctg ggcgaggagg agtacttgaa tgactcgctg ttgagacccg agcgggagaa  10560
gaacttcccc aataacggga tagagagcct ggtggacaag atgagccgct ggaagacgta  10620
tgcgcaggag cacagggacg atccgtcgca gggggccacg agccggggca gcgccgcccg  10680
taaacgccgg tggcacgaca ggcagcgggg actgatgtgg gacgatgagg attccgccga  10740
cgacagcagc gtgttggact tgggtgggag tggtaacccg ttcgctcacc tgcgcccccg  10800
catcgggcgc atgatgtaag agaaaccgaa aataaatgat actcaccaag gccatggcga  10860
ccagcgtgcg ttcgtttctt ctctgttgtt gtatctagta tgatgaggcg tgcgtacccg  10920
gagggtcctc ctccctcgta cgagagcgtg atgcagcagg cgatggcggc ggcggcggcg  10980
atgcagcccc cgctggaggc tccttacgtg cccccgcggt acctggcgcc tacggagggg  11040
cggaacagca ttcgttactc ggagctggca ccccttgtacg ataccacccg gttgtacctg  11100
gtggacaaca agtcggcgga catcgcctcg ctgaactacc agaacgacca cagcaacttc  11160
ctgaccaccg tggtgcagaa caatgacttc acccccacgg aggccagcac ccagaccatc  11220
aactttgacg agcgctcgcg gtggggcggt cagctgaaaa ccatcatgca caccaacatg  11280
cccaacgtga acgagttcat gtacagcaac aagttcaagg cgcgggtgat ggtctcccgc  11340
aagaccccca acggggtgac agtgacagat ggtagtcagg atatcttgga gtatgaatgg  11400
gtggagtttg agctgcccga aggcaacttc tcggtgacca tgaccatcga cctgatgaac  11460
aacgccatca tcgacaatta cttggcggtg gggcggcaga acggggtcct ggagagcgat  11520
atcggcgtga agttcgacac taggaacttc aggctgggct gggaccccgt gaccgagctg  11580
gtcatgcccg gggtgtacac caacgaggcc ttccaccccg atattgtctt gctgcccggc  11640
tgcggggtgg acttcaccga gagccgcctc agcaacctgc tgggcattcg caagaggcag  11700
cccttccagg agggcttcca gatcatgtac gaggatctgg aggggggcaa catccccgcg  11760
```

-continued

```
ctcctggatg tcgacgccta tgagaaaagc aaggaggaga gcgccgccgc ggcgactgca  11820
gctgtagcca ccgcctctac cgaggtcagg ggcgataatt ttgccagccc tgcagcagtg  11880
gcagcggccg aggcggctga aaccgaaagt aagatagtca ttcagccggt ggagaaggat  11940
agcaaggaca ggagctacaa cgtgctgccg gacaagataa acaccgccta ccgcagctgg  12000
tacctggcct acaactatgg cgaccccgag aagggcgtgc gctcctggac gctgctcacc  12060
acctcggacg tcacctgcgg cgtggagcaa gtctactggt cgctgcccga catgatgcaa  12120
gacccggtca ccttccgctc cacgcgtcaa gttagcaact acccggtggt gggcgccgag  12180
ctcctgcccg tctactccaa gagcttcttc aacgagcagg ccgtctactc gcagcagctg  12240
cgcgccttca cctcgctcac gcacgtcttc aaccgcttcc ccgagaacca gatcctcgtc  12300
cgcccgcccg cgcccaccat taccaccgtc agtgaaaacg ttcctgctct cacagatcac  12360
gggaccctgc cgctgcgcag cagtatccgg ggagtccagc gcgtgaccgt tactgacgcc  12420
agacgccgca cctgccccta cgtctacaag gccctgggca tagtcgcgcc gcgcgtcctc  12480
tcgagccgca ccttctaaaa aatgtccatt ctcatctcgc ccagtaataa caccggttgg  12540
ggcctgcgcg cgcccagcaa gatgtacgga ggcgctcgcc aacgctccac gcaacacccc  12600
gtgcgcgtgc gcgggcactt ccgcgctccc tggggcgccc tcaagggccg cgtgcggtcg  12660
cgcaccaccg tcgacgacgt gatcgaccag gtggtggccg acgcgcgcaa ctacaccccc  12720
gccgccgcgc ccgtctccac cgtggacgcc gtcatcgaca gcgtggtggc cgacgcgcgc  12780
cggtacgccc gcgccaagag ccggcggcgg cgcatcgccc ggcggcaccg gagcaccccc  12840
gccatgcgcg cggcgcgagc cttgctgcgc agggccaggc gcacgggacg cagggccatg  12900
ctcagggcgg ccagacgcgc ggcttcaggc gccagcgccg gcaggacccg gagacgcgcg  12960
gccacggcgg cggcagcggc catcgccagc atgtcccgcc cgcggcgagg gaacgtgtac  13020
tgggtgcgcg acgccgccac cggtgtgcgc gtgcccgtgc gcacccgccc ccctcgcact  13080
tgaagatgtt cacttcgcga tgttgatgtg tcccagcggc gaggaggatg tccaagcgca  13140
aattcaagga agagatgctc caggtcatcg cgcctgagat ctacggcccc gcggtggtga  13200
aggaggaaag aaagccccgc aaaatcaagc gggtcaaaaa ggacaaaaag gaagaagatg  13260
acgatctggt ggagtttgtg cgcgagttcg cccccggcg gcgcgtgcag tggcgcgggc  13320
ggaaagtgca cccggtgctg agacccggca ccaccgtggt cttcacgccc ggcgagcgct  13380
ccggcagcgc ttccaagcgc tcctacgacg aggtgtacgg ggacgaggac atcctcgagc  13440
aggcggccga gcgcctgggc gagtttgctt acggcaagcg cagccgcccc gccctgaagg  13500
aagaggcggt gtccatcccg ctggaccacg gcaaccccac gccgagcctc aagcccgtga  13560
ccctgcagca ggtgctgccg agcgcagcgc cgcgccgggg gttcaagcgc gagggcgagg  13620
atctgtaccc caccatgcag ctgatggtgc ccaagcgcca gaagctggaa gacgtgctgg  13680
agaccatgaa ggtggacccg gacgtgcagc ccgaggtcaa ggtgcggccc atcaagcagg  13740
tggccccggg cctgggcgtg cagaccgtgg acatcaagat ccccacggag cccatggaaa  13800
cgcagaccga gcccatgatc aagcccagca ccagcaccat ggaggtgcag acggatccct  13860
ggatgccatc ggctcctagc cgaagacccc ggcgcaagta cggcgcggcc agcctgctga  13920
tgcccaacta cgcgctgcat ccttccatca tccccacgcc gggctaccgc ggcacgcgct  13980
tctaccgcgg tcatacaacc agccgccgcc gcaagaccac cacccgccgc cgccgtcgcc  14040
gcacagccgc tgcatctacc cctgccgccc tggtgcggag agtgtaccgc cgcggccgcg  14100
cgcctctgac cctaccgcgc gcgcgctacc acccgagcat cgccatttaa actttcgcct  14160
gctttgcaga tggccctcac atgccgcctc cgcgttccca ttacgggcta ccgaggaaga  14220
aaaccgcgcc gtagaaggct ggcggggaac gggatgcgtc gccaccacca tcggcggcgg  14280
cgcgccatca gcaagcggtt gggggaggc ttcctgcccg cgctgatccc catcatcgcc  14340
gcggcgatcg gggcgatccc cggcattgct tccgtggcgg tgcaggcctc tcagcgccac  14400
tgagacactt ggaaaacatc ttgtaataaa ccaatggact ctgacgctcc tggtcctgtg  14460
atgtgttttc gtagacagat ggaagacatc aatttttcgt ccctggctcc gcgacacggc  14520
acgcggccgt tcatgggcac ctggagcgac atcggcacca gccaactgaa cgggggcgcc  14580
ttcaattgga gcagtctctg gagcgggctt aagaatttcg ggtccacgct taaaacctat  14640
ggcagcaagg cgtggaacag caccacaggg caggcgctga gggataagct gaaagagcag  14700
aacttccagc agaaggtggt cgatgggctc gcctcgggca tcaacggggt ggtggacctg  14760
gccaaccagg ccgtgcagcg gcagatcaac agccgcctgg acccggtgcc gcccgccggc  14820
tccgtggaga tgccgcaggt ggaggaggag ctgcctcccc tggacaagcg gggcgagaag  14880
cgaccccgcc ccgacgcgga ggagacgctg ctgacgcaca cggacgagcc gcccccgtac  14940
gaggaggcgg tgaaactggg tctgcccacc acgcggccca tcgcgcccct ggccaccggg  15000
gtgctgaaac ccgaaagtaa taagcccgcg accctggact tgcctcctcc cgcttcccgc  15060
ccctctacag tggctaagcc cctgccgccg gtggccgtgg cccgcgcgcg acccgggggc  15120
tccgcccgcc ctcatgcgaa ctggcagagc actctgaaca gcatcgtggg tctgggagtg  15180
cagagtgtga agcgccgccg ctgctattaa acctaccgta gcgcttaact tgcttgtctg  15240
tgtgtgtatg tattatgtcg ccgctgtccg ccagaaggag gagtgaagag gcgcgtcgcc  15300
gagttgcaag atggccaccc catcgatgct gccccagtgg gcgtacatgc acatcgccgg  15360
acaggacgct tcggagtacc tgagtccggg tctggtgcag ttcgcccgcg ccacagacac  15420
ctacttcagt ctggggaaca agtttaggaa ccccacggtg gcgcccacgc acgatgtgac  15480
caccgaccgc agccagcggc tgacgctgcg cttcgtgccc gtggaccgcg aggacaacac  15540
ctactcgtac aaagtgcgct acacgctggc cgtgggcgac aaccgcgtgc tggacatggc  15600
cagcacctac tttgacatcc gcggcgtgct ggatcggggc cctagcttca aaccctactc  15660
cggcaccgcc tacaacagcc tggctcccaa gggagcgccc aattccagcc agtgggagca  15720
aaaaaaggca ggcaatggtg acactatgga aacacacaca tttggtgtgg ccccaatggg  15780
cggtgagaat attacaatcg acggattaca aattggaact gacgctacag ctgatcagga  15840
taaaccaatt tatgctgaca aaacattcca gcctgaacct caagtaggag aagaaaattg  15900
gcaagaaact gaaagctttt atggcggtag ggctcttaaa aaagacacaa gcatgaaacc  15960
ttgctatggc tcctatgcta gacccaccaa tgtaaaggga ggtcaagcta aacttaaagt  16020
tggagctgat ggagttccta ccaaagaatt tgacatagac ctggctttct ttgatactcc  16080
cggtggcaca gtgaatggac aagatgagta taaagcagac attgtcatgt ataccgaaaa  16140
cacgtatctg gaaactccag acacgcatgt ggtatacaaa ccaggcaagg atgatgcaag  16200
ttctgaaatt aacctggttc agcagtccat gcccaataga cccaactata ttgggttcag  16260
agacaacttt attgggctca tgtattacaa cagtactggc aatatggggg tgctggctgg  16320
tcaggcctca cagctgaatg ctgtggtcga cttgcaagac agaaacaccg agctgtcata  16380
ccagctcttg cttgactctt tgggtgacag aacccggtat ttcagtatgt ggaatcaggc  16440
ggtggacagt tatgatcctg atgtgcgcat tattgaaaac catggtgtgg aagacgaact  16500
```

-continued

```
tcccaactat tgcttccccc tggatgggtc tggcactaat gccgcttacc aaggtgtgaa  16560
agtaaaaaat ggtaacgatg gtgatgttga gagcgaatgg gaaaatgatg atactgtcgc  16620
agctcgaaat caattatgca agggcaacat ttttgccatg gaaattaacc tccaagccaa  16680
cctgtggaga agtttcctct actcgaacgt ggccctgtac ctgcccgact cttacaagta  16740
cacgccagcc aacatcaccc tgcccaccaa caccaacact tatgattaca tgaacgggag  16800
agtggtgcct ccctcgctgg tggacgccta catcaacatc ggggcgcgct ggtcgctgga  16860
ccccatggac aacgtcaatc ccttcaacca ccaccgcaac gcgggcctgc gctaccgctc  16920
catgctcctg ggcaacgggc gctacgtgcc cttccacatc caggtgcccc agaaattttt  16980
cgccatcaag agcctcctgc tcctgcccgg gtcctacacc tacgagtgga acttccgcaa  17040
ggacgtcaac atgatcctgc agagctccct cggcaacgac ctgcgcacgg acggggcctc  17100
catctccttc accagcatca acctctacgc caccttcttc cccatggcgc acaacacggc  17160
ctccacgctc gaggccatgc tgcgcaacga caccaacgac cagtccttca acgactacct  17220
ctcggcggcc aacatgctct accccatccc ggccaacgcc accaacgtgc ccatctccat  17280
cccctcgcgc aactgggccg ccttccgcgg ctggtccttc acgcgcctca agaccaagga  17340
gacgccctcg ctgggctccg ggttcgaccc ctacttcgtc tactcgggct ccatccccta  17400
cctcgacggc accttctacc tcaaccacac cttcaagaag gtctccatca ccttcgactc  17460
ctccgtcagc tggcccggca acgaccggct cctgacgccc aacgagttcg aaatcaagcg  17520
caccgtcgac ggcgagggat acaacgtggc ccagtgcaac atgaccaagg actggttcct  17580
ggtccagatg ctggcccact acaacatcgg ctaccagggc ttctacgtgc ccgagggcta  17640
caaggaccgc atgtactcct tcttccgcaa cttccagccc atgagccgcc aggtggtgga  17700
cgaggtcaac tacaaggact accaggccgt caccctggcc taccagcaca acaactcggg  17760
cttcgtcggc tacctcgcgc ccaccatgcg ccagggccag ccctaccccg ccaactaccc  17820
gtacccgctc atcggcaaga gcgccgtcac cagcgtcacc cagaaaaagt tcctctgcga  17880
cagggtcatg tggcgcatcc ccttctccag caacttcatg tccatgggcg cgctcaccga  17940
cctcggccag aacatgctct atgccaactc cgcccacgcg ctagacatga atttcgaagt  18000
cgaccccatg gatgagtcca cccttctcta tgttgtcttc gaagtcttcg acgtcgtccg  18060
agtgcaccag ccccaccgcg gcgtcatcga ggccgtctac ctgcgcaccc ccttctcggc  18120
cggtaacgcc accacctaaa ttgctacttg catgatggct gagcccacag gctccggcga  18180
gcaggagctc agggccatca tccgcgacct gggctgcggg ccctacttcc tgggcacctt  18240
cgataagcgc ttcccgggat tcatggcccc gcacaagctg gcctgcgcca tcgtcaacac  18300
ggccggccgc gagaccgggg gcgagcactg gctggccttc gcctggaacc cgcgctcgaa  18360
cacctgctac ctcttcgacc ccttcgggtt ctcggacgag cgcctcaagc agatctacca  18420
gttcgagtac gagggcctgc tgcgccgtag cgccctggcc accgaggacc gctgcgtcac  18480
cctggaaaag tccacccaga ccgtgcaggg tccgcgctcg gccgcctgcg ggctcttctg  18540
ctgcatgttc ctgcacgcct tcgtgcactg gcccgaccgc cccatggaca agaaccccac  18600
catgaacttg ctgacggggg tgcccaacgg catgctccag tcgccccagg tggaacccac  18660
cctgcgccgc aaccaggagg cgctctaccg cttcctcaac tcccactccg cctactttcg  18720
ctcccaccgc gcgcgcatcg agaaggccac cgccttcgac cgcatgaaca atcaagacat  18780
gtaaaccgtg tgtgtatgtt taaaatatct tttaataaac agcactttaa tgttacacat  18840
gcatctgaga tgattttatt ttagaaatcg aaagggttct gccgggtctc ggcatggccc  18900
gcgggcaggg acacgttgcg gaactggtac ttggccagcc acttgaactc ggggatcagc  18960
agtttgggca gcggggtgtc ggggaaggag tcggtccaca gcttccgcgt cagctgcagg  19020
gcgcccagca ggtcgggcgc ggagatcttg aaatcgcagt tgggacccgc gttctgcgcg  19080
cgagagttgc ggtacacggg gttgcagcac tggaacacca tcagggccgg gtgcttcacg  19140
ctcgccagca ccgccgcgtc ggtgatgctc tccacgtcga ggtcctcggc gttggccatc  19200
ccgaaggggg tcatcttgca ggtctgcctt cccatggtgg gcacgcaccc gggcttgtgg  19260
ttgcaatcgc agtgcagggg gatcagcatc atctgggcct ggtcggcgtt catccccggg  19320
tacatggcct tcatgaaagc ctccaattgc ctgaacgcct gctgggcctt ggctccctcg  19380
gtgaagaaga ccccgcagga cttgctagag aactggttgg tggcacagcc ggcatcgtgc  19440
acgcagcagc gcgcgtcgtt gttggccagc tgcaccacgc tgcgccccca gcggttctgg  19500
gtgatcttgg cccggtcggg gttctccttc agcgcgcgct gcccgttctc gctcgccaca  19560
tccatctcga tcatgtgctc cttctggatc atggtggtcc cgtgcaggca ccgcagtttg  19620
ccctcggcct cggtgcaccc gtgcagccac agcgcgcacc cggtgcactc ccagttcttg  19680
tgggcgatct gggaatgcgc gtgcacgaac ccttgcagga agcggcccat catggtcgtc  19740
agggtcttgt tgctagtgaa ggtcaacggg atgccgcggt gctcctcgtt gatgtacagg  19800
tggcagatgc ggcggtacac ctcgccctgc tcgggcatca gttggaagtt ggctttcagg  19860
tcggtctcca cgcggtagcg gtccatcagc atagtcatga tttccatgcc cttctcccag  19920
gccgagacga tgggcaggct catagggttc ttcaccatca tcttagcact agcagccgcg  19980
gccagggggt cgctctcatc cagggtctca aagctccgct tgccgtcctt ctcggtgatc  20040
cgcaccgggg ggtagctgaa gcccacggcc gccagctcct cctcggcctg tctttcgtcc  20100
tcgctgtcct ggctgacgtc ctgcatgacc acatgcttgg tcttgcgggg tttcttcttg  20160
ggcggcagtg gcggcggaga tgcttgtggc gaggggggagc gcgagttctc gctcaccact  20220
actatctctt cctcttcttg gtccgaggcc acgcggcggt aggtatgtct cttcgggggc  20280
agaggcggag gcgacgggct ctcgccgccg cgacttggcg gatggctggc agagcccctt  20340
ccgcgttcgg gggtgcgctc ccggcggcgc tctgactgac ttcctccgcg gccggccatt  20400
gtgttctcct agggaggaac aacaagcatg gagactcagc catcgccaac ctcgccatct  20460
gcccccaccg ccggcgacga gaagcagcag cagcagaatg aaagcttaac cgccccgccg  20520
cccagccccg cctccgacgc agccgcggtc ccagacatgc aagagatgga ggaatccatc  20580
gagattgacc tgggctatgt gacgcccgcg gagcatgagg aggagctggc agtgcgcttt  20640
caatcgtcaa gccaggaaga taaagaacag ccagagcagg aagcagagaa cgagcagagt  20700
caggctgggc tcgagcatgg cgactacctc cacctgagcg gggaggagga cgcgctcatc  20760
aagcatctgg cccggcaggc caccatcgtc aaggacgcgc tgctcgaccg caccgaggtg  20820
cccctcagcg tggaggagct cagccgcgcc tacgagctca acctcttctc gccgcgcgtg  20880
ccccccaagc gccagcccaa cggcacctgc gagcccaacc cccgcctcaa cttctacccg  20940
gtcttcgcgg tgcccgaggc cctggccacc taccacatct tttcaagaa ccaaaagatc  21000
cccgtctcct gccgcgccaa ccgcacccgc gccgacgccc tcttcaacct gggtcccggc  21060
gcccgcctac ctgatatcgc ctccttggaa gaggttccca agatcttcga gggtctgggc  21120
agcgacgaga ctcgggccgc gaacgctctg caaggagaag gaggaggaga gcatgagcac  21180
cacagcgccc tggtcgagtt ggaaggcgac aacgcgcggc tggcggtgct caaacgcacg  21240
```

-continued

```
gtcgagctga cccatttcgc ctacccggct ctgaacctgc ccccgaaagt catgagcgcg  21300
gtcatggacc aggtgctcat caagcgcgcg tcgcccatct ccgaggacga gggcatgcaa  21360
gactccgagg agggcaagcc cgtggtcagc gacgagcagc tggcccggtg gctgggtcct  21420
aatgctaccc ctcaaagttt ggaagagcgg cgcaagctca tgatggccgt ggtcctggtg  21480
accgtggagc tggagtgcct gcgccgcttc ttcgccgacg cggagaccct gcgcaaggtc  21540
gaggagaacc tgcactacct cttcaggcac gggttcgtgc gccaggcctg caagatctcc  21600
aacgtggagc tgaccaacct ggtctcctac atgggcatct tgcacgagaa ccgcctgggg  21660
cagaacgtgc tgcacaccac cctgcgcggg gaggcccgcc gcgactacat ccgcgactgc  21720
gtctacctct acctctgcca cacctggcag acgggcatgg gcgtgtggca gcagtgtctg  21780
gaggagcaga acctgaaaga gctctgcaag ctcctgcaaa agaacctcaa gggtctgtgg  21840
accgggttcg acgagcggac caccgcctcg gacctggccg acctcatctt ccccgagcgc  21900
ctcaggctga cgctgcgcaa cggcctgccc gactttatga gccaaagcat gttgcaaaac  21960
tttcgctctt tcatcctcga acgctccgga atcctgcccg ccacctgctc cgcgctgccc  22020
tcggacttcg tgccgctgac cttccgcgag tgcccccgc cgctgtggag ccactgctac  22080
ctgctgcgcc tggccaacta cctggcctac cactcggacg tgatcgagga cgtcagcggc  22140
gagggcctgc tcgagtgcca ctgccgctgc aacctctgca cgccgcaccg ctccctggcc  22200
tgcaaccccc agctgctgag cgagacccag atcatcggca ccttcgagtt gcaagggccc  22260
agcgagggcg agggagccaa ggggggtctg aaactcaccc cggggctgtg gacctcggcc  22320
tacttgcgca agttcgtgcc cgaggattac catcccttcg agatcaggtt ctacgaggac  22380
caatcccagc cgcccaaggc cgagctgtcg gcctgcgtca tcacccaggg ggcgatcctg  22440
gcccaattgc aagccatcca gaaatcccgc caagaattct tgctgaaaaa gggccgcggg  22500
gtctacctcg acccccagac cggtgaggag ctcaaccccg gcttccccca ggatgccccg  22560
aggaaacaag aagctgaaag tggagctgcc gcccgtggag gatttggagg aagactggga  22620
gaacagcagt caggcagagg agatggagga agactgggac agcactcagg cagaggagga  22680
cagcctgcaa gacagtctgg aggaagacga ggaggaggca gaggaggagg tggaagaagc  22740
agccgccgcc agaccgtcgt cctcggcggg ggagaaagca agcagcacgg ataccatctc  22800
cgctccgggt cggggtcccg ctcggcccca cagtagatgg gacgagaccg ggcgattccc  22860
gaaccccacc acccagaccg gtaagaagga gcggcaggga tacaagtcct ggcgggggca  22920
caaaaacgcc atcgtctcct gcttgcaggc ctgcgggggc aacatctcct tcacccggcg  22980
ctacctgctc ttccaccgcg gggtgaactt cccccgcaac atcttgcatt actaccgtca  23040
cctccacagc ccctactact tccaagaaga ggcagcagca gcagaaaaag accagaaaac  23100
cagctagaaa atccacagcg gcggcagcgg caggtggact gaggatcgcg gcgaacgagc  23160
cggcgcagac ccgggagctg aggaaccgga tctttcccac cctctatgcc atcttccagc  23220
agagtcgggg gcaggagcag gaactgaaag tcaagaaccg ttctctgcgc tcgctcaccc  23280
gcagttgtct gtatcacaag agcgaagacc aacttcagcg cactctcgag gacgccgagg  23340
ctctcttcaa caagtactgc gcgctcactc ttaaagagta gcccgcgccc gcccagtcgc  23400
agaaaaaggc gggaattacg tcacctgtgc ccttcgccct agccgcctcc acccagcacc  23460
gccatgagca aagagattcc cacgccttac atgtggagct accagcccca gatgggcctg  23520
gccgccggcg ccgcccagga ctactccacc cgcatgaatt ggctcagcgc cgggcccgcg  23580
atgatctcac gggtgaatga catccgcgcc caccgaaacc agatactcct agaacagtca  23640
gcgctcaccg ccacgccccg caatcacctc aatccgcgta attggcccgc cgccctggtg  23700
taccaggaaa ttccccagcc cacgaccgta ctacttccgc gagacgccca ggccgaagtc  23760
cagctgacta actcaggtgt ccagctggcg ggcggcgcca ccctgtgtcg tcaccgcccc  23820
gctcagggta taaagcggct ggtgatccgg ggcagaggca cacagctcaa cgacgaggtg  23880
gtgagctctt cgctgggtct gcgacctgac ggagtcttcc aactcgccgg atcggggaga  23940
tcttccttca cgcctcgtca ggcggtcctg actttggaga gttcgtcctc gcagccccgc  24000
tcgggcggca tcggcactct ccagttcgtg gaggagttca ctccctcggt ctacttcaac  24060
cccttctccg gctcccccgg ccactacccg gacgagttca tcccgaactt tgacgccatc  24120
agcgagtcgg tggacggcta cgattgatta attaatcaac taacccctta cccctttacc  24180
ctccagtaaa aataaagatt aaaaatgatt gaattgatca ataaagaatc acttacttga  24240
aatctgaaac caggtctctg tccatgtttt ctgtcagcag cacttcactc ccctcttccc  24300
aactctggta ctgcaggccc cggcgggctg caaacttcct ccacactctg aaggggatgt  24360
caaattcctc ctgtccctca atcttcattt ttatcttcta tcagatgtcc aaaaagcgcg  24420
cgcgggtgga tgatggcttc gaccccgtgt accccctacga tgcagacaac gcaccgactg  24480
tgcccttcat caaccctccc ttcgtctctt cagatggatt ccaagaaaag cccctggggg  24540
tgttgtccct gcgactggcc gaccccgtca ccaccaagaa tggggctgtc accctcaagc  24600
tgggggaggg ggtggacctc gacgactcgg gaaaactcat ctccaaaaat gccaccaagg  24660
ccactgcccc tctcagtatt tccaacggca ccatttccct taacatggct gccccttttt  24720
acaacaacaa tggaacgtta agtctcaatg tttctacacc attagcagta tttcccactt  24780
ttaacacttt aggtatcagt cttggaaacg gtcttcaaac ttctaataag ttgctgactg  24840
tacagttaac tcatcctctt acattcagct caaatagcat cacagtaaaa acagacaaag  24900
gactctatat taattctagt ggaaacagag ggcttgaggc taacataagc ctaaaaagag  24960
gactgatttt tgatggtaat gctattgcaa cataccttgg aagtggttta gactatggat  25020
cctatgatag cgatgggaaa acaagaccca tcatcaccaa aattggagca ggtttgaatt  25080
ttgatgctaa taatgccatg gctgtgaagc taggcacagg tttaagtttt gactctgccg  25140
gtgccttaac agctggaaac aaagaggatg acaagctaac actttggact acacctgacc  25200
caagccctaa ttgtcaatta ctttcagaca gagatgccaa atttacccta tgtcttacaa  25260
aatgcggtag tcaaatacta ggcactgttg cagtagctgc tgttactgta ggttcagcac  25320
taaatccaat taatgacaca gtaaaaagcg ccatagtatt ccttagattt gactctgacg  25380
gtgtgctcat gtcaaactca tcaatggtag gtgattactg gaactttagg gaaggacaga  25440
ccacccaaag tgtggcctat acaaatgctg tgggattcat gcccaatcta ggtgcatatc  25500
ctaaaaccca aagcaaaaca ccaaaaaata gtatagtaag tcaggtatat ttaaatggag  25560
aaactactat gccaatgaca ctgacaataa ctttcaatgg cactgatgaa aaagacacaa  25620
cacctgtgag cacttactcc atgactttta catggcagtg gactggagac tataaggaca  25680
agaatattac ctttgctacc aactccttta ctttctccta catggcccaa gaataaaccc  25740
tgcatgccaa ccccattgtt cccaccacta tggaaaactc tgaagcagaa aaaaataaag  25800
ttcaagtgtt ttattgattc aacagttttc tcacagaacc ctagtattca acctgccacc  25860
tccctcccaa cacacagagt acacagtcct ttctccccgg ctggccttaa aaagcatcat  25920
atcatgggta acagacatat tcttaggtgt tatattccac acggtttcct gtcgagccaa  25980
```

```
acgctcatca gtgatattaa taaactcccc gggcagctca cttaagttca tgtcgctgtc  26040
cagctgctga gccacaggct gctgtccaac ttgcggttgc ttaacgggcg gcgaaggaga  26100
agtccacgcc tacatggggg tagagtcata atcgtgcatc aggatagggc ggtggtgctg  26160
cagcagcgcg cgaataaact gctgccgccg ccgctccgtc ctgcaggaat acaacatggc  26220
agtggtctcc tcagcgatga ttcgcaccgc ccgcagcata aggcgccttg tcctccgggc  26280
acagcagcgc accctgatct cacttaaatc agcacagtaa ctgcagcaca gcaccacaat  26340
attgttcaaa atcccacagt gcaaggcgct gtatccaaag ctcatggcgg ggaccacaga  26400
acccacgtgg ccatcatacc acaagcgcag gtagattaag tggcgacccc tcataaacac  26460
gctggacata aacattacct cttttggcat gttgtaattc accacctccc ggtaccatat  26520
aaacctctga ttaaacatgg cgccatccac caccatccta aaccagctgg ccaaaacctg  26580
cccgccggct atacactgca gggaaccggg actggaacaa tgacagtgga gagcccagga  26640
ctcgtaacca tggatcatca tgctcgtcat gatatcaatg ttggcacaac acaggcacac  26700
gtgcatacac ttcctcagga ttacaagctc ctcccgcgtt agaaccatat cccagggaac  26760
aacccattcc tgaatcagcg taaatcccac actgcaggga agacctcgca cgtaactcac  26820
gttgtgcatt gtcaaagtgt tacattcggg cagcagcgga tgatcctcca gtatggtagc  26880
gcgggtttct gtctcaaaag gaggtagacg atccctactg tacggagtgc gccgagacaa  26940
ccgagatcgt gttggtcgta gtgtcatgcc aaatggaacg ccggacgtag tcatatttcc  27000
tgaagcaaaa ccaggtgcgg gcgtgacaaa cagatctgcg tctccggtct cgccgcttag  27060
atcgctctgt gtagtagttg tagtatatcc actctctcaa agcatccagg cgccccctgg  27120
cttcgggttc tatgtaaact ccttcatgcg ccgctgccct gataacatcc accaccgcag  27180
aataagccac acccagccaa cctacacatt cgttctgcga gtcacacacg ggaggagcgg  27240
gaagagctgg aagaaccatg attaacttta ttccaaacgg tctcggagca cttcaaaatg  27300
caggtcccgg aggtggcacc tctcgccccc actgtgttgg tggaaaataa cagccaggtc  27360
aaaggtgaca cggttctcga gatgttccac ggtggcttcc agcaaagcct ccacgcgcac  27420
atccagaaac aagaggacag cgaaagcggg agcgtttttct aattcctcaa tcatcatatt  27480
acactcctgc accatcccca gataatttc attttccag ccttgaatga ttcgtattag  27540
ttcctgaggt aaatccaagc cagccatgat aaaaagctcg cgcagagcgc cctccaccgg  27600
cattcttaag cacaccctca taattccaag agattctgct cctggttcac ctgcagcaga  27660
ttaacaatgg gaatatcaaa atctctgccg cgatccctaa gctcctccct caacaataac  27720
tgtatgtaat ctttcatatc atctccgaaa tttttagcca tagggccgcc aggaataaga  27780
gcagggcaag ccacattaca gataaagcga agtcctcccc agtgwgcatt gccaaatgta  27840
agattgaaat aagcatgctg gctagaccct gtgatatctt ccagataact ggacagaaaa  27900
tcaggcaagc aatttttaag aaaatcaaca aaagaaaagt cgtccaggtg caggtttaga  27960
gcctcaggaa caacgatgga ataagtgcaa ggagtgcgtt ccagcatggt tagtgttttt  28020
ttggtgatct gtagaacaaa aaataaacat gcaatattaa accatgctag cctggcgaac  28080
aggtgggtaa atcactcttt ccagcaccag gcaggctacg gggtctccgg cgcgaccctc  28140
gtagaagctg tcgccatgat tgaaaagcat caccgagaga ccttcccggt ggccggcatg  28200
gatgattcga gaagaagcat acactccggg aacattggca tccgtgagtg aaaaaaagcg  28260
acctataaag cctcggggca ctacaatgct caatctcaat tccagcaaag ccacccatg  28320
cggatggagc acaaaattgg caggtgcgta aaaaatgtaa ttactcccct cctgcacagg  28380
cagcaaagcc cccgctccct ccagaaacac atacaaagcc tcagcgtcca tagcttaccg  28440
agcacggcag gcgcaagagt cagagaaaag gctgagctct aacctgactg cccgctcctg  28500
tgctcaatat atagccctaa cctacactga cgtaaaggcc aaagtctaaa aatacccgcc  28560
aaaatgacac acacgcccag cacacgccca gaaaccggtg acacactcaa aaaaatacgt  28620
gcgcttcctc aaacgcccaa accggcgtca tttccgggtt cccacgctac gtcaccgctc  28680
agcgactttc aaattccgtc gaccgttaaa aacgtcactc gccccgcccc taacggtcgc  28740
ccttctctcg gccaatcacc ttcctccctt cccaaattca aacgcctcat ttgcatatta  28800
acgcgcacaa aaagtttgag gtatatattt gaatgatggt ttaaacgcgg ccgccaggcc  28860
tacccactag tcaattcggg aggatcgaaa cggcagatcg caaaaaacag tacatacaga  28920
aggagacatg aacatgaaca tcaaaaaaat tgtaaaacaa gccacagttc tgacttttac  28980
gactgcactt ctggcaggag gagcgactca agccttcgcg aaagaaaata accaaaaagc  29040
atacaaagaa acgtacggcg tctctcatat tacacgccat gatatgctgc agatccctaa  29100
acagcagcaa aacgaaaaat accaagtgcc tcaattcgat caatcaacga ttaaaaataa  29160
ttgagtctga caaaaggact tgatgtg                                     29187
```

```
SEQ ID NO: 41          moltype = DNA  length = 2661
FEATURE                Location/Qualifiers
misc_feature           1..2661
                       note = Vector
source                 1..2661
                       mol_type = other DNA
                       organism = synthetic construct
SEQUENCE: 41
ttaattaacc atcttcaata atatacctca aactttttgt gcgcgttaat atgcaaatga  60
ggcgtttgaa tttggggagg aagggcggtg attggtcgag ggatgagcga ccgttagggg  120
cggggcgagt gacgttttga tgacgtggtt gcgaggagga gccagtttgc aagttctcgt  180
gggaaaagtg acgtcaaacg aggtgtggtt tgaacacgga aatactcaat tttcccgcgc  240
tctctgacag gaaatgaggt gtttctgggc ggatgcaagt gaaaacgggc cattttcgcg  300
cgaaaactga atgaggaagt gaaaatctga gtaatttcgc gtttatggca gggaggagta  360
tttgccgagg gccgagtaga ctttgaccga ttacgtgggg gtttcgatta ccgtgttttt  420
cacctaaatt tccgcgtacg gtgtcaaagt ccggtgtttt tacgcgatcg ctagcgacat  480
cgatcacaag tttgtacaaa aaagcaggct ccaccatggg aacccgcgtt ttgagatttc  540
tgtcgccgac taaattcatg tcgcgcgata gtggtgttta tcgccgatag agatggcgat  600
attggaaaaa tcgatatttg aaaatatggc atattgaaaa tgtcgccgat gtgagtttct  660
gtgtaactga tatcgccatt tttccaaaag tgatttttgg gcatacgcga tatctggcga  720
tagcgcttat atcgtttacg gggggatggcg atagacgact ttggtgactt gggcgattct  780
gtgtgtcgca aatatcgcag tttcgatata ggtgacagac gatatgaggc tatatcgccg  840
atagaggcga catcaagctg gcacatggcc aatgcatatc gatctataca ttgaatcaat  900
attggccatt agccatatta ttcattggtt atatagcata aatcaatatt ggctattggc  960
```

```
cattgcatac gttgtatcca tatcataata tgtacattta tattggctca tgtccaacat  1020
taccgccatg ttgacattga ttattgacta gttattaata gtaatcaatt acggggtcat  1080
tagttcatag cccatatatg gagttccgcg ttacataact tacggtaaat ggcccgcctg  1140
gctgaccgcc caacgacccc cgcccattga cgtcaataat gacgtatgtt cccatagtaa  1200
cgccaatagg gactttccat tgacgtcaat gggtggagta tttacggtaa actgcccact  1260
tggcagtaca tcaagtgtat catatgccaa gtacgccccc tattgacgtc aatgacggta  1320
aatggcccgc ctggcattat gcccagtaca tgaccttatg ggactttcct acttggcagt  1380
acatctacgt attagtcatc gctattacca tggtgatgcg gttttggcag tacatcaatg  1440
ggcgtggata gcggtttgac tcacggggat ttccaagtct ccaccccatt gacgtcaatg  1500
ggagtttgtt ttggcaccaa aatcaacggg actttccaaa atgtcgtaac aactccgccc  1560
cattgacgca aatgggcggt aggcgtgtac ggtgggaggt ctatataagc agagctctcc  1620
ctatcagtga tagagatctc cctatcagtg atagagatcg tcgacgagct cgtttagtga  1680
accgtcagat cgcctggaga cgccatccac gctgttttga cctccataga agacaccggg  1740
accgatccag cctccgcggc cgggaacggt gcattggaac gcggattccc cgtgccaaga  1800
gtgacgtaag taccgcctat agagtctata ggcccacccc cttggcttct tatgcatgct  1860
atactgtttt tggcttgggg tctatacacc cccgcttcct catgttatag gtgatggtat  1920
agcttagcct ataggtgtgg gttattgacc attattgacc actcccctat tggtgacgat  1980
actttccatt actaatccat aacatggctc tttgccacaa ctctctttat tggctatatg  2040
ccaatacact gtccttcaga gactgacacg gactctgtat ttttacagga tggggtctca  2100
tttattattt acaaattcac atatacaaca ccaccgtccc cagtgcccgc agtttttatt  2160
aaacataacg tgggatctcc acgcgaatct cgggtacgtg ttccggacat gggctcttct  2220
ccggtagcgg cggagcttct acatccgagc cctgctccca tgcctccagc gactcatggt  2280
cgctcggcag ctccttgctc ctaacagtgg aggccagact taggcacagc acgatgccca  2340
ccaccaccag tgtgccgcac aaggccgtgg cggtagggta tgtgtctgaa aatgagctcg  2400
gggagcgggc ttgcaccgct gacgcatttg gaagacttaa ggcagcggca gaagaagatg  2460
caggcagctg agttgttgtg ttctgataag agtcagaggt aactcccgtt gcggtgctgt  2520
taacggtgga gggcagtgta gtctgagcag tactcgttgc tgccgcgcgc gccaccagac  2580
ataatagctg acagactaac agactgttcc tttccatggg tcttttctgc agtcaccgtc  2640
cttgacacga agcttggtac c                                            2661
```

```
SEQ ID NO: 42          moltype = DNA  length = 37490
FEATURE                Location/Qualifiers
misc_feature           1..37490
                       note = Vector
source                 1..37490
                       mol_type = other DNA
                       organism = synthetic construct
SEQUENCE: 42
gcggccgctc gagcatgcat ctagagggcc ctattctata gtgtcaccta aatgctagag  60
ctcgctgatc agcctcgact gtgccttcta gttgccagcc atctgttgtt tgcccctccc  120
ccgtgccttc cttgaccctg gaaggtgcca ctcccactgt cctttcctaa taaaatgagg  180
aaattgcatc gcattgtctg agtaggtgtc attctattct ggggggtggg gtggggcagg  240
acagcaaggg ggaggattgg gaagacaata gcaggcatgc tggggatgcg gtgggctcta  300
tggcttctga ggcggaaaga accagctggg gctcgagggg ggatcgatcc cgtcgagata  360
tctagaccca gctttcttgt acaaagtggt gatcgattcg acagatcgcg atcgcaagtg  420
agtagtgttc tggggcgggg gaggacctgc atgagggcca gaataactga aatctgtgct  480
tttctgtgtg ttgcagcagc atgagcggaa gcggctcctt tgagggaggg gtattcagcc  540
cttatctgac ggggcgtctc ccctcctggg cgggagtgcg tcagaatgtg atgggatcca  600
cggtggacgg ccggcccgtg cagcccgcga actcttcaac cctgacctat gcaaccctga  660
gctcttcgtc gttggacgca gctgccgccg cagctgctgc atctgccgcc agcgccgtgc  720
gcggaatggc catgggcgcc ggctactacg gcactctggt ggccaactcg agttccacca  780
ataatcccgc cagcctgaac gaggagaagc tgttgctgct gatggcccag ctcgaggcct  840
tgacccagcg cctgggcgag ctgacccagc aggtggctca gctgcaggag cagacgcggg  900
ccgcggttgc cacggtgaaa tccaaataaa aaatgaatca ataaataaac ggagacggtt  960
gttgatttta acacagagtc tgaatcttta tttgattttt cgcgcgcggt aggccctgga  1020
ccaccggtct cgatcattga gcacccggtg gatcttttcc aggacccggt agaggtgggc  1080
ttggatgttg aggtacatgg gcatgagccc gtcccggggg tggaggtagc tccattgcag  1140
ggcctcgtgc tcgggggtgg tgttgtaaat cacccagtca tagcaggggc gcagggcatg  1200
gtgttgcaca atatctttga ggaggagact gatggccacg ggcagccctt tggtgtaggt  1260
gtttacaaat ctgttgagct gggagggatg catgcggggg gagatgaggt gcatcttggc  1320
ctggatcttg agattggcga tgttaccgcc cagatcccgc ctggggttca tgttgtgcag  1380
gaccaccagc acggtgtatc cggtgcactt ggggaattta tcatgcaact tggaagggaa  1440
ggcgtgaaag aatttggcga cgcctttgtg cccgcccagg ttttccatgc actcatccat  1500
gatgatggcg atgggcccgt gggcggcggc ctgggcaaag acgtttcggg ggtcggacac  1560
atcatagttg tggtcctggg tgaggtcatc ataggccatt ttaatgaatt tggggcggag  1620
ggtgccggac tgggggacaa aggtaccctc gatcccgggg gcgtagttcc cctcacagat  1680
ctgcatctcc caggctttga gctcggaggg ggggatcatg tccacctgcg gggcgataaa  1740
gaacacggtt tccggggcgg gggagatgag ctgggccgaa agcaagttcc ggagcagctg  1800
ggacttgccg cagccggtgg ggccgtagat gaccccgatg accggctgca ggtggtagtt  1860
gagggagaga cagctgccgt cctcccggag gaggggggcc acctcgttca tcatctcgcg  1920
cacgtgcatg ttctcgcgca ccagttccgc caggaggcgc tctcccccca gggataggag  1980
ctcctggagc gaggcgaagt ttttcagcgg cttgagtccg tcggccatgg gcattttgga  2040
gagggtttgt tgcaagagtt ccaggcggtc ccagagctcg gtgatgtgct ctacggcatc  2100
tcgatccagc agacctcctc gtttcgcggg ttgggacggc tgcgggagta gggcaccaga  2160
cgatgggcgt ccagcgcagc cagggtccgg tccttccagg gtcgcagcgt ccgcgtcagg  2220
gtggtctccg tcacggtgaa ggggtgcgcg ccgggctggg cgcttgcgag ggtgcgcttc  2280
aggctcatcc ggctggtcga aaaccgctcc cgatcggcgc cctgcgcgtc ggccaggtag  2340
caattgacca tgagttcgta gttgagcgcc tcggccgcgt ggcctttggc gcggagctta  2400
cctttggaag tctgcccgca ggcgggacag aggagggact tgagggcgta gagcttgggg  2460
```

-continued gcgaggaaga cggactcggg ggcgtaggcg tccgcgccgc agtgggcgca gacggtctcg 2520
cactccacga gccaggtgag gtcgggctgg tcggggtcaa aaaccagttt cccgccgttc 2580
tttttgatgc gtttcttacc tttggtctcc atgagctcgt gtccccgctg ggtgacaaag 2640
aggctgtccg tgtccccgta gaccgacttt atgggccggt cctcgagcgg tgtgccgcgg 2700
tcctcctcgt agaggaaccc cgcccactcc gagacgaaag cccgggtcca ggccagcacg 2760
aaggaggcca cgtgggacgg gtagcggtcg ttgtccacca gcgggtccac cttttccagg 2820
gtatgcaaac acatgtcccc ctcgtccaca tccaggaagg tgattggctt gtaagtgtag 2880
gccacgtgac cgggggtccc ggccgggggg gtataaaagg gtgcgggtcc ctgctcgtcc 2940
tcactgtctt ccggatcgct gtccaggagc gccagctgtt ggggtaggta ttccctctcg 3000
aaggcgggca tgacctcggc actcaggttg tcagtttcta gaaacgagga ggatttgata 3060
ttgacggtgc cggcggagat gcctttcaag agcccctcgt ccatctggtc agaaaagacg 3120
atctttttgt tgtcgagctt ggtggcgaag gagccgtaga gggcgttgga gaggagcttg 3180
gcgatggagc gcatggtctg gttttttttcc ttgtcggcgc gctccttggc ggcgatgttg 3240
agctgcacgt actcgcgcgc cacgcacttc cattcgggga agacggtggt cagctcgtcg 3300
ggcacgattc tgacctgcca gccccgatta tgcagggtga tgaggtccac actggtggcc 3360
acctcgccgc gcaggggctc attagtccag cagaggcgtc cgcccttgcg cgagcagaag 3420
gggggcaggg ggtccagcat gacctcgtcg ggggggtcgg catcgatggt gaagatgccg 3480
ggcaggaggt cggggtcaaa gtagctgatg gaagtggcca gatcgtccag ggcagcttgc 3540
cattcgcgca cggccagcgc gcgctcgtag ggactgaggg gcgtgcccca gggcatggga 3600
tgggtaagcg cggaggcgta catgccgcag atgtcgtaga cgtagagggg ctcctcgagg 3660
atgccgatgt aggtggggta gcagcgcccc ccgcggatgc tggcgcgcac gtagtcatac 3720
agctcgtgcg agggggcgag gagccccggg cccaggttgg tgcgactggg cttttcggcg 3780
cggtagacga tctggcggaa aatggcatgc gagttggagg agatggtggg cctttggaag 3840
atgttgaagt gggcgtgggg cagtccgacc gagtcgcgga tgaagtgggc gtaggagtct 3900
tgcagcttgg cgacgagctc ggcggtgact aggacgtcca gagcgcagta gtcgagggtc 3960
tcctggatga tgtcatactt gagctgtccc ttttgtttcc acagctcgcg gttgagaagg 4020
aactcttcgc ggtccttcca gtactcttcg agggggaacc cgtcctgatc tgcacggtaa 4080
gagcctagca tgtagaactg gttgacggcc ttgtaggcgc agcagccctt ctccacgggg 4140
agggcgtagg cctgggcggc cttgcgcagg gaggtgtgcg tgagggcgaa agtgtccctg 4200
accatgacct tgaggaactg gtgcttgaag tcgatatcgt cgcagccccc ctgctcccag 4260
agctggaagt ccgtgcgctt cttgtaggcg gggttgggca aagcgaaagt aacatcgttg 4320
aagaggatct tgcccgcgcg gggcataaag ttgcgagtga tgcggaaagg ttggggcacc 4380
tcggcccggt tgttgatgac ctgggcggcg agcacgatct cgtcgaagcc gttgatgttg 4440
tggcccacga tgtagagttc cacgaatcgc ggacggccct tgacgtgggg cagtttcttg 4500
agctcctcgt aggtgagctc gtcggggtcg ctgagcccgt gctgctcgag cgcccagtcg 4560
gcgagatggg ggttggcgcg gaggaaggaa gtccagagat ccacggccag ggcggtttgc 4620
agacggtccc ggtactgacg gaactgctgc ccgacggcca ttttttcggg ggtgacgcag 4680
tagaaggtgc gggggtcccc gtgccagcga tcccatttga gctggagggc gagatcgagg 4740
gcgagctcga cgagccggtc gtccccggag agtttcatga ccagcatgaa ggggacgagc 4800
tgcttgccga aggaccccat ccaggtgtag gtttccacat cgtaggtgag gaagagcctt 4860
tcggtgcgag gatgcgagcc gatggggaag aactggatct cctgccacca attggaggaa 4920
tggctgttga tgtgatggaa gtagaaatgc cgacggcgcg ccgaacactc gtgcttgtgt 4980
ttatacaagc ggccacagtg ctcgcaacgc tgcacgggat gcacgtgctg cacgagctgt 5040
acctgagttc ctttgacgag gaatttcagt gggaagtgga gtcgtggcgc ctgcatctcg 5100
tgctgtacta cgtcgtggtg gtcggcctgg ccctcttctg cctcgatggt ggtcatgctg 5160
acgagcccgc gcgggaggca ggtccagacc tcggcgcgag cgggtcggag agcgaggacg 5220
agggcgcgca ggccggagct gtccagggtc ctgagacgct gcggagtcag gtcagtgggc 5280
agcggcggcg cgcggttgac ttgcaggagt ttttccaggg cgcgcgggag gtccagatgg 5340
tacttgatct ccaccgcgcc attggtggcg acgtcgatgg cttgcagggt cccgtgcccc 5400
tggggtgtga ccaccgtccc ccgtttcttc ttgggcggct ggggcgacgg gggcggtgcc 5460
tcttccatgg ttagaagcgg cggcgaggac gcgcgccggg cggcaggggc ggctcggggc 5520
ccggaggcag gggcggcagg ggcacgtcgg cgccgcgcgc gggtaggttc tggtactgcg 5580
cccggagaag actggcgtga gcgacgacgc gacggttgac gtcctggatc tgacgcctct 5640
gggtgaaggc cacgggaccc gtgagtttga acctgaaaga gagttcgaca gaatcaatct 5700
cggtatcgtt gacggcggcc tgccgcagga tctcttgcac gtcgcccgag ttgtcctggt 5760
aggcgatctc ggtcatgaac tgctcgatct cctcctcttg aaggtctccg cggccggcgc 5820
gctccacggt ggccgcgagg tcgttggaga tgcggcccat gagctgcgag aaggcgttca 5880
tgcccgcctc gttccagacg cggctgtaga ccacgacgcc ctcgggatcg ccggcgcgca 5940
tgaccacctg ggcgaggttg agctccacgt ggcgcgtgaa gaccgcgtag ttgcagaggc 6000
gctggtagag gtagttgagc gtggtggcga tgtgctcggt gacgaagaaa tacatgatcc 6060
agcggcggag cggcatctcg ctgacgtcgc ccagcgcctc caaacgttcc atggcctcgt 6120
aaaagtccac ggcgaagttg aaaaactggg agttgcgcgc cgagacggtc aactcctcct 6180
ccagaagacg gatgagctcg gcgatggtgg cgcgcacctc gcgctcgaag gcccccggga 6240
gttcctccac ttcctcttct tcctcctcca ctaacatctc ttctacttcc tcctcaggcg 6300
gcagtggtgg cgggggaggg ggcctgcgtc gccggcggcg cacgggcaga cggtcgatga 6360
agcgctcgat ggtctcgccg cgccggcgtc gcatggtctc ggtgacggcg cgcccgtcct 6420
cgcggggccg cagcgtgaag acgccgccgc gcatctccag gtggccgggg gggtccccgt 6480
tgggcaggga gagggcgctg acgatgcatc ttatcaattg ccccgtaggg actccgcgca 6540
aggacctgag cgtctcgaga tccacgggat ctgaaaaccg ctgaacgaag gcttcgagcc 6600
agtcgcagtc gcaaggtagg ctgagcacgg tttcttctgg cgggtcatgt tggttgggag 6660
cggggcgggc gatgctgctg gtgatgaagt tgaaataggc ggttctgaga cggcggatgg 6720
tggcgaggag caccaggtct ttgggcccgg cttgctggat gcgcagacgg tcggccatgc 6780
cccaggcgtg gtcctgacac ctggccaggt ccttgtagta gtcctgcatg agccgctcca 6840
cgggcacctc ctcctcgccc gcgcggccgt gcatgcgcgt gagcccgaag ccgcgctggg 6900
gctggacgag cgccaggtcg gcgacgacgc gctcggcgag gatggcttgc tggatctggg 6960
tgagggtggt ctggaagtca tcaaagtcga cgaagcggtg gtaggctccg gtgttgatgg 7020
tgtaggagca gttggccatg acggaccagt tgacggtctg gtggcccgga cgcacgagct 7080
cgtggtactt gaggcgcgag taggcgcgcg tgtcgaagat gtagtcgttg caggtgcgca 7140
ccaggtactg gtagccgatg aggaagtgcg gcggcggctg gcggtagagc ggccatcgct 7200

```
cggtggcggg ggcgccgggc gcgaggtcct cgagcatggt gcggtggtag ccgtagatgt  7260
acctggacat ccaggtgatg ccggcggcgg tggtggaggc gcgcgggaac tcgcggacgc  7320
ggttccagat gttgcgcagc ggcaggaagt agttcatggt gggcacggtc tggcccgtga  7380
ggcgcgcgca gtcgtggatg ctctatacgg gcaaaaacga aagcggtcag cggctcgact  7440
ccgtggcctg gaggctaagc gaacgggttg ggctgcgcgt gtaccccggt tcgaatctcg  7500
aatcaggctg gagccgcagc taacgtggta ttggcactcc cgtctcgacc caagcctgca  7560
ccaaccctcc aggatacgga ggcgggtcgt tttgcaactt ttttttggag gccggatgag  7620
actagtaagc gcggaaagcg gccgaccgcg atggctcgct gccgtagtct ggagaagaat  7680
cgccagggtt gcgttgcggt gtgccccggt tcgaggccgg ccggattccg cggctaacga  7740
gggcgtggct gccccgtcgt ttccaagacc ccatagccag ccgacttctc cagttacgga  7800
gcgagcccct cttttgtttt gtttgttttt gccagatgca tcccgtactg cggcagatgc  7860
gcccccacca ccctccaccg caacaacagc cccctccaca gccggcgctt ctgccccogc  7920
cccagcagca acttccagcc acgaccgccg cggccgccgt gagcggggct ggacagagtt  7980
atgatcacca gctggccttg gaagagggcg aggggctggc gcgcctgggg gcgtcgtcgc  8040
cggagcggca cccgcgcgtg cagatgaaaa gggacgctcg cgaggcctac gtgcccaagc  8100
agaacctgtt cagagacagg agcggcgagg agcccgagga gatgcgcgcg gcccggttcc  8160
acgcggggcg ggagctgcgg cgcggcctgg accgaaagag ggtgctgagg gacgaggatt  8220
tcgaggcgga cgagctgacg gggatcagcc ccgcgcgcgc gcacgtggcc gcggccaacc  8280
tggtcacggc gtacgagcag accgtgaagg aggagagcaa cttccaaaaa tccttcaaca  8340
accacgtgcg caccctgatc gcgcgcgagg aggtgaccct gggcctgatg cacctgtggg  8400
acctgctgga ggccatcgtg cagaacccca ccagcaagcc gctgacggcg cagctgttcc  8460
tggtggtgca gcatagtcgg gacaacgaag cgttcaggga ggcgctgctg aatatcaccg  8520
agcccgaggg ccgctggctc ctggacctgg tgaacattct gcagagcatc gtggtgcagg  8580
agcgcgggct gccgctgtcc gagaagctgg cggccatcaa cttctcggtg ctgagtttgg  8640
gcaagtacta cgctaggaag atctacaaga ccccgtacgt gcccatagac aaggaggtga  8700
agatcgacgg gttttacatg cgcatgaccc tgaaagtgct gaccctgagc gacgatctgg  8760
gggtgtaccg caacgacagg atgcaccgtg cggtgagcgc cagcaggcgg cgcgagctga  8820
gcgaccagga gctgatgcat agtctgcagc gggccctgac cggggccggg accgaggggg  8880
agagctactt tgacatgggc gcggacctgc actggcagcc cagccgccgg gccttggagg  8940
cggcggcagg accctacgta gaagaggtgg acgatgaggt ggacgaggag ggcgagtacc  9000
tggaagactg atggcgcgac cgtatttttg ctagatgcaa caacaacagc cacctcctga  9060
tcccgcgatg cgggcggcgc tgcagagcca gccgtccggc attaactcct cggacgattg  9120
gacccaggcc atgcaacgca tcatggcgct gacgacccgc aaccccgaag cctttagaca  9180
gcagccccag gccaaccggc tctcggccat cctggaggcc gtggtgccct cgcgctccaa  9240
ccccacgcac gagaaggtcc tggccatcgt gaacgcgctg gtggagaaca aggccatccg  9300
cggcgacgag gccggcctgg tgtacaacgc gctgctggag cgcgtggccc gctacaacag  9360
caccaacgtg cagaccaacc tggaccgcat ggtgaccgac gtgcgcgagg ccgtggccca  9420
gcgcgagcgg ttccaccgcg agtccaacct gggatccatg gtggcgctga acgccttcct  9480
cagcacccag cccgccaacg tgccccgggg ccaggaggac tacaccaact tcatcagcgc  9540
cctgcgcctg atggtgaccg aggtgcccca gagcgaggtg taccagtccg ggccggacta  9600
cttcttccag accagtcgcc agggcttgca gaccgtgaac ctgagccagg ctttcaagaa  9660
cttgcagggc ctgtggggcg tgcaggcccc ggtcggggac cgcgcgacgg tgtcgagcct  9720
gctgacgccg aactcgcgcc tgctgctgct gctggtggcc cccttcacgg acagcggcag  9780
catcaaccgc aactcgtacc tgggctacct gattaacctg taccgcgagg ccatcggcca  9840
ggcgcacgtg gacgagcaga cctaccagga gatcacccac gtgagccgcg ccctgggcca  9900
ggacgacccg ggcaacctgg aagccaccct gaacttttg ctgaccaacc ggtcgcagaa  9960
gatcccgccc cagtacgcgc tcagcaccga ggaggagcgc atcctgcgtt acgtgcagca  10020
gagcgtgggc ctgttcctga tgcaggaggg ggccaccccc agcgccgcgc tcgacatgac  10080
cgcgcgcaac atggagccca gcatgtacgc cagcaaccgc ccgttcatca ataaactgat  10140
ggactacttg catcgggcgg ccgccatgaa ctctgactat ttcaccaacg ccatcctgaa  10200
tccccactgg ctcccgccgc cggggttcta cacgggcgag tacgacatgc ccgaccccaa  10260
tgacgggttc ctgtgggacg atgtggacag cagcgtgttc tccccccgac cgggtgctaa  10320
cgagcgcccc ttgtggaaga aggaaggcag cgaccgacgc ccgtcctcgg cgctgtccgg  10380
ccgcgagggt gctgccgcgg cggtgcccga ggccgccagt cctttcccga gcttgccctt  10440
ctcgctgaac agtatccgca gcagcgagct gggcaggatc acgcgcccgc gcttgctggg  10500
cgaagaggag tacttgaatg actcgctgtt gagacccgag cgggagaaga acttccccaa  10560
taacgggata gaaagcctgg tggacaagat gagccgctgg aagacgtatg cgcaggagca  10620
cagggacgat ccccgggcgt cgcagggggc cacgagccgg ggcagcgccg cccgtaaacg  10680
ccggtggcac gacaggcagc ggggacagat gtgggacgat gaggactccg ccgacgacag  10740
cagcgtgttg gacttgggtg ggagtggtaa cccgttcgct cacctgcgcc cccgtatcgg  10800
gcgcatgatg taagagaaac cgaaaataaa tgatactcac caaggccatg gcgaccagcg  10860
tgcgttcgtt tcttctctgt tgttgttgta tctagtatga tgaggcgtgc gtacccggag  10920
ggtcctcctc cctcgtacga gagcgtgatg cagcaggcga tggcggcggc ggcgatgcag  10980
cccccgctgg aggctcctta cgtgccccccg cggtacctgg cgcctacgga ggggcggaac  11040
agcattcgtt actcggagct ggcacccttg tacgatacca cccggttgta cctggtggac  11100
aacaagtcgg cggacatcgc ctcgctgaac taccagaacg accacagcaa cttcctgacc  11160
accgtggtgc agaacaatga cttcaccccc acggaggcca gcacccagac catcaacttt  11220
gacgagcgct cgcggtgggg cggccagctg aaaaccatca tgcacaccaa catgcccaac  11280
gtgaacgagt tcatgtacag caacaagttc aaggcgcggg tgatggtctc ccgcaagacc  11340
cccaatgggg tgacagtgac agaggattat gatggtagtc aggatgagct gaagtatgaa  11400
tgggtggaat ttgagctgcc cgaaggcaac ttctcggtga ccatgaccat cgacctgatg  11460
aacaacgcca tcatcgacaa ttacttggcg gtggggcggc agaacggggt gctggagagc  11520
gacatcggcg tgaagttcga cactaggaac ttcaggctgg gctgggaccc cgtgaccgag  11580
ctggtcatgc ccggggtgta caccaacgag gctttccatc ccgatattgt cttgctgccc  11640
ggctgcgggg tggacttcac cgagagccgc ctcagcaacc tgctgggcat tcgcaagagg  11700
cagcccttcc aggaaggctt ccagatcatg tacgaggatc tggagggggg caacatcccc  11760
gcgctcctgg atgtcgacgc ctatgagaaa agcaaggagg atgcagcagc tgaagcaact  11820
gcagccgtag ctaccgcctc taccgaggtc aggggcgata attttgcaag cgccgcagca  11880
gtggcagcgg ccgaggcggc tgaaaccgaa agtaagatag tcattcagcc ggtggagaag  11940
```

-continued

```
gatagcaaga acaggagcta caacgtacta ccggacaaga taaacaccgc ctaccgcagc  12000
tggtacctag cctacaacta tggcgacccc gagaagggcg tgcgctcctg gacgctgctc  12060
accacctcgg acgtcacctg cggcgtggag caagtctact ggtcgctgcc cgacatgatg  12120
caagacccgg tcaccttccg ctccacgcgt caagttagca actacccggt ggtgggcgcc  12180
gagctcctgc ccgtctactc caagagcttc ttcaacgagc aggccgtcta ctcgcagcag  12240
ctgcgcgcct tcacctcgct tacgcacgtc ttcaaccgct tccccgagaa ccagatcctc  12300
gtccgcccgc ccgcgcccac cattaccacc gtcagtgaaa acgttcctgc tctcacagat  12360
cacgggaccc tgccgctgcg cagcagtatc cggggagtcc agcgcgtgac cgttactgac  12420
gccagacgcc gcacctgccc ctacgtctac aaggccctgg gcatagtcgc gccgcgcgtc  12480
ctctcgagcc gcaccttcta aatgtccatt ctcatctcgc ccagtaataa caccggttgg  12540
ggcctgcgcg cgcccagcaa gatgtacgga ggcgctcgcc aacgctccac gcaacacccc  12600
gtgcgcgtgc gcgggcactt ccgcgctccc tggggcgccc tcaagggccg cgtgcggtcg  12660
cgcaccaccg tcgacgacgt gatcgaccag gtggtggccg acgcgcgcaa ctacaccccc  12720
gccgccgcgc ccgtctccac cgtggacgcc gtcatcgaca gcgtggtggc ggacgcgcgc  12780
cggtacgccc gcgccaagag ccggcggcgg cgcatcgccc ggcggcaccg gagcacccccc  12840
gccatgcgcg cggcgcgagc cttgctgcgc agggccaggc gcacgggacg cagggccatg  12900
ctcagggcgg ccagacgcgc ggcttcaggc gccagcgccg gcaggacccg gagacgcgcg  12960
gccacggcgg cggcagcggc catcgccagc atgtcccgcc cgcggcgagg gaacgtgtac  13020
tgggtgcgcg acgccgccac cggtgtgcgc gtgcccgtgc gcacccgccc ccctcgcact  13080
tgaagatgtt cacttcgcga tgttgatgtg tcccagcggc gaggaggatg tccaagcgca  13140
aattcaagga agagatgctc caggtcatcg cgcctgagat ctacggccct gcggtggtga  13200
aggaggaaag aaagccccgc aaaatcaagc gggtcaaaaa ggacaaaaag gaagaagaaa  13260
gtgatgtgga cggattggtg gagtttgtgc gcgagttcgc cccccggcgg cgcgtgcagt  13320
ggcgcgggcg gaaggtgcaa ccggtgctga gacccggcac caccgtggtc ttcacgcccg  13380
gcgagcgctc cggcaccgct tccaagcgct cctacgacga ggtgtacggg gatgatgata  13440
ttctggagca ggcggccgag cgcctgggcg agtttgctta cggcaagcgc agccgttccg  13500
caccgaagga agaggcggtg tccatcccgc tggaccacgg caaccccacg ccgagcctca  13560
agcccgtgac cttgcagcag gtgctgccga ccgcggcgcc gcgccggggg ttcaagcgcg  13620
agggcgagga tctgtacccc accatgcagc tgatggtgcc caagcgccag aagctggaag  13680
acgtgctgga gaccatgaag gtggacccgg acgtgcagcc cgaggtcaag gtgcggccca  13740
tcaagcaggt ggccccgggc ctgggcgtgc agaccgtgga catcaagatt cccacggagc  13800
ccatggaaac gcagaccgag cccatgatca agcccagcac cagcaccatg gaggtgcaga  13860
cggatccctg gatgccatcg gctcctagtc gaagaccccg gcgcaagtac ggcgcggcca  13920
gcctgctgat gcccaactac gcgctgcatc cttccatcat ccccacgccg ggctaccgcg  13980
gcacgcgctt ctaccgcggt cataccagca gccgccgccg caagaccacc actcgccgcc  14040
gccgtcgccg caccgccgct gcaaccaccc ctgccgccct ggtgcggaga gtgtaccgcc  14100
gcggccgcgc acctctgacc ctgccgcgcg cgcgctacca cccgagcatc gccatttaaa  14160
ctttcgccag ctttgcagat caatggccct cacatgccgc cttcgcgttc ccattacggg  14220
ctaccgagga agaaaaccgc gccgtagaag gctggcgggg aacgggatgc gtcgccacca  14280
ccaccggcgg cggcgcgcca tcagcaagcg gttgggggga ggcttcctgc ccgcgctgat  14340
ccccatcatc gccgcggcga tcggggcgat ccccggcatt gcttccgtgg cggtgcaggc  14400
ctctcagcgc cactgagaca cacttggaaa catcttgtaa taaacccatg gactctgacg  14460
ctcctggtcc tgtgatgtgt tttcgtagac agatggaaga catcaatttt tcgtccctgg  14520
ctccgcgaca cggcacgcgg ccgttcatgg gcacctggag cgacatcggc accagccaac  14580
tgaacggggg cgccttcaat tggagcagtc tctggagcgg gcttaagaat ttcgggtcca  14640
cgcttaaaac ctatggcagc aaggcgtgga acagcaccac agggcaggcg ctgagggata  14700
agctgaaaga gcagaacttc cagcagaagg tggtcgatgg gctcgcctcg ggcatcaacg  14760
gggtggtgga cctggccaac caggccgtgc agcggcagat caacagccgc ctggacccgg  14820
tgccgcccgc cggctccgtg gagatgccgc aggtggagga ggagctgcct cccctggaca  14880
agcggggcga gaagcgaccc cgccccgatg cggaggagac gctgctgacg cacacggacg  14940
agccgccccc gtacgaggag gcggtgaaac tgggtctgcc caccacgcgg cccatcgcgc  15000
ccctggccac cggggtgctg aaacccgaaa agcccgcgac cctggacttg cctcctcccc  15060
agccttcccg cccctctaca gtggctaagc ccctgccgcc ggtggccgtg gcccgcgcgc  15120
gacccggggg caccgcccgc cctcatgcga actggcagag cactctgaac agcatcgtgg  15180
gtctgggagt gcagagtgtg aagcgccgcc gctgctatta aacctaccgt agcgcttaac  15240
ttgcttgtct gtgtgtgtat gtattatgtc gccgccgccg ctgtccacca gaaggaggag  15300
tgaagaggcg cgtcgccgag ttgcaagatg gccaccccat cgatgctgcc ccagtgggcg  15360
tacatgcaca tcgccggaca ggacgcttcg gagtacctga gtccgggtct ggtgcagttt  15420
gcccgcgcca cagacaccta cttcagtctg gggaacaagt ttaggaaccc cacggtggcg  15480
cccacgcacg atgtgaccac cgaccgcagc cagcggctga cgctgcgctt cgtgcccgtg  15540
gaccgcgagg acaacaccta ctcgtacaaa gtgcgctaca cgctggccgt gggcgacaac  15600
cgcgtgctgg acatggccag cacctacttt gacatccgcg gcgtgctgga tcggggccct  15660
agcttcaaac cctactccgg caccgcctac aacagtctgg cccccaaggg agcacccaac  15720
acttgtcagt ggacatataa agccgatggt gaaactgcca cagaaaaaac ctatacatat  15780
ggaaatgcac ccgtgcaggg cattaacatc acaaaagatg gtattcaact tggaactgac  15840
accgatgatc agccaatcta cgcagataaa acctatcagc ctgaacctca agtgggtgat  15900
gctgaatggc atgacatcac tggtactgat gaaaagtatg gaggcagagc tcttaagcct  15960
gataccaaaa tgaagccttg ttatggttct tttgccaagc ctactaataa agaaggaggt  16020
caggcaaatg tgaaaacagg aacaggcact actaaagaat atgacataga catggctttc  16080
tttgacaaca gaagtgcggc tgctgctggc ctagctccag aaattgtttt gtatactgaa  16140
aatgtggatt tggaaactcc agatacccat attgtataca aagcaggcac agatgacagc  16200
agctcttcta ttaatttggg tcagcaagcc atgcccaaca gacctaacta cattggtttc  16260
agagacaact ttatcgggct catgtactac aacagcactg gcaatatggg ggtgctggcc  16320
ggtcaggctt ctcagctgaa tgctgtggtt gacttgcaag acagaaacac cgagctgtcc  16380
taccagctct tgcttgactc tctgggtgac agaacccggt atttcagtat gtggaatcag  16440
gcggtggaca gctatgatcc tgatgtgcgc attattgaaa atcatggtgt ggaggatgaa  16500
cttcccaact attgtttccc tctggatgct gttggcagaa cagatactta tcagggaatt  16560
aaggctaatg gaactgatca aaccacatgg accaaagatg acagtgtcaa tgatgctaat  16620
gagataggca agggtaatcc attcgccatg gaaatcaaca tccaagccaa cctgtggagg  16680
```

-continued aacttcctct acgccaacgt ggccctgtac ctgcccgact cttacaagta cacgccggcc 16740
aatgttaccc tgcccaccaa caccaacacc tacgattaca tgaacggccg ggtggtggcg 16800
ccctcgctgg tggactccta catcaacatc ggggcgcgct ggtcgctgga tcccatggac 16860
aacgtgaacc ccttcaacca ccaccgcaat gcggggctgc gctaccgctc catgctcctg 16920
ggcaacgggc gctacgtgcc cttccacatc caggtgcccc agaaattttt cgccatcaag 16980
agcctcctgc tcctgcccgg gtcctacacc tacgagtgga acttccgcaa ggacgtcaac 17040
atgatcctgc agagctccct cggcaacgac ctgcgcacgg acggggcctc catctccttc 17100
accagcatca acctctacgc caccttcttc cccatggcgc acaacacggc ctccacgctc 17160
gaggccatgc tgcgcaacga caccaacgac cagtccttca acgactacct ctcggcggcc 17220
aacatgctct accccatccc ggccaacgcc accaacgtgc ccatctccat cccctcgcgc 17280
aactgggccg ccttccgcgg ctggtccttc acgcgtctca agaccaagga gacgccctcg 17340
ctgggctccg ggttcgaccc ctacttcgtc tactcgggct ccatccccta cctcgacggc 17400
accttctacc tcaaccacac cttcaagaag gtctccatca ccttcgactc ctccgtcagc 17460
tggcccggca acgaccggct cctgacgccc aacgagttcg aaatcaagcg caccgtcgac 17520
ggcgagggct acaacgtggc ccagtgcaac atgaccaagg actggttcct ggtccagatg 17580
ctggcccact acaacatcgg ctaccagggc ttctacgtgc ccgagggcta caaggaccgc 17640
atgtactcct tcttccgcaa cttccagccc atgagccgcc aggtggtgga cgaggtcaac 17700
tacaaggact accaggccgt caccctggcc taccagcaca acaactcggg cttcgtcggc 17760
tacctcgcgc ccaccatgcg ccagggccag ccctaccccg ccaactaccc ctacccgctc 17820
atcggcaaga gcgccgtcac cagcgtcacc cagaaaaagt tcctctgcga cagggtcatg 17880
tggcgcatcc ccttctccag caacttcatg tccatgggcg cgctcaccga cctcggccag 17940
aacatgctct atgccaactc cgcccacgcg ctagacatga atttcgaagt cgaccccatg 18000
gatgagtcca cccttctcta tgttgtcttc gaagtcttcg acgtcgtccg agtgcaccag 18060
ccccaccgcg gcgtcatcga ggccgtctac ctgcgcaccc ccttctcggc cggtaacgcc 18120
accacctaag ctcttgcttc ttgcaagcca tggccgcggg ctccggcgag caggagctca 18180
gggccatcat ccgcgacctg ggctgcgggc cctacttcct gggcaccttc gataagcgct 18240
tcccgggatt catggccccg cacaagctgg cctgcgccat cgtcaacacg gccggccgcg 18300
agaccggggg cgagcactgg ctggccttcg cctggaaccc gcgctcgaac acctgctacc 18360
tcttcgaccc cttcgggttc tcggacgagc gcctcaagca gatctaccag ttcgagtacg 18420
agggcctgct gcgccgcagc gccctggcca ccgaggaccg ctgcgtcacc ctggaaaagt 18480
ccacccagac cgtgcagggt ccgcgctcgg ccgcctgcgg gctcttctgc tgcatgttcc 18540
tgcacgcctt cgtgcactgg cccgaccgcc ccatggacaa gaaccccacc atgaacttgc 18600
tgacgggggt gcccaacggc atgctccagt cgccccaggt ggaacccacc ctgcgccgca 18660
accaggaggc gctctaccgc ttcctcaact cccactccgc ctactttcgc tcccaccgcg 18720
cgcgcatcga gaaggccacc gccttcgacc gcatgaatca agacatgtaa accgtgtgtg 18780
tatgttaaat gtctttaata aacagcactt tcatgttaca catgcatctg agatgattta 18840
tttagaaatc gaaagggttc tgccgggtct cggcatggcc cgcgggcagg gacacgttgc 18900
ggaactggta cttggccagc cacttgaact cggggatcag cagtttgggc agcggggtgt 18960
cggggaagga gtcggtccac agcttccgcg tcagttgcag ggcgcccagc aggtcgggcg 19020
cggagatctt gaaatcgcag ttgggacccg cgttctgcgc gcgggagttg cggtacacgg 19080
ggttgcagca ctggaacacc atcagggccg ggtgcttcac gctcgccagc accgtcgcgt 19140
cggtgatgct ctccacgtcg aggtcctcgg cgttggccat cccgaagggg gtcatcttgc 19200
aggtctgcct tcccatggtg ggcacgcacc cgggcttgtg gttgcaatcg cagtgcaggg 19260
ggatcagcat catctgggcc tggtcggcgt tcatccccgg gtacatggcc ttcatgaaag 19320
cctccaattg cctgaacgcc tgctgggcct tggctccctc ggtgaagaag accccgcagg 19380
acttgctaga gaactggttg gtggcgcacc cggcgtcgtg cacgcagcag cgcgcgtcgt 19440
tgttggccag ctgcaccacg ctgcgccccc agcggttctg ggtgatcttg gcccggtcgg 19500
ggttctcctt cagcgcgcgc tgcccgttct cgctcgccac atccatctcg atcatgtgct 19560
ccttctggat catggtggtc ccgtgcaggc accgcagctt gccctcggcc tcggtgcacc 19620
cgtgcagcca cagcgcgcac ccggtgcact cccagttctt gtgggcgatc tgggaatgcg 19680
cgtgcacgaa gccctgcagg aagcggccca tcatggtggt cagggtcttg ttgctagtga 19740
aggtcagcgg aatgccgcgg tgctcctcgt tgatgtacag gtggcagatg cggcggtaca 19800
cctcgccctg ctcgggcatc agctggaagt tggctttcag gtcggtctcc acgcggtagc 19860
ggtccatcag catagtcatg atttccatac ccttctccca ggccgagacg atgggcaggc 19920
tcatagggtt cttcaccatc atcttagcgc tagcagccgc ggccaggggg tcgctctcgt 19980
ccagggtctc aaagctccgc ttgccgtcct tctcggtgat ccgcaccggg gggtagctga 20040
agcccacggc cgccagctcc tcctcggcct gtctttcgtc ctcgctgtcc tggctgacgt 20100
cctgcaggac cacatgcttg gtcttgcggg gtttcttctt gggcggcagc ggcggcggag 20160
atgttggaga tggcgagggg gagcgcgagt tctcgctcac cactactatc tcttcctctt 20220
cttggtccga ggccacgcgg cggtaggtat gtctcttcgg gggcagaggc ggaggcgacg 20280
ggctctcgcc gccgcgactt ggcggatggc tggcagagcc ccttccgcgt tcgggggtgc 20340
gctcccggcg gcgctctgac tgacttcctc cgcggccggc cattgtgttc tcctagggag 20400
gaacaacaag catggagact cagccatcgc caacctcgcc atctgccccc accgccgacg 20460
agaagcagca gcagcagaat gaaagcttaa ccgccccgcc gcccagcccc gccacctccg 20520
acgcggccgt cccagacatg caagagatgg aggaatccat cgagattgac ctgggctatg 20580
tgacgcccgc ggagcacgag gaggagctgg cagtgcgctt ttcacaagaa gagatacacc 20640
aagaacagcc agagcaggaa gcagagaatg agcagagtca ggctgggctc gagcatgacg 20700
gcgactacct ccacctgagc ggggggggagg acgcgctcat caagcatctg gcccggcagg 20760
ccaccatcgt caaggatgcg ctgctcgacc gcaccgaggt gcccctcagc gtggaggagc 20820
tcagccgcgc ctacgagttg aacctcttct cgccgcgcgt gccccccaag cgccagccca 20880
atggcacctg cgagcccaac ccgcgcctca acttctaccc ggtcttcgcg gtgcccgagg 20940
ccctggccac ctaccacatc tttttcaaga accaaaagat ccccgtctcc tgccgcgcca 21000
accgcacccg cgccgacgcc cttttcaacc tgggtcccgg cgcccgccta cctgatatcg 21060
cctccttgga agaggttccc aagatcttcg agggtctggg cagcgacgag actcgggccg 21120
cgaacgctct gcaaggagaa ggaggagagc atgagcacca cagcgccctg gtcgagttgg 21180
aaggcgacaa cgcgcggctg gcggtgctca aacgcacggt cgagctgacc catttcgcct 21240
acccggctct gaacctgccc cccaaagtca tgagcgcggt catggaccag gtgctcatca 21300
agcgcgcgtc gcccatctcc gaggacgagg gcatgcaaga ctccgaggag ggcaagcccg 21360
tggtcagcga cgagcagctg gcccggtggc tgggtcctaa tgctagtccc cagagtttgg 21420

-continued

```
aagagcggcg caaactcatg atggccgtgg tcctggtgac cgtggagctg gagtgcctgc  21480
gccgcttctt cgccgacgcg gagaccctgc gcaaggtcga ggagaacctg cactacctct  21540
tcaggcacgg gttcgtgcgc caggcctgca agatctccaa cgtggagctg accaacctgg  21600
tctcctacat gggcatcttg cacgagaacc gcctggggca gaacgtgctg cacaccaccc  21660
tgcgcgggga ggcccggcgc gactacatcc gcgactgcgt ctacctctac ctctgccaca  21720
cctggcagac gggcatgggc gtgtggcagc agtgtctgga ggagcagaac ctgaaagagc  21780
tctgcaagct cctgcagaag aacctcaagg gtctgtggac cgggttcgac gagcgcacca  21840
ccgcctcgga cctggccgac ctcattttcc ccgagcgcct caggctgacg ctgcgcaacg  21900
gcctgcccga ctttatgagc caaagcatgt tgcaaaactt tcgctctttc atcctcgaac  21960
gctccggaat cctgcccgcc acctgctccg cgctgccctc ggacttcgtg ccgctgacct  22020
tccgcgagtg cccccgccg ctgtggagcc actgctacct gctgcgcctg gccaactacc  22080
tggcctacca ctcggacgtg atcgaggacg tcagcggcga gggcctgctc gagtgccact  22140
gccgctgcaa cctctgcacg ccgcaccgct ccctggcctg caacccccag ctgctgagcg  22200
agacccagat catcggcacc ttcgagttgc aagggcccag cgaaggcgag ggttcagccg  22260
ccaagggggg tctgaaactc accccggggc tgtggacctc ggcctacttg cgcaagttcg  22320
tgcccgagga ctaccatccc ttcgagatca ggttctacga ggaccaatcc catccgccca  22380
aggccgagct gtcggcctgc gtcatcaccc agggggcgat cctggcccaa ttgcaagcca  22440
tccagaaatc ccgccaagaa ttcttgctga aaaagggccg cggggtctac ctcgaccccc  22500
agaccggtga ggagctcaac ccgggcttcc cccaggatgc cccgaggaaa caagaagctg  22560
aaagtggagc tgccgccccgt ggaggatttg gaggaagact gggagaacag cagtcaggca  22620
gaggaggagg agatggagga agactgggac agcactcagg cagaggagga cagcctgcaa  22680
gacagtctgg aggaagacga ggaggaggca gaggaggagg tggaagaagc agccgccgcc  22740
agaccgtcgt cctcggcggg ggagaaagca agcagcacgg ataccatctc cgctccgggt  22800
cggggtcccg ctcgaccaca cagtagatgg gacgagaccg gacgattccc gaaccccacc  22860
acccagaccg gtaagaagga gcggcaggga tacaagtcct ggcgggggca caaaaacgcc  22920
atcgtctcct gcttgcaggc ctgcgggggc aacatctcct tcacccggcg ctacctgctc  22980
ttccaccgcg gggtgaactt tccccgcaac atcttgcatt actaccgtca cctccacagc  23040
ccctactact tccaagaaga ggcagcagca gcagaaaaag accagcagaa aaccagcagc  23100
tagaaaatcc acagcggcgg cagcaggtgg actgaggatc gcggcgaacg agccggcgca  23160
aacccgggag ctgaggaacc ggatctttcc caccctctat gccatcttcc agcagagtcg  23220
ggggcaggag caggaactga aagtcaagaa ccgttctctg cgctcgctca cccgcagttg  23280
tctgtatcac aagagcgaag accaacttca gcgcactctc gaggacgccg aggctctctt  23340
caacaagtac tgcgcgctca ctcttaaaga gtagcccgcg cccgcccagt cgcagaaaaa  23400
ggcgggaatt acgtcacctg tgcccttcgc cctagccgcc tccacccatc atcatgagca  23460
aagagattcc cacgccttac atgtggagct accagcccca gatgggcctg gccgccggtg  23520
ccgcccagga ctactccacc cgcatgaatt ggctcagcgc cgggcccgcg atgatctcac  23580
gggtgaatga catccgcgcc caccgaaacc agatactcct agaacagtca gcgctcaccg  23640
ccacgccccg caatcacctc aatccgcgta attggcccgc cgccctggtg taccaggaaa  23700
ttccccagcc cacgaccgta ctacttccgc gagacgccca ggccgaagtc cagctgacta  23760
actcaggtgt ccagctggcg ggcggcgcca ccctgtgtcg tcaccgcccc gctcagggta  23820
taaagcggct ggtgatccgg ggcagaggca cacagctcaa cgacgaggtg gtgagctctt  23880
cgctgggtct gcgacctgac ggagtcttcc aactcgccgg atcggggaga tcttccttca  23940
cgcctcgtca ggccgtcctg actttggaga gttcgtcctc gcagccccgc tcgggtggca  24000
tcggcactct ccagttcgtg gaggagttca ctccctcggt ctacttcaac cccttctccg  24060
gctcccccgg ccactacccg gacgagttca tcccgaactt cgacgccatc agcgagtcgg  24120
tggacggcta cgattgagtt taaactcacc cccttatcca gtgaaataaa gatcatattg  24180
atgatgattt tacagaaata aaaaataatc atttgatttg aaataaagat acaatcatat  24240
tgatgatttg agtttaacaa aaaaataaag aatcacttac ttgaaatctg ataccaggtc  24300
tctgtccatg ttttctgcca acaccacttc actcccctct tcccagctct ggtactgcag  24360
gccccggcgg gctgcaaact tcctccacac gctgaagggg atgtcaaatt cctcctgtcc  24420
ctcaatcttc attttatctt ctatcagatg tccaaaaagc gcgtccgggt ggatgatgac  24480
ttcgaccccg tctacccta cgatgcagac aacgcaccga ccgtgccctt catcaacccc  24540
cccttcgtct cttcagatgg attccaagag aagcccctgg gggtgttgtc cctgcgactg  24600
gccgaccccg tcaccaccaa gaacggggaa atcaccctca agctgggaga gggggtggac  24660
ctcgattcct cgggaaaact catctccaac acggccacca aggccgccgc ccctctcagt  24720
ttttccaaca acaccatttc ccttaacatg gatcacccct tttacactaa agatggaaaa  24780
ttatccttac aagtttctcc accattaaat atactgagaa caagcattct aaacacacta  24840
gctttaggtt ttggatcagg tttaggactc cgtggctctg ccttggcagt acagttagtc  24900
tctccactta catttgatac tgatggaaac ataaagctta ccttagacag aggtttgcat  24960
gttacaacag gagatgcaat tgaaagcaac ataagctggg ctaaaggttt aaaatttgaa  25020
gatggagcca tagcaaccaa cattggaaat gggttagagt ttggaagcag tagtacagaa  25080
acaggtgttg atgatgctta cccaatccaa gttaaacttg gatctggcct tagctttgac  25140
agtacaggag ccataatggc tggtaacaaa gaagacgata aactcacttt gtggacaaca  25200
cctgatccat caccaaactg tcaaatactc gcagaaaatg atgcaaaact aacactttgc  25260
ttgactaaat gtggtagtca aatactggcc actgtgtcag tcttagttgt aggaagtgga  25320
aacctaaacc ccattactgg caccgtaagc agtgctcagg tgtttctacg ttttgatgca  25380
aacggtgttc ttttaacaga acattctaca ctaaaaaaat actgggggta taggcaggga  25440
gatagcatag atggcactcc atataccaat gctgtaggat tcatgcccaa tttaaaagct  25500
tatccaaagt cacaaagttc tactactaaa aataatatag tagggcaagt atacatgaat  25560
ggagatgttt caaaacctat gcttctcact ataaccctca atggtactga tgacagcaac  25620
agtacatatt caatgtcatt ttcatacacc tggactaatg gaagctatgt tggagcaaca  25680
tttggggcta actcttatac cttctcatac atcgcccaag aatgaacact gtatcccacc  25740
ctgcatgcca acccttccca ccccactctg tggaacaaac tctgaaacac aaaataaaat  25800
aaagttcaag tgttttattg attcaacagt ttcacagaac cctagtattc aacctgccac  25860
ctccctccca acacacagag tacacagtcc tttctccccg gctggcctta aaaagcatca  25920
tatcatgggt aacagacata ttcttaggtg ttatattcca cacggtttcc tgtcgagcca  25980
aacgctcatc agtgatatta ataaactccc cgggcagctc acttaagttc atgtcgctgt  26040
ccagctgctg agccacaggc tgctgtccaa cttgcggttg cttaacgggc ggcgaaggag  26100
aagtccacgc ctacatgggg gtagagtcat aatcgtgcat caggataggg cggtggtgct  26160
```

```
gcagcagcgc gcgaataaac tgctgccgcc gccgctccgt cctgcaggaa tacaacatgg  26220
cagtggtctc ctcagcgatg attcgcaccg cccgcagcat aaggcgcctt gtcctccggg  26280
cacagcagcg caccctgatc tcacttaaat cagcacagta actgcagcac agcaccacaa  26340
tattgttcaa aatcccacag tgcaaggcgc tgtatccaaa gctcatggcg gggaccacag  26400
aacccacgtg gccatcatac cacaagcgca ggtagattaa gtggcgaccc ctcataaaca  26460
cgctggacat aaacattacc tcttttggca tgttgtaatt caccacctcc cggtaccata  26520
taaacctctg attaaacatg gcgccatcca ccaccatcct aaaccagctg gccaaaacct  26580
gcccgccggc tatacactgc agggaaccgg gactggaaca atgacagtgg agagcccagg  26640
actcgtaacc atggatcatc atgctcgtca tgatatcaat gttggcacaa cacaggcaca  26700
cgtgcataca cttcctcagg attacaagct cctcccgcgt tagaaccata tcccagggaa  26760
caacccattc ctgaatcagc gtaaatccca cactgcaggg aagacctcgc acgtaactca  26820
cgttgtgcat tgtcaaagtg ttacattcgg gcagcagcgg atgatcctcc agtatggtag  26880
cgcgggtttc tgtctcaaaa ggaggtagac gatccctact gtacggagtg cgccgagaca  26940
accgagatcg tgttggtcgt agtgtcatgc caaatggaac gccggacgta gtcatatttc  27000
ctgaagcaaa accaggtgcg ggcgtgacaa acagatctgc gtctccggtc tcgccgctta  27060
gatcgctctg tgtagtagtt gtagtatatc cactctctca aagcatccag gcgccccctg  27120
gcttcgggtt ctatgtaaac tccttcatgc gccgctgccc tgataacatc caccaccgca  27180
gaataagcca cacccagcca acctacacat tcgttctgcg agtcacacac gggaggagcg  27240
ggaagagctg gaagaaccat gattaacttt attccaaacg gtctcggagc acttcaaaat  27300
gcaggtcccg gaggtggcac ctctcgcccc cactgtgttg gtggaaaata acagccaggt  27360
caaaggtgac acggttctcg agatgttcca cggtggcttc cagcaaagcc tccacgcgca  27420
catccagaaa caagaggaca gcgaaagcgg gagcgtttc taattcctca atcatcatat  27480
tacactcctg caccatcccc agataatttt catttttcca gccttgaatg attcgtatta  27540
gttcctgagg taaatccaag ccagccatga taaaaagctc gcgcagagcg ccctccaccg  27600
gcattcttaa gcacaccctc ataattccaa gagattctgc tcctggttca cctgcagcag  27660
attaacaatg ggaatatcaa aatctctgcc gcgatcccta agctcctccc tcaacaataa  27720
ctgtatgtaa tctttcatat catctccgaa atttttagcc atagggccgc caggaataag  27780
agcagggcaa gccacattac agataaagcg aagtcctccc cagtgwgcat tgccaaatgt  27840
aagattgaaa taagcatgct ggctagaccc tgtgatatct tccagataac tggacagaaa  27900
atcaggcaag caatttttaa gaaaatcaac aaaagaaaag tcgtccaggt gcaggtttag  27960
agcctcagga acaacgatgg aataagtgca aggagtgcgt tccagcatgg ttagtgtttt  28020
tttggtgatc tgtagaacaa aaaataaaca tgcaatatta aaccatgcta gcctggcgaa  28080
caggtgggta aatcactctt tccagcacca ggcaggctac ggggtctccg gcgcgaccct  28140
cgtagaagct gtcgccatga ttgaaaagca tcaccgagag accttcccgg tggccggcat  28200
ggatgattcg agaagaagca tacactccgg gaacattggc atccgtgagt gaaaaaaagc  28260
gacctataaa gcctcggggc actacaatgc tcaatctcaa ttccagcaaa gccaccccat  28320
gcggatggag cacaaaattg gcaggtgcgt aaaaaatgta attactcccc tcctgcacag  28380
gcagcaaagc ccccgctccc tccagaaaca catacaaagc ctcagcgtcc atagcttacc  28440
gagcacggca ggcgcaagag tcagagaaaa ggctgagctc taacctgact gcccgctcct  28500
gtgctcaata tatagcccta acctacactg acgtaaaggc caaagtctaa aaatacccgc  28560
caaataatca cacacgccca gcacacgccc agaaaccggt gacacactca aaaaaatacg  28620
cgcacttcct caaacgccca aaactgccgt catttccggg ttcccacgct acgtcatcaa  28680
aacacgactt tcaaattccg tcgaccgtta aaaacgtcac ccgcccgcc cctaacggtc  28740
gcccgtctct cagccaatca gcgccccgca tccccaaatt caaacacctc atttgcatat  28800
taacgcgcac aaaaagtttg aggtatatta ttgatgatgg ttaattaagg atccttctat  28860
agtgtcacct aaatgtcgac ggccaggcgg ccgccaggcc tacccactag tcaattcggg  28920
aggatcgaaa cggcagatcg caaaaaacag tacatacaga aggagacatg aacatgaaca  28980
tcaaaaaaat tgtaaaacaa gccacagttc tgacttttac gactgcactt ctggcaggag  29040
gagcgactca agccttcgcg aaagaaaata accaaaaagc atacaaagaa acgtacggcg  29100
tctctcatat tacacgccat gatatgctgc agatccctaa acagcagcaa aacgaaaaat  29160
accaagtgcc tcaattcgat caatcaacga ttaaaaatat tgagtctgca aaaggacttg  29220
atgtgtggga cagctggccg ctgcaaaacg ctgacggaac agtagctgaa tacaacggct  29280
atcacgttgt gtttgctctt gcgggaagcc cgaaagacgc tgatgacaca tcaatctaca  29340
tgttttatca aaaggtcggc gacaactcaa tcgacagctg gaaaaacgcg ggccgtgtct  29400
ttaaagacag cgataagttc gacgccaacg atccgatcct gaaagatcag acgcaagaat  29460
ggtccggttc tgcaaccttt acatctgacg gaaaaatccg tttattctac actgactatt  29520
ccggtaaaca ttacggcaaa caaagcctga caacagcgca ggtaaatgtg tcaaaatctg  29580
atgacacact caaaatcaac ggagtggaag atcacaaaac gatttttgac ggagacggaa  29640
aaacatatca gaacgttcag cagtttatcg atgaaggcaa ttatacatcc ggcgacaacc  29700
atacgctgag agaccctcac tacgttgaag acaaaggcca taaataccttt gtattcgaag  29760
ccaacacggg aacagaaaac ggataccaag gcgaagaatc tttatttaac aaagcgtact  29820
acggcggcgg cacgaacttc ttccgtaaag aaagccagaa gcttcagcag agcgctaaaa  29880
aacgcgatgc tgagttagcg aacggcgccc tcggtatcat agagttaaat aatgattaca  29940
cattgaaaaa agtaatgaag ccgctgatca cttcaaacac ggtaactgat gaaatcgagc  30000
gcgcgaatgt tttcaaaatg aacggcaaat ggtacttgtt cactgattca cgcggttcaa  30060
aaatgacgat cgatggtatt aactcaaacg atatttacat gcttggttat gtatcaaact  30120
ctttaaccgg cccttacaag ccgctgaaca aaacagggct tgtgctgcaa atgggtcttg  30180
atccaaacga tgtgacattc acttactctc acttcgcagt gccgcaagcc aaaggcaaca  30240
atgtggttat cacaagctac atgacaaaca gaggcttctt cgaggataaa aaggcaacat  30300
ttgcgccaag cttcttaatg aacatcaaag gcaataaaac atccgttgtc aaaaacagca  30360
tcctggagca aggacagctg acagtcaact aataacagca aaaagaaaat gccgatactt  30420
cattggcatt ttcttttatt tctcaacaag atggtgaatt gactagtggg tagatccaca  30480
ggacgggtgt ggtcgccatg atcgcgtagt cgatagtggc tccaagtagc gaagcgagca  30540
ggactgggcg gcggccaaag cggtcggaca gtgctccgag aacgggtgcg catagaaatt  30600
gcatcaacgc atatagcgct agcagcacgc catagtgact ggcgatgctg tcggaatgga  30660
cgatatcccg caagaggccc ggcagtaccg gcataaccaa gcctatgcct acagcatcca  30720
gggtgacggt gccgaggatg acgatgagcg cattgttaga tttcatacac ggtgcctgac  30780
tgcgttagca atttaactgt gataaactac cgcattaaag cttatcgatg ataagctgtc  30840
aaacatgaga attgatccgg aacccttaat ataacttcgt ataatgtatg ctatacgaag  30900
```

-continued

```
ttattaggtc cctcgactat agggtcaccg tcgacagcga cacacttgca tcggatgcag  30960
cccggttaac gtgccggcac ggcctgggta accaggtatt ttgtccacat aaccgtgcgc  31020
aaaatgttgt ggataagcag gacacagcag caatccacag caggcataca accgcacacc  31080
gaggttactc cgttctacag gttacgacga catgtcaata cttgcccttg acaggcattg  31140
atggaatcgt agtctcacgc tgatagtctg atcgacaata caagtgggac cgtggtccca  31200
gaccgataat cagaccgaca acacgagtgg gatcgtggtc ccagactaat aatcagaccg  31260
acgatacgag tgggaccgtg gtcccagact aataatcaga ccgacgatac gagtgggacc  31320
gtggttccag actaataatc agaccgacga tacgagtggg accgtggtcc cagactaata  31380
atcagaccga cgatacgagt gggaccatgg tcccagacta ataatcagac cgacgatacg  31440
agtgggaccg tggtcccagt ctgattatca gaccgacgat acgagtggga ccgtggtccc  31500
agactaataa tcagaccgac gatacgagtg ggaccgtggt cccagactaa taatcagacc  31560
gacgatacga gtgggaccgt ggtcccagtc tgattatcag accgacgata caagtggaac  31620
agtgggccca gagagaatat tcaggccagt tatgctttct ggcctgtaac aaaggacatt  31680
aagtaaagac agataaacgt agactaaaac gtggtcgcat cagggtgctg gcttttcaag  31740
ttccttaaga atggcctcaa ttttctctat acactcagtt ggaacacgag acctgtccag  31800
gttaagcacc attttatcgc ccttatacaa tactgtcgct ccaggagcaa actgatgtcg  31860
tgagcttaaa ctagttcttg atgcagatga cgttttaagc acagaagtta aaagagtgat  31920
aacttcttca gcttcaaata tcaccccagc ttttttctgc tcatgaaggt tagatgcctg  31980
ctgcttaagt aattcctctt tatctgtaaa ggctttttga agtgcatcac ctgaccgggc  32040
agatagttca ccggggtgag aaaaaagagc aacaactgat ttaggcaatt tggcggtgtt  32100
gatacagcgg gtaataatct tacgtgaaat attttccgca tcagccagcg cagaaatatt  32160
tccagcaaat tcattctgca atcggcttgc ataacgctga ccacgttcat aagcacttgt  32220
tgggcgataa tcgttaccca atctggataa tgcagccatc tgctcatcat ccagctcgcc  32280
aaccagaaca cgataatcac tttcggtaag tgcagcagct ttacgacggc gactcccatc  32340
ggcaatttct atgacaccag atactcttcg accgaacgcc ggtgtctgtt gaccagtcag  32400
tagaaaagaa gggatgagat catccagtgc gtcctcagta agcagctcct ggtcacgttc  32460
attacctgac catacccgag aggtcttctc aacactatca ccccggagca cttcaagagt  32520
aaacttcaca tcccgaccac atacaggcaa agtaatggca ttaccgcgag ccattactcc  32580
tacgcgcgca attaacgaat ccaccatcgg ggcagctggt gtcgataacg aagtatcttc  32640
aaccggttga gtattgagcg tatgttttgg aataacaggc gcacgcttca ttatctaatc  32700
tcccagcgtg gtttaatcag acgatcgaaa atttcattgc agacaggttc ccaaatagaa  32760
agagcatttc tccaggcacc agttgaagag cgttgatcaa tggcctgttc aaaaacagtt  32820
ctcatccgga tctgaccttt accaacttca tccgtttcac gtacaacatt ttttagaacc  32880
atgcttcccc aggcatcccg aatttgctcc tccatccacg gggactgaga gccattacta  32940
ttgctgtatt tggtaagcaa aatacgtaca tcaggctcga accctttaag atcaacgttc  33000
ttgagcagat cacgaagcat atcgaaaaac tgcagtgcgg aggtgtagtc aaacaactca  33060
gcaggcgtgg gaacaatcag cacatcagca gcacatacga cattaatcgt gccgataccc  33120
aggttaggcg cgctgtcaat aactatgaca tcatagtcat gagcaacagt ttcaatggcc  33180
agtcggagca tcaggtgtgg atcggtgggc agtttacctt catcaaattt gcccattaac  33240
tcagtttcaa tacggtgcag agccagacag gaaggaataa tgtcaagccc cggccagcaa  33300
gtgggcttta ttgcataagt gacatcgtcc ttttccccaa gatagaaagg caggagagtg  33360
tcttctgcat gaatatgaag atctggtacc catccgtgat acattgaggc tgttccctgg  33420
gggtcgttac cttccacgag caaaacacgt agccccttca gagccagatc ctgagcaaga  33480
tgaacagaaa ctgaggtttt gtaaacgcca cctttatggg cagcaacccc gatcaccggt  33540
ggaaatacgt cttcagcacg tcgcaatcgc gtaccaaaca catcacgcat atgattaatt  33600
tgttcaattg tataaccaac acgttgctca acccgtcctc gaatttccat atccgggtgc  33660
ggtagtcgcc ctgctttctc ggcatctctg atagcctgag aagaaacccc aactaaatcc  33720
gctgcttcac ctattctcca gcgccgggtt attttcctcg cttccgggct gtcatcatta  33780
aactgtgcaa tggcgatagc cttcgtcatt tcatgaccag cgtttatgca ctggttaagt  33840
gtttccatga gtttcattct gaacatcctt taatcattgc tttgcgtttt tttattaaat  33900
cttgcaattt actgcaaagc aacaacaaaa tcgcaaagtc atcaaaaaac cgcaaagttg  33960
tttaaaataa gagcaacact acaaaaggag ataagaagag cacatacctc agtcacttat  34020
tatcactagc gctcgccgca gccgtgtaac cgagcatagc gagcgaactg gcgaggaagc  34080
aaagaagaac tgttctgtca gatagctctt acgctcagcg caagaagaaa tatccaccgt  34140
gggaaaaact ccaggtagag gtacacacgc ggatagccaa ttcagagtaa taaactgtga  34200
taatcaaccc tcatcaatga tgacgaacta acccccgata tcaggtcaca tgacgaaggg  34260
aaagagaagg aaatcaactg tgacaaactg ccctcaaatt tggcttcctt aaaaattaca  34320
gttcaaaaag tatgagaaaa tccatgcagg ctgaaggaaa cagcaaaact gtgacaaatt  34380
accctcagta ggtcagaaca aatgtgacga accaccctca aatctgtgac agataaccct  34440
cagactatcc tgtcgtcatg gaagtgatat cgcggaagga aaatacgata tgagtcgtct  34500
ggcggccttt ctttttctca atgtatgaga ggcgcattgg agttctgctg ttgatctcat  34560
taacacagac ctgcaggaag cggcggcgga agtcaggcat acgctggtaa ctttgaggca  34620
gctggtaacg ctctatgatc cagtcgattt tcagagagac gatgcctgag ccatccggct  34680
tacgatactg acacagggat tcgtataaac gcatggcata cggattggtg atttcttttg  34740
tttcactaag ccgaaactgc gtaaaccggt tctgtaaccc gataaagaag ggaatgagat  34800
atgggttgat atgtacactg taaagccctc tggatggact gtgcgcacgt ttgataaacc  34860
aaggaaaaga ttcatagcct ttttcatcgc cggcatcctc ttcagggcga taaaaaacca  34920
cttccttccc cgcgaaactc ttcaatgcct gccgtatatc cttactggct tccgcagagg  34980
tcaatccgaa tatttcagca tatttagcaa catggatctc gcagataccg tcatgttcct  35040
gtagggtgcc atcagatttt ctgatctggt caacgaacag atacagcata cgtttttgat  35100
cccgggagag actatatgcc gcctcagtga ggtcgtttga ctggacgatt cgcgggctat  35160
ttttacgttt cttgtgattg ataaccgctg tttccgccat gacagatcca tgtgaagtgt  35220
gacaagtttt tagattgtca cactaaataa aaaagagtca ataagcaggg ataactttgt  35280
gaaaaaacag cttcttctga gggcaatttg tcacagggtt aagggcaatt tgtcacagac  35340
aggactgtca tttgagggtg atttgtcaca ctgaaagggc aatttgtcac aacaccttct  35400
ctagaaccag catggataaa ggcctacaag gcgctctaaa aaagaagatc taaaaactat  35460
aaaaaaaata attataaaaa tatccccgtg gataagtgga taaccccaag ggaagttttt  35520
tcaggcatcg tgtgtaagca gaatatataa gtgctgttcc ctggtgcttc ctcgctcact  35580
cgagggcttc gccctgtcgc tcaactgcgg cgagcactac tggctgtaaa aggacagacc  35640
```

```
acatcatggt tctgtgttca ttaggttgtt ctgtccattg ctgacataat ccgctccact  35700
tcaacgtaac accgcacgaa gatttctatt gttcctgaag gcatattcaa atcgttttcg  35760
ttaccgcttg caggcatcat gacagaacac tacttcctat aaacgctaca caggctcctg  35820
agattaataa tgcggatctc tacgataatg ggagattttc ccgactgttt cgttcgcttc  35880
tcagtggata acagccagct tctctgttta acagacaaaa acagcatatc cactcagttc  35940
cacatttcca tataaaggcc aaggcattta ttctcaggat aattgtttca gcatcgcaac  36000
cgcatcagac tccggcatcg caaactgcac ccggtgccgg gcagccacat ccagcgcaaa  36060
aaccttcgtg tagacttccg ttgaactgat ggacttatgt cccatcaggc tttgcagaac  36120
tttcagcggt ataccggcat acagcatgtg catcgcatag gaatggcgga acgtatgtgg  36180
tgtgaccgga acagagaacg tcacaccgtc agcagcagcg gcggcaaccg cctccccaat  36240
ccaggtcctg accgttctgt ccgtcacttc ccagatccgc gctttctctg tccttcctgt  36300
gcgacggtta cgccgctcca tgagcttatc gcgaataaat acctgtgacg gaagatcact  36360
tcgcagaata aataaatcct ggtgtccctg ttgataccgg gaagccctgg gccaactttt  36420
ggcgaaaatg agacgttgat cggcacgtaa gaggttccaa ctttcaccat aatgaaataa  36480
gatcactacc gggcgtattt tttgagttat cgagattttc aggagctaag gaagctaaaa  36540
tggagaaaaa aatcactgga tataccaccg ttgatatatc ccaatggcat cgtaaagaac  36600
attttgaggc atttcagtca gttgctcaat gtacctataa ccagaccgtt cagctggata  36660
ttacggcctt tttaaagacc gtaaagaaaa ataagcacaa gttttatccg gcctttattc  36720
acattcttgc ccgcctgatg aatgctcatc cggagttccg tatggcaatg aaagacggtg  36780
agctggtgat atgggatagt gttcaccctt gttacaccgt tttccatgag caaactgaaa  36840
cgttttcatc gctctggagt gaataccacg acgatttccg gcagtttcta cacatatatt  36900
cgcaagatgt ggcgtgttac ggtgaaaacc tggcctattt ccctaaaggg tttattgaga  36960
atatgttttt cgtctcagcc aatccctggg tgagtttcac cagttttgat ttaaacgtgg  37020
ccaatatgga caacttcttc gcccccgttt tcaccatggg caaatattat acgcaaggcg  37080
acaaggtgct gatgccgctg gcgattcagg ttcatcatgc cgtttgtgat ggcttccatg  37140
tcggcagaat gcttaatgaa ttacaacagt actgcgatga gtggcagggc ggggcgtaat  37200
tttttaagg cagttattgg tgcccttaaa cgcctggttg ctacgcctga ataagtgata  37260
ataagcggat gaatggcaga aattcgatga taagctgtca aacatgagaa ttggtcgacg  37320
gcgcgccaaa gcttgcatgc ctgcagccgc gtaacctggc aaaatcggtt acggttgagt  37380
aataaatgga tgccctgcgt aagcggggca catttcatta cctctttctc cgcacccgac  37440
atagataata acttcgtata gtatacatta tacgaagtta tctagtagac             37490
```

```
SEQ ID NO: 43          moltype = AA  length = 24
FEATURE                Location/Qualifiers
source                 1..24
                       mol_type = protein
                       organism = Foot-and-mouth disease virus
SEQUENCE: 43
APVKQTLNFD LLKLAGDVES NPGP                                          24
```

```
SEQ ID NO: 44          moltype = DNA  length = 143055
FEATURE                Location/Qualifiers
misc_feature           1..143055
                       note = Vector
source                 1..143055
                       mol_type = other DNA
                       organism = synthetic construct
SEQUENCE: 44
tatttattta gtgtctagaa aaaaatgtgt gaccaacgac cgtaggaaac tctagagggt  60
aagaaaaatc aatcgcttta tagagaccat cagaaagagg tttaatattt ttgtgagacc  120
atcgaaggag aaagagataa aactttttta cgactccatc agaaagaggt ttaatatttt  180
tgtgagacca tcgaagagag aaagagataa aactttttta cgactccatc agaaagaggt  240
ttaatatttt tgtgagacca tcgaagagag aaagagataa aactttttta cgactccatc  300
agaaagaggt ttaatatttt tgtgagacca tcgaaggaga aagagataaa actttttac  360
gactccatca gaaagaggtt taatattttt gtgagaccat cgaaggagaa agagataaaa  420
ctttttacg actccatcag aaagaggttt aatatttttg tgagaccatc gaaggagaaa  480
gagataaaac tttttacga ctccatcaga aagaggttta atatttttgt gagaccatcg  540
aagagagaaa gagataaaac tttttacga ctccatcaga aagaggttta atatttttgt  600
gagaccatcg aaggagaaag agataaaact tttttacgac tccatcagaa agaggtttaa  660
tatttttgtg agaccatcga agagagaaag agaataaaaa tattttagtg acaccatcag  720
aaagaggttt aatatttttg tgagaccatc gaagagagaa agagataaaa cttttttacg  780
actccatcag aaagaggttt aatatttttg tgagaccatc gaaggagaaa gagataaaac  840
tttttacga ctccatcaga aagaggttta atatttttgt gagaccatcg aagagagaaa  900
gagataaaac tttttacga ctccatcaga aagaggttta atatttttgt gagaccatcg  960
aagagagaaa gagataaaac tttttacga ctccatcaga aagaccatcg aagagagaaa  1020
gagaaagaga tagttagtct agatattttt cttagtacaa aagtcaatgt tttaaaatat  1080
atggacaaga atttgtctgt ataaaaactt gtgtgaaatt ttgtaccaaa gaaaaaatgt  1140
gagcagtatc ccctacatgg attttactag atcatttata taccaaaaaa tattatacga  1200
tctacgtttt attatatgat tttaacgtgt aaattataaa cattatttta tgatatacaa  1260
ttgtctggta acctagatgg gcatagggga tgagtatatg ttgttggacg ttattgttta  1320
agaaatagtt gatgcatcag aaagaggttt aatatttttg tgagaccatc gaagagagaa  1380
agagataaaa cttttttacg actccatcag aaagaggttt aatatttttg tgagaccatc  1440
gaagagagaa agagataaaa ctttttatg actccattga agagagaatg agaataaaaa  1500
tattttagtg acaccatcag aaagaggttt aatattttt atgagaccat caaagagaga  1560
aagagaataa aaatatttta tgactccatt gaagagagaa agagaaaatg agaataaaaa  1620
tattttagtg acaccatcag aaagaggttt aatattttt atgagaccat caaagagaga  1680
aagagaataa aaatattttt gtaaaacttt ttttatgaga ccatcaaaga gagaaagaga  1740
ataaaaatat ttttgtaaaa cttttttat gagaccatca aagagagaaa gagaataaaa  1800
atatttttgt aaaactttt ttatgagacc atcaaagaga gaaagagaat aaaaatattt  1860
```

-continued

```
ttgtaaaact tttttatga gaccatcaaa gagagaaaga gaataaaaat atttttgtaa 1920
aacttttttt atgagaccat caaagagaga aagagaataa aaatattttt gtaaaacttt 1980
ttttatgaga ccatcaaaga gagaaagaga ataaaaatat ttttgtaaaa cttttttat 2040
gagaccatca aagagagaaa gagaataaaa atattttatg actccattga agagagaaag 2100
agaataaaaa tattttagtg acaccatcag aaagaggttt aatatttttg tgagaccatc 2160
gaagagagaa agagaataaa aatattttat gactccattg aagagagaaa gagaataaaa 2220
atattttagt gacaccatca gaaagaggtt taatattttt tatgagacca tcaaagagag 2280
aaagagaata aaaatatttt tgtaaaactt tttttatgag accatcaaag agagaaagag 2340
aataaaaata tttttgtaaa acttttttta tgagaccatc aaagagagaa agagaataaa 2400
aatatttttg taaaactttt tttatgagac catcaaagag agaaagagaa taaaaatatt 2460
tttgtaaaac tttttttatg agaccatcaa agagagaaag agaataaaaa tatttttgta 2520
aaactttttt tatgagacca tcaaagagag aaagagaata aaaatatttt atgactccat 2580
tgaagagaga atgagaataa aaatatttta gtgacaccat cagaaagagg tttaatattt 2640
ttgtgagacc atcgaagaga gaaagagaat aaaaatattt tatgactcca ttgaagagag 2700
aaagagaata aaaatatttt agtgacacca tcagaaagag gtttaatatt ttttatgaga 2760
ccatcaaaga gagaaagaga ataaaaatat ttttgtaaaa cttttttat gagaccatca 2820
aagagagaaa gagaataaaa atatttttgt aaaacttttt ttatgagacc atcaaagaga 2880
gaaagagaat aaaaatattt ttgtaaaact tttttatga gaccatcaaa gagagaaaga 2940
gaataaaaat atttttgtaa aacttttttt atgagaccat caaagagaga aagagaataa 3000
aaatattttt gtaaaacttt ttttatgaga ccatcaaaga gagaaagaga ataaaaatat 3060
ttttgtaaaa cttttttat gagaccatca aagagagaaa gagaataaaa atatttttgt 3120
aaaacttttt ttatgagacc atcaaagaga gaaagagaat aaaaatattt tatgactcca 3180
ttgaagagag aatgagaata aaaatatttt agtgacacca tcagaaagag gtttaatatt 3240
tttgtgagac catcgaagag agaaagagaa taaaaatatt ttatgactcc attgaagaga 3300
gaatgagaat aaaaatattt tagtgacacc atcagaaaga ggtttaatat tttttatgag 3360
accatcaaag agagaaagag aataaaaata tttttgtaaa acttttttta tgagaccatc 3420
aaagagagaa agagaataaa aatatttttg taaaaattat aaacattatt ttatgatata 3480
caattgtctg gtaacctaga tgggcatagg ggatgttgat aagctcgacg agtatatgtt 3540
gttggacgtt attgtttaag aaatagttga tgcatcagaa agagaataaa aaatatttta 3600
gtgagaccat cgaagagaga aagagataaa actttttac gactccatca gaaagaggtt 3660
taatattttt gtgagaccat cgaagagaga aagagataaa actttttac gactccatca 3720
gaaagaggtt taatattttt gtgagaccat cgaaggagaa agagataaaa cttttttacg 3780
actccatcag aaagaggttt aatatttttg tgagaccatc aaagagagaa agagaataaa 3840
aatatttttg taaaactttt tttatgagac catcaaagag agaaagagaa taaaaatatt 3900
tttgtaaaac tttttttatg agaccatcaa agagagaaag agaataaaaa tatttttgta 3960
aaactttttt tatgagacca tcaaagagag aaagagaata aaaatatttt tgtaaaactt 4020
tttttatgag accatcaaag agagaaagag aataaaaata ttttatgact ccattgaaga 4080
gagaatgaga ataaaaatat tttagtgaca ccatcagaaa gaggtttaat atttttgtga 4140
gaccatcgaa gagagaaaga gaataaaaat attttatgac tccattgaag agagaatgag 4200
aataaaaata ttttagtgac accatcagaa agaggtttaa tatttttat gagaccatca 4260
aagagagaaa gagaataaaa atatttttgt aaaacttttt ttatgagacc atcaaagaga 4320
gaaagagaat aaaaatattt ttgtaaaact tttttatga gaccatcaaa gagagaaaga 4380
gaataaaaat atttttgtaa aacttttttt atgagaccat caaagagaga aagagaataa 4440
aaatattttt gtaaaacttt ttttatgaga ccatcaaaga gagaaagaga ataaaaatat 4500
tttatgactc cattgaagag agaatgagaa taaaaatatt ttagtgacac catcagaaag 4560
aggtttaata tttttgtgag accatcgaag agagaaagag aataaaaata ttttatgact 4620
ccattgaaga gagaaagaga ataaaaatat tttagtgaca ccatcagaaa gaggtttaat 4680
atttttatg agaccatcaa agagagaaag agaataaaaa tatttttgta aaactttttt 4740
tatgagacca tcaaagagag aaagagaata aaaatatttt atgactccat tgaagagaga 4800
atgagaataa aaatatttta gtgacaccat cagaaagagg tttaatattt ttgtgagacc 4860
atcgaagaga gaaagagaat aaaaatattt tatgactcca ttgaagagag aatgagaata 4920
aaaatatttt agtgacacca tcagaaagag gtttaatatt tttgtgagac catcgaagag 4980
agaaagagaa taaaaatatt ttatgactcc attgaagaga gaatgagaat aaaaatattt 5040
tagtgacacc atcagaaaga ggtttaatat tttttatgag accatcaaag agagaaagag 5100
aataaaaata tttttgtaaa acttttttta tgagaccatc aaagagagaa agagaataaa 5160
aatatttttg taaaactttt tttatgagac catcaaagag agaaagagaa taaaaatatt 5220
tttgtaaaac tttttttatg agaccatcaa agagagaaag agaataaaaa tatttttgtg 5280
agaccatcaa agagagaaag agaataaaaa tatttttgtg agaccatcaa agagagaaag 5340
agaataaaaa tatttttgtg agaccatcaa agagagaaag agaataaaaa tattttatga 5400
ctccattgaa gagagaaaga gaataaaaat attttagtga caccatcaga aagaggttta 5460
atatttttgt gagaccatcg aagagagaaa gagaataaaa atattttatg actccattga 5520
agagagaaag agaataaaaa tattttagtg acaccatcag aaagaggttt aatatttttt 5580
atgagaccat caaagagaga aagagaataa aaatattttt tatgagacca tcaaagagag 5640
aaagagaata aaaatatttt atgagaccat caaagagaga aagagaataa aaatattttt 5700
tatgagacca tcaaagagag aaagagaata aaaatatttt atgagaccat caaagagaga 5760
aagagaataa aaatattttt tatgagacca tcaaagagag aaagagaata aaaatatttt 5820
tgtatgagac catcagaaag aggtttaata tttttgtgat accctgaaag gaaataggaa 5880
tagtgtcata atcgtatcac actattgaga cagaaaaaga agaagtcgcg agaggtaact 5940
ttttgttttg caaaccggaa tatagtgtcc ggtacacttt tttaattcgt ggtgtgcctg 6000
aatcgttcga ttaaccctac tcatccaatt tcagatgaat agagttatcg attcagacac 6060
acgctttgag ttttgttgaa tcgatgagtg aagtatcatc ggttgcacct tcagatgccg 6120
atccgtcgac atacttgacc tcaagttcag atgattcctt gcacatgtct ccgatacgaa 6180
cgctaaactc tagattcttg acacattttg tatcgacgat cgttgaaccg atgatatctt 6240
cgtaactcac tttcttatga gagatgttag acccgagtac tggatgggtc ttgatgtcgc 6300
tgtctttctc ttcttcgcta catctgatgt cgatagacac ctcacagtct ttccatcagc 6360
ggattctgag atggatttaa tctgaggaca tttggtgaat ccaaagttca ttctcagacc 6420
tccaccgatg atggagtaat aagtggtagg aggatctaca tcctcgactg attccacctc 6480
gggatctgga tctgactcgg actctgtaat ttccgttacg gattggcaaa tcttatcatc 6540
ggtcggtgtt tggtcttgct ttgtgacttt gataataaca tcgattccca tatgatgttt 6600
```

```
gttttcttct tccgtacacg atgaggatga ttgctgaaga ctggcaggca catgcatgcc  6660
agtacgatat attgtttcat gattgctatt gattgagtac tgttctttat gattctactt  6720
ccttaccgtg caataaatta gaatatattt tctactttta cgagaaatta attattgtat  6780
ttatgggtga aaaacttact ataaaaagcg ggtgggtttg gaattagtga tcagtttatg  6840
tatatcgcaa ctaccgggca tatggctaca ttacccacat gataagagat tgtatcagtt  6900
tcgtagtctt gagtattggt attactatat agtatataga tgtcgacgct agagttactg  6960
tctccgaatg cggcatgata gtatcattct ttgctttcgt taactgtttg gaggaagaat  7020
ctttgttatt gcatttaatc tcgaaattca gagtgcacac ctttctcctg taaagaaacc  7080
tgaagtcgct accttattaa gaagacggga tcgcagtctt tatgattcat agtaatagtt  7140
agttccgacg ttgagatgga ttcgctgaga ccggtagtgg tcgtccgagt acacgatgtg  7200
tcgttaactg gatacaggtt aatttccaca tcgatatagt taaaggtatt tctgggtacg  7260
ggttcgcatt tatctgcgga agagacggtg tgagaatatg ttccgagacc acacggagaa  7320
cagatgacgt ctccggatac tccgtatcct attccacatt ttgtttggga aacacatgcc  7380
ttgcatccat gatcgggaga gcattcacag attctattgt gagtcgtgtt acacgatcgc  7440
gtcgacattg ttgacagaaa cgtgaccttc attcttaccg tcgtccataa atacgttagg  7500
tatgtaccac atactgtcgc gaacgatgcg tccatctcat aatgatttac tttttcataa  7560
ttaaagatgt gaaagaaaac cgaacaatat attttttag taatgtttat gcgagacata  7620
taaaataaac tccgtgttta tgatgccggt aaatgttttt atcatcttgg acggaatcga  7680
ttttgtaata tgccatggaa acaggacatt atcactccat gataaattat ttaatggagt  7740
cgatcctctc attgttcttt gcgtatctca atctgtggcg tttgcttcgt ttaaataata  7800
tatcaaacat ggagacgcct gatatgtagg cattcttcat tctattaatg tctgctctat  7860
agcgctttag ttccttatga cgaccggcga tatcatactt actttagaag gaaaatcatc  7920
atctaggatt aaggcgtatc tgatacaggc gaataatggt tcaggatata gatagcgtat  7980
atctctatta aatgcgtcaa tcatagtctc tagagtggga tggtaactca gtaataaatc  8040
aactagcttc tctttggtaa ctgcttttct ggatggccgt attgattatc gagcgtgaca  8100
ctcgctccat attccaataa ccgctttgca aattgtatat tattgacatc gaccgcgtaa  8160
tatagtagag ttatcgatca tatctatatc atccatgtac ttgcttagta tatcaaatac  8220
atcttcataa cagtgatacc cgcaattatt aaatctcgat aatatcagac cgtacataca  8280
tagacggcca ttgttagata tgtgatttac agccgcgtgt ccatattttc cacgataaac  8340
cttacgacgt ttacatcgac gagattatta ttaacaaagt tgttgtccgt cgtcttatcc  8400
aacatgcatt gaatgatagg tatacttacc atatcgccgt aatgtaagta gtttatcagt  8460
atggcttgta cgatggattc atcctgttgt ctaaatctct ttagaatgtt atcgatgatg  8520
tagtggttat attctctgga atcgtacgaa gtaatactac gcattacgtc gacaagagta  8580
tgacgtctct caataagaag attaacgatt tccatgtcta cattatatgg ggttactcta  8640
aatcgcttgt ttagataata cgcctctaat atagggctga cgtcgtatac tctacacgtg  8700
tccacatcct ttattaataa tctctatatc tatggttgag caagaccagt agtattggat  8760
ggaaacattg ttatcgatca aacatttaat tacatccttg gatagagatt ctctatgaga  8820
cgatatatag taatgaagag agttcttaca catatcactg ttgtacatac aggtacgaaa  8880
tacgtaaccg gtgctgtaac attctgattt aagaagccat agcaatactt ctggtctcgg  8940
attaggcgtc gttacgtata tatccaccaa tccgagacca ttgattgcat aattcgtatt  9000
cttggacgga cgtatccgtt tatccacaat taggtatttt agcagacgta agtcgaaatc  9060
atttatattc gacttgagtt cgttagagga attcgaatag ctggatatca gtagatgcac  9120
aatctgagat tttacgtatc tatgcttact gtatgctcct agcggagtta atccttcgtt  9180
gtttctacaa agtctctcga ctccgcgaga gagtaacagt cgaacaatct taatgtctgt  9240
atcgcattta ttggagacgt aacaatgtag cgcattgttt cctcgtctat ctatatgttt  9300
tgataagttg tgacacgttt caatttctag ttttattttt ttgtacgtca catcttcatc  9360
cagtagacga catagaatac atgtgcaatc catagctatt ctggtgctaa ttattcctca  9420
taagatgata aaaagtgtag tgagagagca tgaaggagat ttagtattta gcagtgcgga  9480
tatgatccaa gagggtgaga tagtcgttct cgttcagaat ctttcgcagc ataagtagta  9540
tgtcgatata cttatcgttg aagactcttc cagagacgat agctgattga gtacaaagtc  9600
caatgattgc acgaagttct tcggcggttt tcatggagtc atttaatgat ctccacggaa  9660
gtgaatcctt caactcacca ccaaagagct ccgttgcatc agttctgaaa gagatgagaa  9720
gcctgtagag agaccctgcg ctttctctat gggtccatct atgagaaacc cacaggatgt  9780
attcagtcag acaatgtctg acgtcggcca cggtattcag ggagtcctta gtagcgtggc  9840
aatgacaggg tctgaactgg gcacaaggaa aggccattgt aaaggtagac ctgtagccgt  9900
ttatgctaat agagggcttt aatttccatt ttttaatggg ttgtggatga ggaatgagag  9960
tgatatcata ttgagatacg tagttatgta gaggtgtatt tcctatatta tttactttcg  10020
gtttcatatt ttaccaactc tttaataaat ttcttttcac gatgcatctt attaaatgac  10080
gttttctcat aagtggacat atagatgcag aagtattacc tctatcatct acataattag  10140
ggtctgctcc taacttatac agtacgtagt agtagtttat cggttttaaa tcaagtctag  10200
aatatatagt ggattaatat atttttatat tagctaaagc atatcattct caacttcatc  10260
atgagttaaa tatttgtgtc tactagtttg tttatatcac agcattctac aaacagtcta  10320
aacaatagag aagacggaca gactttaacg tataaatgac acatgttatc gatattcgtt  10380
gataaatgat tctaacgaca tctctcgcta gagataaaat ctagtatcgt atcatactcg  10440
catagcatag tttttcataa ttaatacaat atttaaaaga cttattcgga aagtatttta  10500
atacatgtat catcgatgga gatccatatg aggagtcact tgtagttctt cagtagtgct  10560
atcatcgata gtataattat atgttgttgt aattggagta actgttggta gttcttccgt  10620
ggaatcaata attatactaa cagcaatagt ataattatat aaatatgttc cgttgatatc  10680
acatatttta atgaactcat ttctaaagcc gtacatccac atctattagg atctgatatt  10740
ttacacaact gtttaataga gtctacattt atatgttctc tatcggtgag atacaaatac  10800
ctagatagtc gcgttatagc acaaatacga tataaataat aataataatt attcagtaat  10860
gtatataaaa atgcattgtg tatttactcc aatactactg tagttgtaag ggttttttca  10920
aaataatagt tgtgtccacg acatttatat gtattaccta tatattcttc agtaacattt  10980
tcaaagtaca aggtcgcctc ggtgataccg cctctactag ttaaaacaga gtatacatca  11040
aaatcgaatc ctataagcca tccggatgga ttttcccatt caatcagtac atcgtcaatc  11100
aataatgacg ttgacacagc agtgcatgtt atattggcag gttctcctat cgttacgttg  11160
atttttggat ctagtattag tttaaacctg tggtcttgcg acggtataac cgtaagtatt  11220
ttacatcttg attctaacgt cgtcgtaatg aacgtaacag ttgtatcttc cactatcttc  11280
taactctgga ttatgaataa ttaatttctt tcccgtttgt gaatacttaa tatcgtcgat  11340
```

-continued

```
attaatttcc ttattatctt tataccaagt tatattatta taatgttttg cgtaaagaat  11400
tccacagtat aagtctatgc catacttatc atgagtacct agttcatatg tttttggaat  11460
gcatgaagga ggtttttttaa tatgagatct aactataccc tgaacacagt caccattctt  11520
tgtagttacg gtacacaaat acctacggtt actgaattta gatgtatagt tggctatcca  11580
taaatcacca tgtttaacac gtttattaga aacctgtcgc cgtctatttt tttctagcct  11640
ctcccattta accacatagt ctttatatct gtgcgataaa agactgtctt caataggagg  11700
acactttgcg ctgaatggct ctcctagagc ggctatatca ttcattgtgc ctccgaacat  11760
acatgctgga ttcaaccatt tagagtcttt agctggtaga gtatctctca ttttattgaa  11820
gaattctgtg atttcatttt cgatgtctat ggcgtaactg tggaatagca ataacaataa  11880
tgatacgaaa tatatatgta ccatcatttt catcgtcatc ttcattatac ggcactaaaa  11940
tatttatata atatcagttt ttttacacac atcgcatgag aaaaatacaa ctatactttg  12000
gtaggtggat acgatatatt ataaagatcg ttaattgtca gcatgtataa tatttcgtat  12060
ataatttctg aaggtagtaa tgttagtaga caatttttat ctgtgaaaac aggaaatagt  12120
ttatcatata cctttgacac gtacatatct ttataatata cattaaggta tctctcattc  12180
ataatattag aatatatttt aaaggactta tcgttattat attttttttaa ctcgttgagg  12240
tatcttctta actttttcga attatggcat cttaaaactg catatagtgt agtgtctaga  12300
acagtggata gtttgagcaa tattgtttct ttatgacatt tagttattat accatcgtat  12360
ttatcaaacg acatgtattt tgaaaatgcg tatcgatacg ttttagaatt gcgattccta  12420
acgtgtctat tgtaaaatgt gtcatctaaa agtatacagt aggatatgaa tttctcaaat  12480
gattttatat cgaagatagg tagagatgga agttgatcca ccaacgatct tatcacattc  12540
ttatctacaa tatatctaag tatatacagt aaacaattaa tggtatatgg ggaattttct  12600
ttgttatcta taatgagttg tgtagcgtgt ttgttattgt cggttaacgc atttatatct  12660
ccgttgatac gtataagata atctattacg tgtgtattat tatattcaca tgctacgtgt  12720
aataatgtct ttccttcata gcgggtataa atatctatat ttttaaacct attcatcaaa  12780
taagttatcg aatctgccgg acgtgtagaa tatgttttga taaactcgaa tacgattata  12840
cgacgctcat ctatcggcat ttctccaaca tttgtttcat agtgatgtat taacataaca  12900
agaatatcgt gttgtatgta gtcggaagtt atataacata gtataggcgt taatccatga  12960
ttattacata ttttgaaatt cggattaaaa gtcaacagca ttttagtcat atgaatatta  13020
ttacacattt caatactaag atacaaatgg aatggtgtat taccacaatt atctaacgcg  13080
tttagattag ctccatgttg tataaacaaa gaaataattc gcttggcctt ttttatcgtt  13140
atcggttttc tacactcacc tggtttataa acgtgtgcga gacacaaata ataataatgt  13200
aacgctgtat atccgtcttg tttaaagtta ggatcgattc ccttatctaa taaagtggat  13260
actatgttct catcgatatc ctcttccttc aataacatgt aacgagattt tatatactct  13320
agtagtaggt tggaatagtc tctatgcgat aagtggtttt tatctttgtc tatcatatct  13380
atcactacat catgtgaaat attacaacat ctagtaagca atatataaac aggcatacgt  13440
ccgctactgg ttttcatcgt tacatccact ccatgattta ataatatctt cagtacatcg  13500
tttgtaaagt aattattata caaatagcag tgtagtgcag tatacccagt tacaggttgt  13560
cgtctgttta gatcatagtt tttaactaca aaatcaagtt ctgtagaagt atggtctata  13620
ttgcaatgac taaaatatgt atatatttca ttctcttgta ttttatgagt tgattcgcgg  13680
ttgatattta aaacataaat cagacgacga ctcattttta tgatgcttg tggtaaaagt  13740
cctcatataa ttgtttaata ttcattatta tagacgattc ccattaacta atctaacatc  13800
tttgatatac ccgtaaatat gtaaatatga tcctaaaata acacggattg taagatgtct  13860
agaaagttta tgcaggtgta tgaatatgac agagagcaat atctcgatga gttcattgaa  13920
gacagatata acgatagttt tatcactagt ccagaatact atagtgcgga aaaatacatg  13980
tgtagatata ctacactaaa tcacaattgt ataaacgtac gacgatgcgc gttagactcc  14040
aagttattac atgatatcat aaccaattgt aaaatatata acaatataga attagttagg  14100
gcgacaaaat ttgtttatta tctggatctg ataaaatgta attgggtatc taaggtaggt  14160
gattcagttc tatatcccgt tatatttata acacatacaa gcactagaaa tttagataaa  14220
gtctctgtaa aaacatacaa gggcgttaaa gtaaaaaaac ttaatagatg cgcggatcat  14280
gctattgtaa ttaatccatt cgtcaagttt aaactaacgt tgccgaacaa aacaagtcat  14340
gcaaaggtat tggttacatt ttgtaagtta agaacggata taacgcagat agaggcaccg  14400
ctttcgggca atgttttagt ttatacattt cctgacatta ataaaagaat tcctggatat  14460
atacatgtca acatagaagg atgtatcgat ggaatgattt atataaattc ttcaaagttc  14520
gcgtgtgttt taaaactaca tagatcaatg tatcgcattc caccctttcc tatagatatc  14580
tgctcttgtt gttcacaata tattaacgat gacatagaaa ttcccattca tgatttaata  14640
aaggatgtgg caatttttaa aaataaggag acggtatatt atctaaaatt aaataataaa  14700
actatagcta gatttacgta ctttaataat atagataccg caattacaca agaacatgag  14760
tatgtcaaaa tagcactagg tatagtctgc aagttaatga ttaataatat gcatagtatc  14820
gtgggagtta atcatagcaa tacgttcgtc aattgtttgt tggaagataa tgtataaaaa  14880
ttcttataaa ctcaattgac atggaaatgt aacaacatac attcacgtta tactaacagt  14940
aactgttttg ctgatgctag gaatagtaaa cgccatacac gtaaacgttg tagcatcttc  15000
ttccttgaca ggattaatgt ttaaccggga tgtaataaca cgtctcttat cggtcatata  15060
gattttattt gctacactta ttctaccgtc tccgtcccca tcatcttctt cgtaatacat  15120
accattactt atccaaaaga cgtctgcatc cgttgtggga ggtctcaacg atactctaca  15180
cgcaatagtc aaattactac ctattgaagt tacaacacct tctggtaatt gcatagtaga  15240
aggtattatt ttatcccgta cctctaattt tacaattctg gttacgttat atgttttgcc  15300
accgtatata tattctaaaa cacatgtata ataaccagca tcatttttttc taacatcttc  15360
tatggtaata attccaggtg tccgttgttt aagtctctta tttctaaggc gtcgatgccc  15420
gctccatata atatctgcgt ttacgttact agcaataaat gcattaatat tgggacatac  15480
catttcgcca gtagatctct catttactat ttgtggatac gagataagat ctatatttga  15540
ttctgagaca gacacgattg tcaaatttaa cgacatcatg tcacagtagg tttcgttcgt  15600
ggtaatgcat atataaatac cagagtctga ttgtgtcggg ttcagaatta gcatattgct  15660
accattatct atcggtataa ttctatcatt atccgctcct cgtttttccc ataaaatatc  15720
taatatatta tatccggatg atagcgtatt tatttgagga catggtaaga ttactggctc  15780
gttttctaac tccatgaatg atgcaaaata ttgccctttg tcgatacatt caggcgcgtt  15840
aaaagtctga acgaatgaag aataaaaaaa tatagaaaga aatataacag gtagtatact  15900
cattttattt tatagtgggt aaaaaaagtt tgtttctggg aaagggagaa gagaagaaag  15960
aagaaaatgt caagatgtac aactcatcaa ttcatacgcc ggaatatgat gttataatcc  16020
acgtaattta gcatctcaag catcacaaac aatgcgttca gactgttact agtgggatgg  16080
```

```
tcttcacctc cccagtaagt agcagcatat gcacaaagtc cgatgatggt tttttgctca  16140
tccggtatat aacaacggat gatttctaca caatctttga catcatccca cggcatattt  16200
tttaccagct cgcgaatgtc gatgaacact aattccgcat catctctaaa agagaggagt  16260
gtggaataca attgtccagc gcattgcctg ttgcggtatg cataggacga ccaataaata  16320
tattcagtca aacattgttt gacgtcatca atactggtca gtctgtcaca tccacagtgc  16380
tgtggtgaaa agacgtgggt actaaagttg gccgtcatct taccaattgc aattggaaga  16440
ataacgacct gcactaatac cacatgtttt ttctattttt ttaaaaaaaa tggttaacaa  16500
ttagttgtcg gagagcaata tctaccaacg aaaaaaattt ttccatcaac atgcctaatc  16560
acatagatga acggatgatc tacacagaac tcatttgtaa ttgttgatgc acagtctgac  16620
accagtgcac aagttgctgc agctgcttct gtatactctt cattgacatc tatatacgtt  16680
ttgtggatca tagcgtcgac actcacatct aaattacaca tattgctata atctccagtt  16740
gaaccgaaca cctctgtcag tcctgacttt actagagtat ccaccagatt atacgagcct  16800
gttaccttaa acttgggaat gtgaacatcg ataaacgtag cttccagaga gttacaccat  16860
ttcttaaaat ttgtatctgt tagattttgt tctatggatt ctaatccatc aatcttgtct  16920
ggaagaatga ccatcatact agtatctcca acatatggca gttctatgat tgaaaagtta  16980
ccgaatgatt cttttacaga tgcgtgatta aatagctcgc cgtacataga catcatactt  17040
acgtctacca tttccgttgg tgatacgtaa aagggataat cactggtaaa ttccttttcg  17100
aatggcgtca accattttgc tttaaagtat acggcactaa ttgctaggag acaattgttc  17160
atccaatagt ggattgattt tcccctcagt aaagatatct acacacttgt tgattgcatc  17220
tatagtgcga caatcagtga agtcaacagt ttgaaactta tcgccaattt ttctcaaaaa  17280
ggaatcttta aacacggcag aatatcgccc atatacttta ttcatggatt tgaatgagat  17340
attctgagcg ctaaccttat ccgtgttctc ctccttttct acatatttg atagctgttc  17400
agcagtggat ccattagctc cataatacag tattgtcaat actgacgaga ttgacgctgg  17460
agaaatgaat acattctctc ctttcataga agatatccat agtaatcgat attggtcgtg  17520
tagcgcgata gagatagtct aatattaata ttagatatcc gtaacactac cacactctat  17580
aaaaaaagaa tatttcaatc ttgtataaac agtctacgta gtctgtcata attaggagtt  17640
tgagaataat ctaacgtgta tactaattct atatatctaa ctaattccag aggttcattt  17700
ccttcaggaa aacagtcctc aaagaaagta gctataaatt ttttatattc ttttttttgt  17760
tttattactt ttatactact ttcgtttttc catggaagtt tgccaccgaa ccattctatc  17820
atgcaatatc ccaacatttc taaatctcct cgttttgaaa ctgttgctcc aagatgattg  17880
tctacacaca tataattgat atttcctgaa gttatcatgt cctcgttgta atctatatgt  17940
gagtttccac tcttgtatag tttgttagtt ctagaatagt caattagtga aagacgttta  18000
tttctaatca gtatattcct cggttctatt tttccatggg taaatcctcg agagtgtata  18060
aactctaacg tgtttatcat agtgacgcat gcttcgaaga ctgattcagt atcctttggg  18120
gcgaatactc ttcccaaatt ctttataacg aagaacatat aatcatcggt ttctccaatt  18180
ccatacagat ctggaatagc caaatacttt ataccacgtt cccgtgtcca gttgtcgata  18240
gtcaaaggat ccaatacaga tatatagaat cgtatttcag acaacaatgg cttgtgtgat  18300
ttgtgatcta tcttcattac gtaattgtag aacgaactag tgaaattttt tctgacctta  18360
tagagtattg aattaccaga atataaagta tttccgataa tccatttctt gccatcgtta  18420
tcaaaacaat acttgaagga ttccatgcct gctatgtaat aacgagttgt tttttatgtt  18480
ttgtattgat tataaaaatt agtagatatg atctatattc ctacatcgtg actgatacat  18540
tctataactt ctttatcaat ggaatcacta ttactacttg tattaataac gagtgcttct  18600
ctaatatatt cattgggatg attcttgtta atgtttttat tattttcaat ttctacattt  18660
tttagtattt cttctttctc tctatctatt tcattcatga tatcttctac atttgtaaca  18720
tctgtatctg tatccatgtt agtagtaagc aataaaacta tagggtaata ctgctataca  18780
taaaaactat ttatattttc attttcaatc aataaggaga agttgataat gcctttatag  18840
cggggagacc atcatacttt tccacatatc caatgtcctt actaaataca tagaagacgt  18900
tatttagttt acacaatgat gatatggata tcttataaat agtatatgaa atatcaaacc  18960
acttattcgt tctaggattg taacaagata tctcgttgtt tttctctaaa ttaccatatt  19020
gttcggtaac ggatagacct ccggcaaaat ataacattcc aaatgtcgag tcgatgccgt  19080
gatataccct agccataggc atttctataa tcgaccattg tttgtcttta taaatgtcaa  19140
gtttttccat attgttaacc acgatcgtgc tattagagtt atttatgaat aatccgccag  19200
ttacgaaaat agtattatta acggaaacag cggacacatt gctttttttta taatttatcg  19260
gtgtttcgta tatccctgaa tccattgcct tcacttgcag ttgggagatg aacactgcaa  19320
tcagttcttt cgggatagaa atctttggca attatacaca accctatttt caatccccat  19380
gtttcctctt cagtcttctc acatcgtcta atagacatgg agtagatgat agaggggaac  19440
agaaggacta taatcaggga cctcatcttg aaaatggtta gagcctataa gggcgttaac  19500
cagtgtataa tatgcagttt tatttcgttt ttgtatcatt aataaaaatt agttatgaat  19560
atttagtcaa gttaagcatg ctaagaaaag tggtaacatc atttgatgtg ctaccgagaa  19620
atttagttaa attttctctt gataactctg gccattttgt ccttgaaatt gggaacatct  19680
tctttggatc taattgcgca tgtatataca ctctttttag gtgtcagaca tactttcgaa  19740
ctccatggag taatttttttc gagaaaccct tctgtggctc cctgtgctgt cacgcacact  19800
ttttctgttg tgacaaagtc tatgctgcaa cctgtagacg tgcaatcgta gtcatcgata  19860
tcatatggta ctggttcttt agaatctccg aatgtgaagt tagccgtata caacaagtag  19920
atatcacaca tgtcaccgcg tttgtaaata ggaatctttt tgctacctct agtagcatac  19980
ggatggtcgt cgtattcagt taatgttaca gtcggtggtc ccgtacaata ctcttccact  20040
ttataatcgc cttgttcaaa tttaacccag aaagatacga aatcattctt tggaaatgcg  20100
gatatgtcgt atgttccttc tggtacattt gtatacattg tttgccacgt cttgatgcca  20160
taatttttaa gggatatatt gtatagacca tccccagtcc attcaatttt ggaatcaaaa  20220
ttgacggatt caaacttata actagttatt ttagcgtgta tactattaat gaacaaaact  20280
gcgagaatta taatatatct catggtgttg tttgttattt gactactgtc actgaagtga  20340
taatatattt taaattttta aaaatcatat tttgaataat atgtattact atgtccatga  20400
cgatcaaata tataagtaga tccaatttta agagtatgtt ttctcaatag agtatcatcg  20460
ttgatcatac ttatttcata ttttattcct ttatagcatt ttccctctgc agtaatagaa  20520
tattgtcgct catcaccatc atatttgtga atataagggt acttatcata atggcatgat  20580
aatttggtag atattctaca cgtgtgacct ctgcgttgaa tagtagacat atcaataatt  20640
ttatagtcgt ttataacatc tatatctatg gaatcaaatc cgacgtcgca tgactctgta  20700
ataatagaaa ttgtgtactc tttaaaattt aacaccaatt cattattatc atcagtatat  20760
gaattttcta tattatctac tccatctata tagagtttta cactcagttt attaaacgga  20820
```

```
gtgtactcat tattcgaata ggatgctaat gcacctatta caaataaaaa cgttattagt  20880
tttttataca tttaaaatct taaaatttta actagtatat tgaaataatt atttatacaa  20940
actaactaga tgcatcaaca gataataaca aacacctcca gcgatcgtgc caatagtagt  21000
tagagatgcg tatccgtaca acttgttaat catatttcta cggatgtata taccatcgtc  21060
gttaaaagcg cttctatatc tctcattagc tagaattata gatacgctat taattatatc  21120
atacattagt tgattgttga tactattttt attgtaatcg aaaaacattt ccatgaatag  21180
tattccggtg ccaacgctta cagaaacatc gcgttcattc atcattatac cattaagtgt  21240
atccatcacc cattgtttaa cacgtgattc atttggcata gtacgtacta tatcatcgaa  21300
cggtataacg gcgcatcttg taaatagcct gtatatatta tgtaatatgg cgttacttct  21360
tccatacaca ataaatctct tgttataata gtgcctgagt aaaaatgctc taacggcatc  21420
gtagatatca acatccactg aagaagacat ctcaattgat tctagctata agtctttaat  21480
cttttgatac ttgtttgtta ttaaattatt aattattaat tattcattat tttaacggat  21540
ttatattcac ggtagcaatt tatggaactt atattggtca ttattttttgt cacaggaaca  21600
aactaatact ataacggaga ttaaaaatat gacgcccata attgttaacg ccactatgat  21660
tatatgataa gttgcttcta acgattctat ttcttgttca tattgtacaa cgtctttcga  21720
gagtttgctc aaatctgtct catcgtcggg accatcatcc actggatcaa atttttcgtt  21780
agatcgtaca catgttggga gtatgggatt ccatttaccg tcgatacatg tggatgatgg  21840
agatcccgtt agtataaaac cacttttaca actaagatgt ataacgccac cgatagaaaa  21900
tgtagatccg gaaattaatc cattagatag agacggtata tcacattttt gttgacatga  21960
tggaataaca ttccaagaat tagctgtaca acttatgtac gaagcaccaa taacctcata  22020
tccaacatca cagttgatag ttatatattc cccaaatgag tatttttctt taactggttg  22080
acacgatccg tgttctaatt gaagaggttg acattccgca ttaggacacg taacagtatc  22140
attccaagaa gtatttccat ttttttcttc gcaacgaaaa tattttgttt cgccgttgca  22200
acttagtgtc atggtggaat tcacttcgta tagcggttta ttatatagtt cagagatgta  22260
atcagaaact gtgcacattt ttttgcatgg attttcgtat ttccatttat ctgtttcgca  22320
gacagcattt ggatccgaag aatgatatcc ctgatcacat gtaaacgtaa ctttctggtt  22380
attattaaac gatgtttcgg tagacgttaa tttagcgtta ttcatagtgg gtacagtaca  22440
tgttgaataa acaacagcag gtagtacgca taacaacgta acaacggaaa tcgttttcat  22500
ttttatttat gagcgttaaa aatagtatac actgtcgagc actaaaagga aacaatgatg  22560
tagtgtgatt ttatatttta atagtgttta taagattttt agatatgtgg acagttcgtt  22620
atcgttatat tttatttcgt taggaaaaca cgaccattta tctccaggat ccagcttctt  22680
ggataataga ctaattaatc tctgacgata tctaatagat gctatgatat tacgtacacg  22740
acttccgtat acgtcgagac tagtgcactt cacgaaagaa ggatgtttac cgtatctcat  22800
taaagtatta atgtctttga tacaaaaaac taattggaat acagttttat tttttatata  22860
acatctcttc atgatatcta tttcatcgaa acatcttaaa atataccatt tatattgctg  22920
tagtgattgt acatctataa gagtatcata atcggtcata cacgcagtat attttataca  22980
cattttcaat aaatctgcat tatgctgttt atgtttagta attgctatca tagactgtat  23040
cataattttc aaagatggtc gtttagacaa tagtacttcc attattattt tgttgttgtt  23100
tgcgactgct tccgaaatac atgtacatcc actagtagta atcgtctcaa aatcaccatt  23160
tctgtttaat agatagacca acgtattata cgcattataa ctgacagcgt cgtaaatagt  23220
acgatagtta atatcaataa ctcctctgga taatagataa tctaaagatt caacagcatc  23280
aaaaattatt aaatgacgaa ctatatgttc attatctatt tctaactctg tgtctgattc  23340
caaatatagt tttataagcg agataccgtg tataattcca caataaaatg gagtagttcc  23400
gaatttatta cgcgcattaa catttgctcc tttagaaatt aataacttta caaaatcata  23460
tttattacga catgagacat aatgaagagg tgtatatcta ttaaagtcta cagagtctat  23520
attagcattc tctaaacata tctcaaacaa ttccacgttg ttgatatcgt gtttacataa  23580
taggataaaa ggtgtgtttc cgtacgtatc ttttttatct acatctgatc cattatttaa  23640
caatatctta attaattcat tgtatgattc tgattctgat tctgatttct tatagtgata  23700
tatacatcta tgtaataatg tacaaccgta actgtcttcg gcatctatat aaaatacata  23760
tatagatatt aactgtatct gatatatagg acaaaaaatg tcttgttcta cgtccatttt  23820
caagcattag tcttatccta ttatctggat gatcattatt aactaattga tatacatatt  23880
cttttatatt aatggatgat gataacctga gattgtgtat aaatgacccg ttcttattaa  23940
tatttaatac tctatctaga aaaaaaatta taatattcgt attagcatca tccatagaat  24000
aaatatgtag aatattttcc ccatattcta aaatatggaa taaatttggc aacctagata  24060
aaaaatcaac tattgtttta tccactttct cgtatgttcg aacgagatta taatcctgta  24120
ttatatggga tgtggaaaaa ttggaaaaca cgcgtgctat ataatgaaga gataaatata  24180
cactccagtc aagtatttcc tttttaaaaa aaatccatat ataatttata ttctgtaaca  24240
tgttatccct tttcaattaa caatgttggt ttataaaaaa ttaaagaagc gaatcaatga  24300
ttaatagatg ttaagaacta taattacgat gtattaatag gtatagttag ttagttaaaa  24360
agagataaca gttactaatt aattgttagt tattgtctat atgatattac aacctattat  24420
ttgttctcta tagttacatt aattaaaatt ttatatgtga cacctattca tctggagaat  24480
acttcttgat accatgattc tggccaatct gcaaacacag cacaacagca tctttccact  24540
ttgatagcgc acacgtatgt cgaggtagcc tcatccccag gtttatatac cttgatgaat  24600
cgacacgtgt acttgatgtc ctctttcttc tcacagaaat acacaacaca aagtcttttg  24660
atatgctttt ctatatcatt ctctatcagt ctgaggtagt cgtaacccac cgtgaatcca  24720
aatactttgt gtgtattatt atcaactcca atgaacaaat atccaccctc tgtgttggca  24780
aaagatgaga gtatacgtgt tcttagttgc ttagctgaaa cagatgtatg tttaacatta  24840
atagatttac cagcctgaag ttctgatcta ttgaagaact cctctaccaa tctctcaatt  24900
gattcagtgt cttccactcc atctggatat tcaaattcct gcatttctgg tctgggactc  24960
catccacctg attccttcag ttcgctaaga tactcatttg aatgcatgat cccatagtct  25020
tcatgtacaa atttgttttt acagtactcg gtataagatt ttgattagac aaatgcgtat  25080
gcacataaca gcattcttta ccattcacaa tatcaaaatg atcatataca acagaccaca  25140
tatggcgtat agattccaaa cgtttcatga gtacatgatt cacactgtct tccagagagg  25200
tggttacctc gatggtgccg ccgatatagt agaagaaaga ttttctgtat cattctcccc  25260
aagtttaact tttaccagat ttgggatcgg aagcaccgca ccctttttga atctcattct  25320
cataatttcc tttccatgta cgtccacagc agtaacttga cagatacaat ctcctatcca  25380
gacgtggtaa tcgatgatag gtcctgaact gagtgcattc atttctttgg ccttctcttt  25440
gatagtagaa taatcatgtt gaacttttcc atatacagcg ttttctgttt caagtacgtg  25500
atgatgaatc cctactcctt ccaaacacaa gtctagactc tcgtacccga ttccgcttag  25560
```

```
agcatagtag tttttgtggc gatatgtgat ttccttcttg atcatggatc ggatctccaa  25620
tttgtagata ttcattgcac tcaaacatag gcagcagtgc tccaatatat ctcttgttca  25680
cctgactgta acaccacata tatttgtctt ttacaatgtc atacttgtta ttataaactg  25740
acatcattgg caacagtcga tgatattcca ggaaaggcat gaagattctc gtcgtaccca  25800
ccgagagcgt gtgcgtaaaa catcgccatg atttcggttg tacacacgag atcaataata  25860
aattaagtta ttttttaatt tttatcgaca aaaattttac atcaaccaaa caccacactt  25920
aataatatac accctgcatt aatatgtgcc gaaacttgtc gtaattgggt tcctcaaaat  25980
atgtcaaaga gtttaccatg gtaatatatt gcagcaattc tctaggtgca tattgcaaac  26040
tggtcattaa caaagtcgca gtattgttaa catatttctg ttttgtggca cttactaatg  26100
cacaattctt tgtttcagat atcttagtcc atggcaagat acctcccaac catctaatca  26160
tacaatatcc aagtgtttct agatctccac gtctagatac aacgtatcct ttatgcgaat  26220
ctataggtgt aaattctaga gtaccgttat ccattttatt tggatttctt ataaatggaa  26280
catgttcgcc attagacatg aatttagaaa ccaatccgta atccactaga tataatttat  26340
tcttatctat ttgatccaag actatattac tcgctttaat atctccgtga gaatatcctt  26400
gctcgtgcat aaattgtatg gtatttaaga tttcgattcc gatcaacatc accgaccttt  26460
ttggtaatct attattattg gctctgatca ccgcatctag atctgcacct aatctattaa  26520
ttaccaagaa tcgatattcc acattaatgg atttgtatag accaaatgcc ttgcacgtga  26580
taagacctac gtgctttata ttgtgagatt ttttccattc ttcgataacg gatggtttaa  26640
gtactctagt ataaaatgcc tgttcggtaa ataatgatcc gttagctttg ggctctattt  26700
ttactacata attattgtca ttagtagtat aaatactacc aaatccacct tttcctatta  26760
atggtccaac gacccattga tttttgcaat tgtcagttaa cacaagtcct tgaaagttca  26820
taatgtgtga tctatctgtc aatgaaatat cattttaaat tttaagtttt acgtggtaag  26880
ttttaatatt taactaatac attagacgtt gaaatagcca catataaaaa cgagttatat  26940
tattaattat caagttttaa gtcttaagtc tctaattagt gttaaaatac attctaatac  27000
ggtcctgtag tatctgaatt aacttactat atgctaaatt cacatcatct tcaatgataa  27060
tagtgtcgaa tagaccggct tcacctgcct catccatgtc agtttttgcc aacatcacac  27120
gacgatgaat ctcatcatcc gcttcagtgt ttctacaacg aagcttggtc tcaaccattt  27180
taagagaggt aggtcttata tacaccgagt aaggcattag gtaagtattt ttaaaacttc  27240
taacaccgtc gatgtttaga tccatcacac aaatacgatt attaatagcc gctgtattca  27300
cagcagtttt agaagttccg taaatatttc ctaaaaactc agtatgttcc ggcggctatt  27360
cccttccaga tggcctctct gttaacgtaa tggtaatcga caccttctcg ttccatagga  27420
cgaggaaatc tagtggtatg ggacaccaca aatccaaata tattcccata gtcttttggc  27480
tatggctgtc tttcctaaac cagatggccc gctcaatatg atagatttta ctatcccaga  27540
catttatgta agtcaaaaat ctagactttg ttctctgttt tgtatttacg tgaacgttta  27600
ttatatatat aatatgtaat acagaatatt gccacggccg acaatataat taatgcggta  27660
ataccaaata tttctacaaa gtccttggtt ttataattgc taatagaggt tgtactaccg  27720
cctacagtag ttgatggtac tgtatcatta tcattgtacg tatcataaag atccgcatca  27780
tcggtggttg atttagtagt gacaattcca gatgatgtac ttactgtagt gtatgagaca  27840
gtgtctgtaa ctgtatgatc ttcttcttta tcagtaattg gttccggagt ctcgtctgtt  27900
gtggattctc cagatgatgc acttactgta ttaatgctat cactagtgta tgtgacggtg  27960
tctgtatgat cttctacatt atcagtaatt ggttccggag tcgcgatttc gaataccgac  28020
gagcaattag aattatctat ataatcaggt ttctcagaac tagtttccgg tgaatgtgta  28080
gatccagata gtattatgtc tatagtcgat tcactatctg tatttacaat caactctgtg  28140
gagtattctt cataatctac tttatcagtg tcatttgtag gcgatgtcat aaagaatgca  28200
catacataag taccggcatc tctagcagtc aatgatttaa ttgtgatagt tgtaactaga  28260
tcatcgtatg gagagtcgta agatatttta tccttggtat aattatcaaa atacaagacg  28320
tcgcttttag cagctaaaag aataatggaa ttgggctcct tataccaagc actcataaca  28380
acgtagtcat ttgtattatt tcgattacat gataaagttg catcatcacc tattttttta  28440
gatgtctgag gaaaaggtgt agcgtatact aatgatatta gtaacaaaag tattggtaat  28500
cgtgtcatat tagtataaaa agtgatttat ttttacaaaa ttatgtattt tgttctatca  28560
actacctata aaactttcca aataccagcc accgaaagag caatcttaat catgtcaggt  28620
tcatatttcc ccaacatact agatccaaat tcgcctacat caggtaaatt catcataata  28680
caatgtctgt tcatatcaca cgatgatcca ttgagcatct catctctatc aagaatccta  28740
atctgtggtt caaaataaca gcatctacac tcatcgttaa ttgtagtatt gtctaatata  28800
tttttgctaa tatttgcgta agttctatta tcagctattg catgcatcac agatccatca  28860
acaaccatat ataatataga acaatagtcg gactttatac ttatgtaaaa cttgaaccaa  28920
ttggaactcg gaagctcgtc atgtagacgc tggtgtctag atataataac attattatcg  28980
gttacacttc ttaagagagg tgccgcatcg atagagaaat caaacaggag aataatcaat  29040
gatgcatttc ctttggtaaa aaaggaaaca tccatgggaa gaatggctac tttatatgaa  29100
tttaactcta tacacgcaca cgctttatca gatgagatta atagttcaca aacatctcta  29160
tcctttccta tggatataat aacaggaatg gcatctttag gtttaaaata attatataca  29220
ccagtaggag tcttgtcatc gtcatctatc tttatcaaat tagcaaatct ggatattctt  29280
gatacattct ttttatacag tgaattgcat acatcggata ccgcattatc catatatggc  29340
aaatctgcaa tcactgtatt gtttttagat tgtccgccaa tgtgaacgtt cttgactttt  29400
tcacaacatg gtttaatcat gaaatcattt tttatatgat ttatttcctc gccatgtttt  29460
actaacgcgt ttagacagta tacaataaca ccatccatgg cgaccaccaa ctaaatagtg  29520
ttattttaat ttgtatgtaa ctattaagat ttagtcaagt ttactaaatc gtttagatga  29580
gtagattctt tccacgtttt atcctctctt atcctagtaa atctaggaaa tctaatggat  29640
attccatttg cggtatggga cttggaagat gtaaactctg ctcctgaaat ttcccatatc  29700
tgagattgtt ttggatcctc tactacaaaa tcgggaatat agattttatt aactactaac  29760
cactctggaa tttttttggg atccttgtta attttaatca tctttaattg gtcttgcaac  29820
tcccttaacg tattatcatc gtgtcctgaa cacttggtaa ccgtcttcca tttaccggat  29880
tcatcgtcgt aacaacccat tagaaagact gccatgatac caccctttgc tcctttacca  29940
tagtaagcac ctagtactac taaatcggca gaatctgcca tggaaccctc gttcaaatag  30000
tctcgcttta tttttaacca tcttctcttt cccggttcgt atactccatt aatatctttt  30060
aagaccaatc cttctaattt tctcgttagt gcatcatcca atacgtcagt taactgagac  30120
tcgttactaa tattcgtcaa ctctgagaat actattctat tgggtatttc aaccataaca  30180
tctttgagaa aagatcttcg ttcgtacaat ggaatgtccg tcatatcgaa tccatcaaag  30240
tacaaacagt caaacacgaa caaacacatg ttagagtttt tatattcttt ctttttgtgt  30300
```

-continued

```
atacctaaac ttccaaacgg gagcggtaca ttatgttcgt ctacaagaac aatttcagaa  30360
tccaatacga tagacgtagc ttttttaaat gctttcggta tgtattcttt gagataatcc  30420
actttatgag agagtactgg tttcatgttt ctactaaaga aggcaaactc gttattattt  30480
ttatgaactt gtactctttc accatcgtat ttgacttccg caaacattcc tgatggaaat  30540
tttttaaacg ccttattgac agaatcacac gattccgcta acatgggatt aattggagtc  30600
ataacagaaa tagatataga gtctagattt tgtttagatg cattttctat tatctctttc  30660
aagttattag attttctaaa cacatcatag gcatgaggac taatagcgtt aagtacgtac  30720
cgagggcccg ctttaatttt tagatcttta tcaataagca tgactacaca ttttaaatca  30780
ttacatgtac aaacggatgc gatatcagtc aataatttta tttgatgcga ttctttagtt  30840
acggatgata acgtagttaa aaaactatcc acttcttcta aagttaaaat gcttttatct  30900
cgtggacgga tttctgtgtt ctctttgaag aaagtcctaa tagtgtctcc tatatatccg  30960
tatcctaaat cttgtagcat atcttcctga gattgtttaa atattatact atataatttt  31020
ataatttgtt tatcgttcat gttataaatt ctatcgtcta atccgggaag caatagctta  31080
atgatcaaat atttatcatc cctatctgtt ataaagtctc taattaattt agatttttct  31140
ttatatcctg atgcgtgata tatatcacag cataattttc taaattcgcg aagcgacgtc  31200
atttaataaa aaaagtattt ttttttaata ttttcacaaa tatcgttcgc ggatattatt  31260
agacaattgt agtatattct cacgtatcac ttgtttaata tctatatccg ctattctgga  31320
accgagtact tcggcatacg tagttttaaa atctggatta ttcattatat attttagagt  31380
aatgatagca tctactatat tttctaggtt atccttataa aagctcataa acttgttaac  31440
tatacaatcg ataatttcat tgtcgtctaa tgaattaatc aattcggtct gatagatctc  31500
ttgatctata atagtatata cagtatctag gaaagagata aatggattat ccaagtttga  31560
tctacacatg ataaaattta caatgtcctt gtttaatata tcattatcta tagtttctat  31620
cttggcaata actaattgag atattgatgc gagttcggta tgcatatcgg acacgtatcc  31680
gagtactgat tccaagttgc cagagtaata tgcttcatcc atttataaaa aatgtaattt  31740
cactattaca tccacagttg ccccactggt ccagtaaccg tgtgtatagc ctctataact  31800
atattcttaa tcaactcctt ctttacatct tcctcgaatt cagaagaaat aatttgccaa  31860
tgaatatctc cttcttcaat cattttttta tattcttgta atacctttttg ttggaatgta  31920
acatcttcat aaatttcctc gccgacgttt ctattaattt ctttgctacc agattccaag  31980
aatataacta agtcgggttt aggcaatcca gattcataac tcttactgag agtcattgac  32040
gcgcctttag cggcggcata cgctactcca gagaatgcgt atctatcaac tattaaagta  32100
attccctgtt ctagttgttc ttgtataaaa gatgcaaact cccatctatt tgcacaaaat  32160
aatagattaa ctatatgatc attataggtt tttttacgag ttagatagtc atctatcatc  32220
tttccagtga cagtggatct ctgaggaaag ttaagatatt ttatcgtgtt tgccggtata  32280
gattccatga tgttcataca ttgtgttgtt tttccagatt tgtccaatcc ttcaaaaacg  32340
attaatgccc cacgagacat ttttgtaaac ctaacatatt ttttacaatt tatgcgtata  32400
ataaaactga aaataaatat atggtcatcc gagacgatta ggtctacctt tatagatcat  32460
gggtaacaaa aatattaaac catctaagga aaatagactg tccatcttgt ccaaggataa  32520
gatggattca tttaagagag gatcctttag agaaaagtcg cgtgcaacca tccaaagatt  32580
ttcatctctt agacgagaac atattaaagt agaccatcct gacaagttcc tggagttaaa  32640
gagagggata tatgaaataa ttcagaaatc gtcgtctata gatgtggaca aacggactaa  32700
gctcatgtcc aacataaaaa cgatgatgat aaatccattc atgatcgagg gtttaatgac  32760
atctttagaa aacttggatc ccgataacaa gatgagctac tcatcggtga tgatattggg  32820
agaattcgac atcatcaata taagcgacaa tgaggcggca ttcgagttca taaacagtct  32880
gttgaaatct cttctcttgg aatactccat tagtaatgac ttgttgtatg cccacataaa  32940
tgcgttggag tatatcataa aaaatacatt taatgttcca gaacggcaac tgattctgag  33000
aggtcaatac ctaactccaa ttttcagtga tttgttaaag tatgcgggtc taaccataaa  33060
gtcaaacata cttatgtgga ataaacagtt tatcaaacca gtatctgacc tctatacatc  33120
tataagactc cttcattgtg ttacagaatc atataaggtg attggaatgg gataaataca  33180
acaattatat tttttatcat atccttcacg ctataaaaaa aattatacat ccgtttccct  33240
gtcggttacg gcagaacatg tagacgaatc atcgtcttca aaataatcaa attcatcctc  33300
tatgctctca gtgtgcccgc gtagatactt acatagattg tatcgtagtc tagatagctc  33360
agatattgga atactatcag atatatgttc ggctaatgcc atacacctat atttttttatt  33420
tgtcaattcc caatgtttag atactagact agatagagct actactattc tagaatcaca  33480
acatatcata tcctttacaa agttgacaaa gtcaaatagt cccgaatcgg agtctacttt  33540
aagtttctca ttaaataata gatcaatgtc tccatactgt ttaatagcca aatcatctag  33600
tgtcatcaat gccgaataaa tattgccgga tatagtattt ctgtgtctta tatattctgc  33660
taaaatcagt ttaaaactat acttattata caagtaagtc atactaaccg gcgtattaac  33720
cgcgcaacca atattagttt cctctggaag caccccctctt atctctatgg agtcattatg  33780
tctattatat gaaataaacg tgtcaactac tttgtcccta tcaaattcga cagtgtagtg  33840
tgtatcatta acttcattac gtatgactaa tttattttgc tgagtagaaa agtaaactaa  33900
tgcatttatt gttttagacg cattaactga tatatcaaac gccattctcg ttaattgtaa  33960
gaaaatgtat tatcttttca tttatgtaag aaataccaat aactccacac gctaatctct  34020
gatcattttt tgaaatagat aacgcctttc caataattgt agatatattt acatctgtat  34080
ctaaataaac atatgctaca ccatatctgt ttacaaagat gttaccgata aatatttctg  34140
gactgcctat ggaatcacat ccttgactaa tatctccgta acgatgaatt atcaaactat  34200
acgttccgga ttttaatcca ataactttat cttttccatg gactggttca aagtaaataa  34260
ctcctctgat attatcgtgg tctattatac aaacagccat tatttagtaa aatagaataa  34320
gtagtctgat attatgagtg gcagcaatgg ccgtgtacgc ggttactggt ggtgccggat  34380
ttctaggcag gtatatagta aaactgttaa ttagtgcaga tgatgttcaa gaaatcagag  34440
tcatagatat tgtagaagat ccacaaccaa taacctcgaa agttaaggtt ataaactata  34500
tacaatgtga tataaacgac tttgataagg taagagaagc gctagatggg gtaaatctga  34560
ttattcatac agctgctcta gtggatgtat ttggaaaata caccgataat gaaatcatga  34620
aagtaaacta ttatggaaca cagactatat tggcagcttg tgtggaccta ggaatcaagt  34680
atttgatcta tactagtagc atggaagcaa taggacccaa taaacacggt gatccattca  34740
tcggccatga gcataccctt tatgatatat caccaggaca tgtatacgca aaaagtaaac  34800
gtatggccga gcaactggtt atgaaagcca ataattccgt aatcatgaat ggagcaaaat  34860
tgtatacttg ttgcctaaga cccactggaa tttacggaga aggagacaaa ttgatgaaag  34920
tcttttacga gcaatgtaag caacacggta acattatgta tcgtacagtc gatgataacg  34980
cggtacatag ccgggtatat gtaggaaatg ctgcatggat gcacgtgttg gctgcaaaat  35040
```

```
atatccagta tccgggatct gagattaaag gaaatgctta cttttgctac gattactctc  35100
catcgtgttc gtacgatatg tttaatcttc tattgatgaa accattggga atagaacaag  35160
gatctaggat tccaagatgg atgctaaaaa tgtacgcgtg caagaatgat atgaagagaa  35220
ttctatttag aaaaccatca ctactcaaca actatacgtt gaagatatcc aacactacat  35280
ttgaggtgcg taccaacaat gcagaactag atttcaacta ctcccctatc tttaacgtcg  35340
atgtggcatt cgaacgaaca cggaaatggc tagaagaatc agaataagta ttttttttta  35400
aaaaaataat cgagtagggt atcaccacta cacagtaaga gtacagtaaa taaaaagtat  35460
ttatatactt atttttatag atcgtattat gcgctttcta catccatatc atcgtcatct  35520
tcaatatcga taatattttt ttcttctacc ttgacatctt ttgcctcttc gacagcaact  35580
gattgcgcta ataatacatc ctttctttt ttctttttag gtgtgacatc aatagttatc  35640
ttttccaagt tatacgatat ggtaacaaca ttaccaattt ttgaatcaac cgtaattttg  35700
attttatcca tttctaatag catagcataa ttaagagttc atttttattt ttttaaacac  35760
gtatatggtc actatcaatg tagacgctat tagcatacat attgcagtaa aatcatagat  35820
gtcatttata tctttatacc atataataga atcgtatcct attatagtaa tacacgtgga  35880
ccgatgtaga gaataagtct tatgtttaga tgttaatata gtagatgtac tcgttgccaa  35940
atttttaatg agacacgata catttactga gcattgtata tcattatatt ttaagtttcc  36000
tgataatgag acaatcaaac taggattaag tgaaccatat ttgtgtttta aaaaataacc  36060
atgtgtaaaa aagacattat cgtctagttc atctacggtt aacgtgcgat taataaaatt  36120
atatctatat ggaatatgcg gattatattt tatatttact acattataga tcctatcaaa  36180
atacaaatgc ccataacata attccacatc ctctgaatga aatctaaaaa tcgatgaact  36240
gtatgccaat accggcatta ttgacatcgt caatatggat attatccatt tcatcatcat  36300
catttaaaat tgacactaca tatgaatatt actttttatt ttaattacca gttgcacgta  36360
cacgggtagc gtgatctcta cacgttctat acacgtcacg tctggatgtt gttggcttac  36420
ccatcaaaaa tataagtgcg gtatgagttc tcgctataac gatcggagat acaggggcgt  36480
acccagtaag caactccata gcatacgtgt tctcatccat tagagagtta gtatatacaa  36540
tacaatattt ctgaccaata agaggtttta gaatattacg attagtgatg agaggattaa  36600
tcttggcaaa tgttctgtta ggaatagcag ctagaacatt ctttgtagtc ttgtaatcaa  36660
cgatggcggc atcctcgaac ttattatttt ttgagatatc ctcgataatt ttatgccatt  36720
cagccattgt tatttattat atatgttttt taataagaca tctattggaa taaacttgac  36780
attagcattc tattcttact acaaaatata aaatataaaa taaaatatac aatccaatac  36840
tcacataatc caactcactc gaacactatt tttccaatta cgataacaat attgcagaat  36900
gtactcgtta ttatttatta ttttgatgtg tataccattt agttttcaaa cagtgtatga  36960
tgataaatcg gtatgcgatt ctgacaataa agaatatatg ggaatcgaag tttacgtaga  37020
agcaacacta gacgaacacc tcagacaaac aacgtgtgaa tccgaaatcc ataaatatgg  37080
cgcatctgta tcaaacggag gattaaatat ttctgttgat ttattaaact gttttcttaa  37140
ttttcataca gttggtgtat acactaatcg cgataccgta tacgcgaagt ttgctagttt  37200
ggatccatgg actacggaac ctataaattc tatgacccat gacgatctag taaaattaac  37260
agaagaatgt atagtggaca tttatttaaa atgtgaagtg gataaaacaa aggatttcat  37320
gaaaactaat ggcaatagat taaaaccaag agactttaaa actgttcctc cttctgatgt  37380
aggaagcatg atagaactac agtctgacta ttgcgtaaac gatgtgactg catacgtcaa  37440
aatatacgat gagtgcggaa acattaaaca gcattccatt ccaacactaa gagattattt  37500
taccaccaag aatggtcaac cacgtaaaat attaaagaaa aaatttgata attgttaatt  37560
gttattttta taaaaacaag aacggtacgg cgatatttat ttttttctaa aacatctaac  37620
cgaagtagtg gtatgataaa aatgtagttt gggagtattc gttgtactac aaatatattt  37680
ccgtttttta gttccattct tcgtggcatt tttagctata aaattatatg gggttgtctg  37740
gtttaatatt tcggattctc ctacccaata tccgcgtcta atgcttctta aaaaacttaa  37800
ctcgtttgga gtctctatct taattagatc cgaatttgga tttagagctt tgcatgcatt  37860
acgtccttcc tcccaggttt ttcgatcagt agataaatgg atacatttat tattatagct  37920
tatccagtca gtaggacaat cttctctaat atatgcatct tttatcgttt tatctattga  37980
tggtgtatga actaatttac gttctacaac ttttaatagt gtcgctgtaa aaataattcc  38040
aacaattaga ccgcatatta cgcagcaagc ataaccagca taatctgtct tatgtttgtt  38100
cattgtcgtg cggtgtactc gattaagatt acattttaag tatttttttc atttgtggca  38160
ttcctactcc tatccctata tctgctataa ataacggttt cgaagttacc attactgaaa  38220
atagtcgcgc atcgacttgc gagctacgag tttgtttaga ttttgtatcg aacgaatata  38280
tagaatttc ttttatgaag tatattctat attcccgatg ttcattttcc ttctccttta  38340
tatcgaacca tttaacacca gacggtcctt cgaagatagg ttggttagat aaaggcttta  38400
taatatcatc tagtacatta tatttttcta tgacttcaaa cgtggtatgt ggaacaactt  38460
ttccagctgg taaacatata ccaggagctg gagacggcaa ttgctttgta tatccttcca  38520
attttgacgt agaaaaagat tgtttaatgg tattcataga ataggtacat aatgcggact  38580
tggaataagg actatcgaag aatacatata gtatcgtatc attatctgtt tttatagttc  38640
tagaatgaat aatttgtcta taacttcttc cgtcgatatc acattctaat tcgactttga  38700
gaaacgtcga ccatctatga ctagacaatg atgatggacc accttcgtcg tttaggcaca  38760
tttgtgctat atacggaatt ttgacaattc tctttgagcc gatagtatca gtgaaaagaa  38820
tgtaaacttt gtcataagta ccatctttat cgacgaatgc tcctcgtaaa ccatcttttg  38880
gaattacgtt atccgccgtg tataaatcat aaccacatgg tccgtcaaat cttctccatc  38940
gtttaattcc ttcttttgat atgtttatgt cagatagtac acatccgttg tgactgatta  39000
tcgttacttt gctattttga taaggagcgt atcctctacc tctatgtttt gggtcgtctg  39060
aaccgtctat tttccaacat ttgggatttc cgttattggt tccgcatcct ctacttttat  39120
agatgttgtt atataattat tattagttaa accagttttg tttagtttat tatttgaaaa  39180
tgtgtatacc gccccattaa cacccgtgta taatacgtcg tctaataagt aagtagaaat  39240
tatttcttca ctcgtttcaa acttatgcca ttcaataccg ttagcaaaat agaataaaat  39300
aaataacaaa ggtatcattt taaataaata aaaaatgtca agagttagaa tatcgttgat  39360
atacctctat acgttggttg ttataacaac tacaaagacc atagagtata cagcatgtaa  39420
tgataccatc attattccgt gtactataga taatccgaca aagtatatta gatggaaatt  39480
ggataaccat gatattttaa cttataataa aacttccaag acgacaatat taagtaaatg  39540
gcatactagt gctagacttc attcgttatc agatagtgat gtctcattga ttatggaata  39600
taaagatatc ttaccaggta cttatacatg cggggataat actggaataa aatctactgt  39660
gaaattagtt caacttcata ctaattggtt taatgattac caaacaatgt tgatgtttat  39720
ctttacgggc attactttat tcttattatt tctcgagatc acttatacat cgatatccgt  39780
```

```
tgtattttct actaatttag gaatcttaca agtatttggt tgtgttattg ccatgataga  39840
gttatgcgga gcatttttgt tttatccgtc aatgtttact ctccggcata ttattggatt  39900
gttgatgatg acgttaccat ctatatttct tataattact aaagtatttt cattttggtt  39960
actgtgtaaa tcatcatgcg ctgtacacct cattatctac tatcaattgg ccggatacat  40020
tttaacggtt ttgggtttgg gattgagttt aaaggaatgt gttgatggta ctctgttatt  40080
atctgggttg ggaactatta tggtgtctga acattttagc ctgttatttc tagtctgctt  40140
tccgtcaacg caaagagact attactaggc atgtgtataa taccacgagc tagtagacgt  40200
ggaagaggaa ccaggaacta ttgttatttt ataataatcc ttgatcttat tcttattctt  40260
tttatcagat tttttgcttc cagttttatc agtagatata caacagagtt tcataaaaag  40320
agaagagaat gaatccattc cgtacagtat ttgataatag ctttttttc gttttatgag  40380
gtatttagag attagagatg attaatgatc cccatactag aaatctatta atccacagaa  40440
atactaatgc tcatatttat attatcaatt ctaccgtaca atatttgttc cttgataggt  40500
acagaattgt acgactgcat tttttgtat actaagtcga atggatgctc gaggttacaa  40560
acatgtatta aagtatcttg ctcgatgcta gaatttatgt acttggcaga ggacatacct  40620
atacagtttg atggaatagg aaactgctta ttgtcgatgg ttataatgga ataccactta  40680
ttattcgcaa atatctgatc gcatatgtgt ctatccaaat agtcggtaac tcgtctaata  40740
atgaatacag acaacggcga ataattaatc agtgatagat tgtttacata cagtatgtcg  40800
tttgtaaacg atgttaccaa tcgtttgcta ggtatatccg ctttaacaac caatatggtt  40860
gtaggaccct tgctaactac gacacattta ctcagtgggg atatgattac agcatgatca  40920
atgggaaagg ttagaatatt tttgccattg acgtcattat ctatagagat aacacatcct  40980
ccgacagaac taatacagag tataatcgtc gataatctat gaggaataag atggtacatc  41040
tcattgtcat ttacaacttc tacgcttaag atgttggtaa gaagtaccgt ttcatccatc  41100
tgtctattga tctcatcaga tataattttt tgatgttctg tatctatata atatctacag  41160
tcattattag caataaaatt gctaatttta gaaatgccga atacagggaa tatctccatt  41220
tgtacaacgt gacggcagca ataatactaa atattacttc aattttataa aaaggaaact  41280
aatcacacca atgattctat atcatcgtgt tcatgatctt gttcttgctt attaagataa  41340
tcatcgctat gtgctcgtct aaacggatta ttctcactaa atttattgtt gagttctgta  41400
atgaacggat ttgacttgct acaaatactg gttttattat aatttacgaa aggattggat  41460
gaatagttag gattctgttt ggtatcttca ttaagtacta ctgtagtgtt ctgataaata  41520
gtctgttcat tacgatcatt atttattagc agcgtgcttc cagcaacact atcgtaaatg  41580
tgttctgtgc taggcgccat aacattggat tcgttatccc atattaaact accagcgaag  41640
ctatcatcgt ccaatatctc attcctagaa atattatcta cgtcattgtt ttgttccata  41700
gcactacagt gatcctccca gtctgattcg ctatcagttg atttactaga tttgctggaa  41760
ttagaactct ttatcttttt taattttgtc atgataattt tattgtcatt atagacagta  41820
cgtatctttt tcctacaaat atataatata taacatacta atattgttcc cgcaactacg  41880
gtcaccgtga taagaggtac cagcatcatt tctgattgct caatatacgt actactagtt  41940
caatatttat tgttttatta tttactttac aacttttatg ataaaaaatt actattgcat  42000
ttcccatcaa ttatgatcca tccattgccg tctgatatgc agaatgaaga attaaacgac  42060
aatttcattt tcagattatc tgaaggattg atgattagat gataatctcc agctgtatac  42120
aggttatacg cttctatgat tgtagcgtta aaaacatcaa tagatgggaa tagataaaat  42180
ggctgatgtt tatcttctat atctaacatg atatcatagt cgcatgctat gatgatggta  42240
tttttgatc tgtatgcggc acaaatgcta taaatgttga atctagccaa atcattagaa  42300
tcctgaggaa ctattttacc cttatagcta aagtagcatt tttgcatgtc ggaatatttt  42360
atatcccgta catctatttg gacagttttt atgttaccta taatgtatgg tcctataaag  42420
tccatgattg agatatcgag atcatcatac aatgtatctg ttatagtcaa cacacccatt  42480
ggagtaataa caaacgcggc gtccatggcg gcgtacgtta acgacttatt attaattcat  42540
tttttgttgt cacttgtaga attttttaac acatagtaca gattgagtac ttttacatac  42600
tgttttaacc agttttccag acttgtatat ataacacgct tcagcatccg tcgtactgtt  42660
tagttgttta aaatttgtta atttactaat atctatatct ttatcattat taatatctaa  42720
ccatttatca ttggtctttt ttaaacttac ccaataatct ttataaaaaa tactaaacaa  42780
tactctcaga tgtctagtat ccggtctagg caatctggct cgtaatttac gacactgata  42840
aaccgcatta tctgtagaca ttttaatgtt agtatctaaa taacaatgtt tatcgtattg  42900
tatccatcca ttggcgcaag cactaggcat cagttcttct ttgtaatgca gaaatgttcc  42960
tatgccacta ataatggttg agagtatcat cattatagcg accggcaccg acaacttctt  43020
aaacctactt acagtttgtc tattaagcga tttcatttat taatgtacaa aaataaatat  43080
tagttcattg ttttaacaca aaaatacttt ctaacttctt gtgatacatc agaatcttga  43140
taatcggatg tagtttttgt aattggatta ccatcagatc cccatgtatc cttaacataa  43200
tcaatgagcc aggtagtcaa gacatcggat ttattgggta gtgttgatga ttccgcagtg  43260
caatttgctt tagcatccga gaataactgg tagtctgaat gtaatatata acaagaaccc  43320
tggtaatata aaccattaca gctttctttg tgatcatatt gcgtagtgct agacgcaacc  43380
tttctatgag tagatgatgc agcagcaacg gcaacagcgg cgtcagtaat agcagcctcg  43440
ttagcagaca tgcattgatt taggcgcact atgagaaacg cggacatggt aatcatagat  43500
agtagtgaaa taaccataga tattctaata catagaccaa tcacgcgttt gcgtttattc  43560
tttccctgaa ttttgtctct gtaaacagta gcggagaaca cagatgtctg ctcttcgtcg  43620
ttttctggtg tcatcatgat aataaatgtt atttatgtca cgatgtgcct tctttgttct  43680
cctccctact aacgacctta gtttccata ttttgattta ttatcaaatt aatttagtaa  43740
ctgtaaatat aattatgaat tgtttccaag aaaaacaatt ttcaagagaa aatttattaa  43800
aaatgccgtt tagaatggtt ttaacgggag gatctggatc tggaaaaact atctatttac  43860
tatctctgtt ttctacacta gttaaaaaat ataaacatgt attcttgttt acacccgttt  43920
ataatccaga ttatgatgga tacatttggc caaatcatat taatttcgtt agtagtcagg  43980
aatctctaga atataatctg atacgaacta aaagtaacat agaaaaatgt attgctgtcg  44040
cacaaaatca taaaaaatca gcacactttt tacttatttt tgatgatgta ggcgataaac  44100
tatcaaaatg caatactcta atagaattct taaactttgg aaggcattta aacacgtcta  44160
ttattctact atgccaaact tatagacacg taccaatatt aggacgggct aacattacgc  44220
atttttgtag ttttaacatt tccatctcag acgcggaaaa tatgctacga tcgatgcctg  44280
taaaggggaa acgaaaggat atattaaaca tgttgaatat gatacagaca gctagatcca  44340
ataatcgatt ggctattatt atcgaagact ccgtattttg tgaaggtgaa ttacgtatat  44400
gtaccgatac cgccgataag gacgttatag aacaaaagtt aaacatagat attttagtaa  44460
atcaatattc gcacatgaaa aagaatctaa acgctatatt agaaagtaaa aaaacaaaat  44520
```

-continued

```
tgtgcaatag cgatcaatca tcatcgtcaa aaaatgtatc ataattataa ttattaactt  44580
ttgtaacaat agtcctattt agagaaagtc tatcgataga cgatcccaat ttgtaaattg  44640
ttccactact tgtcactcca tgatatgata aatccatgta aaatagcatc atctttagat  44700
cattaattgt taccttcccc aatacaacca aatcatcatg atatatacct cctccagaca  44760
agtatttaac aacggtagaa tgctttggct tataaaatac aaatgacatt cccttatgtt  44820
taatcttaat cttttcttta gttattgaat cgttacaatt ataaaatgat gtttttttcca  44880
aaaacctaag tgtatttaaa atagatgcca tgttaaaaat gtccgccgtc gactttttgg  44940
aacgattgat aaaagctggt gtttatattt atgttttacg gacaaagtgt gtaattgcag  45000
ctttactagt aaaaaactat tccataaaag acgaataaga tacaaacaca aatgtttata  45060
taatatttaa atggaagacc ttaacgaggc aaacttctca catttattga taaatttatc  45120
taataataaa gatatcgatg cgcaatacgc gtctacatta tccgtggtac atgaattgct  45180
atccgctata aattttaaaa tatttaatat aaacaaaaag tcgaaaaaga attccaaatc  45240
aatcgaacaa catcccgtcg ttcatcatgc agcatccgcg ggaagagaat tcaatcgtcg  45300
ttgaactcga accctcattg gctacattta tcaaacaagg atttaataat ctcgtaaaat  45360
ggcccttgtt aaacattgga atagttttgt ctaatacatc taccgctgtc aatgaggaat  45420
ggctaactgc ggtagagcat attcccacca tgaagatatt ttacaaacat atacataaga  45480
tacttactag agaaatgggg tttttagtct atttgaaaag atcccaatct gaacgcgata  45540
attatataac tttatacgat tttgattatt atattataga taaggataca aattctgtaa  45600
ctatggtaga taaaccgacc gagttaaagg aaactttgtt acatgtattt caagaatatc  45660
gtttaaagag ttctcaaaca atagagctta tagcgtttag ttcaggtacg gtaataaacg  45720
aagacatagt ttcaaaatta acatttttag atgtggaggt atttaataga gaatataata  45780
atgttaaaac tatcatagat ccggatttttg tatttagatc tccatttata gttatttctc  45840
ctatgggtaa actaactttc ttcgtagaag tatattcgtg gtttgatttt aaatcgtgtt  45900
tcaaagatat tatagatttc ttagaaggtg ctctaatagc caatattcat aatcacatga  45960
ttaaggtagg taattgtgac gaaacagtat cgtcttataa tccagagtct ggaatgttgt  46020
ttgttaatga cttaatgact atgaacatag tcaacttttt cggatgtaat tctaggttag  46080
aatcatacca tcggttcgat atgacaaaag tagatgttga actatttatt aaagcattgt  46140
ctgatgcgtg taaaaaaatt ttgtcagctt ctaatagatt ataaatgaac tctctatcaa  46200
tttttttttat tgtggtagct acggctgcgg tgtgtttact ttttatccag ggttactcaa  46260
tatatgaaaa ttatggcaat attaaggaat ttaatgctac tcatgcagca ttcgaatatt  46320
caaaatctat aggtggaaca ccggcattag ataggagagt tcaagatgtc aacgacacaa  46380
tttctgatgt aaagcaaaag tggagatgtg tggtttatcc aggaaacggt tttgtatccg  46440
cttccatatt tggatttcag gcagaagttg gacccaataa tactagatcc attagaaaat  46500
ttaacacgat gcaacaatgt atagacttta catttttctga tgttattaac atcaatattt  46560
ataatccatg tgttgtacca aatataaata acgcagagtg tcagtttcta aaatctgtac  46620
tttaaatgga cggaactctt ttccccggag atgacgatct tgcaattcca gcaactgaat  46680
ttttttctac aacggctgct aaaaagccag aggctaaacg cgaagcaatt gttaaagccg  46740
atgaagacga caatgaggaa actctcaaac aacggctaac taatttggaa aaaaagatta  46800
ctaatgtaac aacaaagttt gaacaaatag aaaagtgttg taaacgcaac gatgaagttc  46860
tatttaggtt ggaaaatcac gctgaaactc taagagcggc tatgatatct ctggctaaaa  46920
agattgatgt tcagactgga cggcgtccat atgagtaact taactctttt gttaattaaa  46980
agtatattca aaaaatgagt tatataaatg gcgaacatta taaatttatg gaacggaatt  47040
gtaccaacgg ttcaagatgt taatgttgcg agcattactg cgtttaaatc tatgatagat  47100
gaaacatggg ataaaaaaat cgaagcaaat acatgcatca gtagaaaaca tagaaacatt  47160
attcacgaag ttattaggga ctttatgaaa gcctatccta aaatggatga gaataaaaaa  47220
tctccattag gagccccaat gcaatggcta acacaatatt atattttaaa gaatgaatat  47280
cataagacca tgctagcgta tgataatgga tcattgaata caaaatttaa aacgttaaac  47340
atttacatga ttactaacgt gggtcaatat attttatata tagtattttg tataatatct  47400
ggtaagaatc acgatggtac tccttatata tacgattctg aaataacgag caatgataaa  47460
aatcttatta atgatcgtat caagtatgca tgtaagcaaa tattacacgg tcaattaact  47520
atagctctga gaattagaaa taaattcatg tttataggat cacccatgta tttatggttt  47580
aacgtaaacg gatcacaggt atatcacgac atatatgatc gtaatgccgg ttttcataat  47640
aaagagatag gtagactact atacgcattt atgtactatc tatctatcta taagtggtag  47700
atttttgaat gatttcgcac tattaaagtt tacgtattta ggagaatcct ggacatttag  47760
tttgagtgtt cctgaatata tattatatgg tttaggatat tctgttttcg atactattga  47820
aaaatttagc aatgatgcta tactcgttta tattagaaca aacaatagaa atggatatga  47880
ttatgtagag tttaataaaa aaggaattgc taaggtgaca gaagctaaac ccgataacga  47940
taagcgaatt catgctataa gacgcatgaa ggctgaacgt gaaatcgctc gtaaaaactg  48000
cggaggtaac ccatgcgaac gtgaagaggt tggaatatca actagatgcg gagaaagaaa  48060
aagttaagtt ctacaaaaga gaactagaac gtgatcggta tctttctagt agatatctta  48120
cctcttcttc agatccacat gagaaaccat taccaaatta tacatttcct cgcattgaag  48180
tagctccgtt gatgactgag gataaagaac cagaacctgt agaagtggtg cctccatcgt  48240
ccacagacgt taccgaaccg attagtgatg tgacaccatc ggtggatgtc gaaccagaac  48300
atcccccagc tttctgaata tcagacttca gtatcccaag tagcagttac acctccacca  48360
aaacctaaaa ctccacagat tttcgaatat cagacgtccg attctatagt taacaatcca  48420
cgcccatttt ataattcgga tctcgaattt gatgatattg atatgtatct actaccaaac  48480
tagaatatta caccagaaaa gacggtttga gatcaacttt atctaatggt ttataaaacg  48540
aaggaggcct tcgttcgaaa tctaatttaa cttttacgcc tctggcgttc atttgagtaa  48600
gaaatacttt agatacgtgc gtggtatcaa tttttgttaa gagaggagag agattaagtt  48660
ttgaacatct aagacatgta ttaataccct tgatttgtgc tgctatgtct ccacaatttt  48720
cacaaacata cacatcttga taatcttctt ccgaatcttt caaaacttct gtaatagtat  48780
tggctgcacc atgcgctatt aaacagtctc tctccatttc tccgaacttg atacctcctc  48840
cacgttttcg tccctcattc gcctgtctaa tgagcttcgt ctttttacct ctacatctaa  48900
cggttgcctt gtcctgagtt aaatgcctca gacgcaagta ataaattggt ccaaaaaata  48960
ctttggatgc ataaggctta tccgtttcag gatcatagag aatcttttca caaaagattt  49020
tatccgataa ttcttcatca gacaatttcg gatttgaatg ctcataacat tgtttagcga  49080
attgcatata tgtatcgatg gatgtttcgt tactactagg aaaacagaca ggtcggtttt  49140
ctcccttatt gttgtacggc ttagcagaat atgcggctgt taaaataacc tctatcaaca  49200
tagatatagt ttttctagag aagatggatg tagaattaat aatgacatct ggtgtgatac  49260
```

```
cattttcatc gtatggaagt tccgtttcat ccgcgatata cgcgactgtt ccccttttgac  49320
tcgttctagt ggtaaatttg tctcctagaa tgggtcttct ttctttcatg gttaatactc  49380
gtaccttaac tttgtcagta agttctactt gtactcgttc aacgcgagat ttgtacatat  49440
cggtatattt ttcggaaaca tcaaagctaa tctgattatc tctagcaaaa tcatcttcaa  49500
gagttcttga tgagatattt cgtgctatag cgtctccgga ttccaagaaa gcattcagtc  49560
taactaatcc attactttct aattttgaat aggcgttaga cctatctctt tctttgttat  49620
taaagttttc caacggaatt tctacttgat gtttcttggc tgtaacaata tcgagaccgc  49680
ctctctgaat aaattgtttt ttgatgataa ttccatcctc ttgattgata cctttgtacg  49740
acattaatgc tatagtaaca tgttggccga agcaattagc cgcaatcttt gaagtttcta  49800
aagccttact aatcacgatt ggcctctctg gatacatcaa atgaattcca ttgtctattt  49860
tatttcgtat atccgagctc agacaagaga tagcttgttt agcttgagca catccaagaa  49920
tagctctggg tccagaattg tgattgattc ccactagtga agatgctaca tatccatctc  49980
taaattcggc aggaaagtca cataaatcgt attgctttct ttcatccttt gacatcattc  50040
taaatttttg aaccgattca catacgttac taaaagtaaa ttgttctata tctaccattt  50100
cgatgacatg cggaaactct ttctgaatgt cagagaatgt catgtcgtct aatctgcttt  50160
ctaactccgg acacacatcc atcatgagct ctccgttatc cacaaccaag aatggtctga  50220
ctaatcttcc cgctccaata ttaatgcgaa tttcattcat gtgatcccta actaaagtaa  50280
tacctacctc caagttaccg aagaatccca tccgttttct acgtctaaag tcagttacaa  50340
aatcacatat catatttgga ttaagagatg cgactagagc atttctatat gtgattggaa  50400
atcctgtttc aaagtaactt atatcatctt tataatatga tctgatatac tcacaaattt  50460
tcttttccaa atccaaatac tcagacgtta gtatatttgt aatggaactc aagacagaca  50520
attgagatac taaacctacc tgaggacctc tttccggaac gtccgatgaa caaaagtaaa  50580
gatattgact tggatggtat tttctgacag aaaacatctt tgaaatcttt acttgatccg  50640
gataaaatcc aacactccta ggaatagaaa tattctgcat ccatgaatag tgaggatgtg  50700
ttcgataact accgtctgac tttttgaact ttccactcaa tagactagaa aatgcatgat  50760
taagtccagg agttgttagt acatgaatgt ttaccgcgta agtgcctctg ttcttgtgat  50820
tgttcatgat atcgtttcgg atgttgccta tgtaattctc taattcatca tgtgccaacg  50880
tctcaaaata tttgccgtac gttaggatgc gatgacaaac catcgaatct ctatctggat  50940
atctagaagt gtggtagata cagtagagaa actttcttag taaagatatc atataaaatc  51000
cctttagttg atcgggtgta tagttcatat gaggtaaaaa gttatgcagc atttcatatt  51060
tgaactcgtt gatcgttaac tgagattttt gtttaatgtg ttcagcttcc accaggtcat  51120
taatgtatgt atcaatatta aagtcagtaa tagattcagt aattcgttta gcactatcta  51180
ttatcgcgtt tactagatag acaacttctg gaggcatatc gtatgataaa ctacgtctaa  51240
tgaattctag actcactcta gataaatatt gagacagcaa aacaatattg accgttataa  51300
atgtctttgt cgatgatata ttcaacgctt ccaattgtga tatatccaga gatatcttgt  51360
aatggcgata tcttgtcggt aatacattag gaggggatac ggaggaaaac gagaaagtga  51420
atgagtttgg cttaacaacc ctaaattttg gccatgttgt aatcttttct actagattaa  51480
ttcctacttt ttcgacagat tgtttattga taaagactcc acctatgaca ttaggaacaa  51540
gatacttggc tgtatcaagt ggatttttat tcccgtatcc tattagtagc ggaattttta  51600
tcaaatgaga atcttttccc tcataactac ttattttagt gatggatata ccctctttgg  51660
tcattacctc tttaaagata tttacagtga acgtggctaa tgcgtcataa ctcttacctt  51720
taatactcgc gattataggt gagtaatctg gaggagtcac tttaacattg ctaatttcta  51780
tcataattcg ttctgtatta ttcttaaacg ataagagtgg ccgcttgacg gtcaagattt  51840
catgcaatcg atgcaatata aaattagaat acgatacata ttggaaatgt aacggtctat  51900
aaaaaactcc ggctttagga tcaggcacca aaaacttata tccgagtcgt tgatccattt  51960
ctgaattagt gttttttttt cattttagaa gcaattcttt tagacgatct accgattccg  52020
tttctatatc tatgctattt aaaatagtcg atctttcctt catcatttct atcatattct  52080
cggatttagt cacgtaattt atacaatcct ccagagatcg taatgctaca atattgagct  52140
ttttcccctt aaaaaacttt attttgctat cctcatctaa cagagagggg aaaacggtat  52200
gatccaacga cttaataaat gtcaggttaa acatccctat tttgaaattg ctaactccat  52260
aaacatcgtg ttcagccatt ttcttaatta ggaataattt ctcatctaat gccgtagccg  52320
tgagtacgtg gtttacaaca ttagctactt ctttaaagta ctcgttttgg atgatatcct  52380
cgaacaacag aaataaatta taatagacat agaataattt gtcaatcatg tgtatacacc  52440
cctttttcatc cttgtccttg gatagaataa tgtgcatagt agaatccttg aatattttca  52500
cacatgttct attagtaaaa ataatttcta tagtttgtaa tatagagctt tttccacgcg  52560
ttactataga gtgattaatg atatctactc tcattctctt agaaatggtt ttgatccaag  52620
gttgattaat gttggacctg actgtagtgc tcagatactc atcagacttt ttaccggaaa  52680
agtaatttgc attagtgcct ccatgtacag ttttctttat ttccccataa ttgacctttc  52740
tcttcttatt ggtagtttta atatatgata caagagatga cttttccctc tcaaatatct  52800
ctactgtacg agagctaata ttgctattat ctgagtttat atcgaaataa tgacaacatt  52860
tcacttgtga agaatcgtta aataccggat acgtattctg attaataatg tgtttagtaa  52920
gttggatgtc gcaatacact agtttcttaa tggcatgatg tatatcttta ttatacacta  52980
tattatcaaa catatcctct gaggaaatgc gttctttcat aagaccatat atatctccta  53040
tttcatcgca acttattaga tgaaagttaa aaatagttct ggcatatcta tcttctattt  53100
catgtagaaa ggtaaataga ttatccataa tggcgttact aacgttatta cattttttttt  53160
atgtaatttc tagatttaca cctattataa ggtgtataat tagtattcca tttatctaat  53220
acgtatctca tagccaaatt gaaactatcc gctacatcgt ctaatttgcg tctatccgga  53280
acggagtctc gcaatccgaa tgtgtccatc caatcaagaa atgcttcgac cgatctcttt  53340
tttcgatctc tatatgaatt accagacatg acaggcgaga cgcaaataac tttggcagcc  53400
gatgtatgat ataaaaagcc tttaataaaa tagataaatt tgacgtacgg cgaccttcta  53460
ggctgacgtt ctagaagaac tgtagtgtat tcatattgtg acaaatcttt agctatgtgc  53520
ctttcccaat cagaactcca gtctaatttt gatatatcca ataccctaac ggagttatcc  53580
ttgacttcta aaacagttct ggcaggattt tttgcaccta tatcaaaggc gcatattatt  53640
tcactcgaat aatctttttt tgacatcggt gacgatatta aagattgaga cgaactggtt  53700
aaagtttcca tatatagtct caatactcgg gttatttaaa caattagtat tttcaatatt  53760
gaaatttaca accttacaat tttctatttt gaaccgcatg ttattaacta acgttataaa  53820
atccgcttct ggatatccca aacattctct gcttaaatca aatgctgatt ggttttttat  53880
ttttcgtttt acagttccgg atttattaat ctcatcaact aactcatcga cagttgcgca  53940
ctcattaata tctaatttat tagtcaattg ctttaagcct gcactaccaa ccttagagaa  54000
```

```
atactttccg ttaacataat agtctcgtcc tatagtgtct ataattcgtt ttattacttc  54060
tcctctagtt tctgttccgt ttccatcata gtcgtataaa atggaaaatg tgtttttctt  54120
ttttactttt acaaatgtat gttctctaac cttggatcgt attaaatggt ctacatcttt  54180
tactaatatc ttttttcctg attttgttat aacgctagga ataaaaatat tatctcctat  54240
acgatctacc ttgatggact caatatacat gaatgagaat ttgaaaaagt ctacaacttg  54300
ccgcctaagt tctcccaact taatatacga tatggatatt tttggaaatt tatcatcgaa  54360
agagcgttct ataatagagt ataactcgtc gtcaaataat gtgtcttcct ctatttcaat  54420
ttctaaatat ttgggtatgt ttaatccgta ctcactagct agtttaaata tattaactgg  54480
agactgatat tttgatatag catcttccat tatccatcta ttgtttaaca aaacaaatct  54540
cagaaagtct attccgttat cgctgtctaa tactttgtta cacgcacttc gcatatcatc  54600
tggtatttga aaagagtttc cagatccaag ttctaccata tttttaccct tcgaataaat  54660
aaagacgctc ccaaaatata ccggtaagaa aatgtaatag cccggatcaa tattaaacgg  54720
tttatttttt acctcatcat aataatcaga tattgacgtc tcgacattag ctaccttttg  54780
cacgcctatt ttccagtaag tagatgttcc ccattctacc aaagaattat acttttctat  54840
agccgcagaa tctgaaaatt tcaaactttt gtacagacta agtaattctt ttaagttagt  54900
taaatcagcg ctagaagtca tgataacttt atttttaatc ctatgttatt tcattcttat  54960
ttttaatatt atagtacctg caatatctga aaaaatgaga cgcgaacgag ccgcatacgt  55020
aaactacaaa cgtctaaaca agaatttcat ttgtgtcgat gatagactgt ttagttataa  55080
ttttacaaca tctggaatta aggcaaaggt ggccgttgat aacaaaaatg ttcccattcc  55140
atgttccaag ataaacgagg tcaataataa taaagatgtc gatacactat attgtgataa  55200
agatagagac gatataccag gttttgcacg atcgtgctat agggcatatt ctgacttatt  55260
ttttactacc taaatggata gcaccaatgt gcgttccgga atgaagagcc gcaaaaagaa  55320
gcccaagact acagttatcg atgacgatga tgattgcatg acgtgttctg cctgtcagtc  55380
taaattggtt aagatttccg acatcacaaa agtatcattg gattatatta atactatgag  55440
gggtaataca ctggcctgcg cagcatgcgg atcgtcgctt aaacttctta acgattttgc  55500
gagttaaata ttctatttaa tacacgttct tctctggagg atgttgtaca tacagaagtg  55560
ggatcggatt cttgatgttt ccgataactt ttttgtttaa atcctagttt atctacagac  55620
agactaataa ttcgttgaac gaaatttcct atcatgtact ttatttcttt gatggatgtg  55680
ctaggaaata catataccgt cctatctaat agttctgttt ctcgacatac cctccctagt  55740
aattgctcta tttgcatatt gttgattact gccgagcaaa tgaacaaaga atccaaacta  55800
ggaatatcta aaccagtacc ggaataaaat aaggtggata cgaatataaa tctatttagt  55860
tccttgattg atttgaccat atctggagta cgtctatttt gggcgtctcc tataaataca  55920
acctctgatc cgaaaaaatc taataatcgt ttgtagaaga ataccatatg ttcacgtagt  55980
ttagtaataa ctaaaatgcg attaatagtt cctgacttga attcttctac cagggtatta  56040
agaataagtt gatttctagg ctcgtctaca gataataact tctcggtata tatatgatat  56100
ttattagatg gtccatctaa tcgttttatc atatgtctaa tattatctgt ggaatatggc  56160
tcaaaaaaac tatctactgc atagatagtt ttttttagat cggataactt ggcaatatta  56220
ataatactgt tacaataaat tctgttagat ggtctaggtg tagcagttaa aaaataacac  56280
atcatcggag gataatacgc taaaaatctt gtaactgctg tattgttcat cagattatac  56340
gtatgtgatt catccaagat gaacaaatca taatgcttat tgatatattt acaaaaggca  56400
tcgtttgtca gatgtctact gactactatt aatacatccg gactttgagt ctttagttcc  56460
tttaatagac tacttactcc atctatggat atcttatgtt ccaatccgac tgcctctacc  56520
tgtgtcttcc attgatgtat taacatttta ttgggtacgc aaatgacggt ttttctaccg  56580
tgtgtagcca taagataaca cgtggtaata gtcttaccaa atccacacgc caagtgaaga  56640
gtgatgtata gaggacgttt tgattcgatc attttcctca tattagaaac tacttcagat  56700
acgactttgc gttgaagagg atataacttt ggcgcatttg ttggattgat actagtaatt  56760
ttattatcgg tcgttgttaa tgtttcaaat actagactcg tctttacgga aggagaggcg  56820
taaaatccct taggtatcag aaacttaaag gatgatcccg gttcaacttc tacgaaatcc  56880
ccgtcttcgt taaaaagact taggggttga ccacaagtca tttttttag ttcggcataa  56940
agattatact ccatctttaa tagtgacatt ttttaatata taaatgagtt atttaagata  57000
ttacaatatg cttgacgact tctctgcggg tgctggagtg cttgataaag atttatttac  57060
agaggaacag cagcaatcgt ttatgcctaa agatggaggt atgatgcaaa acgattatgg  57120
aggaatgaat gattatttgg gaatcttcaa aaataatgat gttagaacgt tactcggttt  57180
gattttgttc gtcttggctc tatatagccc tcctctaatc tctatattga tgatatttat  57240
ctcatctttt ctattgcctc ttactagctt agttattacc tattgcttag taactcaaat  57300
gtatcgtgga ggtaatggca acactgtggg aatgtctatt gtatgtattg tagctgctgt  57360
aattattatg gcaatcaatg tatttacgaa ttcacagata tttaatatta tttcttacat  57420
tattttgttt attctgttct ttgcatatgt gatgaacatc gaaagacagg actatagaaa  57480
aagtataaat gtaaccattc ctgaacagta tacctgcaac aaaccttata ctgcgggaaa  57540
taaggtaaat gttgatatac caacatttaa cagtttaaat actgacgatt attaaaaatg  57600
ggggcagccg ttactcttaa tagaatcaaa atagcaccag gaatagcaga tatacgagac  57660
aaatatatgg aattaggttt taattatcct gaatataata gagctgttaa gtttgcagaa  57720
gaaagttata cgtactatta tgaaacatct ccgggagaaa ttaaacccaa gttttgtttg  57780
atagatggta tgtcgataga tcattgtagt agttttatag ttcctgaatt tgctaaacaa  57840
tatgtattaa ttcatggaga accatgtagt tctttcaaat ttcgtcctgg atcattaatc  57900
tattatcaga acgaggtaac tcctgaatat attaaggatt taaaacacgc tactgattat  57960
atagcatccg ggcaacgatg tcattttata aaaaaggatt atctcctggg cgatagtgat  58020
agcgtggcaa aatgttgttc taagacaaat accaaacact gtccaaaaat atttaataat  58080
aattacaaga cagaacattg tgatgatttc atgactggat tttgtagaaa cgatcctgga  58140
aaccccaatt gtttagaatg gttacgtgca aaacggaaac cggctatgtc tacttattcc  58200
gatatttgct ccaaacatat ggatgcgaga tattgttctg agtttattag aattattcgt  58260
cctgattatt ttactttttgg ggatacggca ttatacgtct tttgtaacga tcataaagga  58320
aatagaaatt gttggtgcgc gaattatcca aaatctaatt ccggagataa atatttagga  58380
cctagggtat gttggttaca tgagtgcacc gacgaatcta gagatagaaa atggttatat  58440
tataatcaag atgttcaaag aactagatgt aaatacgttg ggtgcacgat taacgttaac  58500
tctttagcgt taaaaaattc ccaagcggaa cttacgtcta attgtactag aactacgtcc  58560
gccgttggtg acgtacatcc aggagaacct gtagtaaaag ataaaaataa actgcctacc  58620
tggttgggcg cggccataac attggttgta atatctgtta ttttctattt tatatctatt  58680
tattcgcgta ctaaaattaa aacaaatgat ataaatgttc gtagacgata attcgttgat  58740
```

```
aatttattct acatggccca gtacattgtc cgattcatcg ggtagagtca tcgttatgcc  58800
agataataga tcattcacgt ttaaggaagg gtttaaatta gatgaatcga taaaatctat  58860
attgttggta aacccgtcgt ctatagatct attaaagatt agagtatata aacatcgcat  58920
aaaatggatg ggtgatatat tcgtattatt tgagcaagaa aatatcccac cacctttcg   58980
tctagtaaat gataagtaat tacgagccgt tgctgctgtt agttataaca tgctgtgtac  59040
tactatttaa ttttaccata tcttcgaaaa caaaaataga tattattttt gcagtacaaa  59100
ctattgtttt tatatggttt atattccact ttgttcattc ggcgatttaa aatttttatt  59160
agttaaatgg atatgatgct tatgattgga aattattttt ccggcgtgct aatcgctgga  59220
atcattcttt tgattctttc gtgtatcttc gcctttattg actttagtaa gtctaccagt  59280
cccactcgta catggaaagt attgagtatt atggcgttta tacttggtat tattatcaca  59340
gtcggaatgc taatttattc tatgtgggga aagcactgcg cgccccacag agttagcgga  59400
gtcattcata ccaatcatag cgatatttcc atgaactaaa ttattatcgt ccatatatct  59460
cgacattgtt gaatcattat tactacttat ttagtgaaaa gatgatatat tgcatacttg  59520
atcaatagtg aagttattgt caataaatga ttggtattct tttgttgatc ggtatttgcg  59580
tagcagttac cgtcgccatc ctatatgcgc tgtataataa gatcaagaac ccacaaaatc  59640
caaatccaag tccgaattta aattcgcctc ctccagaacc aaaaaatacc aagtttgtaa  59700
ataatctgga aaaggatcat attagttcat tgtataatct agttaaatct tctgcataaa  59760
taaaaatatt tttagcttct aaatggcgga taaaaaaaat ttagccgtta gaagcagtta  59820
cgatgattat atcgaaacag ttaataagat tacaccacag cttaaaaatc tactagcgca  59880
aatcggtgga gatgcagccg tcaaaggagg caacaataat cttaattctc aaacagatgt  59940
gactgccggc gcatgtgata caaaatgtat tacatgtaaa ccaaaatcaa aatcctcgtc  60000
ttcttctaca tcaacatcca agggctccaa aaatacttct ggtgctccta gacgtagaac  60060
aacagttact actacatcgt acaatgcgat ggatggtcag attgtccaag ctgttactaa  60120
tgctggtaaa atagtttatg gtaccgtcag agacggccaa ttagaagttc gtggaatggt  60180
cggagagatc aatcacgatc ttctaggtat cgactcagtt aatgctggga aaaagaaacc  60240
atctaaaaag atgcctacta ataaaaagat taatatgtcg tccggtatga gacgacagga  60300
acagattaat ccagacgatt gttgtctgga tatgggaatg tattaaatta aataatttta  60360
attcgtttaa cgaatatctt gagtataaac aatacaatat taagaaccgg actgttaccg  60420
attcctagtt ttgatgctac agcatcgcag tcatctccga tctccacatc gataatttct  60480
gaagtgatat cggtactcag tcctttgatt tcttcaaatc cgagttttag caatgcttgc  60540
tcgataatat ttatgacaat aataatcacg ttagtgacga taatttttcg ttttctactt  60600
tcgtgatatt gtttaatcgt tttatagatt ctatctattt catcctctga acaaacatcc  60660
aagtcctcga ctgataaggg agacccgttc aaatttgcat aattaacgat ggctatacgc  60720
ttattaactt ctgttgattt atacggagtc ttaccaaata gtattctggt aaaattatct  60780
aaattatcag atgattttgt attagatcgt tgatttctaa gattaaccac ttcatcctcc  60840
aacatctgaa ttcttttatc tttatcataa actactccca aggatggtgt ttgtgttggc  60900
atagaagata tcatagatct agattccatt attgcttcag catttttcga tactgtaata  60960
ttaaatcttt tttctcgttg ttgacgttgt tccgatatca ataactctct acgaaacgta  61020
ggaggtggag tatcgtcaat aatagtagta tgaggttgta ctcgttcgat aatagtggcc  61080
ggagaatcat catctggaaa tagatcttca ttaagttgtg aggatatttc ctctggagat  61140
gacactacgg cggcattatg ttctctatct accacgttgt taacgtgagt tagaatagac  61200
atttgacgaa gagttatttc ataattttttg ttagatggat aattatcttc tgaaaactct  61260
gtaattaaat cgttttgtat atccgtcact ggtacggtcg tcatttaata ctaaataaat  61320
gatgcctatt aagtcaatag ttactcttga tcaattagag gactctgaat atttatttcg  61380
tatagtttct accgttcttc cgcatctatg tctagattac aaagtatgtg accaacttaa  61440
aacaaccttc gttcatccgt tcgatatatt gcttaataac tcattaggat ccgtaactaa  61500
acaagatgag cttcaggctg ctatatccaa attgggcatt aattatttaa ttgataccac  61560
gtcacgtgaa ttaaaactgt ttaatgttac acttaacgct ggaaatatag atattattaa  61620
taccccaatt aacattagtt cggaaactaa tcctatcatt aatactcaca gcttttacga  61680
tcttccacct ttcactcaac accttcttaa tattagattg acggatacag aatacagagc  61740
tagatttatc ggtggttata ttaaaccaga tggctccgac tcaatggatg ttctagcaga  61800
aaagaaatat ccagatctta actttgataa cacttatttg tttaacatcc tctataagga  61860
tgttattaat gcaccaataa aagaattcaa ggcaaaaatt gttaacggtg tattaagcag  61920
acaagatttt gataatctta taggtgttag acaatatata acagcacaag atcgaccccg  61980
ctttgacaac gcttataaca tcgcagatgc tgctagacat tatggagtta atcttaatac  62040
attgccatta ccaaacgtag atctcactac tatgccaaca tataaacatc tcatcatgtt  62100
tgaacagtac ttcatttata catatgacag agtggatatt tattacaatg gtaacaaaat  62160
gctcttagat gatgagatta tgaacttttg tatttctatg cgatatcaat ctcttattcc  62220
tagactggta gaattctttc cagatatacc agtaaacaat aacatcgtac ttcatactcg  62280
cgatcctcaa aatgctgcag tgaatgtaac cgtggcgctt ccaaacgtgc aatttgtaga  62340
cataggtaga aaccacaaat tctttattaa tttctttaac ctgttggcga aggaacaaag  62400
atctacggct atcaaagtta ccaaatccat gttttgggac ggtatggatt acgaggaata  62460
caagtctaaa aaccttcagg acatgatgtt tataaattct acctgttatg tattcggtct  62520
ttataatcac aataatacta cttattgctc tatccttttct gatattatct ccgcagagaa  62580
aacacctatt agagtttgtt tgttacctag agtagtcgga ggtaagactg ttactaatct  62640
tatttcagaa actttgaaga gtatttcatc tatgactata cgagagtttc ccaggaaaga  62700
taaatctatc atgcatatag gactttctga gacaggattc atgagattct tccaactact  62760
caggctcatg gctgataaac ctcatgaaac ggctattaaa gaggttgtta tggcttatgt  62820
gggtataaag ttgggtgaca aaggtagtcc gtactatatt agaaaggagt catacccaaga  62880
ctttatctat ctgctatttg catcaatggg ctttaaggtg actactagaa gatccattat  62940
gggaagtaat aatatctcta tcatcagtat tagaccaaga gtaactaaac aatacatcgt  63000
cactacattg atgaaaacta gttgtagtaa aaacgaggca gaaaaattaa ttacttcagc  63060
gtttgatctt ctcaatttca tggtatcagt tagtgacttt agagattatc agagttacag  63120
acagtataga aactattgtc ctagatattt ctatgcagga tctcccgaag gagaggaaac  63180
cattatctgt gactcggaac cgataagtat cttggataga attgatactc gtggtatctt  63240
ttctgcgtat actattaatg aaatgatgga cactgatatc ttttctccag agaataaggc  63300
atttaagaat aatctgagta gatttatcga gagtggaaat attacaggag aagatatttt  63360
ctgcgcaatg ccatacaaca tcttagatag gattattaca aatgctggta cgtgtaccgt  63420
atccataggt gatatgttgg ataacattac aacccagtca gactgtaata tgactaacga  63480
```

```
aatcacagat atgataaacg cctcattgaa gaatacaatt tctaaagata ataatatgct  63540
agtcagccaa gcattggact ctgtagctaa tcgttctaaa caaacgattg gagacttgag  63600
gcaatcatcg tgtaaaatgg cattgttgtt taaaaatctt gctacatcca tctacacaat  63660
agaacgtatt ttcaatgcta aagtaggcga tgatgttaag gcatcgatgt tggagaagta  63720
taaagtattc acagatattt ccatgtcatt gtataaagac ttgatagcta tggagaatct  63780
caaagcgatg ctatacatta ttcgacgaag cggatgcaga atagacgatg cacaaattac  63840
tactgacgat ctagtcaagt cttactcatt gatccgtcct aaaattctaa gtatgataaa  63900
ctattataat gaaatgagta gaggatactt tgaacacatg aaaaaaaatc taaatatgac  63960
agatggtgac tctgtctctt ttgatgatga ataaatgtca tgttatacag ctatattaaa  64020
atctgtagga ggactggcgc tatttcaagt agccaatggc gccatagatt tatgtagaca  64080
tttctttatg tatttttgtg aacaaaagct acgaccaaat tcattttggt tcgtcgttgt  64140
tagagccatt gcaagcatga taatgtattt agtattaggc atagcattgc tgtatatttc  64200
tgaacaagat aacaagaaga atactaataa tgataaacga aatgagtcgt ctataaattc  64260
taactccagt cctaagtaaa atattttagt agcgtatcct tatcgcgttt gcttatcttg  64320
aatgaactgg tctttttaa ctcgttgatg aattttgtaa ataattcatt tctatcttta  64380
agtaatttta ttggaagttt tgattccaca gccaatgaac atgtaaattg tgaatcattt  64440
tctatgacca gttgtaactt ttcatacact gtaatcaata cagtatttac catttgatta  64500
attacagcgc ccgtactagc actccattga acaagatcag attttagatt aattagataa  64560
aatctatatg ttatttcaga taatgaactt accagataac tctcttgacg gatattaaaa  64620
atgccagatg aatgttcatc tcgaatagcc agagctactg tagagtaata cggttcaaaa  64680
tcataaacgt gatagtttcc aaactggtat ccgagttttt cttggatgat ggatacttga  64740
gagttgaatt taaatttctt actatgttca ttatatagtt ctggaaagaa tgcttcaatc  64800
attgtttctg taagtttgca tccttttgat gcgatagtta aaagtgctat ataaggcgcc  64860
acgataatgt tatttttttt ggtaatagtg acgtctttta cagcgtcaac gcatctgaac  64920
aaataatgaa tctctctatg atctaaaaaa taaagtcttt gtaaaaagaa tcgtagtgct  64980
agtttctct catcatcctt agatctatgg gcgaatagac gtctactacg ggatataaaa  65040
ccgctatttt cctttatcat aggtgttgtt tgatctatat ttacctcccc tagttctacg  65100
gaggcctcca aattaagatc tggtactggt tcgaacattg taagacttac atcatcggta  65160
gtagattttc actttacccc acgatataaa tatgcgatat atagtaagtc cgcaattggt  65220
attacaggtg ggtaaggggc aggaggtaga acgagcccta tatctcactc catatgatta  65280
catagatgag aagtcgccca tatattattt tttacgaagt catttaaata tacaacagcc  65340
ggaaatagtt aagagacata ttctattgac gcttcgaatg actcaattaa agggatattt  65400
aggaaatttg ttagatatta aggacgatat tattatctat tctcataaga ataatttgga  65460
atatagttac gttgataata ctatttttaa tcccttcgta tatactcaga aaaaaacact  65520
actaaaaaac gatagctttt tatacaatgt atatcctgga gcgtgtgact ttttggttat  65580
ctgggtggcc agagcgtgcg atacatctat tccggaattt ggatcgtatg aagatgtaga  65640
taataatatt atcaagtttg aaacaatgtt gatggaagta tttccacaac tagatttgga  65700
cattactgta gaatcaaagt ttaacaatat atttcgtacc aatctaaaac taactgggtt  65760
aaaaaagatc attcagcgag ttcaagactt ggacattaat tataagtcgt tgttatctag  65820
atacgatgaa cactttatta atatgaccgg taatcatttt attctaaacg atgaacagtt  65880
aaatctctcc atttgggact tggatggtac attagcgtta tctagcgacg gcgataccgt  65940
gatgattaat aacgtaaaac tatttacaga tcttgtgtcc gatatagata cacaaatgga  66000
acgcatcaag ggagatataa cgtataaggt acatttggcg actcctatca attctagaat  66060
aaaattggat atcgagacta gcttcatttt tatagagacg gcgactaata atattttact  66120
atcctcggat aaaaaaatat ctatcatttt ggccaaaaac catatatcta ttaaagtgaa  66180
aaaccatatt cctaacatag aaaaatattt tacattttta gttattgcca ttaatgccat  66240
gtttaatagc gttcaaaagt ctgctgattt taccaaagtg gaaactgttt actggtctag  66300
gatatgccaa aatacaaaga ataagaatag aaaacccatc attattaatt atctagatcc  66360
tggaatgaaa aaaatcagta acaactttta cagatccgat gagaaagaag tctttattaa  66420
tgataacggc ataatgttta catgcatgga tcctttgggg aaatataata aggtgggatt  66480
tcttaatata tttcatgata tgtggaaata ttgtatccct tgttgttttc tacatgatca  66540
atctcatcga agtacatttt catcgtgtgt tcatcaaatc gacgttgaga aaaagatagt  66600
aagtccgtat atccttaatt ttggtaaagt tgtaacagaa tccaaaatgt catttctccc  66660
tattatcttt gacgccttct taaatgatgg aatgactgct aatatggaac aagataataa  66720
acgactaaag gaaactagtg gatatcatat agttagatgt tgtgctggtg atgatatagt  66780
tcgtttacga actacatctg atattattca gtttgtaaac gaggataaaa atattcttat  66840
agttaacgac atggtatatt ttccaatgaa cgcgtccgat ataggaaaga aaatacatat  66900
actcattcaa gaaatagttc atgaggtaat gatagtaaaa aagaaagagt ctagtgataa  66960
aatcgatttt ttcccaccca actataagtt attgaaggat ctatttccaa aacaaactat  67020
tcaaactcct attcaatctg acgcgggaat ggtgttaaca accgatggat tctacataga  67080
tggaaaactt tttaacgaag atctgtcgtc taaatacgtt acatttacaa aaaatgttat  67140
tgcgtctgat gccgtagcta aatatttttc tcctttgttt aaatacgtta tttcagaagc  67200
taaagataga tttatcaaaa cgtggatgat taatattatg atacatatga acgtagatcc  67260
taataatata ataccgacgt tagaaaaata ctatcccaac tctggaagag cacaaataaa  67320
ttaaacaact aaatctgtaa ataaataatg gacaaactta gagttctata cgatgagttc  67380
gtcaccatta gtaaagataa tcttgaacgc gagactggtc ttagcgcatc agatgttgat  67440
atggattttg atttaaacat ttttatgacg ttggttccag tcttggagaa aaaggtatgc  67500
gctattacac caactataga agatgataaa atcgtaacta tgatgaaata ttgtagttat  67560
cagagttttt cattctggtt ccttaaatct ggtgccgttg tgaaatcggt atataataaa  67620
ctagatgatg tggaaaagga aaagtttgca gccacattta gagacatgtt gcttaatgta  67680
caaactctaa tttctcttaa ctctatgtat actagattgc gtcaagatac cgaagatatt  67740
gtatccgatt ccaaaaaaat aatggagatt gtttcccatt tgagagcgtc gactacagag  67800
aacgcggcgt atcaagttct ccaacaaaac aatagtttta tcatatctac actaaataaa  67860
atcttatctg atgaaaacta tctcttgaaa attattgcag tattcgactc taaactaatt  67920
tctgaaaaag agacattgaa tgaatacaaa caattgtaca ccatttcttc tgaaagtttg  67980
gtatatggaa tcagatgcgt tagtaatctg gatatatcat ctgttcaact gagtaacaat  68040
aaatacgttc tctttgttaa gaaaatgcta cctaaaatca tactgtttca gaataacgac  68100
atcaatgcac aacaattcgc taatgttatt tctaaaattt atacgttgat ttatagacaa  68160
ttgacgtcga atgtcgatgt tggatgtcta ttgacagata cgatagaatc tgccaaaact  68220
```

```
aaaatatctg tagaaaaaat taaacagacg ggtatcaata atgttcaaag tcttatcaaa  68280
ttcatatctg ataacaagaa agaatataag acaataatct ctgaagaata tctatcgaag  68340
gaagatagaa tcattactat tttgcaagat atcgttaatg aacacgatat aaagtacgac  68400
aataaattgc tgaacatgcg agacttgatt gtgacattta gagaacgata ttcgtataaa  68460
ttctaatatc gtttttgaag tttccaaatt ttgataatat agtctagatg gaattttaga  68520
ccatctttgt caaaatcgtt taccgacaac aattctccgt tcttttcgat gactatagga  68580
caagaaccct cctctatctc ttgtataatt acatgtagca tattttgctt catcgtttcg  68640
tcagaaaatt ctgaaactag aggtaatctt cctcgttgaa gcaagttata gctttctgct  68700
attataccg ctatttcaaa tagacttata cgtctagtat agcgtcgttt aagagcagat  68760
atatgattcc ctatatgttt aagattggaa tgcgcatctt ctatatgagt ggatgctgat  68820
tctacaatct tataagaaga tttgggatct atatcactag tttctagtga ctctccatct  68880
tcttcctctt cttcatcatc ctcgtattcg gtgagatcat cggattcata gtcgataata  68940
tcgtctgtgt ctgccattta atcttataat cgcaattcaa ttttaaagcc ttaaatggac  69000
ttctttaaca agttctcaca ggggctggca gaatcctcta caccaaagtc gtcaatctat  69060
tattctgaag aaaaggatcc ggatacgaaa aaggatgaag cgattgaaat aggactaaag  69120
tctcaagagt cgtattatca aagacagttg cgagaacaac tagctagaga taatatgatg  69180
gccgccagca gacagcctat ccaaccgcta caaccaacta ttcatataac tccacagccg  69240
gttccaacag ctacaccggc tcctacacca aaaccacgac aacaaactaa tacatcatct  69300
gatatgtcta atctttttga ttggctgtct gcagatactg atgcgccggc gagttcactc  69360
cttccagcgt tgacgccgag caatgctgtt caggatatta tctctaaatt taataaagat  69420
caaaagacga cgacgccgcc atctacccaa ccttctcaga cgttaccaac aactacatgt  69480
acacaacaat cggatggaag tatttcttgt actactccaa cggttacacc tcctcaacct  69540
cctattgtgg ccactgtatg tactcctaca cctactggtg gtacagtatg tacaacagca  69600
caacaaaatc caaatccagg agcagcatct caacaaaatc tagacgatat ggcccttaag  69660
gatctcatgt cgaatgttga aagagatatg caccaacttc aggccgaaac aaacgatctg  69720
gtgacgaacg tatatgatgc aagggagtat acgcgtaggg caatagatca aattctacaa  69780
ttagtcaaag gttttgaacg attccaaaag taataagatt gaatattaaa atcacgcttt  69840
cgagtaaaaa ctacgaatat aaataatgga agccgtggtc aatagcgatg tttttttaac  69900
atctaacgca ggactaaaat ctagttatac taatcaaact ctttctttgg tagatgaaga  69960
tcatattcac acttctgata aatctttgtc ttgtagtgta tgcaattcat tatccaaaat  70020
tgtagacgat gactttatat ccgcaggggc tagaaatcaa cgtaccaaac ctaaacgtgc  70080
aggaaataat caatctcaac agcctatcaa aaaggattgt atggtttcca tcgacgaagt  70140
agcatccacg catgattgga gtacgagatt gagaaatgat gggaatgcaa ttgctaaata  70200
tctaactact aacaagtatg acacatctaa ctttactatt caggatatgc ttaacattat  70260
gaataaacta aatattgtca gaacaaatag aaacgagcta tttcaactcc ttacccatgt  70320
aaagagcaca ttgaacaatg ctagtgtttc tgtgaaatgt actcatcctt tagtacttat  70380
tcattctcga gctagtccta gaatcggtga ccaactcaaa gagttagata aaatatactc  70440
tccatctaat catcatattc ttctgtcgac tacacgattc caatccatgc attttaccga  70500
tatgtctagt tcacaagatt tgtcttttat ttatagaaaa ccagaaacta attactatat  70560
tcatcctatt ctgatggcac tattcggtat taaacttcct gcgctcgaga acgcgtatgt  70620
acatggagac acctatagcc taatccagca actttatgaa tttagaaaag taaagtctta  70680
taattatatg ttgttggtta atcgtcttac ggaggataat ccgatagtga ttacaggtgt  70740
atcagatcta atttccacag agattcagag agcaaacatg cataccatga ttagaaaagc  70800
aattatgaac attagaatgg gaattttttta ttgtaacgat gatgatgcgg tagatcccca  70860
tctaatgaag attattcata ctggatgctc tcaagttatg acagatgaag aacagatatt  70920
ggcttctatt ttgtctatag ttggatttag acctacgttg gtttctgtgg ctagacctat  70980
aaacggcatc agttacgata tgaaacttca ggcggcacca tacatagttg ttaatcctat  71040
gaagatgatc acaacatccg acagtccgat ttctatcaat tccaaggata tttattctat  71100
ggcattcgat ggcaatagtg gaagagtggt gttcgctcct cctaacatag gatatggaag  71160
atgttctgga gttacacaca ttgatccatt gggaactaat gtgatgggta gtgctgttca  71220
ttcccctgtt atcgttaatg gagcaatgat gttttatgta gaacgacgtc agaataagaa  71280
tatgtttggt ggagaatgtt acaccggctt tagatctcta atagatgata ctccgattga  71340
cgtatcacca gaaatcatgc taaacggtat catgtatagg ttaaagtccg cagtttgtta  71400
caaactcgga gaccaattct ttgattgtgg atcgtctgat atcttcttga agggacatta  71460
tacgattcta tttacagaaa atggaccctg gatgtacgat cctctttctg ttttcaatcc  71520
gggagctaga aatgctagat tgatgcgagc tctcaaaaac cagtacaaga aattatcaat  71580
ggattcagac gatggttttt atgaatggtt gaatggcgac ggttcagtat ttgctgcctc  71640
aaaacagcaa atgttgatga atcacgttgc taactttgac gacgatcttc taactatgga  71700
agaagccatg tcgatgattt cgagacattg ttgtatctta atttatgcac aggattatga  71760
tcaatatatt agcgctagac atattacaga actattttag attatgatat ttaaatgagt  71820
tggtacgaaa aatataacat tgtactgaat ccgcctaagc ggtgttcttc tgcatgtgcg  71880
gataatttaa ctactatatt ggcggaggac ggtaaccata ttagggcgat actttattca  71940
cagcccaaaa aactaaaaat attacaggat tttctggcaa cgtctagaaa taaaatgttt  72000
ttatataaaa tattggacga cgagatacgt agagtgttaa catgaatcta cgattatgta  72060
gcggttgtag acacaacggt atagtatctg aacaaggata tgaatattgt atttttttgcg  72120
agtctgtatt tcaaaaatgt acaaaggtac aaaaaaagtc aaacttccat gtgtctaata  72180
aacttattca tttgagaaat gtattgcgga gattattgtc tcatcaatgt tctggagaaa  72240
ttatctcgga actcttggat atcatggaaa aaaatcaaat atccacggat gatgtagatg  72300
caaattttgt atctagtttt cttaaggcta acgagagaat aaataaaaag gattataagt  72360
tagtctttga aataatcaat caagtaaaag atgagaaact gaatctgagt acagaaaaga  72420
ttaatgaagt agtagaaata tttaagcact tggtattctt ttgccaagaa aacactcctt  72480
ctaagacaat taattattca ttctttttgg ataaaatatt cgatatcact tctgtaacta  72540
aaaatctaaa acctcaaact gttaaaaatt atacgaaaaa taatagtaac caattagtat  72600
gggaaaactt tttagcacat atgagatcta aaaaacgtgt aactatggta gaggattatg  72660
gacacgagta tgtttttgta gatgagaggt tttctacttg ctcattagaa gtataaaaaa  72720
atagttccgt aattaaatgg ctaagcgagt aagccttcca gatgtggtta tttcagcacc  72780
taaagcagtc tttaagcccg ctaaagaaga agcactcgct tgtatactac caaagtatta  72840
taaatctatg gcagatgtgt ctattaagac aaatagtgta attgataagt gttggttttg  72900
taatcaagat ttggttttta gacctattag tattgagaca ttcaagggtg gtgaagttgg  72960
```

```
gtatttctgt tctaaaatat gtagggattc gttggcttct atggttaagt ctcacgtagc  73020
tcttagagaa gaaccaaaaa tttctttgtt gcctttagta ttctatgaag ataaggaaaa  73080
ggtcataaat acaataaacc tactaagaga taaagacggc gtttacggaa gctgttactt  73140
taaggaaaac tcacaaatta tagatatttc tctacggagt ttattgtaag ctttttccat  73200
tttaaataga aaatgaataa tactatcatt aattctttga tcggtgggga tgactctatt  73260
aaacggtcta atgtcttcgc agtcgatagt caaattccaa ctttgtatat gccgcaatat  73320
atttctctat ccggagttat gacaaacgat ggtccagaca atcaggctat cgctagcttc  73380
gaaattaggg atcagtatat tactgcgctt aatcatttgg ttctgagttt ggaacttcca  73440
gaagttaaag gtatgggaag attcggttac gtaccatatg ttggatataa atgtattaat  73500
cacgtatcta tctcttcgtg taacggtgtt atttgggaaa ttgagggcga agaattatat  73560
aataattgta tcaataatac aattgctttg aaacactctg gatattctag tgaacttaat  73620
gatatttcta ttggcctaac tcctaatgac actattaaag aaccatctac agtatacgtt  73680
tatattaaaa ctccgtttga tgtggaagat acattcagca gtcttaaact atccgattca  73740
aaaattaccg taacggtaac cttcaatcca gtatccgata tcgttattcg tgactcttcg  73800
ttcgactttg aaacgttcaa caaagaattt gtttatgttc ctgaattgag ctttattgga  73860
tatatggtta agaatgtaca aattaaacca tcgtttatag agaaacctag gagagtaata  73920
ggtcaaataa accaaccaac ggcgactgta actgaagttc atgcggcaac atcgctctct  73980
gtttatacta aaccttatta tggaaatacg gataataaat ttatttcgta tccagggtac  74040
tcacaagatg aaaaagatta tatagatgca tatgtgagta gattgttgga tgatctagtt  74100
attgttagtg atggcccacc gactggttat ccggagtctg ccgagattgt tgaggttcca  74160
gaagatggta tcgtttctat tcaagatgct gatgtgtatg taaaaattga taatgttcct  74220
gataatatga gtgtttatct tcatactaat ctgctaatgt ttggaacacg aaaaaattct  74280
tttatatata acatttctaa aaagttttcc gccattactg gaacatatag tgatgccact  74340
aagagaacaa tctttgctca catatcacat agtatcaaca tcatcgatac atctattcct  74400
gtaagtcttt ggactagtca acgtaacgtc tataacggag ataatagatc agccgaatca  74460
aaggccaagg atttgttcat taacgatccc ttcatcaagg gaatagattt taagaataag  74520
accgatatta tttctagact agaagttaga tttggaaatg atgttctata ttcagagaac  74580
ggacccatct cgagaattta taatgaacta ctgacaaaaa gcaataatgg aacaagaacc  74640
ctaactttta actttacacc aaagatattc tttaggccga caactattac ggccaatgta  74700
tctaggggga aagataaact atctgttcga gtagtttatt ccaccatgga tgtcaaccat  74760
ccaatctatt atgtacaaaa acaattggta gttgtatgta atgacctgta taaggtatct  74820
tacgatcaag ggtaagtat taccaagatt atgggagata ataactaata ataatgaaaa  74880
caaactatag agttgtaaat ggatgaaatt gtaaaaaata tccgggaggg aacgcatgtc  74940
cttcttccat tttatgaaac attgccagaa cttaacttgt ctttaggtaa aagcccatta  75000
cctagtctgg aatacggagc taattacttt cttcagattt ctagagttaa tgatctaaat  75060
agaatgccga ccgacatgtt aaaacttttt acacatgata tcatgttacc agaaagcgat  75120
ctagataaag tctatgaaat tttaaagatt aatagcgtaa agtattatgg gaggagtact  75180
aaagcggacg ccgtagttgc cgacctcagc gcacacaata aactgttcaa acgtgaacga  75240
gatgctatta aatctaataa tcatctcact gaaaacaatc tatacattag cgattataag  75300
atgttaacct tcgacgtgtt tcgaccatta tttgatttg taaacgaaaa atattgtatt  75360
attaaacttc caactttatt cggtagaggt gtaatcgata ctatgagaat atattgtagt  75420
ctctttaaaa atgttagact gctaaaatgc gtaagcgata gctggttgaa agatagcgcc  75480
attatggtgg ctagtgatgt ttgtaaaaaa aatttggatt tatttatgtc tcatgttaag  75540
tccgtcacta agtcttcttc ttggaaggat gtgaacagtg ttcaatttag tattttaaac  75600
aatccagtgg atacggaatt cattaataag ttcttagagt tttcgaatag agtatacgaa  75660
gctctctatt acgttcactc gttgctttat tctagtatga cttctgattc aaaaagtatc  75720
gaaaacaaac atcagagaag actagttaaa ctactgctgt gatttttaaa acatagttat  75780
tacttatcac tcataaatga gtaaatcaca cgcggcctat atcgattatg cattgcgcag  75840
aactactaat atgcctgttg aaatgatggg aacagacgta gtacgcctca aggattatca  75900
acattttgta gcaagagttt tcttaggatt agacagtatg cattctcttt tattgttcca  75960
tgaaacgggt gttggtaaaa caatgactac tgtatatatt ctcaaacatc ttaaggatat  76020
ttatacgaat tgggctatta tcttattggt gaaaaaggct ttgatagaag atccttggat  76080
gaacactata ctcagatacg ctccagagat aacgaaggat tgtattttta ttaattacga  76140
tgatcaaaat tttagaaata aatttttac taatatcaaa actattaatt ccaagagtag  76200
aatatgcgtc attattgatg aatgtcataa cttcatttct aaatcattaa tcaaagaaga  76260
tggtaagatc cgtcctactc gttcagtata taatttttta tctaagacca tcgcattaaa  76320
aaaccataag atgatttgtt tatcggctac acctatcgtt aatagtgtgc aagaattcac  76380
catgttggtt aacttactac gaccaggatc cttacaacac caatcgctat ttgagaataa  76440
acgtctagtt gatgagaaag aattagtctc caaactagga ggcctatgtt cgtacatagt  76500
taataacgag ttttctattt ttgatgacgt agaagggtct gcatcattcg ctaagaaaac  76560
agtattaatg cgatacgtta atatgtcgaa aaagcaagaa gaaatttatc aaaaggctaa  76620
actcgctgaa ataaaaacag gtatatcatc atttagaatt ctgagacgta tggctactac  76680
gtttacgttc gatagctttc ctgaaagaca aaatcgtgat ccgggcgaat acgcgcaaga  76740
gatagcaaca ctatataatg attttaaaaa ttcattaaga gatagagagt tttctaaatc  76800
cgcattagat acctttaaaa agggagaact attgaaaggg gatgctagtg cggctgatat  76860
ctctctattt actgaattaa aagagaaaag cgtcaaattt atagatgtat gtttgggaat  76920
attagcatcc catggtaaat gtctagtctt tgaaccattt gttaatcagt caggaataga  76980
aatcttatta ctatatttca aagtctttgg tatctctaat atagagttct catctagaac  77040
aaaagatact agaatcaagg cggtggctga gtttaaccaa gaatcaaaca ctaacggaga  77100
atgcattaaa acatgcgtat tctcttctag tggaggcgag ggtattagtt ttttctcaat  77160
taatgatatc ttcattttag atatgacatg gaacgaggcg tctcttcgtc agatagtagg  77220
aagagccatt cgtctcaata gtcacgttct tactcctcca gaacgtagat atgtaaacgt  77280
gcactttata atggctagat tatctaatgg tatgcctact gtagacgaag acctatttga  77340
aatcattcaa agcaaatcaa aagaatttgt ccaattgttt agagtgttta aacatacatc  77400
attagaatgg attcatgcta atgaaaaaga cttctcaccg atcgacaatg agtccggttg  77460
gaaaaccttg gtttcaagag ccatcgatct atcgtctaaa aaaaatatta ccaataaact  77520
aattgagggt actaatattt ggtattccaa ttctaataga ttaatgtcaa taaatagagg  77580
atttaaaggc gtagatggtc gagtatacga tgtagacggt aactatctac atgatatgcc  77640
ggacaatccc gttataaaaa tacacgatgg taaattaatt tatattttct aatcaatcat  77700
```

-continued

```
cctcagttaa tttttttaat gattcgtaat aacatcctct atggccataa catttgagtt  77760
ttgcagtatc tagagcatat tttgcaattt cgtattggag tccattacct gaattcggat  77820
ctaaaaatat tagatccttg atttcatgat tacttttaaa tgtatcaatg atttgatcac  77880
tcgttaaaga tattcttccg acaaagaaga ttacctcaaa aaatttatta ataatggtat  77940
cttctatgat gccatgaata aaaaaccgag tgtctatgaa tacaaaagaa ttgtctatat  78000
taacttcttc tttaatttcc ctggataaac actctggaac attctcaccc cttttgggta  78060
tgccacccgg ataaatagca tctattctat cattatcagt agtagctgga tctagagaaa  78120
aaaatgacga tagtatactt ctttcctgtt tggacaaata attggaataa ttcagaaata  78180
atcgtttctt tctagacatg tttctagttc taattatttc agaatagaga aaactatctc  78240
gtctgttaca tactaatatt ttgttatcag tagttaataa aatagcggac acggatactc  78300
gtttatgaca ccataggcat tggttaacga atgccgtgag tgtaataatt tgagagtcat  78360
cctcgcaaat aatagactta gctagtcgtc tattatactt aataatctga ctaattatac  78420
tagatctgta aaagttcatt tactattaac tagcatatta taaatataag acagatattc  78480
gtatttatcg tcgttaatac aatcatttaa tgatttaatc tttctaattt ctacattgta  78540
aatactagta tgcgataaat cctccaacga ttgattaata aaacacgcca tgcaataact  78600
tatatatact ttattaaata atttatcccg tgttgtaagt tttagaatta catttccaaa  78660
ttcttttact gttatacgtt catcactttc ctcttttaat tctcttctta aacaatcttt  78720
aatagattcc tttttatcta gtttaccacc caataatatt aactcttcaa agtgaggatc  78780
gatatcgttg atagaacctt ttctcaaccg tctaaagatt tctcttagtt cattgtagta  78840
cataaaccgt aatagtttag tggatactct aaagatagaa tctgaatttt gttgagataa  78900
tatcgcttgg aatgcgaatg aagttcttct agctcctatt aacggatatc cgtcacttgt  78960
tatacacgca gcaaacacat gcgtgtcttt tgatcttgga atatctttta ttcgtttaat  79020
agatattaat tctctaggag tttcaaatat cacttcctca tccattgtaa ttcccatact  79080
aagagctatt tttaaacagt tatcatttca tttttactat gccgcaacaa ctatctccta  79140
ttaatataga aactaaaaaa gcaatttcta acgcgcgatt gaagccgtta gacatacatt  79200
ataatgagtc gaaaccaacc actatccaga acactggaaa actagtaagg attaatttta  79260
aaggaggata tataagtgga gggtttctcc ccaatgaata tgtgttatca tcactacgta  79320
tatattgggg aaaggaagac gattatggat ccaatcactt gatagatgtg tacaaatact  79380
ctggagagat taatcttgtt cattggaata agaaaaaata tagttcttat gaagaggcaa  79440
aaaaacacga tgatggactt atcattattt ctatattctt acaagtatcg gatcataaaa  79500
atgtatattt tcaaaagata gttaatcaat tggattccat tagatccacc aatacgtctg  79560
caccgtttga ttcagtattt tatctagaca atttgctgcc tagtaagttg gattatttta  79620
catatctagg aacaactatc aaccactctg cagacgctgt atggataatt tttccaacgc  79680
caataaacat tcattctgat caactatcta aatttagaac actattgtcg tcgtctaatc  79740
atgatggaaa accgcattat ataacagaga actatagaaa tccgtataaa ttgaacgacg  79800
acacgcaagt atattattct ggggagatta tacgagcagc aactacctct ccagcgcgcg  79860
agaactattt tatgagatgg ttgtccgatt tgagagagac atgtttttca tattatcaaa  79920
aatatatcga agggaataaa acattcgcaa ttattgccat agtattcgtg tttatactta  79980
ccgctattct ctttttttatg agtcaacgat attcgcgaga aaaacaaaac tagattcgat  80040
accttgttga gcctccatta gaacggcagt gacttcgctg ccattgtcat acgcattacc  80100
atttcgaaaa aagcagtact ttgaatcgct aaatgataca gtacccgaat ctctacttag  80160
tttacagatt aaatctccac attgaatagt tacatttgat tcatcttcga tgtttaatgt  80220
tcctctgact atatccccaa cgtgataata cgcgtaggtt attacacacg gaacgtttat  80280
aactacagaa ttattaacta tttcgccgag aggtaattcc acgtcttcac gaatttctat  80340
tttcttggcc attttaccac taatttctct atggagatac gtcttatata cggcattcct  80400
aatattagtt tttatgtcta acgtcagctc gtgtggctcc aatgtaactg gaaggtatcc  80460
attggtaaca aagctcgaca tttatttctt tatatatctc atcagtttta tggagaagat  80520
accacgttat attctttacg aaagttaact ccccaaacaa atggttcgta ggaaagtcta  80580
aacggtactg taataatatc gttttcgtat ttgtataaaa gagatttatc aaatacttta  80640
ttcgatacaa agaagtgacc gtttacaata tcatctatgt aattcctagc gtcttcttta  80700
ttttttataa ctgatgtaac cattttaagt aacttggtat cgttatactt aatacgagaa  80760
ttattataaa aaaattgtct gaccaattct cccaataaaa cttttacaat tgatggatgt  80820
ggtggaagag aatacgtttc agacatctct tgaagaatag agtatattct attcgtttct  80880
ttagtcttaa attttagata caacagcttt ttgatgtcaa atggtaaaac attaattaat  80940
tcatcctgtg tgtaatcgtt taatgacgtc acttcgtcat tgaaatcgga atatacggcg  81000
gctaaaagat atacattaac tggttcagaa atatcggcgt aagagaattt tctaatagat  81060
cgtccaagaa tttggttgta ttgagaaaaa gtatctggga tagtcataaa ccaaatatgc  81120
cttacctctt tcagagtata ggattcggac ataatgtttg acgaaaacaa aaacatcaat  81180
tgactgccat catcgtttc aggagaatta tacacatcta atagatcctc taaagacgat  81240
ttcattttac tagtaacgat agcaaatgtt tttggtttgc cgtttatcat atgtggatta  81300
gttccctgag aaccattata ttcagaatat ccattactga gcatgatata tttaattacc  81360
aatccgccat atgtagaatt agaaaagtat ataaaatgtt ttccgttgag tgtctgtatc  81420
cgattaataa agtatttaaa tttggaacta atgtttaacg ttaccaattc ttctccgtat  81480
aacacgccat tatttatttt cagatttggg tacaattcct tatcctgttc ctgaaataaa  81540
gtatctaaat tattcatcag attaagttgt cccaatactg ccattgacac gttatacata  81600
tttttatcaa acatttcatg ataacatagc tgtcgtctag taatcatata atctctctct  81660
tgaagtttag acatgtgaca atatactact ctagtatcta gaaacttacg tccgtgatat  81720
cttatcgttg gtagatcttt atcaggcatt tcgtaatatg atattcttcc tttaagcaaa  81780
tccttaagta cattcacacc tcgttcgtta agaagtgtct gaattacttt cttaccacga  81840
ctaataattt caccaaaatc tatcgtctct tcggacatta aatctataat atgacccaga  81900
gtattaggtg tgttagtaat gggagatcca gacaatagta aaaaaggaat cttgttttta  81960
tttttatcaa cggtcataag ttctccagta ttattcccaa agatattatg tgcctcatca  82020
acgataaaaa tagagttatt gtagcgagat aatccgttat aattaatgac gttatcgtta  82080
taattaagag aataaaaact tgttgtggaa tgaataaaga tattctcagc tatgaattcg  82140
tcattaaaca agttcatagc tacacccata ttataattaa aaattttcaa aatgttaata  82200
ttaggcacta gaatgtaaac ctttttaaat ctggaagcta ccaaggcgaa caacaaagcg  82260
attattgttt tacctgatcc cataatatgg aacaataaca cgcttctgtt ctcatctatg  82320
atagttctaa ctagataatc tagagtagct aactgatgag gtaatatagt tggtatacta  82380
tcaacatgat tatcaaataa atctatgatt ccggtattca tttagatatg tgatatcttc  82440
```

```
tataaatata tgagcatata tttacggaga tgaaatatcc tctatgaata tatattgcag  82500
atattcatca ctaacattgg caaatttctt atgtctattg atgaagctct ctatatcgtg  82560
tccaaatagt ctagaattaa aatacttgga tattttctgt tggaaagtag tcaacggaag  82620
agtaaccaca ttatcgtaca atatatatcc ctttttggag aggtccgtca ttaatggaat  82680
atgctttaca gagctagata ctaacagagt acctatttg agatagaatg caaagtccgg  82740
aatctcttcc ggtgtaggat atagtttcat aataggaaca tgatattttt tgtaccattt  82800
caccaacaag tatagaaatg cgaatctata tctattattt tgtattttac catctaaccc  82860
ctcgtctaat agtttgactt tatcgtacgc gtcattattt tcagcagcct ctctaccaga  82920
aggttgagaa aagtgtgttc tgaatcgcac gacggcaatt cttctcatta atgcgttatc  82980
tatcctatca aagacaggtt tgtaattagt atcgataatg attgtcgcat ggtttctatt  83040
attaatttta ttggagaaac acggtcttcc aatgacacaa ggttctgtca actttttaat  83100
attgtcagat ctaattttct ttgatccact acaggcaaaa tcaggtagtt cgctacagaa  83160
tacagatctt ttcaaatgca tgttagcgat aaatggatta ggtcctttat ccaatacatc  83220
tgttaaaatt gtttgacccg tctcaacaaa caggtcaccg atagcagact ttaacaaacg  83280
tttggttgtc gactttccag ttgcagtttc tccaaaaaag aatgttaaac atcctttggt  83340
agcaccgcat aaacaactag ataaagtttt ttcgtacaac tctctatttt tcttattttc  83400
atccgttaat ggttggatat cgttaatgat attcattaac tcttccattt ctggactgtc  83460
ttcgacgaac tttgtatcgt caaatttaaa tccggttgat acagtacacg tatattttt  83520
agcatcatct ccagagtaaa acattccgtc taccaggtcc aatacaccat ttttaaacgg  83580
aagtttatcc ggataggtat cggtctccac tgaatctatt aacatgtctc gtatgttagc  83640
ttctacagtc tttcgtttcc tcggacagag taattcgctt gaatattcct taggtagttg  83700
atgtcttatt gacagaatta gttttgttat caagggttct tcgctgttaa atttccatga  83760
attattaatc caaactatat ggtctcctcg ttcggttaat aaaacagagt tagtgtctaa  83820
aattctttgt gcaatattaa acagtttatt accatccaac ggaacaattt taactttaca  83880
actatgtgga ttaccagttt tgtaaattct aatagcacca ttttccaacg atagttgatg  83940
cggatgttta tgcgatcgtt ttttacataa tgcacaaggt gttacgtaat ctatgaccag  84000
tggtaccgtt gtaaaattat tttcatcgag atcattaaag tttattatag aattaatgaa  84060
tatttttgaa actcttttta tagcgtcttc gaatgaaata aaccctggtt cccataactt  84120
atcaggaact aaatcctcca atcgtcgttg tagagaaaag taataactat tgttgttcat  84180
atccacgtaa gtgaataggt aatcttctat attatcatgc ggtggttgca ttacatgaat  84240
agtgtcgcaa tttgatttt tcctagtacc tacaacccga agagttgttt ttctcctata  84300
tacggcagtg tctatcgatc tggttagtgg attttcagat gatctactta attctaatag  84360
tgttcgtttc atagctatca atgtatccat agtggtatac gtgtctaaaa agataatatg  84420
aaaacttgtt ttatctctat ttgtagactt agtcaatgaa aaattagatc tcatggattt  84480
tattacattt tcatgaatgg caccgcattc tgtaaacgcg aatctagcta cacagtttga  84540
cacctcgata ataaaatctt gaatagccgt taaataatct atttcgtcta gacacgcgtc  84600
taaatctaca tccatgaaaa ttctgactat agagtatgct tcctcatccc taagactttc  84660
gaatagtgta cattctggat tattctcaat atatctttct aactcgtcgc atttaaatgc  84720
ttctacaaat cttggatctt cattttgtct gcacgctgac gggacaccta tagtcttaag  84780
aacaaagata acatcattac ctctaatagt tgcatccatt tagaacacaa gttaaaattt  84840
cactaaagca ttaataaata aacccttgag cccaatttat aggtgccttg ttgtctaatt  84900
ccagtaaaac gttgataatt tcaaatgatc tatctttctc gaattggcgg tctctagccg  84960
ctggatgata tccgactatg gtagttaccg gggattctaa ctttgcccgt atattcgaga  85020
aatctgtttt acccaaacaa taaagaacac taacgtgttt agttatatgc tgcagcagta  85080
acttggaaat cttatcccag tagatcgcgt gactttttgt ttctcctaat ttacaactta  85140
agtaataatt ccagggtata accccgtcta ttatattaag gttataacct ttataatcaa  85200
ttactccggt taatctagat atagatgaag ctatctcctt aattgatttt tttgtaaaat  85260
ttggtgattc gaacggtaca ccagttccat ctttcggata cggatctata ccacacacac  85320
atactcgttt atttctaagc ggttgtttca actgtataaa gaacttatca ggaataggcg  85380
acgtctcgtc tcgtagcagc caactggcta cttcgttata aaactctacc aattgactca  85440
ttactggttc ccaatcatcg tgataagtaa tagtatatgg cgcgtgtgat acagtcactg  85500
aattcattat atcaaattag atacctttt atacgtatct agtacctttt cattttccga  85560
aacgccgtta aaccaagcga atacaaacgc cttaaactta tctctattat aacatattct  85620
cgttagattt aattcttcgg tatccttgta tctaactatt gttatatgtt tagaaactct  85680
atagtggctt ctaatcagat gttctaataa atattttaaa aatgaatctt gattaaaaat  85740
catatcattg accatttgtc tggctactga attacgataa tacggagaca ataacggatt  85800
agtcaaatag ctatcatctc ctaatgatgg aggcacctgt acaaatacca atcgtttatt  85860
cttgaacgaa tcaaacgtat aaatatcata aatgacaaat ttatcagtgt gcatatcttc  85920
agatatatga ttggatgtag aacaccatct aacttgtctt ccagcatcta taaattcctc  85980
cacctctata tatctaccac cgtgctgaaa actagaccca tttaattcga cgcataaaga  86040
tccatatgta tctggagtca caatatattc agaaaaaaat acatgctcct ttaattttgt  86100
taattttgat ctgataaagt cattgtgatt tcctaaaagt ataaatactt cgttatcgtc  86160
gttatcgact ttgggatact tattatcctt aactataaaa atgtccatca atatcgatat  86220
aaaaaaaata actgatttac tcaacagtag tattttattc ccagatgatg tgcaagaact  86280
tcttcgagag aaatatatag tattagaaag aaaatcaaat ggtacaccta cagtagctca  86340
catctataag acaatggcta gatttgataa taagagtata tatagaatcg ccaagttttt  86400
atttatgaac aggccagatg ttatcaaact tttattttta gaagacgtag aacctctgtt  86460
acccgacaaa agtattaata tatctattaa caatacagag tatccacagt tggaaggtcc  86520
tataggaaca aaaatcgctc tattggaatt atttaatgca tttagaacgg ggatatcaga  86580
acccatacca tattattatt taccgcttag aaaagacata aacaacatag taactaagta  86640
agtcttcgac atctaaacct tcacatttaa tggctcctct atttagttcg aaaaagtttt  86700
ttgtagacgg tctatcttcc attgtagatg cgccattaat aaactttta cttcgttcta  86760
taattgtagc gaaatcaacg ttatctacaa gaacaaatcc gtattcgtta aacactctga  86820
ctatatcgtt ctttttgata atgtattcag tcattggagt agacattgtt gatggattat  86880
ataccactat tctatcatca gctatttttt ctacagacat atagttttcg ctactaggta  86940
aattcttatg aattataaaa gtctttttat ctgttaattt tgataatttg tctccgtcca  87000
tggtagtgat taataccttg cctccagaag cagttagttc ggataagtta ttcatgacgg  87060
tagcataatg tctcggatga aaagaataat ggatagcaaa ctgccagtcg atgatattaa  87120
actttccaaa atagaatact tctctgacac tagagacaaa tgtatcggat cgaatagttt  87180
```

```
cctgaatgta gtcaaatttg tagtacttgg ttttaattcc agagtttaat ttgttgtatc  87240
tttcatttcc tctagctata gcatcagcat ccggatccgt cgctaccaat aacgcaatct  87300
ctccataaaa gtatttttcc aggtccgcac cgtttccaaa atcaatcgcc aatacctttc  87360
gtttgttgga atcgtctaaa aatgttttgg aacaatacat agaaataaga agagtcttga  87420
cgtagtttga taaaattccc aacggtcctc tagttcgttt attcgtaaaa taactaactt  87480
ctggatttaa tctaaattta tcattattgg cgtattgatg tcccacatcc gatagtttat  87540
cctcgttaaa gatatctcct attttgatgc tttgatctct taaatgttcg actatgatat  87600
tatgttgatt tccataataa tcttctgagt taatatattt catggtttta tcaattctag  87660
gtttaagtat ttctccatta actaagaatt ctgctataaa cttaataggt acaaccacgg  87720
acttaatacc cacttcatta tgtgtattaa tatattccaa acaatagata ttatttagat  87780
aattaacgcc gttatataac acaatcttac cagaaccata ttctttagga aagcctttat  87840
cgttgctaaa tttcttatac tctacaaaga tagacgattc tccaaagata attggttcac  87900
tggacatgta cctaaatact acatttgcag tttggtctat agtattttcc tttttaattt  87960
taaaatcaat gttagattta ggtccctttg aatagaacag aataacacct tctggttgct  88020
ttggtaaata tgtagataac atatcgacga cttcactagt tgtagtaaac ggaccttcgt  88080
atttctttga cttgaatact atccgatcac aaatatccac tagtttagat tcaacatact  88140
tactttcttc tagtctatca ttgattgcat tcacaggctc tattagctta atgagatata  88200
cggtccagtt cttatcctta actgcctcac caaagactac tacttcggaa tctattattc  88260
tcttaacagg atatctaata atataaccaa gatgtgtaaa ataacaatac aacccttttg  88320
atgtaactct gatagttata ggaattccgt cagtcttagt tacggcatat agattttcca  88380
gatccaaacc tactatatct tgtttaggca acataaaggt ttttataggc gcgttaatag  88440
gcggagaaag aattacattc tctggagaag ccataaatat atgacgtgat agagtcgtca  88500
attcctttat tagttcatca tatggaactt tttcattgtc tctaggtgtg aattctattt  88560
ccagagatgt attaggcctt gactttggat gattaatagc gtgtaataaa gaacttttag  88620
actgggcacc ggatcctaga aaatatttta gcttaaagtc tatcgtaaag ttttttgttt  88680
ttgcttgaat aagattgact aattctagtc ggatagagga tccatatttc ttgtaatcca  88740
aaaatatatg acgttcctct gtcgatagtc tcaacaagca ttctttgtga agacgatttt  88800
ccgtcactaa tgatttcttt tcccaaacta tgttatctat agcatctact aactgtacat  88860
tttttacatc tagaccatgt accttagata atggaatctt agttctaatt ttaacacctt  88920
ccttattagt aacggtaaat cgaataaacg attcctgaat cgtagagata ttcactacat  88980
ttgtcaaagt aattaatggc ggcttaataa atactagttc caattcatta tttatttcgt  89040
atgcggtaga cctctgttct aattctgaag cattcttcgc taaagcgtct atatacgttg  89100
caatagtaga agatgatact atgttggcat ccatattgtg ttttattata aacgactagt  89160
tttttttcat ttacttatta acaagcgtct tttatatatt cgtaatctat gcctttagct  89220
agagctattt taagcttttc tgtatctcga ctgatacgag tatctgatct attgcggtat  89280
ttttttataa atcgtttaag acggggagta gttttgatat attcgctaat atcctcttta  89340
ataatatcca cacacgccaa ttgttcggct atactcgatg cgtgagtctt gcattcatct  89400
ccagatatcg gagtgagggt cagatccaaa tattgagaag ccttataatt atcgtattcg  89460
aaatcaatca taaactgacc atccttatcc actgaaaaaa tggtattgtt tggatggcgt  89520
ttaaatatag acattatcaa tgccataata tctaatgtgt ttagctctcc gaagaaagct  89580
gtcattgcga gagatttcat acgcttatcc atttccattt atcggtcttg taattatttg  89640
tgtaaagatc tatatcatcc atccgtagat gatttaacgt gatctacgac tatagatagg  89700
aattcatcga acgtagtttt agatactaca tctaaaaaat ttttatcctt taccatttct  89760
aaaatagtcg ttgccatata agctcttttt gaaattgatg gagtatgacc taccacttca  89820
gcagtttgtt tgatagttaa cgctattaac tttttggtg acggaagagg agatatggac  89880
tttacatttg tccaaaaatt atataaaaac gtataattga ctccatacgt tcggagatcc  89940
ttgattctaa taccaaactg tttgatacat tcgtatacct ttcgttcact tagtttgttg  90000
aacagaaatt cttcgggact agaatcatcc gtcagtttca atagcggttt atatagtcta  90060
ttagacttat gaacaacaaa ttcatgtgaa actttgtcct ttcctacaaa cttgataact  90120
atttcatcgg gacttatttc tatgtgttta ttttttagtg ttaataaccc tactgtttca  90180
ttctccttaa gatatttcat tttaccaaat ctaataaaaa acatagtttc cattaacata  90240
aaaaccgcca actgataatt ggaatctgtg gacgatttct ttatattttt gtttataaaa  90300
caattaattc gtttcataac gttatatact ctaacaaaaa tacgatctct tttagcgttg  90360
cgattctgta catgcatttt tccgtaaaag tattgtctac gtccttttga atcacttccc  90420
acaaaaatta atctagttaa cgcctcctcc cacgtttgtt catatactac tacatctgtt  90480
aaatgagtag gaattttaac atgttgcaaa acctcatacg ctggattatc gtctgataca  90540
ggatttaaaa aattattatc ggtaaagagt ttaccatctt tataaaaaag tgcacgcatt  90600
tacttcttac aagttttaac ttttttacga acaactttag attttccctc ggtgactaga  90660
tcagatagtg ttgtaatagc tttagtcata gaagtaaatt gtctagagat accagctgct  90720
tgaacatcct ctagaaccgt cgatactgca gagattctag taataatttt cttaagatct  90780
ttaacgatat tgtcggtagc caccttttagg tcagaaagat cgcttctagc actatgattt  90840
actttaccag cttcaacttg taccataggt tcatcatccc cgtcgctatc atcgagctct  90900
acagcagcca cgctttctac aatgtcgctg actccaggag atggagaatt tttttcagtt  90960
gtttgatgat attcctctat aactacttct tcttccactt cctccttttt ggttgatctt  91020
ttagtagccg ctggtttacg aggagtagtg gctcgtttgg ttttgggctt agtagatgga  91080
attattacat cttccgggaa aatatcctcg tttttatctt tattttcagc gctatttttt  91140
agatgagctc tgatttcagc catctttgtg aagctactag tatccgcttt atttgtaatt  91200
gaccacgcca ttacgataca aacttaacgg atatcgcgat aatgaaataa tttatgatta  91260
tttctcgctt tcaatttaac acaaccctca agaacctttg tatttatttt catttttaaa  91320
gtatagaata aagaatctat aaaaactaaa aaaattatac atcataaacc aatttcctag  91380
ttgtttgtaa ctttaaatgg actctaaaga gactattcta attgagatca ttccaaaaat  91440
aaaagcatat ctactagacg cgaatataag tccaaaatcc tacgatgact ttatctcacg  91500
aaataaaaat attttcgtta tcaaccttta taacgtatcg actatcacag aagaagatat  91560
acgattgtta tacactacga tagaacagaa tattgacgcg gatgatcaaa cactggttgc  91620
tattttttcg tatataggat ataaatttga acaggctgtt aaagaagaga ttagtacgag  91680
tttatccttc aatgacaaga ataccacaga tgaaatgacg tataacttgt atgatctttt  91740
ttttaacaca ttagacatgt atttacgaca aaagaagatc agtattctgg taaatgatga  91800
tgttagaggt gatgtaatcg ttagttataa aaatagtgac ttagtttcat catttaatgc  91860
ggaactagaa ccagagatta agaagatacc gttcaatatg aaaaatctat taccgtactt  91920
```

```
ggaaaagaat ttggaccaac taagattctc taaaaaatat ttagactttg catatttatg  91980
tagacacatc ggtattccca tttccaaaaa aaagtataat gtgcgatatg tatttcttta  92040
taaaatagac ggattatcca ttcctattat cattaaggat tttttagatg ttaagtacgt  92100
atatttggaa aatactggaa aaatttataa aaattctttt tccgaagacc ataacaacag  92160
tctatctgat tggggtaaag tcatcatacc tctcttaaag gatcgtcatc tatatagcta  92220
catctttcta tctagttatc atttacatag ttactataca gatctcatcg cgagagacga  92280
gcctgtgttt gtgaaacgca aaaaactaga tattatagag atcgatgaac ctgaggcatg  92340
gaaaagggat gttagagtgg aattcgcacc gtgtgagcat caaattagat tgaaggaagc  92400
tatgaaagtt gacgctaact atttcactaa aattaataat tttgctaacg aatttattta  92460
ttatgaagat ggtgtggcat attgtagagt gtgtggaata aatataccta tatttaattt  92520
agatgccgct gacgtgatta aaaatacagt tatcgtttcc acgtttaaca agactatatt  92580
cttgagcgaa ccatatagct atttcgttca tagtcagcgc tttatcttta atattatcat  92640
gtcttttgat aatattatga aatctcaaac ttgggtaatg aaatacaaca ttaaccgact  92700
aattcttaac tttcttattg atataaactc tagacgtcag gaatacgaaa aaaagttttc  92760
ttctgaaatt aagagaggtc tgttctttct tcgtttgtct gcaaacttat tcgaaagtca  92820
agtatcgtct acagagttat tttatgtttc caagatgctt aatttaaact atatagttgc  92880
gttagtaatc attcttaaca gtagtgcgga ctttatagtt tcttatatga aatccaagaa  92940
caaaacggta gaagaatcca ctcttaaata cgccatctcc gtggttatat acgatttttt  93000
ggttaagact agaatttgcg agaagggatc gttggatact atagttttat ttaccgatgt  93060
atacacatct ataatgccgg aggaattgga tttacatttt cagagaatca cattagaact  93120
tagaaaacta gtatccattc agagatcggc gttagaaccc aattacgatg tagaaagtcg  93180
cggcgaagag cttccattat ctgcattaaa gtttttcgat acaagcacca ttatagttaa  93240
gacaatggct ccagtacata catacatcga acaaaaaatt gttgcaccta ctccatcggt  93300
cgaaccaact gatgcatctc ttaaaaactt caaagaacta acgtgtgacg aagatattaa  93360
gatctcgatt agagttcatg atactaatgc tacaaaatta gtcatttttc catcacatct  93420
aaaaatagaa atcgagagaa aaaaactaat tataccgcta aagagtttat atattaccaa  93480
tactctcaaa tattattatt ctaactccta tttatacgtt ttcagattcg gagatcctat  93540
gccattcgaa gaagaactca tagatcacga acatgtgcaa tacaaaataa attgttacaa  93600
tattctaaga tatcatttat tgccagacag tgacgtgttt gtatatttta gtaattcatt  93660
aaacagagaa gcattggaat acgcatttta tatcttttg tcgaaatatg taaatgtgaa  93720
acaatggata gacgaaaata taactcgtat taaagagttg tatatgatta atttcaataa  93780
ctaaatggcg gcggtgaaaa ctcctgttat tgttgtgcca gttattgata gacctccatc  93840
agaaacattt cctaatgttc atgagcatat taatgatcag aagttcgatg atgtaaagga  93900
caatgaagtt atgccagaaa aaagaaatgt tgtggtagtc aaggatgatc cagatcatta  93960
caaggattat gcgtttatac agtggactgg aggaaacatt agaaatgatg acaagtatac  94020
tcacttcttt tcagggtttt gtaacactat gtgtacagag gaaacgaaaa gaaatatcgc  94080
tagacattta gccctatggg attctaattt ttttaccgag ttagaaaata aaaaggtaga  94140
atatgtagtt attgtagaaa acgataacgt tattgaggat attacgtttc ttcgtcccgt  94200
cttgaaggca atgcatgaca aaaaaataga tatcctacag atgagagaaa ttattacagg  94260
caataaagtt aaaaccgagc ttgtaatgga caaaaatcat gccatattca catatacagg  94320
agggtatgat gttagcttat cagcctatat tattagagtt actacggcgc tgaacatcgt  94380
agatgaaatt ataaagtctg gaggtctatc atcgggattt tattttgaaa tagccagaat  94440
cgaaaacgaa atgaagatca ataggcagat actggataac gccgccaaat atgtagaaca  94500
cgatcctcga cttgttgcag aataccgttt cgaaaacatg aaaccgaatt tttggtctag  94560
aataggaacg gcagctgcta aacgttatcc aggagttatg tacgcgttta ctactccact  94620
gatttcattt tttggattgt ttgatattaa tgttataggt ttgattgtaa ttttgtttat  94680
tatgtttatg ctcatcttta acgttaaatc taagctgtta tggttcctta caggaacatt  94740
cgttaccgca tttatctaac actattccat attactaaaa tcggaacacc aatgcggtga  94800
cataaaataa ccgctataac ctaattcatt taacatctca ttaccacaag taataacatt  94860
attagacttg tgttttatca aatactgaca aaattgttga gcagatggat cgacctttgc  94920
cgccttttta accatccacg cgtctccagt acctcgccta atagcttgcg gcagatatgt  94980
tttcttatcc aatcgcatag ctataaaata ggcgccgaaa tccacacatt tgaattcgaa  95040
tatatcatcc ttaccagcgg ctagaagtct acctctatca ctttctaatt ttgttttgct  95100
atccgttaat gatttccaat cgttaaccgt atttttaatt cgcatatatc tcgttaattc  95160
attaaagact ggattatcag acgtctgaaa ccagagtaat agcgcactaa ttgccaatat  95220
aataacaaag aatataagtg ttgatgtttt ggctgcttgt acgcctacta tagccttttc  95280
tctaacgtat tctaaattac acgcgtttac cgataaagta gttttatcca tttgtacgtt  95340
ataaatggat aagaaaagtt tgtataaata cttactacta cgttcaactg gagatatgca  95400
caaagccaaa tctcccacta taatgacaag agtaaccaat aatgtgtatt tgggaaatta  95460
taaaaatgct atggatgcac catcatctga agttaagttc aaatatgttt taaatttgac  95520
gatggataaa tatacattac ctaactctaa tattaatatt attcatatac cgttggtaga  95580
tgatacaact accgatatta gtaaatattt tgacgacgta accgcctttt tatctaaatg  95640
tgatcaacga aacgagcccg tgttggttca ttgtgctgcg ggagtaaata gaagcggggc  95700
tatgattttg gcatatctaa tgtctaaaaa taaggagtca ttgcctatgc tatattttt  95760
atacgtgtat cattctatga gggacttgag aggcgcattt gtggaaaatc catcgtttaa  95820
aagacagatc atagaaaaat atgttattga taagaattaa aagtcttctg tttcttccat  95880
ttccttgatc ttttgagaag atatcttatc agatagtttc ctttccattc tcatgagaag  95940
acccaagtcg ataaagtatt tgtaatatcc agttcctata ttagggacct tgctaaaaaa  96000
gtggcagcta ctattatcgt taataggttc tgacttttta tgaagagccg cgtttaacaa  96060
tgctttattg tctccgaacg tagctctctt aagagtacta gctgcgccga acttgaattt  96120
attcactgat tctggttcgt aactagcaca tagtaaacta gcgagaagat cacaaggctg  96180
atacagataa tcgaaccctt ctccataggt gtttaacatg gcttcgcaca agtattcacg  96240
agcggcctcg ataccgaaga tatcgtatgt attccatact ccaggataca cgttgacgtt  96300
ttccaaatcg aaagaaccca attcttttag attcatgagt tctacagtca tcttattgag  96360
cttttttgtt tgattgaagt cgtcatatcc cgtataatca gagataggaa tcttgaattt  96420
actaatcttg cccttgttgg cggcacccgg aagaaccatc ataaacttac taagattcaa  96480
ttcttccggt tcaacgaaat ttaggtagac agtaaatcta atattatcct catcctcaat  96540
gaatgtttcc ataccccatt cctttacaat gacgctaaag gagatgaatc gttcaatcat  96600
atattcgacg actaattcgg taatttctgc tctcttgatg tataatctat tgactattat  96660
```

-continued

```
atctactaca tacctatctg tttcttttcg aagagtgatg tttggattta attctcccaa  96720
acatacaaat tcgaaattaa tcttaacaga ttgaagttta gagatatcat cggataccag  96780
agtgataatt tcggtcttat tcttactcaa attagtcaag ttattaaact cgttgaaacc  96840
aagtttttgt ttgacggcac cactttttttc agtagtgtga aaactggaca gggcttgttg  96900
tgtaaacttc tcagacaata cctgtgcaga aataattcca ataggagttc caccacctag  96960
agtataattg agtttttcat agaacttttc aaagatagtg atagccgttt cttttgtaat  97020
tctaattcta gaaggattaa gatgcgtcaa gaatatatac tccataaaat ctatattaga  97080
taccgtaaag aagtatttct ctctcacatc atcaatgacg ttatgaatca tatcgtacag  97140
atccttaacc ttaatagcat tatcctcagt ggtgggtttg acgaatacta ggaaattaaa  97200
cggcgccaat gtctttttttg caagtttctg tttctgagag taaacgaatc cctgttttat  97260
tttattccac agagcactaa tttccaaata ccaagtcatg gactcatctg gatagataag  97320
atctacaggt ttacatactg agcctagaat tttggtataa ttggcggcgt acttgatgag  97380
cgtattacct ataactactt gtccgtatcc gtcgaccacc atatcctcca tctttttaat  97440
gatttttcta gccagtgttc cggtacgtga tgtttcacag acgatatcag tagattgaga  97500
tcttgcaacc agcatcgaaa agtaatattg agaacccgtt aatccttttg ttaaagaatt  97560
aagaatgtaa cctcttcctt ctggatcctt agagtctgga agatagtaag gtaagactct  97620
acccaatact cgagtctctg ctggttcacc atcaatcctc tgttgtccat aagtacctag  97680
aatatacatt agttctgtgg gatttacttt ataacccgct ttggccattt tcaggaggtt  97740
attatctgga tcatctatca gcgtttgtct catatgttct tctatctctc ggatattaag  97800
atttgtcaag ttggataaca tggattccac atagtccgcc tctaaagctt tagataatgg  97860
aactattttc ccgtctctta catcgttgag atatttggcg tatgcttctt tgataagttc  97920
tatttttttct acgttgatgg cctccaattt attagtgaac gtcgaatttg gtctcagatc  97980
tttgaatgtc accccaaaac cgtaaataga tagatatctc ttaaaaacat aagatgactt  98040
gataataaag ttgatacctt ccacgttcga cttatgatcg gataagagtc cagccaatga  98100
cagatgcctc atagccacaa caaaattact atctacgtcg tttgcaataa tttcaccatc  98160
ctttaagaga cccggataat taatcttttc acctatcaag taagtataga tatctttacc  98220
gctgaattta catttacctt taggatcgaa ctctcttcca tatttcccca agatgttcaa  98280
tacttcatct aaacaaagat cttgtatcct aaacaatgaa tacgctgcta cgatttcatc  98340
ttgaatagat ccataaacgg gggctccatg aatatcgtgt ttgagtaacg tcgtcggata  98400
cataagaata ctttgttcaa ttacggcttt aggattttgc tccaatatca tccattcttc  98460
atctccgtcg aaatcagcat tttgagagtt gacaattccg ggagatattt tgatagtatc  98520
tccttcggta gctctgatag atgaagcgat gacgttgtat ctatgtagag acggctgtct  98580
tccaaaaata atacttgtat attcttgaac agctacttct acccaatcac caggcaataa  98640
atgtatttta tttttgataa actttccttg gcgtattctt gttaattggt ttaatcgttt  98700
attaaagtaa aatttaactt ggtttgacgc taatagttgt ttaactttat ccactgtaaa  98760
ggcattaaca aatatctttt ctgtaagtgt atttctaata tatgcgggca ttcctacctc  98820
attaacggtg atagatgtac tggaccaat tacagatcta gcggtctgat cttttcgccg  98880
ggcgacgata taacttctaa tcatattatt tttgccggat gtgatatatg ataaattgat  98940
actggaagtg ttattagaaa taattttaat atcatcgtat tctattaccg ccttctggat  99000
aacctgttca tcagcattca agttacaatt cttaacgatc atacctaata agtaagttaa  99060
ttcattggtt tctttgggta tactatctat ccaaaaacta atagccggtc taataatcaa  99120
cggagggatg ggaaagtagt ctgtataaaa taagttagct ggatattgat gaatttctaa  99180
taatggccaa aacttttcat gaatagaaat taacttttga tagatgagag aattaggaac  99240
gttaatatca tccaacttgt tgacgaaaca aacctttttc tttgaaaaag taatttttttg  99300
atacggttgc atacattcac tgttccaaca tgacttttttc ttggataata ttttatcctt  99360
taatctccta agagcgtgtc ccgataactc ttttaggtta atatcgtcgg aatacggttc  99420
tcgtgaacgc aataatccgc agtgaataca tatataattc agtaaacgaa taatttctga  99480
aataaattca ggcttaacta tatgagtttt ataaatactt actttacccc agtgaccgaa  99540
acattccaat tccgttttcc cacaagtttt acataatgcc ccatccatag cacctagtct  99600
accatcttta acggtaccga tatcgtcgtc atttttaaca tgactaatga taatatctgt  99660
agcattaatc tctttttgat catatagact atacgtaacc ttagagatta cagccatttt  99720
tatcaagtca gtttctttta aagaaccgaa agtatacaat caaatttccc tttttattac  99780
aactataaaa taatagttat atttacactt taaattttta tcatgacgga cgaacaaatt  99840
tatgcattct gtgatgctaa caaagacgat atacgatgta aatgtattta tcctgataaa  99900
agcatagtac ggataggaat agatacaaga ttaccctatt attgttggta cgagccatgt  99960
aaacgaagcg atgcgttgtt accagcctct ttaaaaaaaa atataacaaa atgcaatgta  100020
tcggattgta ccatttcatt gggaaacgtt tccattacag atagtaaatt agatgtaaat  100080
aatgtttgtg attccaaacg agtagctacc gagaatatag ctgtccgcta tctgaatcag  100140
gaaattagat accctattat agatatcaaa tggcttccga ttggattact agcgttagct  100200
attttaatat tagcattttt ctaaacaaga tataagatat aaaatatatt attgattatt  100260
ataatgttct tatctcatct ctactaattg attaatcagc gactgaaata acagatctat  100320
cggctatctc tactccagtt accatgttat tgcggaaaaa tctaacaatt tttaatggta  100380
tattaggacg gtagagaatc ttgacaacta tttccgtctc taacattttg ggaagacgaa  100440
gagtcttttt accatcgcct gtttgtagta cactattaac tatattagtt tctgtagtat  100500
ctagtctaac aaagctagga aataagtcag atattaccac atctatgtat agaaaattta  100560
caggaaactt gttatgacct ttttgaagat acgatgttat aatgattggt tctccataat  100620
catcatcaac cggagtataa tttatggatg attcgttaaa tacctgaaac acagtttca  100680
tagaatcaat tttatgtcta acggttatta aagtaactaa atcattatac tctatatcgg  100740
tagtatatct cagtagtacg tttctattta ttactgcgta cggatctctt gctatttctg  100800
tttttagaca tagaattttt gctagatatt ttacgttgta ttggttcatg actaactttt  100860
tcagttgatg ttgttggaat atttaagaaa cgaaatatag attgttgtag aaatagtacc  100920
tttgctttag tagtaggaaa tgttttattg cagtacacgg tcctcagcat aaagtacatg  100980
tgaaaatagt catattcctg attaggataa tcaaagttaa caactacttt gttacggacg  101040
atcttattaa ggtagtacat ctttttttca taatttacag cgtctgattt ggtaactcga  101100
gtcagtctca tgttctcacc ggtataaata cttaataatc tcatttcagc tgaatatgaa  101160
ggagcaaaag gttgtaacat tttattaccg tgtgggatat aaaagtcctt gatccattga  101220
tctggaaacg ggcatctcca tttaagacta gacgccacgg ggtttaaaat actaatcatg  101280
acattttgta gagcgtaatt acttagtaaa tccgccgtac taggttcatt tcctcctcgt  101340
ttggatctca catcagaaat taaaataatc ttagaaggat gcagttgttt tttgatggat  101400
```

-continued

```
cgtagatatt cctcatcaac gaaccgagtc actagagtca catcacgcaa tccatttaaa  101460
ataggatcat gatggcggcc gtcaattagc atccatttga tgatcactcc taaattatag  101520
aaatgatctc tcaaataacg tatatgtgta ccgggagcag atcctatata cactacggtg  101580
gcaccatcta atataccgtg tcgctgtaac ttactaagaa aaaataattc tcctagtaat  101640
agttttaact gtccttgata cggcagtttt tttgcgacct catttgcact ttctggttcg  101700
taatctaact cattatcaat ttcctcaaaa tacataaacg gtttatctaa cgacacaaca  101760
tccattttta agtattatat taaaatttaa tcaatgttta tttttagttt tttagataaa  101820
aaatataata ttatgagccg acgtaacact ttctacacac cgattgatac atatcattac  101880
ctcctattat ctctatctcg gtttcctcac ccaatcgttt agaaaaggaa gcctccttaa  101940
agcatttcat acacacagca gttagtttta ccaccatttc agataatgga ataagattca  102000
aaatattatt aaacggttta cgttgaaatg tcccatcgag tgcggctact ataactattt  102060
ttccttcgtt tgccatacgc tcacagaatt caacaatgtc tggaaagaac tgtccttcat  102120
cgatacctat cacggagaaa tctgtaattg attccaagac atcacatagt ttagttgctt  102180
ccaatgcttc aaaattattc ttatcatgcg tccatagtcc cgttccgtat ctattatcgt  102240
tagaatattt tatagtcacg catttatatt gagctatttg ataacgtcta actcgtctaa  102300
ttaattctgt acttttacct gaaaacatgg ggccgattat caactgaata tgtccgccgt  102360
tcatgatgac aataaagaat taattattgt tcactttatt cgactttaat atatccatca  102420
cgttagaaaa tgcgatatcg cgacgaggat ctatgtatct aataggatct attgcggtgg  102480
tagctagaga ggattctttt ttgaatcgca tcaaactaat cacaaagtcg aacaaatatc  102540
ctttattaag tttgaccctt ccatctgtaa caatagggac cttgttaaac agttttttaa  102600
aatcttgaaa gtctgtgaat tttgtcaatt gtctgtattc ctctgaaaga gattcataac  102660
aatgacccac ggcttctaat ttattttttg attggatcaa taataataac agaaagtcta  102720
gatattgagt gatttgcaat atatcagata atgaagattc atcatcttga ctagccaaat  102780
acttaaaaaa tgaatcatca tctgcgaaga acatcgttaa gagatactgg ttgtgatcca  102840
tttattgatc gcaaaagctt tgcacaatct ttatacacta tcggtttact atttattgat  102900
aacgcagatg tttgagttgt catccatggt aatccataga tcattaattt atcgtcttca  102960
cacgctagat tagcacgtcg taatctatca ataggatcgg gtatttttcg tttaggcatg  103020
aagaacatat ttaattcaga tctaaaaaat acatatatta gaatgaatac aatgaatact  103080
tcaaataaaa ctattaatct gtgtttataa acacttaata aagaatgttt aaacgtgggc  103140
tctataaaca caggattaaa gtatacatta ggaacattct ccatttatag taatcaatcc  103200
tttgtcggaa tatctgttag aggaatattc tttttaacac attccaatag tcccagaaaa  103260
tcatttaacc taatgggttc ttgaagaggg ctagaactat acgattctag ttccttatta  103320
gtactaagtt tctctagttt atttttattg gtgaatccgt aaatggcatt caatctcatg  103380
gatgtggaag gagaatacac attcaggaca ttaattcccg catatttaga tatcaaagcc  103440
ttgttgtctc cgataggtgt atactcagtc gacgcggatt ccatatttc tttataaata  103500
ttaatctttt tacgagtttc gaaaatacac aagataggtg atgatccttg acggaaaata  103560
accatgttct tattcttct cctaccactt tttttaggaa tgacggcagt catatccgta  103620
ttattaatga taagaggcat aacctcattg ttaggatcca agaaatagtt ttcaatggct  103680
tcaatagtta gtttatcatc tcctagaccc aaattgtttc ttatattata cattgtggta  103740
aacattgccc ctgtgatatt ctcgttatga atcaactcca actcatattt tgacatcgtt  103800
ctaggtacta tattaaaaat agaaagcata gatcttggaa atttggattt tgcgccggca  103860
ataaccattt gtaaatcatc atactcagat atacttcctg caaaaaatat ggtatcttct  103920
tcgatgaggt tttctagcag tagactcatt tagagaagtt ttttttgtga taaatgaata  103980
cccgtaccga tgttacaaac gataatatag acaaaaatcc aaccaaacga ggtgatagaa  104040
atataccagg aagaaatgaa agatttaatg accaaaatag attcaacaac gatataccaa  104100
agcctaaacc aagactacag cctaatcagc caccgaaaca agataataaa tgcagagaag  104160
agaatggaga ttttatcaat attagattgt gtgcctacga aaaggaatat tgcaatgacg  104220
gatatctatc tcctgcctat tatatgttaa aacaggtgga tgatgaagaa ataagttgct  104280
ggtcagaact atcgtcgttg gtgagatcca gaaaggcggt gggatttcct ctattaaagg  104340
cggctaaacg tatttctcat ggatcgatgc tatattttga acagtttaaa aacagtaaag  104400
ttgtgaaatt aaccccgcaa gttaaatgtt taaatgatac tgttattttt caaactgtag  104460
ttattttata ttccatgtat aaacgtggca tatattctaa cgaattttgt tttgatctgg  104520
tttctattcc cagaacgaac attgtttttt ctgttaatca attaatgttt aacatttgta  104580
cagacatatt ggtagttcta tctatttgcg gcaaccggct ctatagaaca aatctaccac  104640
agtcgtgtta cttaaatttc atacacggcc atgagacaat agcccgtaga ggatatgaac  104700
actccaatta ctttttttgag tggttgataa aaaatcacat atcgctattg accaagcaaa  104760
cgatggatat tctcaaggta aagaaaaagt atgctacagg agcaccagta aataggttgt  104820
tagaacctgg tacactggta tatgtgccca aagaagatta ttactttata ggcatatcac  104880
tcaccgatgt gtcaattagc gataatgtca gagtattatt ttccacagat ggaatagtgt  104940
tagaaataga agactttaat atcaagcatt tatttatggc aggtgagatg tttgttagaa  105000
gtcagtctag tactattata gtataaagta ataaaaaata gttaatgtga tgactagcgc  105060
caccaacgcc aacaacattt gataatttct acttactaga cgtaccgtaa aaatataaat  105120
tactataaca aataatagta tatcaataaa caacctaatt aatggtcgaa gtatagcagg  105180
acattgatgc tctagaccgt gtataacaaa atctacaaat ttttcatccg ctatattttg  105240
tttcactata tcgtctagac gatcagcgat aacttccatg ttaatctatt aaaatattat  105300
caatatattt tcagttttgc atatccgtgg tagcaataac catcggagaa gttctaaaga  105360
atgtgtccat gtaagtagtc caatggacgt tttccttatt ggctaaaata agtttgattt  105420
tatcattggt ggatgtgaac aacatacgct tggcatagta cataaacaac gctgccaata  105480
ttataacacc gataacaatc atataaaact gaactcctgt accagcaact tgtctaggtg  105540
ctatttgagt agtggcctta gtcgtcaatt gcatcaacgc tttaatggca caatttcctt  105600
tgctagatcc tgtattaata aattccaaat ttgttggaga tcctggggct ccgtaacatt  105660
catctatgat tacgttttgt atctttaatt tgttatcgac gaccgcgcta gaattacaag  105720
tctgtttcac ataattttca aaatctctaa caacagtgtt tacactcgtc tgaatgttta  105780
acgcagcagt aaacatagct ggtacgtatg ctttttgttc cggtgttaat ccactatatg  105840
tttctgtagc ggctgataac acagcatcca actgagcatc cgcgtccgca gagcacatat  105900
ttttaacagt gaggttacat ccatggtttt gtcggatata aaaatttccg atttctatat  105960
cacattttgt ttgagcacta gcgttcgctt cttgttctaa tttagacgag atacgttcgc  106020
tgagtgtatt caccgtcgtc tgtatgcttg ccgcggcacc catttaaata gctacaatta  106080
gtatccatat taccaagaga gataataaac tgatcaaatg caattttagg tcgaacgaat  106140
```

```
gtttaatatt atgttgaact acttttgctc tattgacggg aacagtagaa aatctatcac  106200
tattgcttaa tccacatgac aatcttaatg aggaagtttt atccatctgt aagttgttca  106260
cgctagtatt acatcgtaca atattgcaaa gtcctaaatt attataatta cgtgttagta  106320
agaaattaac attggcattc gaacactctg gatcccaaca ttctcgaggt tccgcatatt  106380
ttaatgactc ttctaactta tctctagtgg gataactaca tctcatatat ttctgtttaa  106440
agtccgcaga ctgttgtctt agaatataat cgatcatctc tttgctatct tctgtattgt  106500
gtgcgcgtaa atgatgcaaa aatgattcac atattggtac actagcatct ttactacata  106560
atgtttgcat cttattatac agatttatta acgattgttg accctctaca gttctatcac  106620
tcctattaaa ggctgaaccg atccactgat ggcatatgtt tctatcgaac gtatccccct  106680
gacaccagtc gaataaatca acatcgcatt ttccagtgtc gtgaacgtct ggccaacacg  106740
attctaatac tgcaccctct tcatacttat ctgatatctt tccatccttt ttccaataat  106800
gagtacgatt aaaagtgcga cagcaattgg gtgcggttcc attatacgat tgtcttaaca  106860
atgccgaaag accaccgggt cctgtgttga ctaatctaaa ctctggatat cttttcttta  106920
ctttatcctc tttatctttt gctagtggtc ctatatgcac atattctaaa agcttagcgg  106980
gagctatcac gtcatgcatt ttatccacgt ttaataacat ctcatcagtg ggtactcccg  107040
gaggcggatc ccgtttaggg agctcaacac ttactctgcc acccatattt atctcattga  107100
aagtattaat ctaaaaacgt cataaagatg ttgatcttaa aggattgaac tctatccgaa  107160
aacaacattc ctagaatgtt atcgtcatta tccattacga ttctagtttc aaaaacattg  107220
actctctttt tgaatcctcg tagtttgttg agagacgaga tagctatttt gaaagaaaac  107280
ttttgtagtt cttgagaaca ttcagtcata gaatattccc tggaaaacgc atcagtatta  107340
ccaggagtct tcataataat attgtcatct ttaaacataa tagccaaatg ctgatgctga  107400
ctaatacact tgataaagcc caacaaccat tctaaatgaa tgacggttct accacaacat  107460
ttttcttcat acttgtgaaa attaaacacg taagatttct tttgatctat acttagacaa  107520
atagtagtat ctgtcctaat aggcatcagt tccttgttac aatcgacact tactacatga  107580
taactagaaa gttttactag attattttcc agatcaggtt ctatatctat gatggcatca  107640
ttgtgaaaac tacacaaaca cgattttacc ttggacacag gaagattaaa cacaatgttt  107700
tcggctccgc ggtagaacac tgatgcactg agaggtataa tggcccaaat gtttacagat  107760
ccgcccaagg cggcaaaaat atacattaac tcatccgtcg agtctacatt tatagatact  107820
tcttcactga actctgaaaa atatgccaca atttggcgca gtttatcgat ttttatacgg  107880
atgctcattt taaatttttg taaattattt aaagttaaat ggctgcagaa cagcgtcgtt  107940
ctacaatttt tgacatagtt tcaaaatgta tagtgcaatc tgtattgaga gatatatcta  108000
ttaattctga atacatagag tccaaagcta aacaattgtg ctattgtccg gcatcgaaaa  108060
aggaatcagt gattaatggt atctacaatt gttgcgagtc aaatatagaa ataatggaca  108120
aagagcagct attaaaaata ttggacaatc ttcgatgtca ttcggctcat gtatgtaacg  108180
ccacagattt ctggagacta tataattcgt taaaacggtt tactcatact accgcattct  108240
ttaatacatg caagcccact attctagcca cgctaaacac tttgataacc ctgattttat  108300
ctaacaagtt attgtatgcg gcagaaatgg tagagtatct agagaaccaa ctagattcat  108360
caaataaatc aatgtctcaa gaactagcag aattattgga aatgaaatat gctctcatta  108420
atctggtaca atataggatt ttgccaatga tcatcggtga gcctattata gtagctggat  108480
tttctggtaa agaaccaatt tctgattatt ctgcagaagt ggaaaggcta atggaactac  108540
cagttaaaac tgatatagtg aataccacat atgacttctt agccagaaaa ggtattgata  108600
ctagcaacaa tatagcagaa tatatagccg gcttgaaaat agaagagatt gaaaaggtag  108660
aaaaatattt accagaagtt atatctacaa ttgccaatag taatataata aaaaataaaa  108720
aatctatctt tccggccaat atcaacgata aacagatcat ggaatgctct agaatgttag  108780
acacgagtga gaaatactct aaaggatata aaactgatgg agctgtgact agtccattga  108840
cgggaaataa tacaattaca acatttatac caatttctgc gtccgatatg caaaagttta  108900
ccatttaga atatctttac attatgagag tgatggcaaa caacgttaag aaaaagaacg  108960
agggaaaaaa caacggagga gtagttatgc atattaactc accctttaag gtaatcaatt  109020
tgccaaaatg ttaaattatt agaatcatat atctttatcc atctattatc atctgtgaag  109080
ttttggctca gaaaaatatc tttacctaat attcgtttag acgatgtatc aataccggca  109140
tttttataac attcagctac caatttaaaa caatacattc tattatgacc aaatccatac  109200
ggaataccca ataaagttaa tgacgtatca gctgctattt tcataacttg aatattctct  109260
aacatgtata cttttgcact aagatatcct tcaaaaaaac tatccaatgg gactattcga  109320
actccttttc tataggtaga ttcaactacc aagtgttccg ataataacgt accataataa  109380
atacccacat gtttttctat cgatggattc aaatgacttg ttaatgacat ggtataatta  109440
ataaaaataa tagaacctct aggcgcatat gtcttgataa aattaaccgg atccatatta  109500
gtttatatcc aatagaggtt gcactgttaa gttacgttga ggttctattt gtgtagataa  109560
ttttaaccta caacattcgt tctttacact gacgagtaca tcctttaatg atttttttcg  109620
tataatcaat ttatatcgtt cgtgagaaat atctttgccg cacgtagagc acacgagttg  109680
gaacaccatt tttaatctag taacctatat ttattatatt atcactttta gtattggtta  109740
ttaacagact atcgttaaag taaaatgaac tatttatact cagtagtaaa ttatccttat  109800
agatgccgaa cactatagtg ttacagtttt cgttagaata tccgaagatc gaagatatag  109860
attttataac atcgatatct gatttagtat tttcgaaatc tatataagat gataaagttt  109920
taacttctga aacatcaatc tccttgcgtg gttctaatgc atacattaat tggcagggta  109980
acggaacggt ctctaaataa gatgatttaa aattgttcca tttttcatct aatgcggaaa  110040
atataaattc ttgaacagtg cattgacaag gaggaacata cgagtagaca tcgtctaaat  110100
tagcgtaatc gtttataaac gtaacaatat tacgcacgtc tacggtagag ttagtctttc  110160
tataataatt tttaattgcc aaactagtga ctatattatc gattgtaaaa tcactaaaca  110220
attgtatttt gtttaagttg gtgggtgtta tagatgcccc atagagtcca ggaaagaaat  110280
cacatccatt cactaacgcc gttaattttg ctaaatagtt atcctctgcc gagggaacaa  110340
atttaaacag ttgagttaag ttttttatca tcttaggatg attatcagta gatgcaaata  110400
gcatagtatc ctgatcggta cttattatca acggccattc tcctgtggta gagaaatgtg  110460
ttttagcctc gagacacata acgaattctg cgtctcgttc atcacaataa aataatgtaa  110520
cattctcatt attgttgaaa tgtgttagta tctcattcaa tgatattttt atgttatcag  110580
aatcagataa atatatttga aatgtgagtt tatcgatttt taattgcatt tctgccttta  110640
tttcttcttc cataaatccg gtaacatttt gtatttcgga tgtacacttt tctaattcta  110700
gcatttttct gtccttggtt aatttagaat atttacgtct cttgtctcta acgtcttgtt  110760
taatttttat acttcctcta tcgataaaaa gggttacatg ccctcccttt tttacccatc  110820
cgtttacgta ttttatgaat accgtagtta actcttctaa gtttctgaca caattggcga  110880
```

-continued

```
cggctatata aatactcatt gtatccacaa atattccatt gtatactttg tataaattat  110940
catctaatat cgtcagtgat ttattttcca gcagtaacga ttttaagttt ttgataccca  111000
taaatgaaga acgtactgat tattttcggt aaaccgtatt gtagtatttg tgaaaatgtc  111060
agtgatgcag tagaagaatt aaaatccgag tatgatatac tccatgttga tatcttatca  111120
tttttttaa aggatggtga ttcaagtatg ctgggtgacg taaagcgcgg aaccctaata  111180
ggaaactttg cagcgcatct atctaactac atcgtttcca ttttcaaata caatccacag  111240
acaaaacaaa tggcatttgt ggacattaat aaatccttgg atttcaccaa aaccgataaa  111300
tcgctggtga atttggaaat tctaaaatcc gaaatagaaa aagcaaatta tggagtttgg  111360
ccaccggtta ccgaataaaa tatcttcctg agtattttgt ttattgttcc gcttccttta  111420
tcaaataaat tttgaagtat ttgataattt attggatcga ctagttcatc tatacatttt  111480
ttggaaacga gaacatctac ctttttattt gttgttatat gcgacgttgt atacgccata  111540
aatgtaactt gagaaaatcc acaaagaatt aattttgaac cagttatggg gacgcgctca  111600
ttagaatatg tataaatctg aggagtgtat tccttgagga gatattctat caagtcatca  111660
tttgcttctc taatataaat attcctgtcc tttataacaa ctatgccttt tagattatct  111720
cctaatttat aacacggccg tatacacttg gaatacttgt acaatctaag atagactaaa  111780
tctctcagag ttgtatcatg gaattccata cttaattcct ccgataaatc tacatgttca  111840
aatactttag aaatatattt atggtatttc ctatctggaa agtaagttat caagtcatca  111900
taagatattt caaatcctct acataaggaa gacactatct ccaacgattc ctcatcttct  111960
gtaagtagga atttggacaa gttaaacaaa attagatctc taaatggcat ctttattata  112020
tcttatttta tttttgttat tcgtatgtat ttcttattat tttacatatt atccgaccaa  112080
taaacttcag gcagctgtaa tggaaacaga tagagaaaac gctattatta gacagcgaaa  112140
tgatgaaata ccgactagaa cattagatac agctatattt accgatgcat caaccgtcgc  112200
gagtgcgcaa atacacctat attataattc caatattggt aaaattataa tgtcacttaa  112260
tggtaaaaaa cacaccttta atttatacga tgataacgac atacgaacat tacttcctat  112320
tttactcctt agtaaatgat tgtcttaccg aataaagttc gtattttcat caacgatcgg  112380
atgaaaaagg atatctactt gggaatttct aatttcggat tcgagaatga tatagatgaa  112440
atcttgggaa ttgctcactt gttggaacat ctacttatat cctttgattc tactaatttt  112500
ttagcgaatg cttctacatc tagaagttat atgagttttt ggtgtaaatc cattaattca  112560
gcaacggaat cggacgcaat cagaacatta gtttcgtggt tcttttctaa cggaaaactc  112620
aaagataatt tttccctttc tagtatacga tttcacatta aagaattaga aaacgaatac  112680
tattttagaa atgaagtatt ccattgtatg gatatactaa cgtttcttag cggaggcgat  112740
ttatataacg gtgggagaat agacatgata gataatctta atatagttcg tgatatgctg  112800
gtaaatagaa tgcaaaggat atcgggatcg aatatcgtaa tttttgttaa gagattagga  112860
cctggaacat tggatttctt caaacagaca tttgggtctt taccagcatg tccggagatt  112920
attccttcgt ctattccagt aagtacaaac ggtaaaatag ttatgactcc gtctccattt  112980
tatacagtta tggtaaagat taatccaaca ttagataata ttttagggat tctgtatttg  113040
tacgaaactt accacttaat agactatgag actatcggca accagttata tttaacggta  113100
tcctttatcg atgaaactga atacgagagc tttcttcgtg gcgaggctat attacaaatt  113160
agtcaatgtc aacgtattaa tatgaattat agcgacgatt atatgatgaa catctattta  113220
aattttcctt ggctatcgca tgatttatat gattacatta cacgtattaa tgacgatagc  113280
aagtcgatac taatatcctt gacaaatgaa atatatgcat ctataattaa tagagatatc  113340
atagttattt acccaaactt tagtaaggcc atgtgtaaca ctagagatac ccaacaacat  113400
ccgatagtag ttcttgacgc aaccaatgat ggactgatta agaaacctta tagaagtata  113460
cccctaatga agcgtctaac atctaatgaa atatttatac gatacggaga cgcgtctctc  113520
atggacatga taactttatc attgtctaaa caagatatat cattaaaaag aaatgccgaa  113580
ggaatacgtg taaaacatag tttttcagct gatgatatac aggcaattat ggaatctgat  113640
tcgtttttaa agtatagtag atcaaaacca gctgcgatgt atcaatatat atttctatca  113700
ttttttgcta gtggtaattc catagatgac atattggcaa atagagattc taccttagaa  113760
ttttctaaaa gaactaaaag taaaattttg tttggtagga ataccagata cgacgtcact  113820
gcaaaatcta gttttgtatg tggtatagta cgaggtaaat cattggataa aacgtctctg  113880
gttgaaatga tgtgggatct caagaagaaa ggattaatat attctatgga atttaccaat  113940
ctattgagca agaatacctt ttatctgttc acatttacta tctacactga tgaagtatac  114000
gattatctaa acactaataa actttttttct gcaaaatgtt tagtcgtgtc tacaaaagga  114060
gatgtggaaa attttcatc tctaaaaaaa gatgtggtca ttagagtttg atttttagtt  114120
attatctaca ggaacaaata tagtatctga aatcatattc atatatcccg ttagaggtct  114180
atgataatat atagtagcgt ttgttccgtt atagacaccg aataatattt tacaaaagtg  114240
tatatacgta tcatcatctt tatgtttaaa atttaaaatc ttaattcgta aatttagaga  114300
taaaatggct tcttgtacaa tactagttaa ttctcccgtc ctctcaaaat tatccaactc  114360
ctcagcgaga ataggactta gtacataaag tttagcatac tctatcatct tcatataata  114420
attggataat aatttattcc atgtttctgt actaatatcg aacgagtcta tatattcctt  114480
tgtacgccat agaatatcca aatttgtagg gattataaac aaatcttcgg ggagtgttag  114540
attaaactta ttagcgtaca atatataatt atgtagaaat tctgaatcta ttcgctgtat  114600
agacttcata taagacagat catagaaata tacgtatgtc ccaggattaa ctcttcctac  114660
tcttcctttt cgttgatctc tcatagattt agaaataaat tcttgcgatc ctccaaaagg  114720
agcggggaca aaaactctac ccatatcata aatgtgtgta acattgcgta tagtaacgct  114780
ggattccaaa taaggagtag aaataattat cgatacatta ggtgatgaat acacttttc  114840
taatatttcg tctatatcta agaccttacc atgaataata tacatatcat acggtaatct  114900
tttttctaaa tatgatttat attcgtgaca ctgtgcaacg gatgccacaa agactatacc  114960
ggatgatcca tcaggaggag tatacatctg tatagcagta actaaatttc tcttttcttc  115020
ttctatgtat gccattctgg aagatggatt tatcttatta tgaataaata cctcgctaat  115080
tttaaacagt gtatctccag gaatatgtat aaatgcggga ttaggtaaaa atacttttag  115140
ccgttccctg tcatcctcta acgtggcagt cattaaaaac atagaatcta ttttcgtatg  115200
atgctttctc gctactgcta taataatatc tcctatttga tcatgctcat gaacttcgtc  115260
tataataaga gtgccataac taaatagttt tgttagagat aacttatggg tagaaaatac  115320
aattccatat tttttggtt gtttgtttat taattcttcc ggtatagatc cgtaccgtaa  115380
agaaatagga gatccatcta gtaccttaaa tcccaatgat tttaaaatgg tattgctatg  115440
caatctaact aaagctatcc taggaagaga tagaatgact ggtctttcgt gaaagtcagt  115500
gattttatct agagtagaga atccaccaaa taaataatta aaccaaagca ataacttggg  115560
tacctgtgac gtcttaccca ctccagttcc tccagttaaa actacaggtc tatgagaaat  115620
```

```
ccacgctgaa aatatctctc gttgtgcttt aggagttaat gaggccaatg gaattttgct  115680
aaatggatac ttattcccta gtacacctat agtatctgtt cgtttaccta cggaattgga  115740
aaatatctgt aaactattac cagcttctaa tagtcctctt aatatatact catcgaacga  115800
attgatttct gtatttgtta tacattttag aaaactataa cattcaaagc ttattgtgtg  115860
ttcactgtat atatattgct tcgcggttag gtttatgtgt gcgggttttc ctagtgatgg  115920
aggagatact ttttttccac gtgcttctgt actaactttg tatattcctt tatgttttac  115980
aacgtgtgcg ttatgccatc tatgttttat aactggaaac accgccaatg agaaactatc  116040
acgttccgtt ttactcatat tactgaattc atcttgtgaa tatttgtaag agaatacatt  116100
aacgcagttt ggaaaaaaga agatatctgg taaattcttt tccatgataa atggaaagat  116160
atacagattt agtaattagt aaaataccag aactaggatt taccaattta ttatgtcata  116220
tatattcact agctggatta tgtagcaata tagatgtatc taaattttta acaaattgta  116280
acggatatgt agtggagaaa tatgataaat ctacaaccgc cggcaaagtg tcttgtattc  116340
ctatcggtat gatgttggaa ctagtagagt cggggcacct gagcagaccc aatagtagcg  116400
acgaactcga tcaaaagaaa gagttaaccg acgagttaaa gacgcgttac cattctatat  116460
atgatgtctt tgagttacct actagtatac cgttagcgta tttctttaaa cctcgactac  116520
gggaaaaagt atctaaggcg atagacttct cacaaatgga tttgaaaatc gatgatttat  116580
cacgtaaagg aatacatact ggtgaaaatc caaaggtcgt caagatgaaa atagagcctg  116640
agagaggagc ctggatgagc aatcgaagta ttaagaactt agtctctcag tttgcttatg  116700
gatccgaagt ggattatata ggacaatttg acatgagatt cttaaactcc ttagcgattc  116760
atgaaaaatt tgacgcgttt atgaataaac atatcttatc gtatatactt aaagacaaaa  116820
ttaaaagttc tacctctaga tttgtaatgt ttggattttg ttatttgtct cattggaaat  116880
gtgtaattta tgataaaaaa caatgtttag tatccttta tgactccgga ggcaatattc  116940
caactgaatt ccaccactat aataattttt atttttattc cttctccgat ggttttaaca  117000
cgaatcacaa acattctgta ttggataata caaattgtga catcgatgtt ttattcagat  117060
ttttcgaatg tacatttgga gcgaaaatag gctgtattaa tgtagaagtt aatcagctgt  117120
tggaatctga atgtggaatg tttattagtt tgtttatgat attgtgtact aggacaccac  117180
ctaagagttt caaatctctg aaaaaggttt atacattctt taaattttta gcggataaga  117240
aaatgacatt atttaagagc attctattta acttgcaaga tctatccctg gatataacgg  117300
aaacggataa cgcaggatta aaagaatata aacgtatgga aaaatggacc aaaaagtcaa  117360
ttaatgtgat atgtgataaa ttaactacaa aattaaatag aatagtaaac gacgatgaat  117420
aactttgtta aacaagtagc ttcaaagtct ctaaaaccta ccaaaaaatt gtctccgtca  117480
gatgaggtga tatctttaaa cgaatgcata atatccttta acttggataa cttttattat  117540
tgcaacgatg gactgtttac taagcccatt aatactccgg aggatgttct taaatcactc  117600
ttgatcatgg aatcattcgc ctacgagaag atgataatca aaggattgat aaaaatacta  117660
atatctagag catatattaa tgatatttat tttactccat tcggttggtt gacgggcgtc  117720
gacgatgatc ctgaaacaca cgtggtgata aaaataattt tcaattcatc actaatatct  117780
atcaagtctc aagttataga atatttaaaa ccatacaatg tcaataacct atcggtactt  117840
accacagaaa aagaattaag tattaatacg ttcaatgttc cagattctat acctatgtcg  117900
ataatttcgt ttttcccatt cgatacagat tttatactag ttattttgtt ttttggagta  117960
tataatgact cgtattgtgg aataagctat ataagtccga aagagagact accgtatatc  118020
atcgaaatat taaaaccgtt ggtgtcggaa attaacatgt tatcggatga aataggtaga  118080
acatcatcca ttagaatctt caattccact agcgtcaaaa aatttcctac taatacatta  118140
acatccattt gtgaaattgt ttattcgttt gatgaatcat cctttccgac gcctaagacg  118200
ttcactcctc taaacgcgag tccatacatt cctaaaaaga tagtttcact attggattta  118260
ccatctaatg tggaaataaa agcgatatct agaggcggtg tggatttcat cactcatatt  118320
aataataagc gtctaaacac aatcttggta atagcaaaag ataacttttt aaaaaattct  118380
acattttctg gaacttttat caaagagaat attatttgga agggtatcta tacttataga  118440
ataatcaagt ctagttttcc agttcctact attaagtcgg ttactaataa aaaaaaaata  118500
tgtaagaaac attgtttcgt caattctcag tatacaacta ggactttgtc acatattctt  118560
tgatctaatt tttagatata aatggtggat gctataaccg ttctaactgc gatcggcata  118620
actgtattaa tgcttttgat ggtaatttct ggcgccgcca tgatagtcaa ggagttaaat  118680
cctaatgata tattcactat gcaatcatta aagtttaatc gagccgtaac gattttcaaa  118740
tatataggac tctttatcta tataccagga acgataattt tgtacgctac atacgtcaaa  118800
tccctattaa tgaaaagtta aataattttt tttattacac caacaaaaat gtttgtcatt  118860
aaacgaaatg gatacaagga aaatgtcatg tttgataaaa tcacgtctcg tattagaaaa  118920
ttatgttatg gcttaaacac ggatcatata gatcctatta aaatagctat gaaggttatt  118980
caaggaatat ataatggagt aacaacggta gaattggaca ctctggcagc cgaaatagca  119040
gccacttgta ctacacaaca tccggattat gccattctag ccgccagaat agccgtatca  119100
aatctacaca aggaaacaaa aaaactattt agtgaagtga tggaggattt attcaactat  119160
gttaatccta aaaatgggaa acattctccg attatttcaa gtatcaccat ggatatagtt  119220
aacaaatata aggataaact caactcggtt attatttacg aacgagactt ttcatacaac  119280
tattttggtt ttaaaacttt ggaaaaatcc tacttgttga aataaacaa caagatcgtt  119340
gaaagacctc agcacatgtt aatgcgtgtc gcagtaggaa ttcatcaatg ggatatagac  119400
tcagctattg agacgtacaa tctactttct gaaaaatggt ttacgcacgc ttctcctacc  119460
ttatttaatg cgggaactag tcgtcaccaa atgtctagct gttttctact taacatgatc  119520
gatgatagca tagagggtat ctatgacacg ttaaaacgat gcgcattaat ctctaaaatg  119580
gcaggggga taggtctatc aattagtaat attcgtgcca gtggaagcta tatctccggt  119640
accaatggta tatcaaacgg tattattcca atgttgagag tttataataa caccgctaga  119700
tacatagatc agggaggaaa caaacggcct ggagttatgg ccatatactt ggaaccgtgg  119760
cattctgata ttatggcgtt cctcgatctt aaaaagaata caggaaacga ggaacataga  119820
accagagatc tatttatagc tctttggatt cctgatctct ttatgaaacg agtgaaggat  119880
gacggagagt ggtcgttgat gtgtccggat gaatgtcctg gattggacaa tgtttgggga  119940
gacgagttcg aacgattgta tacactatac gaaagagaaa ggagatacaa atctataata  120000
aaggctcgag tcgtctggaa agcgattata gaatctcaga ttgaaactgg tactccattc  120060
attctttata aggatgcgtg taacaaaaag agtaatcaac aaaatttagg aactatcaag  120120
tgtagtaatc tttgcactga gataatacaa tatgcggatg ctaatgaggt agccgtttgt  120180
aatctggcat ctgttgcctt gaacatgttt gtaatagatg ggcgatttga ttttctcaaa  120240
ctgaaggatg tggtcaaagt aattgtcaga aatctcaata aaattataga tattaattat  120300
tatcctattc cagaagctga aatctctaat aagagacata gacctatcgg tattggtgtt  120360
```

```
caaggattag cggacgcgtt tattctctta aattatccat ttgatagcct ggaagcacaa  120420
gatctaaata agaagatctt cgaaaccatt tattacggtg cattagaggc gagttgtgaa  120480
ctagctgaga aggaaggacc atacgataca tatgtaggat cgtacgccag taacggtatt  120540
ctacaatatg atctttggaa tgttgtaccg tcggatcttt ggaattggga acctctaaaa  120600
gataaaatca gaacatacgg tcttagaaat agtttattgg tggcacctat gccgactgca  120660
tcaactgctc aaattttggg aaataatgag tcggtggaac cgtataccag taatatttac  120720
actcggagag tattgtctgg agaatttcaa gtagttaatc cgcatctcct tagagtttta  120780
accgagagaa aattatggaa tgatgagatc aagaatagga ttatggcaga tggtggatcc  120840
attcagaata caaaccttcc agaagatatt aagcgagttt ataaaactat ttgggaaatt  120900
ccacaaaaga cgatcataaa aatggctgca gacaggggag ccttcatcga tcaaagtcaa  120960
tctatgaata tccatatagc agatccgagt tattccaaac taacgagtat gcatttttac  121020
ggatggagtc tcggtctaaa aacgggaatg tactatctac gtacgaaacc cgcatccgct  121080
cccattcaat tcacattgga caaggataaa ataaaaccac tggtggtttg cgattccgaa  121140
atctgtacat catgcagtgg ttaaacaaaa acatttttat tctcaaatga gataaagtga  121200
aaatatatat cattatatta caaagtacaa ttatttaggt ttaatcatga gtaaggtaat  121260
caagaagaga gttgaaactt caccaagacc tactgcatct agcgattctc tacagacttg  121320
tgcgggtgtt atagagtatg caaaatcgat tagtaaatct aatgcaaaat gtatcgaata  121380
cgttacacta aatgcttctc aatacgctaa ttgttcgtct atctctataa aacttactga  121440
tagtttatct agtcaaatga cttccacttt tattatgttg gaaggagaga ctaaacttta  121500
taaaaataaa tctaaacaag atagaagcga tggatacttt ctaaaaataa aagttaccgc  121560
ggctagtcct atgttgtatc aacttctaga agccgtctat ggaaacatta agcacaagga  121620
acgcattcca aattctttgc atagtctttc ggtggaaact attacagaga aaacatttaa  121680
ggatgaatcc atcttcatca acaaattaaa cggatccatg gtagaatatg tttcgactgg  121740
agaatcatcc attctcagat ctatagaagg tgaactagaa tcactcagta aaagagaaag  121800
acaattggcc aaggcaatta tcacacctat cgtcttctat agatccggaa cggaaacaaa  121860
aattacattc gcactcaaga aactaatcat tgatagagaa gtggtggcta acgttatcgg  121920
actctctgga gatagtgaac gtgtatcaat gactgaaaat gtagaagaag atctggctcg  121980
taatctggga cttgttgata ttgatgatga atatgatgaa gatagcgata aagaaaagcc  122040
aatattcaat gtataaatgg ataagttgta cgccgctata tttggtgtat ttatggggtc  122100
tccggaagat gatttgacag actttataga aattgttaaa tctgttctaa gtgatgagaa  122160
aacagtcaca tcaactaata ataccggttg ttggggttgg tattggttaa ttattatttt  122220
ttttatagtt cttattctac tactattgat atatttgtat ttaaaagttg tttggtgaac  122280
ttaaatggcg gaatttgaag atcaactcgt tttcaatagt atcagtgccc gtgcattgaa  122340
agcttatttc actgctaaaa tcaatgaaat ggtagatgag ttggtcacaa gaaaatgtcc  122400
acaaaagaaa aaatcacaag ctaagaaacc tgaattacgc attcctgtag atcttgtaaa  122460
gtctagtttt gttaaaaagt ttggattgtg caattatgga ggaatcctta tcagtcttat  122520
taatagtcta gtagaaaata atttctttac aaaggatgga aaactggatg atacaggcaa  122580
aaaggaattg gttttgacag atgtcgaaaa acgaattctt aataccatag ataaatcatc  122640
tcctttgtat atcgatatta gtgatgttaa agtattggct gctagactaa aaagaagcgc  122700
tacacaattt aactttaatg gacatacata tcatctggaa aatgataaaa tagaagatct  122760
cattaatcag ttggttaagg acgaatccat tcaactggat gaaaagagtt ctattaaaga  122820
tagtatgtat gtcattcccg atgaacttat cgatgttctc aaaactagat tgtttagatc  122880
tcctcaagtc aaggataata ttatttcgcg tactagattg tatgattatt ttactagagt  122940
tactaagaga gacgaatcgt caatctatgt gattctaaag gatcctagga tcgctagcat  123000
tttgtcacta gaaactgtta aaatgggcgc ctttatgtat acaaaacata gtatgttgac  123060
gaacgctatt tcatctagag tcgatagata ttctaaaaag tttcaagaat ctttttacga  123120
agatattgta gaatttgtta aagaaaatga gagagttaat gtatcgagag tggttgaatg  123180
tttgactgtg cctaatatta ctatatcaag taatgctgaa taaaaatatt tataaatatg  123240
ctcgtcgtaa ttatgttttt tatagcgttt gccttctgta gttggctatc atatagctat  123300
ctgcgtccat atatctcgac taaagagtta aataagtcga gatagtttta tatcacttaa  123360
atattaaaat ggccgaggaa tttgtacaac aaaggttggc caataacaaa gtgacaattt  123420
ttgtcaagta tacatgtcct ttttgtagaa atgcactgga tattctaaat aagtttagtt  123480
tcaaaagagg agcgtatgaa attgtcgata ttaaagaatt taaacccgaa aatgaattgc  123540
gtgactattt tgaacaaatt actggtggta gaactgttcc tagaatcttt tttggaaaaa  123600
cttctattgg tggatatagc gacctgttgg aaatagacaa catggacgca ttgggtgata  123660
ttctatcatc tattggggta ttgagaactt gttgagaaaa taatgaaaaa acaatactta  123720
atcatgtcgc cgacatgttc atgtatccgg aatttgcgag gaaggcttta tcaaagctta  123780
tttcaaaaaa attaaacatt gaaaaggtgt ctagcaagca ccagctcgtg ttactggatt  123840
atggattaca cggactattg ccaaaatcac tgtatctgga agctattaat tccgatattc  123900
tcaatgttag attctttcct cctgaaataa taaacgtcac tgatatcgtt aaggctctcc  123960
aaaattcttg tagagtagat gagtacctaa aatctgtttc cttatatcat aagaattctt  124020
taatggtatc gggaccaaat gtagtcaagc ttatgataga atataatctt cttacacaca  124080
gtgacttgga atggttaatt aatgagaatg tagtcaaggc tacatacctt ttaaaaatca  124140
atgcctatat gattaacttt aaaatagatc taacggttga tgaaatcatt gacttagtta  124200
aagatattcc tgtaggagct acgctacatc tatataatat attaaacaat atagatttgg  124260
acattgttct tcgtatatct gatgaatata atataccacc tgttcacgat attctgtcta  124320
aacttaccga tgaagagatg tgtataaaac tagttacaaa gtatcctatg gacaatgtta  124380
taaattttat taatcaagat gttagatata gtcccacctt catcaagaca attaaagatt  124440
ttgtcaacaa gcatcttcca accatgtacg atggattaaa tgattatcta cattctgtta  124500
ttatcgacga ggacttaata gaggaatata aaattaaatc cgttgccatg tttaatttgg  124560
aatacaaaac tgatgtagat actctaacat tggacgaaca gatatttgta gaggtaaaca  124620
tctcatatta tgattttaga tatagacaat ttgccgatga atttagagat tacattatga  124680
taaaagaaag aagacaaatc accatgcaat ctggtgatag aataagaagg tttagacgtc  124740
ccatgtcatt gagatccact atcatcaaaa aggatactga ttctctagag gatattctcg  124800
cacatataga taatgccaga aaaaatagca aggtatccat tgaagatgtt gagagaatca  124860
tttcatcttt ccgtcttaat ccttgtgttg tcagacgcac catgctgtct gatatagata  124920
tcaaaacaaa gattggaaat cttgtgctct gacactatca gccatcaaag gaattatggt  124980
aacagatacc atcaataccg tgttatccaa aattctgcat catcatagga atgtcttcaa  125040
gtatcttaca tctgtagaga ataaagaaat tgctgtctgt cgctcttcta tagagaatta  125100
```

```
aaaagtgtac gatgtgatct acgcacagat gatggattat tggataggct atacgatctg  125160
actagatacg ccttacacgg aaaaatcaat caaaacttaa tcggtcaacg atgttggggt  125220
ccgttgacag aaatgctgtt taacgagaat aaaaagaaaa aactaaataa tttaatggaa  125280
tacatcaaaa tatcagacat gttggtatac ggacactcta tcgagaagac gcttattcca  125340
attactgatt ctctttcatt caagctatct gttgatacca tgtctgtgtt aaatgatcaa  125400
tatgccaaga ttgtcatctt cttcaatacc atcatagaat atattatagc tactatctat  125460
tatagattga cagtcttgga caattatact aatgtcaaac attttgtatc caaagtgtta  125520
cacactgtca tggaagcatg tggcgtactg ttttcataca ttaaagttaa tgacaaaata  125580
gagcatgaat tggaggagat ggtggacaaa ggtaccgtac cttcttattt gtatcatctg  125640
tccatcaacg tcatttcaat aatattggat gatataaatg gaactcgtta atattttttt  125700
agaaacggat gctggaagag taaagtttgc cataaaaaat accgacgatg tatgtgcctc  125760
ggagttaata aataaatttg tggaactgtt aagtgaatac attcacattg accaatcaga  125820
attttatttg gtggtaaagg ataaggatat tttttatttt aagtgtgata gggggtctat  125880
ttcgattgta aacaatgagt tttatgtctt tgacgaaccc ttgctgtttg ttaaagattt  125940
cactaatgta acgggggttg aattcatagt tacagaaacc atgccgtgta gaattatacc  126000
aaaaaataat cacgcggtta tttcagtcgt gactaatcat aagttttata atgggttaag  126060
tttataaagg gttaaccttt gtcacatcga tcgcgtattt gggatcagat gccaaattgt  126120
taaataatct gatgaaaaaa taataaatat aattcagatc atcgctagac atgacattat  126180
tgtcctctat agcgatagtc gcgtgccgtc tacatgcagg acatggaaga gtgctgacta  126240
tagtatatag ttttcgttta cacgcttcta tgttgccgtc taaacccgct tgcgaaagta  126300
ctataaaaat aatggtccat acggctcttc cccaatgttt gggattcatt taaatgaaaa  126360
tatatttcta aattctataa atggatgttc ggtgcattaa ttggtttgaa agtcacggtg  126420
aaaacagatt tttatatctg aaatccagat gtcgaaatgg cgagaccgta tttatacgat  126480
ttcctcatta cttttattac gtagttacgg acgaaatata tcagtcattg tctcctcctc  126540
catttaatgc gaggccgttg ggaaagatga gaactataga cattgacgag acaataagtt  126600
ataatctaga tattaaagat agaaaatgct ccgtcgcaga tatgtggttg atagaagagc  126660
caaagaaacg cagcatacaa aatgccacca tggatgaatt tctcaatatt agttggtttt  126720
atatttctaa cgggatatct ccagacggat gttactcgtt ggacgagcaa tatttgacaa  126780
agattaacaa tggatgttat cattgtgacg atccacgtaa ctgtttcgct aaaaaaatac  126840
ctagattcga tatcccaaga tcgtacttat ttctagatat agagtgtcac ttcgataaga  126900
agtttccttc tgtatttatt aacccaatct cgcatacaag ttactgttat atcgatttaa  126960
gtggtaaacg attattgttt acgctcatta atgaagagat gttaacggaa caggaaatac  127020
aagaagccgt cgatagagga tgtttgagga tacagtcact aatggaaatg gattacgaac  127080
gagaactagt tctatgttct gaaatagttt tgttacgaat agctaaacaa ttgttggaac  127140
taacgttcga ctacgtcgtt acctttaacg gacataactt tgatctgaga tatattacta  127200
atcgtctaga gttattaaca ggagagaaga ttatctttag atctccggac aaaaaggaag  127260
ctgtacatct ctgtatttat gagagaaatc agtctagtca taagggagta ggcggcatgg  127320
ccaatactac gtttcacgtt aataacaata atggaactat atttttcgat ctatattcat  127380
tcattcaaaa atctgaaaaa ttggattcgt acaaattgga ttctatatcc aagaacgcgt  127440
tcagttgcat gggtaaagta ttaaatagag gagttagaga aatgacgttc atcggtgacg  127500
atactacgga cgcgaaaggc aaagccgctg catttgcaaa ggttttaacc acaggtaatt  127560
atgtgactgt tgatgaggat attatatgta aagtaattcg taaagatatt tgggaaaatg  127620
gatttaaagt cgtactatca tgtcctactt tacctaatga tacatataaa ttatctttcg  127680
gaaaggatga cgttgattta gctcagatgt ataaggatta taatctaaac atagctttag  127740
atatggctag atactgtatt catgatgctt gtttgtgtca gtatttgtgg gagtattatg  127800
gagtagaaac aaaaacagac gcgggtgcgt caacatatgt gcttcctcaa tccatggtat  127860
tcgaatatag agcgagtaca gtcatcaagg gtccactgtt aaagctattg ttggaaacta  127920
aaactatctt agttagatca gaaacaaaac aaaagtttcc ttatgaaggc ggtaaggtat  127980
ttgctccaaa acaaaaaatg tttagtaata atgtattaat ctttgattat aacagtctgt  128040
atcctaatgt gtgtatcttt ggaaatctat ctccggaaac attagtcggt gtcgttgtta  128100
gtaccaatag attggaagaa gaaataaata atcagctctt gcttcagaaa tatccacctc  128160
ctagatatat tacggttcat tgtgaaccta gactaccgaa cctcatctct gaaatagcaa  128220
ttttcgatag atcgatagaa ggaaccattc ctagactatt aagaacattt ttggcagaga  128280
gagccagata taaaaagatg ctaaaacagg ctaccagttc aactgaaaag gccatctatg  128340
attccatgca atatacgtac aagatagtag ccaactcagt atatggtctg atgggattta  128400
gaaatagtgc tctatactca tacgcttcgg ctaagagttg cacatccata ggacgtagaa  128460
tgatcttgta tctagaatcg gtactaaatg gagcagagtt atctaacggt atgttacggt  128520
ttgccaatcc attaagtaat ccattttata tggacgatag agatattaat ccgattgtga  128580
aaacatcgtt gcctatagat tacagatttc gttttcgtag cgtgtatgga gataccgact  128640
ccgtgtttac agagatagac agtcaagatg tcgataagtc tatagaaata gcgaaagagt  128700
tagaacgact gattaataat agagtattgt ttaataattt taaaatagag tttgaggcgg  128760
tatataagaa tctgattatg caatcgaaga agaaatatac aacgatgaaa tactcagcat  128820
cgtcgaattc aaaatctgta cctgagagaa ttaataaagg tactagtgaa actagaagag  128880
atgtttccaa gtttcataag aatatgatta agacatacaa gaccagactg tctgagatgt  128940
tgtctgaagg acggatgaat tctaatcagg tatgtataga tattctccgt tctttagaaa  129000
cagatttacg atccgaattt gatagtagat cgtctcctct agaattattt atgttgagtc  129060
gaatgcatca ctcaaattat aaatccgcag ataaccctaa tatgtatttg gttactgaat  129120
ataataaaaa taatccagaa actatagaac ttggagaacg atattatttt gcatatattt  129180
gtccggctaa tgtaccatgg accaaaaaac ttgtaaatat taaaacatat gaaacaatta  129240
tcgatagaag ttttaaactc ggcagtgatc aaagaatatt ttacgaagtt tactttaaac  129300
gattgacgtc cgaaatagtc aatctattgg ataataaagt tttatgcatc tcattctttg  129360
aaagaatgtt tggttcaaaa cctacatttt acgaagcata aaataattta caacagttgt  129420
acgtcgctct ttgttagatt cagtttatcc attagatatt ctacggctgg agtaattttt  129480
gtagtaattg aatacccagg tacgtaaaac aataaaaaca ttaataccgg atcatacttg  129540
gtaaagtaca atatagtact aatattagct aatgtctcat aatcggatgg acttcttgct  129600
ctactaagat tagggtgatc tatatctttg atacttattg gaacgggacc ggtaaatata  129660
taattctctt tgagacgact aaacaaaggc ttatagtctc ctgtttgatg catataccta  129720
gccaacgcca ggtgtttggc attatctgta tagacgtatc tgaataatgt gtgtttagta  129780
atatcaaact gagtattttt aaaccagaac aagatattat agattggaat ggaagtcagt  129840
```

```
aacaaaaaac taataaactc gtttgttgga agggcagaaa actttcgaag atatgatacg  129900
tatctaccag agaacgatcc attagcaatg aattcagtat ttactttttc ttcatatacg  129960
ggaataggac ctttatatag agacatgaga aactcgaact ttttaagtaa tcccaacgaa  130020
atgggataat agtcacttgc atctaagttt gcgtatctac tactccaaat tgcagtttct  130080
ggtatccatc catacgcgta attatcaaat agatatgtgt ttttcattaa cggtctactt  130140
agacctctac taaaaaatgt ttcttgatct agaattcttc tttgtgcatt tttgtacacg  130200
tcgtcaaaac gcggaacggt ggcagccata atatttatat cctaccgctt tttatcaact  130260
atgttatgtc ttttagttag gttaatattc taataagatg caggtaatac atcaggttaa  130320
agtattagaa tgggattata cttatatatt tagtttatct ttcatcagat aactaaaaaa  130380
tgtataaaac agacgcgtta cattgcctat gctacatgag ttccatgtgc ggagattgtt  130440
aaagtttagg gtagagagtt gttctagcat ccattcattg tctttacatc cgttatatgt  130500
aattatgtca cccatggaca ttataggttt taatagtact tcagatactg gaataagata  130560
ttgttcgtat atgtgtttga taatcatttg ttgcgtttct ggagaacttt tctctgcatg  130620
atttttacat agctttacaa actcgtgatc actttttata atgagagatc tatagtcttc  130680
gtatctgtta cgaaaatcaa tatattcagg attattttct gaatcacttg attcgtcact  130740
aatatacata actatatgat caacaatttt ttccaaaatc atttctgcat tttctttatt  130800
cattaatttg gtgggagtct gaattgttgc agcagttccc atttatcaaa aatgtgtgat  130860
aattatatct atgtatatac aaattattaa taatatattt ggtctgttct atgatctacc  130920
gtgtcttatc aattgaagta tatatttctt atccgtcttg gttagatgga tgcttttatc  130980
caagaattct tctacatgat atagattatc tctcaaaaac ctttgaaata agacgatgat  131040
ggaaatatta taactagcta aaatagtttt gattagcgat ggaagaatac tagggttttt  131100
atctgtagaa aatcgaacga atgcggatac atcctccaca gacttaagat ggtttatcat  131160
tttaactaac aagtctcctt tataatcatc taacacaaga cctagacgag ccaattgtcc  131220
gtctaaataa tattttaaaa tgtttttgct aaacaagttc agccgtctac tcttggattt  131280
tatagatgac agtttcttta gtattccgtt ctctatgacc atgggatccg actcgtgcaa  131340
aaacaggtat gtattgtatt ccttaacata atacgacgta tcctcgttaa agatttgaca  131400
cttcttcata tcatccattg tatctaatgt gatatcgttc acctcataaa ttatattaga  131460
tatataactg ttattaatat ctaactcatc aaatcgttta atgtccgcag cactcgtaga  131520
gaataaagac ataattcgtt cattatcgaa atattcggga tctatttgaa caacaactct  131580
gaataagtcc tcgttaaacg ttctatcact aataaatgta ttaccgttaa taaaattagc  131640
tttataaaaa ctaataaaat atttttccca atcgtcgttt tttgcatcaa taatagatag  131700
gatatctcca ggaatatcat atatgatttc tagcagaagt tctctgatat ctttttcagg  131760
ctcaaagata taaactaact taagcatgtt tttattaacg cgtccttgtt ttatctcaga  131820
gtatatataa ctaagaattt tatcatacat ggtaatggcg tgtctattaa gaacaatatc  131880
cgcatcatta gctatacttt cgtttaacca cacccaatag ctagtcttat ctccgggaaa  131940
gatataatct ctaaacgttt ctgttagatt gctatggact attctaccag tttgttgaaa  132000
tagagtgtat atatcttgtc tatcattatc cgcaaactct atgcctgtat ctttcttgct  132060
taggtaagcc caaataagta atcttataac acttaatttt ttaacaactt tgaagtctgt  132120
tttcttaaac agttttaaaa aaatgatttc catatctttg atgggttccc ctccgtgaaa  132180
taatggatta agaactaagt cataatttac gcctataagt tctcctaatt cgtccatgta  132240
ttcggcaacc tctaaaaatt tttcatcttg tgttagttta tgcacggttt ccttgtacga  132300
ttgtattgcg ttactaaacg ataaataatt cttagtcaat gctttaacgt acaacgtggg  132360
tgcatcaaat gcgtgtcgta aaaccgcttc gtacacttta caacatcgta ccatatgtat  132420
gaaaacaaaa aaattggtat tagctaatac atccttagta ataacgtgtt gaggaaaatt  132480
gctaactaga tacttgagag ctagtacatg attgagggta aaattgttta ctttacttaa  132540
tgtatcatcc tttaaaaaat ctatattatt ttctactgtg tatataagat actttctacg  132600
aataaaatcc atttttatag aagagagtta tctatgatac tacactctta ttctaataat  132660
tatttttact attttatcac taataactat ttatactatc cattattaat ttaacaattt  132720
gaattagtat tggagaaaga tgaaatgcct attcactaac aaagtcaatg cactcttgaa  132780
gatttttacc aataatatgt agcggattct caaagtattt atttaccatt tctttacaca  132840
gtatcttagc cactggccta cgaacaggca tacatggttc aactatatca tgaacaatgt  132900
ttaattttag tgtatccaat ccaataaatc cattttctac atcatcatcg tatctgtacg  132960
ctttgtattc tccactcttg aacaaatctc taaacagtat cttcaacact ttttccacca  133020
attcctggga tgtcacacat tgttctacca tctgtttgat aaagagggta tcttcttcag  133080
attttccctt gattctatac atgggtttta ggttatacct tgcatctatt gtatatttat  133140
cagattcagc tatcaacatt ttatcaactt gtgttccaat tattctccat ttattagatc  133200
tgcattcatt attatagaat ctttcttcca ctaatattct aataagatta agtttgaaag  133260
gagagaagat cttgtgtttg attttactca ttggatgcat tctataacga atgaatctat  133320
gatcatctcc aaacaaattg ggaaacatgt aaagcagcag agcatatacc atcttactcg  133380
gattctgtga tgctttgccg atggctgaaa tgtccgagaa tagtttataa gttttctgat  133440
tatttggaat agatggtgct atatcttcta gagtagtagt cctaatcatt ctcttaaatt  133500
ttatgtatcc tagtttcaat gtctcgtaat gagtttgtgc tgctcttatt gtctgattta  133560
tttcttttac cattttggct ctattctgaa actttatcct cttcttatcc atttttattg  133620
ttgactccgc actatcgatt tgatactttc ttttcagagt aaagctatcg tcattgatca  133680
tcggacactg acttccactc attatgaaat tgtagccgta taaccacaat acaattatta  133740
acatatatat tcacttttgt taatatcaac ataataatga aaaaatataa atgaacaaag  133800
ttaatacata agtgttataa atggaaaatg tatacattag tagttactca tccaatgaac  133860
aaacatcaat ggcggtagcc gctactgata tccgagaatt actatcacaa tatgtggatg  133920
atgccaactt ggaagactta atagaatggg ccatggaaaa atcatcaaag tactacatca  133980
agaatatagg taatacaaaa tctaatatcg aagaaactaa attcgaatca aagaataata  134040
ttggtataga atactcaaag gattccagaa acaaactatc gtatagaaat aaaccgtcta  134100
ttgccacaaa tttggaatat aaaacactat gtgatatgat taagggtact agcggcaccg  134160
aaaaagaatt ccttcgctat ctcttattcg gtataaaatg cattaagaaa ggagtagaat  134220
acaatataga taaaataaag gatgtgagtt acaacgatta ttttaacgtt ctcgacgaga  134280
aatacaatac accgtgtcct aactgtaaaa gtaggaatac tacgccgatg atgattcaaa  134340
ctagagccgc tgacgaacct ccactagtta gacatgcgtg tagagattgc aaacaacact  134400
ttaagcctcc caaatttaga gcatttcgca atcttaatgt tacaacgcaa tcgatacatg  134460
aaaacaagga aataacagag attcttccag ataataatcc atctcctcca gaatctccag  134520
aaccagcatc acctatagat gacgggttaa tcagatccac attcgataga aacgacgaac  134580
```

```
caccagagga tgatgaataa aaaaatgata aaataaatta gttttattgc tggttgtgtt  134640
agttctctct aaaaatgtct aagatctata ttgacgagcg ttctgacgca gagattgtgt  134700
gtgcggctat taaaaacatt ggaatcgaag gagctactgc tgcacaacta actagacaac  134760
ttaatatgga gaagcgagaa gttaataaag ctctgtacga tcttcaacgt agtgctatgg  134820
tgtacagctc cgacgatatt cctcctcgtt ggtttatgac aacggaggcg gataagccgg  134880
atgctgatgt tatggctgac gccataatag atgatgtatc ccgcgaaaaa tcaatgagag  134940
aggatcataa gtcttttgat gatgttattc cggctaaaaa aattattgat tggaaagatg  135000
ctaaccctgt caccattatt aatgagtact gccaaataac taagagagat tggtcttttc  135060
gtattgaatc agtggggcct agtaactctc ctacatttta tgcctgtgta gatatcgacg  135120
gaagagtatt cgataaggca gatggaaaat ctaaacgaga tgctaaaaat aatgcagcta  135180
aattggcagt agataaactt cttggttacg tcatcattag attctgattc tagttatcaa  135240
taacagttag tagtttagtt atacattgaa tcatacatat taattttttt attgagatag  135300
attaaaaaat acaaattgta gtactattaa cgcgactagt atattctcta aagatgatat  135360
ctgtcacaga tattcgtaga gcgtttctag acaatgaatg ccatactatc acaaaagcgt  135420
ttggatatct gcacgaggac aaggctatcg cattaattaa aataggattt catcccactt  135480
atctacccaa agtcctttat aataatgttg tagaattcgt tccagaaaaa ctatatctgt  135540
ttaagccaag aactgtagct ccattggatt tgatatctac tataacaaaa ttaaagaacg  135600
tggacaaatt tgcctcacac ataaattatc acaagaatag tatattgata acaggagaca  135660
agtctctaat tgttaaatgt atgccttaca tgattatttc agatgatgat atacgattca  135720
taagagaaca gtttgttggt acaaattcta ttgagtatat tctatccttc atcaacaagg  135780
aaagcatata tagaatgagt taccaatttt cagagaatga aatagtcact atcatcaata  135840
gagatcattt catgtatgaa ccaatatatg aacatcaggt cttagattct gactttctta  135900
aaactatgtt agatagatac ggaatagttc ccattaattc tggtataata gatgaattat  135960
gtccagaagc tataatagag atattaatgg cagtagttcg tcctagggac gctatccgtt  136020
tcttagatat agtgaataag aatcaattga cagaagatag tgtcaaaaac tatatcatta  136080
atgatatcag aagaggtaaa atagattatt atattccata cgttgaagat tttttagaag  136140
atagaactga agacttggga atatatgcga atatattttt tgaggatgct atagatatta  136200
cgaaactaga catcacaaag acagagttgg aacatatatc gaaatacatg aattattaca  136260
ctacttatat agatcacata gttaacatca tcttacaaaa taattatata gatatcttgg  136320
catctataat agattacgtg caagacgtat taacagaaga attatgtatt agaatagttt  136380
gcgaatcaac aaaccctgtt cccgttacat ctcttcctat acattctacg ttagtaatgg  136440
ttatgtgtat acaaatgaaa tatgtcgata tagttgaatt cttagacgag atcgacatcg  136500
atactttaat agaaaaagga gcagatccga taaccgaata cacatttaca acaagatggt  136560
acaataaaca caatgatttg atcactcttt acattaagaa atatggattc tgtccaatga  136620
tgatgaaacg gttaatgttc gaatatccat tgactaaaga agccagtgat catttactta  136680
aaaccatgga tgaaaacagg ggagctatta tgttttttcc gcgtactatt tgcacacttc  136740
cttatctatt atgttgtaat tataaactaa ttcaaaaacc tattccattc aaagaagaaa  136800
atcgtaacat cgtatataag aaaaccaaca gagtattatg ctttgactcg ttggagaact  136860
ctgcgtttaa aagcctcatt aaaatagatt ctattccagg attaaaaact tataacatga  136920
aagacattac atacgaaaag tctaataata taatttgtgt taggtttata cctcaagaat  136980
caattcataa tgaagagcga agaataaaat tacagttatt cgacattgct agattggcat  137040
cctatggact atattatatt ccctctagat atttatcatc gtggacacca gtagtgaaca  137100
tgatagaggg aagagagtac actaatccac aaaaaaataga atgtctagtt attttggatt  137160
tattttcaga ggaattcata gaatatcaaa atctgggcaa tgcggtatct aataaatatg  137220
aactggaata tactatatct aattatcaag ctgccataaa ctgcctaatg agcacgttat  137280
taatatatct agttctagga tcaatcagat cgatatcaaa aactgaagat tttgtattat  137340
ctatattaaa tatcttctat aaaggactga aaattaatga attactttct gaaccagtat  137400
caggagtttg tatcgaatta aataaaaataa aagatagagc gagctctgga gacagtagtt  137460
ttatatttct taagaaaaac gagttatcaa aaactctatc gctctgtgaa aaagtttgtg  137520
ttgagaccat attagacaat aatcagagtt ttaaatcctc aaaatgaata ggaatcctga  137580
tcagaatact tttcctaata ttacattaaa gattatagaa acctatttag gcagagtacc  137640
tagtgtgaac gaatatcata tgttaaaatt acaagctaga aatattcaga aaataactgt  137700
ttttaacaaa gacatatttg tatctttagt aaaaaagaat aaaaaaagat ttttttccga  137760
tgttgataca tctgcatcag aaataaaaga tcgtatactt agctactttt ctaaacagac  137820
tcaaacatat aatataggta aattatttac gattatagaa ctacaatctg tattagtgac  137880
cacatacacg gacatattag gagttcttac tattaaagct ccaaatgtaa tttcatctaa  137940
aatttcttat aatgtaacat caatggaaga attggcaaga gatatgctaa attctatgaa  138000
cgtcgcagta atagacaagg caaaagtaat gggacgtcat aatgtatctt ccctagtcaa  138060
aaatgttaat aagttgatgg aagaatatct tagacgccat aataaaagtt gtatatgtta  138120
cggatcatat tctctatatc taattaatcc aaatatacgg tacggcgata tagatattct  138180
tcaaactaat tcgaggactt ttcttataga tttggcattt ctaataaaat ttattacggg  138240
aaataatatt atattaagta aaatcccata tcttagaaac tatatggtga taaaagatga  138300
aaacgataat catatcattg atagttttaa tattcgccag gataccatga acgtagttcc  138360
taaaatcttt atagataata tctatatagt ggatccgacg tttcaactat tgaacatgat  138420
aaaaatgttt tctcaaatag atagattgga agatctatcc aaagatcctg aaaagtttaa  138480
tgcgcgtatg gcaaccatgc tagaatacgt tagatataca catggtatag tctttgatgg  138540
taagcgtaat aatatgccga tgaaatgtat catcgatgaa aataatcgca tagttactgt  138600
tactactaaa gactatttta gctttaaaaa atgtctagtg tatctagatg aaaatgtgtt  138660
atcgagtgat atattagatc ttaacgccga cacatcgtgt gatttcgaga gtgttacaaa  138720
ttctgtatat ctaattcatg ataaatatcat gtatacatat ttctcaaata ctattctcct  138780
tagtgataag gggaaggtac atgaaataag tgccagaggt ttatgtgcac atatattgtt  138840
gtatcagatg ctgacatctg gagaatacaa acaatgttta tcggatctct taaattcgat  138900
gatgaataga gataaaatac ctatctattc acatactgaa agagataaaa aacctggacg  138960
acacggattt attaatatcg aaaaggatat aattgtattt taggacaaaa gtctagaagc  139020
tacattatcg cgattagccg cgaacatatt ttgtagcatg tccgtcctca taaacggaac  139080
ttgttttcct gggttattca ttctctcgca tctggaaggg gacgaaggtc ttctctcaca  139140
cgcgggtgat gagggtttat ctactttgag tacgcaggaa gctttacttc cttcgcattc  139200
tacagttcta acatcgcata ctttaacggc ttttagaacc agatatcttc cttctttggt  139260
attgatataa aacggagtat gagcagatgc aaaatgagaa ttcatttata gcatagaaaa  139320
```

```
aaaacaaaat gaaattctac tatattttta catatatata ttctaaatat gaaagtggtg  139380
attgtgacta gcgtagcatc gcttctagac gcatctattc agtttcaaaa aacggcatgt  139440
aggcatcact gtaattacct atctatgcaa gtagttaaag agatagaaga atttggtact  139500
atcaatgaaa aaaatttgga atttgacact tggaaagacg ttatacaaaa cgatgaaata  139560
gatgcattag tattttatag agtaaaacaa attagtattt ctacgggtgt tctatataaa  139620
tctatgatgc gcaatagaac aaaacctatt tccatgtact ttgtacgtga ttgtctggca  139680
tttgatggag atcctccgtc ttttagaatg acgtcttgca atatcaacgc atacaatcgt  139740
agtaagatta aagatttaat aatcctaatg aatatgaaaa catgtaataa aaaaattatc  139800
ggtgagttta taatagacaa ttttggaagc gtcgatgcat tactatcgat agttaattcc  139860
aatgttacgt ggattacatc agttataaat aatagtaacg gcaggggtat taatatcagg  139920
gtatcaaata ataaaatgtt aactataact agttttcgac gattcgtcaa taaacttaaa  139980
atgtacaaaa ctactaaatg cgcttctcaa ttggataatc tatgtaccga gatgaacaaa  140040
atggatatta tagacaaaaa atgaaacgta atgaggagta ttgcggggct acataaatta  140100
aaaatggaaa tttttaatgt agaagaattg ataaatatga aacctttaa gaatatgaat   140160
aaaataacaa ttaatcaaaa tgataattgt atattagcaa atcgatgctt tgttaaaata  140220
gatactccta gatacatacc atcgacatcc attagcagtt ctaatatcat cagaatacgg  140280
aatcatgatt ttacattatc tgaattattg tattcaccgt ttcattttca acagcctcag  140340
tttcaatatc tccttcctgg gtttgtatta acgtgtattg ataaagtttc gaaacagcaa  140400
aaaaaatgta aatattgtat ctctaatcgt ggagatgatg atagtttaag cattaatcta  140460
tttattccga ctattaacaa gtctatatat attattatcg gtttacggat gaaaaatttt  140520
tggaagccta aattcgaaat agaataatgt ttttatatta tacatgttct aaaagaataa  140580
tcgatacagt ttaagtgaaa gctagagagg ggtttttaaa tggtcatcgg tttagtcata  140640
ttcgtgtctg tggcggccgc catcgtcggt gtgttgtcta acgtattgga catgtttatg  140700
tacgtagaag aaaataatga agaggatgct agaatcaagg aggagcaaga actactgttg  140760
ctatattgat acataattga aaatctacca acttaaatac accgcctata aatttacaat  140820
gaaacacaga ttgtattctg aaggattgag tattagtaat gatttaaact cgataatcgg  140880
tcaacaatct acaatggata cggatataga aatagacgaa gatgacatca tggaacttct  140940
taatatattg actgagttag gttgtgatgt cgactttgat gaaaatttta gcgatatagc  141000
cgatgatatt ctagaatcgt tgatagaaca ggatgtataa gtttttatgt taactaaatg  141060
tggccatttg caccggtacc tgcgggagca aaatgtaggc tggtagaaac actaccagaa  141120
aatatggatt ttagatccga tcatttaaca acatttgaat gttttaacga aattatcact  141180
ctagctaaga aatatatata catagcatct ttttgttgta atcctctgag tacgactagg  141240
ggagcgctta tttttgataa actaaaagag gcatctgaaa aagggattaa aataatagtt  141300
ttgctagatg aacgagggaa aagaaatctg ggagagctac aaagtcactg cccggatata  141360
aattttataa ccgttaatat agataaaaaa aataatgtgg gactactact cggttgtttt  141420
tgggtgtcag ataatgaaag atgttatgta ggaaacgcgt catttactgg aggatctata  141480
catacgatta aaacgttagg tgtatattct gattatcccc cgctggccac agatcttcgt  141540
agaagatttg atactttaa agcctttaat agcgcaaaaa attcatggtt gaatttatgc   141600
tctgcggctt gttgtctgcc agttagcact gcgtatcata ttaagaatcc tataggtgga  141660
gtgttcttta ctgattctcc ggaacaccta ttgggatatt ctagagatct agacactgat  141720
gtagttattg ataaactcaa gtcggctaag actagtatag atattgaaca tttggccata  141780
gttcccacta cacgtgtcga cggtaatagc tactattggc ccgacattta caactccatt  141840
atagaagcag ccattaatag aggagttaag atcagacttc tagttggtaa ttgggataag  141900
aacgacgtat attctatggc aaccgccaga agtctagacg cgttgtgtgt tcaaaatgat  141960
ctatctgtga aggttttcac tattcagaat aatacaaaat tgttgatagt cgacgacgaa  142020
tatgttcata tcacttcggc aaatttcgac ggaacccatt accaaaatca cggattcgtc  142080
agttttaata gtatagataa acagcttgta agcgaggcta aaaaaatatt tgagagagat  142140
tgggtatcta gccacagtaa atcgttaaaa atttaaaaaa tagaaacgta tagaacgcca  142200
tcatgttaaa caggatacaa accttgatga aaacagctaa caattatgaa actattgaga  142260
tattgcgtaa ctatttaaga ctgtatatca ttttggcacg aaatgaagaa ggtcatggta  142320
tactaatata cgatgataac atagatagtg ttatgtcgat gatgaatatt acaatattag  142380
aagttatagg attgacgact cattgcacaa aattaagatc atcgcctcca attcctatgt  142440
ctagattgtt tatggacgaa atagatcatg agtcatatta ttctccaaaa acttcagatt  142500
atccgttgat cgatattata cgaaagcgtt ctcacgaaca gggagatata gcactggctt  142560
tagaacgata cggtattgag aatacagatt ccatatcaga aattaatgaa tggttgtcgt  142620
caaaaggttt agcatgttat agatttgtaa aatttaacga ttataggaaa cagatgtatc  142680
gtaagttctc taggtgtact atagttgaca gtatgataat agggcatata ggtcatcatt  142740
atatttggat taaaaattta gaaacatata cgcgtcccga aattgatgtg ttaccgtttg  142800
atattaaata catatctaga gatgaattgt gggcgcgaat ttcttcctcg ttagatcaaa  142860
cacatataaa aaccatcgcc gtatcagttt atggagctat tactgataat ggaccaatac  142920
catatatgat atccacgtat ccgggtaata cctttgttaa ctttaacagt gtaaaaaatc  142980
taattttaaa tttcttagat tggattaaag atattatgac tagtacacga actatcattc  143040
tagtaggtta catga                                                   143055
```

```
SEQ ID NO: 45          moltype = DNA  length = 31690
FEATURE                Location/Qualifiers
misc_feature           1..31690
                       note = Vector
source                 1..31690
                       mol_type = other DNA
                       organism = synthetic construct
SEQUENCE: 45
tggctggaat cattaacaag aaaataaaaa acaatttcaa agttaaacat aactggtatt  60
acgatttcca tttctttgtt catactttat taaaaacata tccagaaatc gaaaaagata  120
tcgaatttag tacggcattg gaagaattca tcatgtgtac caaaacagac tgtgataaat  180
atagattaaa ggtttccatt cttcacccaa ttagtttctt ggaaaaattt attatgagag  240
acattttctc agactggata aatggcggaa actaaagagt ttaaaacttt gtataatctt  300
tttatagata gttatttaca aaaattagct caacattcta tccctactaa tgtcacttgt  360
gctattcata taggagaggt tataggacag tttaaaaatt gcgcgctccg aataactaac  420
```

-continued

```
aaatgcatga gtaattctcg acttagtttc acactcatgg ttgaatcatt tattgaagtg  480
atttcattgc ttccggaaaa ggatagaaga gctatcgctg aggaaatagg aatagatcta  540
gacgatgtac ctagtgcggt atccaagcta gaaaagaact gtaatgcgta tgcggaggtt  600
aataatatta tagatataca gaaattggat atcggagaat gttcggctcc gcccggtcaa  660
catatgcttt tacagatagt taatacagga tccgcggaag caaattgtgg tttacagaca  720
attgttaagt ccttaaataa aatatacgtt ccacctatta tcgaaaaccg attgccgtat  780
tacgatccgt ggtttctagt gggtgtagca attattctag ttatttttac tgtagctatt  840
tgttctatta gacgaaatct ggctcttaaa tacagatacg gaacgttttt atacgtttaa  900
ttaataaaaa aatttaatta caaggtataa aatagtactc catctacgca atcgcgataa  960
tggagggatc taaacgcaga cacgacagtc ggcgactaca acaagaacag gagcagcctc  1020
gtccacgtac accgccatca tatgaagaaa ttgcaaaata tggacactca tttaacgtga  1080
aaagatttac gaatgaagaa atgtgtctta agaatgatta tccacgaatt atatcatata  1140
atcctccacc aaaatagagt atatatatat catcatttca tgatgtatac tactgacata  1200
gtttcaatgt gaacttttca ctttcttgcc ggttatgaag aatattttta ttttaatggt  1260
cattactaat cgtatattat aattgaaaat ggattagttt aatatgacgc tcgtcatggg  1320
atcctgctgt ggtagattct gtgacgctaa gaataagaat aagaaggaag atgtagaaga  1380
gggaagagaa ggatgttaca attataagaa ccttaatgat ctggatgaat ccgaagcacg  1440
tgtagaattt ggaccattat atatgataaa tgaagaaaaa tcagacataa atacattgga  1500
tataaaaaga agatatagac acacgataga gtctgtatat ttctaaaagt ttttataaaa  1560
aatgagtaaa atactcacgt ttgttaaaaa taagataatt gacttgatta ataatgacca  1620
aattaaatat tctagagtta taatgataga agagtccgat agtcttttac cggttgatga  1680
ggtgcatgct aaccacggat ttgactgtgt ggagatgata gatgaaaata taagcaatga  1740
gaatatcgaa cagtataaaa ccgaatcttt ttttacaata aattgaaatc aaaacattta  1800
ttaaaccgca tcaagatggg tacgaacggc gttagagtat ttgtcatttt atatttgttg  1860
gctgtatgcg gatgtatcga atacgacgta gacgataatg tacatatttg tacccacact  1920
aacgtgtcac atattaatca cactagttgg tattataatg ataaggttat agcgctagcc  1980
accgaggata aaacttctgg ttatatatca tcattcataa aacgcgttaa tatctcatta  2040
acttgtttaa atatatcgag tttgaggtac gaagattctg gtacatacaa aggagtatcg  2100
catctaaaag atggagtcat cgttacgact actatgaata tatctgtaaa ggctaatatc  2160
attgacttga ctggtagagt gcgttatcta accagaaatt attgcgaagt taaaatacga  2220
tgcgaaataa catctttcgc gcttaatggt tctactacac caccacatat gatattagga  2280
acagtagata aatggaaata tcttccattt cctacagatg attatagata cgtaggggaa  2340
ctgaaaagat atatatctgg aaacccatat ccaacagagt cgctagcgtt agaaattagc  2400
tcgacgttta atcggtttac tatcgttaaa aatttgaacg atgacgagtt ttcttgttat  2460
ctgtttccat aaaatgttga acgcgcgcca tatttgtgaa tccgaatggg aggctttaaa  2520
taataataac gataattcat cctccatgcc cgcttcccac aacaatctcg caaacgattt  2580
atctagtatg atgtcacaat tacaaaatga taataacgat aatttaatta tgatagtact  2640
aataacaatg ctatcaataa tacttgtaat tattgtagtg attgcggcga tatcgatgta  2700
caaaagatcc aagtacaggc atatagataa ctgaaaaaaa atttattgtt attgttaatt  2760
tagttatgga acccatcctt gcaccaaatc caaatagatt tgttattttc ccaatccaat  2820
atcatgacat ctggaacatg tataaaaagg cagaggcatc attttggaca gtggaagaag  2880
tagatatatc taaagatatc aatgattgga ataaactaac accagacgaa aaatatttta  2940
taaaacatgt attggcgttt tttgcagcca gtgacggaat agtgaatgaa aatttggcgg  3000
aacgattttg tacagaagta cagattaccg aggctagatg tttctacgga tttcagatgg  3060
ccattgaaaa cattcattcg gaaatgtata gtcttttgat cgatacttat gttaaagata  3120
gtaatgaaaa aaactatctc tttaatgcca tagaaacgat gccttgtgta aaaaagaagg  3180
ccgattgggc tcaaaagtgg atacatgaca gcgccggtta tggagagaga cttattgcct  3240
ttgctgcagt agaaggaatc ttcttttccg gatcattcgc ttccatattt tggcttaaaa  3300
agcgtggcct aatgcccgga ctcacgtttt ccaacgaatt gattagtaga gacgagggtc  3360
tacactgcga cttcgcatgt ttgatgttta aacatttatt gcatccaccg agtgaagaaa  3420
ccgttagatc tattataaca gatgcggtat ccattgaaca agaatttctt actgcggctc  3480
ttccagttaa acttatagga atgaattgtg aaatgatgaa aacatatata gaattcgtcg  3540
cggatagatt gatttctgaa ttgggattta aaaaaattta taatgttacc aatccgtttg  3600
atttcatgga aaatatatca ttagaaggta aaactaattt tttcgaaaaa cgtgtgggtg  3660
aataccaaaa aatgggagtt atgtctcaag aagataatca tttttcttta gatgttgact  3720
tttaaagaaa cataaatgcc gatatttgtc aatactgtgt actgtaagaa tatattagca  3780
ttgtctatga ctaagaaatt caaaacaatt attgatgcca taggaggcaa tataatagtc  3840
aattctacga tattgaaaaa gttatctcct tactttcgca cacatttacg tcaaaaatac  3900
acgaaaaata aagatccagt tacgagggtt tgtctagacc ttgacattca cagtctaact  3960
tctatagtta tttactcata tactggaaag gtatatatag atagtcataa cgtcgtcaat  4020
ttattacgtg cttctatatt aacctctgta gaatttatca tctacacttg tataaacttt  4080
atcctacgag attttagaaa ggaatattgt gtcgagtgtt acatgatggg tatagaatac  4140
ggactatcca atctcttatg tcatactaaa aactttattg ccaaacactt tttggaactg  4200
gaagatgaca tcatagacaa ttttgattat ctatctatga aacttattct agaaagcgat  4260
gaactaaatg ttccagatga ggattttgtc attaagtggt atataaagcg aagaaataaa  4320
ttaggaaatc tgctactcct tatcaaaaat gtaatcaggt caaattatct ttctcccaga  4380
ggtataaata atgtaaaatg gatactagac tgtaccaaaa tatttcattg tgataaacaa  4440
ccacgcaaat catacaagta tccattcata gagtatccta tgaacatgga tcaaattata  4500
gatatattcc atatgtgtac aagtactcat gttggagaag tagtatatct catcggtgga  4560
tggatgaaca atgaaataca taacaatgct atagctgtaa attatatatc aaacaattgg  4620
attccaattc ctccgatgaa tagccccaga ctgtatgcta gcgggatacc cgctaacaat  4680
aaattatacg tagtaggagg tctaccaaat cccacatctg ttgagcgttg gttccacggg  4740
gatgctgctt gggttaatat gccgagtctt ctgaaaccta gatgtaatcc agcagtggca  4800
tccataaaca atgttatata cgtaatggga ggacattctg aaactgatac aactacagaa  4860
tatttgctac ccaatcatga tcagtggcag tttggaccat ccacttatta tcctcattat  4920
aaatcatgcg cgttagtgtt cggtagaagg ttattcttgg ttggtagaaa tgcggaattt  4980
tattgtgaat ccagcaatac atggactctg atagatgatc ctatttatcc gagggataat  5040
ccagaattga tcatagtgga taataaactg ctattgatag gaggatttta tcgtgaatcg  5100
tatatagata ctatagaagt gtacaatcat cacacttatt catggaatat atgggatggt  5160
```

```
aaataatttt gaaataaaat attagtttta tgttcaacat gaatattaac tcaccagtta  5220
gatttgttaa ggaaactaac agagctaaat ctcctactag gcaatcgccg ggtgctgccg  5280
gatatgattt gtatagcgct tacgattata ctatccctcc aggagaaaga cagttaatta  5340
agacagatat tagtatgtcc atgcctaaga tttgctatgg tagaatagct cctaggtctg  5400
gtctgtcact aaaaggcatt gatataggag gtggtgtaat agacgaagat tataggggaa  5460
acataggagt cattcttatt aataatggaa aatgtacgtt taatgtaaat actggagata  5520
gaatagctca gctaatctat caacgtatat attatccaga actggaagaa gtacaatctc  5580
tagatagtac aaatagagga gatcaagggt ttggatcaac aggacttaga taataaacaa  5640
tagtatgttg tcgatgttta tgtgtaataa tatcgtagat tatgtagatg gtatagtaca  5700
ggatatagaa gatgaggcta gcaataatgt tgatcacgac tatgtatatc cacttccaga  5760
aaatatggta tatagatttg acaagtccac taacatactc gattatctat caacggaacg  5820
ggaccatgta atgatggctg ttcgatacta tatgagtaaa caacgtttag acgacttgta  5880
tagacagttg cccacaaaga ctagatcata tatagatatt atcaacatat attgtgataa  5940
agttagtaat gattataata gggacatgaa tatcatgtat gatatggcat ctacaaaatc  6000
atttacagtt tatgacataa ataacgaagt taatactata ctaatggata acaaggggtt  6060
gggtgtaaga ttggcgacaa tttcattcat aaccgaattg ggtagacgat gtatgaatcc  6120
agtaaaaact ataaaaatgt ttactctact atcgcatact atatgcgatg attgttttgt  6180
agattatata acggacattt caccaccaga taataccatc cctaacacta gcacgcgtga  6240
atatctaaag cttattggca tcacagctat catgtttgct acatataaaa ctctcaaata  6300
catgatagga taattttttt taacacggat atagaatgct aacgtaataa ttatgcgtta  6360
tgaagacccc tatatcatca attcaatttt ttttctagaa aaagtatcaa gatgtttata  6420
ttatcgtcgg tcatcagatc tgtaatgttt cccaatgatt ggaatctaga ttctgaaatc  6480
tttttgtatc cccaatgttc agtgatttta gcacatattc ctatggtagc gaataaactt  6540
tcctgatcat ggacttttgt aaaattgatg tagtggtctc cttcgctcat agcttcgaca  6600
atctcattaa ttttatcaat accatagtac cgtatagcga catcatcgaa cttcatcaat  6660
tccttgtaca gtcttccaca actggtaata tctttgttaa acactataac atgatttctc  6720
cacgtaatat attcatctat tagatcgatg atggagtcgc gactacatat tttatcatca  6780
tccacaaagt aaaaaacagc atcctcataa tctaatttag tcgccatgac tatctcacaa  6840
aagacagtag ccgtctcctt cctctatatt gatttaattg tatgttttta caattatcaa  6900
taaaacataa aaataatatg atcatcaaac gaactgttaa tattgatagt tatataacgt  6960
gaatcatgag tgcaaactgt atgttcaatc tggacaatga ttacatatcc taaggcatta  7020
gtattcataa gtcatggagc tggtaaacat tctggacgtt atgacgaact agctgaaaac  7080
atatcatcgt taggaatttt agtattctca catgatcata ttggacatgg aagaagtaat  7140
ggtgaaaaaa tgatgattga tgactttggt acagcacgtg gtaactatta aatctactta  7200
ttgggtcatt ccatgggagc aacaatttct atactagcct cttacgataa tccaaacttg  7260
tttacagcaa tgattctaat gtctcctcta gttaatgcag atgctgtttc aagactgaat  7320
ctgctagctg ccaaacttat gggaaccatc acaccaaatg cgccagtcgg aaagctatgt  7380
ccagaatcag tatctagaga tatggataaa gtttataaat accaatacga cccattaatc  7440
aatcatgaaa aaattaaggc tggatttgct agtcaggtct tgaaggctac caacaaggtt  7500
agaaaaataa tttccaagat taacaccccg actctcatac tccagggaac aaacaatgag  7560
attagcgatg ttttaggtgc atattatttc atgcaacatg caaattgtaa tagagaaata  7620
aaaatttatg aaggtgccaa acatcatctt cataaggaaa cggatgaagt taaaaaatca  7680
gtcatgaaag aaatagaaac ttggattttt aatagagtga agtgatatag gattattctt  7740
ttaacaaata aaatgaatcc ggataataca atcgcagtga ttacagagac tattcctata  7800
ggtatgcaat ttgataaagt atatttgtct acatttaaca tgtggaggga aattctatcc  7860
aataccacaa aaacactaga tatatcatct ttttattgga gtttatcgga tgaagtgggt  7920
acgaatttcg gcacgataat attaaacgag attgtacaat tacccaaaag aggagtacga  7980
gttagagtag ccgtcaataa atctaacaaa ccattaaagg atgttgaaag actacaaatg  8040
gccggagttg aagtacgata catagatatt acaaatatcc taggaggagt tcttcataca  8100
aaattttgga tatctgataa tacacatatt tatttaggaa gcgctaacat ggattggaga  8160
tcactaactc aggtcaaaga attgggtatt gcgatcttca ataataggaa cttggcagcg  8220
gatctcactc aaatttttga ggtatactgg tatcttggag ttaacaatct accatataat  8280
tggaaaaact tttatccgtc gtattataat acagatcatc ctcttagtat taacgtaagt  8340
ggtgttccac actctgtatt tattgcttct gcaccgcaac aactatgtac tatggaaaga  8400
accaatgatt taaccgcttt attgtcatgt attagaaatg cgagtaaatt cgtttatgta  8460
tctgttatga actttatccc tattatttat tcgaaggcgg gtaaaatttt gttttggcct  8520
tatatagaag atgaattaag aagatccgct atagacagac aagtatccgt taagctattg  8580
attagttgct ggcaacgatc ttcgtttatc atgagaaact tttaagatc tatcgctatg  8640
ctaaaatcta aaaacataaa tatagaagta aagctattta ttgtaccaga tgctgatcct  8700
cccattccgt attctagggt aaaccatgcc aaatatatgg taaccgataa aacggcctat  8760
ataggtacct caaattggac aggaaattac tttacggata catgtggagc atctattaat  8820
attacaccgg atgatggatt aggtcttcgt caacaattag aagatatttt tatgcgtgat  8880
tggaattcaa aatacagcta tgaattgtac gatactagtc ctactaaaag gtgtaaacta  8940
ttaaaaaata tgaaacaatg tacaaatgat atatactgcg atgagataca accggaaaaa  9000
gaaattcctg aatattctct tgaataaaat agatataaaa acataatttt tatcccaatt  9060
tacgagcccg ttaacaagat gcttgcattt tgttattcgt tgcccaatgc gggcgatgta  9120
ataaagggca gagtatacga gaatgattat gctctatata tttatctttt tgactatcct  9180
cactctgaag ctatcttggc agagagtgtt aagatgcata tggatagata tgttgaatat  9240
agggataaac tggtagggaa aactgtaaaa gttaaagtga ttagagttga ttatacaaaa  9300
ggatatatag atgtcaatta caaaaggatg tgtagacatc aataattttt ataccgaaca  9360
taaaaataag gttaattatt aataccataa aatcatgatt gcgttattga tactatcgtt  9420
aacgtgttca gcgtctacct atcgtctaca aggatttacc aatgccggta tagtagcgta  9480
taaaaatatt caagatgata atattgtctt ctcaccgttt ggttattcgt tttctatgtt  9540
tatgtcgcta ttgcctgcat caggtaatac tagaatagaa ttattgaaga ctatggattt  9600
gagaaaaaga gatctgggtc cagcatttac agaattaata tcaggattag ctaagctgaa  9660
aacatctaaa tatacgtaca ctgatctaac ttatcaaagt ttcgtagata atactgtgtg  9720
tattaaaccg tcgtattatc aacaatatca tagattcggc ctatatagat taaactttag  9780
acgagatgcg gttaataaaa ttaattctat agtagaacgt agatccggta tgtctaatgt  9840
agtagattct aatatgctcg acaataatac tctatgggca atcattaata ctatatattt  9900
```

```
taaaggtata tggcaatatc cgtttgatat cactaaaaca cgcaatgcta gttttactaa  9960
taagtacggt acgaaaacgg ttcccatgat gaacgtagtt actaaattgc aaggaaatac  10020
aatcacaatc gatgacaaag aatatgacat ggtacgcctt ccgtataagg atgctaatat  10080
tagtatgtac ctggcaatag gtgataatat gacccatttc acagattcta ttacggctgc  10140
aaaattagac tattggtcgt ttcaattagg gaataaagtg tacaatctta aactccctaa  10200
attttctatc gaaaataaga gggatattaa gtcgatagcc gaaatgatgg ctcctagtat  10260
gtttaatcca gataatgcgt cgtttaaaca tatgactagg gacccattat atatttataa  10320
aatgtttcag aatgcaaaga tagatgtcga cgaacaagga actgtagcag aggcatctac  10380
tattatggta gctacggcga gatcatctcc tgaaaaactg gaatttaata caccatttgt  10440
gttcatcatc agacatgata ttactggatt tatattgttt atgggtaagg tagaatctcc  10500
ttaatatggg tacggtgtaa ggaatcatta ttttatttat attgatgggt acgtgaaatc  10560
tgaatttttct taataaatat tatttttatt aaatgtgtat atgttgtttt gcgatagcca  10620
tgtatctact aatcagatct attagagata ttattaattc tggtgcaata tgacaaaaat  10680
tatacactaa ttagcgtctc gtttcagaca tggatctgtc acgaattaat acttggaagt  10740
ctaagcagct gaaaagcttt ctctctagca aagatgcatt taaggcggat gtccatggac  10800
atagtgcctt gtattatgca atagctgata ataacgtgcg tctagtatgt acgttgttga  10860
acgctggagc attgaaaaat cttctagaga atgaatttcc attacatcag gcagccacat  10920
tggaagatac caaaatagta aagattttgc tattcagtgg actggatgat tcgtattcga  10980
tgattatttt taacaaaata acataaaaat aatatatttt tttaggatgc gatcatgacg  11040
tcctctgcaa tggataacaa tgaacctaaa gtactagaaa tggtatatga tgctacaatt  11100
ttacccgaag gtagtagcat ggattgtata aacagacaca tcaatatgtg tatacaacgc  11160
acctatagtt ctagtataat tgccatattg gatagattcc taatgatgaa caaggatgaa  11220
ctaaataata cacagtgtca tataattaaa gaatttatga catacgaaca aatggcgatt  11280
gaccattatg gagaatatgt aaacgctatt ctatatcaaa ttcgtaaaag acctaatcaa  11340
catcacacca ttaatctgtt taaaaaaata aaaagaaccc ggtatgacac ttttaaagtg  11400
gatcccgtag aattcgtaaa aaaagttatc ggatttgtat ctatcttgaa caaatataaa  11460
ccggtttata gttacgtcct gtacgagaac gtcctgtacg atgagttcaa atgtttcatt  11520
gactacgtgg aaactaagta tttctaaaat taatgatgca ttaattttttg tattgattct  11580
caatcctaaa aactaaaata tgaataagta ttaaacatag cggtgtacta attgatttaa  11640
cataaaaaat agttgttaac taatcatgag gactctactt attagatata ttctttggag  11700
aaatgacaac gatcaaacct attataatga tgattttaaa aagcttatgt tgttggatga  11760
attggtagat gacggcgatg tatgtacatt gattaagaac atgagaatga cgctgtccga  11820
cggtccattg ctagatagat tgaatcaacc agttaataat atagaagacg ctaagcgaat  11880
gatcgctatt agtgccaaag tggctagaga cattggtgaa cgttcagaaa ttagatatag  11940
agaaaatagc tccagaatac agacaatgct tacaggatct ataccatatg aaaattacgc  12000
gtcctagaca ctttgataac tagttatgtc attctcgttt ttatagagtg tactcgttac  12060
taaatattaa ttaatgaaat aataacaatt attaagacat actattcatc caacttaaac  12120
aacgaaaaac atttttcatt aagtttatca tgaatgcgta taataaagcc gattcgtttt  12180
ctttagagtc tgattctatc aaagatgtta tacacgatta tatttgttgg ctcagtatga  12240
ctgatgaaat gagaccatct atcggaaacg tctttaaagc gatggaaacg tttaagatag  12300
acgcggttag atattacgat ggtaacatat acgatttagc taaagatata aatgcgatgt  12360
cattcgacag ttttataaga tctctacaaa atatctcttc aaagaaagat aaactcactg  12420
tttatggaac catgggactg ctgtctattg tcgtagatat taacaaaggt tgtgatatat  12480
ccaatatcaa gttcgctgcc ggaataatca ttttaatgga gtatattttt gatgacacgg  12540
atatgtctca tcttaaagta gcactctatc gtagaataca gagacgtgat gatgtagata  12600
gatatttttt tttcctaaac tgatttctct gtttaaattc gtagcgatat ataaaacaac  12660
atgtaattaa ttaataaact ttaagacatg tgtgttatac taagatggtt ggcttattcc  12720
atagtagctt gtggaattta taaacttatg atagtaaaac tagtacccaa tatgtaaaga  12780
tgaaaaagta aattactatt aacgccgtcg gtattcgttc atccattcag tatgggtata  12840
cagcacgaat tcgacatcat tattaatgga gatatcgcgt tgagaaattt acagttacat  12900
aaaggggata actacggatg caaactaaaa attatttcga atgattacaa gaaattaaag  12960
tttagattca ttatacgccc agattggtcg gaaatcgacg aggtcaaagg attaaccgta  13020
tttgcaaaca actatgcggt gaaagttaat aaggtagatg acacgttcta ttacgtaata  13080
tatgaggctg taatacatct gtataacaaa aaaacagaga tattgattta ttctgatgat  13140
gagaacgaac tctttaaaca ctattaccca tacatcagtc taaatatgat tagtaaaaag  13200
tataaagtta aagaagaaaa ctactcatcc ccgtatatag aacatccgtt aatcccgtat  13260
agagattatg agtccatgga ttaatatgag tatagtgtta aatgacactt actaaatagc  13320
caaggtgatt attcgtattt ttttaaggag taaccatgtc cgcaattaga tttattgcat  13380
gtctatatct catttccatc ttcggaaatt gtcatgagga tccatattat caaccatttg  13440
ataaattaaa cattactcta gatatataca cttatgagga tctagtacca tacaccgtag  13500
acaatgacac aacttctttc gttaagatat actttaaaaa tttttggatt acggttatga  13560
ctaaatggtg tgctccgttt attgataccg ttagcgtata cacatctcat gataatctga  13620
atatacaatt ttatagtagg gacgaatatg atacacaaag cgaggataaa atttgtacca  13680
ttgatgttaa agcacgatgc aaacatctaa caaaacgaga agttacagta caacaagaag  13740
cctacagata ttcattatct tctgacctat cgtgttttga ttctatagat ctagagattg  13800
atcttattga aactaatagt actgacacta cagtactgaa atcatatgag ctcatgcttc  13860
ccaaacgtgc taaatccata cataactgaa atgaaagaaa ccaaaaaatg cgatagcatc  13920
aacaaccaat catggttaac gataagatac tctatgatag ttgtaaaaca tttaacatcg  13980
atgccagcag tgcacaatca ttgatagaaa gtggtgcaaa tccattatat gagtatgatg  14040
gtgaaactcc attaaaggca tacgttacca agaaaaataa taatatcaaa aacgatgttg  14100
tgattttgtt attgtcgtca gtcgactata aaaatatcaa tgattttgat atactcgaat  14160
atctatgttc tgataacatc gatatagact tattgaaatt actaatttcg aaaggtatag  14220
aaataaatag tatcaaaaat ggtattaata ttgtagaaaa atacgctaca acatcaaatc  14280
ccaatgtaga tgtgtttaaa ctattattgg ataaaggaat acctacatgt agcaacatac  14340
agtatggata caagatcaaa atagaacaga ttagacgtgc tggtgaatat tataattggg  14400
atgatgaatt agacaattac gattacgact acaccactga ttatgatgat agaatgggta  14460
aaacagttct ctattattat attattacta ggtcacaaga tggttatgct acatctttgg  14520
acgtaataaa ctatttaatt tcacacgaaa aagagatgcg ttattatact tatcgtgaac  14580
ataccacact ctattattat cttgacaaat gcgatattaa acgggaaata tttgacgcgt  14640
```

```
tattcgatag taactatagt ggtcatgaac taatgaatat tctatctaac tatttacgta  14700
aacagtttag gaagaaaaat cacaaaatcg ataattatat agttgatcaa ctattattcg  14760
accgtgatac gttttatatt ttagaattgt gtaatagttt acgtaataat atccacaatt  14820
cttaaaagat atacagattc tatacaagat ctattgttag aatatgtatc ttatcataca  14880
gtatacatca atgttattaa atgtatgatt gatgaaggag ctacattata tagatttaag  14940
catataaata aatattttca aaaatttggc aatagagatc ctaaagttgt cgagtatatt  15000
ttaaaaaatg gaaacttagt tgtagataat gacaatgatg ataacctaat aaatattatg  15060
ccattattcc ctaccttctc tatgcgtgag ttggatgtgt tatcgatact aaaactttgt  15120
aagccgtata ttgatgatat aaacatggat gtagtatact ttatcattgt attaagtcgc  15180
atagtgtcag cctagtagaa tggttaatag ataatggcgc agacattaat ataataacaa  15240
aatatgggtt tacatgtatt actatttgtg ttatactggc agataaatat atcccagaaa  15300
tagcagaatt atatattaag atattggaaa ttattctgag taaattacca accatcgaat  15360
gtattaagaa aacagttgat tacctagacg atcacaggta cttattcata ggtggtaata  15420
ataaatcgtt actgaaaata tgtatcaagt acttcatatt agtcgattat aagtacacat  15480
gtagcatgta tccatcatat atagaattta taaccgactg cgaaaaagaa attgcggata  15540
tgcgtcaaat taaaataaat ggtacggaca tgcttacagt gatgtacatg ttaaataaac  15600
ctacaaagaa acgatatgtt aataatccga tatttacaga ttgggctaat aagcaatata  15660
agttttataa tcaaataata tataatgcta ataagttaat agaacaaagt aagaaaatag  15720
acgacatgat agaggaggta tccattgacg ataatcgttt atcaacacta ccgttagaaa  15780
ttagacattt gattttctcg tacgcgttcc tataaaaata gaaactataa tcatataata  15840
gtgtaggttg gtagtattgc tcttgtgact agagacttta gttaaggtac tgtaaaaata  15900
gaaactataa tcatataata gtgtaggttg gtagtagggt actcgtgatt aattttattg  15960
ttaaacttgt ccttaagtct tattaatatg tcttctaaag gggtagtgg cggcatgtgg  16020
agtgtcttta tccatggaca tgatggtagt aataaaggat ctaaaactta tacatctggt  16080
ggcggtggaa tgtggggagg aggatcgtcc agtggtgtaa aaagtggggt taacggaggt  16140
gtaaaatctg gaactggtaa aatttaaaca ctaaattatt tttattaata attgtacaag  16200
tttttgacat gatatttaat gacattagtt gtgtgggtgt atagagttca cagtagctca  16260
ttcagtcaaa atgtttgact atttggaaaa tgaggaggtg gctctcgatg aacttaaaca  16320
gatgttgaga gacagagatc ctaatgatac caggaaccaa ttcaagaata atgctttaca  16380
cgcatacctt tttaatgagc attgtaataa tgtcgaggtc gtcaaactac tactagacag  16440
tggcactaat ccattacgca aaaattggag acagctaccc cattagaaga atacacaaat  16500
agtagacatg ttaaagttaa aggatatagc gatggctcta ctagaagcca ctggatttag  16560
caacataaat gactttaata tattcagcta tatgaaatcc aaaaatgtag acgttgactt  16620
gataaaggtg ttggtagaac atggatttga cttgagtgtt aaatgtgaaa accatcgttc  16680
agttatagaa aattatgtaa tgacagatga tcctgttcct gaaattattg atttgttcat  16740
agaaaatggc tgcagtgttc tttatgagga cgagtactga tacgcgtatg atgattatca  16800
actacgaaat tgcggtaccg tattgcatct gtatatcatc tctcatctgt attcagagtc  16860
ggatacgaga gcatatgtgc gtccggaagt tgttaaatgt ctaattaatc acggaatcaa  16920
gccgtctttt atagataaaa actattgtac agctcttcaa tattatatta agtcatctca  16980
tatagatata gacatcgtta aattgttaat gaaaggaata gataacacgg cttattcata  17040
tatagacgat ctaacatgtt gcactcgagt aattatggct gattatctaa atagtgatta  17100
tagatacaat aaagatgtag atttggtcaa attgtttttg gaaaatggaa agccgcacgg  17160
aataatgtgt agtattgtac cactatggag aaatgataag gaaaccatct ttttgatatt  17220
gaaaacaatg aactcggatg tcctccaaca tatactaatt gagtatatga cattcggcga  17280
tatccctcta gtggaatatg gaactgtggt aaataaagag gctatacacg gatactttag  17340
aaatattaat attgattctt acacgatgaa atatctacta aaaaaggaag ggagatgcca  17400
tcaattatct cgatgatgga gagatcccga ttggacacct atgtaaatcc aactatgaat  17460
gttataattt ttacacttat acatacaaaa agggtctttg tgacatgtct tatgcttgcc  17520
caattcttag tactataaac atttgcctac cttatcttaa agacattaac atgattgaca  17580
aacgaggaga aacacttctt cacaaggctg ttagatataa taaacaatct ctagtatctt  17640
tactgctaga atccggttca gatgtcaaca ttagatcaaa taacggatat acatgtatag  17700
ccattgccat caacgaatct aaaaacattg aactgctgaa aatgctatta tgtcataaac  17760
ctacattaga ttgtgtgatt gattcattga gagaaatatc taacatcgta gataacgact  17820
atgctataaa acaatgtatt aaatatgcca tgattataga tgactgtaca tcgtctaaga  17880
ttccagagtc cataagtcaa cgctataatg attatataga tctttgcaat taagaattga  17940
atgagatgaa aaaaataatg gtaggtggta atactatgtt ctcattaata tttactgatc  18000
atggagctaa aattattcat agatatgtca ataatccaga attacgtgag tattatgagt  18060
taaaacaaaa taaaatatat gtggaagcat atgatattat ttccaacgca atagtgaaac  18120
atgatagaat acataaaacc atagaatcag ttgatgataa tacctacatt tctaatcttc  18180
cgtataccat caaatacaaa atattcgagc aacaataagt attttttata cctttaaaat  18240
tgataaataa atttttttcta gtgatatttt ggcaagatga aaatcctatt tctcatcgct  18300
ttcatgtatg ggtgtgttca ctcatatgtt aacgcggttg aaaccaaatg tccaaatcta  18360
gacattgtaa catcttctgg agaatttcat tgttcaggat gtgtggaaca tatgcctgag  18420
tttagctata tgtattggtt ggcaaaggat accaagttta tagaacatct gggtgatggc  18480
atcaaagaag atgaaaccgt tcgtaccaca gatagtggaa tcaccactct acgtaaagtc  18540
cttcatgtaa ccgatactaa taaatttgct cattataggt tcacttgtgt cctcactacg  18600
atagatggcg tttcaaaaaa gaatatttgg ctgaagtagt gcgtgctact atttttattt  18660
atgatataat ctaatggaat taatttgaat tgatatttat ccaatactaa agattatatt  18720
agaatcaaat taatctttta tacgagaaaa aataacgaca tacgtcgtca acaaattaaa  18780
ctttttattt attagttaac ttgctcattg ttatgtttct aaaacgggta cgacatatag  18840
gacaattatc cgacgcaccg gtttctcttc gtgttctatg ccatatattg atgcatgtta  18900
tgcaaaatat atgattacac gaatccaata aaccaaagta tctatcgttt tgagtaaaca  18960
acttcatagc aaatttcaca ttctttttct ttacttactc tatacacgtc ctcgtattta  19020
tccagtattt tgatgatatc caactcagaa atggttgttg tattattggg tgtataggta  19080
ttattagcta tgtaccaatt taccaacctt cttaatattg attgataatc acatcggtta  19140
tccaattaat aactaaattg tagtgtatat atagaccata tatgtttcta tttttttgac  19200
agtttcagta agttttgatt gttgtattcc tgtatctcta gataagttag tcatatagtc  19260
ccttccggcg atacgttttt tccaagcccg aaattgatta gccaaatgtg gatttatttt  19320
tgtgataatg catactgtta gtcttatatc atttggttca tctatgtatt gtaatattgt  19380
```

```
tacatgatct atagatgatg tattgatttt ggcaggatcg aattccatat ccgcgactaa  19440
acagtgaaaa aaatgtaaat aattttaaat tagtaaaact tttttttatt ttttatgatt  19500
ccaaaaaaac tgaatacaaa gtcctaaatt ataaatatgg agatcatact accacaactt  19560
attattatgt atacaaggcc ggtgtaatag atagatatat ataattctat tacaccggca  19620
gacaattacc gatcggtatt tgtcgttacc aacataccgt ataatatgta atatacaatt  19680
ccataaccca ttgacagttg ttatacatca aaattgcaat tcttttgatt acgatgttat  19740
aagaatgtag ttaattgatg tatgatgtta atgtgtcctc tttcctctta taacatcgta  19800
atcaaaaact tttttataat atatacctaa taatgtgtct taatagttct cgtgattcgt  19860
caaacaatca ttcttataaa atataataaa gcaacgtaaa aacacataaa aataagcgta  19920
actaataaga caatggatat ttacgacgat aaaggtctac agactattaa actgtttaat  19980
aatgaatttg attgtataag gaatgacatc agagaattat ttaaacatgt aactgattcc  20040
gatagtatac aacttccgat ggaagacaat tctgatatta tagaaaatat cagaaaaata  20100
ctatatagac gattaaaaaa tgtagaatgt gttgacatcg atagtacaat aacttttatg  20160
aaatacgatc caaatgatga taataagcgt acgtgttcta attgggtacc cttaactaat  20220
aactatatgg aatattgtct agtaatatat ttggaaacac cgatatgtgg aggcaaaata  20280
aaattatacc accctacagg aaatataaag tcggataagg atattatgtt tgcaaagact  20340
ctagacttta aatcaacgaa agtgttaact ggacgtaaaa caattgccgt tctagacata  20400
tccgtttcat ataatagatc aatgactact attcactaca acgacgacgt tgatatagat  20460
atacatactg ataaaaacgg aaaagagtta tgttattgtt atataacaat agatgatcat  20520
tacttggttg atgtggaaac tataggagtt atagtcaata gatctggaaa atgtctgtta  20580
gtaaataacc atctaggtat aggtatcgtt aaagataaac gtataagcga tagttttgga  20640
gatgtatgta tggatacaat atttgacttt tctgaagcac gagagttatt ttcattaact  20700
aatgatgata acaggaatat agcatgggac gatgatacag atatatggac tcccgtcaca  20760
gaagatgatt acaaatttct ttctagacta gtattgtatg caaaatctca atcggatact  20820
gtattcgact attatgttct tactggtgat acggaaccac ccactgtatt catttttcaag  20880
gtaactagat tttactttaa tatgccgaaa taaaaaattt ttgtataata tctagaggta  20940
gaggtattgt ttagataaat acaaataaca tagatacatc gcatatttag catttttata  21000
aatatacata agacatacac tttatacatt tttgtaaaaa tactcataaa aaaaatttat  21060
aaaaattatg gcacaaccat atcttgtata ggtagtttag ttcgtcgagt gaacctataa  21120
acagataata gacaacacgt aataataata atgcctacta atacaagcat aataccggga  21180
gatgggatat atgacgttgt agtgtttggt ttttctgaac gttgatagtc tactaatact  21240
acatgctgac atctaatgcc tgtataacca tgagagcatc tacaatacat accgtcgata  21300
tctctagcgt ggatacagtc accgtgtaaa caatatccat ctccctctgg accgcataat  21360
ctgatagctg gaatatctgt tgtagcgttt gtaatttctg gcgatgtcgt ttcgatagcg  21420
ttaccactat cggcgaatga tctgattatc atagcagcga acaacaacat cagataattt  21480
atcaacattt ttgatggatt ttgtgtttat gctgtttctc agtgtgtgtt tatgacaaga  21540
ttgggaattt tatattatta attcagtaat ataaactaat aatatattgt taattgtgta  21600
aataatataa aaataacaat acaatattga atgtgttgct gttaaaaatg tatgtgttaa  21660
tataatagaa taaaataaat gagtatgatc attttagata acgattgatt ttatcattac  21720
cgcttcattc ttatattctt tgcttacgga acctatattt agaaacatct actaacgatt  21780
ttttatgctt gcattattaa tggtatgtaa taccaatttg ttaagtatga atacggggta  21840
caaacataaa ctgaaattta gatcattaaa tgtttcatca gaaatgactc catgaaaacc  21900
gccgaagaac ttcgtgcaat cattggactt tgtactcaat cagctatcgt ctctggaaga  21960
gtcttcaacg ataagtatat cgacatacta cttatgctgc gaaagattct gaacgagaac  22020
gactatctca ccctcttgga tcatatccgc actgctaaat actaaatctc cttcatgctc  22080
tctcactaca ctttttatca tcttatgagg aataattagc accagaatag ctatggattg  22140
cacatgtatt ctatgtcgtc tactggatga agatgtgacg tacaaaaaaa taaaactaga  22200
aattgaaacg tgtcacaact tatcaaaaca tatagataga cgaggaaaca atgcgctaca  22260
ttgttacgtc tccaataaat gcgatacaga cattaagatt gttcgactgt tactctctcg  22320
cggagtcgag agactttgta gaaacaacga aggattaact ccgctaggag catacagtaa  22380
gcatagatac gtaaaatctc agattgtgca tctactgata tccagctatt cgaattcctc  22440
taacgaactc aagtcgaata taaatgattt cgacttacgt ctgctaaaat acctaattgt  22500
ggataaacgg atacgtccgt ccaagaatac gaattatgca atcaatggtc tcggattggt  22560
ggatatatac gtaacgacgc ctaatccgag accagaagta ttgctatggc ttcttaaatc  22620
agaatgttac agcaccggtt acgtatttcg tacctgtatg tacaacagtg atatgtgtaa  22680
gaactctctt cattactata tatcgtctca tagagaatct ctatccaagg atgtaattaa  22740
atgtttgatc gataacaatg tttccatcca atactactgg tcttgctcaa ccatagatat  22800
agagattatt aataaaggat gtggacacgt gtagagtata cgacgtcagc cctatattag  22860
aggcgtatta tctaaacaag cgatttagag taaccccata taatgtagac atggaaatcg  22920
ttaatcttct tattgagaga cgtcatactc ttgtcgacgt aatgcgtagt attacttcgt  22980
acgattccag agaatataac cactacatca tcgataacat tctaaagaga tttagacaac  23040
aggatgaatc catcgtacaa gccatactga taaactactt acattacggc gatatggtaa  23100
gtatacctat cattcaatgc atgttggata agacgacgga caacaacttt gttaataata  23160
atctcgtcga tgtaaacgtc gtaaggttta tcgtggaaaa tatggacacg cggctgtaaa  23220
tcacatatct aacaatggcc gtctatgtat gtacggtctg atattatcga gatttaataa  23280
ttgcgggtat cactgttatg aagatgtatt tgatatacta agcaagtaca tggatgatat  23340
agatatgatc gataactcta ctatattacg cggtcgatgt caataatata caatttgcaa  23400
agcggttatt ggaatatgga gcgagtgtca cgctcgataa tcaatacggc catccagaaa  23460
agcagttacc aaagagaagc tagttgattt attactgagt taccatccca ctctagagac  23520
tatgattgac gcatttaata gagatatacg ctatctatat cctgaaccat tattcgcctg  23580
tatcagatac gccttaatcc tagatgatga ttttccttct aaagtaagta tgatatcgcc  23640
ggtcgtcata aggaactaaa gcgctataga gcagacatta atagaatgaa gaatgcctac  23700
atatcaggcg tctccatgtt tgatatatta tttaaacgaa gcaaacgcca cagattgaga  23760
tacgcaaaga acaatgagag gatcgactcc attaaataat ttatcatgga gtgataatgt  23820
cctgtttcca tggcatatta caaaatcgat tccgtccaag atgataaaaa catttaccgg  23880
catcataaac acggagttta ttttatatgt ctcgcataaa cattactaaa aaaatatatt  23940
gttcggtttt ctttcacatc tttaattatg aaaaagtaaa tcattatgag atggacgcat  24000
cgttcgcgac agtatgtggt acatacctaa cgtatttatg gacgacggta agaatgaagg  24060
tcacgtttct gtcaacaatg tcgacgcgat cgtgtaacac gactcacaat agaatctgtg  24120
```

-continued aatgctctcc cgatcatgga tgcaaggcat gtgtttccca aacaaaatgt ggaataggat 24180
acggagtatc cggagacgtc atctgttctc cgtgtggtct cggaacatat tctcacaccg 24240
tctcttccgc agataaatgc gaacccgtac ccagaaatac ctttaactat atcgatgtgg 24300
aaattaacct gtatccagtt aacgacacat cgtgtactcg gacgaccact accggtctca 24360
gcgaatccat ctcaacgtcg gaactaacta ttactatgaa tcataaagac tgcgatcccg 24420
tcttcttaat aaggtagcga cttcaggttt ctttacagga gaaaggtgtg cactctgaat 24480
ttcgagatta aatgcaataa caaagattct tcctccaaac agttaacgaa agcaaagaat 24540
gatactatca tgccgcattc ggagacagta actctagcgt cgacatctat atactatata 24600
gtaataccaa tactcaagac tacgaaactg atacaatctc ttatcatgtg ggtaatgtag 24660
ccatatgccc ggtagttgcg atatacataa actgatcact aattccaaac ccacccgctt 24720
tttatagtaa gtttttcacc cataaataca ataattaatt tctcgtaaaa gtagaaaata 24780
tattctaatt tattgcacgg taaggaagta gaatcataaa gaacagtact caatcaatag 24840
caatcatgaa acaatatatc gtactggcat gcatgtgcct gccagtcttc agcaatcatc 24900
ctcatcgtgt acggaagaag aaaacaaaca tcatatggga atcgatgtta ttatcaaagt 24960
cacaaagcaa gaccaaacac cgaccgatga taagatttgc caatccgtaa cggaaattac 25020
agagtccgag tcagatccag atcccgaggt ggaatcagtc gaggatgtag atcctcctac 25080
cacttattac tccatcatcg gtggaggtct gagaatgaac tttggattca ccaaatgtcc 25140
tcagattaaa tccatctcag aatccgctga tggaaagact gtgaggtgtc tatcgacatc 25200
agatgtagcg aagaagagaa agacagcgac atcaagaccc atccagtact cgggtctaac 25260
atctctcata agaaagtgag ttacgaagat atcatcggtt caacgatcgt cgatacaaaa 25320
tgtgtcaaga atctagagtt tagcgttcgt atcggagaca tgtgcaagga atcatctgaa 25380
cttgaggtca agtatgtcga cggatcggca tctgaaggtg caaccgatga tacttcactc 25440
atcgattcaa caaaactcaa agcgtgtgtc tgaatcgata actctattca tctgaaattg 25500
gatgagtagg gttaatcgaa cgattcaggc acaccacgaa ttaaaaaagt gtaccggaca 25560
ctatattccg gtttgcaaaa caaaaagtta cctctcgcga cttcttcttt ttctgtctca 25620
atagtgtgat acgattatga cactattcct atttcctttc agggtatcac aaaaatatta 25680
aacctctttc tgatggtctc atacaaaaat atttttattc tctttctctc tttgatggtc 25740
tcataaaaaa tatttttatt ctctttctct ctttgatggt ctcataaaat atttttattc 25800
tctttctctc tttgatggtc tcataaaaaa tatttttatt ctctttctct ctttgatggt 25860
ctcataaaat atttttattc tctttctctc tttgatggtc tcataaaaaa tatttttatt 25920
ctctttctct ctttgatggt ctcataaaaa atattaaacc tctttctgat ggtgtcacta 25980
aaatattttt attctctttc tctcttcaat ggagtcataa aatattttta ttctctttct 26040
ctcttcgatg gtctcacaaa aatattaaac ctctttctga tggtgtcact aaaatatttt 26100
tattctcttt ctctcttcaa tggagtcata aaatattttt attctctttc tctctttgat 26160
ggtctcacaa aaatattttt attctctttc tctctttgat ggtctcacaa aaatattttt 26220
attctctttc tctctttgat ggtctcacaa aaatattttt attctctttc tctctttgat 26280
ggtctcataa aaaaagtttt acaaaaatat ttttattctc tttctctctt tgatggtctc 26340
ataaaaaaag ttttacaaaa atatttttat tctctttctc tctttgatgg tctcataaaa 26400
aaagttttac aaaaatattt ttattctctt tctctctttg atggtctcat aaaaaatatt 26460
aaacctcttt ctgatggtgt cactaaaata tttttattct cattctctct tcaatggagt 26520
cataaaatat ttttattctc tttctctctt cgatggtctc acaaaaatat taaacctctt 26580
tctgatggtg tcactaaaat atttttattc tcattctctc ttcaatggag tcataaaata 26640
tttttattct ctttctctct tcgatggtct cacaaaaata ttaaacctct ttctgatggt 26700
gtcactaaaa tatttttatt ctcattctct cttcaatgga gtcataaaat atttttattc 26760
tctttctctc tttgatggtc tcataaaaaa agttttacaa aaatattttt attctctttc 26820
tctctttgat ggtctcataa aaaatattaa acctctttct gatggtgtca ctaaaatatt 26880
tttattctct ttctctcttc aatggagtca taaaatattt ttattctctt tctctcttcg 26940
atggtctcac aaaaatatta aacctctttc tgatggtgtc actaaaatat ttttattctc 27000
attctctctt caatggagtc ataaaatatt tttattctct ttctctcttt gatggtctca 27060
taaaaaaagt tttacaaaaa tatttttatt ctctttctct ctttgatggt ctcataaaaa 27120
aagttttaca aaaatatttt tattctcttt ctctctttga tggtctcata aaaaaagttt 27180
tacaaaaata tttttattct ctttctctct ttgatggtct cataaaaaaa gttttacaaa 27240
aatattttta ttctctttct ctctttgatg gtctcataaa aaatattaaa cctctttctg 27300
atggtgtcac taaaatattt ttattctcat tctctcttca atggagtcat aaaatatttt 27360
tattctcttt ctctcttcga tggtctcaca aaaatattaa acctctttct gatggtgtca 27420
ctaaaatatt tttattctca ttctctcttc aatggagtca taaaatattt ttattctctt 27480
tctctctttg atggtctcat aaaaaaagtt ttacaaaaat atttttattc tctttctctc 27540
tttgatggtc tcataaaaaa agttttacaa aaatattttt attctctttc tctctttgat 27600
ggtctcataa aaaaagtttt acaaaaatat ttttattctc tttctctctt tgatggtctc 27660
ataaaaaaag ttttacaaaa atatttttat tctctttctc tctttgatgg tctcacaaaa 27720
atattaaacc tctttctgat ggagtcgtaa aaaagtttta tctctttctc cttcgatggt 27780
ctcacaaaaa tattaaacct ctttctgatg gagtcgtaaa aaagttttat ctctttctct 27840
cttcgatggt ctcacaaaaa tattaaacct ctttctgatg gagtcgtaaa aaagttttat 27900
ctctttctct cttcgatggt ctcactaaaa tatttttat tctctttctg atgcatcaac 27960
tatttcttaa acaataacgt ccaacaacat atactcgtcg agcttatcaa catcccctat 28020
gcccatctag gttaccagac aattgtatat cataaaataa tgtttataat ttttacaaaa 28080
atatttttat tctctttctc tctttgatgg tctcataaaa aaagttttac aaaaatattt 28140
ttattctctt tctctctttg atggtctcat aaaaaatatt aaacctcttt ctgatggtgt 28200
cactaaaata tttttattct cattctctct tcaatggagt cataaaatat ttttattctc 28260
tttctctctt cgatggtctc acaaaaatat taaacctctt tctgatggtg tcactaaaat 28320
atttttattc tcattctctc ttcaatggag tcataaaata tttttattct ctttctctct 28380
ttgatggtct cataaaaaaa gttttacaaa aatattttta ttctctttct ctctttgatg 28440
gtctcataaa aaaagtttta caaaaatatt tttattctct ttctctcttt gatggtctca 28500
taaaaaaagt tttacaaaaa tatttttatt ctctttctct ctttgatggt ctcataaaaa 28560
aagttttaca aaaatatttt tattctcttt ctctctttga tggtctcata aaaaaagttt 28620
tacaaaaata tttttattct ctttctctct ttgatggtct cataaaaaaa gttttacaaa 28680
aatattttta ttctctttct ctctttgatg gtctcataaa aaaagtttta caaaaatatt 28740
tttattctct ttctctcttt gatggtctca taaaaaatat taaacctctt tctgatggtg 28800
tcactaaaat atttttattc tctttctctc ttcaatggag tcataaaata tttttattct 28860
ctttctctct tcgatggtct cacaaaaata ttaaacctct ttctgatggt gtcactaaaa 28920
tatttttatt ctcattctct cttcaatgga gtcataaaat atttttattc tctttctctc 28980
tttgatggtc tcataaaaaa agttttacaa aaatattttt attctctttc tctctttgat 29040
ggtctcataa aaaaagtttt acaaaaatat ttttattctc tttctctctt tgatggtctc 29100
ataaaaaaag ttttacaaaa atatttttat tctctttctc tctttgatgg tctcataaaa 29160
aaagttttac aaaaatattt ttattctctt tctctctttg atggtctcat aaaaaaagtt 29220
ttacaaaaat atttttattc tctttctctc tttgatggtc tcataaaaaa tattaaacct 29280
ctttctgatg gtgtcactaa aatattttta ttctctttct ctcttcaatg gagtcataaa 29340
atatttttat tctctttctc tcttcgatgg tctcacaaaa atattaaacc tctttctgat 29400
ggtgtcacta aaatattttt attctctttc tctcttcaat ggagtcataa aatattttta 29460
ttctctttct ctctttgatg gtctcataaa aaaagtttta caaaaatatt tttattctct 29520
ttctctcttt gatggtctca taaaaaaagt tttacaaaaa tatttttatt ctctttctct 29580
ctttgatggt ctcataaaaa aagttttaca aaaatatttt tattctcttt ctctctttga 29640
tggtctcata aaaaaagttt tacaaaaata tttttattct ctttctctct ttgatggtct 29700
cataaaaaaa gttttacaaa aatattttta ttctctttct ctctttgatg gtctcataaa 29760
aaaagtttta caaaaatatt tttattctct ttctctcttt gatggtctca taaaaaaagt 29820
tttacaaaaa tatttttatt ctctttctct ctttgatggt ctcataaaaa atattaaacc 29880
tctttctgat ggtgtcacta aaatattttt attctcattt tctctttctc tcttcaatgg 29940
agtcataaaa tatttttatt ctctttctct ctttgatggt ctcataaaaa atattaaacc 30000
tctttctgat ggtgtcacta aaatattttt attctcattc tctcttcaat ggagtcataa 30060
aaaagtttta tctctttctc tcttcgatgg tctcacaaaa atattaaacc tctttctgat 30120
ggagtcgtaa aaaagtttta tctctttctc tcttcgatgg tctcacaaaa atattaaacc 30180
tctttctgat gcatcaacta tttcttaaac aataacgtcc aacaacatat actcatcccc 30240
tatgcccatc taggttacca gacaattgta tatcataaaa taatgtttat aatttacacg 30300
ttaaaatcat ataataaaac gtagatcgta taatattttt tggtatataa atgatctagt 30360
aaaatccatg taggggatac tgctcacatt ttttctttgg tacaaaattt cacacaagtt 30420
tttatacaga caaattcttg tccatatatt ttaaaacatt gacttttgta ctaagaaaaa 30480
tatctagact aactatctct ttctctttct ctcttcgatg gtctttctga tggagtcgta 30540
aaaaagtttt atctctttct ctcttcgatg gtctcacaaa aatattaaac ctctttctga 30600
tggagtcgta aaaaagtttt atctctttct ctcttcgatg gtctcacaaa aatattaaac 30660
ctctttctga tggagtcgta aaaaagtttt atctctttct ccttcgatgg tctcacaaaa 30720
atattaaacc tctttctgat ggagtcgtaa aaaagtttta tctctttctc tcttcgatgg 30780
tctcacaaaa atattaaacc tctttctgat ggtgtcacta aaatattttt attctctttc 30840
tctcttcgat ggtctcacaa aaatattaaa cctctttctg atggagtcgt aaaaaagttt 30900
tatctctttc tccttcgatg gtctcacaaa aatattaaac ctctttctga tggagtcgta 30960
aaaaagtttt atctctttct ctcttcgatg gtctcacaaa aatattaaac ctctttctga 31020
tggagtcgta aaaaagtttt atctctttct ccttcgatgg tctcacaaaa atattaaacc 31080
tctttctgat ggagtcgtaa aaaagtttta tctctttctc cttcgatggt ctcacaaaaa 31140
tattaaacct ctttctgatg gagtcgtaaa aaagttttat ctctttctcc ttcgatggtc 31200
tcacaaaaat attaaacctc tttctgatgg agtcgtaaaa aagttttatc tctttctctc 31260
ttcgatggtc tcacaaaaat attaaacctc tttctgatgg agtcgtaaaa aagttttatc 31320
tctttctctc ttcgatggtc tcacaaaaat attaaacctc tttctgatgg agtcgtaaaa 31380
aagttttatc tctttctcct tcgatggtct cacaaaaata ttaaacctct ttctgatggt 31440
ctctataaag cgattgattt ttcttaccct ctagagtttc ctacggtcgt tggtcacaca 31500
ttttttttcta gacactaaat aaatatttaa aatataatat taatatacta aaatttatgt 31560
attattaatt tataatatta atatactaaa atttatgtat tattaattta tctaactaaa 31620
gttagtaaat catatacata attttataat taatattata tacataattt tataattaat 31680
ttaatcttac 31690

SEQ ID NO: 46 moltype = DNA length = 4590
FEATURE Location/Qualifiers
misc_feature 1..4590
note = Vaccine construct
source 1..4590
mol_type = other DNA
organism = synthetic construct
SEQUENCE: 46
cccgccgcca ccatgtctct gctgtggggc ggagtgacag tgctggccgc catgctgatt 60
gctggccagg tggcctccgt ggtgttcctc gtgaaaggcg gaggacctgg cggcggaatg 120
cagctgtttc acctgtgcct gatcatcagc tgtagctgcc ccaccgtgca ggccagcaag 180
ctgtgtctgg gatggctgtg gggaatggac atcgacccct acaaagaatt cggcgccagc 240
gtggaactgc tgagcttcct gcccagcgac ttcttcccct ccatccggga cctgctggat 300
acagccagcg ccctgtatag agaggccctg gaaagccccg agcactgcag ccctcatcac 360
accgctctga gacaggccat cctgtgctgg ggcgagctga tgaacctggc cacttgggtg 420
ggaagcaacc tggaagatcc cgccagccgg gaactggtgg tgtcttacgt gaacgtgaac 480
atgggcctga agatccggca gctgctgtgg ttccacatct cctgcctgac cttcggccgg 540
gaaaccgtgc tggaatacct ggtgtccttc ggcgtgtgga tcagaacccc ccctgcctac 600
agacccccca acgcccctat cctgagcacc ctgcctgaga caacagtcgt gcggcggaga 660
ggcagaagcc ccagaagaag aacccccagc cccagacgca gaagaagcca gtcccctcgg 720
cggagaagat cccagagcag ggaaagccag tgtggcggag gctctggggg aggcatgcca 780
ctgagctacc agcacttcag aaaactgctg ctgctggacg acgaggccgg acccctggaa 840
gaggaactgc ctagactggc cgacgagggc ctgaacagaa gagtggccga ggacctgaac 900
ctgggcaacc tgaacgtgtc catcccctgg acccacaaag tgggcaactt caccggcctg 960
gcctccagca ccgtgcccgt gtttaatccc gagtggcaga cccccagctt cccccacatc 1020
catctgcagg aagatatcat caaccgctgc cagcagtacg tgggccccct gaccgtgaac 1080
gagaagcgga gactgaagct gatcatgccc gccagattct accccaacct gaccaagtac 1140
ctgcccctgg acaagggcat caagccctac taccctgagc acgccgtgaa ccactacttc 1200
aagacccggc actacctgca caccctgtgg aaggccggca tcctgtacaa gagagagaca 1260
accagaagcg ccagcttctg cggcagcccc tacagctggg agcaggaact gcagcacggc 1320

```
cggctggtgt ttcagaccag cacaagacac ggcgacgagt ctttctgcag ccagagcagc  1380
gggatcctgt ccagatctcc tgtgggccct tgtgtgcgga gccagctgaa gcagagcaga  1440
ctgggactgc agcctcagca gggaagcctg gccagaggca agtctggcag aagcggcagc  1500
atccgggcca gagtgcaccc taccaccaga cggtcctttg gcgtggaacc tagcggcagc  1560
ggccacatcg ataacagcgc cagcagcacc tccagctgcc tgcatcagtc tgccgtgcgc  1620
aagaccgcct acagccacct gtccaccagc aagagacaga gcagctctgg ccacgctgtg  1680
gaactgcaca acatccccc tagcagcgcc agaagccaga gcgagggccc tatctttagc  1740
gcctggtggc tgcagtttcg gaacagcaag cccgccagcg actacgccct gacccacatc  1800
gtgaacctgc tggaagattg gggccctgcc acagagcacg gcgagcacaa tatccggatc  1860
cccagaaccc ctgccagagt gacaggcggc gtgttcctgg tggataagaa tccccacaac  1920
accaccgaga gcaggctggt ggtggacttc agccagttca gcagaggcag cacccacgtg  1980
tcctggccca agttcgccgt gcccaatctg cagagcctga ccaacctgct gagcagcaac  2040
ctgagctggc tgagcctgga cgtgtccgcc gccttctacc acatcccact gcatcctgcc  2100
gctatgcccc atctgctcgt gggcagttct ggcctgccta gatatgtggc ccggctgtct  2160
agcaccagca gaaacatcaa ttaccagcac ggcaccatgc aggacctgca cgacagctgc  2220
agccggaatc tgtacgtgtc cctcctgctg ctgtacaaaa ccttcggcag aaagctgcac  2280
ctgtactccc accccatcat cctgggcttc agaaagatcc ccatgggcgt gggcctgagc  2340
ccattcctgc tggcccagtt taccagcgcc atctgtagcg tcgtgcggag agccttccct  2400
cactgcctgg cctttagcta catggacgac gtggtgctgg gcgccaagag cgtgcagcac  2460
ctggaatccc tgtttacctc catcaccaac tttctgctgt ccctgggcat ccacctgaac  2520
cccaacaaga ccaagaggtg gggctacagc ctgaacttca tgggctacgt gatcggcagc  2580
tggggcacac tgcctcagga acacatcgtg ctgaagatca agcagtgctt tcggaagctg  2640
cccgtgaacc ggcccatcga ctggaaagtg tgccagcgga tcgtggggct gctgggattt  2700
gccgcccctt ttacccagtg cggctacccc gctctgatgc cctgtacgc ctgcattcag  2760
agcaagcagg ccttcacctt cagccctacc tacaaggcct ttctgtgcaa gcagtatctg  2820
aacctgtacc ccgtggctcg gcagagaagc ggcctgtgtc aggtgttcgc cgatgccaca  2880
cctacaggat ggggcctggc catcggacac agagccatga gaggcacctt cgtggcccct  2940
ctgcctattc acacagccga gctgctggct gcctgtttcg ccagatctag aagcggcgcc  3000
aagctgatcg gcaccgacaa ctctgtggtg ctgagccgga agtacacctc cttcccttgg  3060
ctgctgggct gcgccgccaa ctggatcctg agaggaacca gcttcgtgta cgtgccaagc  3120
gccctgaacc ctgccgccga tcctagtgct ggaaggctgg gcctgtaccg gccactgctg  3180
catctgcctt tcagacccac caccggccgg accagtctgt atgccgtgtc tcctagcgtg  3240
cccagccatc tgcccgacag agtgcatttc gccagccctc tgcatgtggc ctggcggcct  3300
ccaagaaaaa gacgggcccc tgtgaagcag accctgaatt tcgacctgct gaagctggcc  3360
ggcgacgtgg aaagcaaccc tggccctatg ggcggctggt ccagcaagcc tagacagggc  3420
atgggcacca acctgtccgt gcctaacccc ctgggattct tcccagacca ccagctggac  3480
cctgccttcg gagccaacag caacaacccc gactgggatt tcaaccctaa caaggaccac  3540
tggcccgagg ccaaccaagt gggagctggc gcatttggcc ctggcttcac acctcctcat  3600
ggcggactgc tggggtggtc acctcaggct cagggcatcc tgactacagt gcctgccgct  3660
cctcctcccg cctccaccaa tagacagagc ggcagacagc ccacccccat cagccctcca  3720
ctgagagata gccacccccca ggccatgcag tggaacagca ccacctttca ccaggccctg  3780
ctggacccaa gagtgcgcgg cctgtatttt cctgccggcg gaagctctag cggcaccgtg  3840
aatcctgtgc ctaccaccgc cagcccaatc agcagcatct tctccagaac cggcgaccct  3900
gcccccaaca tggagaacac cacctccggc tttctgggcc cactgctggt gctgcaggcc  3960
ggctttttc tgctgacccg gatcctgacc atcccccagt ccctggactc ttggtggacc  4020
tccctgaact ttctgggagg cgcccctaca tgtcccggcc agaatagcca gagccccacc  4080
tccaatcaca gcccaaccag ctgcccccct atctgccccg gctatcggtg gatgtgcctg  4140
cggcggttca tcatctttct gttcattctg ctgctgtgtc tgatcttcct gctggtgctg  4200
ctggactacc agggcatgct gcctgtgtgc cctctgctgc ctggcacctc taccacaagc  4260
accggccctt gcaagacttg caccatccca gcccagggca ccagcatgtt ccccagctgt  4320
tgctgcacca agccctccga cggcaactgt acctgcatcc ccatcccaag cagctgggcc  4380
ttcgcccggt ttctgtggga atgggccagc gtgcggttct cctggctgag tctgctggtg  4440
cctttcgtgc agtggttcgt gggactgtcc cctaccgtgt ggctgagcgt gatctggatg  4500
atgtggtact ggggcccctc cctgtacaat atcctgtccc ccttcctgcc cctgctgccc  4560
atcttctttt gcctgtgggt gtacatctga                                4590
```

```
SEQ ID NO: 47          moltype = DNA  length = 4578
FEATURE                Location/Qualifiers
misc_feature           1..4578
                       note = Vaccine construct
source                 1..4578
                       mol_type = other DNA
                       organism = synthetic construct
SEQUENCE: 47
cccgccgcca ccatgtctct gctgtggggc ggagtgacag tgctggccgc catgctgatt  60
gctggccagg tggcctccgt ggtgttcctc gtgaagggcg gatctatggg cggctggtcc  120
agcaagccta gacagggcat gggcaccaac ctgagcgtgc ccaatcccct gggattcttc  180
ccagaccacc agctggatcc tgccttcggc gccaacagca acaaccccga ctgggacttc  240
aaccccaaca aggaccactg gcccgaggcc aaccaagtgg gagctggcgc ttttggccct  300
ggcttcacac ctcctcatgg cggactgctg ggatggtcac ctcaggccca gggcatcctg  360
acaacagtgc ctgctgctcc acctcccgcc agcaccaata gacagagcgg cagacagccc  420
accccatca gccctccact gagagatagc cacccccagg ccatgcagtg gaacagcacc  480
acctttcacc aggccctgct ggaccctaga gtgcggggcc tgtattttcc tgccggcgga  540
agcagcagcg gcaccgtgaa tcctgtgcct accaccgcca gccccatctc cagcatcttc  600
agcagaaccg gcgaccctgc ccccaacatg gagaacacca ccagcggctt tctgggcccc  660
ctgctggtgc tgcaggccgg cttttttctg ctgacccgga tcctgaccat tccccagagc  720
ctggactcct ggtggacctc cctgaacttc ctgggcggag cccctacatg ccctggccag  780
aatagccaga gccccaccag caaccacagc cctaccagct gccctcctat ctgccccggc  840
tacaggtgga tgtgcctgcg gcggttcatc atctttctgt tcatcctgct gctgtgcctg  900
```

```
atctttctgc tggtgctgct ggactatcag ggcatgctgc ccgtgtgccc tctgctgcct  960
ggcaccagca caacaagcac cggcccttgc aagacctgca ccatccctgc ccagggaacc  1020
agcatgttcc ccagctgctg ctgcaccaag cccagcgacg gcaactgcac ctgtatcccc  1080
atcccttcca gctgggcctt cgccagattc ctgtgggagt gggccagcgt gcggttcagc  1140
tggctgtcac tgctggtgcc cttcgtgcag tggttcgtgg gcctgtctcc taccgtgtgg  1200
ctgagcgtga tctggatgat gtggtactgg ggcccctccc tgtacaatat cctgagcccc  1260
ttcctgcccc tgctgcccat cttcttttgc ctgtgggtgt acatccggaa gcggagagcc  1320
cccgtgaagc agacccctgaa tttcgacctg ctgaagctgg ccggcgacgt ggaaagcaac  1380
cctggcccta tgcagctgtt tcacctgtgt ctgatcatca gctgtagctg ccccaccgtg  1440
caggccagca agctgtgtct gggatggctg tgggggatgg acatcgaccc ctacaaagaa  1500
ttcggcgcct ctgtggaact gctgagcttc ctgcctagcg acttcttccc ctccatccgg  1560
gacctgctgg atacagccag cgccctgtat agagaggccc tggaaagccc cgagcactgc  1620
agccctcatc acaccgctct gaggcaggcc atcctgtgtt ggggcgagct gatgaacctg  1680
gccacttggg tgggaagcaa cctggaagat cccgcctccc gggaactggt ggtgtcttac  1740
gtgaacgtga acatgggcct gaagatccgg cagctgctgt ggttccacat ctcctgcctg  1800
accttcggcc gggaaaccgt gctggaatac ctggtgtcct tcggcgtgtg gatcagaacc  1860
ccccctgcct acagaccccc caacgcccct atcctgtcca ccctgcctga gacaactgtc  1920
gtgcggcgga gaggcagaag ccccagaaga agaaccccca gccccagacg cagaagaagc  1980
cagtcccctc ggcggagaag atcccagagc agggaaagcc agtgtggcgg aggatctggc  2040
ggcggaatgc ctctgagcta ccagcacttc cggaaactgc tgctgctgga tgacgaggcc  2100
ggacccctgg aagaggaact gcctagactg gccgacgagg gcctgaacag aagagtggcc  2160
gaggacctga acctgggcaa cctgaatgtg tctatcccct ggacccacaa agtgggcaac  2220
ttcaccggcc tggcctccag caccgtgccc gtgtttaatc ccgagtggca gacccccagc  2280
ttcccccaca tccatctgca ggaagatatc atcaaccgct gccagcagta cgtgggccct  2340
ctgaccgtga acgagaagcg cagactgaag ctgatcatgc ccgccaggtt ctaccccaac  2400
ctgaccaagt acctgcctct ggacaagggc atcaagccct actaccctga gcacgccgtg  2460
aaccactact tcaagacccg gcactacctg cacaccctgt ggaaggccgg catcctgtat  2520
aagcgggaaa caaccagatc cgccagcttc tgcggctccc cctacagctg ggagcaggaa  2580
ctgcagcacg gccggctggt gtttcagacc tctaccagac acggcgacga gtctttctgc  2640
agccagagca gcgggatcct gagcagatct ccagtgggcc cttgtgtgcg gtcccagctg  2700
aagcagagta gactgggcct gcagcctcag cagggctctc tggctagagg caagtctggc  2760
agaagcggca gcatccgggc cagagtgcac cctaccacca gacggtcctt tggcgtggaa  2820
cctagcggca gcggccacat cgataacagc gcctctagca cctccagctg cctgcatcag  2880
tccgccgtgc ggaaaaccgc ctacagccac ctgagcacaa gcaagagaca gagcagctcc  2940
ggccacgccg tggaactgca caatatcccc cctagcagcg ccagaagcca gagcgagggc  3000
cctatcttta gcgcctggtg gctgcagttt cggaacagca agcccgccag cgactacgcc  3060
ctgacccaca tcgtgaacct gctggaagat tggggccctg ccacagagca cggcgagcac  3120
aacatccgga tccccagaac ccctgccaga gtgacaggcg gcgtgttcct ggtggataag  3180
aaccctcaca acaccaccga gagcagactg gtggtggact tcagccagtt cagccggggc  3240
tctacccacg tgtcctggcc taagttcgcc gtgcccaacc tgcagagcct gaccaacctg  3300
ctgtccagca acctgtcctg gctgtccctg gatgtgtccg ccgccttcta ccacatccca  3360
ctgcatcccg ccgctatgcc ccatctgctc gtgggaagta gcggcctgcc tagatacgtg  3420
gccagactga gcagcacctc ccggaacatc aattaccagc acggcaccat gcaggatctg  3480
cacgacagct gcagccggaa cctgtacgtg tcccttctgc tgctgtacaa gaccttcggc  3540
agaaagctgc atctgtactc ccaccccatc atcctgggct ttagaaagat ccccatgggc  3600
gtgggactgt ccccattcct gctggcccag ttcaccagcg ccatctgttc cgtcgtgcgc  3660
agagccttcc ctcactgcct ggcctttagc tacatggacg acgtggtgct gggcgccaag  3720
agcgtgcagc acctggaatc cctgtttacc agcatcacca actttctgct gagcctgggc  3780
atccacctga accctaacaa gaccaagcgc tggggctaca gcctgaactt tatgggctac  3840
gtgatcggct cctggggcac actgcctcag gaacacatcg tgctgaaaat caagcagtgc  3900
tttcggaagc tgcctgtgaa ccggcccatc gactggaaag tgtgccagcg gattgtgggc  3960
ctgctgggct ttgccgcccc ttttacacag tgcggctacc ccgctctgat gcccctgtac  4020
gcctgcattc agagcaagca ggccttcacc ttcagcccaa cctacaaggc cttcctgtgc  4080
aagcagtacc tgaatctgta ccccgtggcc cggcagagaa gcggcctgtg tcaggtgttc  4140
gccgatgcca cacctacagg atggggcctg gccatcggac acagagccat gagaggcacc  4200
ttcgtggccc cactgcctat tcacacagcc gagctgctgg ctgcctgttt cgccaggtct  4260
agaagcggcg ccaagctgat cggcaccgac aactctgtgg tgctgagccg gaagtacacc  4320
tccttccctt ggctgctggg ctgcgccgcc aactggatcc tgagaggcac aagcttcgtg  4380
tacgtgccct ccgccctgaa tcctgccgac gatcctagtg ctggacggct gggactgtac  4440
cggcctctgc tgcatctgcc cttcagaccc accaccggca gaaccagcct gtatgccgtg  4500
tcccctagcg tgccaagcca tctgcccgac agagtgcatt tcgcctcccc cctgcatgtg  4560
gcttggaggc cccccttaa                                               4578

SEQ ID NO: 48          moltype = DNA  length = 4704
FEATURE                Location/Qualifiers
misc_feature           1..4704
                       note = Vaccine construct
source                 1..4704
                       mol_type = other DNA
                       organism = synthetic construct
SEQUENCE: 48
cccgccgcca ccatgtcttt gctttggggc ggagtgacag tgctggccgc catgcttatt  60
gctggacagg tggccagcgt ggtgttcctg gtcaaaggcg gaggacctgg cggaggcatg  120
cagctgtttc acctgtgcct gatcatcagc tgtagctgcc ctacagtgca ggccagcaag  180
ctgtgtcttg gatggctgtg gggcatggac atcgacccct acaaagaatt cggcgcctcc  240
gtggaactgc tgagcttcct gcctagcgac ttcttcccct ccatccggga tctgctggat  300
acagccagcg cactgtatag agaggccctg gaaagccccg agcactgttc tccacatcac  360
acagccctga gacaggccat cctgtgttgg ggcgagctga tgaatctggc cacatgggtc  420
ggaagcaacc tggaagatcc cgccagcaga gaactggtgg tgtcctacgt gaacgtgaac  480
```

-continued

```
atgggcctga agatccggca gctgctgtgg ttccacatct cctgcctgac cttcggcaga  540
gaaaccgtgc tggaatacct ggtgtccttc ggcgtgtgga tcagaacccc tccagcctac  600
agacctccta acgctcccat cctgagcacc ctgcctgaga caacagtcgt gcggagaaga  660
ggcagaagcc ccagaagaag aaccccatct cctcggaggc ggagatctca gtcccctcgg  720
agaagaagat cccagagcag ggaaagccag tgcggtggtg gaagtggtgg cggaatgcct  780
ctgagctacc agcacttcag aaaactgctg ctgctggacg acgaggccgg acctcttgag  840
gaagaactgc ctagactggc cgacgagggc ctgaatagaa gagtggccga ggacctgaac  900
ctgggcaacc tgaatgtgtc tatcccctgg acacacaaag tgggcaactt cacaggcctg  960
gccagctcta ccgtgcctgt gttcaatccc gagtggcaga cccctagctt ccctcacatc  1020
catctgcaag aggacatcat caaccggtgc cagcagtacg tgggccctct gaccgtgaac  1080
gagaagcgga gactgaagct gatcatgccc gccagattct accccaacct gaccaagtac  1140
ctgcctctgg acaagggcat caagccttac taccctgagc acgccgtgaa ccactacttc  1200
aagacccggc actacctgca caccctgtgg aaggccggca tcctgtacaa gagagagaca  1260
accagaagcg ccagcttctg cggcagccct tactcttggg agcaagagct gcagcacggc  1320
agactggtgt tccagacctc tacaagacac ggcgacgagt ctttctgcag ccagagcagc  1380
gggatcctgt ctagatctcc tgtgggacct tgtgtgcgga gccagctgaa acagagcaga  1440
ctgggactgc agcctcagca gggatctctg gctagaggca agtctggcag aagcggcagc  1500
atcagagcca gagtgcaccc taccaccaga cggtcctttg gcgtggaacc tagcggcagc  1560
ggccacatcg ataatagcgc cagcagcacc agcagctgtc tgcatcagtc tgctgtgcgc  1620
aagaccgcct acagccacct gagcacaagc aagagacaga gcagctctgg ccacgccgtc  1680
gagctgcaca atatccctcc aagcagcgcc agaagccaga gcgagggccc tattttttct  1740
gcctggtggc tgcagttcag aaacagcaag cccgccagcg actacgccct gacacacatc  1800
gtgaacctgc tggaagattg gggccctgcc acagaacacg gcgagcacaa catcagaatc  1860
cccaggactc ccgccagagt gaccggcgga gttttcctgg tggacaagaa ccctcacaac  1920
accaccgaga gcaggctggt ggtggacttc agccagttta gcagaggcag cacccacgtg  1980
tcctggccta aattcgccgt gcctaacctg cagagcctga ccaatctgct gagcagcaac  2040
ctgagctggc tgagcctgga tgtgtccgcc gccttctatc acatcccact gcatcctgcc  2100
gctatgcccc atctgcttgt gggaagttct ggcctgccta gatatgtggc ccggctgtcc  2160
tctaccagcc ggaacatcaa ttaccagcac gggaccatgc aggacctgca cgatagctgc  2220
tcccggaacc tgtacgttag cctgctcctg ctgtacaaaa ccttcggccg gaagctgcac  2280
ctgtactctc accctatcat cctgggcttc agaaagatcc ccatgggcgt gggactgagc  2340
ccatttctgc tggcccagtt taccagcgcc atctgcagtg ttgtgcggag agcctttcct  2400
cactgcctgg ccttcagcta catggacgat gtggtgctgg gcgccaagtc tgtgcagcac  2460
ctggaatctc tgtttacctc catcaccaac tttctgctgt ccctgggaat ccatctgaac  2520
cccaacaaga caaagagatg ggctacagc ctgaacttca tgggctacgt gatcggcagc  2580
tggggcacac tgcctcaaga gcacatcgtg ctgaagatca agcagtgctt tagaaagctg  2640
cccgtgaaca gacccatcga ctggaaagtg tgccagcgga ttgtgggcct gctgggattt  2700
gccgctcctt tcacacagtg cggctacccc gctctcatgc ctctgtacgc ctgcatccag  2760
tccaagcagg ccttcacatt cagccctacc tacaaggcct tcctgtgcaa gcagtacctg  2820
aatctgtacc ccgtggctag acagagaagc ggcctgtgtc aggtgttcgc cgatgccaca  2880
cctacaggat ggggactcgc cattggacac agggccatga gaggaacctt tgtggcccct  2940
ctgcctattc acaccgccga attgctggct gcctgtttcg ccagatctag aagcggcgcc  3000
aagctgatcg gcaccgacaa ttcagtggtg ctgagccgga agtacaccag ctttccatgg  3060
ctgctgggct gtgccgccaa ctggattctg agaggcacca gcttcgtgta cgtgcccagc  3120
gctcttaacc ctgccgctga tcctagtgct ggacggctgg gactctacag accactgctg  3180
catctgccct tcagacccac cacaggcaga accagcctgt atgccgtgtc tcctagcgtg  3240
ccaagccatc tgcctgatcg ggtgcacttt gcctctccac tgcatgtggc ttggcggcct  3300
ccaaagagcc ccaacagcaa caaccccgac tgggatttca accctaacaa ggaccactgg  3360
cctgaggcca atcaagttgg agccggcgct tttggccctg gctttacacc tcctcatggc  3420
ggactgcttg gatggtcacc tcaggctcag ggcatcctga ctacagtgcc tgctgctcca  3480
cctcctgcca gcaccaatag acagtcaggc agacagccca cacctatcag ccctccactg  3540
cgggatagtc acccacaggc catgcaatgg aacagcacca ccttccatca ggccctgctg  3600
gatcctagag tgcggggcct gtattttcct gccggcggat ctagctccgg caccgtgaat  3660
cctgtgccta caaccgcctc tcctatcagc agcatcttca gccggacagg cgaccctgct  3720
cctaatggct ctaagggcaa gagaaagcgg agggcccctg tgaaacagac cctgaatttc  3780
gacctgctga agctggccgg cgacgtggaa tctaaccctg gacctatggg cggctggtcc  3840
agcaaaccta gacaaggcat gggcaccaat ctgagcgtgc ccaatccact gggattcttc  3900
ccagaccacc agctggaccc tgccttcggc gccaatagca acaatcctga ttgggacttt  3960
aatcccaaca aagatcattg gcccgaagct aatcaagtcg gcctggaagg cggaagcggc  4020
ggcatggaga ataccacatc tggctttctg ggcccactgc tggttctcca ggccggcttt  4080
tttctcctga cacggatcct gacaatccct cagagcctgg actcttggtg gacctctctg  4140
aacttccttg gcggagcccc tacctgtcct ggacagaata gccagtctcc taccagcaat  4200
cacagcccca caagctgccc tccaatctgc cctggctatc ggtggatgtg cctgcggcgg  4260
ttcatcatct ttctgttcat cctgctgctg tgtctgatct tcctgctggt cctcctggac  4320
taccagggca tgctgccagt ttgtcctctg ctgcctggca cctccacaac atctacaggc  4380
ccttgcaaga cctgtacaat ccccgctcag ggaaccagca tgttccccag ctgttgctgc  4440
accaagccaa gcgacggcaa ctgcacatgc atccccattc ctagcagctg ggcctttgcc  4500
agatttctgt gggagtgggc ctccgtgcgg tttagctggc tgtctctgct cgtgcctttc  4560
gtgcagtggt tcgtcggact gtctccaacc gtgtggctga gcgtgatctg gatgatgtgg  4620
tactggggcc ctagcctgta caatattctg agccccttcc tgcctctcct gccaatcttc  4680
ttttgtctgt gggtgtacat ctga                                        4704
```

```
SEQ ID NO: 49          moltype = DNA  length = 4800
FEATURE                Location/Qualifiers
misc_feature           1..4800
                       note = Vaccine construct
source                 1..4800
                       mol_type = other DNA
                       organism = synthetic construct
```

-continued

SEQUENCE: 49
cccgccgcca ccatgtcttt gctttggggc ggagtgacag tgctggccgc catgcttatt 60
gctggacagg tggccagcgt ggtgttcctg gtcaaaggcg gaggacctgg cggaggcatg 120
cagctgtttc acctgtgcct gatcatcagc tgtagctgcc ctacagtgca ggccagcaag 180
ctgtgtcttg gatggctgtg gggcatggac atcgacccct acaaagaatt cggcgcctcc 240
gtggaactgc tgagcttcct gcctagcgac ttcttcccct ccatccggga tctgctggat 300
acagccagcg cactgtatag agaggccctg gaaagccccg agcactgttc tccacatcac 360
acagccctga gacaggccat cctgtgttgg ggcgagctga tgaatctggc cacatgggtc 420
ggaagcaacc tggaagatcc cgccagcaga gaactggtgg tgtcctacgt gaacgtgaac 480
atgggcctga agatccggca gctgctgtgg ttccacatct cctgcctgac cttcggcaga 540
gaaaccgtgc tggaatacct ggtgtccttc ggcgtgtgga tcagaacccc tccagcctac 600
agacctccta acgctcccat cctgagcacc ctgcctgaga caacagtcgt gcggagaaga 660
ggcagaagcc ccagaagaag aaccccatct cctcggaggc ggagatctca gtcccctcgg 720
agaagaagat cccagagcag ggaaagccag tgcggtggtg gaagtggtgg cggaatgcct 780
ctgagctacc agcacttcag aaaactgctg ctgctggacg acgaggccgg acctcttgag 840
gaagaactgc ctagactggc cgacgagggc ctgaatagaa gagtggccga ggacctgaac 900
ctgggcaacc tgaatgtgtc tatcccctgg acacacaaag tgggcaactt cacaggcctg 960
gccagctcta ccgtgcctgt gttcaatccc gagtggcaga cccctagctt ccctcacatc 1020
catctgcaag aggacatcat caaccggtgc cagcagtacg tgggccctct gaccgtgaac 1080
gagaagcgga gactgaagct gatcatgccc gccagattct accccaacct gaccaagtac 1140
ctgcctctgg acaagggcat caagccttac taccctgagc acgccgtgaa ccactacttc 1200
aagacccggc actacctgca caccctgtgg aaggccggca tcctgtacaa gagagagaca 1260
accagaagcg ccagcttctg cggcagccct tactcttggg agcaagagct gcagcacggc 1320
agactggtgt tccagacctc tacaagacac ggcgacgagt ctttctgcag ccagagcagc 1380
gggatcctgt ctagatctcc tgtgggacct tgtgtgcgga gccagctgaa acagagcaga 1440
ctgggactgc agcctcagca gggatctctg gctagaggca agtctggcag aagcggcagc 1500
atcagagcca gagtgcaccc taccaccaga cggtcctttg gcgtggaacc tagcggcagc 1560
ggccacatcg ataatagcgc cagcagcacc agcagctgtc tgcatcagtc tgctgtgcgc 1620
aagaccgcct acagccacct gagcacaagc aagagacaga gcagctctgg ccacgccgtc 1680
gagctgcaca atatccctcc aagcagcgcc agaagccaga gcgagggccc tatttttct 1740
gcctggtggc tgcagttcag aaacagcaag cccgccagcg actacgccct gacacacatc 1800
gtgaacctgc tggaagattg ggccctgcc acagaacacg gcgagcacaa catcagaatc 1860
cccaggactc ccgccagagt gaccggcgga gttttcctgg tggacaagaa ccctcacaac 1920
accaccgaga gcaggctggt ggtggacttc agccagttta gcagaggcag cacccacgtg 1980
tcctggccta aattcgccgt gcctaacctg cagagcctga ccaatctgct gagcagcaac 2040
ctgagctggc tgagcctgga tgtgtccgcc gccttctatc acatcccact gcatcctgcc 2100
gctatgcccc atctgcttgt gggaagttct ggcctgccta gatatgtggc ccggctgtcc 2160
tctaccagcc ggaacatcaa ttaccagcac gggaccatgc aggacctgca cgatagctgc 2220
tcccggaacc tgtacgttag cctgctcctg ctgtacaaaa ccttcggccg gaagctgcac 2280
ctgtactctc accctatcat cctgggcttc agaaagatcc ccatgggcgt gggactgagc 2340
ccatttctgc tggcccagtt taccagcgcc atctgcagtg ttgtgcggag agcctttcct 2400
cactgcctgg ccttcagcta catggacgat gtggtgctgg gcgccaagtc tgtgcagcac 2460
ctggaatctc tgtttacctc catcaccaac tttctgctgt ccctgggaat ccatctgaac 2520
cccaacaaga caaagagatg ggctacagc ctgaacttca tgggctacgt gatcggcagc 2580
tggggcacac tgcctcaaga gcacatcgtg ctgaagatca agcagtgctt tagaaagctg 2640
cccgtgaaca gacccatcga ctggaaagtg tgccagcgga ttgtgggcct gctgggattt 2700
gccgctcctt tcacacagtg cggctacccc gctctcatgc ctctgtacgc ctgcatccag 2760
tccaagcagg ccttcacatt cagccctacc tacaaggcct tcctgtgcaa gcagtacctg 2820
aatctgtacc ccgtggctag acagagaagc ggcctgtgtc aggtgttcgc cgatgccaca 2880
cctacaggat ggggactcgc cattggacac agggccatga gaggaacctt tgtggcccct 2940
ctgcctattc acaccgccga attgctggct gcctgtttcg ccagatctag aagcggcgcc 3000
aagctgatcg gcaccgacaa ttcagtggtg ctgagccgga agtacaccag ctttccatgg 3060
ctgctgggct gtgccgccaa ctggattctg agaggcacca gcttcgtgta cgtgcccagc 3120
gctcttaacc ctgccgctga tcctagtgct ggacggctgg gactctacag accactgctg 3180
catctgccct tcagacccac cacaggcaga accagcctgt atgccgtgtc tcctagcgtg 3240
ccaagccatc tgcctgatcg ggtgcacttt gcctctccac tgcatgtggc ttggcggcct 3300
ccaaagagcc ccaacagcaa caaccccgac tgggatttca accctaacaa ggaccactgg 3360
cctgaggcca atcaagttgg agccggcgct tttggccctg gctttacacc tcctcatggc 3420
ggactgcttg gatggtcacc tcaggctcag ggcatcctga ctacagtgcc tgctgctcca 3480
cctcctgcca gcaccaatag acagtcaggc agacagccca cacctatcag ccctccactg 3540
cgggatagtc acccacaggc catgcaatgg aacagcacca ccttccatca ggccctgctg 3600
gatcctagag tgcggggcct gtattttcct gccggcggat ctagctccgg caccgtgaat 3660
cctgtgccta caaccgcctc tcctatcagc agcatcttca gccggacagg cgaccctgct 3720
cctaatggct ctaagggcaa gagaaagcgg agggcccctg tgaaacagac cctgaatttc 3780
gacctgctga agctggccgg cgacgtggaa tctaaccccg gacctatgga cgccatgaag 3840
aggggcctgt gttgtgtcct gctgctgtgt ggcgctgtgt tcgtgtctcc cagccaagag 3900
atccacgcca gatttcggag aatgggcggc tggtccagca agcctagaca aggcatgggc 3960
accaatctga gcgtgcccaa tccactggga ttcttcccag accaccagct ggaccctgcc 4020
ttcggcgcca atagcaacaa tcctgattgg gactttaatc ccaacaaaga tcattggccc 4080
gaagctaatc aagtcggcct ggaaggcgga agcggcggca tggagaatac cacatctggc 4140
tttctgggcc cactgctggt tctccaggcc ggctttttc tcctgacacg gatcctgaca 4200
atccctcaga gcctggacag ttggtggacc tctctgaact tccttggcgg agcccctacc 4260
tgtcctggac agaatagcca gtctcctacc agcaatcaca gccccacaag ctgccctcca 4320
atctgccctg gctatcggtg gatgtgcctg cggcggttca tcatctttct gttcattctg 4380
ctgctttgcc tgatcttcct gctggtcctc ctggactacc agggcatgct gccagtttgt 4440
cctctgctgc ctggcacctc cacaacctct acaggccctt gcaagacctg tacaatcccc 4500
gctcagggaa ccagcatgtt ccccagctgt tgctgcacca agccaagcga cggcaactgc 4560
acatgcatcc ccattcctag cagctgggcc tttgccagat tcctctggga atgggcctcc 4620
gtgcggttta gctggctgtc tctgctcgtg cctttcgtgc agtggttcgt cggactgtct 4680

```
ccaaccgtgt ggctgagcgt gatctggatg atgtggtact ggggccctag cctgtacaat  4740
attctgagcc ccttcctgcc tctcctgcca atcttctttt gtctgtgggt gtacatctga  4800

SEQ ID NO: 50          moltype = DNA  length = 2100
FEATURE                Location/Qualifiers
misc_feature           1..2100
                       note = Promoter
source                 1..2100
                       mol_type = other DNA
                       organism = synthetic construct
SEQUENCE: 50
tgagatttct gtcgccgact aaattcatgt cgcgcgatag tggtgtttat cgccgataga  60
gatggcgata ttggaaaaat cgatatttga aaatatggca tattgaaaat gtcgccgatg  120
tgagtttctg tgtaactgat atcgccattt ttccaaaagt gatttttggg catacgcgat  180
atctggcgat agcgcttata tcgtttacgg gggatggcga tagacgactt tggtgacttg  240
ggcgattctg tgtgtcgcaa atatcgcagt ttcgatatag gtgacagacg atatgaggct  300
atatcgccga tagaggcgac atcaagctgg cacatggcca atgcatatcg atctatacat  360
tgaatcaata ttggccatta gccatattat tcattggtta tatagcataa atcaatattg  420
gctattggcc attgcatacg ttgtatccat atcataatat gtacatttat attggctcat  480
gtccaacatt accgccatgt tgacattgat tattgactag ttattaatag taatcaatta  540
cggggtcatt agttcatagc ccatatatgg agttccgcgt tacataactt acggtaaatg  600
gcccgcctgg ctgaccgccc aacgaccccc gcccattgac gtcaataatg acgtatgttc  660
ccatagtaac gccaataggg actttccatt gacgtcaatg ggtggagtat ttacggtaaa  720
ctgcccactt ggcagtacat caagtgtatc atatgccaag tacgccccct attgacgtca  780
atgacggtaa atggcccgcc tggcattatg cccagtacat gaccttatgg gactttccta  840
cttggcagta catctacgta ttagtcatcg ctattaccat ggtgatgcgg ttttggcagt  900
acatcaatgg gcgtggatag cggtttgact cacggggatt tccaagtctc caccccattg  960
acgtcaatgg gagtttgttt tggcaccaaa atcaacggga ctttccaaaa tgtcgtaaca  1020
actccgcccc attgacgcaa atgggcggta ggcgtgtacg gtgggaggtc tatataagca  1080
gagctctccc tatcagtgat agagatctcc ctatcagtga tagagatcgt cgacgagctc  1140
gtttagtgaa ccgtcagatc gcctggagac gccatccacg ctgttttgac ctccatagaa  1200
gacaccggga ccgatccagc ctccgcggcc gggaacggtg cattggaacg cggattcccc  1260
gtgccaagag tgacgtaagt accgcctata gagtctatag gcccaccccc ttggcttctt  1320
atgcatgcta tactgttttt ggcttggggt ctatacaccc ccgcttcctc atgttatagg  1380
tgatggtata gcttagccta taggtgtggg ttattgacca ttattgacca ctcccctatt  1440
ggtgacgata ctttccatta ctaatccata acatggctct ttgccacaac tctctttatt  1500
ggctatatgc caatacactg tccttcagag actgacacgg actctgtatt tttacaggat  1560
ggggtctcat ttattattta caaattcaca tatacaacac caccgtcccc agtgcccgca  1620
gtttttatta aacataacgt gggatctcca cgcgaatctc gggtacgtgt tccggacatg  1680
ggctcttctc cggtagcggc ggagcttcta catccgagcc ctgctcccat gcctccagcg  1740
actcatggtc gctcggcagc tccttgctcc taacagtgga ggccagactt aggcacagca  1800
cgatgcccac caccaccagt gtgccgcaca aggccgtggc ggtagggtat gtgtctgaaa  1860
atgagctcgg ggagcgggct tgcaccgctg acgcatttgg aagacttaag gcagcggcag  1920
aagaagatgc aggcagctga gttgttgtgt tctgataaga gtcagaggta actcccgttg  1980
cggtgctgtt aacggtggag ggcagtgtag tctgagcagt actcgttgct gccgcgcgcg  2040
ccaccagaca taatagctga cagactaaca gactgttcct ttccatgggt cttttctgca  2100

SEQ ID NO: 51          moltype = DNA  length = 673
FEATURE                Location/Qualifiers
misc_feature           1..673
                       note = Promoter
source                 1..673
                       mol_type = other DNA
                       organism = synthetic construct
SEQUENCE: 51
cctttcactc attagatgca tgtcgttaca taacttacgg taaatggccc gcctggctga  60
ccgcccaacg acccccgccc attgacgtca ataatgacgt atgttcccat agtaacgcca  120
atagggactt tccattgacg tcaatgggtg gagtatttac ggtaaactgc ccacttggca  180
gtacatcaag tgtatcatat gccaagtacg ccccctattg acgtcaatga cggtaaatgg  240
cccgcctggc attatgccca gtacatgacc ttatgggact ttcctacttg gcagtacatc  300
tacgtattag tcatcgctat taccatggtg atgcggtttt ggcagtacat caatgggcgt  360
ggatagcggt ttgactcacg gggatttcca agtctccacc ccattgacgt caatgggagt  420
ttgttttgga accaaaatca acgggacttt ccaaaatgtc gtaacaactc cgccccattg  480
acgcaaatgg gcggtaggcg tgtacggtgg gaggtctata taagcagagc tctccctatc  540
agtgatagag atctccctat cagtgataga gatcgtcgac gagctcgttt agtgaaccgt  600
cagatcgcct ggagacgcca tccacgctgt tttgacctcc atagaagaca ccgggaccga  660
tccagcctcc ggt                                                    673

SEQ ID NO: 52          moltype = AA  length = 119
FEATURE                Location/Qualifiers
source                 1..119
                       mol_type = protein
                       organism = Hepatitis B virus
SEQUENCE: 52
MGGWSSKPRQ GMGTNLSVPN PLGFFPDHQL DPAFGANSNN PDWDFNPNKD HWPEANQVGA  60
GAFGPGFTPP HGGLLGWSPQ AQGILTTVPA APPPASTNRQ SGRQPTPISP PLRDSHPQA   119

SEQ ID NO: 53          moltype = AA  length = 55
FEATURE                Location/Qualifiers
```

```
source                  1..55
                        mol_type = protein
                        organism = Hepatitis B virus
SEQUENCE: 53
MQWNSTTFHQ ALLDPRVRGL YFPAGGSSSG TVNPVPTTAS PISSIFSRTG DPAPN       55

SEQ ID NO: 54           moltype = AA  length = 25
FEATURE                 Location/Qualifiers
source                  1..25
                        mol_type = protein
                        organism = Hepatitis B virus
SEQUENCE: 54
FLGPLLVLQA GFFLLTRILT IPQSL                                        25

SEQ ID NO: 55           moltype = AA  length = 19
FEATURE                 Location/Qualifiers
source                  1..19
                        mol_type = protein
                        organism = Hepatitis B virus
SEQUENCE: 55
FIIFLFILLL CLIFLLVLL                                               19

SEQ ID NO: 56           moltype = AA  length = 25
FEATURE                 Location/Qualifiers
source                  1..25
                        mol_type = protein
                        organism = Hepatitis B virus
SEQUENCE: 56
RFLWEWASVR FSWLSLLVPF VQWFV                                        25

SEQ ID NO: 57           moltype = AA  length = 22
FEATURE                 Location/Qualifiers
source                  1..22
                        mol_type = protein
                        organism = Hepatitis B virus
SEQUENCE: 57
TVWLSVIWMM WYWGPSLYNI LS                                           22

SEQ ID NO: 58           moltype = DNA  length = 7239
FEATURE                 Location/Qualifiers
misc_feature            1..7239
                        note = Vaccine construct
source                  1..7239
                        mol_type = other DNA
                        organism = synthetic construct
SEQUENCE: 58
gtaatctatt cgatataccg ttgctaacag tatactggcc caataactgt ggatggaaaa  60
tctataataa tacattaata tcatccgatg gtgctagggt tatttggatg gatgcgtata  120
aattttcttg cggtttatct ttacaagact attgttatca ttggggtagc aaaccagaga  180
gccgaccatt cgatttaata aaaaaatcag atgctaaacg caattctaaa tcgttggtca  240
aagaatctat ggcatccttg aaatccttgt acgaggcatt cgagacacaa tcaggagcgt  300
tagaagtttt aatgagtcca tgtaggatgt tttcgttttc tagaatagaa gacatgttct  360
taactagtgt cattaataga gtatccgaga atactggaat ggggatgtat tatcctacca  420
acgatatacc ttctctattt atcgaatcat ctatctgtct agattatatt atagtaaata  480
atcaggaatc caacaaatat cgtatcaaat ctgttctcga tatcatttct tcaaaacaat  540
accctgcagg acgtcccaac tacgttaaaa atggtacaaa aggaaagtta tatatcgcgt  600
tgtgtaaagt taccgtacct actaacgacc atattccagt agtttatcac gatgatgaca  660
atactaccac ctttattaca gtattgacgt ccgtcgatat tgaaactgct atcagagcag  720
gatattcgat agtcgaatta ggggctttac aatgggataa taatattcca gaacttaaaa  780
acggtttact ggatagtatc aagatgattt atgacttgaa cgcagttaca acaaataatt  840
tattggaaca gctcatagaa aatattaact ttaacaactc tagtataatt tcgttgtttt  900
atacatttgc cattagttat tgccgagcat tcatttactc aattatggaa accatagatc  960
cggtgtatat atctcagttc agttataaag aattatacgt tagtagctct tataaagata  1020
ttaatgaatc catgagtcag atggtaaaat tataaaaagt gaaaaaacaat attattttta  1080
tcgttggttg ttacactatg tcacttcttt ggggcggagt tacagttctt gctgctatgc  1140
ttattgctgg acaagttgct tctgttgtgt ttcttgtttc taaatctgga cctccttctg  1200
gaaaatctaa ttctaacaat cctgattggg atttcaatcc taacaaagat cattggcctg  1260
aagctaatca agttggagct ggtgcttttg gacctggttt tacacctcct catggtggat  1320
tgcttggatg gtcacctcaa gctcagggaa ttcttacaac agttccagct gctcctcctc  1380
ctgcttctac aaatagacaa tctggtagac aacctacacc tatttctcca cctcttagag  1440
attctcatcc tcaagctatg caatggaatt ctactacatt tcatcaagct ttgcttgatc  1500
ctagagttag aggactttat tttcctgctg gtggaagttc ttctggaaca gttaatcctg  1560
ttcctacaac agcttctcca atttcttcta tattttctag aacaggcgat cctgctccta  1620
atggatcaaa atctggatca aaaatgcctc tgtcttatca acactttaga aaattgctgc  1680
ttcttgatga tgaagctgga cctcttgaag aagaattgcc tagacttgct gatgaaggac  1740
ttaatagaag agttgctgaa gatcttaatc tgggaaatct taatgtttct attccttgga  1800
cacacaaagt tggaaatttc acaggacttg catcttctac agtgcctgtt tttaatcctg  1860
aatggcaaac accttctttt ccacatattc atctgcaaga ggatatcatc aatagatgtc  1920
aacaatatgt tggaccactg acagttaatg agaagagaag gcttaaactt attatgcctg  1980
```

```
ctagattcta tcctaatctt acaaagtatt tgcctctgga taagggaatc aaaccttatt  2040
atcctgaaca tgctgtgaat cactacttta aaacaagaca ttatctgcat acactgtgga  2100
aagctggtat tctttacaaa agagaaacaa caagatctgc ttcattttgt ggatctccat  2160
attcttggga acaagaactt caacatggta gacttgtttt tcaaacatct acaagacatg  2220
gggatgaatc attttgttct caaagttctg gaattctttc tagatctcct gttggacctt  2280
gtgttagatc tcaacttaaa caatctagac ttggacttca acctcaacaa ggatctcttg  2340
ctagaggaaa aagtggaaga tctggatcta ttagagctag agttcatcct acaactagaa  2400
gatcttttgg agttgaacct tctggatctg gacatattga taattctgcc tcttctacat  2460
cttcttgtct gcatcaatct gctgttagaa agacagctta ttctcatttg tctacttcta  2520
agagacaatc atcttctgga catgctgttg aacttcataa tattcctcca agtagtgcta  2580
gaagtcaatc tgaaggacca atattttcag cttggtggct tcaattcaga aattctaaac  2640
ctgcttctga ttatgctctg acacatatag ttaatttgct tgaagattgg ggacctgcta  2700
cagaacatgg cgaacacaat attagaatac ctagaactcc tgctagagtt acaggcggag  2760
tctttttggt tgataagaat cctcataata ccacagaatc aagacttgtt gttgattttt  2820
cacagttttc tagaggatct acacatgttt cttggcctaa atttgctgtt ccaaatcttc  2880
aatctcttac aaatttgctt tcatctaatc tttcttggct gtctcttgat gtttctgctg  2940
ccttttatca tattcctctt catcctgctg caatgcctca tttgcttgtt ggatcatctg  3000
gacttccaag atatgttgct agacttagct ctacatctag aaatatcaat tatcagcatg  3060
gaacaatgca ggatcttcac gattcttgta gtaggaatct gtatgtttct ttgcttctgc  3120
tgtataagac atttggaaga aaacttcatc tgtattctca ccctattatt ctgggtttta  3180
gaaagattcc tatgggagtt ggactttctc cttttttgct tgctcaattc acatctgcta  3240
tttgttctgt tgttagaagg gcttttcctc attgtcttgc attttcttat atggatgatg  3300
ttgttcttgg agctaaatct gttcaacatc ttgaaagtct gtttacctct attactaatt  3360
ttctgctttc tctgggaatt catctgaatc caaacaaaac aaagagatgg ggatattctc  3420
ttaatttcat gggatatgtt attggatctt ggggaacact tcctcaagaa catatcgttt  3480
tgaaaatcaa gcaatgtttc agaaaactgc ctgtgaatag acctattgat tggaaagttt  3540
gtcaaagaat tgtgggactt cttggatttg ctgctccttt tacacaatgt ggatatcctg  3600
ctcttatgcc actttatgct tgtattcaat ctaaacaggc ttttacattt tctccaacat  3660
acaaagcttt tctgtgtaaa cagtatctga atctttatcc tgtggctaga caaagatctg  3720
gtctttgtca agtttttgct gatgctacac caacaggatg gggacttgct attggacata  3780
gagctatgag aggaacattt gttgctccat tgcctattca tacagctgaa ttgcttgctg  3840
cttgttttgc tagatctaga agcggagcaa aacttattgg tacagataat agtgttgtcc  3900
tgagtagaaa gtacacatct tttccatggt tgttgggatg tgctgctaat tggattctta  3960
gaggaacttc ttttgtttat gttccttctg ctcttaatcc tgcagctgat ccatctgctg  4020
gtagattggg actgtataga ccacttcttc atttgccttt tagaccaaca actggaagaa  4080
catctcttta tgctgtttct ccttctgttc catctcattt gcctgataga gttcattttg  4140
cttctccact tcatgttgct tggaggccac catctaaatc tccaggttct ggaccaccta  4200
tgcaactttt tcatttgtgt ttgatcatta gctgttcttg tcctacagtt caagcttcta  4260
aactttgtct tggatggctt tggggaatgg atattgatcc atacaaagaa tttggagcta  4320
gtgttgaatt gctgtcattt cttccatctg atttttcccc ttctattcgt gatcttcttg  4380
atacagcatc tgctctgtat agagaagctc ttgaatctcc tgaacactgt tctccacatc  4440
atacagcact tagacaagct attctttgtt ggggagaact tatgaatctt gctacatggg  4500
ttggatctaa tttggaagat ccagcttcta gagaattggt ggtttcttat gttaatgtga  4560
atatgggact gaaaattaga caactgcttt ggtttcatat ctcttgtctt acatttggta  4620
gagaaacagt tttggaatat ttggtttctt ttggcgtttg gattagaaca cctccagctt  4680
atagacctcc taatgctcct attttgtcta cacttcctga aacaacagtc gttagaagaa  4740
gaggaagatc tccaagaaga agaacaccaa gtcctagaag aagaagatct caatcaccaa  4800
gaagaagaag aagtcaatct agagaatctc aatgttgatt tttgttcgac attaaaaatt  4860
gaaaataaat acaaaggttc ttgagggttg tgttaaattg aaagcgagaa ataatcataa  4920
atatgattca ggtgacggat ccatggatgc tatgaagcga ggactttgtt gtgttttgct  4980
tctttgtggt gctgtgtttg tttctccatc tcaagaaatt catgccagat tcagaagaat  5040
gggaggctgg tcatctaaac ctagacaagg catgggaaca aatctttctg ttcctaatcc  5100
tttgggattc tttcctgatc atcaattgga tccagcattt ggagcaaata gtaacaatcc  5160
agattgggac tttaacccaa acaaagatca ttggccagaa gctaatcaag ttggagcatc  5220
taaaggtgga aaaagtggaa tggaaaacac tacatctgga tttcttggac ctttgcttgt  5280
tcttcaagct ggatttttcc tgttgacaag aatacttaca attcctcaat cactggattc  5340
ttggtggaca agtcttaatt ttcttggagg tgctcctaca tgtcctggac aaaattctca  5400
atctccaact tctaatcatt ctcctacatc ttgtcctcca atttgtcctg gatatagatg  5460
gatgtgtctt agaagattca ttatctttct tttcatactg ctgctgtgtc tgatttttct  5520
tcttgttttg ttggattatc agggaatgct tcctgtttgt cctttgcttc ctggaacttc  5580
tacaacaagt acaggacctt gtaaaacatg tacaattcca gcacagggaa catctatgtt  5640
tccaagttgt tgttgtacaa aaccttctga tggaaattgc acatgtattc ctattccaag  5700
ttcttgggca tttgctagat ttctttggga atgggcttct gttagattca gttggttgtc  5760
tcttttggtt ccatttgttc agtggtttgt tggattgtct cctacagttt ggctttctgt  5820
tatttggatg atgtggtatt ggggaccttc tctttacaat attttgagtc cttttctccc  5880
tttgctgcca atttctcttt gtctttgggt ttacatttga ttaaccgagt ttctgcatta  5940
ttgtaattcg tatgctggca ccatcaaaga atcacttcta aaagatatca atatcacaca  6000
tacaaatatt actaccctat tgaatgagac agccaaggtt atcaagttag taaaatctct  6060
ggtagataaa gaagatactg atattgtgaa taatttcatt accaaagaaa ttaaaaacag  6120
agacaaaata gttaatagtt tgtctctatc aaacctggac tttcgtttgt aaattggggc  6180
tttttgtaca ataaatgggt gttgccaatg attcatcccc tgaatatcaa tggatgtctc  6240
cccatagatt atcagatact gttatattag gagactgttt gtattttaac aatataatgt  6300
cccaattaga tttacaccaa aattgggctc catcagttag attgttaaat tattttaaga  6360
attttaataa ggaaacacta ctaaagatag aagagaatga ttacattaat tcatcctttt  6420
tccaacaaaa ggataaacga ttttatccta taaacgacga tttttatcac atatctacag  6480
gaggatatgg tatagtcttt aagatagata actatgtagt aaaatttgta ttcgaggcca  6540
caaaattata tagtcccatg gaaactacgg cggagttcac agtacccaaa tttctataca  6600
acaatctaaa gggagatgaa aaaaaattaa tcgtgtgtgc gtgggccatg ggattaaact  6660
ataaattaac atttttacat actctgtata aacgtgttct tcatatgttg ctattattga  6720
```

```
tacaaactat ggatggtcag gaactatcat tgagatattc ttctaaagtt tttttaaagg  6780
cgtttaacga gagaaaggac agtatcaaat tcgtgaaatt actatcccac ttttatccgg  6840
cagttattaa cagtaatatt aatgttataa actattttaa ccgcatgttt cactttttcg  6900
aacatgaaaa gagaactaac tacgaatacg aaagaggaaa tattataatt tttcccctag  6960
cactgtattc ggcagataaa gtagataccg agctagctat caaattagga tttaaatctt  7020
tggtacaata cataaagttt atctttttac agatggctct gttatacatt aaaatttacg  7080
aactaccatg ctgcgacaac tttttacacg cagatcttaa acccgataat atcttacttt  7140
ttgattccaa tgaaccaata ataattcatc taaaggataa aaagtttgtt tttaatgaac  7200
gtattaaatc ggcattaaac gactttgact tttcccaag                         7239

SEQ ID NO: 59          moltype = DNA  length = 3741
FEATURE                Location/Qualifiers
misc_feature           1..3741
                       note = Vaccine construct
source                 1..3741
                       mol_type = other DNA
                       organism = synthetic construct
SEQUENCE: 59
atgtcacttc tttggggcgg agttacagtt cttgctgcta tgcttattgc tggacaagtt  60
gcttctgttg tgtttcttgt ttctaaatct ggacctcctt ctggaaaatc taattctaac  120
aatcctgatt gggatttcaa tcctaacaaa gatcattggc ctgaagctaa tcaagttgga  180
gctggtgctt ttggacctgg ttttacacct cctcatggtg gattgcttgg atggtcacct  240
caagctcagg gaattcttac aacagttcca gctgctcctc ctcctgcttc tacaaataga  300
caatctggta gacaacctac acctatttct ccacctctta gagattctca tcctcaagct  360
atgcaatgga attctactac atttcatcaa gctttgcttg atcctagagt tagaggactt  420
tattttcctg ctggtggaag ttcttctgga acagttaatc ctgttcctac aacagcttct  480
ccaatttctt ctatattttc tagaacaggc gatcctgctc ctaatggatc aaaatctgga  540
tcaaaaatgc ctctgtctta tcaacacttt agaaaattgc tgcttcttga tgatgaagct  600
ggacctcttg aagaagaatt gcctagactt gctgatgaag gacttaatag aagagttgct  660
gaagatctta atctgggaaa tcttaatgtt tctattcctt ggacacacaa agttggaaat  720
ttcacaggac ttgcatcttc tacagtgcct gtttttaatc ctgaatggca aacaccttct  780
tttccacata ttcatctgca agaggatatc atcaatagat gtcaacaata tgttggacca  840
ctgacagtta atgagaagag aaggcttaaa cttattatgc ctgctagatt ctatcctaat  900
cttacaaagt atttgcctct ggataaggga atcaaacctt attatcctga acatgctgtg  960
aatcactact ttaaaacaag acattatctg catacactgt ggaaagctgg tattctttac  1020
aaaagagaaa caacaagatc tgcttcattt tgtggatctc catattcttg ggaacaagaa  1080
cttcaacatg gtagacttgt tttcaaaca tctacaagac atggggatga atcattttgt  1140
tctcaaagtt ctggaattct ttctagatct cctgttggac cttgtgttag atctcaactt  1200
aaacaatcta gacttggact tcaacctcaa caaggatctc ttgctagagg aaaaagtgga  1260
agatctggat ctattagagc tagagttcat cctacaacta gaagatcttt tggagttgaa  1320
ccttctggat ctggacatat tgataattct gcctcttcta catcttcttg tctgcatcaa  1380
tctgctgtta gaaagacagc ttattctcat ttgtctactt ctaagagaca atcatcttct  1440
ggacatgctg ttgaacttca taatattcct ccaagtagtg ctagaagtca atctgaagga  1500
ccaatatttt cagcttggtg gcttcaattc agaaattcta aacctgcttc tgattatgct  1560
ctgacacata tagttaattt gcttgaagat tggggacctg ctacagaaca tggcgaacac  1620
aatattagaa tacctagaac tcctgctaga gttacaggcg gagtcttttt ggttgataag  1680
aatcctcata ataccacaga atcaagactt gttgttgatt tttcacagtt ttctagagga  1740
tctacacatg tttcttggcc taaatttgct gttccaaatc ttcaatctct tacaaatttg  1800
ctttcatcta atctttcttg gctgtctctt gatgtttctg ctgcctttta tcatattcct  1860
cttcatcctg ctgcaatgcc tcatttgctt gttggatcat ctggacttcc aagatatgtt  1920
gctagactta gctctacatc tagaaatatc aattatcagc atggaacaat gcaggatctt  1980
cacgattctt gtagtaggaa tctgtatgtt tctttgcttc tgctgtataa gacatttgga  2040
agaaaacttc atctgtattc tcaccctatt attctgggtt ttagaaagat tcctatggga  2100
gttggacttt ctccttttt gcttgctcaa ttcacatctg ctatttgttc tgttgttaga  2160
agggcttttc ctcattgtct tgcattttct tatatggatg atgttgttct tggagctaaa  2220
tctgttcaac atcttgaaag tctgtttacc tctattacta attttctgct ttctctggga  2280
attcatctga atccaaacaa aacaaagaga tggggatatt ctcttaattt catgggatat  2340
gttattggat cttggggaac acttcctcaa gaacatatcg ttttgaaaat caagcaatgt  2400
ttcagaaaac tgcctgtgaa tagacctatt gattggaaag tttgtcaaag aattgtggga  2460
cttcttggat ttgctgctcc ttttacacaa tgtggatatc ctgctcttat gccactttat  2520
gcttgtattc aatctaaaca ggcttttaca ttttctccaa catacaaagc ttttctgtgt  2580
aaacagtatc tgaatcttta tcctgtggct agacaaagat ctggtctttg tcaagttttt  2640
gctgatgcta caccaacagg atggggactt gctattggac atagagctat gagaggaaca  2700
tttgttgctc cattgcctat tcatacagct gaattgcttg ctgcttgttt tgctagatct  2760
agaagcggag caaaacttat tggtacagat aatagtgttg tcctgagtag aaagtacaca  2820
tcttttccat ggttgttggg atgtgctgct aattggattc ttagaggaac ttcttttgtt  2880
tatgttcctt ctgctcttaa tcctgcagct gatccatctg ctggtagatt gggactgtat  2940
agaccacttc ttcatttgcc ttttagacca acaactggaa gaacatctct ttatgctgtt  3000
tctccttctg ttccatctca tttgcctgat agagttcatt ttgcttctcc acttcatgtt  3060
gcttggaggc caccatctaa atctccaggt tctggaccac ctatgcaact ttttcatttg  3120
tgtttgatca ttagctgttc ttgtcctaca gttcaagctt ctaaactttg tcttggatgg  3180
ctttggggaa tggatattga tccatacaaa gaatttggag ctagtgttga attgctgtca  3240
tttcttccat ctgatttttt cccttctatt cgtgatcttc ttgatacagc atctgctctg  3300
tatagagaag ctcttgaatc tcctgaacac tgttctccac atcatacagc acttagacaa  3360
gctattcttt gttggggaga acttatgaat cttgctacat gggttggatc taatttggaa  3420
gatccagctt ctagagaatt ggtggtttct tatgttaatg tgaatatggg actgaaaatt  3480
agacaactgc tttggtttca tatctcttgt cttacatttg gtagagaaac agttttggaa  3540
tatttggttt cttttggcgt ttggattaga acacctccag cttatagacc tcctaatgct  3600
cctattttgt ctacacttcc tgaaacaaca gtcgttagaa gaagaggaag atctccaaga  3660
```

-continued

```
agaagaacac caagtcctag aagaagaaga tctcaatcac caagaagaag aagaagtcaa  3720
tctagagaat ctcaatgttg a                                            3741

SEQ ID NO: 60          moltype = DNA  length = 96
FEATURE                Location/Qualifiers
misc_feature           1..96
                       note = TPA encoded
source                 1..96
                       mol_type = other DNA
                       organism = synthetic construct
SEQUENCE: 60
atggatgcta tgaagcgagg actttgttgt gttttgcttc tttgtggtgc tgtgtttgtt  60
tctccatctc aagaaattca tgccagattc agaaga                            96

SEQ ID NO: 61          moltype = DNA  length = 882
FEATURE                Location/Qualifiers
misc_feature           1..882
                       note = Vaccine construct
source                 1..882
                       mol_type = other DNA
                       organism = synthetic construct
SEQUENCE: 61
atgggaggct ggtcatctaa acctagacaa ggcatgggaa caaatctttc tgttcctaat  60
cctttgggat tctttcctga tcatcaattg gatccagcat ttggagcaaa tagtaacaat  120
ccagattggg actttaaccc aaacaaagat cattggccag aagctaatca agttggagca  180
tctaaaggtg gaaaaagtgg aatggaaaac actacatctg gatttcttgg acctttgctt  240
gttcttcaag ctggattttt cctgttgaca agaatactta caattcctca atcactggat  300
tcttggtgga caagtcttaa ttttcttgga ggtgctccta catgtcctgg acaaaattct  360
caatctccaa cttctaatca ttctcctaca tcttgtcctc caatttgtcc tggatataga  420
tggatgtgtc ttagaagatt cattatcttt cttttcatac tgctgctgtg tctgattttc  480
cttcttgttt tgttggatta tcagggaatg cttcctgttt gtcctttgct tcctggaact  540
tctacaacaa gtacaggacc ttgtaaaaca tgtacaattc cagcacaggg aacatctatg  600
tttccaagtt gttgttgtac aaaaccttct gatggaaatt gcacatgtat tcctattcca  660
agttcttggg catttgctag atttctttgg gaatgggctt ctgttagatt cagttggttg  720
tctcttttgg ttccatttgt tcagtggttt gttggatttgt ctcctacagt ttggctttct  780
gttatttgga tgatgtggta ttggggacct tctctttaca atattttgag tccttttctc  840
cctttgctgc caattttctt ttgtctttgg gtttacattt ga                     882
```

HBV VACCINE

CROSS-REFERENCE TO RELATED APPLICATIONS

This application is a Continuation of U.S. patent application Ser. No. 16/604,221, filed Oct. 10, 2019, which is the National Stage of International Application No. PCT/GB2018/050948, filed Apr. 10, 2018, which claims the priority to GB 1705765.4, filed Apr. 10, 2017, which are entirely incorporated herein by reference.

SEQUENCE LISTING

This application contains a sequence listing filed in electronic form as a Sequence Listing XML file entitled "JDM86936P.USPC1_ST26.XML", created on Aug. 30, 2023, and having a size of 391 KB. The content of the sequence listing is incorporated herein in its entirety.

FIELD OF THE DISCLOSURE

This invention relates to multi-antigen HBV immunogen for viral vectored vaccines for therapeutic vaccination of chronic hepatitis B.

BACKGROUND

Hepatitis B is a viral infection that attacks the liver and can cause both acute and chronic disease. The Hepatitis B virus (HBV) is transmitted through contact with the blood or other body fluids of an infected person. There is no specific treatment for acute hepatitis B. Therefore, care is aimed at maintaining comfort and adequate nutritional balance, including replacement of fluids lost from vomiting and diarrhoea. However, the mainstay of tackling acute Hepatitis B is by prevention using vaccination. Once established, chronic hepatitis B infection can be treated with drugs, including oral antiviral agents. Treatment can slow the progression of cirrhosis, reduce incidence of liver cancer and improve long-term survival. However, once chronic infection is established spontaneous viral control is rare. A major goal therefore is to develop immunotherapeutic HBV vaccines to induce viral control or cure.

Currently, there are few different T-cell inducing vaccines in Phase I and Phase II clinical trials, all of which are based on either one or two full length HBV-antigens or multiple truncated or full length chimeric HBV-antigens or synthetic peptides based on the HBV-proteome. GS-4774, by GlobeImmune is currently in Phase II clinical trial (GS-4774 has heat-inactivated yeast cells expressing a chimera of HBx HBsAg and HBcAg. TG1050, by Transgene is currently in Phase I clinical trial (TG1050 is a human adenovirus serotype 5 based vaccine encoding a chimera of truncated version of three HBV antigens, core-Polymerase-Envelope). HepTcell™, by Altimmune is currently in Phase I clinical trial (HepTcell is a completely synthetic peptide product, based on 9 synthetic 32-40 mer peptides derived from conserved regions of HBV protein). INO-1800, by Inovio is currently in Phase I clinical trial (INO-1800 is a multi-antigen SynCon® DNA immunotherapy targeting hepatitis B virus clades A & C surface antigens & HBV core antigens). Currently available prophylactic HBV vaccines (generally based on HBV protein vaccines) have no therapeutic effect on chronically infected HBV individuals and hence they fail to control chronic HBV infection. Therefore, an aim of the present invention is to provide an improved vaccine for HBV infection.

SUMMARY OF THE DISCLOSURE

According to a first aspect of the invention, there is provided a multi-HBV immunogen viral vector vaccine comprising:

a viral vector comprising an immunogen expression cassette, wherein the expression of a protein encoded by the expression cassette is arranged to be driven by a promoter, wherein the immunogen expression cassette encodes:

a) HBV Core;

b) a modified HBV polymerase ($P_{mut}$), wherein the modification is a mutation to wild-type HBV polymerase to substantially remove polymerase function;

c) HBV surface antigen (HbsAg); and d) an intergenic sequence that is arranged to cause expression of at least the HBV surface antigen (HbsAg) as a separate protein from the HBV core and the modified HBV polymerase ($P_{mut}$), wherein the intergenic sequence is downstream (3') of the sequences encoding the HBV core and the modified HBV polymerase ($P_{mut}$) and upstream (5') of the sequence encoding the HBV surface antigen (HbsAg).

The intergenic sequence may comprise a cleavage domain, an IRES (Internal Ribosomal Entry Site), a splicing signal, or a secondary promoter. In one embodiment, the intergenic sequence comprises a cleavage domain comprising a sequence arranged to cause ribosome skipping. In another embodiment, the intergenic sequence comprises a secondary promoter to promote expression of at least the surface antigen (HbsAg).

Induction of a strong, multi-antigen specific T cell response against different HBV proteins is thought to play a major role in viral clearance of a resolving chronic HBV infection. For induction of a multi-antigen T-cell response, it can be important to have maximal number of T-cell epitopes, which requires encoding full-length HBV proteins within a T-cell inducing HBV vaccine. Some of the current HBV vaccines under development do not encode full-length HBV antigens. The present invention vaccine can encode 3 full-length proteins of HBV (namely the Core, optionally with Pre-Core region, Polymerase and Surface proteins). In addition, the vaccine design utilizes an at least two-protein expression, for example using an F2A peptide cleavage strategy to encode a separate surface protein, which in addition to the induction of T-cell response could also induce an antibody response that could possibly have a role in potentiating the therapeutic effect of T-cell vaccine, with possible help in clearance of the virus within a chronically infected individual. Inducing antibodies based on a mammalian system (compared to other systems, for e.g. Yeast) has a selective advantage of providing the mammalian-type glycosylation that could induce antibodies appropriate for the natural host.

The invention advantageously provides a single vaccine encoding full-length multiple-HBV antigens that could induce broad T-cell response and in-addition could also induce antibodies to the surface protein. The new HBV immunogen at least encompasses three full length HBV-antigens (namely the Core, Polymerase and Surface) and encoded them into a viral vector, such as the Chimpanzee adeno and MVA viral vectors. In addition, the HBV-polymerase protein in the immunogen is provided with mutations that abolish its function, which avoids its participation in HBV genome replication and improves safety for the vaccine.

By using a peptide cleavage strategy, for example by using a Furin-2A cleavage sequence, or a secondary promoter, the transgene cassette can generate at least two proteins, a fused core and polymerase protein and a separate surface protein, both of which generates a T-cell immune response. The encoded surface protein, in addition to the generation of T-cell immune response can also generate an antibody response.

Immunogen Expression Cassette

The skilled person will recognize that the cleavage domain may not lead to cleavage on all occasions, for example F2A based ribosomal skipping events may occur in a small proportion of expressions, such that a small proportion of proteins made will be a fusion of all the HBV proteins/antigens that would otherwise be separated by the cleavage. Therefore, in one embodiment, the immunogen expression cassette may further encode a fusion protein comprising at least the HBV Core, modified HBV polymerase ($P_{mut}$) and HBV surface antigen.

In one embodiment, the immunogen expression cassette further encodes HBV Pre-Core (PreC). In another embodiment, the immunogen expression cassette further encodes HBV PreS1, and/or a truncated form thereof. In another embodiment, the immunogen expression cassette further encodes HBV PreS2.

In one embodiment, the immunogen expression cassette further encodes HBV Pre-Core (PreC) and HBV PreS1, or a truncated form of HBV PreS1. In another embodiment, the immunogen expression cassette further encodes HBV Pre-Core (PreC) and HBV PreS2. In one embodiment, the immunogen expression cassette further encodes HBV Pre-Core (PreC) and HBV PreS1, and a truncated form of PreS1. In one embodiment, the immunogen expression cassette further encodes HBV Pre-Core (PreC), HBV PreS1, and/or a truncated form thereof, and HBV PreS2.

In an embodiment wherein the HBV Pre-core and Core are encoded, the immunogen expression cassette may be capable of expressing the HBV e-Antigen. The skilled person in the art will recognise that HBV e-Antigen comprises or consists of the 10 C-terminal amino acids of Pre-Core and the 149 N-terminal amino acids of the Core. For the expression of HBV e-Antigen, the Pre-Core and Core are expressed together and this whole expressed protein undergoes N-terminal and C-terminal cleavage.

In one embodiment, the HBV Core and modified polymerase ($P_{mut}$) are arranged to be expressed as a fusion protein. In an embodiment wherein the immunogen expression cassette encodes HBV Pre-core, the HBV Pre-core, HBV Core and modified polymerase ($P_{mut}$) are arranged to be expressed as a fusion protein.

In one embodiment the immunogen expression cassette encodes at least two proteins, comprising a first fusion protein comprising at least the HBV Core and the modified HBV polymerase ($P_{mut}$), and a second protein comprising at least the HBV surface antigen (HbsAg). In another embodiment the immunogen expression cassette encodes only two proteins, comprising a first fusion protein comprising at least the HBV Core and the modified HBV polymerase ($P_{mut}$), and a second protein comprising at least the HBV surface antigen (HbsAg).

In one embodiment, the immunogen expression cassette does not encode HBV X protein.

In one embodiment, the immunogen expression cassette may comprise a nucleic acid sequence encoding any one of:

SIi-HBV-CPmutS;
SIi-HBV-SCPmut;
HBV-CPmutS
SIi-HBV-CPmutPreS-S(sh);
SIi-HBV-CPmutPreS-TPA-S(sh);
SIi-HBV-PreS-Pmut-C;
MVA-SIi-HBV-PreS-Pmut-C-S(sh); or
MVA-SIi-HBV-PreS-Pmut-C-TPA-S(sh), as described herein.

In one embodiment, the immunogen expression cassette comprises SEQ ID NO: 46 (SIi-HBV-CPmutS) or a variant thereof. A variant of SEQ ID NO: 46 may comprise a sequence having at least 70%, 75%, 80%, 85%, 90%, 95%, 98%, 99%, or 99.5% identity with SEQ ID NO: 46. The variant of SEQ ID NO: 46 may encode protein that substantially retains the immunogenicity of equivalent protein encoded by SEQ ID NO: 46.

In one embodiment, the immunogen expression cassette comprises SEQ ID NO: 47 (SIi-HBV-SCPmut) or a variant thereof. A variant of SEQ ID NO: 47 may comprise a sequence having at least 70%, 75%, 80%, 85%, 90%, 95%, 98%, 99%, or 99.5% identity with SEQ ID NO: 47. The variant of SEQ ID NO: 47 may encode protein that substantially retains the immunogenicity of equivalent protein encoded by SEQ ID NO: 47.

In another embodiment, the immunogen expression cassette comprises SEQ ID NO: 48 (SIi-HBV-CPmutPreS-S(sh)) or a variant thereof. A variant of SEQ ID NO: 48 may comprise a sequence having at least 70%, 75%, 80%, 85%, 90%, 95%, 98%, 99%, or 99.5% identity with SEQ ID NO: 48. The variant of SEQ ID NO: 48 may encode protein that substantially retains the immunogenicity of equivalent protein encoded by SEQ ID NO: 48.

In another embodiment, the immunogen expression cassette comprises SEQ ID NO: 49 (SIi-HBV-CPmutPreS-TPA-S(sh)) or a variant thereof. A variant of SEQ ID NO: 49 may comprise a sequence having at least 70%, 75%, 80%, 85%, 90%, 95%, 98%, 99%, or 99.5% identity with SEQ ID NO: 49. The variant of SEQ ID NO: 49 may encode protein that substantially retains the immunogenicity of equivalent protein encoded by SEQ ID NO: 49.

In one embodiment, the immunogen expression cassette comprises SEQ ID NO: 59 (SIi-HBV-PreS-Pmut-C) or a variant thereof. A variant of SEQ ID NO: 59 may comprise a sequence having at least 70%, 75%, 80%, 85%, 90%, 95%, 98%, 99%, or 99.5% identity with SEQ ID NO: 59. The variant of SEQ ID NO: 59 may encode protein that substantially retains the immunogenicity of equivalent protein encoded by SEQ ID NO: 59.

In one embodiment, the immunogen expression cassette comprises SEQ ID NO: 24 (MVA-SIi-HBV-PreS-Pmut-C-S(sh)) or a variant thereof. A variant of SEQ ID NO: 24 may comprise a sequence having at least 70%, 75%, 80%, 85%, 90%, 95%, 98%, 99%, or 99.5% identity with SEQ ID NO: 24. The variant of SEQ ID NO: 24 may encode protein that substantially retains the immunogenicity of equivalent protein encoded by SEQ ID NO: 24.

In one embodiment, the immunogen expression cassette comprises SEQ ID NO: 27 (MVA-SIi-HBV-PreS-Pmut-C-TPA-S(sh)) or a variant thereof. A variant of SEQ ID NO: 27 may comprise a sequence having at least 70%, 75%, 80%, 85%, 90%, 95%, 98%, 99%, or 99.5% identity with SEQ ID NO: 27. The variant of SEQ ID NO: 27 may encode protein that substantially retains the immunogenicity of equivalent protein encoded by SEQ ID NO: 27. In one embodiment, the immunogen expression cassette comprises SEQ ID NO: 58 (MVA-SIi-HBV-PreS-Pmut-C-TPA-S(sh)) or a variant thereof. A variant of SEQ ID NO: 58 may comprise a sequence having at least 70%, 75%, 80%, 85%, 90%, 95%, 98%, 99%, or 99.5% identity with SEQ ID NO: 58. The variant of SEQ ID NO: 58 may encode protein that substantially retains the immunogenicity of equivalent protein encoded by SEQ ID NO: 58.

Viral Vector

The viral vector may comprise a virus. The immunogen expression cassette sequence of the invention may be cloned into any suitable viral vector that is known to elicit good immune response. Suitable viral vectors have been described in Dicks et al (Vaccine. 2015 Feb. 25; 33(9):1121-8. doi: 10.1016/j.vaccine.2015.01.042. Epub 2015 Jan. 25), Antrobus et al (Mol Ther. 2014 March; 22(3):668-74. doi: 10.1038/mt.2013.284. Epub 2013 Dec. 30), and (Warimwe et al. (Virol J. 2013 Dec. 5; 10:349. doi: 10.1186/1743-422X-10-349), which are incorporated herein by reference.

The viral vector may be an attenuated viral vector. The viral vector may comprise an adenovirus, such as a human or simian adenovirus. In one embodiment, the viral vector comprises an adenovirus, such as a group E simian adenovirus, when used in a prime vaccine of a prime boost regime. The viral vector may comprise a group E simian adenovirus. The viral vector may comprise ChAdOx1 (a group E simian adenovirus, like the AdCh63 vector used safely in malaria trials) or ChAdOx2. The skilled person will be familiar with ChAdOx1 based viral vectors, for example from patent publication WO2012172277, which is herein incorporated by reference. The viral vector may comprise AdCh63. The viral vector may comprise AdC3 or AdH6. In one embodiment, the viral vector is a human serotype. In another embodiment, the viral vector comprises Modified Vaccinia Ankara (MVA). The viral vector may comprise MVA when used as a vaccine boost in a prime boost regime. In one embodiment, the viral vector comprises an adenovirus, such as a group E simian adenovirus, when used in a prime vaccine of a prime boost regime, and may comprise MVA when used as a vaccine boost in a prime boost regime. The skilled person will be familiar with MVA based viral vectors, for example from US patent publication U.S. Pat. No. 9,273,327, which is herein incorporated by reference.

MVA advantageously allows expression of more than one protein using different pox viral promoters.

In an alternative embodiment, the viral vector may comprise Adeno-associated virus (AAV) or Lentivirus. In another embodiment, the viral vector may comprise any of Vaccinia virus, fowlpox virus or canarypox virus (e.g. members of Poxviridae and the genus *Avipoxvirus*), or New York attenuated vaccinia virus (Tartaglia et al. Virology. 1992 May; 188(1):217-32, which is herein incorporated by reference). In another embodiment, the viral vector may comprise any of Herpes simplex virus, Human Cytomegalo virus, Measles virus (MeV), Sendai virus (SeV), Flavivirus (e.g. Yellow Fever Virus—17D), or alphavirus vectors, such as Sindibis virus (SINV), Venezuelan equine encephalitis virus, or Semliki forest virus.

In one embodiment, the viral vector may comprise nucleic acid comprising the sequence of SEQ ID NO: 39 and 40 (ChAdOx1) or a variant thereof. A variant of SEQ ID NO: 39 and 40 may comprise a sequence having at least 70%, 75%, 80%, 85%, 90%, 95%, 98%, 99%, or 99.5% identity with SEQ ID NO: 39 and 40. The variant of SEQ ID NO: 39 and 40 may encode a viral vector that substantially retains the function of the viral vector of SEQ ID NO: 39 and 40 (ChAdOx1).

In one embodiment, the viral vector may comprise nucleic acid comprising the sequence of SEQ ID NO: 41 and 42 (ChAdOx2) or a variant thereof. A variant of SEQ ID NO: 41 and 42 may comprise a sequence having at least 70%, 75%, 80%, 85%, 90%, 95%, 98%, 99%, or 99.5% identity with SEQ ID NO: 41 and 42. The variant of SEQ ID NO: 41 and 42 may encode a viral vector that substantially retains the function of the viral vector of SEQ ID NO: 41 and 42 (ChAdOx2).

In one embodiment, the viral vector may comprise nucleic acid comprising the sequence of SEQ ID NO: 44 and 45 (MVA) or a variant thereof. A variant of SEQ ID NO: 44 and 45 may comprise a sequence having at least 70%, 75%, 80%, 85%, 90%, 95%, 98%, 99%, or 99.5% identity with SEQ ID NO: 44 and 45. The variant of SEQ ID NO: 44 and 45 may encode a viral vector that substantially retains the function of the viral vector of SEQ ID NO: 44 and 45 (MVA).

In one embodiment, the viral vector encodes any one of:

SIi-HBV-CPmutS;

SIi-HBV-SCPmut;

SIi-HBV-CPmutPreS-S(sh);

SIi-HBV-CPmutPreS-TPA-S(sh);

MVA-SIi-HBV-PreS-Pmut-C-S(sh); or

MVA-SIi-HBV-PreS-Pmut-C-TPA-S(sh), as described herein.

In one embodiment, the viral vector encodes SEQ ID NO: 3 (SIi-HBV-CPmutS) or a variant thereof. A variant of SEQ ID NO: 3 may comprise a sequence having at least 70%, 75%, 80%, 85%, 90%, 95%, 98%, 99%, or 99.5% identity with SEQ ID NO: 3. The variant of SEQ ID NO: 3 may substantially retain the immunogenicity of SEQ ID NO: 3.

In one embodiment, the viral vector encodes SEQ ID NO: 11 (SIi-HBV-SCPmut) or a variant thereof. A variant of SEQ ID NO: 11 may comprise a sequence having at least 70%, 75%, 80%, 85%, 90%, 95%, 98%, 99%, or 99.5% identity with SEQ ID NO: 11. The variant of SEQ ID NO: 11 may substantially retain the immunogenicity of SEQ ID NO: 11.

In one embodiment, the viral vector encodes SEQ ID NO: 13 (SIi-HBV-CPmutPreS-S(sh)) or a variant thereof. A variant of SEQ ID NO: 13 may comprise a sequence having at least 70%, 75%, 80%, 85%, 90%, 95%, 98%, 99%, or 99.5% identity with SEQ ID NO: 13. The variant of SEQ ID NO: 13 may substantially retain the immunogenicity of SEQ ID NO: 13.

In one embodiment, the viral vector encodes SEQ ID NO: 25 (SIi-HBV-CPmutPreS-TPA-S(sh)) or a variant thereof. A variant of SEQ ID NO: 25 may comprise a sequence having at least 70%, 75%, 80%, 85%, 90%, 95%, 98%, 99%, or 99.5% identity with SEQ ID NO: 25. The variant of SEQ ID NO: 25 may substantially retain the immunogenicity of SEQ ID NO: 25.

In one embodiment, the viral vector encodes SEQ ID NO: 23 (MVA-SIi-HBV-PreS-Pmut-C-S(sh)) or a variant thereof. A variant of SEQ ID NO: 23 may comprise a sequence having at least 70%, 75%, 80%, 85%, 90%, 95%, 98%, 99%, or 99.5% identity with SEQ ID NO: 23. The variant of SEQ ID NO: 23 may substantially retain the immunogenicity of SEQ ID NO: 23.

In one embodiment, the viral vector encodes SEQ ID NO: 26 (MVA-SIi-HBV-PreS-Pmut-C-TPA-S(sh)) or a variant thereof. A variant of SEQ ID NO: 26 may comprise a sequence having at least 70%, 75%, 80%, 85%, 90%, 95%, 98%, 99%, or 99.5% identity with SEQ ID NO: 26. The variant of SEQ ID NO: 26 may substantially retain the immunogenicity of SEQ ID NO: 26.

In one embodiment, the viral vector comprises the nucleic acid sequence of SEQ ID NO: 46 (SIi-HBV-CPmutS) or a variant thereof. A variant of SEQ ID NO: 46 may comprise a sequence having at least 70%, 75%, 80%, 85%, 90%, 95%, 98%, 99%, or 99.5% identity with SEQ ID NO: 46.

In one embodiment, the viral vector comprises the nucleic acid sequence of SEQ ID NO: 47 (SIi-HBV-SCPmut) or a variant thereof. A variant of SEQ ID NO: 47 may comprise a sequence having at least 70%, 75%, 80%, 85%, 90%, 95%, 98%, 99%, or 99.5% identity with SEQ ID NO: 47.

In one embodiment, the viral vector comprises the nucleic acid sequence of SEQ ID NO: 48 (SIi-HBV-CPmutPreS-S (sh)) or a variant thereof. A variant of SEQ ID NO: 48 may comprise a sequence having at least 70%, 75%, 80%, 85%, 90%, 95%, 98%, 99%, or 99.5% identity with SEQ ID NO: 48.

In one embodiment, the viral vector comprises the nucleic acid sequence of SEQ ID NO: 49 (SIi-HBV-CPmutPreS-TPA-S(sh)) or a variant thereof. A variant of SEQ ID NO: 49 may comprise a sequence having at least 70%, 75%, 80%, 85%, 90%, 95%, 98%, 99%, or 99.5% identity with SEQ ID NO: 49.

In one embodiment, the viral vector comprises the nucleic acid sequence of SEQ ID NO: 24 (MVA-SIi-HBV-PreS-Pmut-C-S(sh)) or a variant thereof. A variant of SEQ ID NO: 24 may comprise a sequence having at least 70%, 75%, 80%, 85%, 90%, 95%, 98%, 99%, or 99.5% identity with SEQ ID NO: 24.

In one embodiment, the viral vector comprises the nucleic acid sequence of SEQ ID NO: 27 (MVA-SIi-HBV-PreS-Pmut-C-TPA-S(sh)) or a variant thereof. A variant of SEQ ID NO: 27 may comprise a sequence having at least 70%, 75%, 80%, 85%, 90%, 95%, 98%, 99%, or 99.5% identity with SEQ ID NO: 27. In one embodiment, the viral vector comprises the nucleic acid sequence of SEQ ID NO: 58 (MVA-SIi-HBV-PreS-Pmut-C-TPA-S(sh)) or a variant thereof. A variant of SEQ ID NO: 58 may comprise a sequence having at least 70%, 75%, 80%, 85%, 90%, 95%, 98%, 99%, or 99.5% identity with SEQ ID NO: 58.

Promoter

In one embodiment, the promoter is encoded in the immunogen expression cassette, for example the promoter may be encoded at, or adjacent to, the 5' end of the immunogen expression cassette. Alternatively, the promoter may be encoded as part of the viral vector nucleic acid outside of the immunogen expression cassette. For example the promoter may be encoded upstream (5') of the immunogen expression cassette.

The promoter may promote the expression of all the encoded protein of the immunogen expression cassette. In an alternative embodiment wherein the immunogen expression cassette comprises a secondary promoter, the promoter may be a primary promoter that is arranged to promote expression of at least the HBV core and modified polymerase ($P_{mut}$), and optionally not the HBV surface antigen (HbsAg) which may be arranged to be promoted separately by the secondary promoter.

The skilled person will recognise that any suitable promoter may be used as the primary and/or secondary promoter as appropriate for the host for expression. In one embodiment, the promoter comprises a CMV promoter. The CMV promoter may comprise the long or short CMV promoter. In an embodiment wherein the viral vector comprises an Adenoviral vector, such as ChAdOx1 or 2, the promoter may comprise a CMV promoter, SV40 promoter, or EF1a promoter. In an embodiment wherein the viral vector comprises an Adenoviral vector, such as ChAdOx1 or 2, the promoter may comprise a CMV promoter.

The promoter element(s) used in the vector, for example adenoviral vector, (such as ChAdOx1 or 2) may comprise a tetracycline operator (tetO) sequence. A tetracycline operator (tetO) sequence is helpful for generation of viral vectors that can express foreign proteins that are toxic to cells within which they are generated.

In another embodiment, the promoter comprises a pox viral promoter. In an embodiment wherein the viral vector comprises MVA, the promoter may comprise a pox viral promoter, such as F11. In one embodiment, the promoter comprises early Flt promoter. Alternatively, the pox viral promotor may comprise an early promoter, for example selected from any of B8R, K6L, A44L, C11R, and B2R, a promoter with early and late activity, for example selected from mH5, p7.5, and SSP, or a late promoter, for example FP4b.

Early promoter based transgene expression is can be useful for an immunogen intended primarily for T-cell response (there is a higher magnitude of T-cell induction upon usage of these early promoters). However promoters with both early and late activity can be used for an immunogen intended for inducing antibody response. However, these early and late activity promoters can also be used for an immunogen intended for T-cell induction.

In one embodiment, the promoter comprises or consists of the nucleic acid sequence of SEQ ID NO: 50 or 52 (CMV long or short promoter) or variants thereof. A variant of SEQ ID NO: 50 or 52 may comprise a sequence having at least 70%, 75%, 80%, 85%, 90%, 95%, 98%, 99%, or 99.5% identity with SEQ ID NO: 50 or 52 respectively. The variant may substantially retain the promoter function of SEQ ID NO: 50 or 52).

In one embodiment, the promoter comprises or consists of a sequence located in the F11 Left flank sequence (SEQ ID NO: 35) or a variant thereof. A variant may comprise a sequence having at least 70%, 75%, 80%, 85%, 90%, 95%, 98%, 99%, or 99.5% identity with the promoter sequence located in the F11 Left flank sequence (SEQ ID NO: 35). The variant may substantially retain the promoter function of the promoter located in the F11 Left flank sequence (SEQ ID NO: 35).

Secondary Promoter

In one embodiment, the immunogen expression cassette encodes a secondary promoter. In an embodiment wherein a secondary promoter is provided in addition to the first/primary promoter, the secondary promoter may be encoded by/within the immunogen expression cassette. The secondary promoter may be encoded 3' of the first/primary promoter. The secondary promoter may be encoded 3' of the first protein/antigen to be expressed, for example downstream of the HBV core and HBV modified polymerase and upstream of the HBV surface antigen. The secondary promoter may promote the expression of at least the HBV surface antigen.

The secondary promoter may comprise a pox viral promoter. The secondary promoter may comprise pox viral early promoters, such as any of B8R, K6L, A44L, C11R, and B2R, or pox viral promoters with early and late activity, such as mH5, p7.5 or SSP, or a late promoter such as FP4b.

In one embodiment, the secondary promoter comprises early/late promoter mH5. In one embodiment, the secondary promoter comprises or consists of the nucleic acid sequence of SEQ ID NO: 28 (mH5 promoter) or a variant thereof. A variant of SEQ ID NO: 28 may comprise a sequence having at least 70%, 75%, 80%, 85%, 90%, 95%, 98%, 99%, or 99.5% identity with SEQ ID NO: 28. The variant may substantially retain the secondary promoter function of SEQ ID NO: 28).

In another embodiment, the secondary promoter may comprise a SV40 promoter or EF1a promoter.

Cleavage Domain

In one embodiment, the immunogen expression cassette encodes a cleavage domain. In one embodiment, the cleavage domain is a post-translation proteolytic cleavage domain, which allows for the cleavage of a translated protein, for example by a proteolytic cleavage enzyme. The cleavage enzyme may be provided by the host, for example the host being vaccinated, such as a human. In another embodiment, the cleavage enzyme may be encoded in the immunogen expression cassette or viral vector. In one embodiment, the cleavage domain comprises a non-HBV sequence, for example, a mammalian sequence. In one embodiment, the cleavage domain comprises a human derived sequence.

In one embodiment, the cleavage domain comprises a ribosome skipping cleavage domain. In one embodiment, the cleavage domain comprises a Furin recognition site comprising or consisting of the sequence RXRR, where X could be any amino acid. In one embodiment, the cleavage domain comprises a Furin recognition site and a 2A peptide sequence. The 2A peptide sequence may comprise FMDV (Foot and Mouth Disease Virus) 2A peptide sequence (APVKQTLNFDLLKLAGDVESNPGP—SEQ ID NO: 43). Alternatively, 2A peptides may be selected from P2A (porcine teschovirus-1 2A), T2A (Thoseaasigna virus 2A), and E2A (equine rhinitis A virus [ERAV] 2A). Any picorna virus 2A peptide sequence may be provided for, and function as, a peptide cleavage site. Therefore, the cleavage domain may comprise a sequence encoding picorna virus 2A peptide sequence.

In one embodiment, the cleavage domain comprises or consists of Furin-2A (F2A) peptide sequence or a functional variant thereof. The cleavage domain may comprise or consists of the sequence of SEQ ID NO: 9 or a variant thereof. A variant of SEQ ID NO: 9 may comprise a sequence having at least 70%, 75%, 80%, 85%, 90%, 95%, 98%, 99%, or 99.5% identity with SEQ ID NO: 9. The variant of SEQ ID NO: 9 may substantially retain the cleavage function of SEQ ID NO: 9.

F2A is advantageously short (only 28 amino acids), which helps to provide appropriate inserts and express more than one protein from vectors that can have a size limit, such as Adenovirus based vectors, including ChAdOx1/2.

In an embodiment where the viral vector is MVA, or otherwise a viral vector is used as a boost vaccination following a prime vaccination, a different cleavage domain may be provided to avoid any potential boosting of T-cell responses to the cleavage domain of the prime vaccination. Alternatively a secondary promoter may be used instead of a cleavage domain in order to avoid any potential boosting of T-cell responses to a cleavage domain of a prime vaccination.

IRES (Internal Ribosomal Entry Site)

In one embodiment, the immunogen expression cassette encodes an Internal Ribosome Entry Site (IRES). The skilled person will recognise that an IRES is an RNA structures that allows cap independent initiation of translation, and is able to initiate translation in the middle of a messenger RNA.

Splicing Signal

In one embodiment, the immunogen expression cassette encodes an mRNA splicing signal. The skilled person will be familiar with commonly used splicing signals that are appropriate for this use. One such example of an mRNA splicing signal that may be used is a chimeric intron composed of the 5' donor site from the first intron of the human β-globin gene and the branch and 3' acceptor site from the intron of an immunoglobulin gene heavy chain variable region in the expression vector pCI-neo Mammalian Expression Vector (Promega).

HBV Pre-Core (PreC)

The HBV PreC may comprise or consist of a full length wild-type HBV PreC sequence, or a variant thereof. The HBV PreC variant may comprise or consist of a truncated HBV PreC sequence.

The HBV PreC may comprise or consist of the sequence of SEQ ID NO: 16 or a variant thereof. A variant of SEQ ID NO: 16 may comprise a sequence having at least 70%, 75%, 80%, 85%, 90%, 95%, 98%, 99%, or 99.5% identity with SEQ ID NO: 16. The variant of SEQ ID NO: 16 may substantially retain the immunogenicity of SEQ ID NO: 16. The variant of SEQ ID NO: 16 may substantially retain the tertiary structure of SEQ ID NO: 16.

HBV Core

The HBV Core may comprise or consist of a full length wild-type HBV Core sequence, or a variant thereof. The HBV Core variant may comprise or consist of a truncated HBV Core sequence. The HBV Core may not comprise HBV Pre-Core.

The HBV Core may comprise or consist of the sequence of SEQ ID NO: 6 or a variant thereof. A variant of SEQ ID NO: 6 may comprise a sequence having at least 70%, 75%, 80%, 85%, 90%, 95%, 98%, 99%, or 99.5% identity with SEQ ID NO: 6. The variant of SEQ ID NO: 6 may substantially retain the immunogenicity of SEQ ID NO: 6. The variant of SEQ ID NO: 6 may substantially retain the tertiary structure of SEQ ID NO: 6.

HBV e-Antigen (HBeAg)

The HBV e-Antigen (HBeAg) may comprise or consist of a full length wild-type HBV e-Antigen sequence, or a variant thereof. The HBV e-Antigen variant may comprise or consist of a truncated HBV e-Antigen sequence.

The HBV e-Antigen (HBeAg) may comprise or consist of the sequence:

```
                                          (SEQ ID NO: 17)
SKLCLGWLWGMDIDPYKEFGASVELLSFLPSDFFPSIRDLLDTASALYRE

ALESPEHCSPHHTALRQAILCWGELMNLATWVGSNLEDPASRELVVSYVN

VNMGLKIRQLLWFHISCLTFGRETVLEYLVSFGVWIRTPPAYRPPNAPIL

STLPETTVV.
```

The HBV e-Antigen (HBeAg) may comprise or consist of the sequence of SEQ ID NO: 17 or a variant thereof. A variant of SEQ ID NO: 17 may comprise a sequence having at least 70%, 75%, 80%, 85%, 90%, 95%, 98%, 99%, or 99.5% identity with SEQ ID NO: 17. The variant of SEQ ID NO: 17 may substantially retain the immunogenicity of SEQ ID NO: 17. The variant of SEQ ID NO: 17 may substantially retain the tertiary structure of SEQ ID NO: 17.

Modified HBV Polymerase

The modified HBV polymerase ($P_{mut}$) may comprise or consist of a truncated HBV polymerase. In particular, the mutation to wild-type HBV polymerase to substantially remove polymerase function may comprise a sequence encoding a truncated HBV polymerase. Alternatively or additionally, the mutation comprises one or more point mutations to the encoded HBV polymerase sequence. The modification may comprise one or more amino acid substitutions, deletions or additions in the encoded HBV polymerase sequence. In one embodiment, the modified HBV polymerase ($P_{mut}$) is not a truncated form of HBV polymerase (i.e. it is full length relative to wildtype HBV polymerase).

The modified HBV polymerase ($P_{mut}$) may comprise or consist of the sequence of SEQ ID NO: 8 or a variant thereof. A variant of SEQ ID NO: 8 may comprise a sequence having at least 70%, 75%, 80%, 85%, 90%, 95%, 98%, 99%, or 99.5% identity with SEQ ID NO: 8. The variant of SEQ ID NO: 8 may substantially retain the immunogenicity of SEQ ID NO: 8. The variant of SEQ ID NO: 8 may substantially retain the tertiary structure of SEQ ID NO: 8.

The modification may be a mutation that prevents protein priming. Additionally or alternatively mutations may be provided in the reverse transcriptase and/or RNAase domains to prevent their function. Further additionally or alternatively the mutation may be structural such that is disrupts the correct protein folding of the polymerase. The modifications may comprise one or more, or all of Y63, C323, C334, C338, C352, R714, D788, R792, or equivalent residues thereof, by reference to wild-type HBV polymerase consensus sequence herein (i.e. SEQ ID NO: 19). In one embodiment the modifications may comprise one or more, or all of Y63A, C323A, C334A, C338A, C352A, R714A, D788A, R792A, or equivalent residues thereof, by reference to wild-type HBV polymerase consensus sequence herein (i.e. SEQ ID NO: 19). In another embodiment, the modifications may comprise one or more, or all of R714, D788, and R792, or equivalent residues thereof, by reference to wild-type HBV polymerase consensus sequence herein (i.e. SEQ ID NO: 19). In one embodiment the modifications may comprise one or more, or all of R714A, D788A, and R792A, or equivalent residues thereof, by reference to wild-type HBV polymerase consensus sequence herein (i.e. SEQ ID NO: 19). Reference to equivalent residues is understood to mean that the HBV polymerase may be based on an alternative sequence than the HBV polymerase sequence provided herein, and that numbering or identity of amino acid residues may differ between the sequences. Such differences and equivalency may be readily determined by an alignment of the HBV polymerase sequence with the wild-type HBV polymerase consensus sequence herein (i.e. SEQ ID NO: 19).

Mutations R714A, D788A, R792A advantageously stop polymerase function. However, one or more, or all of, additional mutations of Y63 and other cysteine mutations of C323, C334, C338, and C352 may be added as an extra measure in the event of a reversion within those functional mutations. The additional mutations may comprise Y63A, C323A, C334A, C338A, and/or C352A.

The mutations advantageously provide that the HBV polymerase function is disrupted by (a) RNAase H functional mutations, to stop its enzyme activity, and/or (b) Y63A mutation to stop the first step of replication (Priming of DNA synthesis), and/or (c) cysteine mutations to disrupt its native conformation and stop the HBV polymerase from participating in the initial steps of viral replication (protein priming, RNA binding and RNA packaging).

The skilled person will be familiar with various HBV polymerase modifications that can be provided which significantly reduce or ablate function, and can be provided in the modified polymerase according to the invention. Such modifications are for example described in WO2016020538, WO2013007772, and WO2011015656, which are incorporated herein by reference.

In one embodiment, the modified polymerase is modified so as to exhibit a reduced reverse-transcriptase (RTase) enzymatic activity with respect to a wild-type HBV polymerase. The reduction of RTase activity may be provided by one or more mutation(s) in the domain responsible for RTase enzymatic activity. Four residues have been found to be involved in RTase activity, forming a motif "YMDD" (for Tyr, Met, Asp and Asp residues) at approximately position 538 to approximately position 541 of a wild-type HBV polymerase. The present invention encompasses any mutation(s) in this motif, or elsewhere in the RTase domain, that provides a significant reduction (e.g. at least a 10 fold reduction) or ablation of the RTase activity. Representative examples of suitable RTase-deficient polymerase mutants are described in Radziwill et al. (1990, J. Virol. 64:613), in Bartenschlager et al. (1990, J. Virol. 64:5324) and in Jeong et al. (1996, Biochem Bioph Res Commun. 223(2):264), which are incorporated herein by reference. In one embodiment, the modified polymerase may comprise the substitution of the first Asp residue of the YMDD motif or of the amino acid residue located in an equivalent position in a native HBV polymerase to any amino acid residue other than Asp, with an optional substitution to a His residue (D540H mutation).

Additionally or alternatively, the modified polymerase may be modified to provide a reduced RNase H enzymatic activity with respect to wild-type HBV polymerase. The reduction of RNase H activity may be provided by one or more mutation(s) in the domain responsible for RNase H enzymatic activity. The functional domain involved in RNase H activity is within the C-terminal portion of HBV polymerase, approximately from position 680 to the C-terminal position 832 of wild-type polymerase, and the modified polymerase of the present invention may encompasses any mutation(s) in this domain that provides a significant reduction (e.g. at least a 10 fold reduction) or ablation of the RNase H activity. Representative examples of suitable RNase H-deftcient polymerase mutants are described in Radziwill et ai. (1990, J. Virol. 64:613), in Bartenschlager at al. (1990, J. Virol. 64:5324).

HBV Surface Antigen (HbsAg)

The skilled person will understand that PreS1 and PreS2 are components of the Large (L) form of RBA/surface protein (e.g. L form=PreS1+PreS2+S). The medium (M) form of HBV surface protein has PreS2-'S. Having such sequences together means that T-Cell epitopes are included in those sequential order.

The HbsAg may comprise or consist of a full length wild-type HbsAg sequence, or a variant thereof. The HbsAg variant may comprise or consist of a truncated HbsAg sequence.

The HbsAg including the PreS1 and PreS2 sequences may comprise or consist of the sequence of SEQ ID NO: 10 or a variant thereof. A variant of SEQ ID NO: 10 may comprise a sequence having at least 70%, 75%, 80%, 85%, 90%, 95%, 98%, 99%, or 99.5% identity with SEQ ID NO: 10. The variant of SEQ ID NO: 10 may substantially retain the immunogenicity of SEQ ID NO: 10. The variant of SEQ ID NO: 10 may substantially retain the tertiary structure of SEQ ID NO: 10.

In another embodiment, the HbsAg may comprise the surface antigen without PreS1 and/or PreS2. The HbsAg may comprise or consist of the sequence of SEQ ID NO: 18 or a variant thereof. A variant of SEQ ID NO: 18 may comprise a sequence having at least 70%, 75%, 80%, 85%, 90%, 95%, 98%, 99%, or 99.5% identity with SEQ ID NO: 18. The variant of SEQ ID NO: 18 may substantially retain the immunogenicity of SEQ ID NO: 18. The variant of SEQ ID NO: 18 may substantially retain the tertiary structure of SEQ ID NO: 18.

In one embodiment, the HbsAg may comprise or consist of any one or all of the four known transmembrane regions in HbsAg (amino acids 1-226), which are amino acids (8-32) FLGPLLVLQAGFFLLTRILTIPQSL (SEQ ID NO: 54), amino acids (80-98) FIIFLFILLLCLIFLLVLL (SEQ ID NO: 55), amino acids (160-184) RFLWEWASVRFSWLSLLVPFVQWFV (SEQ ID NO: 56), and amino acids (189-210) TVWLSVIWMMWYWGPSLYNILS (SEQ ID NO: 57) respectively. In one embodiment, the HbsAg may at least comprise or consist of the HbsAg transmembrane region of amino acids (8-32) FLGPLLVLQAGFFLLTRILTIPQSL (SEQ ID NO: 54).

HBV PreS1

The HBV PreS1 may comprise or consist of a full length wild-type HBV PreS1 sequence, or a variant thereof. The HBV PreS1 may comprise or consist of the sequence of SEQ ID NO: 52 or a variant thereof. A variant of SEQ ID NO: 52 may comprise a sequence having at least 70%, 75%, 80%, 85%, 90%, 95%, 98%, 99%, or 99.5% identity with SEQ ID NO: 52. The variant of SEQ ID NO: 52 may substantially retain the immunogenicity of SEQ ID NO: 52. The variant of SEQ ID NO: 52 may substantially retain the tertiary structure of SEQ ID NO: 52.

The HBV PreS1 variant may comprise or consist of a truncated HBV PreS1 sequence, for example CΔPreS1 or NΔPreS1 described herein (CΔPreS1 refers to C-terminal truncated PreS1 and NΔPreS1 refers to N-terminal truncated PreS1). In one embodiment, the immunogen expression cassette may encode both NΔPreS1 and CΔPreS1. In an embodiment wherein the immunogen expression cassette encodes both NΔPreS1 and CΔPreS1, the NΔPreS1 may be encoded upstream (5') of intergenic sequence and the CΔPreS1 may be encoded downstream (3') of intergenic sequence. In an embodiment wherein the immunogen expression cassette encodes NΔPreS1 upstream (5') of intergenic sequence, it may be fused with PreS2 and/or the modified polymerase ($P_{mut}$). In an embodiment wherein the immunogen expression cassette encodes NΔPreS1 upstream (5') of intergenic sequence, it may be fused with PreS2 and/or the modified polymerase ($P_{mut}$) and the CΔPreS1 encoded downstream (3') of intergenic sequence may be fused with the surface antigen (HbsAg).

CΔPreS1

In one embodiment, the immunogen expression cassette encodes a truncated form of HBV PreS1. The truncation may comprise a C-terminal truncation. In one embodiment, the truncated HBV PreS1 comprises CΔPreS1 (SEQ ID NO: 21) described herein. In one embodiment, the truncated PreS1, such as CΔPreS1 described herein, is arranged to be expressed a fusion protein with the HBV surface antigen (S/HbsAg). A linker sequence, such as a linker described herein, may be provided between the truncated PreS1 and surface antigen (S/HbsAg). For example, CΔPreS1+linker+S (described herein as S(sh)). The nucleotide sequence encoding S(sh) may comprise or consist of SEQ ID NO: 61 or SEQ ID NO: 38.

The CΔPreS1 may comprise or consist of the sequence of SEQ ID NO: 21 or a variant thereof. A variant of SEQ ID NO: 21 may comprise a sequence having at least 70%, 75%, 80%, 85%, 90%, 95%, 98%, 99%, or 99.5% identity with SEQ ID NO: 21. The variant of SEQ ID NO: 21 may substantially retain the immunogenicity of SEQ ID NO: 21. The variant of SEQ ID NO: 21 may substantially retain the tertiary structure of SEQ ID NO: 21.

In one embodiment, the truncated PreS1, such as CΔPreS1 described herein, optionally with a fused surface antigen, is encoded downstream (3') of the intergenic sequence.

The PreS1 truncation advantageously favours antibody generation for both T-cell and antibody response for the HEW antigens provided in the immunogen expression cassette. Without being bound by theory, antibody generation is possibly due to proper folding of PreS1 and Surface antigens.

NΔPreS1

In one embodiment, the truncated PreS1 comprises NΔPreS1 as described herein. The NΔPreS1 and PreS2 fusion may comprise or consist of SEQ ID NO: 15, or a variant thereof. A variant of SEQ ID NO: 15 may comprise a sequence having at least 70%, 75%, 80%, 85%, 90%, 95%, 98%, 99%, or 99.5% identity with SEQ ID NO: 15. The variant of SEQ ID NO: 15 may substantially retain the immunogenicity of SEQ ID NO: 15.

In one embodiment, the truncated PreS1 comprises NΔPreS1 as described herein. The NΔPreS1 and PreS2 fusion may be encoded by nucleic acid comprising or consisting of SEQ ID NO: 38 or 61, or a variant thereof. A variant of SEQ ID NO: 38 or 61 may comprise a sequence having at least 70%, 75%, 80%, 85%, 90%, 95%, 98%, 99%, or 99.5% identity with SEQ ID NO: 38 or 61. The encoded variant of SEQ ID NO: 38 or 61 may substantially retain the immunogenicity of peptide encoded by SEQ ID NO: 38 or 61.

The NΔPreS1 and PreS2 fusion sequence advantageously provides a good T-cell response. NΔPreS1 advantageously includes amino acids in a sequence that would still preserve T-cell epitopes (8-11 amino acids for CD8 T-cell epitopes and slightly longer (12-16) for CD4 T-cell epitopes.

In an embodiment wherein the immunogen expression cassette encodes NΔPreS1 fused with PreS2 upstream (5') of intergenic sequence, it may be further fused with the modified polymerase ($P_{mut}$). A linker sequence, such as a linker described herein, may be provided between the PreS2 and modified polymerase ($P_{mut}$). For example, NΔPreS1+PreS2+linker+Pmut.

HBV PreS2

The HBV PreS2 may comprise or consist of a full length wild-type HBV PreS2 sequence, or a variant thereof. The HBV PreS2 variant may comprise or consist of a truncated HBV PreS2 sequence.

The HBV PreS2 may comprise or consist of the sequence of SEQ ID NO: 53 or a variant thereof. A variant of SEQ ID NO: 53 may comprise a sequence having at least 70%, 75%, 80%, 85%, 90%, 95%, 98%, 99%, or 99.5% identity with SEQ ID NO: 53. The variant of SEQ ID NO: 53 may substantially retain the immunogenicity of SEQ ID NO: 53. The variant of SEQ ID NO: 53 may substantially retain the tertiary structure of SEQ ID NO: 53.

Peptide Adjuvant

The immunogen expression cassette may further encode a peptide adjuvant. The peptide adjuvant may comprise TPA (tissue plasminogen activator). In one embodiment, the peptide adjuvant may comprise a human or non-human invariant chain (Ii), or a fragment thereof. A fragment of the long isoform (isoform (b)) of the human CD74 molecule, is also known as the invariant chain (Nucleic Acids Res. 1985 Dec. 20; 13(24): 8827-8841). It is known that N-terminal fragments of the invariant chain (1i) which comprise at least the transmembrane domain thereof, provide a surprisingly effective adjuvant function when expressed as a fusion protein with an antigen of interest. Fragments encompassing the transmembrane domain and the cytoplasmic domain, and preferably including the N-terminal 16 amino acids of the long isoform of the protein are particularly efficacious.

The invariant chain may comprise or consist of a shark invariant chain (SIi), or fragment or a functional variant thereof. The variant shark invariant chain (SIi) may comprise a truncated invariant shark invariant chain. Other non-human animal sources of an invariant chain, or fragment thereof, include chicken, quail, trout, zebrafish, carp, frog, grouper, shark, mandarin fish or mallard. The skilled person will be familiar with appropriate invariant chains, or fragments thereof, for use as peptide adjuvants encoded in an expression cassette/vector, for example the invariant chain may be any invariant chain as provided in WO2015082922, which is incorporated herein by reference.

The peptide adjuvant may comprise or consist of the sequence of SEQ ID NO: 4 (SIi) or a variant thereof. A variant of SEQ ID NO: 4 may comprise a sequence having at least 70%, 75%, 80%, 85%, 90%, 95%, 98%, 99%, or 99.5% identity with SEQ ID NO: 4. The variant of SEQ ID NO: 4 may substantially retain the adjuvant function of SEQ ID NO: 4.

The peptide adjuvant may be encoded by a sequence comprising or consists of the sequence of SEQ ID NO: 29 (TPA nucleic acid sequence) or a variant thereof. A variant of SEQ ID NO: 29 may comprise a sequence having at least 70%, 75%, 80%, 85%, 90%, 95%, 98%, 99%, or 99.5% identity with SEQ ID NO: 29. The variant of SEQ ID NO: 29 may encode a peptide adjuvant that substantially retains the adjuvant function of the TPA encoded by SEQ ID NO: 29. The peptide adjuvant may be encoded by a sequence comprising or consists of the sequence of SEQ ID NO: 60 (TPA nucleic acid sequence) or a variant thereof. A variant of SEQ ID NO: 60 may comprise a sequence having at least 70%, 75%, 80%, 85%, 90%, 95%, 98%, 99%, or 99.5% identity with SEQ ID NO: 60. The variant of SEQ ID NO: 60 may encode a peptide adjuvant that substantially retains the adjuvant function of the TPA encoded by SEQ ID NO: 60.

The peptide adjuvant may comprise or consist of the sequence of SEQ ID NO: 30 (TPA) or a variant thereof. A variant of SEQ ID NO: 30 may comprise a sequence having at least 70%, 75%, 80%, 85%, 90%, 95%, 98%, 99%, or 99.5% identity with SEQ ID NO: 30. The variant of SEQ ID NO: 30 may substantially retain the adjuvant function of SEQ ID NO: 30.

The peptide adjuvant may be encoded at an N-terminal position of a protein/antigen to be expressed from the immunogen expression cassette. A first peptide adjuvant may be encoded at an N-terminal position of a first protein/antigen (such as the Core and Polymerase fusion) to be expressed from the immunogen expression cassette, and a second peptide adjuvant may be encoded at an N-terminal position of a second protein/antigen (such as surface antigen) to be expressed from the immunogen expression cassette.

HBV Genotype

The HBV may be HBV genotype C. In another embodiment, the HBV may be of any one of the 10 genotypes (A-J). All of the encoded HBV proteins/antigens may be derived from one genotype, for example HBV genotype C.

Linkers

In one embodiment, linker residues may be encoded between one or more, or all, of the protein/antigen sequences that are provided in a fusion protein (e.g. providing junctions between the sequences in the protein). In an embodiment comprising a peptide adjuvant, a linker may be encoded between the peptide adjuvant and the downstream encoded protein/antigen. In one embodiment, a linker is encoded between the sequences of the HBV core and modified HBV polymerase.

The linker residues may comprise random amino acid sequences, or amino-acids that have been selected to be non-immunogenic based on epitope prediction computer programs or experiments in animal models. For example, a linker may not be considered if it is predicted or known to be an epitope (i.e. in order to avoid an immune response to epitopes, e.g. artificial epitopes, not found in HBV. The linker may be flexible. The linker may comprise or consist of K, G, P or S amino acid residues, or combinations thereof. In one embodiment, the linker may comprise or consist of G and/or P amino acid residues. The linker residues may be between 1 and 10 amino acids in length. In another embodiment, the linker residues may be between 2 and 8 residues in length. In another embodiment, the linker residues may be between 1 and 6 residues in length.

A linker may comprise or consist of any of the sequences KGGGPGGG (SEQ ID NO: 5), GGGSGGG (SEQ ID NO: 7), KGGS (SEQ ID NO: 14), KSP, GSKGK (SEQ ID NO: 20), LEGGSGG (SEQ ID NO: 22), SKSGPPSGKS (SEQ ID NO: 31), GSKSGSK (SEQ ID NO: 32), SKSPGSGPP (SEQ ID NO: 33), or ASKGGKSG (SEQ ID NO: 34).

In one embodiment, a linker may comprise the sequence KGGGPGGG (SEQ ID NO: 5). In another embodiment, a linker may comprise the sequence GGGSGGG (SEQ ID NO: 7). In another embodiment, a linker may comprise the sequence KGGS (SEQ ID NO: 14). In another embodiment, a linker may comprise the sequence KSP. In another embodiment, a linker may comprise the sequence GSKGK (SEQ ID NO: 20). In another embodiment, a linker may comprise the sequence LEGGSGG (SEQ ID NO: 22). In another embodiment, a linker may comprise the sequence SKSGPPSGKS (SEQ ID NO: 31). In another embodiment, a linker may comprise the sequence GSKSGSK (SEQ ID NO: 32). In another embodiment, a linker may comprise the sequence SKSPGSGPP (SEQ ID NO: 33). In another embodiment, a linker may comprise the sequence ASKGGKSG (SEQ ID NO: 34).

Advantageously, the use of linkers can avoid generation of peptides with homology to human proteome (which could potentially generate immune response to self-antigen) and they avoid immune-dominant artificial epitopes. Additionally, linkers can provide a flexible hinge between segments of protein, so that they can fold into their native conformation. For example, a linker between CΔPreS1 and S allows independent folding of CΔPreS1 and S, so that they could generate antibodies for conformational epitopes for the respective proteins.

Linkers may be varied between different immunogen expression cassettes. Using different linkers avoids boosting of any T-cell response created to any potential artificial epitopes (i.e. by changing linkers or changing junctions). For example, when vaccines are used in prime boost vaccination strategies, changing the linkers or the order of proteins within the immunogen layout, helps to overcome boosting of artificial epitope response.

Other Elements of the Immunogen Expression Cassette(s)

In an embodiment wherein the immunogen expression cassette is for use in an MVA vector, the immunogen expression cassette may further comprise F11 left and right flanking sequences to allow insertion into the MVA F11 locus by homologous recombination.

The F11-left flank sequence may comprise or consist of the sequence of SEQ ID NO: 35, or a variant thereof. The F11-right flank sequence may comprise or consist of the sequence of SEQ ID NO: 36, or a variant thereof. A variant of SEQ ID NO: 35 or 36 may comprise a sequence having at least 70%, 75%, 80%, 85%, 90%, 95%, 98%, 99%, or 99.5% identity with SEQ ID NO: 35 or 36 respectively. The variant of SEQ ID NO: 35 or 36 may substantially retain the homologous recombination function of SEQ ID NO: 35 or 36 respectively. The skilled person will appreciate that 1, 2, 3, 4, 5 or more amino acid residues may be substituted, added or removed without affecting function. For example, conservative substitutions may be considered.

The immunogen expression cassette may further comprise a transcription terminator sequence. The transcription terminator sequence may be provided in embodiments of the immunogen expression cassette comprising a secondary promoter. For example, the transcription terminator sequence may be provided downstream of a protein expressed by the primary promoter, but before (upstream of) the secondary promoter. The transcription terminator sequence may comprise or consist of the sequence TTTTTGT, or variants thereof.

In one embodiment, the immunogen expression cassette described herein may be isolated or provided in a non-viral vector.

Therefore, according to another aspect of the present invention there is provided a nucleic acid comprising the immunogen expression cassette described herein, optionally wherein the nucleic acid is isolated nucleic acid.

According to another aspect of the invention there is provided a composition comprising the viral vector according to the invention, optionally wherein the composition is a pharmaceutically acceptable composition.

The composition may be immunogenic, for example in a mammal, such as a human. The composition may comprise a pharmaceutically acceptable carrier. The composition may be a pharmaceutical composition comprising a pharmaceutically acceptable carrier. The composition may be for use in the prophylaxis or treatment of HBV infection.

According to another aspect of the invention there is provided a method of treatment or prophylaxis of HBV infection comprising the administration of the viral vector, nucleic acid or composition according to the invention.

The method of treatment or prophylaxis of HBV infection may be a method of vaccination.

According to another aspect of the invention there is provided a viral vector, nucleic acid or composition according to the invention for use in the treatment or prevention of HBV infection, optionally wherein the use is in a vaccine.

According to another aspect of the invention there is provided a vaccine comprising the viral vector, nucleic acid or composition according to the invention.

The vaccine may be a prime vaccine. The vaccine may be a boost vaccine. Where a boost vaccine is provided following a prime vaccine, the viral vector may be a different viral vector according to the invention.

Advantageously, the provision of a different viral vector between prime and boost vaccines can avoid the provision of "false" epitopes formed across junctions of one protein/antigen sequence with another. i.e. the same junction may not occur in a re-ordered protein.

According to another aspect of the invention, there is provided a prime boost vaccination kit comprising a prime vaccination according to the invention;

a boost vaccination according to the invention.

The prime and boost vaccination may comprise different viral vectors.

The viral vector may be used in a vaccine in combination with another therapeutically or prophylactically active ingredient. The viral vector may be used in a vaccine in combination with an adjuvant.

The viral vector, nucleic acid encoding the viral vector may be provided in a pharmaceutically acceptable carrier.

The viral vector or composition according to the invention may not comprise wild-type HBV, or the nucleic acid according to the invention may not encode wild-type HBV.

Reference to sequence "identity" used herein may refer to the percentage identity between two aligned sequences using standard NCBI BLASTp parameters.

The term "immunogenic", when applied to the viral vector, nucleic acid or composition of the present invention means capable of eliciting an immune response in a human or animal body. The immune response may be protective of HBV. The term "protective" means prevention of Hepatitis B disease, a reduced risk of Hepatitis B disease, reduced risk of HBV infection, transmission and/or progression, reduced severity of Hepatitis B disease, a cure of Hepatitis B, an alleviation of symptoms of Hepatitis B, or a reduction in severity of Hepatitis B disease symptoms.

The term "prophylaxis" means prevention of or protective treatment for Hepatitis B. The prophylaxis may include a reduced risk of HBV infection, transmission and/or Hepatitis B disease progression, or reduced severity of Hepatitis B disease.

The term "treatment", means a cure of Hepatitis B, an alleviation of symptoms, or a reduction in severity of Hepatitis B disease or Hepatitis B disease symptoms.

With reference to "variant" nucleic acid sequences, the skilled person will appreciate that 1, 2, 3, 4, 5 or more codons may be substituted, added or removed without affecting function. For example, conservative substitutions may be considered.

With reference to "variant" amino acid sequences, the skilled person will appreciate that 1, 2, 3, 4, 5 or more amino acids may be substituted, added or removed without affecting function. For example, conservative substitutions may be considered.

The skilled person will understand that optional features of one embodiment or aspect of the invention may be applicable, where appropriate, to other embodiments or aspects of the invention.

BRIEF DESCRIPTION OF THE DRAWINGS

Embodiments of the invention will now be described in more detail, by way of example only, with reference to the accompanying drawings.

FIGS. 1A-1B: (A) Phylogenetic relationship of 1447 HBV genotype C sequences used to generate consensus sequence (B) Comparison of HBV genotype C consensus (SEQ ID NO: 1) and KP017269.1 HBV isolate JP-02 (SEQ ID NO: 2). 1447 HBV genotype C nucleotide sequences, downloaded from HBV data base were aligned using MAFFT (a multiple sequence alignment program), to generate the HBV genotype C consensus sequence and a phylogenetic tree and. Alignment of 3215 nucleotide sequences of the consensus and chosen patient's sequence (KP017269.1 HBV isolate JP-02) showed three nucleotide differences (at positions 52, 1053 and 2699), which are highlighted in grey colour. The sequence of the HBV genotype C consensus sequence generated from 1447 genotype c isolate jp-02 is provided below.

DETAILED DESCRIPTION

Figure 1A:
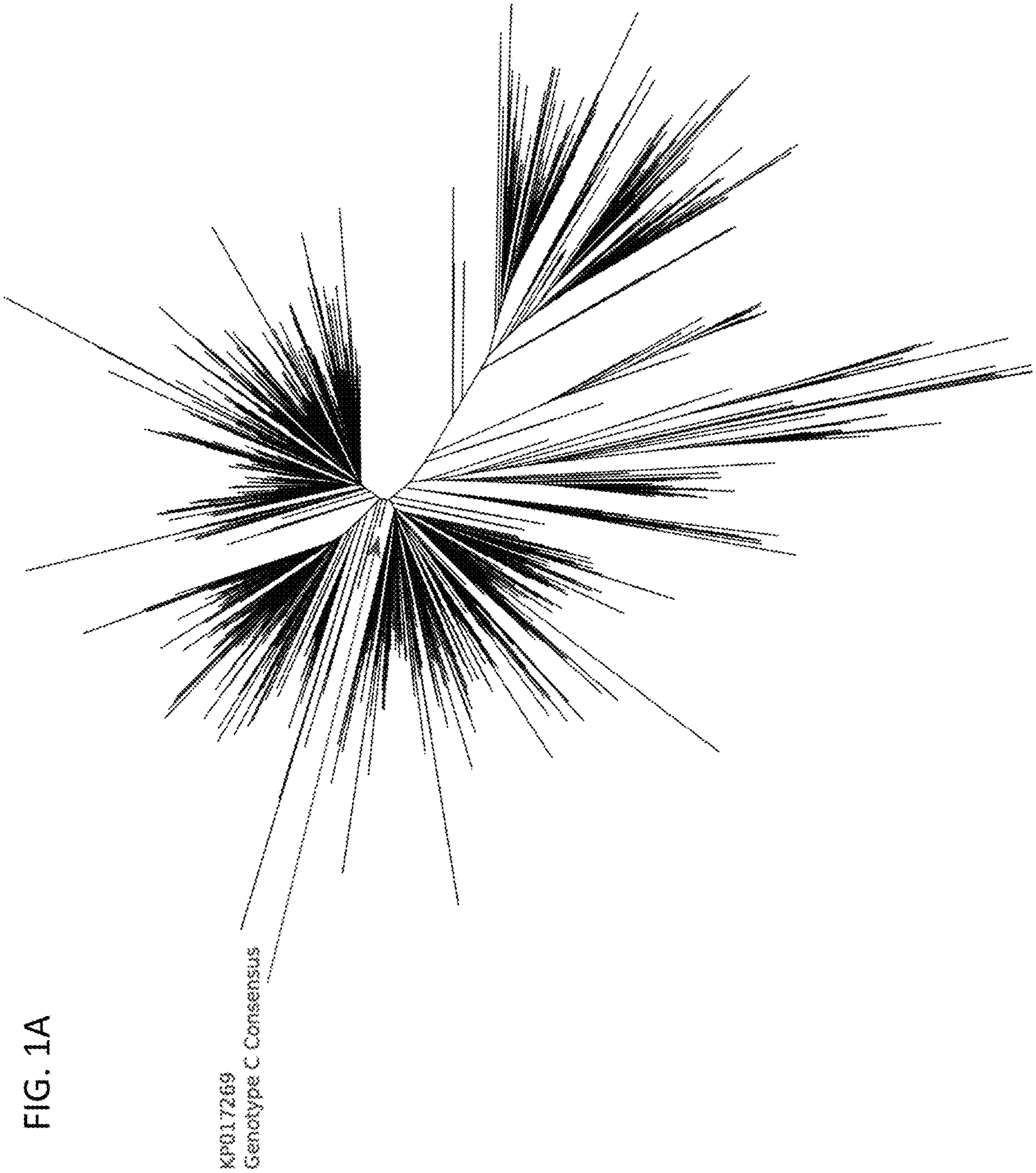

A HBV vaccine was generated based on the HBV genotype C, one of the commonest HBV genotypes in South East Asia that has more frequent association with chronic HBV infection. To design the HBV immunogen, a patient's HBV genotype C sequence (GeneBank: KP017269.1) was selected that was closest to the consensus, this was generated by aligning 1447 HBV-genotype-C sequences from HBVdb, a Hepatitis Virus B database (FIGS. 1A and 1B). The chosen HBV genotype C sequence had only three nucleotide changes compared to the consensus, of which two were silent mutations and one had a mutation in the polymerase protein (FIG. 1C).

Figure 2A:
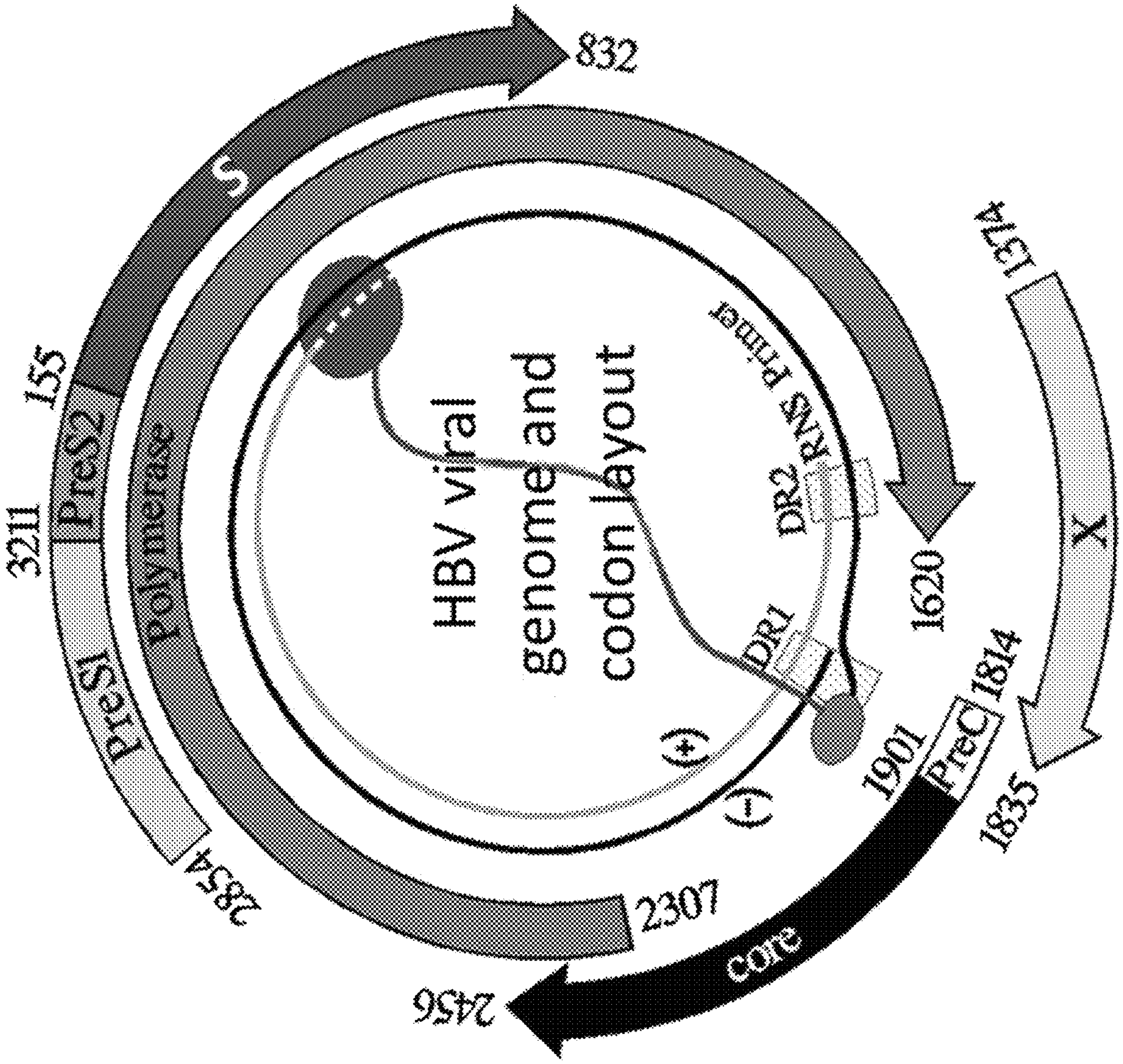
FIGS. 2A-2D: (A) HBV viral genome and codon layout. The HBV virion has a partial double stranded DNA (having a full length negative strand DNA and a partially synthesised positive strand DNA attached to the polymerase protein). The genome is approximately 3.2 Kb in length and has four major codons: core (including the precore region), polymerase, surface (including the preS1 and preS2 region) and X. (B) HBV Immunogen Layout. Two immunogens SIi-HBV-CPmutS and SIi-HBV-SCPmut were designed. Both immunogens encodes HBV codons (encompassing precore, core, polymerase [Pmut], preS1, preS2 and surface proteins) and non HBV codons (comprising of a truncated Shark Invariant chain [SIi], two linkers [represented in Turquoise blue colour] and a Furin 2A [F2A] peptide sequence). Within the mammalian expression cassette, the immunogen codon sequences are placed next to CMV promoter. (C) Invitro expression analysis. Plasmids encoding SIi-HBV-CPmutS and SIi-HBV-SCPmut were transfected into HEK293A cells. 24 hours post-transfection, cells were lysed and the lysates were analysed in Western blot experiments using mouse anti-HBV-PreS1 and mouse anti-HBV-Polymerase antibodies. Blots probed with mouse anti-GAPDH served as loading controls. (D) ChAdOX2-SIi-HBV-CPmutS. The mammalian expression cassette with SIi-HBV-CPmutS immunogen codons was inserted into the replication deficient ChAdOx2 vector. Recombinant ChAdOX2-SIi-HBV-CPmutS virus was generated by transfecting the ChAdOX2-SIi-HBV-CPmutS vector into T-REx™-293 cells (Thermo Fisher Scientific) using standard methods as previously described.
Figure 2B:
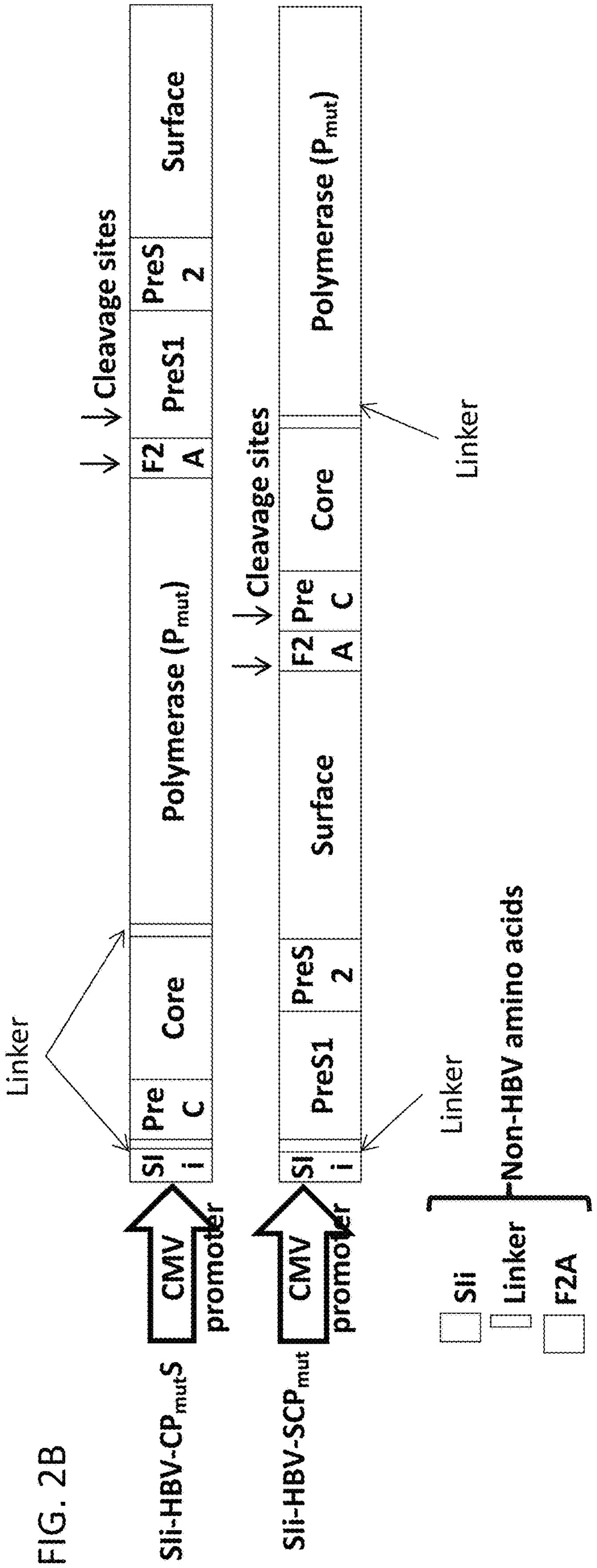

A strong and multi-antigen specific T cell response against different HBV proteins is believed to play a major role in viral clearance of a resolving HBV infection. Based on this HBV immunogens have been designed that encode all major proteins of the virus, namely the core (including the Pre-core region), a non-functional polymerase Pmut (Pmut: HBV polymerase with functional mutations, aiming to discourage the vaccine encoded polymerase's ability to participate in HBV viral replication) and the surface protein (including its PreS1 and PreS2 regions). FIGS. 2A and 2B shows the codon layout of HBV genome and a schematic representation of the first two HBV vaccine immunogen designs respectively. The layout has been designed to encode pre-core, core and Pmut as a fusion protein and a separate surface protein using a furin 2A (F2A) peptide cleavage mechanism, which by causing ribosomal skipping events, helps to encode two proteins from a single open reading frame.

Figure 2C:
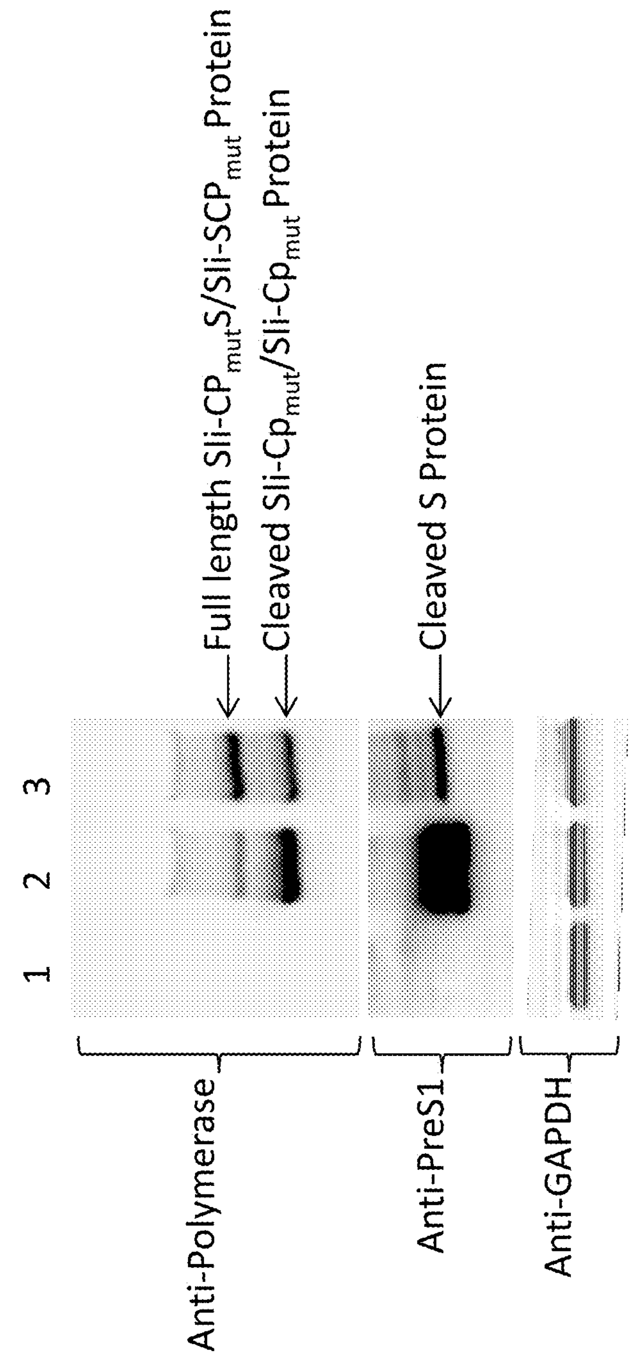

Encoding multiple proteins within a single transgene cassette requires careful design, where the proximity of codon sequence to CMV promoter plays an important role in the level of expression of the encoded proteins. To analyse this two immunogens (FIG. 2B), SIi-HBV-CPmutS and SIi-HBV-SCPmut, we generated which encodes the surface protein either at the end or the beginning of the immunogen cassette respectively and tested them in Western blot expression studies. Western blot expression analysis showed that layout SIi-HBV-CPmutS has the best F2A cleavage possibility, which generates large amounts of the expected CPmut and S proteins when compared to the SIi-HBV-SCPmut (FIG. 2*c*).

Figure 2D:
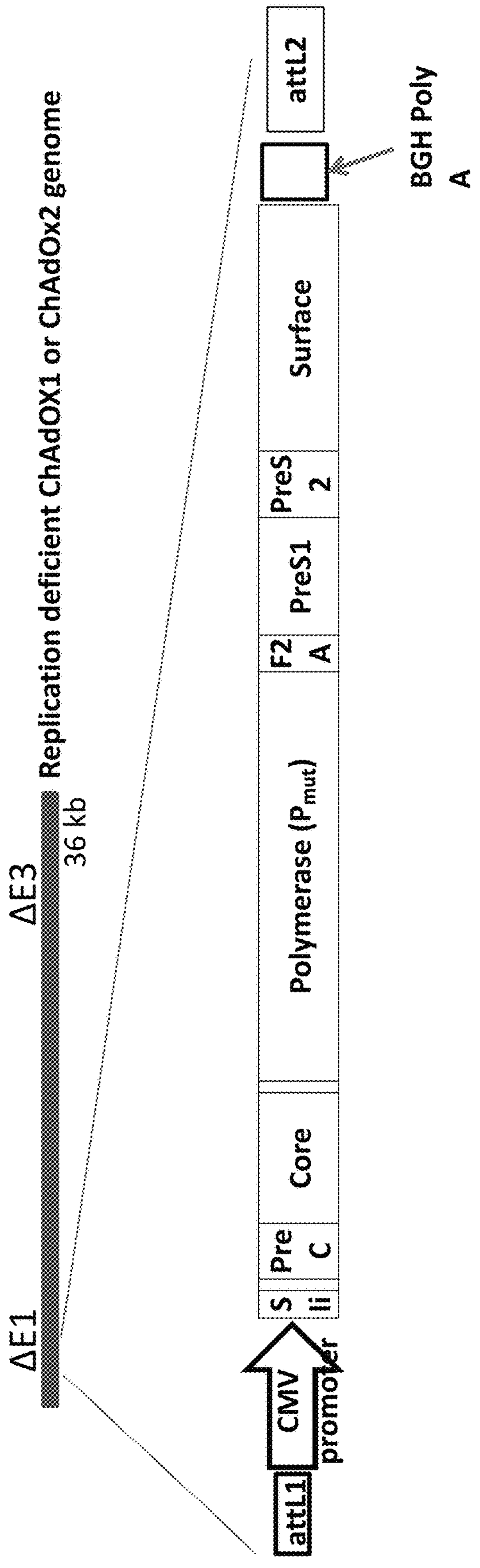
Figure 3A:
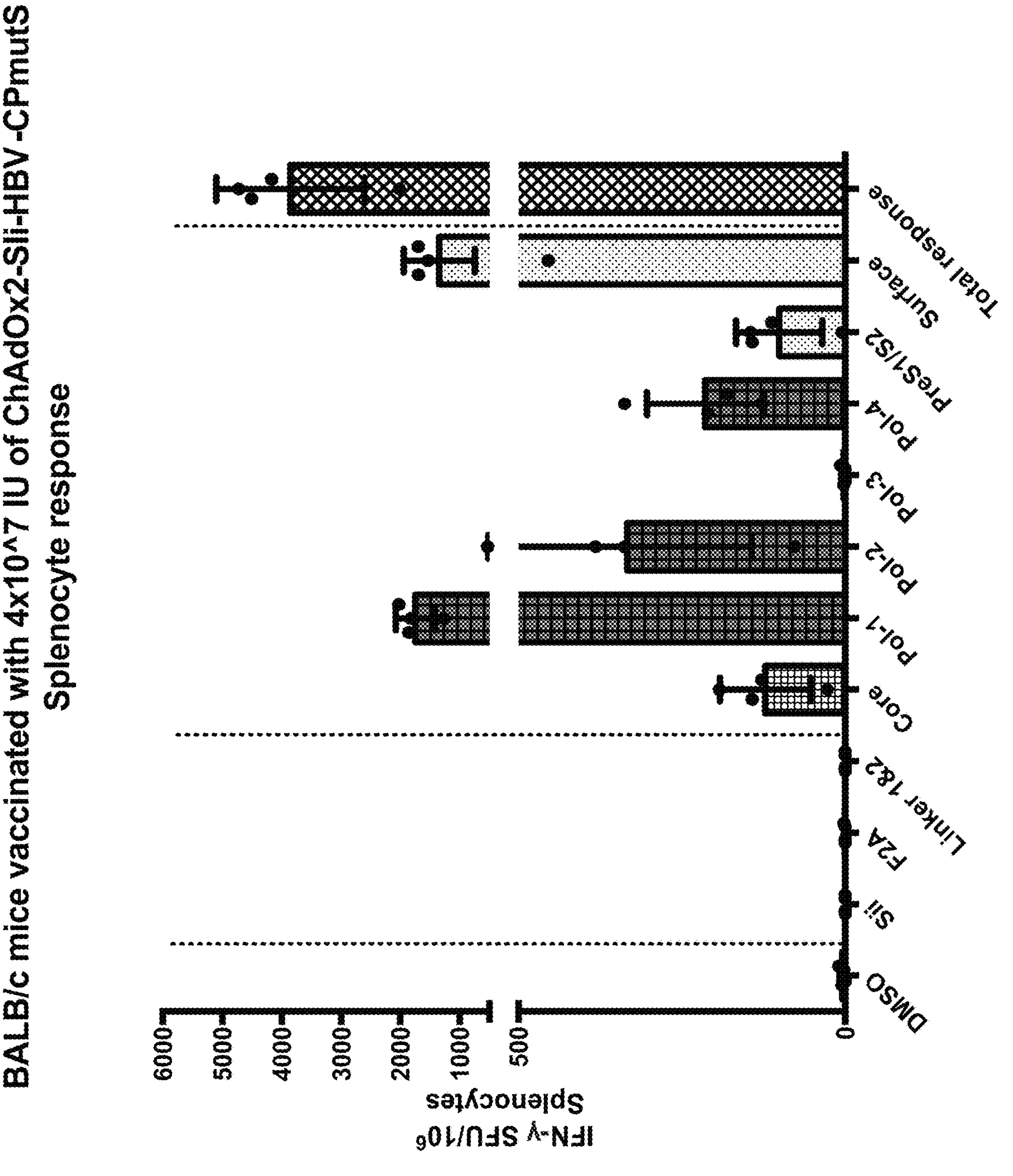
FIGS. 3A-3D: Testing ChAdOx2-SIi-HBV-CPmutS vaccine in naive mice models. (A) Splenocyte responses in BALB/c mice (B) Intra Hepatic Lymphocyte responses in BALB/c mice (C) Splenocyte responses in CD1 mice (D) Intra Hepatic Lymphocyte responses in CD1 mice. BALB/c mice (4 mice at the age of 7 weeks) and CD1 (2 mice at age of 18 weeks and 5 mice at age of 13 weeks) were vaccinated by intramuscular injections with $4\times10^7$ IU and $5\times10^7$ IU per mice respectively of ChAdOx2-SIi-HBV-CPmutS vaccine. 14 days post-vaccination, mice were sacrificed, splenocytes and intra hepatic lymphocytes (IHL) were isolated from spleen and liver according to standard protocol. $2\times10^5$ splenocytes and $1\times10^5$ IHL's were plated on to ELSIPOT plates (pre-coated with Anti-mouse INFγ monoclonal antibody, by overnight incubation) along with DMSO (1%) or non-HBV peptide pool (A, I, L at a concentration of 3 μg/ml) or HBV peptide pool (Core, Pol-1, Poi-2, Poi-3, Pol-4, PreS1/S2 and Surface at a concentration of 3 μg/ml) or a positive control mitogen (PHA or Concanavalin A at a concentration of 10 μg/ml and 12.5 μg/ml respectively). After an overnight 15 hours incubation at 37° C., the plates were washed 7× with PBS and incubated with Biotin conjugated mouse anti-INFγ for 2 hours at room temperature, followed by 4× wash with PBS and AP conjugated anti-biotin incubation for 2 hours at room temperature. The plates were then washed 4× with PBS and developed with BCIP/NBT substrate until spots appeared on the wells. After a final wash with water and drying the spot forming units (SFU) per million cells from individual wells were counted on a automated ELISpot plate reader. ELISPOT responses for each peptide pool stimulus with splenocytes and IHL's from BALB/c and CD1 mice are represented in separate charts. Total responses from HBV peptide stimulus were also calculated by combining ELISPOT responses to all HBV peptide pools (Core, Pol-1, Poi-2, Poi-3, Poi-4, PreS1/S2 and Surface).
Figure 3B:
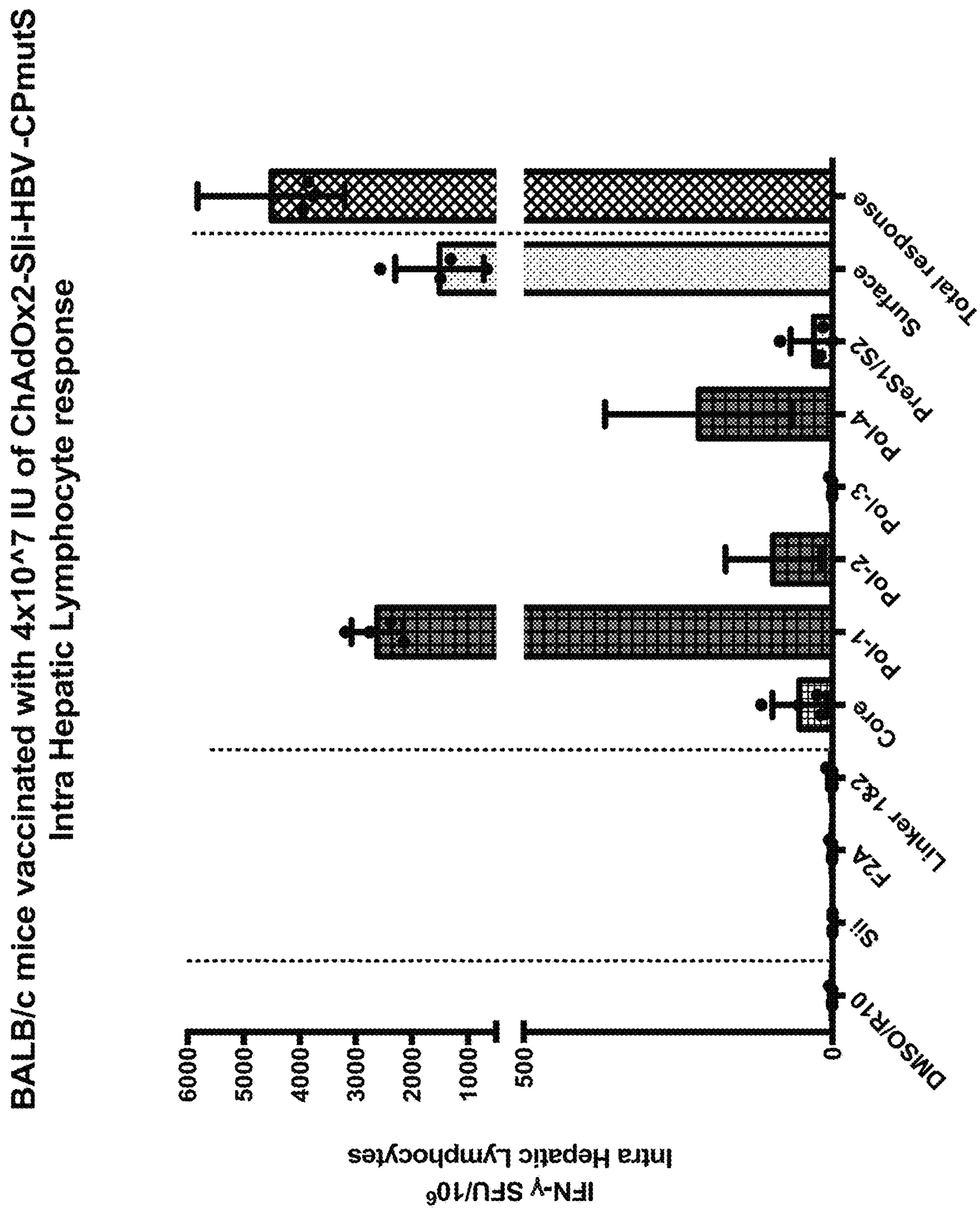
Figure 3C:
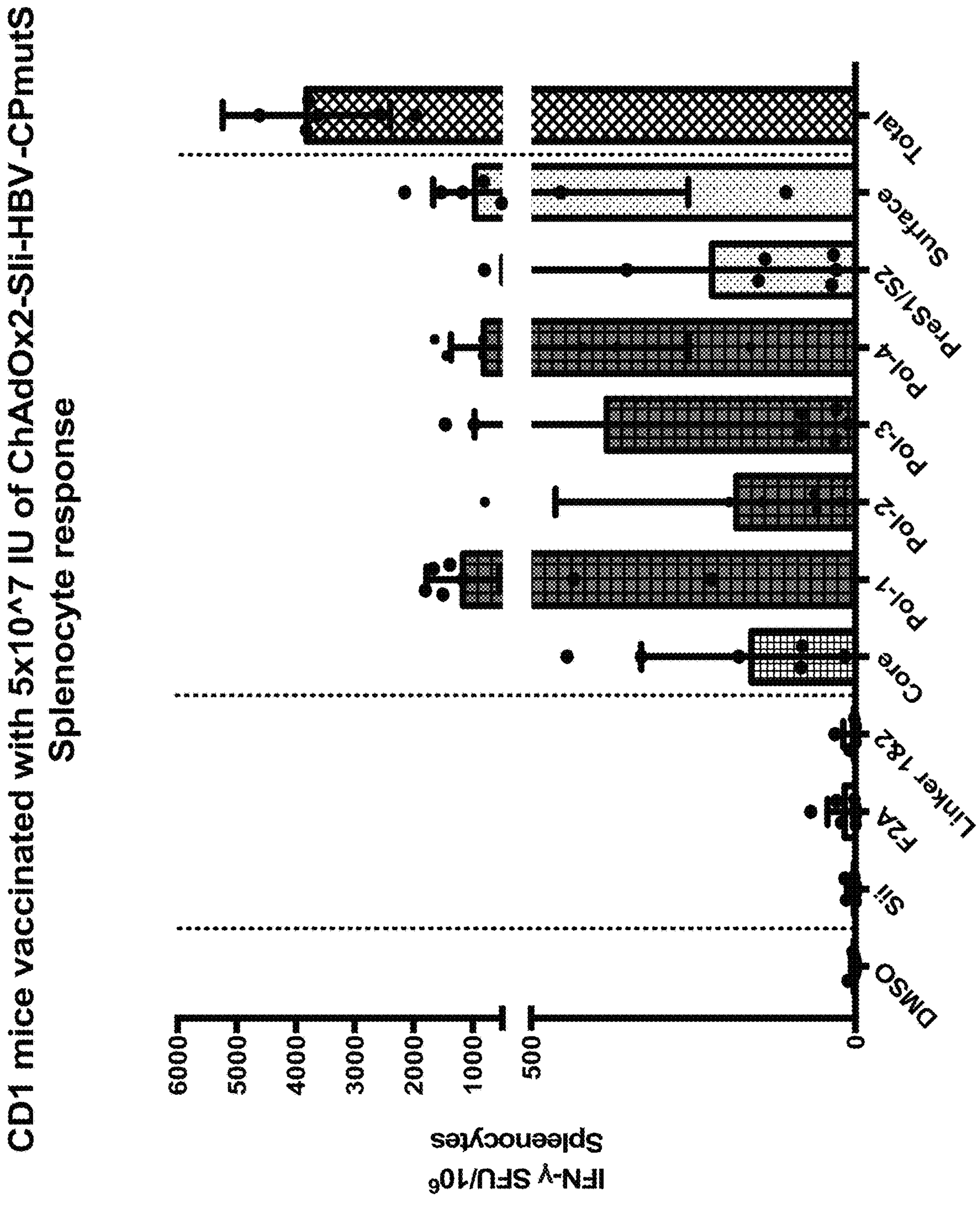
Figure 3D:
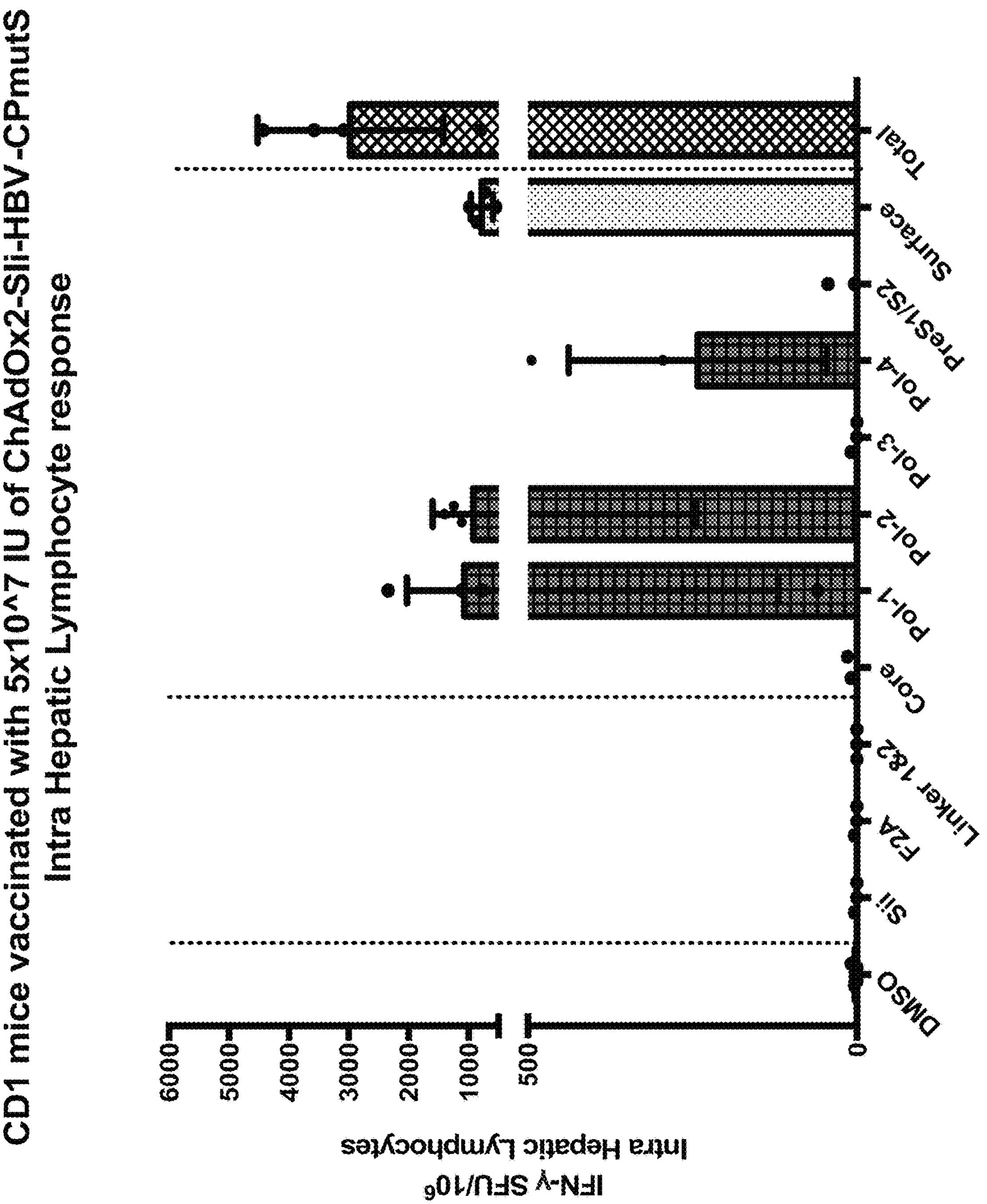

Based on this observation, we decided to take forward SIi-HBV-CPmutS immunogen layout for the generation of chimpanzee adenovirus (ChAdOx2) based T-cell inducing HBV vaccine (FIG. 2D). A small scale batch of ChAdOx2-SIi-HBV-CPmutS was manufactured at the viral vector core facility of the Jenner Institute, University of Oxford, following good manufacturing practices, and used in mice immunogenicity studies.

The ability of ChAdOx2-SIi-HBV-CPmutS vaccine to generate a T-cell immune response was tested using naive mice models. Naive BALB/c and CD1 mice were immunized with $4\times10^7$ IU and $5\times10^7$ IU per mice respectively of ChAdOx2-SIi-HBV-CPmutS vaccine by intra-muscular injections. 14 days post vaccination mice were sacrificed and IFN-γ ELISPOT assays were performed with splenocytes and intra hepatic lymphocytes (IHL) isolated from spleen and liver. Synthetic peptides of 15mers, overlapping by 11 amino acids, generated across the whole of SIi-HBV-CPmutS immunogen, were combined into specific pools (representing different regions of the SIi-HBV-CPmutS immunogen) and used as a stimulant in IFN-γ ELISPOT assays. Results showed that the ChAdOx2-SIi-HBV-CPmutS vaccine generated a good IFN-γ ELISPOT response to SIi-HBV-CPmutS immunogen (FIG. 3). Both BALB/c and CD1 mice showed stronger responses to the polymerase and surface proteins, a weak response to the core protein and negligible or no response to the non-HBV proteins (Shark Invariant chain [SIi], F2A and linkers) in the immunogen.

Figure 4A:
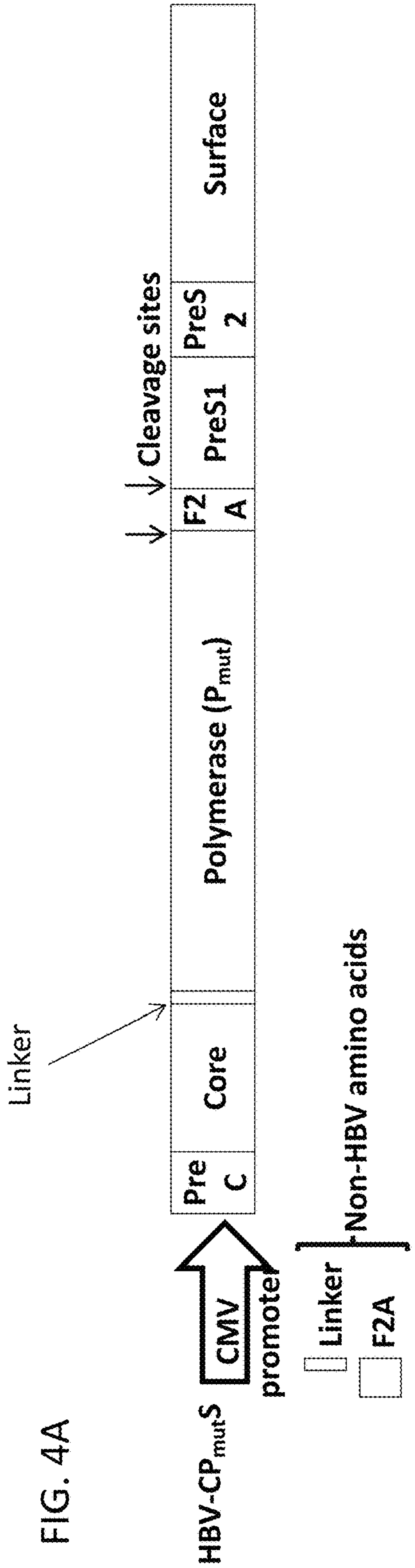
FIGS. 4A-4C: Comparison of the immunogenicity of HBV immunogen SIi-HBV-CPmutS with and without Shark Invariant chain (SIi). (A) HBV-CPmutS immunogen layout. The immunogens HBV-CPmutS was generated by deleting the SIi and first linker present in SIi-HBV-CPmutS. HBV-CPmutS has exactly the same amino acids, except that it lacks the SIi and first linker sequence that is present in the SIi-HBV-CPmutS immunogen. (B) Splenocyte responses in CD1 mice. (C) Intra Hepatic Lymphocyte responses in CD1 mice. ChAdOX2-HBV-CPmutS was generated as described earlier and CD1 mice (10 mice at age of 7 weeks) were vaccinated by intramuscular injections with $5\times10^7$ IU per mice ChAdOx2-HBV-CPmutS vaccine and 14 days post-vaccination mice were sacrificed and splenocytes and intra hepatic lymphocytes response data were generated, as described earlier. Data from 5 and 10 CD1 mice vaccinated with ChAdOx2-SIi-HBV-CPmutS and ChAdOx2-HBV-CPmutS respectively were compared and represented in charts for ease of comparison.
Figure 4B:
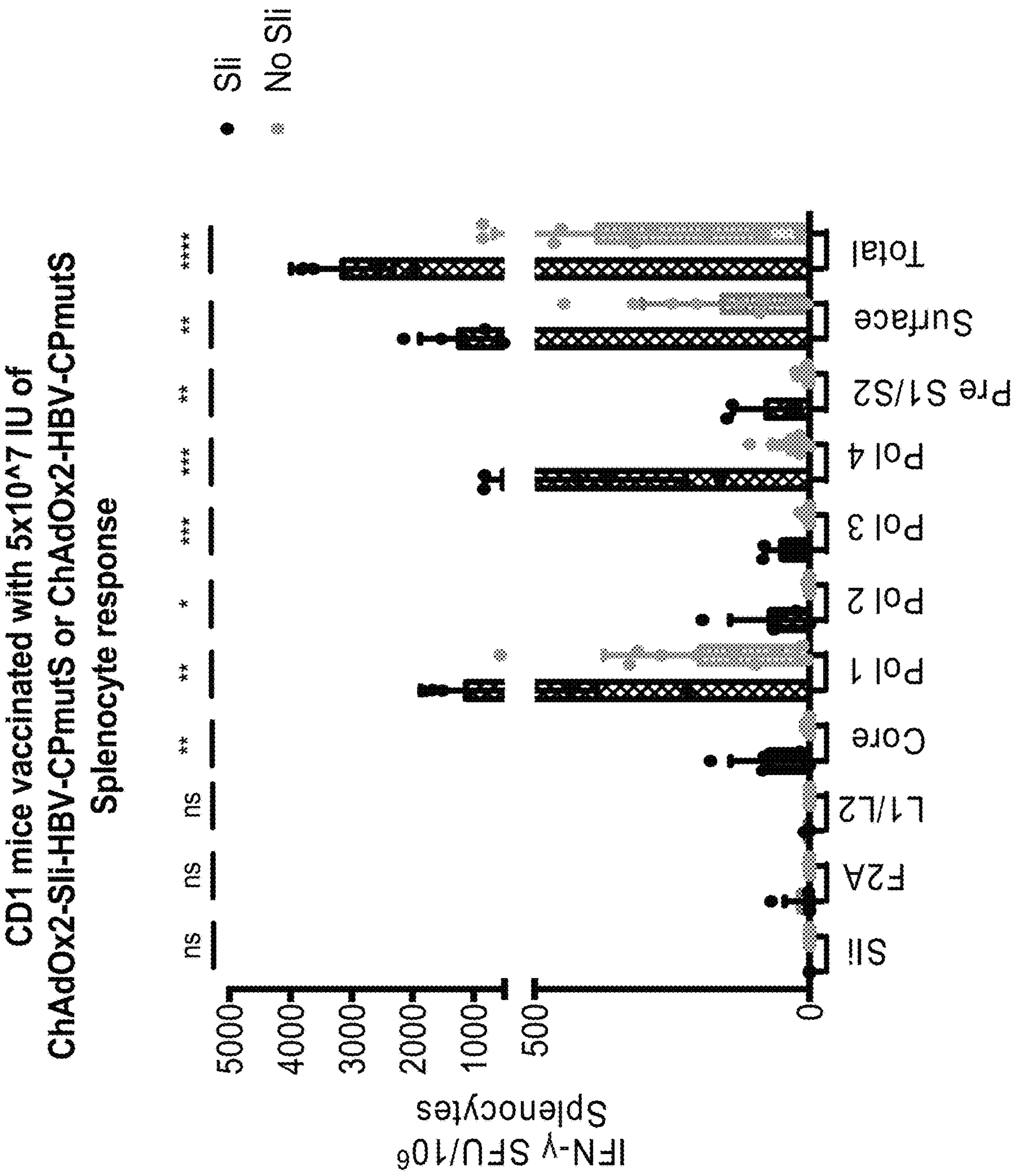
Figure 4C:
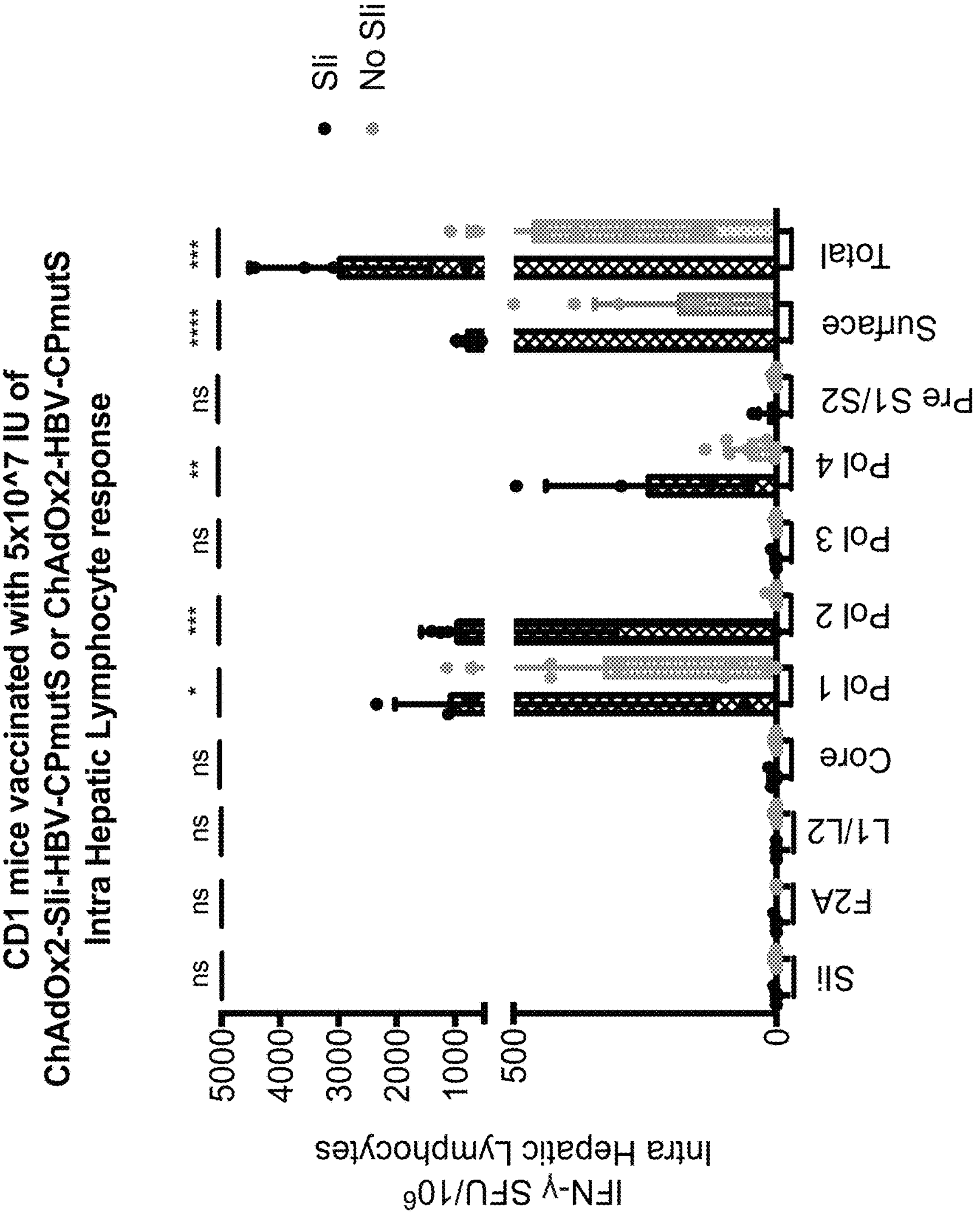

Previous studies have shown that the shark invariant chain (SIi), when placed at the N-terminus of the immunogen, functions as a molecular adjuvant and increases the overall T-cell immune response to the immunogen. To test this, we generated a HBV immunogen without SIi (HBV-CPmutS vaccine) (FIG. 4A), and then generated a ChAdOx2-HBV-CPmutS vaccine and tested them in similar CD1 mice immunogenicity experiments. Results showed that the SIi vaccine (ChAdOx2-SIi-HBV-CPmutS) generates a higher magnitude of IFN-γ ELISPOT response (both Splenocyte and Intra Hepatic Lymphocyte IFN-γ ELISPOT response, represented in FIG. 4B, 4C) compared to the Non-SIi vaccine (ChAdOx2-HBV-CPmutS).

Figure 5A:
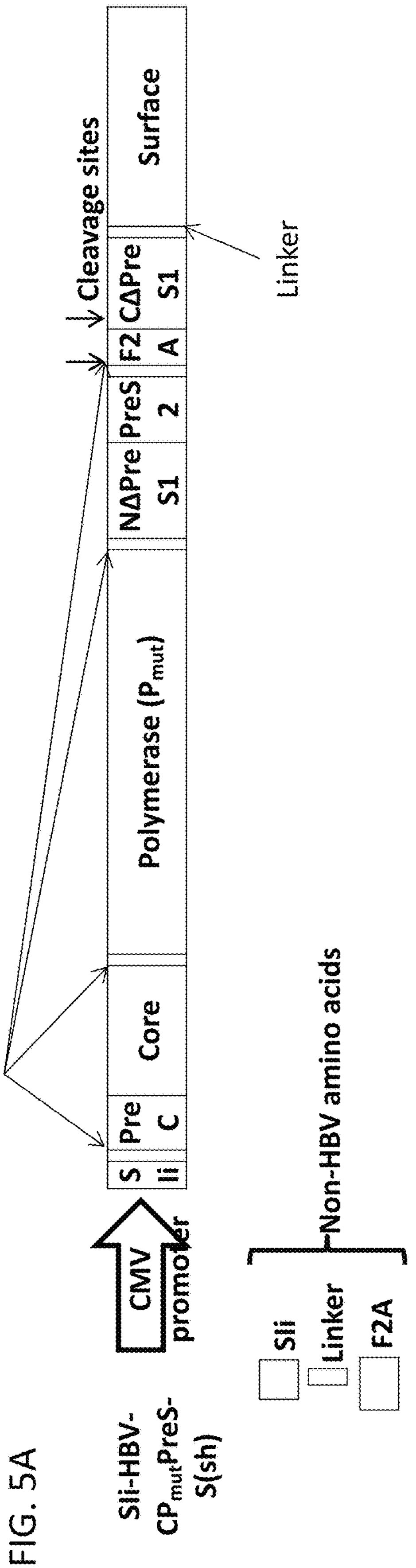
FIG. 5A: Schematic layout of SIi-HBV-CPmutPreS-S (sh).
Figure 5B:
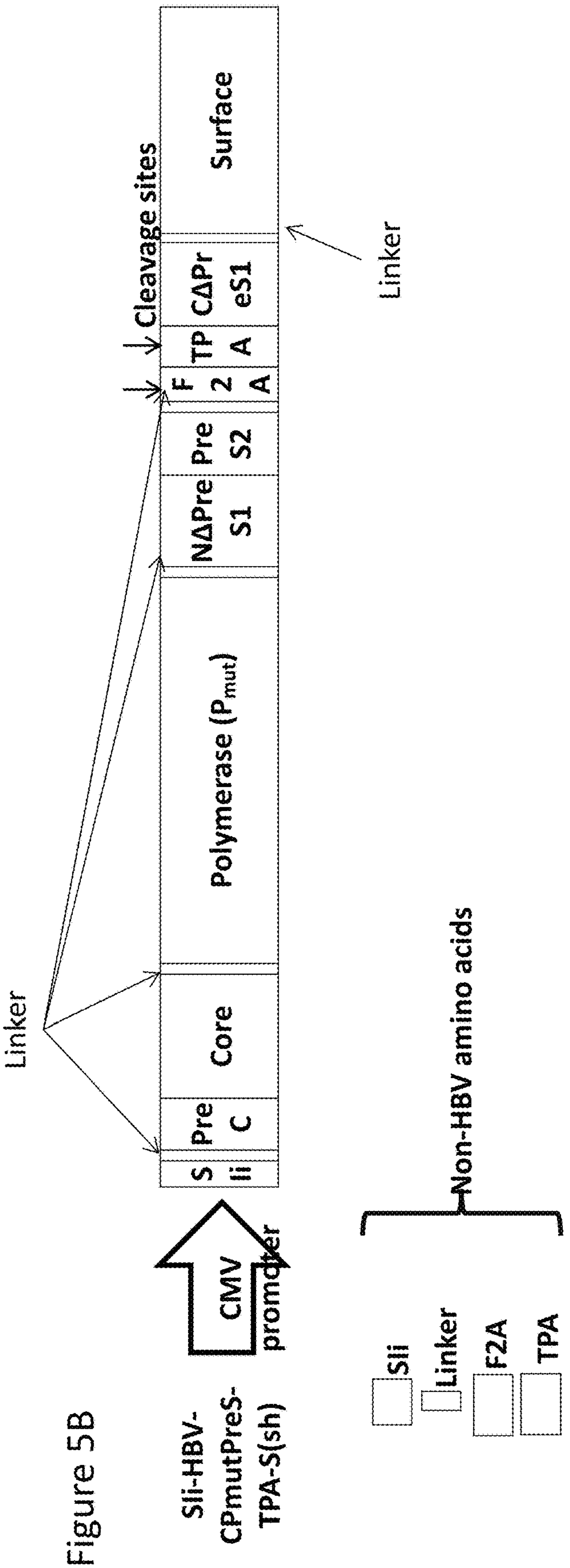
FIG. 5B: Schematic layout of SIi-HBV-CPmutPreS-TPA-S(sh).

The main aim of the viral vectored HBV vaccine design is to generate both T-cell and antibody response to the HBV immunogen. In order to generate a successful antibody response, the immunogen encoded protein has to fold into its native conformation. To provide this, HBV immunogens, SIi-HBV-CPmutPreS-S(sh) and SIi-HBV-CPmutPreS-TPA-S(sh) (FIGS. 5A and 5B) were designed, which encode the N-terminal half of PreS1 domain fused with a linker to the S domain of surface protein, as the antibody inducing immunogen component, and the remaining peptide sequences of the surface protein (the C-terminal half of PreS1 domain and the whole PreS2 domain) were fused to the PreCore/Core/Pmut, in order to preserve the T-cell epitopes that would be required for generation of T-cell immune response. FIGS. 5A and 5B shows a schematic layout of SIi-HBV-CPmutPreS-S(sh).

Figure 6A:
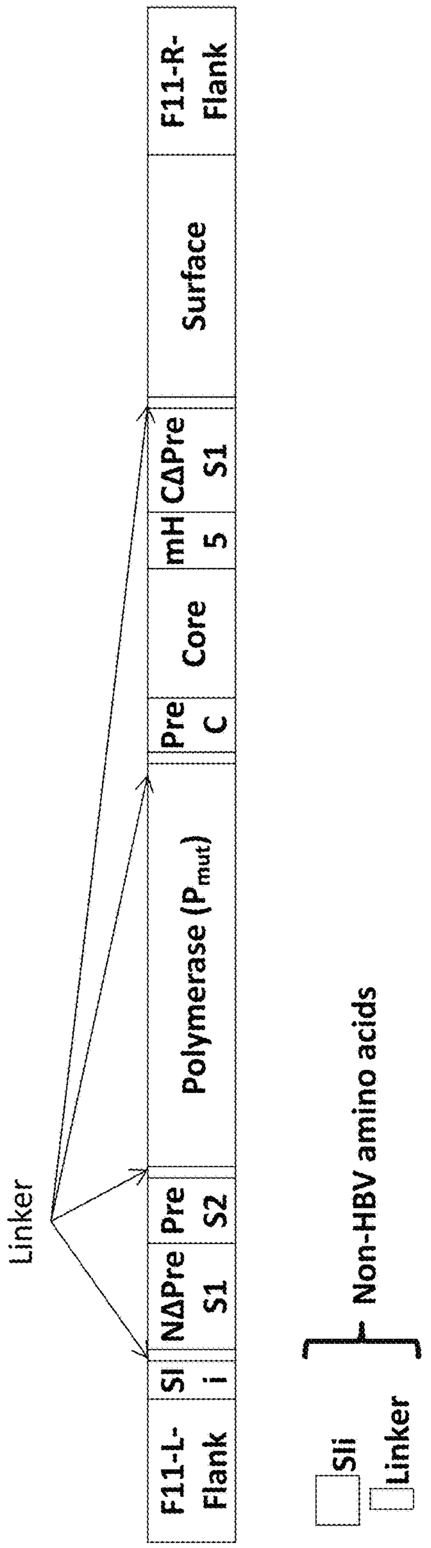
FIG. 6A: Schematic layout of MVA-SIi-HBV-PreS-$P_{mut}$-C-S(sh).
Figure 6B:
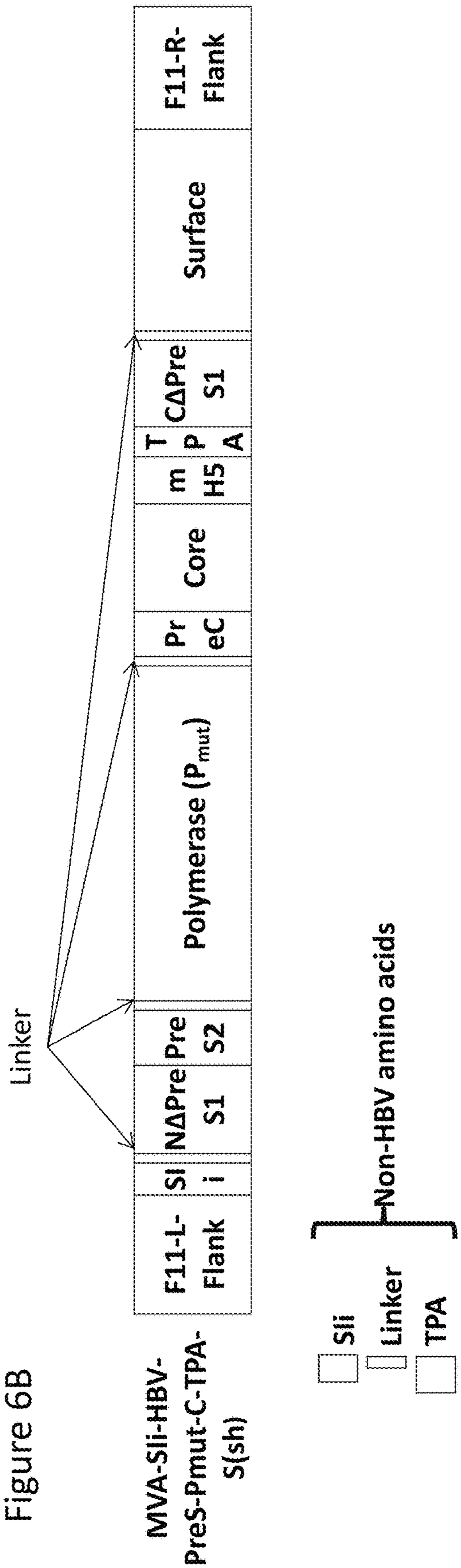
FIG. 6B: Schematic layout of MVA-SIi-HBV-PreS-Pmut-C-TPA-S(sh).

MVA-HBV immunogens were also designed, which followed designs similar to SIi-HBV-CPmutPreS-S(sh) and and SIi-HBV-CPmutPreS-TPA-S(sh). However, the T-cell component of HBV immunogen SIi-HBV-CPmutPreS is encoded by the early promoter F11 and the antibody inducing component S(sh) or TPA-S(sh) is encoded by the early/late promoter mH5. The cloning cassette also has F11-left flank and F11-right flank sequences, to allow insertion into the F11 locus, by homologous recombination. FIGS. 6A and 6B shows schematic layouts of MVA-SIi-HBV-PreS-Pmut-C-S(sh) and MVA-SIi-HBV-CPmutPreS-TPA-S(sh) respectively.

Conclusion: The novel multi-antigen HBV immunogen based ChAdOx2-SIi-HBV-CPmutS are highly immunogenic in naive mice models. These studies pave way for future studies in chronic HBV mice models, to assess their ability to overcome chronic HBV infection through immunotherapeutic approaches.

Sequences

HBV genotype C consensus sequence generated from 1447 genotype C sequences (3215 base pairs) is provided as SEQ ID NO: 1. The Sequence of KP017269.1 HBV isolate JP-02 is provided as SEQ ID NO: 2.

Example Cassettes

Figure 10A:
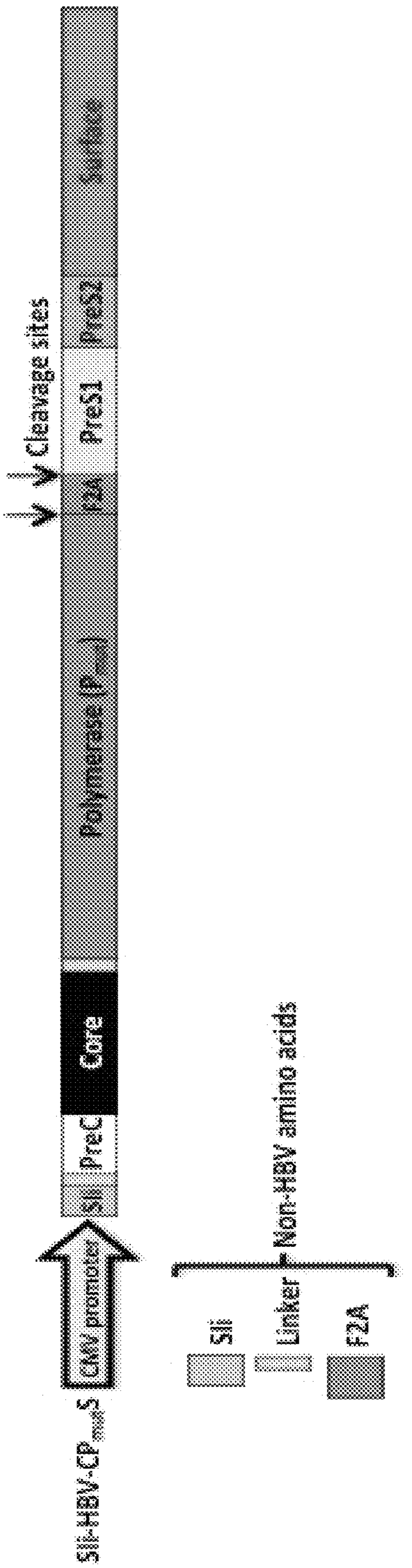
FIGS. 10A-10G: show immunogen layout for (A) SIi-HBV-CPmutS; (B) SIi-HBV-SCP$_{mut}$ (C) HBV-CPmutS (D) SIi-HBV-CP$_{mut}$ PreS-S(sh) (E) MVA-SIi-HBV-PreS-P$_{mut}$-C-S(sh) (F) SIi-HBV-CP$_{mut}$ PreS-TPA-S(sh), and (G) MVA-SIi-HBV-PreS-P$_{mut}$-C-TPA-S(sh).

1. SIi-HBV-CP$_{mut}$S 1.1. SIi-HBV-CP$_{mut}$S: Immunogen Layout is Shown in FIG. 10A 1.2. SIi-HBV-CP$_{mut}$S: Amino acid sequence (SEQ ID NO: 3)

MSLLWGGVTVLAAMLIAGQVASVVFLVKGGGPGGGMQLFHLCLIISCS

CPTVQASKLCLGWLWGMDIDPYKEFGASVELLSFLPSDFFPSIRDLLD

TASALYREALESPEHCSPHHTALRQAILCWGELMNLATWVGSNLEDPA

SRELVVSYVNVNMGLKIRQLLWFHISCLTFGRETVLEYLVSFGVWIRT

PPAYRPPNAPILSTLPETTVVRRRGRSPRRRTPSPRRRRSQSPRRRRS

QSRESQCGGGSGGGMPLSYQHFRKLLLLDDEAGPLEEELPRLADEGLN

RRVAEDLNLGNLNVSIPWTHKVGNFTGLASSTVPVFNPEWQTPSFPHI

HLQEDIINRCQQYVGPLTVNEKRRLKLIMPARFYPNLTKYLPLDKGIK

PYYPEHAVNHYFKTRHYLHTLWKAGILYKRETTRSASFCGSPYSWEQE

LQHGRLVFQTSTRHGDESFCSQSSGILSRSPVGPCVRSQLKQSRLGLQ

PQQGSLARGKSGRSGSIRARVHPTTRRSFGVEPSGSGHIDNSASSTSS

CLHQSAVRKTAYSHLSTSKRQSSSGHAVELHNIPPSSARSQSEGPIFS

AWWLQFRNSKPASDYALTHIVNLLEDWGPATEHGEHNIRIPRTPARVT

GGVFLVDKNPHNTTESRLVVDFSQFSRGSTHVSWPKFAVPNLQSLTNL

LSSNLSWLSLDVSAAFYHIPLHPAAMPHLLVGSSGLPRYVARLSSTSR

NINYQHGTMQDLHDSCSRNLYVSLLLLYKTFGRKLHLYSHPIILGFRK

IPMGVGLSPFLLAQFTSAICSVVRRAFPHCLAFSYMDDVVLGAKSVQH

LESLFTSITNFLLSLGIHLNPNKTKRWGYSLNFMGYVIGSWGTLPQEH

IVLKIKQCFRKLPVNRPIDWKVCQRIVGLLGFAAPFTQCGYPALMPLY

ACIQSKQAFTFSPTYKAFLCKQYLNLYPVARQRSGLCQVFADATPTGW

GLAIGHRAMRGTFVAPLPIHTAELLAACFARSRSGAKLIGTDNSVVLS

RKYTSFPWLLGCAANWILRGTSFVYVPSALNPAADPSAGRLGLYRPLL

HLPFRPTTGRTSLYAVSPSVPSHLPDRVHFASPLHVAWRPPRKRRAPV

KQTLNFDLLKLAGDVESNPGPMGGWSSKPRQGMGTNLSVPNPLGFFPD

HQLDPAFGANSNNPDWDFNPNKDHWPEANQVGAGAFGPGFTPPHGGLL

GWSPQAQGILTTVPAAPPPASTNRQSGRQPTPISPPLRDSHPQAMQWN

STTFHQALLDPRVRGLYFPAGGSSSGTVNPVPTTASPISSIFSRTGDP

APNMENTTSGFLGPLLVLQAGFFLLTRILTIPQSLDSWWTSLNFLGGA

PTCPGQNSQSPTSNHSPTSCPPICPGYRWMCLRRFIIFLFILLLCLIF

LLVLLDYQGMLPVCPLLPGTSTTSTGPCKTCTIPAQGTSMFPSCCCTK

PSDGNCTCIPIPSSWAFARFLWEWASVRFSWLSLLVPFVQWFVGLSPT

VWLSVIWMMWYWGPSLYNILSPFLPLLPIFFCLWVYI

-continued 1.3. SIi-HBV-CP$_{mut}$S: Description for amino acid sequences of HBV immunogen 1.3.1. First amino acid of polypeptide = M 1.3.2. Shark Invariant chain (SIi) =

(SEQ ID NO: 4)

SLLWGGVTVLAAMLIAGQVASVVFLV 1.3.3. Linker =

(SEQ ID NO: 5)

KGGGPGGG

1.3.4. C =

1.3.4.1. PreC =

(SEQ ID NO: 16)

MQLFHLCLIISCSCPTVQASKLCLGWLWG 1.3.4.2. Core =

(SEQ ID NO: 6)

MDIDPYKEFGASVELLSFLPSDFFPSIRDLLDTASALYREALESPEHC

SPHHTALRQAILCWGELMNLATWVGSNLEDPASRELVVSYVNVNMGLK

IRQLLWFHISCLTFGRETVLEYLVSFGVWIRTPPAYRPPNAPILSTLP

ETTVVRRRGRSPRRRTPSPRRRRSQSPRRRRSQSRESQC 1.3.5. Linker =

(SEQ ID NO: 7)

GGGSGGG

1.3.6. Pmut = (mutations: Y63A, C323A, C334A, C338A, C352A, R714A, D788A, R792A)

(SEQ ID NO: 8)

MPLSYQHFRKLLLLDDEAGPLEEELPRLADEGLNRRVAEDLNLGNLNV

SIPWTHKVGNFTGLASSTVPVFNPEWQTPSFPHIHLQEDIINRCQQYV

GPLTVNEKRRLKLIMPARFYPNLTKYLPLDKGIKPYYPEHAVNHYFKT

RHYLHTLWKAGILYKRETTRSASFCGSPYSWEQELQHGRLVFQTSTRH

GDESFCSQSSGILSRSPVGPCVRSQLKQSRLGLQPQQGSLARGKSGRS

GSIRARVHPTTRRSFGVEPSGSGHIDNSASSTSSCLHQSAVRKTAYSH

LSTSKRQSSSGHAVELHNIPPSSARSQSEGPIFSAWWLQFRNSKPASD

YALTHIVNLLEDWGPATEHGEHNIRIPRTPARVTGGVFLVDKNPHNTT

ESRLVVDFSQFSRGSTHVSWPKFAVPNLQSLTNLLSSNLSTFGRKLHL

YSHPIILGFRKIPMGVGLSPFLLAQFTSAICSVVRRAFPHCLAFSYMD

DVVLGAKSVQHLESLFTSITNFLLSLGIHLNPNKTKRWGYSLNFMGYV

IGSWGTLPQEHIVLKIKQCFRKLPVNRPIDWKVCQRIVGLLGFAAPFT

QCGYPALMPLYACIQSKQAFTFSPTYKAFLCKQYLNLYPVARQRSGLC

QVFADATPTGWGLAIGHRAMRGTFVAPLPIHTAELLAACFARSRSGAK

LIGTDNSVVLSRKYTSFPWLLGCAANWILRGTSFVYVPSALNPAADPS

AGRLGLYRPLLHLPFRPTTGRTSLYAVSPSVPSHLPDRVHFASPLHVA

WRPP 1.3.7. Furin 2A (F2A) =

(SEQ ID NO: 9)

RKRRAPVKQTLNFDLLKLAGDVESNPGP

-continued 1.3.8. Surface proteins (S) =

1.3.8.1. PreS1 =

(SEQ ID NO: 52)

MGGWSSKPRQGMGTNLSVPNPLGFFPDHQLDPAFGANSNNPDWDFNPN

KDHWPEANQVGAGAFGPGFTPPHGGLLGWSPQAQGILTTVPAAPPPAS

TNRQSGRQPTPISPPLRDSHPQA 1.3.8.2. PreS2 =

(SEQ ID NO: 53)

MQWNSTTFHQALLDPRVRGLYFPAGGSSSGTVNPVPTTASPISSIFSR

TGDPAPN 1.3.8.3. Surface (S) =

(SEQ ID NO: 10)

MENTTSGFLGPLLVLQAGFFLLTRILTIPQSLDSWWTSLNFLGGAPTC

PGQNSQSPTSNHSPTSCPPICPGYRWMCLRRFIIFLFILLLCLIFLLV

LLDYQGMLPVCPLLPGTSTTSTGPCKTCTIPAQGTSMFPSCCCTKPSD

GNCTCIPIPSSWAFARFLWEWASVRFSWLSLLVPFVQWFVGLSPTVWL

SVIWMMWYWGPSLYNILSPFLPLLPIFFCLWVYI

The SIi-HBV-CPmutS nucleotide sequence is provided as SEQ ID NO: 46.

Figure 10B:
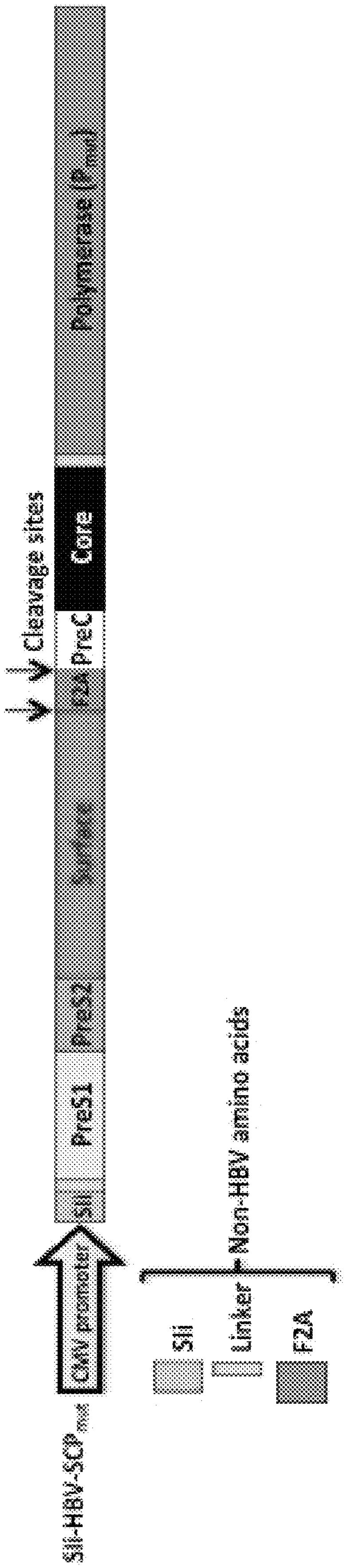

2. SIi-HBV-SCP$_{mut}$ 2.1. SIi-HBV-SCP$_{mut}$: Immunogen Layout is Shown in FIG. 10B 2.2. SIi_HBV-SCP$_{mut}$: Amino acid sequence (SEQ ID NO: 11)

MSLLWGGVTVLAAMLIAGQVASVVFLVKGGSMGGWSSKPRQGMGTNLS

VPNPLGFFPDHQLDPAFGANSNNPDWDFNPNKDHWPEANQVGAGAFGP

GFTPPHGGLLGWSPQAQGILTTVPAAPPPASTNRQSGRQPTPISPPLR

DSHPQAMQWNSTTFHQALLDPRVRGLYFPAGGSSSGTVNPVPTTASPI

SSIFSRTGDPAPNMENTTSGFLGPLLVLQAGFFLLTRILTIPQSLDSW

WTSLNFLGGAPTCPGQNSQSPTSNHSPTSCPPICPGYRWMCLRRFIIF

LFILLLCLIFLLVLLDYQGMLPVCPLLPGTSTTSTGPCKTCTIPAQGT

SMFPSCCCTKPSDGNCTCIPIPSSWAFARFLWEWASVRFSWLSLLVPF

VQWFVGLSPTVWLSVIWMMWYWGPSLYNILSPFLPLLPIFFCLWVYIR

KRRAPVKQTLNFDLLKLAGDVESNPGPMQLFHLCLIISCSCPTVQASK

LCLGWLWGMDIDPYKEFGASVELLSFLPSDFFPSIRDLLDTASALYRE

ALESPEHCSPHHTALRQAILCWGELMNLATWVGSNLEDPASRELVVSY

VNVNMGLKIRQLLWFHISCLTFGRETVLEYLVSFGVWIRTPPAYRPPN

APILSTLPETTVVRRRGRSPRRRTPSPRRRRSQSPRRRRSQSRESQCG

GGSGGGMPLSYQHFRKLLLLDDEAGPLEEELPRLADEGLNRRVAEDLN

LGNLNVSIPWTHKVGNFTGLASSTVPVFNPEWQTPSFPHIHLQEDIIN

RCQQYVGPLTVNEKRRLKLIMPARFYPNLTKYLPLDKGIKPYYPEHAV

NHYFKTRHYLHTLWKAGILYKRETTRSASFCGSPYSWEQELQHGRLVF

QTSTRHGDESFCSQSSGILSRSPVGPCVRSQLKQSRLGLQPQQGSLAR

GKSGRSGSIRARVHPTTRRSFGVEPSGSGHIDNSASSTSSCLHQSAVR

KTAYSHLSTSKRQSSSGHAVELHNIPPSSARSQSEGPIFSAWWLQFRN

-continued

SKPASDYALTHIVNLLEDWGPATEHGEHNIRIPRTPARVTGGVFLVDK

NPHNTTESRLVVDFSQFSRGSTHVSWPKFAVPNLQSLTNLLSSNLSWL

SLDVSAAFYHIPLHPAAMPHLLVGSSGLPRYVARLSSTSRNINYQHGT

MQDLHDSCSRNLYVSLLLLYKTFGRKLHLYSHPIILGFRKIPMGVGLS

PFLLAQFTSAICSVVRRAFPHCLAFSYMDDVVLGAKSVQHLESLFTSI

TNFLLSLGIHLNPNKTKRWGYSLNFMGYVIGSWGTLPQEHIVLKIKQC

FRKLPVNRPIDWKVCQRIVGLLGFAAPFTQCGYPALMPLYACIQSKQA

FTFSPTYKAFLCKQYLNLYPVARQRSGLCQVFADATPTGWGLAIGHRA

MRGTFVAPLPIHTAELLAACFARSRSGAKLIGTDNSVVLSRKYTSFPW

LLGCAANWILRGTSFVYVPSALNPAADPSAGRLGLYRPLLHLPFRPTT

GRTSLYAVSPSVPSHLPDRVHFASPLHVAWRPP 2.3. SIi-HBV-SCP$_{mut}$: Description for amino acid sequences of HBV immunogen 2.3.1. First amino acid of polypeptide = M 2.3.2. Shark Invariant chain (SIi) =

(SEQ ID NO: 4)

SLLWGGVTVLAAMLIAGQVASVVFLV 2.3.3. Linker =

(SEQ ID NO: 14)

KGGS

2.3.4. Surface proteins (S) =

2.3.4.1. PreS1 =

(SEQ ID NO: 52)

MGGWSSKPRQGMGTNLSVPNPLGFFPDHQLDPAFGANSNNPDWDFNPN

KDHWPEANQVGAGAFGPGFTPPHGGLLGWSPQAQGILTTVPAAPPPAS

TNRQSGRQPTPISPPLRDSHPQA 2.3.4.2. PreS2 =

(SEQ ID NO: 53)

MQWNSTTFHQALLDPRVRGLYFPAGGSSSGTVNPVPTTASPISSIFSR

TGDPAPN 2.3.4.3. Surface (S) =

(SEQ ID NO: 10)

MENTTSGFLGPLLVLQAGFFLLTRILTIPQSLDSWWTSLNFLGGAPTC

PGQNSQSPTSNHSPTSCPPICPGYRWMCLRRFIIFLFILLLCLIFLLV

LLDYQGMLPVCPLLPGTSTTSTGPCKTCTIPAQGTSMFPSCCCTKPSD

GNCTCIPIPSSWAFARFLWEWASVRFSWLSLLVPFVQWFVGLSPTVWL

SVIWMMWYWGPSLYNILSPFLPLLPIFFCLWVYI 2.3.5. Furin 2A (F2A) =

(SEQ ID NO: 9)

RKRRAPVKQTLNFDLLKLAGDVESNPGP

2.3.6. C =

2.3.6.1. PreCore =

(SEQ ID NO: 16)

MQLFHLCLIISCSCPTVQASKLCLGWLWG 2.3.6.2. Core =

(SEQ ID NO: 6)

MDIDPYKEFGASVELLSFLPSDFFPSIRDLLDTASALYREALESPEHC

SPHHTALRQAILCWGELMNLATWVGSNLEDPASRELVVSYVNVNMGLK

-continued

IRQLLWFHISCLTFGRETVLEYLVSFGVWIRTPPAYRPPNAPILSTLP

ETTVVRRRGRSPRRRTPSPRRRRSQSPRRRRSQSRESQC 2.3.7. Linker =

(SEQ ID NO: 7)

GGGSGGG

2.3.8. Pmut = (mutations: Y63A, C323A, C334A, C338A, C352A, R714A, D788A, R792A)

(SEQ ID NO: 8)

MPLSYQHFRKLLLLDDEAGPLEEELPRLADEGLNRRVAEDLNLGNLNV

SIPWTHKVGNFTGLASSTVPVFNPEWQTPSFPHIHLQEDIINRCQQYV

GPLTVNEKRRLKLIMPARFYPNLTKYLPLDKGIKPYYPEHAVNHYFKT

RHYLHTLWKAGILYKRETTRSASFCGSPYSWEQELQHGRLVFQTSTRH

GDESFCSQSSGILSRSPVGPCVRSQLKQSRLGLQPQQGSLARGKSGRS

GSIRARVHPTTRRSFGVEPSGSGHIDNSASSTSSCLHQSAVRKTAYSH

LSTSKRQSSSGHAVELHNIPPSSARSQSEGPIFSAWWLQFRNSKPASD

YALTHIVNLLEDWGPATEHGEHNIRIPRTPARVTGGVFLVDKNPHNTT

ESRLVVDFSQFSRGSTHVSWPKFAVPNLQSLTNLLSSNLSTFGRKLHL

YSHPIILGFRKIPMGVGLSPFLLAQFTSAICSVVRRAFPHCLAFSYMD

DVVLGAKSVQHLESLFTSITNFLLSLGIHLNPNKTKRWGYSLNFMGYV

IGSWGTLPQEHIVLKIKQCFRKLPVNRPIDWKVCQRIVGLLGFAAPFT

QCGYPALMPLYACIQSKQAFTFSPTYKAFLCKQYLNLYPVARQRSGLC

QVFADATPTGWGLAIGHRAMRGTFVAPLPIHTAELLAACFARSRSGAK

LIGTDNSVVLSRKYTSFPWLLGCAANWILRGTSFVYVPSALNPAADPS

AGRLGLYRPLLHLPFRPTTGRTSLYAVSPSVPSHLPDRVHFASPLHVA

WRPP

Figure 10C:
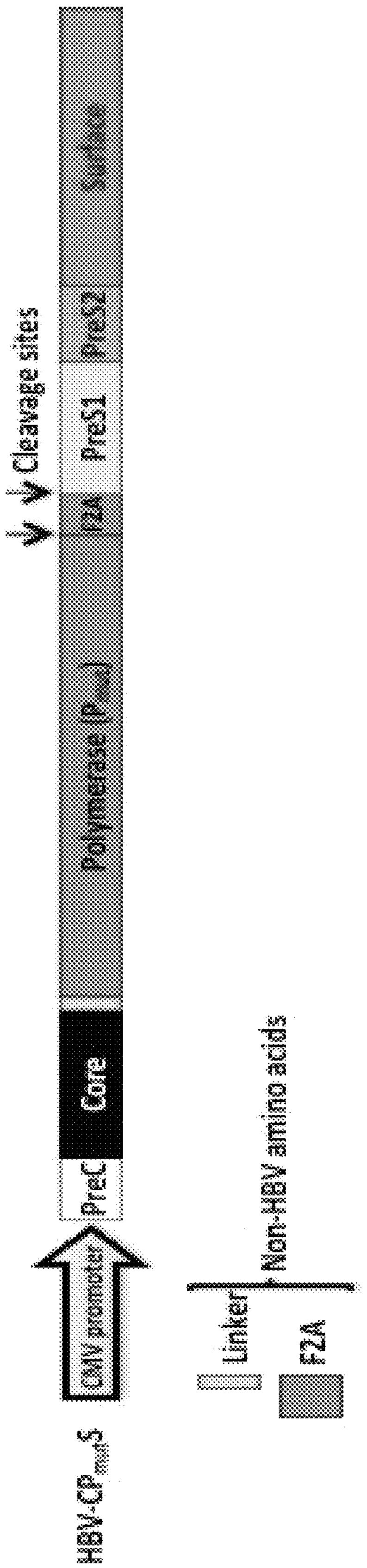

The SIi-HBV-SCPmut nucleotide sequence is provided as SEQ ID NO: 47:

3. HBV-CP$_{mut}$S 3.1. HBV-CP$_{mut}$S: Immunogen layout is shown in FIG. 10C 3.2. HBV-CP$_{mut}$S: Amino acid sequence (SEQ ID NO: 12)

MQLFHLCLIISCSCPTVQASKLCLGWLWGMDIDPYKEFGASVELLSFL

PSDFFPSIRDLLDTASALYREALESPEHCSPHHTALRQAILCWGELMN

LATWVGSNLEDPASRELVVSYVNVNMGLKIRQLLWFHISCLTFGRETV

LEYLVSFGVWIRTPPAYRPPNAPILSTLPETTVVRRRGRSPRRRTPSP

RRRRSQSPRRRRSQSRESQCGGGSGGGMPLSYQHFRKLLLLDDEAGPL

EEELPRLADEGLNRRVAEDLNLGNLNVSIPWTHKVGNFTGLASSTVPV

FNPEWQTPSFPHIHLQEDIINRCQQYVGPLTVNEKRRLKLIMPARFYP

NLTKYLPLDKGIKPYYPEHAVNHYFKTRHYLHTLWKAGILYKRETTRS

ASFCGSPYSWEQELQHGRLVFQTSTRHGDESFCSQSSGILSRSPVGPC

VRSQLKQSRLGLQPQQGSLARGKSGRSGSIRARVHPTTRRSFGVEPSG

SGHIDNSASSTSSCLHQSAVRKTAYSHLSTSKRQSSSGHAVELHNIPP

SSARSQSEGPIFSAWWLQFRNSKPASDYALTHIVNLLEDWGPATEHGE

-continued

HNIRIPRTPARVTGGVFLVDKNPHNTTESRLVVDFSQFSRGSTHVSWP

KFAVPNLQSLTNLLSSNLSWLSLDVSAAFYHIPLHPAAMPHLLVGSSG

LPRYVARLSSTSRNINYQHGTMQDLHDSCSRNLYVSLLLLYKTFGRKL

HLYSHPIILGFRKIPMGVGLSPFLLAQFTSAICSVVRRAFPHCLAFSY

MDDVVLGAKSVQHLESLFTSITNFLLSLGIHLNPNKTKRWGYSLNFMG

YVIGSWGTLPQEHIVLKIKQCFRKLPVNRPIDWKVCQRIVGLLGFAAP

FTQCGYPALMPLYACIQSKQAFTFSPTYKAFLCKQYLNLYPVARQRSG

LCQVFADATPTGWGLAIGHRAMRGTFVAPLPIHTAELLAACFARSRSG

AKLIGTDNSVVLSRKYTSFPWLLGCAANWILRGTSFVYVPSALNPAAD

PSAGRLGLYRPLLHLPFRPTTGRTSLYAVSPSVPSHLPDRVHFASPLH

VAWRPPRKRRAPVKQTLNFDLLKLAGDVESNPGPMGGWSSKPRQGMGT

NLSVPNPLGFFPDHQLDPAFGANSNNPDWDFNPNKDHWPEANQVGAGA

FGPGFTPPHGGLLGWSPQAQGILTTVPAAPPPASTNRQSGRQPTPISP

PLRDSHPQAMQWNSTTFHQALLDPRVRGLYFPAGGSSSGTVNPVPTTA

SPISSIFSRTGDPAPNMENTTSGFLGPLLVLQAGFFLLTRILTIPQSL

DSWWTSLNFLGGAPTCPGQNSQSPTSNHSPTSCPPICPGYRWMCLRRF

IIFLFILLLCLIFLLVLLDYQGMLPVCPLLPGTSTTSTGPCKTCTIPA

QGTSMFPSCCCTKPSDGNCTCIPIPSSWAFARFLWEWASVRFSWLSLL

VPFVQWFVGLSPTVWLSVIWMMWYWGPSLYNILSPFLPLLPIFFCLWV

YI 3.3. HBV-CP$_{mut}$S: Description for amino acid sequences of HBV immunogen 3.3.1. C =

3.3.1.1. PreCore =

(SEQ ID NO: 16)

MQLFHLCLIISCSCPTVQASKLCLGWLWG 3.3.1.2. Core =

(SEQ ID NO: 6)

MDIDPYKEFGASVELLSFLPSDFFPSIRDLLDTASALYREALESPEHC

SPHHTALRQAILCWGELMNLATWVGSNLEDPASRELVVSYVNVNMGLK

IRQLLWFHISCLTFGRETVLEYLVSFGVWIRTPPAYRPPNAPILSTLP

ETTVVRRRGRSPRRRTPSPRRRRSQSPRRRRSQSRESQC 3.3.2. Linker =

(SEQ ID NO: 7)

GGGSGGG

3.3.3. Pmut = (mutations: Y63A, C323A, C334A, C338A, C352A, R714A, D788A, R792A)

(SEQ ID NO: 8)

MPLSYQHFRKLLLLDDEAGPLEEELPRLADEGLNRRVAEDLNLGNLNV

SIPWTHKVGNFTGLASSTVPVFNPEWQTPSFPHIHLQEDIINRCQQYV

GPLTVNEKRRLKLIMPARFYPNLTKYLPLDKGIKPYYPEHAVNHYFKT

RHYLHTLWKAGILYKRETTRSASFCGSPYSWEQELQHGRLVFQTSTRH

GDESFCSQSSGILSRSPVGPCVRSQLKQSRLGLQPQQGSLARGKSGRS

GSIRARVHPTTRRSFGVEPSGSGHIDNSASSTSSCLHQSAVRKTAYSH

LSTSKRQSSSGHAVELHNIPPSSARSQSEGPIFSAWWLQFRNSKPASD

YALTHIVNLLEDWGPATEHGEHNIRIPRTPARVTGGVFLVDKNPHNTT

-continued

ESRLVVDFSQFSRGSTHVSWPKFAVPNLQSLTNLLSSNLSTFGRKLHL
YSHPIILGFRKIPMGVGLSPFLLAQFTSAICSVVRRAFPHCLAFSYMD
DVVLGAKSVQHLESLFTSITNFLLSLGIHLNPNKTKRWGYSLNFMGYV
IGSWGTLPQEHIVLKIKQCFRKLPVNRPIDWKVCQRIVGLLGFAAPFT
QCGYPALMPLYACIQSKQAFTFSPTYKAFLCKQYLNLYPVARQRSGLC
QVFADATPTGWGLAIGHRAMRGTFVAPLPIHTAELLAACFARSRSGAK
LIGTDNSVVLSRKYTSFPWLLGCAANWILRGTSFVYVPSALNPAADPS
AGRLGLYRPLLHLPFRPTTGRTSLYAVSPSVPSHLPDRVHFASPLHVA
WRPP 3.3.4. Furin 2A (F2A) =

(SEQ ID NO: 9)
RKRRAPVKQTLNFDLLKLAGDVESNPGP

3.3.5. Surface proteins (S) =

3.3.5.1. PreS1 =

(SEQ ID NO: 52)
MGGWSSKPRQGMGTNLSVPNPLGFFPDHQLDPAFGANSNNPDWDFNPN
KDHWPEANQVGAGAFGPGFTPPHGGLLGWSPQAQGILTTVPAAPPPAS
TNRQSGRQPTPISPPLRDSHPQA 3.3.5.2. PreS2 =

(SEQ ID NO: 53)
MQWNSTTFHQALLDPRVRGLYFPAGGSSSGTVNPVPTTASPISSIFSR
TGDPAPN 3.3.5.3. Surface (S)

(SEQ ID NO: 10)
MENTTSGFLGPLLVLQAGFFLLTRILTIPQSLDSWWTSLNFLGGAPTC
PGQNSQSPTSNHSPTSCPPICPGYRWMCLRRFIIFLFILLLCLIFLLV
LLDYQGMLPVCPLLPGTSTTSTGPCKTCTIPAQGTSMFPSCCCTKPSD
GNCTCIPIPSSWAFARFLWEWASVRFSWLSLLVPFVQWFVGLSPTVWL
SVIWMMWYWGPSLYNILSPFLPLLPIFFCLWVYI

4. SIi-HBV-CP$_{mut}$PreS-S(sh)

Figure 10D:
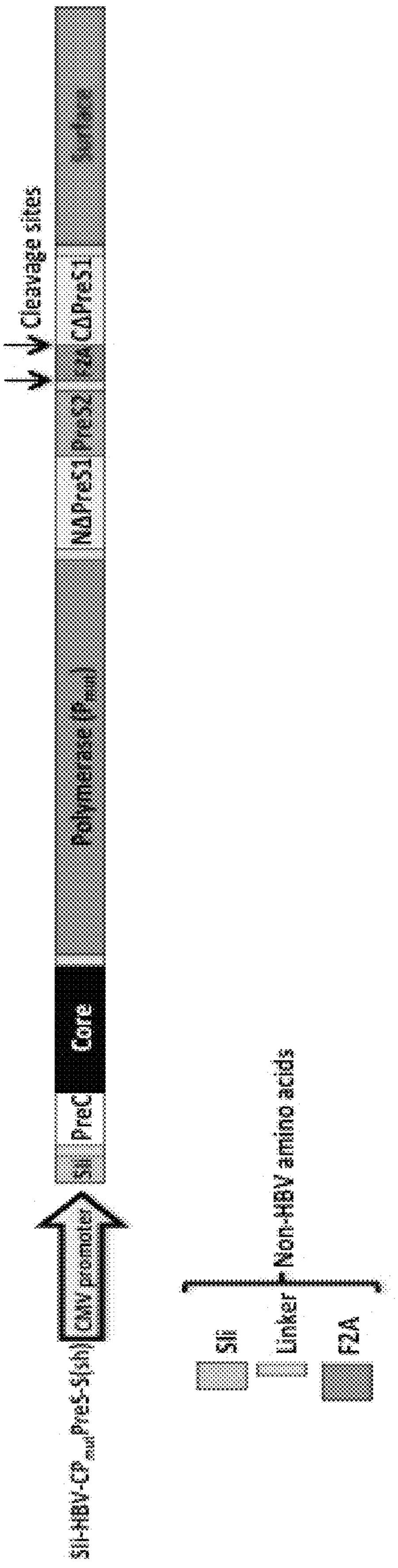
Figure 10E:
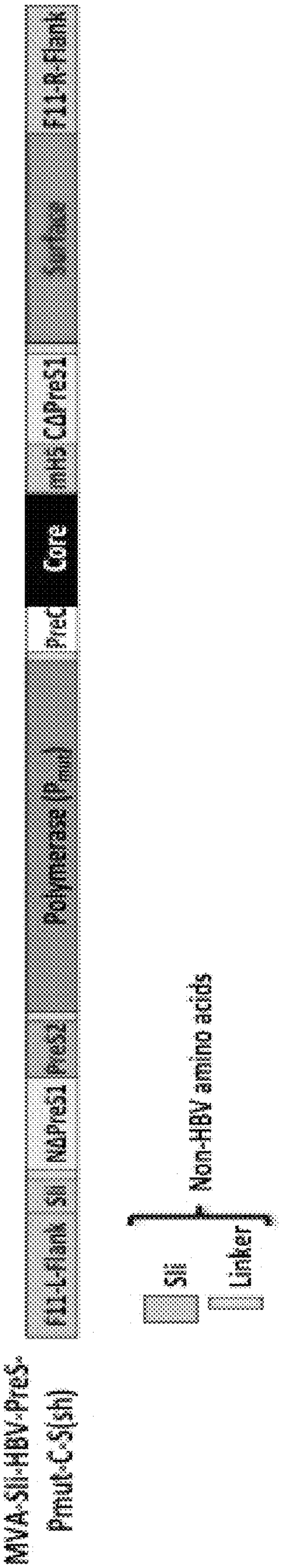

4.1. SIi-HBV-CP$_{mut}$PreS-S(sh): Immunogen layout is shown in FIG. 10D 4.2. SIi-HBV-CP$_{mut}$PreS-S(sh): Amino acid sequence (SEQ ID NO: 13)
MSLLWGGVTVLAAMLIAGQVASVVFLVKGGGPGGGMQLFHLCLIISCS
CPTVQASKLCLGWLWGMDIDPYKEFGASVELLSFLPSDFFPSIRDLLD
TASALYREALESPEHCSPHHTALRQAILCWGELMNLATWVGSNLEDPA
SRELVVSYVNVNMGLKIRQLLWFHISCLTFGRETVLEYLVSFGVWIRT
PPAYRPPNAPILSTLPETTVVRRRGRSPRRRTPSPRRRRSQSPRRRRS
QSRESQCGGGSGGGMPLSYQHFRKLLLLDDEAGPLEEELPRLADEGLN
RRVAEDLNLGNLNVSIPWTHKVGNFTGLASSTVPVFNPEWQTPSFPHI
HLQEDIINRCQQYVGPLTVNEKRRLKLIMPARFYPNLTKYLPLDKGIK
PYYPEHAVNHYFKTRHYLHTLWKAGILYKRETTRSASFCGSPYSWEQE
LQHGRLVFQTSTRHGDESFCSQSSGILSRSPVGPCVRSQLKQSRLGLQ
PQQGSLARGKSGRSGSIRARVHPTTRRSFGVEPSGSGHIDNSASSTSS -continued CLHQSAVRKTAYSHLSTSKRQSSSGHAVELHNIPPSSARSQSEGPIFS
AWWLQFRNSKPASDYALTHIVNLLEDWGPATEHGEHNIRIPRTPARVT
GGVFLVDKNPHNTTESRLVVDFSQFSRGSTHVSWPKFAVPNLQSLTNL
LSSNLSTFGRKLHLYSHPIILGFRKIPMGVGLSPFLLAQFTSAICSVV
RRAFPHCLAFSYMDDVVLGAKSVQHLESLFTSITNFLLSLGIHLNPNK
TKRWGYSLNFMGYVIGSWGTLPQEHIVLKIKQCFRKLPVNRPIDWKVC
QRIVGLLGFAAPFTQCGYPALMPLYACIQSKQAFTFSPTYKAFLCKQY
LNLYPVARQRSGLCQVFADATPTGWGLAIGHRAMRGTFVAPLPIHTAE
LLAACFARSRSGAKLIGTDNSVVLSRKYTSFPWLLGCAANWILRGTSF
VYVPSALNPAADPSAGRLGLYRPLLHLPFRPTTGRTSLYAVSPSVPSH
LPDRVHFASPLHVAWRPPKSPNSNNPDWDFNPNKDHWPEANQVGAGAF
GPGFTPPHGGLLGWSPQAQGILTTVPAAPPPASTNRQSGRQPTPISPP
LRDSHPQAMQWNSTTFHQALLDPRVRGLYFPAGGSSSGTVNPVPTTAS
PISSIFSRTGDPAPNGSKGKRKRRAPVKQTLNFDLLKLAGDVESNPGP
MGGWSSKPRQGMGTNLSVPNPLGFFPDHQLDPAFGANSNNPDWDFNPN
KDHWPEANQVGLEGGSGGMENTTSGFLGPLLVLQAGFFLLTRILTIPQ
SLDSWWTSLNFLGGAPTCPGQNSQSPTSNHSPTSCPPICPGYRWMCLR
RFIIFLFILLLCLIFLLVLLDYQGMLPVCPLLPGTSTTSTGPCKTCTI
PAQGTSMFPSCCCTKPSDGNCTCIPIPSSWAFARFLWEWASVRFSWLS
LLVPFVQWFVGLSPTVWLSVIWMMWYWGPSLYNILSPFLPLLPIFFCL
WVYI 4.3. SIi-HBV-CP$_{mut}$PreS-S(sh): Description for amino acid sequences of HBV immunogen 4.3.1. First amino acid of polypeptide = M 4.3.2. Shark Invariant chain (SIi) =

(SEQ ID NO: 4)
SLLWGGVTVLAAMLIAGQVASVVFLV 4.3.3. Linker =

(SEQ ID NO: 5)
KGGGPGGG

4.3.4. C =

4.3.4.1. PreCore =

(SEQ ID NO: 16)
MQLFHLCLIISCSCPTVQASKLCLGWLWG 4.3.4.2. Core =

(SEQ ID NO: 6)
MDIDPYKEFGASVELLSFLPSDFFPSIRDLLDTASALYREALESPEHC
SPHHTALRQAILCWGELMNLATWVGSNLEDPASRELVVSYVNVNMGLK
IRQLLWFHISCLTFGRETVLEYLVSFGVWIRTPPAYRPPNAPILSTLP
ETTVVRRRGRSPRRRTPSPRRRRSQSPRRRRSQSRESQC 4.3.5. Linker =

(SEQ ID NO: 7)
GGGSGGG

4.3.6. Pmut = (mutations: Y63A, C323A, C334A, C338A, C352A, R714A, D788A, R792A)

(SEQ ID NO: 8)
MPLSYQHFRKLLLLDDEAGPLEEELPRLADEGLNRRVAEDLNLGNLNV
SIPWTHKVGNFTGLASSTVPVFNPEWQTPSFPHIHLQEDIINRCQQYV

-continued

GPLTVNEKRRLKLIMPARFYPNLTKYLPLDKGIKPYYPEHAVNHYFKT

RHYLHTLWKAGILYKRETTRSASFCGSPYSWEQELQHGRLVFQTSTRH

GDESFCSQSSGILSRSPVGPCVRSQLKQSRLGLQPQQGSLARGKSGRS

GSIRARVHPTTRRSFGVEPSGSGHIDNSASSTSSCLHQSAVRKTAYSH

LSTSKRQSSSGHAVELHNIPPSSARSQSEGPIFSAWWLQFRNSKPASD

YALTHIVNLLEDWGPATEHGEHNIRIPRTPARVTGGVFLVDKNPHNTT

ESRLVVDFSQFSRGSTHVSWPKFAVPNLQSLTNLLSSNLSTFGRKLHL

YSHPIILGFRKIPMGVGLSPFLLAQFTSAICSVVRRAFPHCLAFSYMD

DVVLGAKSVQHLESLFTSITNFLLSLGIHLNPNKTKRWGYSLNFMGYV

IGSWGTLPQEHIVLKIKQCFRKLPVNRPIDWKVCQRIVGLLGFAAPFT

QCGYPALMPLYACIQSKQAFTFSPTYKAFLCKQYLNLYPVARQRSGLC

QVFADATPTGWGLAIGHRAMRGTFVAPLPIHTAELLAACFARSRSGAK

LIGTDNSVVLSRKYTSFPWLLGCAANWILRGTSFVYVPSALNPAADPS

AGRLGLYRPLLHLPFRPTTGRTSLYAVSPSVPSHLPDRVHFASPLHVA

WRPP 4.3.7. Linker =

KSP

4.3.8. NΔPreS1 and PreS2 =

(SEQ ID NO: 15)

NSNNPDWDFNPNKDHWPEANQVGAGAFGPGFTPPHGGLLGWSPQAQGI

LTTVPAAPPPASTNRQSGRQPTPISPPLRDSHPQAMQWNSTTFHQALL

DPRVRGLYFPAGGSSSGTVNPVPTTASPISSIFSRTGDPAPN 4.3.9. Linker =

(SEQ ID NO: 20)

GSKGK

4.3.10. Furin 2A (F2A) =

(SEQ ID NO: 9)

RKRRAPVKQTLNFDLLKLAGDVESNPGP

4.3.11. S(sh) =

4.3.11.1. CΔPreS1 =

(SEQ ID NO: 21)

MGGWSSKPRQGMGTNLSVPNPLGFFPDHQLDPAFGANSNNPDWDFNPN

KDHWPEANQVG 4.3.11.2. Linker =

(SEQ ID NO: 22)

LEGGSGG

4.3.11.3. Surface (S) =

(SEQ ID NO: 18)

MENTTSGFLGPLLVLQAGFFLLTRILTIPQSLDSWWTSLNFLGGAPTC

PGQNSQSPTSNHSPTSCPPICPGYRWMCLRRFIIFLFILLLCLIFLLV

LLDYQGMLPVCPLLPGTSTTSTGPCKTCTIPAQGTSMFPSCCCTKPSD

GNCTCIPIPSSWAFARFLWEWASVRFSWLSLLVPFVQWFVGLSPTVWL

SVIWMMWYWGPSLYNILSPFLPLLPIFFCLWVYI

The SIi-HBV-CPmutPreS-S(sh) nucleotide sequence is provided as SEQ ID NO: 48.

5. MVA-SIi-HBV-PreS-$P_{mut}$-C-S(sh)

5.1. MVA-SIi-HBV-PreS-$P_{mut}$-C-S(Sh): Immunogen Layout is Shown in FIG.

5.2. MVA-SIi-HBV-PreS-$P_{mut}$-C-S(sh): Amino acid sequence (SEQ ID NO: 23)

MSLLWGGVTVLAAMLIAGQVASVVFLVSKSGPPSGKSNSNNPDWDFNP

NKDHWPEANQVGAGAFGPGFTPPHGGLLGWSPQAQGILTTVPAAPPPA

STNRQSGRQPTPISPPLRDSHPQAMQWNSTTFHQALLDPRVRGLYFPA

GGSSSGTVNPVPTTASPISSIFSRTGDPAPNGSKSGSKMPLSYQHFRK

LLLLDDEAGPLEEELPRLADEGLNRRVAEDLNLGNLNVSIPWTHKVGN

FTGLASSTVPVFNPEWQTPSFPHIHLQEDIINRCQQYVGPLTVNEKRR

LKLIMPARFYPNLTKYLPLDKGIKPYYPEHAVNHYFKTRHYLHTLWKA

GILYKRETTRSASFCGSPYSWEQELQHGRLVFQTSTRHGDESFCSQSS

GILSRSPVGPCVRSQLKQSRLGLQPQQGSLARGKSGRSGSIRARVHPT

TRRSFGVEPSGSGHIDNSASSTSSCLHQSAVRKTAYSHLSTSKRQSSS

GHAVELHNIPPSSARSQSEGPIFSAWWLQFRNSKPASDYALTHIVNLL

EDWGPATEHGEHNIRIPRTPARVTGGVFLVDKNPHNTTESRLVVDFSQ

FSRGSTHVSWPKFAVPNLQSLTNLLSSNLSWLSLDVSAAFYHIPLHPA

AMPHLLVGSSGLPRYVARLSSTSRNINYQHGTMQDLHDSCSRNLYVSL

LLLYKTFGRKLHLYSHPIILGFRKIPMGVGLSPFLLAQFTSAICSVVR

RAFPHCLAFSYMDDVVLGAKSVQHLESLFTSITNFLLSLGIHLNPNKT

KRWGYSLNFMGYVIGSWGTLPQEHIVLKIKQCFRKLPVNRPIDWKVCQ

RIVGLLGFAAPFTQCGYPALMPLYACIQSKQAFTFSPTYKAFLCKQYL

NLYPVARQRSGLCQVFADATPTGWGLAIGHRAMRGTFVAPLPIHTAEL

LAACFARSRSGAKLIGTDNSVVLSRKYTSFPWLLGCAANWILRGTSFV

YVPSALNPAADPSAGRLGLYRPLLHLPFRPTTGRTSLYAVSPSVPSHL

PDRVHFASPLHVAWRPPSKSPGSGPPMQLFHLCLIISCSCPTVQASKL

CLGWLWGMDIDPYKEFGASVELLSFLPSDFFPSIRDLLDTASALYREA

LESPEHCSPHHTALRQAILCWGELMNLATWVGSNLEDPASRELVVSYV

NVNMGLKIRQLLWFHISCLTFGRETVLEYLVSFGVWIRTPPAYRPPNA

PILSTLPETTVVRRRGRSPRRRTPSPRRRRSQSPRRRRSQSRESQC

MGGWSSKPRQGMGTNLSVPNPLGFFPDHQLDPAFGANSNNPDWDFNPN

KDHWPEANQVGASKGGKSGMENTTSGFLGPLLVLQAGFFLLTRILTIP

QSLDSWWTSLNFLGGAPTCPGQNSQSPTSNHSPTSCPPICPGYRWMCL

RRFIIFLFILLLCLIFLLVLLDYQGMLPVCPLLPGTSTTSTGPCKTCT

IPAQGTSMFPSCCCTKPSDGNCTCIPIPSSWAFARFLWEWASVRFSWL

SLLVPFVQWFVGLSPTVWLSVIWMMWYWGPSLYNILSPFLPLLPIFFC

LWVYI

-continued 5.3. MVA-SIi-HBV-PreS-$P_{mut}$-C-S(sh): Description for amino acid sequences of HBV immunogen 5.3.1.1. First amino acid of polypeptide = M 5.3.1.2. Shark Invariant chain (SIi) =

(SEQ ID NO: 4)
SLLWGGVTVLAAMLIAGQVASVVFLV 5.3.1.3. Linker =

(SEQ ID NO: 31)
SKSGPPSGKS

5.3.1.4. NΔPreS1 and PreS2 =

(SEQ ID NO: 15)
NSNNPDWDFNPNKDHWPEANQVGAGAFGPGFTPPHGGLLGWSPQAQGI

LTTVPAAPPPASTNRQSGRQPTPISPPLRDSHPQAMQWNSTTFHQALL

DPRVRGLYFPAGGSSSGTVNPVPTTASPISSIFSRTGDPAPN 5.3.1.5. Linker =

(SEQ ID NO: 32)
GSKSGSK

5.3.1.6. Pmut = (mutations: Y63A, C323A, C334A, C338A, C352A, R714A, D788A, R792A)

(SEQ ID NO: 8)
MPLSYQHFRKLLLLDDEAGPLEEELPRLADEGLNRRVAEDLNLGNLNV

SIPWTHKVGNFTGLASSTVPVFNPEWQTPSFPHIHLQEDIINRCQQYV

GPLTVNEKRRLKLIMPARFYPNLTKYLPLDKGIKPYYPEHAVNHYFKT

RHYLHTLWKAGILYKRETTRSASFCGSPYSWEQELQHGRLVFQTSTRH

GDESFCSQSSGILSRSPVGPCVRSQLKQSRLGLQPQQGSLARGKSGRS

GSIRARVHPTTRRSFGVEPSGSGHIDNSASSTSSCLHQSAVRKTAYSH

LSTSKRQSSSGHAVELHNIPPSSARSQSEGPIFSAWWLQFRNSKPASD

YALTHIVNLLEDWGPATEHGEHNIRIPRTPARVTGGVFLVDKNPHNTT

ESRLVVDFSQFSRGSTHVSWPKFAVPNLQSLTNLLSSNLSTFGRKLHL

YSHPIILGFRKIPMGVGLSPFLLAQFTSAICSVVRRAFPHCLAFSYMD

DVVLGAKSVQHLESLFTSITNFLLSLGIHLNPNKTKRWGYSLNFMGYV

IGSWGTLPQEHIVLKIKQCFRKLPVNRPIDWKVCQRIVGLLGFAAPFT

QCGYPALMPLYACIQSKQAFTFSPTYKAFLCKQYLNLYPVARQRSGLC

QVFADATPTGWGLAIGHRAMRGTFVAPLPIHTAELLAACFARSRSGAK

LIGTDNSVVLSRKYTSFPWLLGCAANWILRGTSFVYVPSALNPAADPS

AGRLGLYRPLLHLPFRPTTGRTSLYAVSPSVPSHLPDRVHFASPLHVA

WRPP 5.3.1.7. Linker =

(SEQ ID NO: 33)
SKSPGSGPP

5.3.1.8. C =

5.3.1.8.1. PreCore (SEQ ID NO: 16)
MQLFHLCLIISCSCPTVQASKLCLGWLWG 5.3.1.8.2. Core =

(SEQ ID NO: 6)
MDIDPYKEFGASVELLSFLPSDFFPSIRDLLDTASALYREALESPEHC

SPHHTALRQAILCWGELMNLATWVGSNLEDPASRELVVSYVNVNMGLK

-continued

IRQLLWFHISCLTFGRETVLEYLVSFGVWIRTPPAYRPPNAPILSTLP

ETTVVRRRGRSPRRRTPSPRRRRSQSPRRRRSQSRESQC 5.3.1.9. S(sh)

5.3.1.9.1. CΔPreS1 =
MGGWSSKPRQGMGTNLSVPNPLGFFPDHQLDPAFGANSNNPDWDFNPN

KDHWPEANQVG 5.3.1.9.2. Linker =

(SEQ ID NO: 34)
ASKGGKSG

5.3.1.9.3. Surface =

(SEQ ID NO: 18)
MENTTSGFLGPLLVLQAGFFLLTRILTIPQSLDSWWTSLNFLGGAPTC

PGQNSQSPTSNHSPTSCPPICPGYRWMCLRRFIIFLFILLLCLIFLLV

LLDYQGMLPVCPLLPGTSTTSTGPCKTCTIPAQGTSMFPSCCCTKPSD

GNCTCIPIPSSWAFARFLWEWASVRFSWLSLLVPFVQWFVGLSPTVWL

SVIWMMWYWGPSLYNILSPFLPLLPIFFCLWVYI 5.4. Nucleotide sequence of MVA-SIi-HBV-PreS-$P_{mut}$-C-S(sh) is provided as SEQ ID NO: 24.

5.5. Description for nucleotide sequences of MVA-SIi-HBV-PreS-$P_{mut}$-C-S(sh):

5.5.1. F11-L-Flank = bases 1-1097 (SEQ ID NO: 35)

5.5.2. SIi-HBV-PreS-$P_{mut}$-C = bases 1098-4838 (SEQ ID NO: 37)

5.5.3. Transcription terminator sequence = bases 4839-4845
TTTTTGT 5.5.4. mH5 promoter = bases 4846-4942 (SEQ ID NO: 28)

5.5.5. S(sh) = bases 4943-5824 (SEQ ID NO: 38)

5.5.6. F11-R-Flank = bases 5825-7143 (SEQ ID NO: 36)

6. SIi-HBV-CPQ$_{mut}$PreS-TPA-S(sh)

Figure 10F:
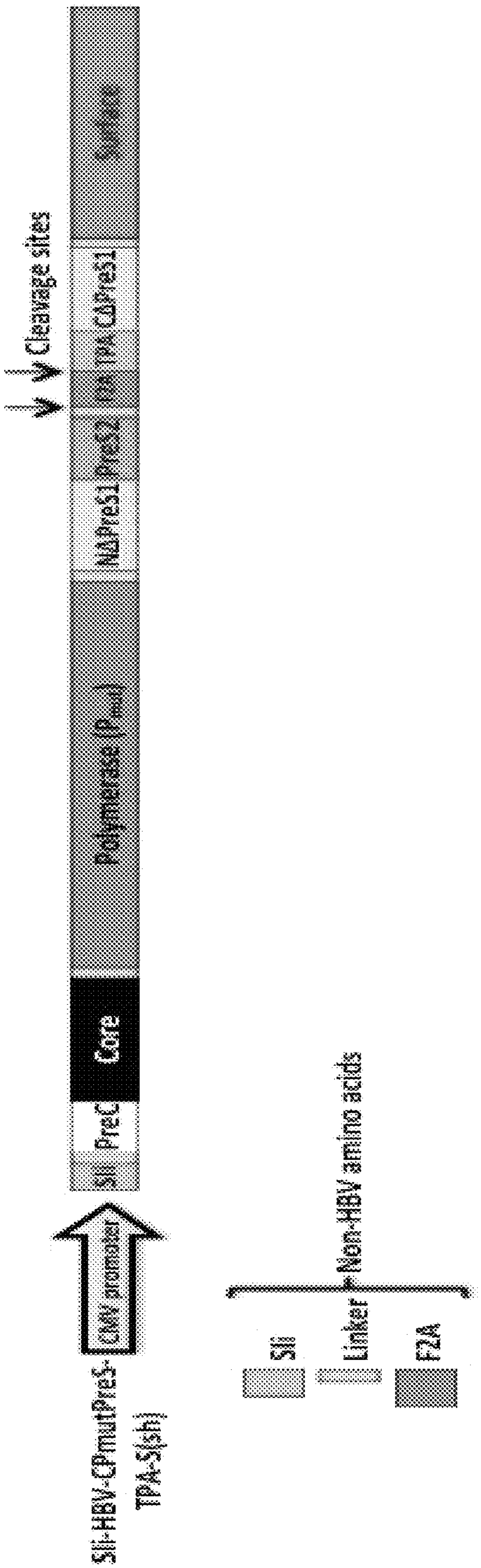

6.1. SIi-HBV-CP$_{mut}$PreS-TPA-S(Sh): Immunogen Layout is Shown in FIG. 10F 6.2. SIi-HBV-CP$_{mut}$PreS-TPA-S(sh): Amino acid sequence (SEQ ID NO: 25)
MSLLWGGVTVLAAMLIAGQVASVVFLVKGGGPGGGMQLFHLCLIISCS

CPTVQASKLCLGWLWGMDIDPYKEFGASVELLSFLPSDFFPSIRDLLD

TASALYREALESPEHCSPHHTALRQAILCWGELMNLATWVGSNLEDPA

SRELVVSYVNVNMGLKIRQLLWFHISCLTFGRETVLEYLVSFGVWIRT

PPAYRPPNAPILSTLPETTVVRRRGRSPRRRTPSPRRRRSQSPRRRRS

QSRESQCGGGSGGGMPLSYQHFRKLLLLDDEAGPLEEELPRLADEGLN

RRVAEDLNLGNLNVSIPWTHKVGNFTGLASSTVPVFNPEWQTPSFPHI

HLQEDIINRCQQYVGPLTVNEKRRLKLIMPARFYPNLTKYLPLDKGIK

PYYPEHAVNHYFKTRHYLHTLWKAGILYKRETTRSASFCGSPYSWEQE

LQHGRLVFQTSTRHGDESFCSQSSGILSRSPVGPCVRSQLKQSRLGLQ

-continued

PQQGSLARGKSGRSGSIRARVHPTTRRSFGVEPSGSGHIDNSASSTSS
CLHQSAVRKTAYSHLSTSKRQSSSGHAVELHNIPPSSARSQSEGPIFS
AWWLQFRNSKPASDYALTHIVNLLEDWGPATEHGEHNIRIPRTPARVT
GGVFLVDKNPHNTTESRLVVDFSQFSRGSTHVSWPKFAVPNLQSLTNL
LSSNLSTFGRKLHLYSHPIILGFRKIPMGVGLSPFLLAQFTSAICSVV
RRAFPHCLAFSYMDDVVLGAKSVQHLESLFTSITNFLLSLGIHLNPNK
TKRWGYSLNFMGYVIGSWGTLPQEHIVLKIKQCFRKLPVNRPIDWKVC
QRIVGLLGFAAPFTQCGYPALMPLYACIQSKQAFTFSPTYKAFLCKQY
LNLYPVARQRSGLCQVFADATPTGWGLAIGHRAMRGTFVAPLPIHTAE
LLAACFARSRSGAKLIGTDNSVVLSRKYTSFPWLLGCAANWILRGTSF
VYVPSALNPAADPSAGRLGLYRPLLHLPFRPTTGRTSLYAVSPSVPSH
LPDRVHFASPLHVAWRPPKSPNSNNPDWDFNPNKDHWPEANQVGAGAF
GPGFTPPHGGLLGWSPQAQGILTTVPAAPPPASTNRQSGRQPTPISPP
LRDSHPQAMQWNSTTFHQALLDPRVRGLYFPAGGSSSGTVNPVPTTAS
PISSIFSRTGDPAPNGSKGKRKRRAPVKQTLNFDLLKLAGDVESNPGP
MDAMKRGLCCVLLLCGAVFVSPSQEIHARFRRMGGWSSKPRQGMGTNL
SVPNPLGFFPDHQLDPAFGANSNNPDWDFNPNKDHWPEANQVGLEGGS
GGMENTTSGFLGPLLVLQAGFFLLTRILTIPQSLDSWWTSLNFLGGAP
TCPGQNSQSPTSNHSPTSCPPICPGYRWMCLRRFIIFLFILLLCLIFL
LVLLDYQGMLPVCPLLPGTSTTSTGPCKTCTIPAQGTSMFPSCCCTKP
SDGNCTCIPIPSSWAFARFLWEWASVRFSWLSLLVPFVQWFVGLSPTV
WLSVIWMMWYWGPSLYNILSPFLPLLPIFFCLWVYI 6.3. SIi-HBV-$CP_{mut}$PreS-TPA-S(sh): Description for amino acid sequences of HBV immunogen 6.3.1. First amino acid of polypeptide = M 6.3.2. Shark Invariant chain (SIi) = (SEQ ID NO: 4)

SLLWGGVTVLAAMLIAGQVASVVFLV 6.3.3. Linker = (SEQ ID NO: 5)

KGGGPGGG

6.3.4. C =

6.3.4.1. PreCore (SEQ ID NO: 16)

MQLFHLCLIISCSCPTVQASKLCLGWLWG 6.3.4.2. Core = (SEQ ID NO: 6)

MDIDPYKEFGASVELLSFLPSDFFPSIRDLLDTASALYREALESPEHC
SPHHTALRQAILCWGELMNLATWVGSNLEDPASRELVVSYVNVNMGLK
IRQLLWFHISCLTFGRETVLEYLVSFGVWIRTPPAYRPPNAPILSTLP
ETTVVRRRGRSPRRRTPSPRRRRSQSPRRRRSQSRESQC 6.3.5. Linker = (SEQ ID NO: 7)

GGGSGGG

-continued 6.3.6. Pmut = (mutations: Y63A, C323A, C334A, C338A, C352A, R714A, D788A, R792A) (SEQ ID NO: 8)

MPLSYQHFRKLLLLDDEAGPLEEELPRLADEGLNRRVAEDLNLGNLNV
SIPWTHKVGNFTGLASSTVPVFNPEWQTPSFPHIHLQEDIINRCQQYV
GPLTVNEKRRLKLIMPARFYPNLTKYLPLDKGIKPYYPEHAVNHYFKT
RHYLHTLWKAGILYKRETTRSASFCGSPYSWEQELQHGRLVFQTSTRH
GDESFCSQSSGILSRSPVGPCVRSQLKQSRLGLQPQQGSLARGKSGRS
GSIRARVHPTTRRSFGVEPSGSGHIDNSASSTSSCLHQSAVRKTAYSH
LSTSKRQSSSGHAVELHNIPPSSARSQSEGPIFSAWWLQFRNSKPASD
YALTHIVNLLEDWGPATEHGEHNIRIPRTPARVTGGVFLVDKNPHNTT
ESRLVVDFSQFSRGSTHVSWPKFAVPNLQSLTNLLSSNLSTFGRKLHL
YSHPIILGFRKIPMGVGLSPFLLAQFTSAICSVVRRAFPHCLAFSYMD
DVVLGAKSVQHLESLFTSITNFLLSLGIHLNPNKTKRWGYSLNFMGYV
IGSWGTLPQEHIVLKIKQCFRKLPVNRPIDWKVCQRIVGLLGFAAPFT
QCGYPALMPLYACIQSKQAFTFSPTYKAFLCKQYLNLYPVARQRSGLC
QVFADATPTGWGLAIGHRAMRGTFVAPLPIHTAELLAACFARSRSGAK
LIGTDNSVVLSRKYTSFPWLLGCAANWILRGTSFVYVPSALNPAADPS
AGRLGLYRPLLHLPFRPTTGRTSLYAVSPSVPSHLPDRVHFASPLHVA
WRPP 6.3.7. Linker =
KSP

6.3.8. NΔPreS1 and PreS2 = (SEQ ID NO: 15)

NSNNPDWDFNPNKDHWPEANQVGAGAFGPGFTPPHGGLLGWSPQAQGI
LTTVPAAPPPASTNRQSGRQPTPISPPLRDSHPQAMQWNSTTFHQALL
DPRVRGLYFPAGGSSSGTVNPVPTTASPISSIFSRTGDPAPN 6.3.9. Linker = (SEQ ID NO: 20)

GSKGK

6.3.10. Furin 2A (F2A) = (SEQ ID NO: 9)

RKRRAPVKQTLNFDLLKLAGDVESNPGP

6.3.11. TPA = (SEQ ID NO: 30)

MDAMKRGLCCVLLLCGAVFVSPSQEIHARFRR 6.3.12. S(sh) =

6.3.12.1. CΔPreS1 = (SEQ ID NO: 21)

MGGWSSKPRQGMGTNLSVPNPLGFFPDHQLDPAFGANSNNPDWDFNPN
KDHWPEANQVG 6.3.12.2. Linker = (SEQ ID NO: 22)

LEGGSGG

6.3.12.3. Surface (S) = (SEQ ID NO: 18)

MENTTSGFLGPLLVLQAGFFLLTRILTIPQSLDSWWTSLNFLGGAPTC
PGQNSQSPTSNHSPTSCPPICPGYRWMCLRRFIIFLFILLLCLIFLLV
LLDYQGMLPVCPLLPGTSTTSTGPCKTCTIPAQGTSMFPSCCCTKPSD

-continued

```
GNCTCIPIPSSWAFARFLWEWASVRFSWLSLLVPFVQWFVGLSPTVWL
SVIWMMWYWGPSLYNILSPFLPLLPIFFCLWVYI
```

The SIi-HBV-CPmutPreS-TPA-S(sh) nucleotide sequence is provided as SEQ ID NO: 49.

7. MVA-SIi-HBV-PreS-P$_{mut}$-C-TPA-S(sh)

Figure 7:
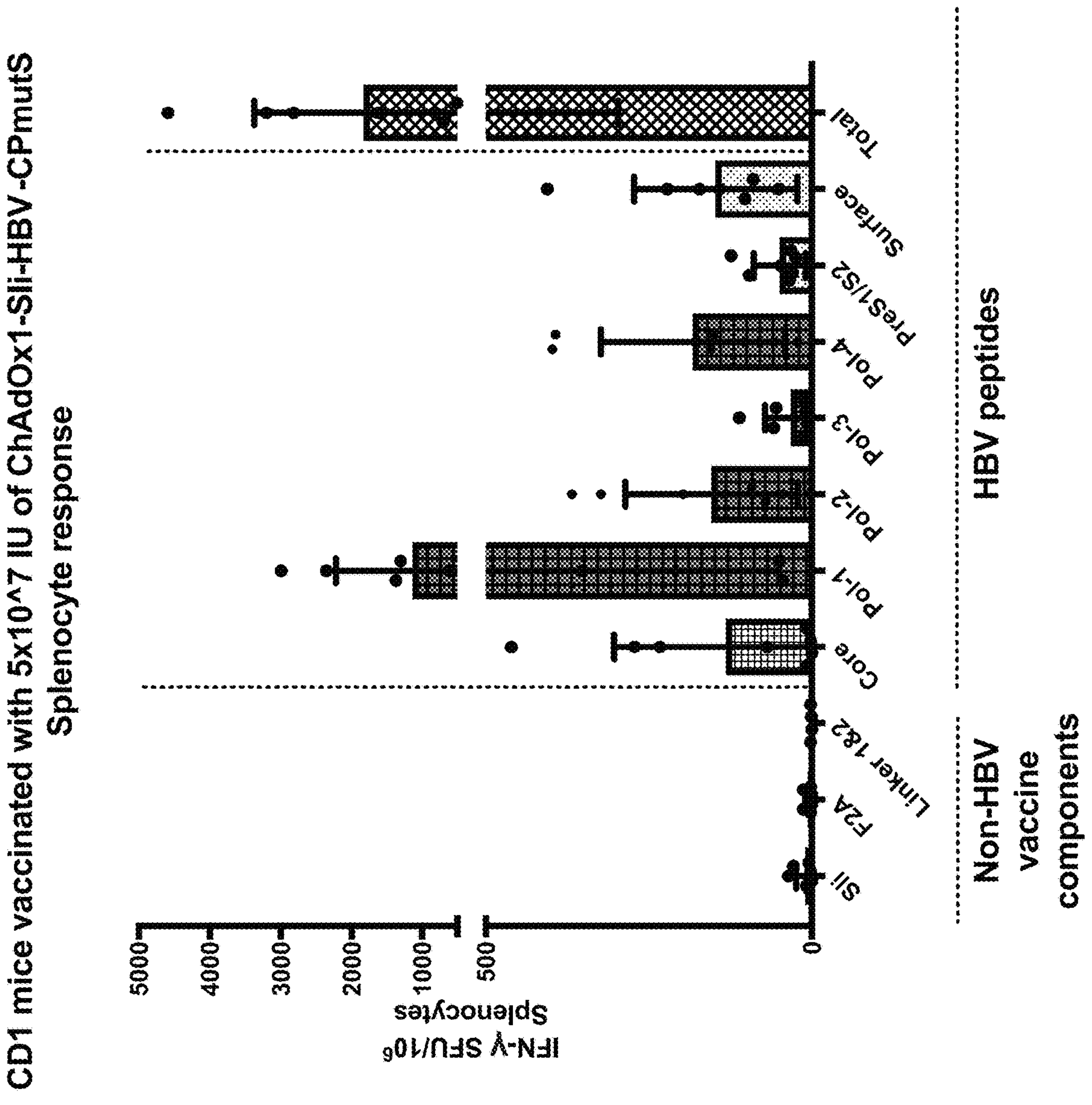
FIG. 7: Testing ChAdOx1-SIi-HBV-CPmutS vaccine in BALB/c mice, splenocyte response: BALB/c mice (8 mice at the age of 8 weeks) were vaccinated by intramuscular injections with $5\times10^7$ IU per mice of ChAdOx1-SIi-HBV-CPmutS vaccine. 14 days post-vaccination, mice were sacrificed; splenocyte response data were generated, as described earlier. Splenocyte T-cell response for each peptide pool stimulus and pooled total response from all HBV-peptide pools are represented in the bar chart.
Figure 8:
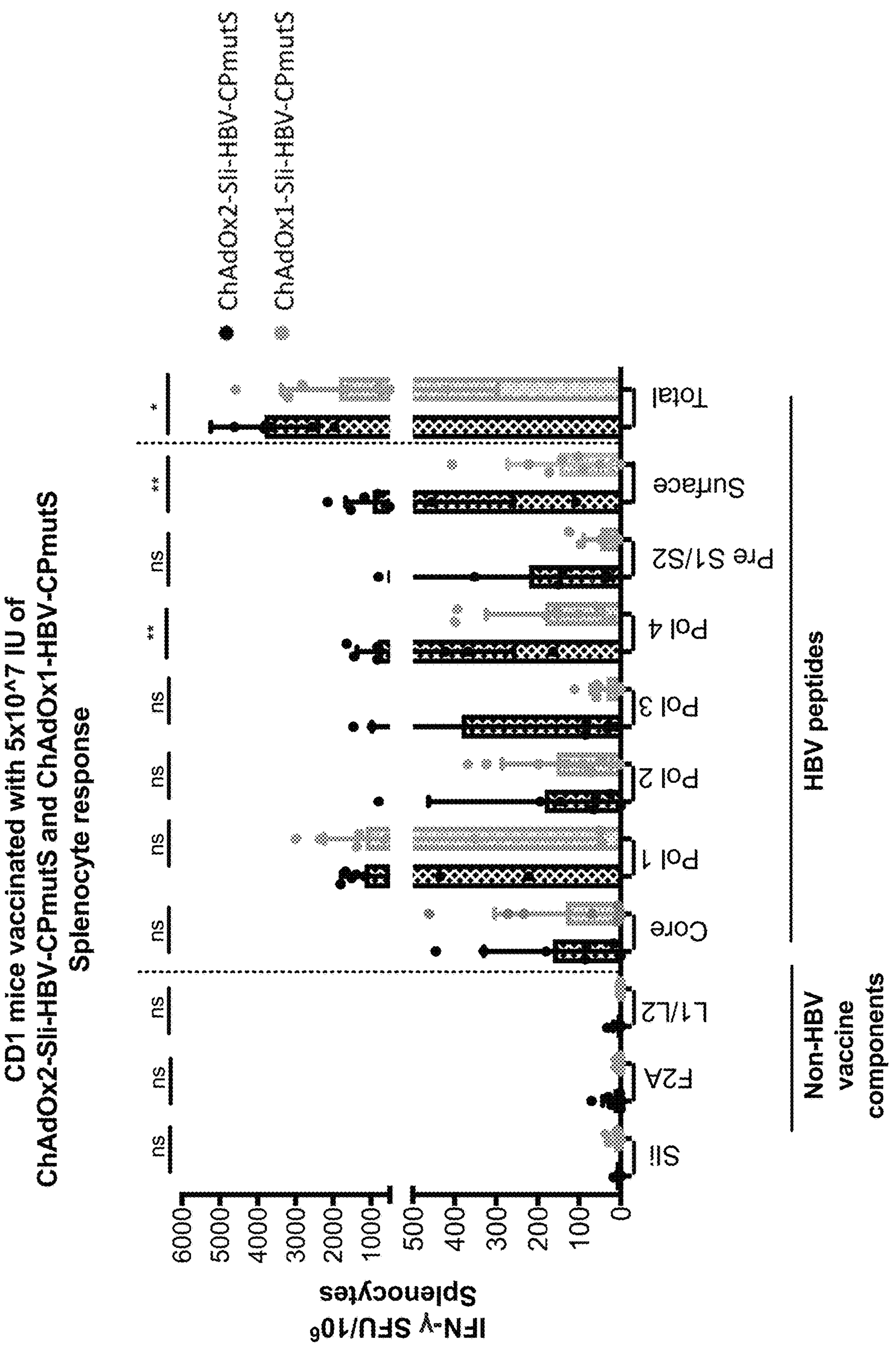
FIG. 8: Comparison of the immunogenicity of HBV immunogen SIi-HBV-CPmutS encoded via ChAdOx1 and ChAdOx2. HBV-CPmutS immunogen encoding ChAdOx1 and ChAdOx2 viral vectored vaccines were generated, as previously described (FIG. 2D). 10 CD1 mice at age of 7 weeks and 8 CD1 mice at age of 8 weeks were vaccinated by intramuscular injections with $5\times10^7$ IU per mice of ChAdOx2-HBV-CPmutS and ChAdOx1-HBV-CPmutS vaccine, respectively, and 14 days post-vaccination mice were sacrificed and splenocyte response data were generated, as described earlier. Data from 10 and 8 CD1 mice vaccinated with ChAdOx2-SIi-HBV-CPmutS and ChAdOx1-HBV-CPmutS were compared and represented in charts for ease of comparison. A statistically significant higher magnitude of total splenocyte T-cell response was observed in mice vaccinated with ChAdOx2-HBV-CPmutS vaccine, compared to the ChAdOx1-HBV-CPmutS vaccine.
Figure 9:
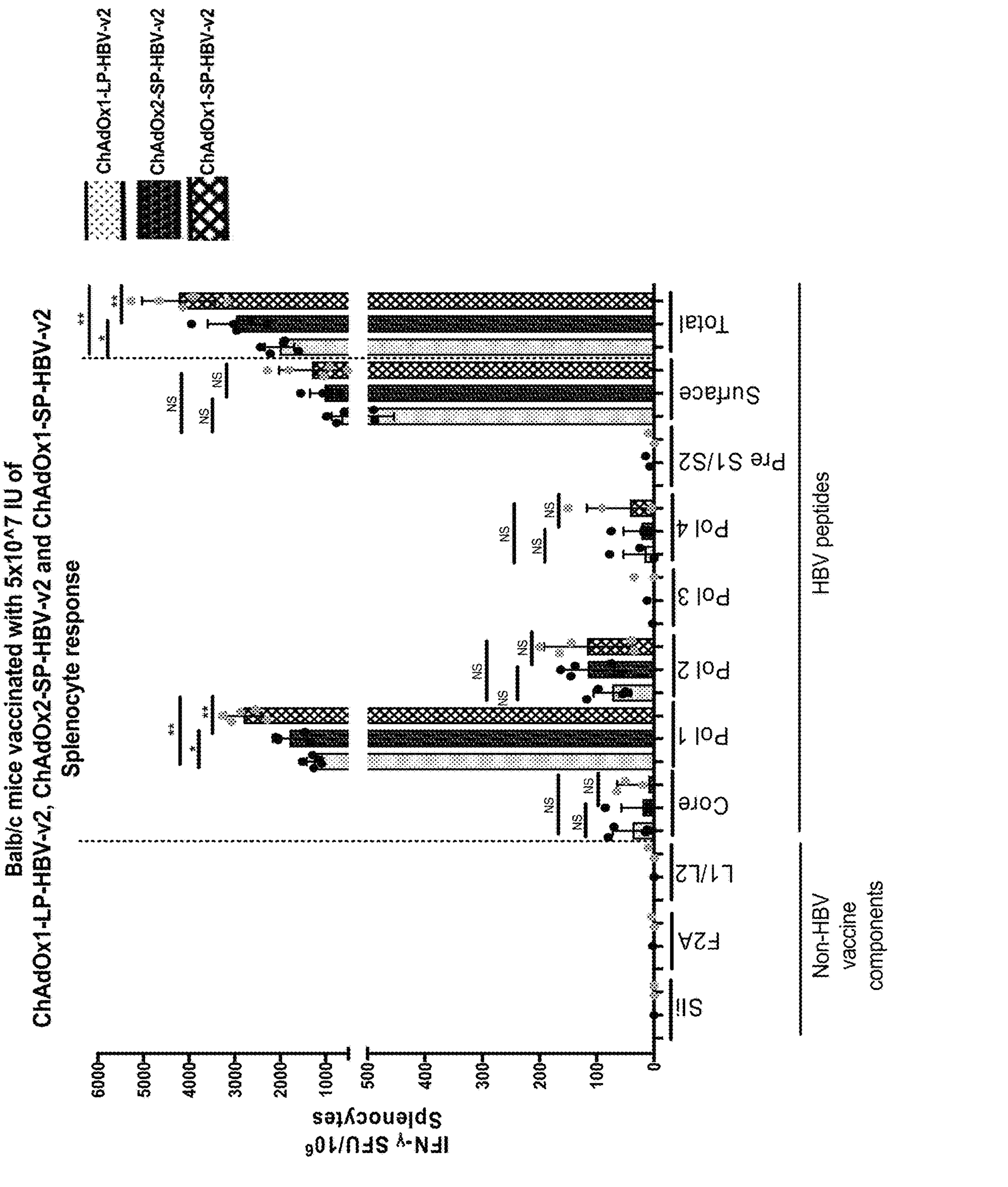
FIG. 9: Comparison of the immunogenicity of HBV immunogen SIi-HBV-CPmutPreS-S(sh) (termed as HBV-v2) encoded via ChAdOx1 and ChAdOx2 viral vectors using either a short CMV promoter or long CMV promoter. Two short CMV promoter and one long CMV promoter based SIi-HBV-CPmutPreS-S(sh) immunogen (termed as HBV-v2) encoding ChAdOx1 (ChAdOx1-LP-HBV-v2 and ChAdOx1-SP-HBV-v2) and ChAdOx2 (ChAdOx2-SP-HBV-v2) vaccines were generated as previously described. 15 Balbc mice at age of 8 weeks were split into 3 groups (5 mice per group) and vaccinated by intramuscular injections with $5\times10^7$ IU of ChAdOx1-SP-HBV-v2 or ChAdOx2-SP-HBV-v2 or ChAdOx1-LP-HBV-v2 vaccine. 14 days post-vaccination mice were sacrificed and splenocyte response data were generated as previously described. Comparative data from all three HBV-v2 vaccines are represented in the same chart for ease of comparison. A statistically significant higher magnitude of total splenocyte T-cell response was observed in mice vaccinated with ChAdOx1-SP-HBV-v2 vaccine, compared to the other two HBV-v2 vaccines. In addition, the ChAdOx2-SP-HBV-v2 vaccine showed a statistically significant higher magnitude of total splenocyte T-cell response compared to the ChAdOx1-LP-HBV-v2 vaccine.
Figure 10G:
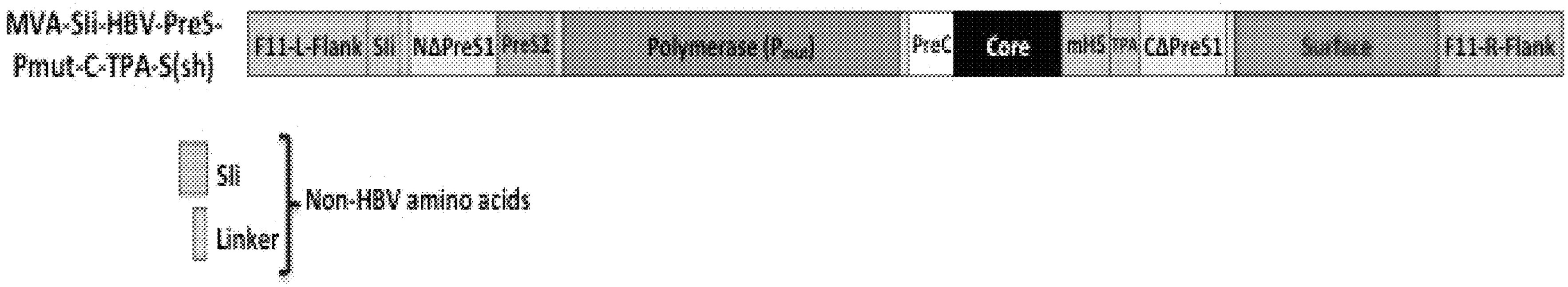

7.1. MVA-SIi-HBV-PreS-P$_{mut}$-C-TPA-S(Sh): Immunogen Layout is Shown in FIG. 10G 7.2. MVA-SIi-HBV-PreS-P$_{mut}$-C-TPA-S(sh): Amino acid sequence (SEQ ID NO: 26)

MSLLWGGVTVLAAMLIAGQVASVVFLVSKSGPPSGKSNSNNPDWDFNP
NKDHWPEANQVGAGAFGPGFTPPHGGLLGWSPQAQGILTTVPAAPPPA
STNRQSGRQPTPISPPLRDSHPQAMQWNSTTFHQALLDPRVRGLYFPA
GGSSSGTVNPVPTTASPISSIFSRTGDPAPNGSKSGSKMPLSYQHFRK
LLLLDDEAGPLEEELPRLADEGLNRRVAEDLNLGNLNVSIPWTHKVGN
FTGLASSTVPVFNPEWQTPSFPHIHLQEDIINRCQQYVGPLTVNEKRR
LKLIMPARFYPNLTKYLPLDKGIKPYYPEHAVNHYFKTRHYLHTLWKA
GILYKRETTRSASFCGSPYSWEQELQHGRLVFQTSTRHGDESFCSQSS
GILSRSPVGPCVRSQLKQSRLGLQPQQGSLARGKSGRSGSIRARVHPT
TRRSFGVEPSGSGHIDNSASSTSSCLHQSAVRKTAYSHLSTSKRQSSS
GHAVELHNIPPSSARSQSEGPIFSAWWLQFRNSKPASDYALTHIVNLL
EDWGPATEHGEHNIRIPRTPARVTGGVFLVDKNPHNTTESRLVVDFSQ
FSRGSTHVSWPKFAVPNLQSLTNLLSSNLSWLSLDVSAAFYHIPLHPA
AMPHLLVGSSGLPRYVARLSSTSRNINYQHGTMQDLHDSCSRNLYVSL
LLLYKTFGRKLHLYSHPIILGFRKIPMGVGLSPFLLAQFTSAICSVVR
RAFPHCLAFSYMDDVVLGAKSVQHLESLFTSITNFLLSLGIHLNPNKT
KRWGYSLNFMGYVIGSWGTLPQEHIVLKIKQCFRKLPVNRPIDWKVCQ
RIVGLLGFAAPFTQCGYPALMPLYACIQSKQAFTFSPTYKAFLCKQYL
NLYPVARQRSGLCQVFADATPTGWGLAIGHRAMRGTFVAPLPIHTAEL
LAACFARSRSGAKLIGTDNSVVLSRKYTSFPWLLGCAANWILRGTSFV
YVPSALNPAADPSAGRLGLYRPLLHLPFRPTTGRTSLYAVSPSVPSHL
PDRVHFASPLHVAWRPPSKSPGSGPPMQLFHLCLIISCSCPTVQASKL
CLGWLWGMDIDPYKEFGASVELLSFLPSDFFPSIRDLLDTASALYREA
LESPEHCSPHHTALRQAILCWGELMNLATWVGSNLEDPASRELVVSYV
NVNMGLKIRQLLWFHISCLTFGRETVLEYLVSFGVWIRTPPAYRPPNA
PILSTLPETTVVRRRGRSPRRRTPSPRRRRSQSPRRRRSQSRESQCMD
AMKRGLCCVLLLCGAVFVSPSQEIHARFRRMGGWSSKPRQGMGTNLSV
PNPLGFFPDHQLDPAFGANSNNPDWDFNPNKDHWPEANQVGASKGGKS
GMENTTSGFLGPLLVLQAGFFLLTRILTIPQSLDSWWTSLNFLGGAPT
CPGQNSQSPTSNHSPTSCPPICPGYRWMCLRRFIIFLFILLLCLIFLL
VLLDYQGMLPVCPLLPGTSTTSTGPCKTCTIPAQGTSMFPSCCCTKPS
DGNCTCIPIPSSWAFARFLWEWASVRFSWLSLLVPFVQWFVGLSPTVW
LSVIWMMWYWGPSLYNILSPFLPLLPIFFCLWVYI

-continued 7.3. MVA-SIi-HBV-PreS-P$_{mut}$-C-TPA-S(sh): Description for amino acid sequences of HBV immunogen 7.3.1.1. First amino acid of polypeptide = M 7.3.1.2. Shark Invariant chain (SIi) =

(SEQ ID NO: 4)

SLLWGGVTVLAAMLIAGQVASVVFLV 7.3.1.3. Linker =

(SEQ ID NO: 31)

SKSGPPSGKS

7.3.1.4. NΔPreS1 and PreS2 =

(SEQ ID NO: 15)

NSNNPDWDFNPNKDHWPEANQVGAGAFGPGFTPPHGGLLGWSPQAQGI
LTTVPAAPPPASTNRQSGRQPTPISPPLRDSHPQAMQWNSTTFHQALL
DPRVRGLYFPAGGSSSGTVNPVPTTASPISSIFSRTGDPAPN 7.3.1.5. Linker =

(SEQ ID NO: 32)

GSKSGSK

7.3.1.6. Pmut = (mutations: Y63A, C323A, C334A, C338A, C352A, R714A, D788A, R792A)

(SEQ ID NO: 8)

MPLSYQHFRKLLLLDDEAGPLEEELPRLADEGLNRRVAEDLNLGNLNV
SIPWTHKVGNFTGLASSTVPVFNPEWQTPSFPHIHLQEDIINRCQQYV
GPLTVNEKRRLKLIMPARFYPNLTKYLPLDKGIKPYYPEHAVNHYFKT
RHYLHTLWKAGILYKRETTRSASFCGSPYSWEQELQHGRLVFQTSTRH
GDESFCSQSSGILSRSPVGPCVRSQLKQSRLGLQPQQGSLARGKSGRS
GSIRARVHPTTRRSFGVEPSGSGHIDNSASSTSSCLHQSAVRKTAYSH
LSTSKRQSSSGHAVELHNIPPSSARSQSEGPIFSAWWLQFRNSKPASD
YALTHIVNLLEDWGPATEHGEHNIRIPRTPARVTGGVFLVDKNPHNTT
ESRLVVDFSQFSRGSTHVSWPKFAVPNLQSLTNLLSSNLSTFGRKLHL
YSHPIILGFRKIPMGVGLSPFLLAQFTSAICSVVRRAFPHCLAFSYMD
DVVLGAKSVQHLESLFTSITNFLLSLGIHLNPNKTKRWGYSLNFMGYV
IGSWGTLPQEHIVLKIKQCFRKLPVNRPIDWKVCQRIVGLLGFAAPFT
QCGYPALMPLYACIQSKQAFTFSPTYKAFLCKQYLNLYPVARQRSGLC
QVFADATPTGWGLAIGHRAMRGTFVAPLPIHTAELLAACFARSRSGAK
LIGTDNSVVLSRKYTSFPWLLGCAANWILRGTSFVYVPSALNPAADPS
AGRLGLYRPLLHLPFRPTTGRTSLYAVSPSVPSHLPDRVHFASPLHVA
WRPP 7.3.1.7. Linker =

(SEQ ID NO: 33)

SKSPGSGPP

7.3.1.8. C =

7.3.1.8.1. PreCore =

(SEQ ID NO: 16)

MQLFHLCLIISCSCPTVQASKLCLGWLWG 7.3.1.8.2. Core =

(SEQ ID NO: 6)

MDIDPYKEFGASVELLSFLPSDFFPSIRDLLDTASALYREALESPEHC
SPHHTALRQAILCWGELMNLATWVGSNLEDPASRELVVSYVNVNMGLK

-continued

IRQLLWFHISCLTFGRETVLEYLVSFGVWIRTPPAYRPPNAPILSTLP

ETTVVRRRGRSPRRRTPSPRRRRSQSPRRRRSQSRESQC 7.3.1.9. TPA =

(SEQ ID NO: 30)

MDAMKRGLCCVLLLCGAVFVSPSQEIHARFRR 7.3.1.10. S(sh)_ =

7.3.1.10.1. CΔPreS1 =

(SEQ ID NO: 21)

MGGWSSKPRQGMGTNLSVPNPLGFFPDHQLDPAFGANSNNPDWDFNPN

KDHWPEANQVG 7.3.1.10.2. Linker =

(SEQ ID NO: 34)

ASKGGKSG

7.3.1.10.3. Surface (S) =

(SEQ ID NO: 18)

MENTTSGFLGPLLVLQAGFFLLTRILTIPQSLDSWWTSLNFLGGAPTC

PGQNSQSPTSNHSPTSCPPICPGYRWMCLRRFIIFLFILLLCLIFLLV

LLDYQGMLPVCPLLPGTSTTSTGPCKTCTIPAQGTSMFPSCCCTKPSD

GNCTCIPIPSSWAFARFLWEWASVRFSWLSLLVPFVQWFVGLSPTVWL

SVIWMMWYWGPSLYNILSPFLPLLPIFFCLWVYI 7.4. Nucleotide sequences of MVA-SIi-HBV-PreS-$P_{mut}$-C-TPA-S(sh) is provided as SEQ ID NO: 27

7.5. Description for nucleotide sequences of MVA-SIi-HBV-PreS-$P_{mut}$-C-TPA-S(sh):

7.5.1. F11-L-Flank = bases 1-1097 (SEQ ID NO: 35)

7.5.2. SIi-HBV-PreS-$P_{mut}$-C = bases 1098-4838 (SEQ ID NO: 37)

7.5.3. Transcription terminator sequence = bases 4839-4845
TTTTTGT 7.5.4. mH5 promoter = bases 4846-4942 (SEQ ID NO: 28)

7.5.5. TPA = bases 4943-5038 (SEQ ID NO: 29)

7.5.6. S(sh) = bases 5039-5920 (SEQ ID NO: 38)

7.5.7. F11-R-Flank = bases 5921-7239 (SEQ ID NO: 36)

8. Nucleotide sequences of low GC content version MVA-SIi-HBV-PreS-Pmut-C-TPA-S(sh) (SEQ ID NO: 58):

gtaatctattcgatataccgttgctaacagtatactggcccaataact gtggatggaaaatctataataatacattaatatcatccgatggtgcta gggttatttggatggatgcgtataaattttcttgcggtttatctttac aagactattgttatcattggggtagcaaaccagagagccgaccattcg atttaataaaaaaatcagatgctaaacgcaattctaaatcgttggtca aagaatctatggcatccttgaaatccttgtacgaggcattcgagacac aatcaggagcgttagaagttttaatgagtccatgtaggatgttttcgt tttctagaatagaagacatgttcttaactagtgtcattaatagagtat -continued ccgagaatactggaatggggatgtattatcctaccaacgatatacctt ctctatttatcgaatcatctatctgtctagattatattatagtaaata atcaggaatccaacaaatatcgtatcaaatctgttctcgatatcattt cttcaaaacaataccctgcaggacgtcccaactacgttaaaaatggta caaaaggaaagttatatatcgcgttgtgtaaagttaccgtacctacta acgaccatattccagtagtttatcacgatgatgacaatactaccacct ttattacagtattgacgtccgtcgatattgaaactgctatcagagcag gatattcgatagtcgaattaggggctttacaatgggataataatattc cagaacttaaaaacggtttactggatagtatcaagatgatttatgact tgaacgcagttacaacaaataatttattggaacagctcatagaaaata ttaactttaacaactctagtataatttcgttgttttatacatttgcca ttagttattgccgagcattcatttactcaattatggaaaccatagatc cggtgtatatatctcagttcagttataaagaattatacgttagtagct cttataaagatattaatgaatccatgagtcagatggtaaaattataaa aagtgaaaaacaatattatttttatcgttggttgttacactATGTCAC

TTCTTTGGGGCGGAGTTACAGTTCTTGCTGCTATGCTTATTGCTGGAC

AAGTTGCTTCTGTTGTGTTTCTTGTTTCTAAATCTGGACCTCCTTCTG

GAAAATCTAATTCTAACAATCCTGATTGGGATTTCAATCCTAACAAAG

ATCATTGGCCTGAAGCTAATCAAGTTGGAGCTGGTGCTTTTGGACCTG

GTTTTACACCTCCTCATGGTGGATTGCTTGGATGGTCACCTCAAGCTC

AGGGAATTCTTACAACAGTTCCAGCTGCTCCTCCTCCTGCTTCTACAA

ATAGACAATCTGGTAGACAACCTACACCTATTTCTCCACCTCTTAGAG

ATTCTCATCCTCAAGCTATGCAATGGAATTCTACTACATTTCATCAAG

CTTTGCTTGATCCTAGAGTTAGAGGACTTTATTTTCCTGCTGGTGGAA

GTTCTTCTGGAACAGTTAATCCTGTTCCTACAACAGCTTCTCCAATTT

CTTCTATATTTTCTAGAACAGGCGATCCTGCTCCTAATGGATCAAAAT

CTGGATCAAAAATGCCTCTGTCTTATCAACACTTTAGAAAATTGCTGC

TTCTTGATGATGAAGCTGGACCTCTTGAAGAAGAATTGCCTAGACTTG

CTGATGAAGGACTTAATAGAAGAGTTGCTGAAGATCTTAATCTGGGAA

ATCTTAATGTTTCTATTCCTTGGACACACAAAGTTGGAAATTTCACAG

GACTTGCATCTTCTACAGTGCCTGTTTTTAATCCTGAATGGCAAACAC

CTTCTTTTCCACATATTCATCTGCAAGAGGATATCATCAATAGATGTC

AACAATATGTTGGACCACTGACAGTTAATGAGAAGAGAAGGCTTAAAC

TTATTATGCCTGCTAGATTCTATCCTAATCTTACAAAGTATTTGCCTC

TGGATAAGGGAATCAAACCTTATTATCCTGAACATGCTGTGAATCACT

ACTTTAAAACAAGACATTATCTGCATACACTGTGGAAAGCTGGTATTC

TTTACAAAAGAGAAACAACAAGATCTGCTTCATTTTGTGGATCTCCAT

ATTCTTGGGAACAAGAACTTCAACATGGTAGACTTGTTTTTCAAACAT

CTACAAGACATGGGGATGAATCATTTTGTTCTCAAAGTTCTGGAATTC

TTTCTAGATCTCCTGTTGGACCTTGTGTTAGATCTCAACTTAAACAAT

CTAGACTTGGACTTCAACCTCAACAAGGATCTCTTGCTAGAGGAAAAA

-continued

GTGGAAGATCTGGATCTATTAGAGCTAGAGTTCATCCTACAACTAGAA

GATCTTTTGGAGTTGAACCTTCTGGATCTGGACATATTGATAATTCTG

CCTCTTCTACATCTTCTTGTCTGCATCAATCTGCTGTTAGAAAGACAG

CTTATTCTCATTTGTCTACTTCTAAGAGACAATCATCTTCTGGACATG

CTGTTGAACTTCATAATATTCCTCCAAGTAGTGCTAGAAGTCAATCTG

AAGGACCAATATTTTCAGCTTGGTGGCTTCAATTCAGAAATTCTAAAC

CTGCTTCTGATTATGCTCTGACACATATAGTTAATTTGCTTGAAGATT

GGGGACCTGCTACAGAACATGGCGAACACAATATTAGAATACCTAGAA

CTCCTGCTAGAGTTACAGGCGGAGTCTTTTTGGTTGATAAGAATCCTC

ATAATACCACAGAATCAAGACTTGTTGTTGATTTTTCACAGTTTTCTA

GAGGATCTACACATGTTTCTTGGCCTAAATTTGCTGTTCCAAATCTTC

AATCTCTTACAAATTTGCTTTCATCTAATCTTTCTTGGCTGTCTCTTG

ATGTTTCTGCTGCCTTTTATCATATTCCTCTTCATCCTGCTGCAATGC

CTCATTTGCTTGTTGGATCATCTGGACTTCCAAGATATGTTGCTAGAC

TTAGCTCTACATCTAGAAATATCAATTATCAGCATGGAACAATGCAGG

ATCTTCACGATTCTTGTAGTAGGAATCTGTATGTTTCTTTGCTTCTGC

TGTATAAGACATTTGGAAGAAAACTTCATCTGTATTCTCACCCTATTA

TTCTGGGTTTTAGAAAGATTCCTATGGGAGTTGGACTTTCTCCTTTTT

TGCTTGCTCAATTCACATCTGCTATTTGTTCTGTTGTTAGAAGGGCTT

TTCCTCATTGTCTTGCATTTTCTTATATGGATGATGTTGTTCTTGGAG

CTAAATCTGTTCAACATCTTGAAAGTCTGTTTACCTCTATTACTAATT

TTCTGCTTTCTCTGGGAATTCATCTGAATCCAAACAAAACAAAGAGAT

GGGGATATTCTCTTAATTTCATGGGATATGTTATTGGATCTTGGGGAA

CACTTCCTCAAGAACATATCGTTTTGAAAATCAAGCAATGTTTCAGAA

AACTGCCTGTGAATAGACCTATTGATTGGAAAGTTTGTCAAAGAATTG

TGGGACTTCTTGGATTTGCTGCTCCTTTTACACAATGTGGATATCCTG

CTCTTATGCCACTTTATGCTTGTATTCAATCTAAACAGGCTTTTACAT

TTTCTCCAACATACAAAGCTTTTCTGTGTAAACAGTATCTGAATCTTT

ATCCTGTGGCTAGACAAAGATCTGGTCTTTGTCAAGTTTTTGCTGATG

CTACACCAACAGGATGGGGACTTGCTATTGGACATAGAGCTATGAGAG

GAACATTTGTTGCTCCATTGCCTATTCATACAGCTGAATTGCTTGCTG

CTTGTTTTGCTAGATCTAGAAGCGGAGCAAAACTTATTGGTACAGATA

ATAGTGTTGTCCTGAGTAGAAAGTACACATCTTTTCCATGGTTGTTGG

GATGTGCTGCTAATTGGATTCTTAGAGGAACTTCTTTTGTTTATGTTC

CTTCTGCTCTTAATCCTGCAGCTGATCCATCTGCTGGTAGATTGGGAC

TGTATAGACCACTTCTTCATTTGCCTTTTAGACCAACAACTGGAAGAA

CATCTCTTTATGCTGTTTCTCCTTCTGTTCCATCTCATTTGCCTGATA

GAGTTCATTTTGCTTCTCCACTTCATGTTGCTTGGAGGCCACCATCTA

AATCTCCAGGTTCTGGACCACCTATGCAACTTTTTCATTTGTGTTTGA

TCATTAGCTGTTCTTGTCCTACAGTTCAAGCTTCTAAACTTTGTCTTG

-continued

GATGGCTTTGGGGAATGGATATTGATCCATACAAAGAATTTGGAGCTA

GTGTTGAATTGCTGTCATTTCTTCCATCTGATTTTTTCCCTTCTATTC

GTGATCTTCTTGATACAGCATCTGCTCTGTATAGAGAAGCTCTTGAAT

CTCCTGAACACTGTTCTCCACATCATACAGCACTTAGACAAGCTATTC

TTTGTTGGGGAGAACTTATGAATCTTGCTACATGGGTTGGATCTAATT

TGGAAGATCCAGCTTCTAGAGAATTGGTGGTTTCTTATGTTAATGTGA

ATATGGGACTGAAAATTAGACAACTGCTTTGGTTTCATATCTCTTGTC

TTACATTTGGTAGAGAAACAGTTTTGGAATATTTGGTTTCTTTTGGCG

TTTGGATTAGAACACCTCCAGCTTATAGACCTCCTAATGCTCCTATTT

TGTCTACACTTCCTGAAACAACAGTCGTTAGAAGAAGAGGAAGATCTC

CAAGAAGAAGAACACCAAGTCCTAGAAGAAGAAGATCTCAATCACCAA

GAAGAAGAAGAAGTCAATCTAGAGAATCTCAATGTTGATTTTTGTTCG

ACATTAAAAATTGAAAATAAATACAAAGGTTCTTGAGGGTTGTGTTAA

ATTGAAAGCGAGAAATAATCATAAATATGATTCAGGTGACGGATCCAT

GGATGCTATGAAGCGAGGACTTTGTTGTGTTTTGCTTCTTTGTGGTGC

TGTGTTTGTTTCTCCATCTCAAGAAATTCATGCCAGATTCAGAAGAAT

GGGAGGCTGGTCATCTAAACCTAGACAAGGCATGGGAACAAATCTTTC

TGTTCCTAATCCTTTGGGATTCTTTCCTGATCATCAATTGGATCCAGC

ATTTGGAGCAAATAGTAACAATCCAGATTGGGACTTTAACCCAAACAA

AGATCATTGGCCAGAAGCTAATCAAGTTGGAGCATCTAAAGGTGGAAA

AAGTGGAATGGAAAACACTACATCTGGATTTCTTGGACCTTTGCTTGT

TCTTCAAGCTGGATTTTTCCTGTTGACAAGAATACTTACAATTCCTCA

ATCACTGGATTCTTGGTGGACAAGTCTTAATTTTCTTGGAGGTGCTCC

TACATGTCCTGGACAAAATTCTCAATCTCCAACTTCTAATCATTCTCC

TACATCTTGTCCTCCAATTTGTCCTGGATATAGATGGATGTGTCTTAG

AAGATTCATTATCTTTCTTTTCATACTGCTGCTGTGTCTGATTTTCCT

TCTTGTTTTGTTGGATTATCAGGGAATGCTTCCTGTTTGTCCTTTGCT

TCCTGGAACTTCTACAACAAGTACAGGACCTTGTAAAACATGTACAAT

TCCAGCACAGGGAACATCTATGTTTCCAAGTTGTTGTTGTACAAAACC

TTCTGATGGAAATTGCACATGTATTCCTATTCCAAGTTCTTGGGCATT

TGCTAGATTTCTTTGGGAATGGGCTTCTGTTAGATTCAGTTGGTTGTC

TCTTTTGGTTCCATTTGTTCAGTGGTTTGTTGGATTGTCTCCTACAGT

TTGGCTTTCTGTTATTTGGATGATGTGGTATTGGGGACCTTCTCTTTA

CAATATTTTGAGTCCTTTTCTCCCTTTGCTGCCAATTTTCTTTTGTCT

TTGGGTTTACATTTGAttaaccgagtttctgcattattgtaattcgta tgctggcaccatcaaagaatcacttctaaaagatatcaatatcacaca tacaaatattactaccctattgaatgagacagccaaggttatcaagtt agtaaaatctctggtagataaagaagatactgatattgtgaataattt cattaccaaagaaattaaaaacagagacaaaatagttaatagtttgtc tctatcaaacctggactttcgtttgtaaattggggctTtttgtacaat aaatgggtgttgccaatgattcatcccctgaatatcaatggatgtctc -continued

```
cccatagattatcagatactgttatattaggagactgtttgtatttta

acaatataatgtcccaattagatttacaccaaaattgggctccatcag

ttagattgttaaattattttaagaattttaataaggaaacactactaa

agatagaagagaatgattacattaattcatcctttttccaacaaaagg

ataaacgattttatcctataaacgacgattttatcacatatctacag

gaggatatggtatagtctttaagatagataactatgtagtaaaatttg

tattcgaggccacaaaattatatagtcccatggaaactacggcggagt

tcacagtacccaaatttctatacaacaatctaaagggagatgaaaaaa

aattaatcgtgtgtgcgtgggccatgggattaaactataaattaacat

ttttacatactctgtataaacgtgttcttcatatgttgctattattga

tacaaactatggatggtcaggaactatcattgagatattcttctaaag

tttttttaaaggcgtttaacgagagaaaggacagtatcaaattcgtga

aattactatcccacttttatccggcagttattaacagtaatattaatg

ttataaactattttaaccgcatgtttcacttttttcgaacatgaaaaga

gaactaactacgaatacgaaagaggaaatattataatttttcccctag

cactgtattcggcagataaagtagataccgagctagctatcaaattag

gatttaaatctttggtacaatacataaagtttatctttttacagatgg

ctctgttatacattaaaatttacgaactaccatgctgcgacaactttt

tacacgcagatcttaaacccgataatatcttacttttttgattccaatg

aaccaataataattcatctaaaggataaaaagtttgtttttaatgaac

gtattaaatcggcattaaacgactttgacttttcccaag
```

8.1 Description for Nucleotide Sequences of Low GC Content Version of MVA-SIi-HBV-PreS-Pmut-C-S (Sh):

8.1.1 F11-L-Flank=bases 1-1097 (SEQ ID NO: 35)

8.1.2 SIi-HBV-PreS-Pmut-C=bases 1098-4838 (SEQ ID NO: 59)

8.1.3 Transcription terminator sequence=bases 4839-4845 TTTTTGT 8.1.4 mH5 promoter=bases 4846-4942 (SEQ ID NO: 28)

8.1.5 TPA=bases 4943-5038 (SEQ ID NO: 60)

8.1.6 S(sh)=bases 5039-5920 (SEQ ID NO: 61)

8.1.7 F11-R-Flank=bases 5921-7239 (SEQ ID NO: 36)

The Sequence of wild-type HBV Polymerase is provided as SEQ ID NO: 19.

ChAdOx1 Sequence

ChAdOx1 sequence 5' to the immunogen cassette is provided as SEQ ID NO: 39.

ChAdOx1 sequence 3' to the immunogen cassette is provided as SEQ ID NO: 40.

ChAdOx2 Sequence

ChAdOx2 sequence 5' to the immunogen cassette is provided as SEQ ID NO: 41.

ChAdOx2 sequence 3' to the immunogen cassette is provided as SEQ ID NO: 42.

MVA Sequence

MVA sequence 5' to the immunogen cassette is provided as SEQ ID NO: 44. MVA sequence 3' to the immunogen cassette is provided as SEQ ID NO: 45

The CMV long promoter with Tetron Operator sequence is provided as SEQ ID NO: 50. The CMV short promoter with Tetron Operator sequence is provided as SEQ ID NO: 51.

```
PreS1 sequence (SEQ ID NO: 52):
MGGWSSKPRQGMGTNLSVPNPLGFFPDHQLDPAFGANSNNPDWDFNPN

KDHWPEANQVGAGAFGPGFTPPHGGLLGWSPQAQGILTTVPAAPPPAS

TNRQSGRQPTPISPPLRDSHPQA

PreS2 sequence (SEQ ID NO: 53):
MQWNSTTFHQALLDPRVRGLYFPAGGSSSGTVNPVPTTASPISSIFSR

TGDPAPN
```

The invention claimed is:

1. A multi-HBV immunogen viral vector vaccine comprising: a viral vector comprising an immunogen expression cassette, wherein the expression of a protein encoded by the expression cassette is arranged to be driven by a promoter, wherein the immunogen expression cassette comprises nucleic acid comprising the sequence of:

SEQ ID NO: 46 (SIi-HBV-CPmutS);
SEQ ID NO: 47 (SIi-HBV-SCPmut);
SEQ ID NO: 48 (SIi-HBV-CPmutPreS-S(sh));
SEQ ID NO: 49 (SIi-HBV-CPmutPreS-TPA-S(sh));
SEQ ID NO: 24 (MVA-SIi-HBV-PreS-Pmut-C-S(sh)), or
SEQ ID NO: 27 or SEQ ID NO: 58 (MVA-SIi-HBV-PreS-Pmut-C-TPA-S(sh)).

2. The multi-HBV immunogen viral vector vaccine according to claim 1, wherein (i) the viral vector encodes the amino acid sequence of:
SEQ ID NO: 3 (SIi-HBV-CPmutS);
SEQ ID NO: 11 (SIi-HBV-SCPmut);
SEQ ID NO: 13 (SIi-HBV-CPmutPreS-S(sh));
SEQ ID NO: 25 (SIi-HBV-CPmutPreS-TPA-S(sh));
SEQ ID NO: 23 (MVA-SIi-HBV-PreS-Pmut-C-S(sh));
SEQ ID NO: 26 (MVA-SIi-HBV-PreS-Pmut-C-TPA-S(sh)); or
(ii) the viral vector comprises an adenovirus vector or Modified Vaccinia Ankara (MVA) vector; or
(iii) the viral vector comprises a group E simian adenovirus vector.

3. A nucleic acid comprising or consisting of an HBV immunogen expression cassette, wherein the immunogen expression cassette comprises the sequence of:

SEQ ID NO: 46 (SIi-HBV-CPmutS);
SEQ ID NO: 47 (SIi-HBV-SCPmut);
SEQ ID NO: 48 (SIi-HBV-CPmutPreS-S(sh));
SEQ ID NO: 49 (SIi-HBV-CPmutPreS-TPA-S(sh));
SEQ ID NO: 24 (MVA-SIi-HBV-PreS-Pmut-C-S(sh)); or
SEQ ID NO: 27 or SEQ ID NO: 58 (MVA-SIi-HBV-PreS-Pmut-C-TPA-S(sh)).

4. The nucleic acid according to claim 3, wherein
the immunogen expression cassette is isolated or provided in a non-viral vector.

5. A method of treatment or prophylaxis of HBV infection comprising the administration of the viral vector according to claim 1, to a subject.

6. The method according to claim 5, wherein the administration of the viral vector is in combination with the administration of another therapeutically or prophylactically active ingredient.

* * * * *